(12) United States Patent
Goddard et al.

(10) Patent No.: US 7,304,136 B2
(45) Date of Patent: Dec. 4, 2007

(54) PRO4407 POLYPEPTIDES

(75) Inventors: Audrey Goddard, San Francisco, CA (US); Austin L. Gurney, Belmont, CA (US); Victoria Smith, Burlingame, CA (US); Colin K. Watanabe, Moraga, CA (US); William I. Wood, Hillsborough, CA (US)

(73) Assignee: Genentech, inc., South San Francisco, CA (US)

( * ) Notice: Subject to any disclaimer, the term of this patent is extended or adjusted under 35 U.S.C. 154(b) by 373 days.

(21) Appl. No.: 10/242,653

(22) Filed: Sep. 11, 2002

(65) Prior Publication Data
US 2003/0108996 A1 Jun. 12, 2003

Related U.S. Application Data

(63) Continuation of application No. 10/197,942, filed on Jul. 18, 2002, now abandoned, which is a continuation of application No. PCT/US01/27099, filed on Aug. 29, 2001, which is a continuation-in-part of application No. PCT/US99/28551, filed on Dec. 2, 1999.

(60) Provisional application No. 60/162,506, filed on Oct. 29, 1999, provisional application No. 60/131,271, filed on Apr. 27, 1999.

(51) Int. Cl.
*C07K 14/435* (2006.01)
*C07K 19/00* (2006.01)
*C07H 21/04* (2006.01)

(52) U.S. Cl. .................... 530/350; 530/387.1; 536/23.1

(58) Field of Classification Search ................ 530/350; 536/23.5; 535/23.5
See application file for complete search history.

(56) References Cited

U.S. PATENT DOCUMENTS 5,536,637 A 7/1996 Jacobs ........................... 435/6

OTHER PUBLICATIONS

Haynes et al., Electrophoresis 1998, vol. 19(11): pp. 1862-1871.*
Chen et al., Mol Cell Proteomics 2002, vol. 1(4): pp. 304-313.*
Luck et al., Molecular Endocrinology 1991, vol. 5(12): pp. 1880-1886.*
Stuart et al., Lancet. 2004, vol. 364(9442): pp. 1343-1360.*
LaBaer, J. (2003). Mining the literature and large datasets. Nature Biotechnology. 21(9):976-977.*
Lichtinghagen et al. (2002). Different mRNA and protein expression of matrix metalloproteinases 2 and 9 and tissue inhibitor of metalloproteanases 1 in benign and malignant prostate tissue. European Urolog. 42:398-406.*
Lian et al. (2001). Genomic and proteomic analysis of the myeloid differentiation program. Blood. 98:513-524.*
Fessler et al. (2002). A genomic and proteomic analysis of activation of the human neutrophil by lipopolysaccharide and its mediation by p38 mitogen-activated protein kinase. The Journal of Biological Chemistry. 277(35):31291-31302.*
Feroze-Meroug et al. (2001). Molecular profiling in prostate cancer. Cancer and Metastasis Reviews. 20:165-171.*
Gygi et al. (1999). Correlation between protein and mRNA abundance in yeast. Molecular and Cellular Biology. 19(3):1720-1730.*
Madoz-Gurpide et al. (2003). Molecular analysis of cancer using DNA and protein microarrays. Adv. Exp. Med. Biol. 532:51-58.*
Celis et al. (2000). Gene expression profiling: monitoring transcription and translation products using DNA microarrays and proteomics. FEBS Letters. 480:2-16.*
Bustin et al. (2002). The value of microarray techniques for quantitative gene profiling in molecular diagnostics. TRENDS in Molecular Medicine. 8(6):269-272.*
Valle et al. (2003). New approaches for biomarker discovery in lung cancer. Expert Rev. Mol. Diagn. 3(1):55-67.*
Hittelman W.M. (2001). Genetic instability in epithelial tissues at risk for cancer. Ann. N Y Acad. Sci. 952:1-12.*
Fleischhacker et al. (1995) DNA aneuploidy in morphologically normal colons from patients with colon cancer. Mod. Pathol. 8(4):360-365.*
Hu et al. (2003). Analysis of genomic and proteomic data using advanced literature mining. Journal of Proteome Research. 2:405-412.*
Quackenbush, J. (2002). Microarray data normalization and transformation. Nature Genetic Supplement. 32:496-501.*
Hegde et al. (2000). A concise guide to cDNA microarray analysis. Bio Techniques. 29(3):548-;550; 552-554; 556; 558-560;562.*
Lilley et al. "Proteomics". Molecular Biology in Cellular Pathology, (2003) England: John Wiley & Sons, p. 351-352.*
Wildsmith et al. "Gene Expression Analysis Using Microarrays". Molecular Biology in Cellular Pathology, (2003) England: John Wiley & Sons, pp. 269-286.*
King, H.C. (2001). Gene expression profile analysis by DNA microarrays: promise and pitfalls. JAMA. 286(18):2280-2288.*
Steiner et al. Proteomics: Applications and opportunities in preclinical drug development. Electrophoresis 21: 2099-2104, 2000.*
Database Search, DNA sequence alignments [BLASTN 2.1.2 (Jan. 8, 2002), NCBI].
Database Search, protein sequence alignments [BLASTP 2.2.2 (Jan. 8, 2002), NCBI].
Klein et al., "Selection for genes encoding secreted proteins and receptors" Proc. Nat. Acad. Sci. USA 93:7108-7113 (1996).
Dayhoff, Accession No. P_ABG34048, WO 200224888-A2, Pub Date: Mar. 28, 2002, K. P. Baker et al.

(Continued)

*Primary Examiner*—Bridget Bunner
(74) *Attorney, Agent, or Firm*—Mark T. Kresnak; Elizabeth M. Barnes; Ginger R. Dreger, Esq.

(57) ABSTRACT

The present invention is directed to novel polypeptides and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention.

6 Claims, 115 Drawing Sheets

OTHER PUBLICATIONS

Dayhoff, Accession No. P_AAY57952, WO 9961471-A2, Pub Date: Dec. 2, 1999, Y. T. Tang et al.
Dayhoff, Accession No. P_AAB24036, WO 200053750-A1, Pub Date: Sep. 14, 2000, D. Botstein et al.
Dayhoff, Accession No. P_AAB12136, WO 200029448-A2, Pub Date: May 25, 2000, S. Kato et al.
Dayhoff, Accession No. AAH35517.1, Direct Submission, Submitted: Jul. 31, 2002, National Institute of Health.
Dayhoff, Accession No. NP_699176.1, Science, 300(5620), 767-772, 2003, S. W. Scherer et al.
Dayhoff, Accession No. P_AAM93501, EP 1130094-A2, Pub Date: Sep. 5, 2001, T. Ota et al.
Dayhoff, Accession No. BAC11382.1, Direct Submission, Submitted: Mar. 25, 2002, T. Isogal et al.
GenBank, Accession No. P_ABK69979, WO 200224888-A2, Pub Date: Mar. 28, 2002, K. P. Baker et al.
GenBank, Accession No. P_AAC58118, WO 200053750-A1, Pub Date: Sep. 14, 2000, D. Botstein et al.
GenBank, Accession No. BC035517, Proc. Natl. Acad. Sci. USA 99 (26), 16899-16903, 2002, R. L. Strausberg et al.
GenBank, Accession No. FLJ90586, Otsuki et al. Jul. 9, 2005.
GenBank, Accession No. XM_072433, Aug. 1, 2002.
GenBank, Accession No. P_AAA62019, WO 2000294488-A2, Pub Date: May 25, 2000, S. Kato et al.
GenBank, Accession No. P_AAK94429, EP 1130094-A2, Pub Date: Sep. 5, 2001, T. Ota et al.
GenBank, Accession No. AK075067, Direct Submission, Submitted: Mar. 25, 2002, T. Isogai et al.
GenBank, Accession No. BD127458, JP 2002017375, Pub Date: Jan. 22, 2002, T. Ota et al.
GenBank, Accession No. P_AAZ56773, WO 9961471-A2, Pub Date: Dec. 2, 1999, Y. T. Tang et al.
Beer et al, "Gene-expression profiles predict survival of patients with lung adenocarcinoma", Nature Biomedicine vol. 98, No. 8, Aug. 2002.
Saito-Hisaminato, "Genome-Wide Profiling of Gene Expression in 29 Normal Human Tissues with cDNA Microarray", DNA Research, vol. 9, pp. 35-45, 2002.
Abe, N., et al., "An Increased High-Mobility Group A2 Expression Level is Associated with malignant Phenotype in Pancreatic Exocrine Tissue," Br J Cancer—89(11):2104-9 (2003) Abstract.
Ando, M., et al., "Selective Apoptosis of Natural Killer-Cell Tumours by I-Asparaginase," Br J Haematol.,—130(6):860-8 (2005) Abstract.
Barnes, V.L., et al., "Expression of Embryonic Fibronectin Isoform EIIIA Parallels Alpha-Smooth Muscle Actin in Maturing and Diseased Kidney," J Histochem Cytochem.—47(6):787-98 (1999) Abstract.
Blaschke, V., et al., "Rapid Quantitation of Proinflammatory and Chemoattractant Cytokine Expression in Small Tissue Samples and Monocyte-Derived Dendritic Cells: Validation of New Real-Time RT-PCR Technology," J Immunol Methods.—246(1-2):79-90 (2000) Abstract.
Buckley, A.R., et al., "Butyrate-Induced Reversal of Dexamethasone Resistance in Autonomouse Rat Nb2 Lymphoma Cells," Apoptosis.—2(6):518-28 (1997) Abstract.
Caberlotto, L. et al.,"Alterations in Neuropeptide Y Levels and Y1 Binding Sites in the Flinders Sensitive Line Rats, A Genetic Animal Model of Depression," Neurosci Lett.—265(3):191-4 (1999) Abstract.
Caberlotto, L., et al., "Neurokinin 1 Receptor and Relative Abundance of the Short and Long Isoforms in the Human Brain," Eur J Neurosci.—17(9):1736-46 (2003) Abstract.
Choi, D., et al., "Characterization of Cyclin D2 Expression in Human Endometrium," J Soc Gynecol Investig.—9(1):41-6 (2002) Abstract.
Couvelard, A., et al., "Human Chorionic Gonadotrophin Beta Expression in Malignant Barret's Oesophagus," Virchos Arch.—445(3):279-84 (2004) Abstract.
Dagenais, A., et al., "Downregulation of EnaC Activity and Expression by TNF-Alpha in Alveolar Epithelial Cells," Am J. Physio Lung Cell Mol Physiol.—286(2):L301-11 (2004) Abstract.
De Boer, C.J., et al., "Involement of CCNDI Gene in Hairy Cell Leukemia," Ann Oncol.—7(3):251-6 (1996) Abstract.
Debieve, F., et al., "Inhibin and Activin Production and Subunit Expression in Human Placental Cells Cultured in Vitro," Mol Hum Reprod.—6(8):743-9 (2000) Abstract.
Dong, Z., et al., "Expression of Membrane-Type Matrix Metalloproteinases 4, 5, and 6 in Mouse Corneas Infected with P. aeruginosa," Invest Opthamol Vis Sci—42(13):3223- (2001) Abstract.
Duchrow, M., et al., "Assessment of Proliferative Activity in Colorectal Carcinomas by Quantitative Reverse Transcriptase-Polymerase Chain Reaction (RT-PCR)," Cancer Invest.—19(6):588-96 (2001) Abstract.
Dyer, J., et al., "Molecular Characterization of Carbohydrate Digestion and Absorption in Equine Small Intestine," Equine Vet J.—34(4):349-58 (2002) Abstract.
Egwuagu, C.E., et al., "Suppressors of Cytokine Signaling Proteins are Differentially Expressed in Th1 and Th2 Cells: Implications for Th Cell Lineage Commitment and Maintenance," J Immunol.—168(7):3181-7 (2002) Abstract.
El-Ghrably, I.A., et al., "Intravitreal Invading Cells Contribute to Vitreal Cytokine Milieu in Proliferative Vitreoretinopathy," Br J Opthamol.—85(4):461-70 (2001) Abstract.
Eleore, L., et al., "Modulation of the Glutamatergic Receptors (AMPA and NMDA) and of Glutamate Vesicular Transporter 2 in the Rat Facial Nucleus after Axotomy," Neuroscience—136(1):147-60 (2005) Abstract.
Forsberg, H., et al., "Altered Levels of Scavenging Enzymes in Embryos Subjected to a Diabetic Environment," Free Radic Res.—24(6):451-9 (1996) Abstract.
Freyschuss, B., et al., "Induction of the Estrogen Receptor by Growth Hormone and Glucocorticoid Substitution in Priminary Cultures of Rat Hepatocytes," Endocrinology—133(4):1548-54 (1993) Abstract.
Fu, K., et al., "Cyclin D1-Negative Mantle Cell Lymphoma: A Clinocopathologic Study Based on Gene Expression Profiling," Blood—106(13):4315-21 (2005) Abstract.
Fuchs, A.R., et al., "Oxtocin Receptors in Bovine Cervix: Distrubution and Gene Expression During the Estrous Cycle," Biol Reprod.—54(3):700-8 (1996) Abstract.
Furuta, J., et al., "Silencing of the Thrombomodulin Gene in Human Malignant Melanoma," Melanoma Res.—15(1):15-20 (2005) Abstract.
George, J., et al., "Pre-translational Regulation of Cytochrome P450 Genes is Responsible for Disease-Specific Changes of Individual P450 Enzymes Among Patients with Cirrhosis," Biochem Pharmacol.—49(7):873-81 (1995) Abstract.
Giroux, M., et al., "Cyclooxygenase-2 Expression in Macrophages: Modulation by Protein Kinase C-alpha," J immunol.—165(7):3985-91 (2000) Abstract.
Godbout, R., et al., "Overexpression of DEAD Box Protein (DDX1) in Neuroblastoma and Retinoblastoma Cell Lines," J Biol Chem,—273(33):21161-8 (1998) Abstract.
Goldenberg, R.C., et al., "Modulation of Gap Junction Mediated Intercellular Communication in TM3 Leydig Cells," J Endocrinol.—177(2):327-35 (2003) Abstract.
Golebiowski, F., et al., "Expression Level of Ubc9 Protein in Rat Tissues," Acta Biochim Pol.—50(4):1065-73 (2003) Abstract.
Grem, J.L., et al., "Thymidine Kinase, Thymidylate Synthase, and Dihydropyrimidine Dehydrogenase Profiles of Cell Lines of the National Cancer Institute's Anticancer Drug Screen," Clin Cancer Res.—7(4):999-1009 (2001) Abstract.
Grenback, E., et al., "Galanin Pituitary Ademonas," Regul Pept,—117(2):127-39 (2004) Abstract.
Non-Invasive and Invasive Bladder Transitional Cell Carcinomas, Int J. Oncol.—13(2):379-83 (1998) Abstract.
Guo, Y., et al., "The Pathogenic Role of Macrophage Migration Inhibitory Factor in Acute Respiratory Distress Syndrome," Zhinghua Jie He He Hu Xi Za Zhi—25(6):337-40 (2002) Abstract.

Habu, Y., et al., "Restored Expression and Activity of Organic Ion Transporters rOAT1, rOAT3 and rOCT2 after Hyperuricemia in the Rat Kidney," *Biochem Pharmacol—69*(6):993-9 (2005) Abstract.

Hahn, M.E., et al., "Regulation of Cytochrome P4501A1 In Teleosts: Sustained Induction of CYP1A1 mRNA, Protein, and Catalytic Activity by 2,3,7,8-Tetrachlorodibenzofuran in the Marine Fish Stenotomus Chrysops," *Toxicol Appl Pharmacol.— 127*(2):187-98 (1994) Abstract.

Hamilton, L.M., et al., "The role of the Epidermal Growth Factor Receptor in Sustaining Neutrophil Inflammation in Severe Asthma," *Clin Exp Allergy.—33*(2):233-40 (2003) Abstract.

Hassett, C., et al., "Human Hepatic Microsomal Epoxide Hydrolase: Comparative Analysis of Polymorphic Expression," *Arch Biochem Biophys.—337*(2):275-83 (1997) Abstract.

Huang, Y.H., et al., "Tissue Plasminogen Activator Induced by Dengue Virus Infection of Human Endothelial Cells," *J Med Virol.—70*(4):610-6 (2003) Abstract.

Huettner, P.C., et al., "Neu Oncogene Expression in Ovarian Tumors: A Quantitative Study," *Mod Pathol.—5*(3):250-6 (1992) Abstract.

Hui, P., et al., "Real-time Quantitative RT-PCT of Cyclin D1 mRNA in Mantle Cell Lymphoma: Comparison with FISH and Immunohistochemstry," Leuk Lymphoma. 44(8):1385-94 (2003) Abstract.

Husain, I., et al., "Elevation of Topoisomerase I Messenger RNA, Protein, aand Catalytic Activity in Human Tumors: Demonstration of Tumor-Type Specificity and Implications for Cancer Chemotherapy," *Cancer Res.—54*(2):539-46 (1994) Abstract.

Ihmann, T., et al., "High-level mRNA Quantification of Proliferation marker pKi-67 is Correlated with Favorable Prognosis in Colorectal Carcinoma," *J Cancer Res Clin Oncol.—130*(12):749-56 (2004) Abstract.

Ikegami, T., et al., "Modulation of Glucagon Receptor Expression and Response in Transfected Human Embryonic Kidney Cells," *Am J Physiol Cell Physiol.—281*(4):C1396-402 (2001) Abstract.

Jacquemin, E., et al., "Developmental Regulation of Acidic Fibroblast Growth Factor (aFGF) Expression in Bovine Retina," *Int J Biol.—37*(3):417-23 (1993) Abstract.

Jaime, M., et al., "The p21 (Cip1) Protein, A Cyclin Inhibitor, Regulates the Levels and the Intracellular Localization of CDC25A in Mice Regenerating Livers," *Hepatology—35*(5):1063-71 (2002) Abstract.

Jungbluth, A.A., et al., "Immunohistochemical Analysis of NY-ESO-1 Antigen Expression in Normal and Malignant Human Tissues," *Int J. Cancer—92*(6):856-60 (2001) Abstract.

Kalabis, G.M., et al., "Multidrug Resistance Phosphoglycoprotein (ABCB1) in the Mouse Placenta: Fetal Protection," *Biol Reprod.—73*(4):591-7 (2005) Abstract.

Khal, J., et al., "Expression of the Ubiquitin-Proteasome Pathway and Muscle Loss in Experimental Cancer Cachexi," *Br J Cancer—93*(7):774-80 (2005), Abstract.

Khal, J., et al., "Increased Expression of Proteasome Subunits in Skeletal Muscle of Cancer Patients with Weight Loss," *Int J. Biochem Cell Biol.—37*(10):2196-206 (2005) Abstract.

Kogo, H., et al., "Cell Type-Specific Occurrence of Caveolin-1alpha and -1beta in the Lung caused by Expression of Distict mRNAs," *J Biol Chem.—279*(24):25574-81 (2004) Abstract.

Kommoss, F., et al., "Ocogene and Growth Factor Expression in Ovarian Cancer," *Acta Obstet Gynecol Scand Suppl.—155*:19-24 (1992) Abstract.

Kumar, U., et al., "Somatostatin Receptors in Primary Human Breast Cancer: Quantitative Analysis of mRNA for Subtypes 1-5 and Correlation with Receptor Protein Expression and Tumor Pathology," *Breast Cancer Res. Treat.—92*(2):175-86 (2005) Abstract.

Landmark, B.F., et al., "Cellular Location and Age-dependent Changes of the regulatory Subunits of cAMP-dependent Protein Kinase in Rat Testis," *J Reprod Fertil.—99*(2):323-34 (1993) Abstract.

Lassmann, S., et al., "Quantification of CK20 Gene and Protein Expression in Colorectal Cancer by RT-PCR and Immunohistochemistry Reveals inter- and Intratumour Heterogeneity," *J Pathol.—198*(2):198-206 (2002) Abstract.

Legrand, O., et al., "Expression of the Multidrug Resistance-Associated Protein (MRP) mRNA and Protein in Normal Peripheral Blood and Bone Marrow Haemopoietic Cells," *Br J, Haematol.— 94*(1):23-33 (1996) Abstract.

Lemstrom, K.B., et al., "Vascular Endothelial Growth Factor Enhances Cardiac Allograft Arteriosclerosis," *Circulation—105*(21):2524-30 (2002) Abstract.

Li, Z.B., et al., "Enhanced Expressions of Arachidonic Acid-Sensitive Tandem-Pore Domain Potassium Channels in Rat Experimental Acute Cerebral Ischemia," *Biochem Biophys Res Commun.—327*(4):1163-9 (2005) Abstract.

Li, Y., et al., "Retinal Preconditioning and the Induction of Heat-Shock Protein 27," *Invest Opthalmol Vis Sci.—44*(3):1299-304 (2003) Abstract.

Lindberg, P., et al., "Increasing Expression of Tissue Plasminogen Activator and Plasminogen Activator Inhibitor Type 2 in Dog Gingival Tissues with Progressive Inflammation," *Arch Oral Biol.—46*(1):23-31 (2001) Abstract.

Macabeo-Ong, M., et al., "Effect of Duration of Fixation of Quantitative Reverse Transcription Polymerase Chain Reaction Analyses," 15(9):979-87 (2002) Abstract.

Meehan, T.P., et al., "Tightly Regulated and Inducible Expression of a Yoked Hormone-Receptor Complex in HEK 293 Cells," *J Mol Endocrinol.—32*(1):247-55 (2004) Abstract.

Mendoza-Rodriguez, C.A., et al., "C-fos and Estrogen Receptor Gene Expression Pattern in the Rat Uterine Epithelium During the Estrous Cycle," *Mol Reprod Dev. 64*(4):379-88 (2003) Abstract.

Meoni, P., et al., "[3H]MK-801 Binding and the mRNA for the NMDAR1 Subunit of the NMDA Receptor are Differentially Distributed in Human and Rat Forebrain," *Brain Res Mol Res.—54*(1):13-23 (1998) Abstract.

Mezzano, S.A., et al., "Overexpression of Chemokines, Fibrogenic Cytokines, and Myofibroblasts in Human Membranous Nephropathy," *Kiney Int.—57*(1):147-58 (2000) Abstract.

Mingrone, G., et al., "Decreased Uncoupling Protein Expression and Intramyocytic Triglyceride Depletion in Formerly Obese Subjects," *Obes Res.—11*(5):632-40 (2003) Abstract.

Miralles, C.P., et al., "Differential Expression of the Short and Long Forms of the Gamma 2 Subunit of the GABAA/benzodiazepine Receptors," *Brain Res Mol Res.—24*(1-4):129-39 (1994) Abstract.

Mizrachi, D., et al., "Follicle-stimulating Hormone Receptor and Its Messenger Ribonucleic Acid are Present in the Bovine Cervix and Can Regulate Cervical Prostanoid Synthesis," *Biol Reprod.— 61*(3):776-84 (1999) Abstract.

Monaghan, P., et al., "The Alpha(v)beta6 Integrin Receptor for Foot-and-Mouth Disease Virus is Expressed Constitutively on the Epithelial Cells Targeted in Cattle," *J Gen Virol.—86*(Pt 10):2769-80 (2005) Abstract.

Montuori, N., et al., "Urokinase-Mediated Posttranscriptional Regualtion of Urokinase-Receptor Expression in Non Small Cell Lung Carcinoma," *Int J Cancer—105*(3):353-60 (2003) Abstract.

Nie, Y., et al., "DNA Hypermethylation is a Mechanism for Loss of Expression of the HLA Class I Genes in Human Esophageal Squamous Cell Carcinomas," *Carcinogenesis—22*(10):1615-23 (2001) Abstract.

Oberringer, M., et al., "Differential Expression of Heat Shock Portein 70 in Well Healing and Chronic Human Wound Tissue," *Biochem Biophys Res Commun.—214*(3):1009-14 (1995) Abstract.

Orntoft, T.F., et al., "Genome-Wide Study of Gene Copy Numbers, Transcripts, and Protein Levels in Pairs of Non-Invasive and Invasive Human Transitional Cell Carcinomas," *Molecular & Cellular Proteomics—1*:37-45 (2002).

Pachmann, K., et al., "Expression of bcr-abl mRNA in Individual Chronic Mylogenous Leukaemia Cells as determined by Situ Amplification," *Br J. Haematol—112*(3):749-59 (2001) Abstract.

Pairon, J.C., et al., "Cell Localization and Regulation of Expression of Cytochrome P450 1A1 and 2B1 and Rat Lung after Induction with 3-Methylcholanthrene Using mRNA Hybridization and Immunohistochemistry," *Am J Respir Cell Mol Biol.—11*(4):386-96 (1994) Abstract.

Papotti, M., et al., "Expression of Somatostatin Receptor Types 1-5 in 81 Cases if Gastrointestinal and Pancreatic Endocrine Tumors. A correlative Immunohistochemical and Reverse-Transcriptase Polymerase Chain Reaction Analysis," *Virchows Arch.—440*(5):461-75 (2002) Abstract.

Paredes, J., et al., "P-Cadherin Overexpression is an Indicator of Clinical Outcome in Invasive Breast Carcinomas and is Associated with CDH3 Promoter Hypomethylation," *Clin Cancer Res.—11*(16):5869-77 (2005) Abstract.

Politis, I., et al., "Mammary-Derived Growth Inhibitor Protein and Messenger Ribonucleic Acid Concentrations in Different Physiological States of the Gland," *J Dairy Sci.—75*(6):1423-9 (1992) Abstract.

Preesman, A.H., et al., "T-Cell Receptor V Beta-family Usage in Primary Cutaneous and Primary Nodal T-cell non-Hodgkin's Lymphomas," *J Invest Dermatol.—99*(5):587-93 (1992) Abstract.

Pullig, O., et al., "Matrilin-3 in Human Articular Cartilage: Increased Expression in Osteoarthritis," *Osteoarthritis Cartilage—10*(4):253-63 (2002) Abstract.

Rey, C., et al., "Up-regulation of Mitochondrial Peripheral Benzodiazepine Receptor Expression by Tumor Necrosis Factor Alpha in Testicular Leydig Cells. Possible Involvement in Cell Survival," *Biochem Pharmacol.—60*(11):1636-46 (2000) Abstract.

Rudlowski, C., et al., "GLUT1 Messenger RNA and Protein Induction Rrelates to the Malignant Transformation of Cervical Cancer," *Am J. Clin Pathol.—120*(5):691-8 (2003) Abstract.

Sasaki, T., et al., "Expression and Distribution of Laminin Alpha1 and Alpha2 Chains in Embryonic and Adult Mouse Tissues: An Immunochemical Approach," *Exp Cell Res.—275*(2):189-99 (2002) Abstract.

Sedelies, K.A., et al., "Discordant Regulation of Granzyme H and Granzyme B Expression in Human Lymphocytes," *J Biol Chem.—279*(25):26581-7 (2004) Abstract.

Shen, Y., et al., "BCL2 Protein Expression Parallels its mRNA level in normal and Maligent B Cells," *Blood—104*(9):2936-9 (2004) Abstract.

Shinohara, Y., et al., "Quantitative Determinations of the Steady Transcript Levels of Hexokinase Isozymes and Glucose Transporter Isoforms in Normal Rat Tissues and the Malignant Tumor Cell Line AH130," *Biochim Biophys Acta—1368*(1):129-36 (1998) Abstract.

Silvers, A.L., et al., "UVA Irradiation-Induced Activation of Activator Protein-1 is Correlated with Induced Expression of AP-1 Family Members in the Human Keratinocyte Cell Line HaCat," *Photochem Photbiol.—75*(3):302-10 (2002) Abstract.

Song, L., et al., "Rat Kidney Glutamyl Aminopeptidase (aminopeptidase A): Molecular Identity and Cellular Localization," *Am J Physiol.—267*(4 Pt 2):F546-57 (1994) Abstract.

Spaziani, E.P., et al., "Tumor Necrosis Factor-Alpha Upregulates the Prostaglandin E2 EP1 Receptor Subtype and the Cyclooxygenase-2 Isoform in Cultured Amnion WISH Cells," *J Interferon Cytokine Res.—18*(12):1039-44 (1998) Abstract.

Spika, I., et al., "Transcriptional Activity of Potent Glucocorticoids: Relevance of Glucocorticord Receptor Isoforms and Drug Metabolites," *Skin Pharmacol Appl Skin Physiol.—16*(3):143-50 (2003) Abstract.

Splinter, P.L., et al., "Specific Inhibition of AQP1 Water Channels in Isolated Rat Intrahepatic Bile Duct Units by Small Interfering RNAs," *J Biol Chem—278*(8):6268-74 (2003) Abstract.

Stearns, M.E., et al., "Type IV Collagenase (M(r) 72,000) Expression in Human Prostate: Benign and Malignant Tissue," *Cancer Res.—53*(4):878-83 (1993) Abstract.

Stein, R., et al., "The Decompensated Detrusor III: Impact of Bladder Outlet Obstruction on Sarcoplasmic Endoplasmic Reticulum Protein and Gene Expression," *J. Urol.—164*(3 Pt 2):1026-30 (2000) Abstract.

Strickland, I., et al., "TNF-Alpha and IL-8 are Upregulated in the Epidermis of Normal Human Skin after UVB Exposure: Correlation with Nuetrophil Accumulation and E-Selectin Expression," *J Invest Dermatol.—108*(5):763-8 (1997) Abstract.

Strutz, F., et al., "Basic Fibroblast Growth Factor Expression is Increased in Human Renal Fibrogenesis and May Mediated Acutocrine Fibroblast Proliferation," *Kidney Int.—57*(4):1521-38 (2000) Abstract.

Takahashi, K., et al., "Adiposity Elevates Plasma MCP-1 Levels Leading to the Increased CD11b-Positive Monocytes in Mice," *J. Biol. Chem.—278*(47):46654-60 (2003) Abstract.

Takimoto, Y., et al., "Augmented Expression of Neuronal Nitric Oxide Synthase in the Atria Parasympthetically Decreases Heart Rate During Acute Myocardial Infarction in Rats," *Circulation—105*(4):490-6 (2002) Abstract.

Telek, G., et al., "Differential Upregulation of Cellular Adhesion Molecules at the Sites of Oxidative Stress in Experimental Acute Pancreatitis," *J Surg Res.—96*(1):56-67 (2001) Abstract.

Timchenko, L., et al., "Myotonic Dystrophy: An Unstable CTG Repeat in a Protein Kinase Gene," *Semin Cell Biol.—6*(1):13-9 (1995) Abstract.

Torronen, R., et al., "Induction of Class 3 Aldehyde Dehydrogenase in the Mouse Hepatoma Cell Line Hepa-1 by Various Chemicals," *Chem Biol. Interact.—83*(2):107-19 (1992) Abstract.

Ullmannova, V., et al., "Relationship Between Cyclin D1 and p21 (Waf1/Cip1) During Differentiation of Human Myeloid Leukemia Cell Lines," *Leuk Res.—27*(12):1115-23 (2003) Abstract.

Van Beers, E.H., et al., "Intestinal Carbamoyl Phosphate Synthase I in Human and Rat. Expression during Development Shows Species Differences and Mosaic Expression in Duodenum of Both Species," *J Histochem Cytochem.—46*(2):231-40 (1998) Abstract.

Van Der Wilt, C.L., et al., "Expression of Deoxycytidine Kinase in Leukaemic Cells Compared with Solid Tumour Cell Lines, Liver Metastases and Normal Liver," *Eur J Cancer—39*(5):691-7 (2003) Abstract.

Waldherr, R., et al., "Expression of Cytokines and Growth Factors in Human Glomerulonephritides," *Pediatr Nephrol.—7*(4):471-8 (1993) Abstract.

Wang, J., et al., "Cell Proliferation in Human Soft Tissue Tumors Correlates with Platelet-derived Growth Factor B Chain Expression: An Immunohistochemical and in Situ Hybridization Study," *Cancer Res.—54*(2):560-4 (1994) Abstract.

Wang, L.G., et al., "Down-Regulation of Prostate-Specific Antigen Expression by Finasteride through Inhibition of Complex Formation Between Androgen Receptor and Steroid Receptor-binding Consensus in the Promoter of the PSA Gene in LNCaP Cells," *Cancer Res.—57*(4)714-9 (1997) Abstract.

Weterman, M.A., et al., "Expression of Calcyclin in Human Melanocytic Lesions," *Cancer Res.—53*(24):6061-6 (1993) Abstract.

Williams, E.T., et al., "Estrogen Regulation of the Cytochrome P450 3A Subfamily in Humans," J Pharmacol Exp Ther. 311(2):728-35 (2004) Abstract.

Wojtaszek, P.A., et al., "Severely Decreased MARCKS Expression Correlates with Ras Reversion but not with Mitogenic Responsiveness" *Oncogene—8*(3):755-60 (1993) Abstract.

Zhong, W., et al., "Expression of Superoxide Dismutases, Catalase, and Glutathione Peroxidase in Glioma Cells," *Free Radic Biol Med.—27*(11-12):1334-45 (1999) Abstract.

Xi, L., et al., "Expression of Human Telomerase Reverse Transcriptase in Cervix Cancer and its Significance,"Zhonghua Fu Chan Ke Za Zhi—40(6):407-10 (2005) Abstract.

Alberts, B., et al., Molecular Biology of the Cell (3rd ed. 1994) Cell 3rd at 453 Figre 9-2 of Cell 3rd Cell 3rd at 403.

Alberts, B., et al., Molecular Biology of the Cell (4rd ed.) In Cell 4th, Figure 6-3 on p. 302 Figure 6-90 on p. 364 of Cell 4th Cell 4 th at 364 Cell 4th at 379, 2002.

Aust, G., et al., "Human Throid Carcinoma Cell Lines and Normal Thyrocytes: Expression and Regulation of Matrix Metalloproteinase-1 and Tissue Matrix Metalloproteinase Inhibitor- Messenger-RNA and Protein," *Thyroid—7*(5):713-724 (1997).

Beà, S., et al., "BMI-1 Gene Amplification and Overexpression in Hematological Malignancies Occur Mainly in Mantle Cell Limphomas," *Cancer Research—61*:2409-2412 (2001).

Beer, et al, "Gene-expression profiles predict survival of patients with lung adenocarcinoma," *Nature Biomedicine—98*(6):816-824 (2002).

Futcher, B., et al., "A Sampling of the Yeast Proteome," *Molecular and Cellular Biology—19*(11):7357-7368 (1999).

Golub, T.R., et al., "Molecular Classification of Cancer: Class Discovery and Class Prediction by Gene Expression Monitoring," *Science—286*:531-537 (1999).

Gnatenko, D.V., et al., "Transcript Profiling of Human Platelets Using Microarray and Serial Analysis of Gene Expression," *Blood—101*(6):2285-2293 (2003).

Greenbaum, D., et al., "Analysis of mRNA Expression and Protein Abundance Data: An Approach for the Comparison of the Enrichment of Features in the Cellular Population of Proteins and Transcripts," *Bioinformaticsl—18*(4):585-496 (2002).

Gromova, I., et al., "Protein Abundancy and mRNA Levels of the Adiopcyte-Type Fatty Acid Binding Protein Correlate in Non-Invasive and Invasive Bladder Transitional Cell Carcinomas," *International Journal of Oncology—13*(2):379-383 (1998).

Hähnel, E., et al., "Expression of the pS2 Gene in Breast Tissues Assessed by pS2-mRNA Analysis and pS2-Protein Radioimmunoassay," *Breast Cancer Research and Treatment—24*:71-74 (1992).

Hirsch, F.R., et al., "Early Detection of Lung Cancer: Clinical Perspectives of Recent Advances in Biology and Radiology," *Clinical Cancer Research—7*:5-22 (2001).

Holten-Andersen, M.D., et al., "Localization of Tissue Inhibitor of Metalloproteinases 1 (TIMP-1) in Human Colorectal Adenoma and Adenocarcinoma," *Int. J. Cancerl—113*:198-206 (2005).

Janssens, N., et al., "Alteration of Frizzled Expression in Renal Cell Carcinoma," *Tumor Biology—25*:161-171 (2004).

Kammori, M., et al., "Expression of Human Telomerase Reverse Transcriptase Gene and Protein, and of Estrogen and Progesterone Receptors, in Breast Tumors: Preliminary Data from Neo-Adjuvant Chemotherapy", Interanational *Journal of Oncology—27*(5):1257-1263 (2005).

Kuo, C.C., et al., "A Transcriptomic and Proteomic Analysis of the Effect of CpG-ODN on Human THP-1 Monocytic Leukemia Cells," *Proteomics—5*:894-906 (2005).

Lewin, B., Genes VI (1997 *Genes VI* at 847-848.

Meric, F., et al., "Translation Initiation in Cancer: A Novel Target for Therapy," *Molecular Cancer Therapeutics—1*:971-979 (2002).

Munaut, C., et al., "Vascular Endothelial Growth Factor Expression Correlates With Matrix Metalloproteinases MT1-NMP, MNP-2 and NMP-9 in Human Glioblastomas," *Int. J. Cancer—106*:848-855 (2003).

Maruyama, H., et al., "Id-1 and Id-2 are Overexpressed in Pancreatic Cancer and in Dysplastic Lesions in Chronic Pancreatitis," *American Journal of Pathology—155*(3):815-822 (1999).

Nuciforo, P. G., et al., "Molecular and Immunohistochemical Analysis of HER2/neu Oncogene in Synovial Sarcoma," *Human Pathology—34*(7):639-645 (2003).

Papotti, M., et al., "Correlative Immunohistochemical and Reverse Transcriptase Polymerase Chain Reaction Analysis of Somatostatin Receptor Type 2 in Neuroendocrine Tumors of the Lung," *Diagnostic Molecular Pathology—9*(1):47-57 (2000).

Walmer, D. K., et al., "Malignant Transformation of the Human Endometrium is Associated with Overexpression of Lactoferrin Messenger RNA and Protein," *Cancer Research—55*(5):1168-1174 (1995).

Wang, J., et al., "Expression of Cadherins and Catenins in Paired Tumor and non-Neoplastic Primary Prostate Cultures and Corresponding Prostatectomy Specimens," *Urol Resl—28*:308-315 (2000).

Wen-Hsiang, W., et al., "Comparison of *TP53* Mutations Identified by Oligonucleotide Microarray and Conventional DNA Sequenc Analysis," *Cancer Research—60*:2716-2722 (2000).

Zhigang, Z., et al., "Prostate Stem Cell Antigen (PSCA) Express in Human Prostate Cancer Tissues and its Potential Role in Prostate Carinogenesis and Progession of Prostate Cancer," *World Journal of Surgical Oncology—2*-13 (2004).

* cited by examiner

FIGURE 1

CGGACGCGTGGGTGCGAGGCGAAGGTGACCGGGGACCGAGCATTTCAGATCTGCTCGGTAGA
CCTGGTGCACCACCACCATGTTGGCTGCAAGGCTGGTGTGTCTCCGGACACTACCTTCTAGG
GTTTTCCACCCAGCTTTCACCAAGGCCTCCCTGTTGTGAAGAATTCCATCACGAAGAATCA
ATGGCTGTTAACACCTAGCAGGGAATATGCCACCAAAACAAGAATTGGGATCCGGCGTGGGA
GAACTGGCCAAGAACTCAAAGAGGCAGCATTGGAACCATCGATGGAAAAAATATTTAAAATT
GATCAGATGGGAAGATGGTTTGTTGCTGGAGGGGCTGCTGTTGGTCTTGGAGCATTGTGCTA
CTATGGCTTGGGACTGTCTAATGAGATTGGAGCTATTGAAAGGCTGTAATTTGGCCTCAGT
ATGTCAAGGATAGAATTCATTCCACCTATATGTACTTAGCAGGGAGTATTGGTTTAACAGCT
TTGTCTGCCATAGCAATCAGCAGAACGCCTGTTCTCATGAACTTCATGATGAGAGGCTCTTG
GGTGACAATTGGTGTGACCTTTGCAGCCATGGTTGGAGCTGGAATGCTGGTACGATCAATAC
CATATGACCAGAGCCCAGGCCCAAAGCATCTTGCTTGGTTGCTACATTCTGGTGTGATGGGT
GCAGTGGTGGCTCCTCTGACAATATTAGGGGGTCCTCTTCTCATCAGAGCTGCATGGTACAC
AGCTGGCATTGTGGGAGGCCTCTCCACTGTGGCCATGTGTGCGCCCAGTGAAAGTTTCTGA
ACATGGGTGCACCCCTGGGAGTGGGCCTGGGTCTCGTCTTTGTGTCCTCATTGGGATCTATG
TTTCTTCCACCTACCACCGTGGCTGGTGCCACTCTTTACTCAGTGGCAATGTACGGTGGATT
AGTTCTTTTCAGCATGTTCCTTCTGTATGATACCCAGAAAGTAATCAAGCGTGCAGAAGTAT
CACCAATGTATGGAGTTCAAAAATATGATCCCATTAACTCGATGCTGAGTATCTACATGGAT
ACATTAAATATATTTATGCGAGTTGCAACTATGCTGGCAACTGGAGGCAACAGAAAGAAATG
AAGTGACTCAGCTTCTGGCTTCTCTGCTACATCAAATATCTTGTTTAATGGGGCAGATATGC
ATTAAATAGTTTGTACAAGCAGCTTTCGTTGAAGTTTAGAAGATAAGAAACATGTCATCATA
TTTAAATGTTCCGGTAATGTGATGCCTCAGGTCTGCCTTTTTTCTGGAGAATAAATGCAGT
AATCCTCTCCCAAATAAGCACACACATTTTCAATTCTCATGTTTGAGTGATTTAAAATGTT
TTGGTGAATGTGAAAACTAAAGTTTGTGTCATGAGAATGTAAGTCTTTTTTCTACTTTAAAA
TTTAGTAGGTTCACTGAGTAACTAAAATTTAGCAAACCTGTGTTTGCATATTTTTTGGAGT
GCAGAATATTGTAATTAATGTCATAAGTGATTTGGAGCTTTGGTAAAGGGACCAGAGAGAAG
GAGTCACCTGCAGTCTTTTGTTTTTTTAAATACTTAGAACTTAGCACTTGTGTTATTGATTA
GTGAGGAGCCAGTAAGAAACATCTGGGTATTTGGAAACAAGTGGTCATTGTTACATTCATTT
GCTGAACTTAACAAAACTGTTCATCCTGAAACAGGCACAGGTGATGCATTCTCCTGCTGTTG
CTTCTCAGTGCTCTCTTTCCAATATAGATGTGGTCATGTTTGACTTGTACAGAATGTTAATC
ATACAGAGAATCCTTGATGGAATTATATATGTGTGTTTTACTTTTGAATGTTACAAAAGGAA
ATAACTTTAAAACTATTCTCAAGAGAAAATATTCAAAGCATGAAATATGTTGCTTTTTCCAG
AATACAAACAGTATACTCATG

FIGURE 2

```
MLAARLVCLRTLPSRVFHPAFTKASPVVKNSITKNQWLLTPSREYATKTRIGIRRGRTGQEL
KEAALEPSMEKIFKIDQMGRWFVAGGAAVGLGALCYYGLGLSNEIGAIEKAVIWPQYVKDRI
HSTYMYLAGSIGLTALSAIAISRTPVLMNFMMRGSWVTIGVTFAAMVGAGMLVRSIPYDQSP
GPKHLAWLLHSGVMGAVVAPLTILGGPLLIRAAWYTAGIVGGLSTVAMCAPSEKFLNMGAPL
GVGLGLVFVSSLGSMFLPPTTVAGATLYSVAMYGGLVLFSMFLLYDTQKVIKRAEVSPMYGV
QKYDPINSMLSIYMDTLNIFMRVATMLATGGNRKK
```

FIGURE 3

```
CCAATCGCCCGGTGCGGTGGTGCAGGGTCTCGGGCTAGTCATGGCGTCCCCGTCTCGGAGACTGCAGACTAAAC
CAGTCATTACTTGTTTCAAGAGCGTTCTGCTAATCTACACTTTTATTTTCTGGATCACTGGCGTTATCCTTCTT
GCAGTTGGCATTTGGGGCAAGGTGAGCCTGGAGAATTACTTTTCTCTTTTAAATGAGAAGGCCACCAATGTCCC
CTTCGTGCTCATTGCTACTGGTACCGTCATTATTCTTTTGGGCACCTTTGGTTGTTTGCTACCTGCCGAGCTT
CTGCATGGATGCTAAAACTGTATGCAATGTTTCTGACTCTCGTTTTTTTGGTCGAACTGGTCGCTGCCATCGTA
GGATTTGTTTTCAGACATGAGATTAAGAACAGCTTTAAGAATAATTATGAGAAGGCTTTGAAGCAGTATAACTC
TACAGGAGATTATAGAAGCCATGCAGTAGACAAGATCCAAAATACGTTGCATTGTTGTGGTGTCACCGATTATA
GAGATTGGACAGATACTAATTATTACTCAGAAAAAGGATTTCCTAAGAGTTGCTGTAAACTTGAAGATTGTACT
CCACAGAGAGATGCAGACAAAGTAAACAATGAAGGTTGTTTTATAAAGGTGATGACCATTATAGAGTCAGAAAT
GGGAGTCGTTGCAGGAATTTCCTTTGGAGTTGCTTGCTTCCAACTGATTGGAATCTTTCTCGCCTACTGCCWCT
CTCGTGCCATAACAAATAACCAGTATGAGATAGTGTAACCCAATGTATCTGTGGGCCTATTCCTCTCTACCTTT
AAGGACATTTAGGGTCCCCCCTGTGAATTAGAAAGTTGCTTGGCTGGAGAACTGACAACACTACTTACTGATAG
ACCAAAAAACTACACCAGTAGGTTGATTCAATCAAGATGTATGTAGACCTAAAACTACACCAATAGGCTGATTC
AATCAAGATCCGTGCTCGCAGTGGGCTGATTCAATCAAGATGTATGTTTGCTATGTTCTAAGTCCACCTTCTAT
CCCATTCATGTTAGATCGTTGAAACCCTGTATCCCTCTGAAACACTGGAAGAGCTAGTAAATTGTAAATGAAGT
```

FIGURE 4

MASPSRRLQTKPVITCFKSVLLIYTFIFWITGVILLAVGIWGKVSLENYFSLLNEKATNVPF
VLIATGTVIILLGTFGCFATCRASAWMLKLYAMFLTLVFLVELVAAIVGFVFRHEIKNSFKN
NYEKALKQYNSTGDYRSHAVDKIQNTLHCCGVTDYRDWTDTNYYSEKGFPKSCCKLEDCTPQ
RDADKVNNEGCFIKVMTIIESEMGVVAGISFGVACFQLIGIFLAYCXSRAITNNQYEIV

Important features of the protein:
Signal peptide:
amino acids 1-42

Transmembrane domains:
amino acids 19-42, 61-83, 92-114, 209-230,

N-glycosylation site.
amino acids 134-138

Tyrosine kinase phosphorylation site.
amino acids 160-168, 160-169

N-myristoylation site.
amino acids 75-81, 78-84, 210-216, 214-220, 226-232

Prokaryotic membrane lipoprotein lipid attachment site.
amino acids 69-80, 211-222

FIGURE 5

GGGGCCGCGGTCTAGGGCGGCTACGTGTGTTGCCATAGCGACCATTTTGCATTAACTGGTTG
GTAGCTTCTATCCTGGGGGCTGAGCGACTGCGGGCCAGCTCTTCCCCTACTCCCTCTCGGCT
CCTTGTGGCCCAAAGGCCTAACCGGGGTCCGGCGGTCTGGCCTAGGGATCTTCCCCGTTGCC
CCTTTGGGGCGGGATGGCTGCGGAAGAAGAAGACGAGGTGGAGTGGGTAGTGGAGAGCATCG
CGGGGTTCCTGCGAGGCCCAGACTGGTCCATCCCCATCTTGGACTTTGTGGAACAGAAATGT
GAAGTTAACTGCAAAGGAGGGCATGTGATAACTCCAGGAAGCCCAGAGCCGGTGATTTTGGT
GGCCTGTGTTCCCCTTGTTTTTGATGATGAAGAAGAAAGCAAATTGACCTATACAGAGATTC
ATCAGGAATACAAAGAACTAGTTGAAAAGCTGTTAGAAGGTTACCTCAAAGAAATTGGAATT
AATGAAGATCAATTTCAAGAAGCATGCACTTCTCCTCTTGCAAAGACCCATACATCACAGGC
CATTTTGCAACCTGTGTTGGCAGCAGAAGATTTTACTATCTTTAAAGCAATGATGGTCCAGA
AAAACATTGAAATGCAGCTGCAAGCCATTCGAATAATTCAAGAGAGAAATGGTGTATTACCT
GACTGCTTAACCGATGGCTCTGATGTGGTCAGTGACCTTGAACACGAAGAGATGAAAATCCT
GAGGGAAGTTCTTAGAAAATCAAAGAGGAATATGACCAGGAAGAAGAAAGGAAGAGGAAAA
AACAGTTATCAGAGGCTAAAACAGAAGAGCCCACAGTGCATTCCAGTGAAGCTGCAATAATG
AATAATTCCCAAGGGGATGGTGAACATTTTGCACACCCACCCTCAGAAGTTAAAATGCATTT
TGCTAATCAGTCAATAGAACCTTTGGGAAGAAAAGTGGAAGGTCTGAAACTTCCTCCCTCC
CACAAAAAGGCCTGAAGATTCCTGGCTTAGAGCATGCGAGCATTGAAGGACCAATAGCAAAC
TTATCAGTACTTGGAACAGAAGAACTTCGGCAACGAGAACACTATCTCAAGCAGAAGAGAGA
TAAGTTGATGTCCATGAGAAAGGATATGAGGACTAAACAGATACAAAATATGGAGCAGAAAG
GAAAACCCACTGGGGAGGTAGAGGAAATGACAGAGAAACCAGAAATGACAGCAGAGGAGAAG
CAAACATTACTAAAGAGGAGATTGCTTGCAGAGAAACTCAAGAAGAAGTTATTAATAAGTA
ATAATTAAGAACAATTTAACAAAATGGAAGTTCAAATTGTCTTAAAAATAAATTATTTAGTC
CTTACACTG

FIGURE 6

MAAEEEDEVEWVVESIAGFLRGPDWSIPILDFVEQKCEVNCKGGHVITPGSPEPVILVACVP
LVFDDEEESKLTYTEIHQEYKELVEKLLEGYLKEIGINEDQFQEACTSPLAKTHTSQAILQP
VLAAEDFTIFKAMMVQKNIEMQLQAIRIIQERNGVLPDCLTDGSDVVSDLEHEEMKILREVL
RKSKEEYDQEEERKRKKQLSEAKTEEPTVHSSEAAIMNNSQGDGEHFAHPPSEVKMHFANQS
IEPLGRKVERSETSSLPQKGLKIPGLEHASIEGPIANLSVLGTEELRQREHYLKQKRDKLMS
MRKDMRTKQIQNMEQKGKPTGEVEEMTEKPEMTAEEKQTLLKRRLLAEKLKEEVINK

N-glycosylation sites.
amino acids 224-228, 246-250, 285-289

N-myristoylation site.
amino acids 273-279

Amidation site.
amino acids 252-256

Cytosolic fatty-acid binding proteins.
amino acids 78-108

FIGURE 7

GGGAACGGAAAATGGCGCCTCACGGCCCGGGTAGTCTTACGACCCTGGTGCCCTGGGCTGCCGCCCTGCTCCTC
GCTCTGGGCGTGGAAAGGGCTCTGGCGCTACCCGAGATATGCACCCAATGTCCAGGGAGCGTGCAAAATTTGTC
AAAAGTGGCCTTTTATTGTAAAACGACAGGAGAGCTAATGCTGCATGCCCGTTGCTGCCTGAATCAGAAGGGCA
CCATCTTGGGGCTGGATCTCCAGAACTGTTCTCTGGAGGACCCTGGTCCAAACTTTCATCAGGCACATACCACT
GTCATCATAGACCTGCAAGCAAACCCCCTCAAAGGTGACTTGGCCAACACCTTCCGTGGCTTTACTCAGCTCCA
GACTCTGATACTGCCACAACATGTCAACTGTCCTGGAGGAATTAATGCCTGGAATACTATCACCTCTTATATAG
ACAACCAAATCTGTCAAGGGCAAAAGAACCTTTGCAATAACACTGGGGACCCAGAAATGTGTCCTGAGAATGGA
TCTTGTGTACCTGATGGTCCAGGTCTTTTGCAGTGTGTTTGTGCTGATGGTTTCCATGGATACAAGTGTATGCG
CCAGGGCTCGTTCTCACTGCTTATGTTCTTCGGGATTCTGGGAGCCACCACTCTATCCGTCTCCATTCTGCTTT
GGGCGACCCAGCGCCGAAAAGCCAAGACTTCATGAACTACATAGGTCTTACCATTGACCTAAGATCAATCTGAA
CTATCTTAGCCCAGTCAGGGAGCTCTGCTTCCTAGAAAGGCATCTTTCGCCAGTGGATTCGCCTCAAGGTTGAG
GCCGCCATTGGAAGATGAAAAATTGCACTCCCTTGGTGTAGACAAATACCAGTTCCCATTGGTGTTGTTGCCTA
TAATAAACACTTTTTCTTTTTTNAAAAAAAAAAAAAAAAAAAAAA

FIGURE 8

Signal Peptide:
Amino acids 1-30

Transmembrane:
Amino acids 198-212

```
MAPHGPGSLTTLVPWAAALLLALGVERALALPEICTQCPGSVQNLSKVAFYCKTTRELMLHA
RCCLNQKGTILGLDLQNCSLEDPGPNFHQAHTTVIIDLQANPLKGDLANTFRGFTQLQTLIL
PQHVNCPGGINAWNTITSYIDNQICQGQKNLCNNTGDPEMCPENGSCVPDGPGLLQCVCADG
FHGYKCMRQGSFSLLMFFGILGATTLSVSILLWATQRRKAKTS
```

FIGURE 9

```
GGGGGAGAAGGCGGCCGAGCCCCAGCTCTCCGAGCACCGGGTCGGAAGCCGCGACCCGAGCC
GCGCAGGAAGCTGGGACCGGAACCTCGGCGGACCCGGCCCCACCCAACTCACCTGCGCAGGT
CACCAGCACCCTCGGAACCCAGAGGCCCGCGCTCTGAAGGTGACCCCCCTGGGGAGGAAGGC
GATGGCCCCTGCGAGGACGATGGCCCGCGCCCGCCTCGCCCCGGCCGGCATCCCTGCCGTCG
CCTTGTGGCTTCTGTGCACGCTCGGCCTCCAGGGCACCCAGGCCGGGCCACCGCCCGCGCCC
CCTGGGCTGCCCGCGGGAGCCGACTGCCTGAACAGCTTTACCGCCGGGGTGCCTGGCTTCGT
GCTGGACACCAACGCCTCGGTCAGCAACGGAGCTACCTTCCTGGAGTCCCCCACCGTGCGCC
GGGGCTGGGACTGCGTGCGCGCCTGCTGCACCACCCAGAACTGCAACTTGGCGCTAGTGGAG
CTGCAGCCCGACCGCGGGGAGGACGCCATCGCCGCCTGCTTCCTCATCAACTGCCTCTACGA
GCAGAACTTCGTGTGCAAGTTCGCGCCCAGGGAGGGCTTCATCAACTACCTCACGAGGGAAG
TGTACCGCTCCTACCGCCAGCTGCGGACCCAGGGCTTTGGAGGGTCTGGGATCCCCAAGGCC
TGGGCAGGCATAGACTTGAAGGTACAACCCCAGGAACCCCTGGTGCTGAAGGATGTGGAAAA
CACAGATTGGCGCCTACTGCGGGGTGACACGGATGTCAGGGTAGAGAGGAAAGACCCAAACC
AGGTGGAACTGTGGGGACTCAAGGAAGGCACCTACCTGTTCCAGCTGACAGTGACTAGCTCA
GACCACCCAGAGGACACGGCCAACGTCACAGTCACTGTGCTGTCCACCAAGCAGACAGAAGA
CTACTGCCTCGCATCCAACAAGGTGGGTCGCTGCCGGGGCTCTTTCCCACGCTGGTACTATG
ACCCCACGGAGCAGATCTGCAAGAGTTTCGTTTATGGAGGCTGCTTGGGCAACAAGAACAAC
TACCTTCGGGAAGAAGAGTGCATTCTAGCCTGTCGGGGTGTGCAAGGTGGGCCTTTGAGAGG
CAGCTCTGGGGCTCAGGCGACTTTCCCCAGGGCCCCTCCATGGAAAGGCGCCATCCAGTGT
GCTCTGGCACCTGTCAGCCCACCCAGTTCCGCTGCAGCAATGGCTGCTGCATCGACAGTTTC
CTGGAGTGTGACGACACCCCCAACTGCCCCGACGCCTCCGACGAGGCTGCCTGTGAAAAATA
CACGAGTGGCTTTGACGAGCTCCAGCGCATCCATTTCCCCAGTGACAAAGGGCACTGCGTGG
ACCTGCCAGACACAGGACTCTGCAAGGAGAGCATCCCGCGCTGGTACTACAACCCCTTCAGC
GAACACTGCGCCCGCTTTACCTATGGTGGTTGTTATGGCAACAAGAACAACTTTGAGGAAGA
GCAGCAGTGCCTCGAGTCTTGTCGCGGCATCTCCAAGAAGGATGTGTTTGGCCTGAGGCGGG
AAATCCCCATTCCCAGCACAGGCTCTGTGGAGATGGCTGTCACAGTGTTCCTGGTCATCTGC
ATTGTGGTGGTGGTAGCCATCTTGGGTTACTGCTTCTTCAAGAACCAGAGAAAGGACTTCCA
CGGACACCACCACCACCCACCACCCACCCCTGCCAGCTCCACTGTCTCCACTACCGAGGACA
CGGAGCACCTGGTCTATAACCACACCACCCGGCCCCTCTGAGCCTGGGTCTCACCGGCTCTC
ACCTGGCCCTGCTTCCTGCTTGCCAAGGCAGAGGCCTGGGCTGGGAAAAACTTTGGAACCAG
ACTCTTGCCTGTTTCCCAGGCCCACTGTGCCTCAGAGACCAGGGCTCCAGCCCCTCTTGGAG
AAGTCTCAGCTAAGCTCACGTCCTGAGAAAGCTCAAAGGTTTGGAAGGAGCAGAAAACCCTT
GGGCCAGAAGTACCAGACTAGATGGACCTGCCTGCATAGGAGTTTGGAGGAAGTTGGAGTTT
TGTTTCCTCTGTTCAAAGCTGCCTGTCCCTACCCCATGGTGCTAGGAAGAGGAGTGGGGTGG
TGTCAGACCCTGGAGGCCCCAACCCTGTCCTCCCGAGCTCCTCTTCCATGCTGTGCGCCCAG
GGCTGGGAGGAAGGACTTCCCTGTGTAGTTTGTGCTGTAAAGAGTTGCTTTTTGTTTATTTA
ATGCTGTGGCATGGGTGAAGAGGAGGGGAAGAGGCCTGTTTGGCCTCTCTGTCCTCTCTTCC
TCTTCCCCCAAGATTGAGCTCTCTGCCCTTGATCAGCCCCACCCTGGCCTAGACCAGCAGAC
AGAGCCAGGAGAGGCTCAGCTGCATTCCGCAGCCCCCACCCCCAAGGTTCTCCAACATCACA
GCCCAGCCCACCCACTGGGTAATAAAAGTGGTTTGTGGAAAAAAAAAAAAAAAAAAAAAAAA
```

FIGURE 10

MAPARTMARARLAPAGIPAVALWLLCTLGLQGTQAGPPPAPPGLPAGADCLNSFTAGVPGFV
LDTNASVSNGATFLESPTVRRGWDCVRACCTTQNCNLALVELQPDRGEDAIAACFLINCLYE
QNFVCKFAPREGFINYLTREVYRSYRQLRTQGFGGSGIPKAWAGIDLKVQPQEPLVLKDVEN
TDWRLLRGDTDVRVERKDPNQVELWGLKEGTYLFQLTVTSSDHPEDTANVTVTVLSTKQTED
YCLASNKVGRCRGSFPRWYYDPTEQICKSFVYGGCLGNKNNYLREEECILACRGVQGGPLRG
SSGAQATFPQGPSMERRHPVCSGTCQPTQFRCSNGCCIDSFLECDDTPNCPDASDEAACEKY
TSGFDELQRIHFPSDKGHCVDLPDTGLCKESIPRWYYNPFSEHCARFTYGGCYGNKNNFEEE
QQCLESCRGISKKDVFGLRREIPIPSTGSVEMAVTVFLVICIVVVVAILGYCFFKNQRKDFII
GHHHHPPPTPASSTVSTTEDTEHLVYNHTTRPL signal sequence:
Amino acids 1-35 transmembrane domain:
Amino acids 466-483

N-glycosylation sites:
Amino acids 66-70;235-239;523-527

N-myristoylation sites:
Amino acids 29-35;43-49;161-167;212-218;281-287;282-288;285-291;
310-316;313-319;422-428;423-429;426-432

Cell attachment sequence:
Amino acids 193-199

Pancreatic trypsin inhibitor (Kunitz) family signatures:
Amino acids 278-298;419-438

FIGURE 11

```
GTGCTGGGCTTTTTCAGACAAGTGCATCTCCTAACCAGGTCACATTTCAGCCGCGACCCACTCTCCGCCAGTCA
CCGGAGGCAGACCGCGGGAGGAGAGCTGAGGACAGCCGCGTGCGCTTCGCCAGCAGCGGGGTGGGAGGAAGGAC
ATTAAAATACTGCAGAAGTCAAGACCCCCCCAGGTCGAACCCAGACCACGATGCGCGCCCCGGGCTGCGGGCGG
CTGGTGCTGCCGCTGCTGCTCCTGGCCGCGGCAGCCCTGGCCGAAGGCGACGCCAAGGGGCTCAAGGAGGGCGA
GACCCCCGGCAATTTCATGGAGGACGAGCAATGGCTGTCGTCCATCTCGCAGTACAGCGGCAAGATCAAGCACT
GGAACCGCTTCCGAGACGAAGTGGAGGATGACTATATCAAGAGCTGGAGGACAATCAGCAAGGAGATGAAGCC
CTGGATACCACCAAGGACCCCTGCCAGAAGGTGAAGTGCAGCCGCCACAAGGTGTGCATTGCCCAGGGCTACCA
GCGGGCCATGTGCATCAGTCGCAAGAAGCTGGAGCACAGGATCAAGCAGCCGACCGTGAAACTCCATGGAAACA
AAGACTCCATCTGCAAGCCCTGCCACATGGCCCAGCTTGCCTCTGTCTGCGGCTCAGATGGCCACACTTACAGC
TCTGTGTGTAAGCTGGAGCAACAGGCGTGCCTGAGCAGCAAGCAGCTGGCGGTGCGATGCGAGGGCCCCTGCCC
CTGCCCCACGGAGCAGGCTGCCACCTCCACCGCCGATGGCAAACCAGAGACTTGCACCGGTCAGGACCTGGCTG
ACCTGGGAGATCGGCTGCGGGACTGGTTCCAGCTCCTTCATGAGAACTCCAAGCAGAATGGCTCAGCCAGCAGT
GTAGCCGGCCCGGCCAGCGGGCTGGACAAGAGCCTGGGGGCCAGCTGCAAGGACTCCATTGGCTGGATGTTCTC
CAAGCTGGACACCAGTGCTGACCTCTTCCTGGACCAGACGGAGCTGGCCGCCATCAACCTGGACAAGTACGAGG
TCTGCATCCGTCCCTTCTTCAACTCCTGTGACACCTACAAGGATGGCCGGGTCTCTACTGCTGAGTGGTGCTTC
TGCTTCTGGAGGGAGAAGCCCCCCTGCCTGGCAGAGCTGGAGCGCATCCAGATCCAGGAGGCCGCCAAGAAGAA
GCCAGGCATCTTCATCCCGAGCTGCGACGAGGATGGCTACTACCGGAAGATGCAGTGTGACCAGAGCAGCGGTG
ACTGCTGGCGTGTGGACCAGCTGGGCCTGGAGCTGACTGGCACGCGCACGCATGGGAGCCCCGACTGCGATGAC
ATCGTGGGCTTCTCGGGGGACTTTGGAAGCGGTGTCGGCTGGGAGGATGAGGAGGAGAAGGAGACGGAGGAAGC
AGGCGAGGAGGCCGAGGAGGAGGAGGGCGAGGCAGGCGAGGCTGACGACGGGGGCTACATCTGGTAGACGCCCT
CAGGAGCCGGCTGCCGGGGGGGACTCAACAGCAGAGCTCTGAGCAGCAGCAGGCAACTTCGAGAACGGATCCAG
AAATGCAGTCAGAAGGACCCTGCTCCACCTGGGGGGACTGGGAGTGTGAGTGTGCATGGCATGTGTGTGGCACA
GATGGCTGGGACGGGTGACAGTGTGAGTGCATGTGTGCATGCATGTGTGTATGTGTGTGTGTGTGGCATGCG
CTGACAAATGTGTCCTTGATCCACACTGCTCCTGGCAGAGTGAGTCACCCAAAGGCCCCTTCGGCCTCCTTGTA
GCTGTTTTCTTTCCTTTTGTTGTTGGTTTTAAAATACATTCACACACAAATACAAAAAAAAAAAAAAAAAAAAA
AAAAAAAAAAAAAAAAAAAAAAAAAAAAAAAAAAAAAAAAAAAAAAA
```

FIGURE 12

MRAPGCGRLVLPLLLLAAAALAEGDAKGLKEGETPGNFMEDEQWLSSISQYSGKIKHWNRFRDEVEDDYIKSWE
DNQQGDEALDTTKDPCQKVKCSRHKVCIAQGYQRAMCISRKKLEHRIKQPTVKLHGNKDSICKPCHMAQLASVC
GSDGHTYSSVCKLEQQACLSSKQLAVRCEGPCPCPTEQAATSTADGKPETCTGQDLADLGDRLRDWFQLLHENS
KQNGSASSVAGPASGLDKSLGASCKDSIGWMFSKLDTSADLFLDQTELAAINLDKYEVCIRPFFNSCDTYKDGR
VSTAEWCFCFWREKPPCLAELERIQIQEAAKKKPGIFIPSCDEDGYYRKMQCDQSSGDCWRVDQLGLELTGTRT
HGSPDCDDIVGFSGDFGSGVGWEDEEEKETEEAGEEAEEEEGEAGEADDGGYIW

FIGURE 13

```
TGCGGCGACCGTCGTACACCATGGGCCTCCACCTCCGCCCCTACCGTGTGGGGCTGCTCCCG
GATGGCCTCCTGTTCCTCTTGCTGCTGCTAATGCTGCTCGCGGACCCAGCGCTCCCGGCCGG
ACGTCACCCCCCAGTGGTGCTGGTCCCTGGTGATTTGGGTAACCAACTGGAAGCCAAGCTGG
ACAAGCCGACAGTGGTGCACTACCTCTGCTCCAAGAAGACCGAAAGCTACTTCACAATCTGG
CTGAACCTGGAACTGCTGCTGCCTGTCATCATTGACTGCTGGATTGACAATATCAGGCTGGT
TTACAACAAAACATCCAGGGCCACCCAGTTTCCTGATGGTGTGGATGTACGTGTCCCTGGCT
TTGGGAAGACCTTCTCACTGGAGTTCCTGGACCCCAGCAAAAGCAGCGTGGGTTCCTATTTC
CACACCATGGTGGAGAGCCTTGTGGGCTGGGGCTACACACGGGGTGAGGATGTCCGAGGGGC
TCCCTATGACTGGCGCCGAGCCCCAAATGAAAACGGGCCCTACTTCCTGGCCCTCCGCGAGA
TGATCGAGGAGATGTACCAGCTGTATGGGGCCCCGTGGTGCTGGTTGCCCACAGTATGGGC
AACATGTACACGCTCTACTTTCTGCAGCGGCAGCCGCAGGCCTGGAAGGACAAGTATATCCG
GGCCTTCGTGTCACTGGGTGCGCCCTGGGGGGCGTGGCCAAGACCCTGCGCGTCCTGGCTT
CAGGAGACAACAACCGGATCCCAGTCATCGGGCCCCTGAAGATCCGGGAGCAGCAGCGGTCA
GCTGTCTCCACCAGCTGGCTGCTGCCCTACAACTACACATGGTCACCTGAGAAGGTGTTCGT
GCAGACACCCACAATCAACTACACACTGCGGGACTACCGCAAGTTCTTCCAGGACATCGGCT
TTGAAGATGGCTGGCTCATGCGGCAGGACACAGAAGGGCTGGTGGAAGCCACGATGCCACCT
GGCGTGCAGCTGCACTGCCTCTATGGTACTGGCGTCCCCACACCAGACTCCTTCTACTATGA
GAGCTTCCCTGACCGTGACCCTAAAATCTGCTTTGGTGACGGCGATGGTACTGTGAACTTGA
AGAGTGCCCTGCAGTGCCAGGCCTGGCAGAGCCGCCAGGAGCACCAAGTGTTGCTGCAGGAG
CTGCCAGGCAGCGAGCACATCGAGATGCTGGCCAACGCCACCACCCTGGCCTATCTGAAACG
TGTGCTCCTTGGGCCCTGACTCCTGTGCCACAGGACTCCTGTGGCTCGGCCGTGGACCTGCT
GTTGGCCTCTGGGGCTGTCATGGCCCACGCGTTTTGCAAAGTTTGTGACTCACCATTCAAGG
CCCCGAGTCTTGGACTGTGAAGCATCTGCCATGGGGAAGTGCTGTTTGTTATCCTTTCTCTG
TGGCAGTGAAGAAGGAAGAAATGAGAGTCTAGACTCAAGGGACACTGGATGGCAAGAATGCT
GCTGATGGTGGAACTGCTGTGACCTTAGGACTGGCTCCACAGGGTGGACTGGCTGGGCCCTG
GTCCCAGTCCCTGCCTGGGGCCATGTGTCCCCTATTCCTGTGGGCTTTTCATACTTGCCTA
CTGGGCCCTGGCCCCGCAGCCTTCCTATGAGGGATGTTACTGGGCTGTGGTCCTGTACCCAG
AGGTCCCAGGGATCGGCTCCTGGCCCCTCGGGTGACCCTTCCCACACACCAGCCACAGATAG
GCCTGCCACTGGTCATGGGTAGCTAGAGCTGCTGGCTTCCTGTGGCTTAGCTGGTGGCCAG
CCTGACTGGCTTCCTGGGCGAGCCTAGTAGCTCCTGCAGGCAGGGCAGTTTGTTGCGTTCT
TCGTGGTTCCCAGGCCCTGGGACATCTCACTCCACTCCTACCTCCCTTACCACCAGGAGCAT
TCAAGCTCTGGATTGGGCAGCAGATGTGCCCCAGTCCCGCAGGCTGTGTTCCAGGGGCCCT
GATTTCCTCGGATGTGCTATTGGCCCCAGGACTGAAGCTGCCTCCCTTCACCCTGGGACTGT
GGTTCCAAGGATGAGAGCAGGGGTTGGAGCCATGGCCTTCTGGGAACCTATGGAGAAAGGGA
ATCCAAGGAAGCAGCCAAGGCTGCTCGCAGCTTCCCTGAGCTGCACCTCTTGCTAACCCCAC
CATCACACTGCCACCCTGCCCTAGGGTCTCACTAGTACCAAGTGGGTCAGCACAGGGCTGAG
GATGGGGCTCCTATCCACCCTGGCCAGCACCCAGCTTAGTGCTGGGACTAGCCCAGAAACTT
GAATGGGACCCTGAGAGAGCCAGGGGTCCCCTGAGGCCCCCTAGGGGCTTTCTGTCTGCCC
CAGGGTGCTCCATGGATCTCCCTGTGGCAGCAGGCATGGAGAGTCAGGGCTGCCTTCATGGC
AGTAGGCTCTAAGTGGGTGACTGGCCACAGGCCGAGAAAAGGGTACAGCCTCTAGGTGGGGT
TCCCAAAGACGCCTTCAGGCTGGACTGAGCTGCTCTCCCACAGGGTTTCTGTGCAGCTGGAT
TTTCTCTGTTGCATACATGCCTGGCATCTGTCTCCCCTTGTTCCTGAGTGGCCCCACATGGG
GCTCTGAGCAGGCTGTATCTGGATTCTGGCAATAAAAGTACTCTGGATGCTGTAAAAAAAA
AAAAAAAAAAAAA
```

FIGURE 14

```
></usr/seqdb2/sst/DNA/Dnaseqs.min/ss.DNA44189
><subunit 1 of 1, 412 aa, 1 stop
><MW: 46658, pI: 6.65, NX(S/T): 4
MGLHLRPYRVGLLPDGLLFLLLLLMLLADPALPAGRHPPVVLVPGDLGNQLEAKLDKPTV
VHYLCSKKTESYFTIWLNLELLLPVIIDCWIDNIRLVYNKTSRATQFPDGVDVRVPGFGK
TFSLEFLDPSKSSVGSYFHTMVESLVGWGYTRGEDVRGAPYDWRRAPNENGPYFLALREM
IEEMYQLYGGPVVLVAHSMGNMYTLYFLQRQPQAWKDKYIRAFVSLGAPWGGVAKTLRVL
ASGDNNRIPVIGPLKIREQQRSAVSTSWLLPYNYTWSPEKVFVQTPTINYTLRDYRKFFQ
DIGFEDGWLMRQDTEGLVEATMPPGVQLHCLYGTGVPTPDSFYYESFPDRDPKICFGDGD
GTVNLKSALQCQAWQSRQEHQVLLQELPGSEHIEMLANATTLAYLKRVLLGP
```

Signal peptide:
Amino acids          1-28

Potential lipid substrate binding site:
Amino acids          147-164

N-glycosylation sites:
Amino acids          99-103;273-277;289-293;398-402

Lipases, serine proteins family:
Amino acids          189-202

Beta-transducin family Trp-Asp repeat:
Amino acids          353-366

Tyrosine kinase phosphorylation site:
Amino acids          165-174;178-186

N-myristoylation sites:
Amino acids          200-206;227-233;232-238;316-322

FIGURE 15

CAGAGCAGATAATGGCAAGCATGGCTGCCGTGCTCACCTGGGCTCTGGCTCTTCTTTCAGCG
TTTTCGGCCACCCAGGCACGGAAAGGCTTCTGGGACTACTTCAGCCAGACCAGCGGGGACAA
AGGCAGGGTGGAGCAGATCCATCAGCAGAAGATGGCTCGCGAGCCCGCGACCCTGAAAGACA
GCCTTGAGCAAGACCTCAACAATATGAACAAGTTCCTGGAAAAGCTGAGGCCTCTGAGTGGG
AGCGAGGCTCCTCGGCTCCCACAGGACCCGGTGGGCATGCGGCGGCAGCTGCAGGAGGAGTTG
GAGGAGGTGAAGGCTCGCCTCCAGCCCTACATGGCAGAGCCGCACGAGCTGGTGGGCTGGAA
TTTGGAGGGCTTGCGGCAGCAACTGAAGCCCTACACGATGGATCTGATGGAGCAGGTGGCCC
TGCGCGTGCAGGAGCTGCAGGAGCAGTTGCGCGTGGTGGGGGAAGACACCAAGGCCCAGTTG
CTGGGGGGCGTGGACGAGGCTTGGGCTTTGCTGCAGGGACTGCAGAGCCGCGTGGTGCACCA
CACCGGCCGCTTCAAAGAGCTCTTCCACCCATACGCCGAGAGCCTGGTGAGCGGCATCGGGC
GCCACGTGCAGGAGCTGCACCGCAGTGTGGCTCCGCACGCCCCGCCAGCCCCGCGCGCCTC
AGTCGCTGCGTGCAGGTGCTCTCCCGGAAGCTCACGCTCAAGGCCAAGGCCCTGCACGCACG
CATCCAGCAGAACCTGGACCAGCTGCGCGAAGAGCTCAGCAGAGCCTTTGCAGGCACTGGGA
CTGAGGAAGGGGCCGGCCCGGACCCCTAGATGCTCTCCGAGGAGGTGCGCCAGCGACTTCAG
GCTTTCCGCCAGGACACCTACCTGCAGATAGCTGCCTTCACTCGCGCCATCGACCAGGAGAC
TGAGGAGGTCCAGCAGCAGCTGGCGCCACCTCCACCAGGCCACAGTGCCTTCGCCCCAGAGT
TTCAACAAACAGACAGTGGCAAGGTTCTGAGCAAGCTGCAGGCCCGTCTGGATGACCTGTGG
GAAGACATCACTCACAGCCTTCATGACCAGGGCCACAGCCATCTGGGGGACCCCTGAGGATC
TACCTGCCCAGGCCCATTCCCAGCTTCTTGTCTGGGGAGCCTTGGCTCTGAGCCTCTAGCAT
GGTTCAGTCCTTGAAAGTGGCCTGTTGGGTGGAGGGTGGAAGGTCCTGTGCAGGACAGGGAG
GCCACCAAAGGGGCTGCTGTCTCCTGCATATCCAGCCTCCTGCGACTCCCCAATCTGGATGC
ATTACATTCACCAGGCTTTGCAAAAAAAAAAAAAAAAAAAAAAAAAAAAAAAAAAAAAAAAA
AAAAAA

FIGURE 16

```
></usr/seqdb2/sst/DNA/Dnaseqs.min/ss.DNA48303
><subunit 1 of 1, 274 aa, 1 stop
><MW: 30754, pI: 7.77, NX(S/T): 0
MASMAAVLTWALALLSAFSATQARKGFWDYFSQTSGDKGRVEQIHQQKMAREPATLKDSL
EQDLNNMNKFLEKLRPLSGSEAPRLPQDPVGMRRQLQEELEEVKARLQPYMAEAHELVGW
NLEGLRQQLKPYTMDLMEQVALRVQELQEQLRVVGEDTKAQLLGGVDEAWALLQGLQSRV
VHHTGRFKELFHPYAESLVSGIGRHVQELHRSVAPHAPASPARLSRCVQVLSRKLTLKAK
ALHARIQQNLDQLREELSRAFAGTGTEEGAGPDP
```

Important features of the protein:
Signal peptide:
Amino acids          1-23

Glycosaminoglycan attachment site:
Amino acids          200-204 cAMP- and cGMP-dependent protein kinase phosphorylation site:
Amino acids          233-237

N-myristoylation sites:
Amino acids          165-171;265-271

FIGURE 17

CTAAGAGGACAAGATGAGGCCCGGCCTCTCATTTCTCCTAGCCCTTCTGTTCTTCCTTGGCC
AAGCTGCAGGGGATTTGGGGGATGTGGGACCTCCAATTCCCAGCCCCGGCTTCAGCTCTTTC
CCAGGTGTTGACTCCAGCTCCAGCTTCAGCTCCAGCTCCAGGTCGGGCTCCAGCTCCAGCCG
CAGCTTAGGCAGCGGAGGTTCTGTGTCCCAGTTGTTTTCCAATTTCACCGGCTCCGTGGATG
ACCGTGGGACCTGCCAGTGCTCTGTTTCCTGCCAGACACCACCTTTCCCGTGGACAGAGTG
GAACGCTTGGAATTCACAGCTCATGTTCTTTCTCAGAAGTTTGAGAAAGAACTTTCTAAAGTG
AGGGAATATGTCCAATTAATTAGTGTGTATGAAAAGAAACTGTTAAACCTAACTGTCCGAAT
TGACATCATGGAGAAGGATACCATTTCTTACACTGAACTGGACTTCGAGCTGATCAAGGTAG
AAGTGAAGGAGATGGAAAAACTGGTCATACAGCTGAAGGAGAGTTTTGGTGGAAGCTCAGAA
ATTGTTGACCAGCTGGAGGTGGAGATAAGAAATATGACTCTCTTGGTAGAGAAGCTTGAGAC
ACTAGACAAAAACAATGTCCTTGCCATTCGCCGAGAAATCGTGGCTCTGAAGACCAAGCTGA
AAGAGTGTGAGGCCTCTAAAGATCAAACACCCCTGTCGTCCACCCTCCTCCCACTCCAGGG
AGCTGTGGTCATGGTGGTGTGGTGAACATCAGCAAACCGTCTGTGGTTCAGCTCAACTGGAG
AGGGTTTTCTTATCTATATGGTGCTTGGGGTAGGGATTACTCTCCCCAGCATCCAAACAAAG
GACTGTATTGGGTGGCGCCATTGAATACAGATGGGAGACTGTTGGAGTATTATAGACTGTAC
AACACACTGGATGATTTGCTATTGTATATAAATGCTCGAGAGTTGCGGATCACCTATGGCCA
AGGTAGTGGTACAGCAGTTTACAACAACAACATGTACGTCAACATGTACAACACCGGGAATA
TTGCCAGAGTTAACCTGACCACCAACACGATTGCTGTGACTCAAACTCTCCCTAATGCTGCC
TATAATAACCGCTTTTCATATGCTAATGTTGCTTGGCAAGATATTGACTTTGCTGTGGATGA
GAATGGATTGTGGGTTATTTATTCAACTGAAGCCAGCACTGGTAACATGGTGATTAGTAAAC
TCAATGACACCACACTTCAGGTGCTAAACACTTGGTATACCAAGCAGTATAAACCATCTGCT
TCTAACGCCTTCATGGTATGTGGGGTTCTGTATGCCACCCGTACTATGAACACCAGAACAGA
AGAGATTTTTTACTATTATGACACAAACACAGGGAAAGAGGGCAAACTAGACATTGTAATGC
ATAAGATGCAGGAAAAGTGCAGAGCATTAACTATAACCCTTTTGACCAGAAACTTTATGTC
TATAACGATGGTTACCTTCTGAATTATGATCTTTCTGTCTTGCAGAAGCCCAGTAAGCTGT
TTAGGAGTTAGGGTGAAAGAGAAAATGTTTGTTGAAAAAATAGTCTTCTCCACTTACTTAGA
TATCTGCAGGGGTGTCTAAAAGTGTGTTCATTTTGCAGCAATGTTTAGGTGCATAGTTCTAC
CACACTAGAGATCTAGGACATTTGTCTTGATTTGGTGAGTTCTCTTGGGAATCATCTGCCTC
TTCAGGCGCATTTTGCAATAAAGTCTGTCTAGGGTGGGATTGTCAGAGGTCTAGGGGCACTG
TGGGCCTAGTGAAGCCTACTGTGAGGAGGCTTCACTAGAAGCCTTAAATTAGGAATTAAGGA
ACTTAAAACTCAGTATGGCGTCTAGGGATTCTTTGTACAGGAAATATTGCCCAATGACTAGT
CCTCATCCATGTAGCACCACTAATTCTTCCATGCCTGGAAGAAACCTGGGGACTTAGTTAGG
TAGATTAATATCTGGAGCTCCTCGAGGGACCAAATCTCCAACTTTTTTTTCCCCTCACTAGC
ACCTGGAATGATGCTTTGTATGTGGCAGATAAGTAAATTTGGCATGCTTATATATTCTACAT
CTGTAAAGTGCTGAGTTTTATGGAGAGAGGCCTTTTTATGCATTAAATTGTACATGGCAAATAA
ATCCCAGAAGGATCTGTAGATGAGGCACCTGCTTTTTCTTTTCTCTCATTGTCCACCTTACT
AAAAGTCAGTAGAATCTTCTACCTCATAACTTCCTTCCAAAGGCAGCTCAGAAGATTAGAAC
CAGACTTACTAACCAATTCCACCCCCACCAACCCCCTTCTACTGCCTACTTTAAAAAAATT
AATAGTTTTCTATGGAACTGATCTAAGATTAGAAAATTAATTTTCTTTAATTTCATTATGG
ACTTTTATTTACATGACTCTAAGACTATAAGAAATCTGATGGCAGTGACAAAGTGCTAGCA
TTTATTGTTATCTAATAAAGACCTTGGAGCATATGTGCAACTTATGAGTGTATCAGTTGTTG
CATGTAATTTTTGCCTTTGTTTAAGCCTGGAACTTGTAAGAAAATGAAATTTAATTTTTTT
TTCTAGGACGAGCTATAGAAAAGCTATTGAGAGTATCTAGTTAATCAGTGCAGTAGTTGGAA
ACCTTGCTGGTGTATGTGATGTGCTTCTGTGCTTTTGAATGACTTATCATCTAGTCTTTGT
CTATTTTTCCTTTGATGTTCAAGTCCTAGTCTATAGGATTGGCAGTTTAAATGCTTTACTCC
CCCTTTTAAAATAAATGATTAAATGTGCTTTGAAAAAAAAAAAAAAAAAAAAAAAAAA

FIGURE 18

```
</usr/seqdb2/sst/DNA/Dnaseqs.min/ss.DNA48320
<subunit 1 of 1, 510 aa, 1 stop
<MW: 57280, pI: 5.61, NX(S/T): 6
MRPGLSFLLALLFFLGQAAGDLGDVGPPIPSPGFSSFPGVDSSSSFSSSSRSGSSSSRSL
GSGGSVSQLFSNFTGSVDDRGTCQCSVSLPDTTFPVDRVERLEFTAHVLSQKFEKELSKV
REYVQLISVYEKKLLNLTVRIDIMEKDTISYTELDFELIKVEVKEMEKLVIQLKESFGGS
SEIVDQLEVEIRNMTLLVEKLETLDKNNVLAIRREIVALKTKLKECEASKDQNTPVVHPP
PTPGSCGHGGVVNISKPSVVQLNWRGFSYLYGAWGRDYSPQHPNKGLYWVAPLNTDGRLL
EYYRLYNTLDDLLLYINARELRITYGQGSGTAVYNNNMYVNMYNTGNIARVNLTTNTIAV
TQTLPNAAYNNRFSYANVAWQDIDFAVDENGLWVIYSTEASTGNMVISKLNDTTLQVLNT
WYTKQYKPSASNAFMVCGVLYATRTMNTRTEEIFYYYDTNTGKEGKLDIVMHKMQEKVQS
INYNPFDQKLYVYNDGYLLNYDLSVLQKPQ
```

Important features:
Signal peptide:
Amino acids          1-20

N-glycosylation sites:
Amino acids          72-76;136-140;193-197;253-257;352-356;
                     411-415

Tyrosine kinase phosphorylation site:
Amino acids          449-457

N-myristoylation sites:
Amino acids          16-22;39-45;53-59;61-67;63-69;81-87;
                     249-255;326-332;328-334;438-444

Legume lectins beta-chain proteins:
Amino acids          20-40

HBGF/FGF family proteins:
Amino acids          338-366

FIGURE 19

GCACCGCAGACGGCGCGGATCGCAGGGAGCCGGTCCGCCGCCGGAACGGGAGCCTGGGTGTG
CGTGTGGAGTCCGGACTCGTGGGAGACGATCGCGATGAACACGGTGCTGTCGCGGGCGAACT
CACTGTTCGCCTTCTCGCTGAGCGTGATGGCGGCGCTCACCTTCGGCTGCTTCATCACCACC
GCCTTCAAAGACAGGAGCGTCCCGGTGCGGCTGCACGTCTCGCGGATCATGCTAAAAAATGT
AGAAGATTTCACTGGACCTAGAGAAGAAGTGATCTGGATTTATCACATTTGATATAACTG
CTGATCTAGAATATATTTGATTGGAATGTTAAGCAGTTGTTTCTTTATTTATCAGCAGAA
TATTCAACAAAAAATAATGCTCTGAACCAAGTTGTCCTATGGGACAAGATTGTTTTGAGAGG
TGATAATCCGAAGCTGCTGCTGAAAGATATGAAAACAAAATATTTTTTCTTTGACGATGGAA
ATGGTCTCAAGGGAAACAGGAATGTCACTTTGACCCTGTCTTGGAACGTCGTACCAAATGCT
GGAATTCTACCTCTTGTGACAGGATCAGGACACGTATCTGTCCCATTTCCAGATACATATGA
AATAACGAAGAGTTATTAAATTATTCTGAATTTGAAACAAAAA

FIGURE 20

```
></usr/seqdb2/sst/DNA/Dnaseqs.min/ss.DNA56049
><subunit 1 of 1, 180 aa, 1 stop
><MW: 20313, pI: 8.91, NX(S/T): 1
MNTVLSRANSLFAFSLSVMAALTFGCFITTAFKDRSVPVRLHVSRIMLKNVEDFTGPRER
SDLGFITFDITADLENIFDWNVKQLFLYLSAEYSTKNNALNQVVLWDKIVLRGDNPKLLL
KDMKTKYFFFDDGNGLKGNRNVTLTLSWNVVPNAGILPLVTGSGHVSVPFPDTYEITKSY
```

Important features of the protein:
Signal peptide:
Amino acids              1-25

Transmembrane domain:
Amino acids              149-164

N-glycosylation site:
Amino acids              141-145

N-myristoylation sites:
Amino acids              25-31;135-141

Cell attachment sequence:
Amino acids              112-115

TonB-dependent receptor proteins signature 1:
Amino acids              1-21

FIGURE 21

AAACTTGACGCCATGAAGATCCCGGTCCTTCCTGCCGTGGTGCTCCTCTCCCTCCTGGTGCT
CCACTCTGCCCAGGGAGCCACCCTGGGTGGTCCTGAGGAAGAAAGCACCATTGAGAATTATG
CGTCACGACCCGAGGCCTTTAACACCCCGTTCCTGAACATCGACAAATTGCGATCTGCGTTT
AAGGCTGATGAGTTCCTGAACTGGCACGCCCTCTTTGAGTCTATCAAAAGGAAACTTCCTTT
CCTCAACTGGGATGCCTTTCCTAAGCTGAAAGGACTGAGGAGCGCAACTCCTGATGCCCAG**T
GA**CCATGACCTCCACTGGAAGAGGGGGCTAGCGTGAGCGCTGATTCTCAACCTACCATAACT
CTTTCCTGCCTCAGGAACTCCAATAAAACATTTTCCATCCAAA

FIGURE 22

```
></usr/seqdb2/sst/DNA/Dnaseqs.min/ss.DNA57694
><subunit 1 of 1, 99 aa, 1 stop
><MW: 11050, pI: 7.47, NX(S/T): 0
MKIPVLPAVVLLSLLVLHSAQGATLGGPEEESTIENYASRPEAFNTPFLNIDKLRSAFKA
DEFLNWHALFESIKRKLPFLNWDAFPKLKGLRSATPDAQ
```

Important features:
Signal peptide:
Amino acids                 1-22

N-myristoylation sites:
Amino acids                 22-28;90-96

Homologous region to Perioxdase:
Amino acids                 16-48

FIGURE 23

TCTCAGACTCTTGGAAGGGGCTATACTAGACACACAAAGACAGCCCCAAGAAGGACGGTGGA
GTAGTGTCCTCGCTAAAAGACAGTAGATATGCAACGCCTCTTGCTCCTGCCCTTTCTCCTGC
TGGGAACAGTTTCTGCTCTTCATCTGGAGAATGATGCCCCCCATCTGGAGAGCCTAGAGACA
CAGGCAGACCTAGGCCAGGATCTGGATAGTTCAAAGGAGCAGGAGAGAGACTTGGCTCTGAC
GGAGGAGGTGATTCAGGCAGAGGGAGAGGAGGTCAAGGCTTCTGCCTGTCAAGACAACTTTG
AGGATGAGGAAGCCATGGAGTCGGACCCAGCTGCCTTAGACAAGGACTTCCAGTGCCCCAGG
GAAGAAGACATTGTTGAAGTGCAGGGAAGTCCAAGGTGCAAGACCTGCCGCTACCTATTGGT
GCGGACTCCTAAAACTTTTGCAGAAGCTCAGAATGTCTGCAGCAGATGCTACGGAGGCAACC
TTGTCTCTATCCATGACTTCAACTTCAACTATCGCATTCAGTGCTGCACTAGCACAGTCAAC
CAAGCCCAGGTCTGGATTGGAGGCAACCTCAGGGGCTGGTTCCTGTGGAAGCGGTTTTGCTGG
ACTGATGGGAGCCACTGGAATTTTGCTTACTGGTCCCCAGGGCAACCTGGGAATGGGCAAGG
CTCCTGTGTGGCCCTATGCACCAAAGGAGGTTATTGGCGACGAGCTCAATGCGACAAGCAAC
TGCCCTTCGTCTGCTCCTTCTAAGCCAGCGGCACGGAGACCCTGCCAGCAGCTCCCTCCCGT
CCCCCAACCTCTCCTGCTCATAAATCCAGACTTCCCACAGCAAAAAAAAAAAAAAAAA

FIGURE 24

```
</usr/seqdb2/sst/DNA/Dnaseqs.min/ss.DNA59208
<subunit 1 of 1, 225 aa, 1 stop
<MW: 25447, pI: 4.79, NX(S/T): 0
MQRLLLLPFLLLGTVSALHLENDAPHLESLETQADLGQDLDSSKEQERDLALTEEVIQAE
GEEVKASACQDNFEDEEAMESDPAALDKDFQCPREEDIVEVQGSPRCKTCRYLLVRTPKT
FAEAQNVCSRCYGGNLVSIHDFNFNYRIQCCTSTVNQAQVWIGGNLRGWFLWKRFCWTDG
SHWNFAYWSPGQPGNGQGSCVALCTKGGYWRRAQCDKQLPFVCSF
```

Important features:
Signal peptide:
Amino acids          1-17

N-myristoylation sites:
Amino acids          13-19;103-109;134-140;164-170;
                     180-186;191-197;194-200;196-202;
                     198-204

C-type lectin domain signature:
Amino acids          200-224

FIGURE 25

```
CAACAGAAGCCAAGAAGGAAGCCGTCTATCTTGTGGCGATCATGTATAAGCTGGCCTCCTGC
TGTTTGCTTTTCACAGGATTCTTAAATCCTCTCTTATCTCTTCCTCTCCTTGACTCCAGGGA
AATATCCTTTCAACTCTCAGCACCTCATGAAGACGCGCGCTTAACTCCGGAGGAGCTAGAAA
GAGCTTCCCTTCTACAGATATTGCCAGAGATGCTGGGTGCAGAAAGAGGGGATATTCAGG
AAAGCAGACTCAAGTACCAACATTTTTAACCCAAGAGGAAATTTGAGAAAGTTTCAGGATTT
CTCTGGACAAGATCCTAACATTTTACTGAGTCATCTTTTGGCCAGAATCTGGAAACCATACA
AGAAACGTGAGACTCCTGATTGCTTCTGGAAATACTGTGTCTGAAGTGAAATAAGCATCTGT
TAGTCAGCTCAGAAACACCCATCTTAGAATATGAAAAATAACACAATGCTTGATTTGAAAAC
AGTGTGGAGAAAAACTAGGCAAACTACACCCTGTTCATTGTTACCTGGAAAATAAATCCTCT
ATGTTTTGCACAAAAAAAAAAAAAAA
```

FIGURE 26

```
</usr/seqdb2/sst/DNA/Dnaseqs.min/ss.DNA59214
<subunit 1 of 1, 124 aa, 1 stop
<MW: 14284, pI: 8.14, NX(S/T): 0
MYKLASCCLLFTGFLNPLLSLPLLDSREISFQLSAPHEDARLTPEELERASLLQILPEML
GAERGDILRKADSSTNIFNPRGNLRKFQDFSGQDPNILLSHLLARIWKPYKKRETPDCFW
KYCV
```

Important features:
Signal peptide:
Amino acids              1-20

Urotensin II signature:
Amino acids              118-124

Cell attachment sequence:
Amino acids              64-67 cAMP- and cGMP-dependent protein kinase phosphorylation site:
Amino acids              112-116

N-myristoylation sites:
Amino acids              61-67;92-98

FIGURE 27

CAAGTAAATGCAGCACTAGTGGGTGGGATTGAGGTATGCCCTGGTGCATAAATAGAGACTCA
GCTGTGCTGGCACACTCAGAAGCTTGGACCGCATCCTAGCCGCCGACTCACACAAGGCAGGT
GGGTGAGGAAATCCAGAGTTGCCATGGAGAAAATTCCAGTGTCAGCATTCTTGCTCCTTGTG
GCCCTCTCCTACACTCTGGCCAGAGATACCACAGTCAAACCTGGAGCCAAAAAGGACACAA
GGACTCTCGACCCAAACTGCCCCAGACCCTCTCCAGAGGTTGGGGTGACCAACTCATCTGGA
CTCAGACATATGAAGAAGCTCTATATAAATCCAAGACAAGCAACAAACCCTTGATGATTATT
CATCACTTGGATGAGTGCCCACACAGTCAAGCTTTAAAGAAAGTGTTTGCTGAAAATAAAGA
AATCCAGAAATTGGCAGAGCAGTTTGTCCTCCTCAATCTGGTTTATGAAACAACTGACAAAC
ACCTTTCTCCTGATGGCCAGTATGTCCCCAGGATTATGTTTGTTGACCCATCTCTGACAGTT
AGAGCCGATATCACTGGAAGATATTCAAATCGTCTCTATGCTTACGAACCTGCAGATACAGC
TCTGTTGCTTGACAACATGAAGAAGCTCTCAAGTTGCTGAAGACTGAATTGTAAAGAAAAA
AAATCTCCAAGCCCTTCTGTCTGTCAGGCCTTGAGACTTGAAACCAGAAGAAGTGTGAGAAG
ACTGGCTAGTGTGGAAGCATAGTGAACACACTGATTAGGTTATGGTTTAATGTTACAACAAC
TATTTTTTAAGAAAACAAGTTTTAGAAATTTGGTTTCAAGTGTACATGTGTGAAAACAATA
TTGTATACTACCATAGTGAGCCATGATTTTCTAAAAAAAAAAATAAATGTTA

FIGURE 28

```
></usr/seqdb2/sst/DNA/Dnaseqs.min/ss.DNA59485
><subunit 1 of 1, 175 aa, 1 stop
><MW: 19979, pI: 9.26, NX(S/T): 0
MEKIPVSAFLLLVALSYTLARDTTVKPGAKKDTKDSRPKLPQTLSRGWGDQLIWTQTYEE
ALYKSKTSNKPLMIIHHLDECPHSQALKKVFAENKEIQKLAEQFVLLNLVYETTDKHLSP
DGQYVPRIMFVDPSLTVRADITGRYSNRLYAYEPADTALLLDNMKKALKLLKTEL
```

Important features:
Signal peptide:
Amino acids           1-20 cAMP- and cGMP-dependent protein kinase phosphorylation site:
Amino acids           30-34

FIGURE 29

AAGACCCTCTCTTTCGCTGTTTGAGAGTCTCTCGGCTCAAGGACCGGGAGGTAAGAGGTT
TGGGACTGCCCCGGCAACTCCAGGGTGTCTGGTCCACGACCTATCCTAGGCGCATGGGT
GTGATAGGTATACAGCTGGTTGTTACCATGGTGATGGCCAGTGTCATGCAGAAGATTATA
CCTCACTATTCTCTTGCTCGATGGCTACTCTGTAATGGCAGTTTGAGGTGGTATCAACAT
CCTACAGAAGAAGAATTAAGAATTCTTGCAGGGAAACAACAAAAAGGGAAAACCAAAAAA
GATAGGAAATATAATGGTCACATTGAAAGTAAGCCATTAACCATTCCAAAGGATATTGAC
CTTCATCTAGAAACAAAGTCAGTTACAGAAGTGGATACTTTAGCATTGCATTACTTTCCA
GAATACCAGTGGCTGGTGGATTTCACAGTGGCTGCTACAGTTGTGTATCTAGTAACTGAA
GTCTACTACAATTTTATGAAGCCTACACAGGAAATGAATATCAGCTTAGTCTGGTGCCTA
CTTGTTTTGTCTTTTGCAATCAAAGTTCTATTTTCATTAACTACACACTATTTTAAAGTA
GAAGATGGTGGTGAAAGATCTGTTTGTGTCACCTTTGGATTTTTTTTCTTTGTCAAAGCA
ATGGCAGTGTTGATTGTAACAGAAAATTATCTGGAATTTGGACTTGAAACAGGGTTTACA
AATTTTTCAGACAGTGCGATGCAGTTTCTTGAAAAGCAAGGTTTAGAATCTCAGAGTCCT
GTTTCAAAACTTACTTTCAAATTTTTCCTGGCTATTTTCTGTTCATTCATTGGGGCTTTT
TTGACATTTCCTGGATTACGACTGGCTCAAATGCATCTGGATGCCCTGAATTTGGCAACA
GAAAAAATTACACAAACTTTACTTCATATCAACTTCTTGGCACCTTTATTTATGGTTTTG
CTCTGGGTAAAACCAATCACCAAAGACTACATTATGAACCCACCACTGGGCAAAGAAATT
TCCCCATCTGGAAGATGAAGATAATAGTATCTAACTCACAAGGTTATCATTGGAATAAAT
GAAAGAACACATGTAATGCAACCAGCTGGAATTAAGTGCTTAATAAATGTTCTTTTCACT
GCTTTGCCTCATCAGAATTAAAATAGAAATACTTGACTAGT

FIGURE 30

```
</usr/seqdb2/sst/DNA/Dnaseqs.full/ss.DNA64966
<subunit 1 of 1, 307 aa, 1 stop
<MW: 35098, pI: 8.11, NX(S/T): 3
MGVIGIQLVVTMVMASVMQKIIPHYSLARWLLCNGSLRWYQHPTEEELRILAGKQQKGKT
KKDRKYNGHIESKPLTIPKDIDLHLETKSVTEVDTLALHYFPEYQWLVDFTVAATVVYLV
TEVYYNFMKPTQEMNISLVWCLLVLSFAIKVLFSLTTHYFKVEDGGERSVCVTFGFFFFV
KAMAVLIVTENYLEFGLETGFTNFSDSAMQFLEKQGLESQSPVSKLTFKFFLAIFCSFIG
AFLTFPGLRLAQMHLDALNLATEKITQTLLHINFLAPLFMVLLWVKPITKDYIMNPPLGK
EISPSGR
```

Important features:
Signal peptide:
Amino acids          1-15

Transmembrane domains:
Amino acids          134-157;169-189;230-248;272-285

N-glycosylation sites:
Amino acids          34-38;135-139;203-207

ATP/GTP-binding site motif A (P-loop):
Amino acids          53-61

Tyrosine kinase phosphorylation site:
Amino acids          59-67

N-myristoylation sites:
Amino acids          165-171;196-202;240-246;247-253

FIGURE 31

GTAGCATAGTGTGCAGTTCACTGGACCAAAAGCTTTGGCTGCACCTCTTCTGGAAAGCTGGCC
ATGGGGCTCTTCATGATCATTGCAATTCTGCTGTTCCAGAAACCCACAGTAACCGAACAACT
TAAGAAGTGCTGGAATAACTATGTACAAGGACATTGCAGGAAAATCTGCAGAGTAAATGAAG
TGCCTGAGGCACTATGTGAAAATGGGAGATACTGTTGCCTCAATATCAAGGAACTGGAAGCA
TGTAAAAAAATTACAAAGCCACCTCGTCCAAAGCCAGCAACACTTGCACTGACTCTTCAAGA
CTATGTTACAATAATAGAAAATTTCCCAAGCCTGAAGACACAGTCTACATAAATCAAATACA
ATTTCGTTTTCACTTGCTTCTCAACCTAGTCTAATAAACTAAGGTGATGAGATATACATCTT
CTTCCTTCTGGTTTCTTGATCCTTAAAATGACCTTCGAGCATATTCTAATAAAGTGCATTGC
CAGTTAAAAAAAAAAA

FIGURE 32

></usr/seqdb2/sst/DNA/Dnaseqs.min/ss.DNA82403
><subunit 1 of 1, 99 aa, 1 stop
><MW: 11343, pI: 9.17, NX(S/T): 0
MGLFMIIAILLFQKPTVTEQLKKCWNNYVQGHCRKICRVNEVPEALCENGRYCCLNIKEL
EACKKITKPPRPKPATLALTLQDYVTIIENFPSLKTQST cAMP- and cGMP-dependent protein kinase phosphorylation site:
Amino acids                64-68

FIGURE 33

```
CGGACGCGTGGGCGCTGAGCCCCGGAGGCCAGGGCGTCCGGGGCTGCGCCACTTCCGAGGGC
CGAGCGCTGCCGGTCCCGGCGGTGCGACACGGCCGGGAGGAGGAGAACAACGCAAGGGGCTC
AACCGTCGGTCGCTGGAGCCCCCCCGGGGCGTGGCCTCCCGCCCCCTCAGCTGGGGAGGGC
GGGGCTCGCTGCCCCTGCTGCCGACTGCGACCCTTACAGGGGAGGGAGGGCGCAGGCCGCG
CGGAGATGAGGAGGAGGCTGCGCCTACGCAGGGACGCATTGCTCACGCTGCTCCTTGGCGCC
TCCCTGGGCCTCTTACTCTATGCGCAGCGCGACGGCGCGGCCCCGACGGCGAGCGCGCCGCG
AGGGCGAGGGAGGGCGGCACCGAGGCCCACCCCCGGACCCCGCGCGTTCCAGTTACCCGACG
CGGGTGCAGCCCCGCCGGCCTACGAAGGGGACACACCGGCGCCGCCCACGCCTACGGGACCC
TTTGACTTCGCCCGCTATTTGCGCGCCAAGGACCAGCGGCGGTTTCCACTGCTCATTAACCA
GCCGCACAAGTGCCGCGGCGACGGCGCACCCGGTGGCCGCCCGGACCTGCTTATTGCTGTCA
AGTCGGTGGCAGAGGACTTCGAGCGGCGCCAAGCCGTGCGCCAGACGTGGGGCGCGGAGGGT
CGCGTGCAGGGGCGCTGGTGCGCCGCGTGTTCTTGCTGGGCGTGCCCAGGGGCGCAGGCTC
GGGCGGGGCCGACGAAGTTGGGGAGGGCGCGCGAACCCACTGGCGCGCCCTGCTGCGGCCG
AGAGCCTTGCGTATGCGGACATCCTGCTCTGGGCCTTCGACGACACCTTTTTAACCTAACG
CTCAAGGAGATCCACTTTCTAGCCTGGGCCTCAGCTTTCTGCCCCGACGTGCGCTTCGTTTT
TAAGGGCGACGCAGATGTGTTCGTGAACGTGGGAAATCTCCTGGAGTTCCTGGCGCCGCGGGAC
CCGGCGCAAGACCTGCTTGCTGGTGACGTAATTGTGCATGCGCGGCCCATCCGCACGCGGGC
TAGCAAGTACTACATCCCCGAGGCCGTGTACGGCCTGCCCGCCTATCCGGCCTACGCGGGCG
GCGGTGGCTTTGTGCTTTCCGGGGCCACGCTGCACCGCCTGGCTGGCGCCTGTGCGCAGGTC
GAGCTCTTCCCCATCGACGACGTCTTTCTGGGCATGTGTCTGCAGCGCCTGCGGCTCACGCC
CGAGCCTCACCCTGCCTTCCGCACCTTTGGCATCCCCAGCCTTCAGCCGCGCCGCATTTGA
GCACCTTCGACCCCTGCTTTTACCGTGAGCTGGTTGTAGTGCACGGGCTCTCGGCCGCTGAC
ATCTGGCTTATGTGGCGCCTGCTGCACGGGCCGCATGGGCCAGCCTGTGCGCATCCACAGCC
TGTCGCTGCAGGCCCCTTCCAATGGGACTCCTAGCTCCCCACTACAGCCCCAAGCTCCTAAC
TCAGACCCAGAATGGAGCCGGTTTCCCAGATTATTGCCGTGTATGTGGTTCTTCCCTGATCA
CCAGGTGCCTGTCTCCACAGGATCCCAGGGGATGGGGGTTAAGCTTGGCTCCTGGCGGTCCA
CCCTGCTGGAACCAGTTGAAACCCGTGTAATGGTGACCCTTTGAGCGAGCCAAGGCTGGGTG
GTAGATGACCATCTCTTGTCCAACAGGTCCCAGAGCAGTGGATATGTCTGGTCCTCCTAGTA
GCACAGAGGTGTGTTCTGGTGTGGTGGCAGGGACTTAGGGAATCCTACCACTCTGCTGGATT
TGGAACCCCCTAGGCTGACGCGGACGTATGCAGAGGCTCTCAAGGCCAGGCCCCACAGGGAG
GTGGAGGGGCTCCGGCCGCCACAGCCTGAATTCATGAACCTGGCAGGCACTTTGCCATAGCT
CATCTGAAAACAGATATTATGCTTCCCACAACCTCTCCTGGGCCCAGGTGTGGCTGAGCACC
AGGGATGGAGCCACACATAAGGGACAAATGAGTGCACGGTCCTACCTAGTCTTTCCTCACCT
CCTGAACTCACACAACAATGCCAGTCTCCCACTGGAGGCTGTATCCCCTCAGAGGAGCCAAG
GAATGTCTTCCCTGAGATGCCACCACTATTAATTTCCCCATATGCTTCAACCACCCCTTG
CTCAAAAAACCAATACCCACACTTACCTTAATACAAACATCCCAGCAACAGCACATGGCAGG
CCATTGCTGAGGGCACAGGTGCTTTATTGGAGAGGGGATGTGGGCAGGGGATAAGGAAGGTTCC
CCCATTCCAGGAGGATGGGAACAGTCCTGGCTGCCCCTGACAGTGGGGATATGCAAGGGGCT
CTGGCCAGGCCACAGTCCAAATGGAAGACACCAGTCAGTCACAAAAGTCGGGAGCGCCACA
CAAACCTGGCTATAAGGCCCAGGAACCATATAGGAGCCTGAGACAGGTCCCCTGCACATTCA
TCATTAAACTATACAGGATGAGGCTGTACATGAGTTAATTACAAAAGAGTCATATTTACAAA
AATCTGTACACACATTTGAAAAACTCACAAAATTGTCATCTATGTATCACAAGTTGCTAGAC
CCAAAATATTAAAAATGGGATAAAATTNNTTTAAAAAAAAAAAAAAAAAAAAAAAAAAAA
AAAAAAAAAAAAA
```

FIGURE 34

```
></usr/seqdb2/sst/DNA/Dnaseqs.min/ss.DNA83505
><subunit 1 of 1, 402 aa, 1 stop
><MW: 43751, pI: 9.42, NX(S/T): 1
MRRRLRLRRDALLTLLLGASLGLLLYAQRDGAAPTASAPRGRGRAAPRPTPGPRAFQLPD
AGAAPPAYEGDTPAPPTPTGPFDFARYLRAKDQRRFPLLINQPHKCRGDGAPGGRPDLLI
AVKSVAEDFERRQAVRQTWGAEGRVQGALVRRVFLLGVPRGAGSGGADEVGEGARTHWRA
LLRAESLAYADILLWAFDDTFFNLTLKEIHFLAWASAFCPDVRFVFKGDADVFVNVGNLL
EFLAPRDPAQDLLAGDVIVHARPIRTRASKYYIPEAVYGLPAYPAYAGGGGFVLSGATLH
RLAGACAQVELFPIDDVFLGMCLQRLRLTPEPHPAFRTFGIPQPSAAPHLSTFDPCFYRE
LVVVHGLSAADIWLMWRLLHGPHGPACAHPQPVAAGPFQWDS
```

Important features of the protein:
Signal peptide:
Amino acids            1-27

N-glycosylation site:
Amino acids            203-207

N-myristoylation sites:
Amino acids            18-24;31-37;110-116;157-163;161-167
                       163-169;366-372

Cell attachment sequence:
Amino acids            107-110

FIGURE 35

AGCAGCCTCTGCCCGACCCGGCTCGTGCGGACCCCAGGACCGGGCGCGGGACGCGTGCGTCC
AGCCTCCGGCGCTGCGGAGACCCGCGGCTGGGTCCGGGGAGGCCCCAAACCCGCCCCCGCCA
GAACCCCGCCCCAAATTCCCACCTCCTCCAGAAGCCCCGCCCACTCCCGAGCCCCGAGAGCT
CCGCGCACCTGGGCGCCATCCGCCCTGGCTCCGCTGCACGAGCTCCACGCCCGTACCCCGGC
GTCACGCTCAGCCCGCGGTGCTCGCACACCTGAGACTCATCTCGCTTCGACCCCGCCGCCGC
CGCCGCCCGGCATCCTGAGCACGGAGACAGTCTCCAGCTGCCGTTCATGCTTCCTCCCCAGC
CTTCCGCAGCCCACCAGGGAAGGGGCGGTAGGAGTGGCCTTTTACCAAAGGGACCGGCGATG
CTCTGCAGGCTGTGCTGGCTGGTCTCGTACAGCTTGGCTGTGCTGTTGCTCGGCTGCCTGCT
CTTCCTGAGGAAGGCGGCCAAGCCCGCAGGAGACCCCACGGCCCACCAGCCTTTCTGGGCTCCC
CCAACACCCCGTCACAGCCGGTGTCCACCCAACCACACAGTGTCTAGCGCCTCTCTGTCCCT
GCCTAGCCGTCACCGTCTCTTCTTGACCTATCGTCACTGCCGAAATTTCTCTATCTTGCTGG
AGCCTTCAGGCTGTTCCAAGGATACCTTCTTGCTCCTGGCCATCAAGTCACAGCCTGGTCAC
GTGGAGCGACGTGCGGCTATCCGCAGCACGTGGGGCAGGGTGGGGGGATGGGCTAGGGGCCG
GCAGCTGAAGCTGGTGTTCCTCCTAGGGGTGGCAGGATCCGCTCCCCCAGCCCAGCTGCTGG
CCTATGAGAGTAGGGAGTTTGATGACATCCTCCAGTGGGACTTCACTGAGGACTTCTTCAAC
CTGACGCTCAAGGAGCTGCACCTGCAGCGCTGGGTGGTGGCTGCCTGCCCCAGGCCCATTT
CATGCTAAAGGGAGATGACGATGTCTTTGTCCACGTCCCCAACGTGTTAGAGTTCCTGGATG
GCTGGGACCCAGCCCAGGACCTCCTGGTGGGAGATGTCATCCGCCAAGCCCTGCCCAACAGG
AACACTAAGGTCAAATACTTCATCCCACCCTCAATGTACAGGGCCACCCACTACCCACCCTA
TGCTGGTGGGGAGGATATGTCATGTCCAGAGCCACAGTGCGGCGCCTCCAGGCTATCATGG
AAGATGCTGAACTCTTCCCCATTGATGATGTCTTTGTGGGTATGTGCCTGAGGAGGCTGGGG
CTGAGCCCTATGCACCATGCTGGCTTCAAGACATTTGGAATCCGGCGGCCCCTGGACCCCTT
AGACCCCTGCCTGTATAGGGGGCTCCTGCTGGTTCACCGCCTCAGCCCCCTCGAGATGTGGA
CCATGTGGGCACTGGTGACAGATGAGGGGCTCAAGTGTGCAGCTGGCCCCATACCCCAGCGC
TGAAGGGTGGGTTGGGCAACAGCCTGAGAGTGGACTCAGTGTTGATTCTCTATCGTGATGCG
AAATTGATGCCTGCTGCTCTACAGAAATGCCAACTTGGTTTTTTAACTCCTCTCACCCTGT
TAGCTCTGATTAAAAACACTGCAACCCAA

FIGURE 36

```
></usr/seqdb2/sst/DNA/Dnaseqs.min/ss.DNA84927
><subunit 1 of 1, 378 aa, 1 stop
><MW: 42310, pI: 9.58, NX(S/T): 3
MLPPQPSAAHQGRGGRSGLLPKGPAMLCRLCWLVSYSLAVLLLGCLLFLRKAAKPAGDPT
AHQPFWAPPTPRHSRCPPNHTVSSASLSLPSRHRLFLTYRHCRNFSILLEPSGCSKDTFL
LLAIKSQPGHVERRAAIRSTWGRVGGWARGRQLKLVFLLGVAGSAPPAQLLAYESREFDD
ILQWDFTEDFFNLTLKELHLQRWVVAACPQAHFMLKGDDDVFVHVPNVLEFLDGWDPAQD
LLVGDVIRQALPNRNTKVKYFIPPSMYRATHYPPYAGGGGYVMSRATVRRLQAIMEDAEL
FPIDDVFVGMCLRRLGLSPMHHAGFKTFGIRRPLDPLDPCLYRGLLLVHRLSPLEMWTMW
ALVTDEGLKCAAGPIPQR
```

Important features of the protein:
Signal peptide:
Amino acids                1-39

Transmembrane domain:
Amino acids                146-171

N-glycosylation sites:
Amino acids                79-83;104-108;192-196

N-myristoylation sites:
Amino acids                14-20;160-166;367-373

Prokaryotic membrane lipoprotein lipid attachment site:
Amino acids                35-46

FIGURE 37

```
ATGAAAGTGATAATCAGGCAGCCCAAATGATTGTTAATAAGGATCAAATGAGATCGTGTATG
TGGGTCCAATCAATTGATTCTACACAAAGGAGCCTGGGGAGGGGCCATGGTGCCAATGCACT
TACTGGGGAGACTGGAGAAGCCGCTTCTCCTCCTGTGCTGCGCCTCCTTCCTACTGGGGCTG
GCTTTGCTGGGCATAAAGACGGACATCACCCCCGTTGCTTATTTCTTTCTCACATTGGGTGG
CTTCTTCTTGTTTGCCTATCTCCTGGTCCGGTTTCTGGAATGGGGGCTTCGGTCCCAGCTCC
AATCAATGCAGACTGAGAGCCCAGGGCCCTCAGGCAATGCACGGGACAATGAAGCCTTTGAA
GTGCCAGTCTATGAAGAGGCCGTGGTGGGACTAGAATCCCAGTGCCGCCCCAAGAGTTGGA
CCAACCACCCCCTACAGCACTGTTGTGATACCCCAGCACCTGAGGAGGAACAACCTAGCC
ATCCAGAGGGGTCCAGGAGAGCCAAACTGGAACAGAGGCGAATGGCCTCAGAGGGTCCATG
GCCCAGGAAGGAAGCCCTGGAAGAGCTCCAATCAACCTTCGGCTTCGGGGACCACGGGCTGT
GTCCACTGCTCCTGATCTGCAGAGCTTGGCGGCAGTCCCCACATTAGAGCCTCTGACTCCAC
CCCCTGCCTATGATGTCTGCTTTGGTCACCCTGATGATGATAGTGTTTTTTATGAGGACAAC
TGGGCACCCCCTTAAATGACTCTCCCAAGATTTCTCTTCTCTCCACACCAGACCTCGTTCAT
TTGACTAACATTTTCCAGCGCCTACTATGTGTCAGAAACAAGTGTTTCTGCCTGGACATCAT
AAATGGGGACTTGGACCCTGAGGAGAGTCAGGCCACGGTAAGCCCTTCCCAGCTGAGATATG
GGTGGCATAATTTGAGTCTTCTGGCAACATTTGGTGACCTACCCCATATCCAATATTTCCAG
CGTTAGATTGAGGATGAGGTAGGGAGGTGATCCAGAGAAGGCGGAGAAGGAAGAAGTAACCT
CTGAGTGGCGGCTATTGCTTCTGTTCCAGGTGCTGTTCGAGCTGTTAGAACCCTTAGGCTTGAC
AGCTTTGTGAGTTATTATTGAAAAATGAGGATTCCAAGAGTCAGAGGAGTTTGATAATGTGC
ACGAGGGCACACTGCTAGTAAATAACATTAAAATAACTGGAATGAA
```

FIGURE 38

```
></usr/seqdb2/sst/DNA/Dnaseqs.min/ss.DNA92264
><subunit 1 of 1, 216 aa, 1 stop
><MW: 23729, pI: 4.73, NX(S/T): 0
MVPMHLLGRLEKPLLLLCCASFLLGLALLGIKTDITPVAYFFLTLGGFFLFAYLLVRFLE
WGLRSQLQSMQTESPGPSGNARDNEAFEVPVYEEAVVGLESQCRPQELDQPPPYSTVVIP
PAPEEEQPSHPEGSRRAKLEQRRMASEGSMAQEGSPGRAPINLRLRGPRAVSTAPDLQSL
AAVPTLEPLTPPPAYDVCFGHPDDDSVFYEDNWAPP
```

Important features of the protein:
Signal peptide:
Amino acids            1-25

Transmembrane domain:
Amino acids            41-59

N-myristoylation site:
Amino acids            133-139

FIGURE 39

```
CCCACGCGTCCGGCGGCTACACACCTAGGTGCGGTGGGCTTCGGGTGGGGGGCCTGCAGCTA
GCTGATGGCAAGGGAGGAATAGCAGGGGTGGGGATTGTGGTGTGCGAGAGGTCCCGCGGACG
GGGGGCTCGGGGGTCTCTTCAGACGAGATTCCCTTCAGGCTTGGGCCGGGTCCCTTCGCACG
GAGATCCCAATGAACGCGGCCCCTGGAGGCCGGTGGTTGGGGCTTCTCCGCGTCGGGGATG
GGGCCGGTACCCTAGCCCGTTTCCAGCGCCTCAGTCGGTTCCCCATGCCCTCAGAGGTGGCC
CGGGGCAAGCGCGCCGCCCTCTTCTTCGCTGCGGTGGCCATCGTGCTGGGGCTACCGCTCTG
GTGGAAGACCACGGAGACCTACCGGGCCTCGTTGCCTTACTCCAGATCAGTGGCCTGAATG
CCCTTCAGCTCCGCCTCATGGTGCCTGTCACTGTCGTGTTTACGCGGGAGTCAGTGCCCCTG
GACGACCAGGAGAAGCTGCCCTTCACCGTTGTGCATGAAAGAGAGATTCCTCTGAAATACAA
AATGAAAATCAAATGCCGTTTCCAGAAGGCCTATCGGAGGGCTTTGGACCATGAGGAGGAGG
CCCTGTCATCGGGCAGTGTGCAAGAGGCAGAAGCCATGTTAGATGAGCCTCAGGAACAAGCG
GAGGGCTCCCTGACTGTGTACGTGATATCTGAACACTCCTCACTTCTTCCCCAGGACATGAT
GAGCTACATTGGGCCCAAGAGGACAGCAGTGGTGCGGGGGATAATGCACCGGGAGGCCTTTA
ACATCATTGGCCGCCGCATAGTCCAGGTGGCCCAGGCCATGTCTTTGACTGAGGATGTGCTT
GCTGCTGCTCTGGCTGACCACCTTCCAGAGGACAAGTGGAGCGCTGAGAAGAGGCGGCCTCT
CAAGTCCAGCTTGGGCTATGAGATCACCTTCAGTTTACTCAACCCAGACCCCAAGTCCCATG
ATGTCTACTGGGACATTGAGGGGCTGTCCGGCGCTATGTGCAACCTTTCCTGAATGCCCTC
GGTGCCGCTGGCAACTTCTCTGTGGACTCTCAGATTCTTTACTATGCAATGTTGGGGGTGAA
TCCCCGCTTTGACTCAGCTTCCTCCAGCTACTATTTGGACATGCACAGCCTCCCCATGTCA
TCAACCCAGTGGAGTCCCGGCTGGGATCCAGTGCTGCCTCCTTGTACCCTGTGCTCAACTTT
CTACTCTACGTGCCTGAGCTTGCACACTCACCGCTGTACATTCAGGACAAGGATGGCGCTCC
AGTGGCCACCAATGCCTTCCATAGTCCCCGCTGGGGTGGCATTATGGTATATAATGTTGACT
CCAAAACCTATAATGCCTCAGTGCTGCCAGTGAGAGTCGAGGTGGACATGGTGCGAGTGATG
GAGGTGTTCCTGGCACAGTTGCGGTTGCTCTTTGGGATTGCTCAGCCCCAGCTGCCTCCAAA
ATGCCTGCTTTCAGGGCCTACGAGTGAAGGGCTAATGACCTGGGAGCTAGACCGGCTGCTCTGG
GCTCGGTCAGTGGAGAACCTGGCCACAGCCACCACCACCCTTACCTCCCTGGCGCAGCTTCT
GGGCAAGATCAGCAACATTGTCATTAAGGACGACGTGGCATCTGAGGTGTACAAGGCTGTAG
CTGCCGTCCAGAAGTCGGCAGAAGAGTTGGCGTCTGGGCACCTGGCATCTGCCTTTGTCGCC
AGCCAGGAAGCTGTGACATCCTCTGAGCTTGCCTTCTTTGACCCGTCACTCCTCCACCTCCT
TTATTTCCCTGATGACCAGAAGTTTGCCATCTACATCCCACTCTTCCTGCCTATGGCTGTGC
CCATCCTCCTGTCCCTGGTCAAGATCTTCCTGGAGACCCGCAAGTCCTGGAGAAAGCCTGAG
AAGACAGACTGAGCAGGGCAGCACCTCCATAGGAAGCCTTCCTTTCTGGCCAAGGTGGGCGG
TGTTAGATTGTGAGGCACGTACATGGGGCCTGCCGGAATGACTTAAATATTTGTCTCCAGTC
TCCACTGTTGGCTCTCCAGCAACCAAAGTACAACACTCCAAGATGGGTTCATCTTTTCTTCC
TTTCCCATTCACCTGGCTCAATCCTCCTCCACCACCAGGGGCCTCAAAAGGCACATCATCCG
GGTCTCCTTATCTTGTTTGATAAGGCTGCTGCCTGTCTCCCTCTGTGGCAAGGACTGTTTGT
TCTTTTGCCCCATTTCTCAACATAGCACACTTGTGCACTGAGAGGAGGGAGCATTATGGGAA
AGTCCCTGCCTTCCACACCTCTCTCTAGTCCCTGTGGGACAGCCCTAGCCCCTGCTGTCATG
AAGGGGCCAGGCATTGGTCACCTGTGGGACCTTCTCCCTCACTCCCCTCCCTCCTAGTTGGC
TTTGTCTGTCAGGTGCAGTCTGGCGGGAGTCCAGGAGGCAGCAGCTCAGGACATGGTGCTGT
GTGTGTGTGTGTGTGTGTGTGTGTGTGTGTGTCAGAGGTTCCAGAAAGTTCCAGATTT
GGAATCAAACAGTCCTGAATTCAAATCCTTGTTTTTGCACTTATTGTCTGGAGAGCTTTGGA
TAAGGTATTGAATCTCTCTGAGCCTCAGTTTTTCATTTGTTCAAATGGCACTGATGATGTCT
CCCTTACAAGATGGTTGTGAGGAGTAAATGTGATCAGCATGTAAAGTGTCTGGCGTGTAGTA
GGCTCTTAATAAACACTGGCTGAATATGAATTGGAATGAT
```

FIGURE 40

```
></usr/seqdb2/sst/DNA/Dnaseqs.min/ss.DNA94713
><subunit 1 of 1, 547 aa, 1 stop
><MW: 61005, pI: 6.34, NX(S/T): 2
MPSEVARGKRAALFFAAVAIVLGLPLWWKTTETYRASLPYSQISGLNALQLRLMVPVTVV
FTRESVPLDDQEKLPFTVVHEREIPLKYKMKIKCRFQKAYRRALDHEEEALSSGSVQEAE
AMLDEPQEQAEGSLTVYVISEHSSLLPQDMMSYIGPKRTAVVRGIMHREAFNIIGRRIVQ
VAQAMSLTEDVLAAALADHLPEDKWSAEKRRPLKSSLGYEITFSLLNPDPKSHDVYWDIE
GAVRRYVQPFLNALGAAGNFSVDSQILYYAMLGVNPRFDSASSSYYLDMHSLPHVINPVE
SRLGSSAASLYPVLNFLLYVPELAHSPLYIQDKDGAPVATNAFHSPRWGGIMVYNVDSKT
YNASVLPVRVEVDMVRVMEVFLAQLRLLFGIAQPQLPPKCLLSGPTSEGLMTWELDRLLW
ARSVENLATATTTLTSLAQLLGKISNIVIKDDVASEVYKAVAAVQKSAEELASGHLASAF
VASQEAVTSSELAFFDPSLLHLLYFPDDQKFAIYIPLFLPMAVPILLSLVKIFLETRKSW
RKPEKTD
```

Important features of the protein:
Signal peptide:
Amino acids                  1-23

Transmembrane domain:
Amino acids                  511-530

N-glycosylation sites:
Amino acids                  259-263;362-366

N-myristoylation sites:
Amino acids                  255-261;304-310;335-341

Amidation sites:
Amino acids                  7-11;174-178

FIGURE 41

CCAGCTGCAGAGAGGAGGAGGTGAGCTGCAGAGAAGAGGAGGTTGGTGTGGAGCACAGGCAG
CACCGAGCCTGCCCCGTGAGCTGAGGGCCTGCAGTCTGCGGCTGGAATCAGGATAGACACCA
AGGCAGGACCCCAGAGATGCTGAAGCCTCTTTGGAAAGCAGCAGTGGCCCCACATGGCCA
TGCTCCATGCCGCCCCGCCGCCCGTGGGACAGAGAGGCTGGCACGTTGCAGGTCCTGGGAGC
GCTGGCTGTGCTGTGGCTGGGCTCCGTGGCTCTTATCTGCCTCCTGTGGCAAGTGCCCCGTCCT
CCCACCTGGGGCCAGGTGCAGCCCAAGGACGTGCCCAGGTCCTGGGAGCATGGCTCCAGCCC
AGCTTGGGAGCCCCTGGAAGCAGAGGCCAGGCAGCAGAGGGACTCCTGCCAGCTTGTCCTTG
TGGAAAGCATCCCCCAGGACCTGCCATCTGCAGCCGGCAGCCCCTCTGCCCAGCCTCTGGGC
CAGGCCTGGCTGCAGCTGCTGGACACTGCCCAGGAGAGCGTCCACGTGGCTTCATACTACTG
GTCCCTCACAGGGCCTGACATCGGGGTCAACGACTCGTCTTCCCAGCTGGGAGAGGCTCTTC
TGCAGAAGCTGCAGCAGCTGCTGGGCAGGAACATTTCCCTGGCTGTGGCCACCAGCAGCCCG
ACACTGGCCAGGACATCCACCGACCTGCAGGTTCTGGCTGCCCGAGGTGCCCATGTACGACA
GGTGCCCATGGGGCGGCTCACCAGGGGTGTTTTGCACTCCAAATTCTGGGTTGTGGATGGAC
GGCACATATACATGGGCAGTGCCAACATGGACTGGCGGTCTCTGACGCAGGTGAAGGAGCTT
GGCGCTGTCATCTATAACTGCAGCCACCTGGCCCAAGACCTGGAGAAGACCTTCCAGACCTA
CTGGGTACTGGGGGTGCCCAAGGCTGTCCTCCCCAAAACCTGGCCTCAGAACTTCTCATCTC
ACTTCAACCGTTTCCAGCCCTTCCACGGCCTCTTTGATGGGGTGCCCACCACTGCCTACTTC
TCAGCGTCGCCACCAGCACTCTGTCCCCAGGGCCGCACCCGGGACCTGGAGGCGCTGCTGGC
GGTGATGGGGAGCGCCCAGGAGTTCATCTATGCCTCCGTGATGGAGTATTTCCCCACCACGC
GCTTCAGCCACCCCCCGAGGTACTGGCCGGTGCTGGACAACGCGCTGCGGGCGGCAGCCTTC
GGCAAGGGCGTGCGCGTGCGCCTGCTGGTCGGCTGCGGACTCAACACGGACCCCACCATGTT
CCCCTACCTGCGGTCCCTGCAGGCGCTCAGCAACCCCGCGGCCAACGTCTCTGTGGACGTGA
AAGTCTTCATCGTGCCGGTGGGGAACCATTCCAACATCCCATTCAGCAGGGTGAACCACAGC
AAGTTCATGGTCACGGAGAAGGCAGCCTACATAGGCACCTCCAACTGGTCGGAGGATTACTT
CAGCAGCACGGCGGGGGTGGGCTTGGTGGTCACCCAGAGCCCTGGCGCGCAGCCCGCGGGGG
CCACGGTGCAGGAGCAGCTGCGGCAGCTCTTTGAGCGGGACTGGAGTTCGCGCTACGCCGTC
GGCCTGGACGGACAGGCTCCGGGCCAGGACTGCGTTTGGCAGGGCTGAGGGGGGCCTCTTTT
TCTCTCGGCGACCCCGCCCCGCACGCGCCCTCCCCTCTGACCCCGGCCTGGGCTTCAGCCGC
TTCCTCCCGCAAGCAGCCCGGGTCCGCACTGCGCCAGGAGCCGCCTGCGACCGCCCGGGCGT
CGCAAACCGCCCGCCTGCTCTCTGATTTCCGAGTCCAGCCCCCCCTGAGCCCCACCTCCTCC
AGGGAGCCCTCCAGGAAGCCCCTTCCCTGACTCCTGGCCCACAGGCCAGGCCTAAAAAAAAC
TCGTGGCTTCAAAAAAAAAAAAAAAAAAAAAAAAAAAAAA

FIGURE 42

```
></usr/seqdb2/sst/DNA/Dnaseqs.min/ss.DNA96869
><subunit 1 of 1, 489 aa, 1 stop
><MW: 53745, pI: 8.36, NX(S/T): 8
MPPRRPWDREAGTLQVLGALAVLWLGSVALICLLWQVPRPPTWGQVQPKDVPRSWEHGSS
PAWEPLEAEARQQRDSCQLVLVESIPQDLPSAAGSPSAQPLGQAWLQLLDTAQESVHVAS
YYWSLTGPDIGVNDSSSQLGEALLQKLQQLLGRNISLAVATSSPTLARTSTDLQVLAARG
AHVRQVPMGRLTRGVLHSKFWVVDGRHIYMGSANMDWRSLTQVKELGAVIYNCSHLAQDL
EKTFQTYWVLGVPKAVLPKTWPQNFSSHFNRFQPFHGLFDGVPTTAYFSASPPALCPQGR
TRDLEALLAVMGSAQEFIYASVMEYFPTTRFSHPPRYWPVLDNALRAAAFGKGVRVRLLV
GCGLNTDPTMFPYLRSLQALSNPAANVSVDVKVFIVPVGNHSNIPFSRVNHSKFMVTEKA
AYIGTSNWSEDYFSSTAGVGLVVTQSPGAQPAGATVQEQLRQLFERDWSSRYAVGLDGQA
PGQDCVWQG
```

Important features of the protein:
Signal peptide:
Amino acids          1-29

N-glycosylation sites:
Amino acids          133-137;154-158;232-236;264-268;
                     386-390;400-404;410-414;427-431

N-myristoylation sites:
Amino acids          58-64;94-100;131-137;194-200;251-257;
                     277-283;281-287;361-367;399-405;
                     440-446;448-454;478-484

FIGURE 43

GGGCCTGGCGATCCGGATCCCGCAGGCGCGCTGGCTGCGCTGCCCGGCTGTCTGTCGTCATG
GTGGGGCCCTGGGTGTATCTGGTGGCGGCAGTTTTGCTCATCGGCCTGATCCTCTTCCTGAC
TCGCAGCCGGGGTCGGGCGGCAGCAGCTGACGGAGAACCACTGCACAATGAGGAAGAGAGGG
CAGGAGCAGGCCAGGTAGGCCGCTCTTTGCCCCAGGAGTCTGAAGAACAGAGAACTGGAAGC
AGACCCCGGCGTCGGAGGGACTTGGGCAGCCGTCTACAGGCCCAGCGTCGAGCCCAGCGAGT
GGCCTGGGAAGACGGGGATGAGAATGTGGGTCAAACTGTTATTCCAGCCCAGGAGGAAGAAG
GCATTGAGAAGCCAGCAGAAGTTCACCCAACAGGGAAAATTGGAGCCAAGAAACTACGGAAG
CTAGAGGAAAAACAGGCTCGAAAGGCTCAGCGAGAGGCAGAGGAGGCTGAACGTGAAGAACG
GAAACGCCTAGAGTCCCAACGTGAGGCCGAATGGAAGAAGGAAGAGGAACGGCTTCGCCTGA
AGGAAGAACAGAAGGAGGAGGAAGAGAGGAAGGCTCAGGAGGAGCAGGCCCGGCGGGATCAC
GAGGAGTACCTGAAACTGAAGGAGGCCTTCGTGGTAGAAGAAGAAGGTGTTAGCGAAACCAT
GACTGAGGAGCAGTCTCACAGCTTCCTGACAGAATTCATCAATTACATCAAGAAGTCCAAGG
TTGTGCTTTTGGAAGATCTGGCTTTCCAGATGGGCCTAAGGACTCAGGACGCCATAAACCGC
ATCCAGGACCTGCTGACGGAGGGGACTCTAACAGGTGTGATTGACGACCGGGGCAAGTTTAT
CTACATAACCCCAGAGGAACTGGCTGCCGTGGCCAATTTCATCCGACAGCGGGGCCGGGTGT
CCATCACAGAGCTTGCCCAGGCCAGCAACTCCCTCATCTCCTGGGGCCAGGACCTCCCTGCC
CAGGCTTCAGCCTGACTCCAGTCCTTCCTTGAGTGTATCCTGTGGCCTACATGTGTCTTCAT
CCTTCCCTAATGCCGTCTTGGGGCAGGGATGGAATATGACCAGAAAGTTGTGGATTAAAGGC
CTGTGAATACTGAA

FIGURE 44

```
></usr/seqdb2/sst/DNA/Dnaseqs.min/ss.DNA96881
><subunit 1 of 1, 315 aa, 1 stop
><MW: 35963, pI: 5.38, NX(S/T): 0
MVGPWVYLVAAVLLIGLILFLTRSRGRAAAADGEPLHNEEERAGAGQVGRSLPQESEEQR
TGSRPRRRRDLGSRLQAQRRAQRVAWEDGDENVGQTVIPAQEEEGIEKPAEVHPTGKIGA
KKLRKLEEKQARKAQREAEEAEREERKRLESQREAEWKKEEERLRLKEEQKEEEERKAQE
EQARRDHEEYLKLKEAFVVEEEGVSETMTEEQSHSFLTEFINYIKKSKVVLLEDLAFQMG
LRTQDAINRIQDLLTEGTLTGVIDDRGKFIYITPEELAAVANFIRQRGRVSITELAQASN
SLISWGQDLPAQASA
```

Important features of the protein:
Signal peptide:
Amino acids                 1-26

N-myristoylation sites:
Amino acids                 203-209;257-263

FIGURE 45

ACGGGCCGCAGCGGCAGTGACGTAGGGTTGGCGCACGGATCCGTTGCGGCTGCAGCTCTGCA
GTCGGGCCGTTCCTTCGCCGCCGCCAGGGGTAGCGGTGTAGCTGCGCAGCGTCGCGCGCGCT
ACCGCACCCAGGTTCGGCCCGTAGGCGTCTGGCAGCCCGGCGCCATCTTCATCGAGCGCAT
GGCCGCAGCCTGCGGGCCGGGAGCGGCCGGGTACTGCTTGCTCCTCGGCTTGCATTTGTTTC
TGCTGACCGCGGGCCCTGCCCTGGGCTGGAACGACCCTGACAGAATGTTGCTGCGGGATGTA
AAAGCTCTTACCCTCCACTATGACCGCTATACCACCTCCCGCAGGCTGGATCCCATCCCACA
GTTGAAATGTGTTGGAGGCACAGCTGGTTGTGATTCTTATACCCCAAAAGTCATACAGTGTC
AGAACAAAGGCTGGGATGGGTATGATGTACAGTGGGAATGTAAGACGGACTTAGATATTGCA
TACAAATTTGGAAAAACTGTGGTGAGCTGTGAAGGCTATGAGTCCTCTGAAGACCAGTATGT
ACTAAGAGGTTCTTGTGGCTTGGAGTATAATTTAGATTATACAGAACTTGGCCTGCAGAAAC
TGAAGGAGTCTGGAAAGCAGCACGGCTTTGCCTCTTTCTCTGATTATTATTATAAGTGGTCC
TCGGCGGATTCCTGTAACATGAGTGGATTGATTACCATCGTGGTACTCCTTGGGATCGCCTT
TGTAGTCTATAAGCTGTTCCTGAGTGACGGGCAGTATTCTCCTCCACCGTACTCTGAGTATC
CTCCATTTTCCCACCGTTACCAGAGATTCACCAACTCAGCAGGACCTCCTCCCCAGGCTTT
AAGTCTGAGTTCACAGGACCACAGAATACTGGCCATGGTGCAACTTCTGGTTTTGGCAGTGC
TTTTACAGGACAACAAGGATATGAAAATTCAGGACCAGGGTTCTGGACAGGCTTGGGAACTG
GTGGAATACTAGGATATTTGTTTGGCAGCAATAGAGCGGCAACACCCTTCTCAGACTCGTGG
TACTACCCGTCCTATCCTCCCTCCTACCCTGGCACGTGGAATAGGGCTTACTCACCCCTTCA
TGGAGGCTCGGGCAGCTATTCGGTATGTTCAAACTCAGACACGAAACCAGAACTGCATCAG
GATATGGTGGTACCAGGAGACGATAAAGTAGAAAGTTGGAGTCAAACACTGGATGCAGAAAT
TTTGGATTTTTCATCACTTTCTCTTTAGAAAAAAGTACTACCTGTTAACAATTGGGAAAAG
GGGATATTCAAAAGTTCTGTGGTGTTATGTCCAGTGTAGCTTTTTGTATTCTATTATTTGAG
GCTAAAAGTTGATGTGTGACAAAATACTTATGTGTTGTATGTCAGTGTAACATGCAGATGTA
TATTGCAGTTTTTGAAAGTGATCATTACTGTGGAATGCTAAAAATACATTAATTTCTAAAAC
CTGTGATGCCCTAAGAAGCATTAAGAATGAAGGTGTTGTACTAATAGAAACTAAGTACAGAA
AATTTCAGTTTTAGGTGGTTGTAGCTGATGAGTTATTACCTCATAGAGACTATAATATTCTA
TTTGGTATTATATTATTTGATGTTTGCTGTTCTTCAAACATTTAAATCAAGCTTTGGACTAA
TTATGCTAATTTGTGAGTTCTGATCACTTTTGAGCTCTGAAGCTTTGAATCATTCAGTGGTG
GAGATGGCCTTCTGGTAACTGAATATTACCTTCTGTAGGAAAAGGTGGAAAATAAGCATCTA
GAAGGTTGTTGTGAATGACTCTGTGCTGGCAAAAATGCTTGAAACCTCTATATTTCTTTCGT
TCATAAGAGGTAAAGGTCAAATTTTTCAACAAAAGTCTTTTAATAACAAAAGCATGCAGTTCTC
TGTGAAATCTCAAATATTGTTGTAATAGTCTGTTTCAATCTTAAAAAGAATCA

FIGURE 46

```
></usr/seqdb2/sst/DNA/Dnaseqs.min/ss.DNA96889
><subunit 1 of 1, 339 aa, 1 stop
><MW: 36975, pI: 7.85, NX(S/T): 1
MAAACGPGAAGYCLLLGLHLFLLTAGPALGWNDPDRMLLRDVKALTLHYDRYTTSRRLDP
IPQLKCVGGTAGCDSYTPKVIQCQNKGWDGYDVQWECKTDLDIAYKFGKTVVSCEGYESS
EDQYVLRGSCGLEYNLDYTELGLQKLKESGKQHGFASFSDYYYKWSSADSCNMSGLITIV
VLLGIAFVVYKLFLSDGQYSPPPYSEYPPFSHRYQRFTNSAGPPPPGFKSEFTGPQNTGH
GATSGFGSAFTGQQGYENSGPGFWTGLGTGGILGYLFGSNRAATPFSDSWYYPSYPPSYP
GTWNRAYSPLHGGSGSYSVCSNSDTKTRTASGYGGTRRR
```

Important features of the protein:
Signal peptide:
Amino acids                         1-30

Transmembrane domain:
Amino acids                         171-190

N-glycosylation site:
Amino acids                         172-176

Glycosaminoglycan attachment sites:
Amino acids                         244-248;259-263;331-335

Tyrosine kinase phosphorylation site:
Amino acids                         98-106

N-myristoylation sites:
Amino acids                         68-74;69-75;131-137;241-247;
                                    247-253;266-272;270-276;278-284;
                                    312-318

FIGURE 47

CCCGGAGCCGGGGAGGGAGGGAGCGAGGTTCGGACACCGGCGGCGGCTGCCTGGCCTTTCCA
TGAGCCCGCGGCGGACCCTCCCGCGCCCCTCTCGCTCTGCCTCTCCCTCTGCCTCTGCCTC
TGCCTGGCCGCGGCTCTGGGAAGTGCGCAGTCCGGGTCGTGTAGGGATAAAAAGAACTGTAA
GGTGGTCTTTTCCCAGCAGGAACTGAGGAAGCGGCTAACACCCCTGCAGTACCATGTCACTC
AGGAGAAAGGGACCGAAAGTGCCTTTGAAGGAGAATACACACATCACAAAGATCCTGGAATA
TATAAATGTGTTGTTTGTGGAACTCCATTGTTTAAGTCAGAAACCAAATTTGACTCCGGTTC
AGGTTGGCCTTCATTCCACGATGTGATCAATTCTGAGGCAATCACATTCACAGATGACTTTT
CCTATGGGATGCACAGGGTGGAAACAAGCTGCTCTCAGTGTGGTGCTCACCTTGGGCACATT
TTTGATGATGGGCCTCGTCCAACTGGGAAAAGATACTGCATAAATTCGGCTGCCTTGTCTTT
TACACCTGCGGATAGCAGTGGCACCGCCGAGGGAGGCAGTGGGGTCGCCAGCCCGGCCCAGG
CAGACAAAGCGGAGCTCTAGAGTAATGGAGAGTGATGGAAACAAAGTGTACTTAATGCACAG
CTTATTAAAAAAATCAAAATTGTTATCTTAATAGATATATTTTTTCAAAAACTATAAGGGCA
GTTTTGTGCTATTGATATTTTTTCTTCTTTTGCTTAAACAGAAGCCCTGGCCATCCATGTAT
TTTGCAATTGACTAGATCAAGAACTGTTTATAGCTTTAGCAAATGGAGACAGCTTTGTGAAA
CTTCTTCACAAGCCACTTATACCCTTTGGCATTCTTTTCTTTGAGCACATGGCTTCTTTTGC
AGTTTTTCCCCCTTTGATTCAGAAGCAGAGGGTTCATGGTCTTCAAACATGAAAATAGAGAT
CTCCTCTGCAGTGTAGAGACCAGAGCTGGGCAGTGCAGGGCATGGAGACCTGCAAGACACAT
GGCCTTGAGGCCTTTGCACAGACCCACCTAAGATAAGGTTGGAGTGATGTTTTAATGAGACT
GTTCAGCTTTGTGGAAAGTTTGAGCTAAGGTCATTTTTTTTTTCTCACTGAAAGGGTGTGA
AGGTCTAAAGTCTTTCCTTATGTTAAATTGTTGCCAGATCCAAAGGGGCATACTGAGTGTTG
TGGCAGAGAAGTAAACATTACCACACTGTTAGGCCTTTATTTTATTTTATTTTCCATCGAAA
GCATTGGAGGCCCAGTGCAATGGCTCACGCCTGTGATCCCAGCACTTTGGGAGGCCAAGGCG
GGTGGATCACGAGGTCAGGAGATGGAGACCATCCTGGCTAACATGGTGAAACCCCGTCTCTA
CTAAAAATACGAAAATTAGCCAGGCGTGGTGGTGGGCACCTGTAGTCCCAGCTACTCAGGAGG
CTGAGGCAGGAGAATGGCGTGAACCCGGAAGGCGGAGCTTGCAGTTAGCCGAGATCATGCCA
CTGCACTCCAGCCTACATGACAATGTGACACTCCATCTCAAAAAATAATAATAATAACAATA
TAAGAACTAGCTGGGCATGGTGGCGCATGCATGTAGTCCCAGCTACTCCTGAGGCTCAGTCA
GGAGAATCGCTTGAACTTGGGAGGCGGAGGTTGCAGTGAGCTGAGCTCATACCACTGCACTC
CAGCCTGAACAGAGTGAGATCCTGTCAA

FIGURE 48

```
></usr/seqdb2/sst/DNA/Dnaseqs.min/ss.DNA96898
><subunit 1 of 1, 192 aa, 1 stop
><MW: 20702, pI: 7.50, NX(S/T): 0
MSPRRTLPRPLSLCLSLCLCLAAALGSAQSGSCRDKKNCKVVFSQQELRKRLTPLQYH
VTQEKGTESAFEGEYTHHKDPGIYKCVVCGTPLFKSETKFDSGSGWPSFHDVINSEAITF
TDDFSYGMHRVETSCSQCGAHLGHIFDDGPRPTGKRYCINSAALSFTPADSSGTAEGGSG
VASPAQADKAEL
```

```
Important features of the protein:
Signal peptide:
Amino acids                     1-24

Glycosaminoglycan attachment site:
Amino acids                     102-106 cAMP- and cGMP-dependent protein kinase phosphorylation site:
Amino acids                     52-56

N-myristoylation sites:
Amino acids                     28-34;66-72;82-88;139-145;
                                173-179;178-184

Amidation site:
Amino acids                     153-157
```

FIGURE 49

```
CCCAAAGAGGTGAGGAGCCGGCAGCGGGGCGGCTGTAACTGTGAGGAAGGCTGCAGAGTGG
CGACGTCTACGCCGTAGGTTGGAGGCTGTGGGGGGTGGCCGGGCGCCAGCTCCCAGGCCGCA
GAAGTGACCTGCGGTGGAGTTCCCTCCTCGCTGCTGGAGAACGGAGGGAGAAGGTTGCTGGC
CGGGTGAAAGTGCCTCCCTCTGCTTGACGGGGCTGAGGGGCCCGAAGTCTAGGGCGTCCGTA
GTCGCCCCGGCCTCCGTGAAGCCCCAGGTCTAGAGATATGACCCGAGAGTGCCCATCTCCGG
CCCCGGGGCCTGGGGCTCCGCTGAGTGGATCGGTGCTGGCAGAGGCGGCAGTAGTGTTTGCA
GTGGTGCTGAGCATCCACGCAACCGTATGGGACCGATACTCGTGGTGCGCCGTGGCCCTCGC
AGTGCAGGCCTTCTACGTCAATACAAGTGGGACCGGCTGCTACAGCAGGGAAGCGCCGTCT
TCCAGTTCCGAATGTCCGCAAACAGTGGCCTATTGCCCGCCTCCATGGTCATGCCTTTGCTT
GGACTAGTCATGAAGGAGCGGTGCCAGACTGCTGGGAACCCGTTCTTTGAGCGTTTTGGCAT
TGTGGTGGCAGCCACTGGCATGGCAGTGGCCCTCTTCTCATCAGTGTTGGCGCTCGGCATCA
CTCGCCCAGTGCCAACCAACACTTGTGTCATCTTGGGCTTGGCTGGAGGTGTTATCATTTAT
ATCATGAAGCACTCGTTGAGCGTGGGGGAGGTGATCGAAGTCCTGGAAGTCCTTCTGATCTT
CGTTTATCTCAACATGATCCTGCTGTACCTGCTGCCCCGCTGCTTCACCCCTGGTGAGGCAC
TGCTGGTATTGGGTGGCATTAGCTTTGTCCTCAACCAGCTCATCAAGCGCTCTCTGACACTG
GTGGAAAGTCAGGGGGACCCAGTGGACTTCTTCCTGCTGGTGGTGGTAGTAGGGATGGTACT
CATGGGCATTTTCTTCAGCACTCTGTTTGTCTTCATGGACTCAGGCACCTGGGCCTCCTCCA
TCTTCTTCCACCTCATGACCTGTGTGCTGAGCCTTGGTGTGGTCCTACCCTGGCTGCACCGG
CTCATCCGCAGGAATCCCCTGCTCTGGCTTCTTCAGTTTCTCTTCCAGACAGACACCCGCAT
CTACCTCCTAGCCTATTGGTCTCTGCTGGCCACCTTGGCCTGCCTGGTGGTGCTGTACCAGA
ATGCCAAGCGGTCATCTTCCGAGTCCAAGAAGCACCAGGCCCCCACCATCGCCCGAAAGTAT
TTCCACCTCATTGTGGTAGCCACCTACATCCCAGGTATCATCTTTGACCGGCCACTGCTCTAT
GTAGCCGCCACTGTATGCCTGGCGGTCTTCATCTTCCTGGAGTATGTGCGCTACTTCCGCAT
CAAGCCTTTGGGTCACACTCTACGGAGCTTCCTGTCCCTTTTTCTGGATGAACGAGACAGTG
GACCACTCATTCTGACACACATCTACCTGCTCCTGGGCATGTCTCTTCCCATCTGGCTGATC
CCCAGACCCTGCACACAGAAGGGTAGCCTGGGAGGAGCCAGGGCCCTCGTCCCCTATGCCGG
TGTCCTGGCTGTGGGTGTGGGTGATACTGTGGCCTCCATCTTCGGTAGCACCATGGGGGAGA
TCCGCTGGCCTGGAACCAAAAGACTTTTGAGGGACCATGACATCTATATTTGCGCAGATC
ATTTCTGTAGCTCTGATCTTAATCTTTGACAGTGGAGTGGACCTAAACTACAGTTATGCTTG
GATTTTGGGGTCCATCAGCACTGTGTCCCTCCTGGAAGCATACACTACACAGATAGACAATC
TCCTTCTGCCTCTCTACCTCCTGATATTGCTGATGGCCTAGCTGTTACAGTGCAGCAGCAGT
GACGGAGGAAACAGACATGGGGAGGGTGAACAGTCCCCACAGCAGACAGCTACTTGGGCATG
AAGAGCCAAGGTGTGAAAAGCAGATTTGATTTTTCAGTTGATTCAGATTTAAAATAAAAAGC
AAAGCTCTCCTAGTTCTA
```

FIGURE 50

```
></usr/seqdb2/sst/DNA/Dnaseqs.min/ss.DNA97003
><subunit 1 of 1, 538 aa, 1 stop
><MW: 59268, pI: 8.94, NX(S/T): 1
MTRECPSPAPGPGAPLSGSVLAEAAVVFAVVLSIHATVWDRYSWCAVALAVQAFYVQYKW
DRLLQQGSAVFQFRMSANSGLLPASMVMPLLGLVMKERCQTAGNPFFERFGIVVAATGMA
VALFSSVLALGITRPVPTNTCVILGLAGGVIIYIMKHSLSVGEVIEVLEVLLIFVYLNMI
LLYLLPRCFTPGEALLVLGGISFVLNQLIKRSLTLVESQGDPVDFFLLVVVVGMVLMGIF
FSTLFVFMDSGTWASSIFFHLMTCVLSLGVVLPWLHRLIRRNPLLWLLQFLFQTDTRIYL
LAYWSLLATLACLVVLYQNAKRSSSESKKHQAPTIARKYFHLIVVATYIPGIIFDRPLLY
VAATVCLAVFIFLEYVRYFRIKPLGHTLRSFLSLFLDERDSGPLILTHIYLLLGMSLPIW
LIPRPCTQKGSLGGARALVPYAGVLAVGVGDTVASIFGSTMGEIRWPGTKKTFEGTMTSI
FAQIISVALILIFDSGVDLNYSYAWILGSISTVSLLEAYTTQIDNLLLPLYLLILLMA
```

Important features of the protein:
Signal peptide:
Amino acids                      1-36

Transmembrane domains:
Amino acids                      77-95;111-133;161-184;225-248;
                                           255-273;299-314;348-373;406-421;
                                           435-456;480-497

N-glycosylation sites:
Amino acids                      500-504 cAMP- and cGMP-dependent protein kinase phosphorylation site:
Amino acids                      321-325

N-myristoylation sites:
Amino acids                      13-19;18-24;80-86;111-117;
                                           118-124;145-151;238-244;251-257;
                                           430-436;433-439;448-454;458-464;
                                           468-474;475-481;496-502;508-514

Prokaryotic membrane lipoprotein lipid attachment site:
Amino acids                      302-313

FIGURE 51

```
GCTCTATGCCGCCTACCTTGCTCTCGCCGCTGCTGCCGGAGCCGAAGCAGAGAAGGCAGCGGGTCCCGTGACCG
TCCCGAGAGCCCCGCGCTCCCGACCAGGGGCGGGGCGGCCCCGGGGAGGGCGGGGCAGGGGCGGGGGGAAGA
AAGGGGGTTTTGTGCTGCGCCGGGAGGGCCGGCGCCCTCTTCCGAATGTCCTGCGGCCCCAGCCTCTCCTCACG
CTCGCGCAGTCTCCGCCGCAGTCTCAGCTGCAGCTGCAGGACTGAGCCGTGCACCCGGAGGAGACCCCCGGAGG
AGGCGACAAACTTCGCAGTGCCGCGACCCAACCCCAGCCCTGGGTAGCCTGCAGCATGGCCCAGCTGTTCCTGC
CCCTGCTGGCAGCCCTGGTCCTGGCCCAGGCTCCTGCAGCTTTAGCAGATGTTCTGGAAGGAGACAGCTCAGAG
GACCGCGCTTTTCGCGTGCGCATCGCGGGCGACGCGCCACTGCAGGGCGTGCTCGGCGGCGCCCTCACCATCCC
TTGCCACGTCCACTACCTGCGGCCACCGCCGAGCCGCCGGGCTGTGCTGGGCTCTCCGCGGGTCAAGTGGACTT
TCCTGTCCCGGGGCCGGGAGGCAGAGGTGCTGGTGGCGCGGGGAGTGCGCGTCAAGGTGAACGAGGCCTACCGG
TTCCGCGTGGCACTGCCTGCGTACCCAGCGTCGCTCACCGACGTCTCCCTGGCGCTGAGCGAGCTGCGCCCCAA
CGACTCAGGTATCTATCGCTGTGAGGTCCAGCACGGCATCGATGACAGCAGCGACGCTGTGGAGGTCAAGGTCA
AAGGGGTCGTCTTTCTCTACCGAGAGGGCTCTGCCCGCTATGCTTTCTCCTTTTCTGGGGCCCAGGAGGCCTGT
GCCCGCATTGGAGCCCACATCGCCACCCCGGAGCAGCTCTATGCCGCCTACCTTGGGGGCTATGAGCAATGTGA
TGCTGGCTGGCTGTCGGATCAGACCGTGAGGTATCCCATCCAGACCCCACGAGAGGCCTGTTACGGAGACATGG
ATGGCTTCCCCGGGGTCCGGAACTATGGTGTGGTGGACCCGGATGACCTCTATGATGTGTACTGTTATGCTGAA
GACCTAAATGGAGAACTGTTCCTGGGTGACCCTCCAGAGAAGCTGACATTGGAGGAAGCACGGGCGTACTGCCA
GGAGCGGGGTGCAGAGATTGCCACCACGGGCCAACTGTATGCAGCCTGGGATGGTGGCCTGGACCACTGCAGCC
CAGGGTGGCTAGCTGATGGCAGTGTGCGCTACCCCATCGTCACACCCAGCCAGCGCTGTGGTGGGGCTTGCCT
GGTGTCAAGACTCTCTTCCTCTTCCCCAACCAGACTGGCTTCCCCAATAAGCACAGCCGCTTCAACGTCTACTG
CTTCCGAGACTCGGCCCAGCCTTCTGCCATCCCTGAGGCCTCCAACCCAGCCTCCAACCCAGCCTCTGATGGAC
TAGAGGCTATCGTCACAGTGACAGAGACCCTGGAGGAACTGCAGCTGCCTCAGGAAGCCACAGAGAGTGAATCC
CGTGGGGCCATCTACTCCATCCCCATCATGGAGGACGGAGGAGGTGGAAGCTCCACTCCAGAAGACCCAGCAGA
GGCCCCTAGGACGCTCCTAGAATTTGAAACACAATCCATGGTACCGCCCACGGGGTTCTCAGAAGAGGAAGGTA
AGGCATTGGAGGAAGAAGAGAAATATGAAGATGAAGAAGAGAAAGAGGAGGAAGAAGAAGAGGAGGAGGTGGAG
GATGAGGCTCTGTGGGCATGGCCCAGCGAGCTCAGCAGCCCGGGCCCTGAGGCCTCTCTCCCCACTGAGCCAGC
AGCCCAGGAGAAGTCACTCTCCCAGGCGCCAGCAAGGGCAGTCCTGCAGCCTGGTGCATCACCACTTCCTGATG
GAGAGTCAGAAGCTTCCAGGCCTCCAAGGGTCCATGGACCACCTACTGAGACTCTGCCCACTCCCAGGGAGAGG
AACCTAGCATCCCCATCACCTTCCACTCTGGTTGAGGCAAGAGAGGTGGGGGAGGCAACTGGTGGTCCTGAGCT
ATCTGGGGTCCCTCGAGGAGAGAGCGAGGAGACAGGAAGCTCCGAGGGTGCCCCTTCCCTGCTTCCAGCCACAC
GGGCCCCTGAGGGTACCAGGGAGCTGGAGGCCCCTCTGAAGATAATTCTGGAAGAACTGCCCCAGCAGGGACC
TCAGTGCAGGCCCAGCCAGTGCTGCCCACTGACAGCGCCAGCCGAGGTGGAGTGGCCGTGGTCCCCGCATCAGG
TGACTGTGTCCCCAGCCCCTGCCACAATGGTGGGACATGCTTGGAGGAGGAGGAAGGGGTCCGCTGCCTATGTC
TGCCTGGCTATGGGGGGACCTGTGCGATGTTGGCCTCCGCTTCTGCAACCCCGGCTGGGACGCCTTCCAGGGC
GCCTGCTACAAGCACTTTTCCACACGAAGGAGCTGGGAGGAGGCAGAGACCCAGTGCCGGATGTACGCGCGCA
TCTGGCCAGCATCAGCACACCCGAGGAACAGGACTTCATCAACAACCGGTACCGGGAGTACCAGTGGATCGGAC
TCAACGACAGGACCATCGAAGGCGACTTCTTGTGGTCGGATGGCGTCCCCCTGCTCTATGAGAACTGGAACCCT
GGGCAGCCTGACAGCTACTTCCTGTCTGGAGAGAACTGCGTGGTCATGGTGTGGCATGATCAGGGACAATGGAG
TGACGTGCCCTGCAACTACCACCTGTCCTACACCTGCAAGATGGGGCTGGTGTCCTGTGGGCCGCCACCGGAGC
TGCCCCTGGCTCAAGTGTTCGGCCGCCCACGGCTGCGCTATGAGGTGGACACTGTGCTTCGCTACCGGTGCCGG
GAAGGACTGGCCCAGCGCAATCTGCCGCTGATCCGATGCCAAGAGAACGGTCGTTGGGAGGCCCCCCAGATCTC
CTGTGTGCCCAGAAGACCTGCCCGAGCTCTGCACCCAGAGGAGGACCCAGAAGGACGTCAGGGGAGGCTACTGG
GACGCTGGAAGGCGCTGTTGATCCCCCCTTCCAGCCCCATGCCAGGTCCCTAGGGGCAAGGCCTTGAACACTGCCG
GCCACAGCACTGCCCTGTCACCCAAATTTTCCCTCACACCTTGCGCTCCGCCACCACAGGAAGTGACAACATG
ACGAGGGTGGTGCTGGAGTCCAGGTGACAGTTCCTGAAGGGCTTCTGGGAAATACCTAGGAGGCTCCAGCCC
AGCCCAGGCCCTCTCCCCCTACCCTGGGCACCAGATCTTCCATCAGGGCCGGAGTAAATCCCTAAGTGCCTCAA
CTGCCCTCTCCCTGGCAGCCATCTTGTCCCCTCTATTCCTCTAGGGAGCACTGTGCCCACTCTTTCTGGGTTTT
CCAAGGGAATGGGCTTGCAGGATCGAGTGTCTGTAAAATCAACAGGAAATAAAACTGTGTATGAGCCCA
```

FIGURE 52

```
></usr/seqdb2/sst/DNA/Dnaseqs.min/ss.DNA98565
><subunit 1 of 1, 911 aa, 1 stop
><MW: 99117, pI: 4.62, NX(S/T): 2
MAQLFLPLLAALVLAQAPAALADVLEGDSSEDRAFRVRIAGDAPLQGVLGGALTIPCHVH
YLRPPPSRRAVLGSPRVKWTFLSRGREAEVLVARGVRVKVNEAYRFRVALPAYPASLTDV
SLALSELRPNDSGIYRCEVQHGIDDSSDAVEVKVKGVVFLYREGSARYAFSFSGAQEACA
RIGAHIATPEQLYAAYLGGYEQCDAGWLSDQTVRYPIQTPREACYGDMDGFPGVRNYGVV
DPDDLYDVYCYAEDLNGELFLGDPPEKLTLEEARAYCQERGAEIATTGQLYAAWDGGLDH
CSPGWLADGSVRYPIVTPSQRCGGGLPGVKTLFLFPNQTGFPNKHSRFNVYCFRDSAQPS
AIPEASNPASNPASDGLEAIVTVTETLEELQLPQEATESESRGAIYSIPIMEDGGGGSST
PEDPAEAPRTLLEFETQSMVPPTGFSEEEGKALEEEEKYEDEEEKEEEEEEEVEDEALW
AWPSELSSPGPEASLPTEPAAQEKSLSQAPARAVLQPGASPLPDGESEASRPPRVHGPPT
ETLPTPRERNLASPSPSTLVEAREVGEATGGPELSGVPRGESEETGSSEGAPSLLPATRA
PEGTRELEAPSEDNSGRTAPAGTSVQAQPVLPTDSASRGGVAVVPASGDCVPSPCHNGGT
CLEEEEGVRCLCLPGYGGDLCDVGLRFCNPGWDAFQGACYKHFSTRRSWEEAETQCRMYG
AHLASISTPEEQDFINNRYREYQWIGLNDRTIEGDFLWSDGVPLLYENWNPGQPDSYFLS
GENCVVMVWHDQGQWSDVPCNYHLSYTCKMGLVSCGPPPELPLAQVFGRPRLRYEVDTVL
RYRCREGLAQRNLPLIRCQENGRWEAPQISCVPRRPARALHPEEDPEGRQGRLLGRWKAL
LIPPSSPMPGP
```

Important features of the protein:

Signal peptide:
Amino acids                      1-15
N-glycosylation sites:
Amino acids                      130-134;337-341
Tyrosine kinase phosphorylation sites:
Amino acids                      128-136;451-460
N-myristoylation sites:
Amino acids                      47-53;50-56;133-139;142-148;
                                          174-180;183-189;281-287;288-294;
                                          297-303;324-330;403-409;414-420;
                                          415-421;576-582;586-592;677-683;
                                          684-690;720-726;772-778;811-817
EGF-like domain cysteine pattern signature:
Amino acids                      670-682
C-type lectin domain signature:
Amino acids                      784-809
Immunoglobulins and major histocompatibility complex proteins signature:
Amino acids                      135-142
Link domain proteins:
Amino acids                      166-216;264-314
Calcium-binding EGF-like domain proteins pattern proteins.
Amino acids                      655-676
C-type lectin domain proteins:
Amino acids                      791-800

FIGURE 53

CTGCCAGGTGACAGCCGCCAAGATGGGGTCTTGGGCCCTGCTGTGGCCTCCCCTGCTGTTCACCGGGCTGCTCG
TCCGACCCCCGGGGACCATGGCCCAGGCCCAGTACTGCTCTGTGAACAAGGACATCTTTGAAGTAGAGGAGAAC
ACAAATGTCACCGAGCCGCTGGTGGACATCCACGTCCCGGAGGGCCAGGAGGTGACCCTCGGAGCCTTGTCCAC
CCCCTTTGCATTTCGGATCCAGGGAAACCAGCTGTTTCTCAACGTGACTCCTGATTACGAGGAGAAGTCACTGC
TTGAGGCTCAGCTGCTGTGTCAGAGCGGAGGCACATTGGTGACCCAGCTAAGGGTGTTCGTGTCAGTGCTGGAC
GTCAATGACAATGCCCCCGAATTCCCCTTTAAGACCAAGGAGATAAGGGTGGAGGAGGACACGAAAGTGAACTC
CACCGTCATCCCTGAGACGAACTGCAGGCTGAGGACCGCGACAAGGACGACATTCTGTTCTACACCCTCCAGG
AAATGACAGCAGGTGCCAGTGACTACTTCTCCCTGGTGAGTGTAAACCGTCCCGCCCTGAGGCTGGACCGGCCC
CTGGACTTCTACGAGCGGCCGAACATGACCTTCTGGCTGCTGGTGCGGGACACTCCAGGGGAGAATGTGGAACC
CAGCCACACTGCCACCGCCACACTAGTGCTGAACGTGGTGCCCGCCGACCTGCGGCCCCGTGGTTCCTGCCCT
GCACCTTCTCAGATGGCTACGTCTGCATTCAAGCTCAGTACCACGGGCTGTCCCACGGGGCACATACTGCCA
TCTCCCCTCGTCCTGCGTCCCGGACCCATCTACGCTGAGGACGGAGACCGCGGCATCAACCAGCCCATCATCTA
CAGCATCTTTAGGGGAAACGTGAATGGTACATTCATCATCCACCCAGACTCGGGCAACCTCACCGTGGCCAGGA
GTGTCCCCAGCCCCATGACCTTCCTTCTGCTGGTGAAGGGCAACAGGCCGACCTTGCCCGCTACTCAGTGACC
CAGGTCACCGTGGAGGCTGTGGCTGCGGCCGGGAGCCCGCCCCGCTTCCCCAGAGCCTGTATCGTGGCACCGT
GGCGCGTGGCGCTGGAGCGGGCGTTGTGGTCAAGGATGCAGCTGCCCCTTCTCAGCCTCTGAGGATCCAGGCTC
AGGACCCGGAGTTCTCGGACCTCAACTCGGCCATCACATATCGAATTACCAACCACTCACACTTCCGGATGGAG
GGAGAGGTTGTGCTGACCACCACCACACTGGCACAGGCGGGAGCCTTCTACGCAGAGGTTGAGGCCCACAACAC
GGTGACCTCTGGCACCGCAACCACAGTCATTGAGATACAAGTTTCCGAACAGGAGCCCCCTCCACAGAGGCTG
GAGGAACAACTGGGCCCTGGACCAGCACCACTTCCGAGGTCCCCAGACCCCCTGAGCCCTCCCAGGGACCCTCC
ACGACCAGCTCTGGGGGAGGCACAGGCCCTCATCCACCCTCTGGCACAACTCTGAGGCCACCAACCTCGTCCAC
ACCCGGGGGCCCCGGGTGCAGAAAACAGCACCTCCCACCAACCAGCCACTCCCGGTGGGGACACAGCACAGA
CCCCAAAGCCAGGAACCTCTCAGCCGATGCCCCCGGTGTGGGAACCAGCACCTCCCACCAACCAGCCACACCC
AGTGGGGCACAGCACAGACCCCAGAGCCAGGAACCTCTCAGCCGATGCCCCCAGTATGGGAACCAGCACCTC
CCACCAACCAGCCACACCCGGTGGGGGCACAGCACAGACCCCAGAGGCAGGAACCTCTCAGCCGATGCCCCCG
GTATGGGAACCAGCACCTCCCACCAACCAACCACACCCGGTGGGGGCACAGCACAGACCCCAGAGCCAGGAACC
TCTCAGCCGATGCCCCTCAGCAAGAGCACCCCATCTTCAGGTGGCGGCCCCTCGGAGGACAAGCGCTTCTCGGT
GGTGGATATGGCGGCCCTGGGCGGGTGCTGGGTGCGCTGCTGCTGCTGGCTCTCCTTGGCCTCGCCGTCCTTG
TCCACAAGCACTATGGCCCCCGGCTCAAGTGCTGCTCTGGCAAAGCTCCGGAGCCCCAGCCCCAAGGCTTTGAC
AACCAGGCGTTCCTCCCTGACCACAAGGCCAACTGGGCGCCCGTCCCCAGCCCCACGCACGACCCCAAGCCCGC
GGAGGCACCGATGCCCGCAGAGCCCGCACCCCCGGCCCTGCCTCCCCAGGCGGTGCCCCTGAGCCCCCCGCAG
CGGCCCGAGCTGGCGGAAGCCCCACGGCGGTGAGGTCCATCCTGACCAAGGAGCGGCGGCCGGAGGGCGGGTAC
AAGGCCGTCTGGTTTGGCGAGGACATCGGGACGGAGGCAGACGTGGTCGTTCTCAACGCGCCCACCCTGGACGT
GGATGGCGCCAGTGACTCCGGCAGCGGCGACGAGGGCGAGGGCGCGGGAGGGGTGGGGGTCCCTACGATGCAC
CCGGTGGTGATGACTCCTACATCTAAGTGGCCCCTCCACCCTCTCCCCAGCCGCACGGGCACTGGAGGTCTCG
CTCCCCCAGCCTCCGACCCGAGGCAGAATAAAGCAAGGCTCCCGAAACCCAGGCCATGGCGTGGGGCAGGCGCG
TGGGTCCCTGGGGGCCCCATTCACTCAGTCCCCTGTCGTCATTAGCGCTTGAGCCCAGGTGTGCAGATGAGGCG
GTGGGTCTGGCCACGCTGTCCCCACCCCAAGGCTGCAGCACTTCCCGTAAACCACCTGCAGTGCCCGCCGCCTT
CCCGAGGCTCTGTGCCAGCTAGTCTGGGAAGTTCCTCTCCCGCTCTAACCACAGCCCGAGGGGGCTCCCCTCC
CCCGACCTGCACCAGAGATCTCAGGCACCCGGCTCAACTCAGACCTCCCGCTCCCGACCCTACACAGAGATTGC
CTGGGGAGGCTGAGGAGCCGATGCAAACCCCAAGGCGACGCACTTGGGAGCCGGTGGTCTCAAACACCTGCCG
GGGGTCCTAGTCCCCTTCTGAAATCTACATGCTTGGGTTGGAGCGCAGCAGTAAACACCCTGCCCAGTGACCTG
GACTGAGGCGCGCTGGGGGTGGGTGCGCCGTGTGGCCTGAGCAGGAGCCAGACCAGGAGGCCTAGGGTGAGAG
ACACATTCCCCTCGCTGCTCCCAAAGCCAGAGCCCAGGCTGGGCGCCCATGCCCAGAACCATCAAGGGATCCCT
TGCGGCTTGTCAGCACTTTCCCTAATGGAAATACACCATTAATTCCTTTCCAAATGTTTT

FIGURE 54

```
></usr/seqdb2/sst/DNA/Dnaseqs.min/ss.DNA102846
><subunit 1 of 1, 839 aa, 1 stop
><MW: 87546, pI: 4.84, NX(S/T): 8
MGSWALLWPPLLFTGLLVRPPGTMAQAQYCSVNKDIFEVEENTNVTEPLVDIHVPEGQEV
TLGALSTPFAFRIQGNQLFLNVTPDYEEKSLLEAQLLCQSGGTLVTQLRVFVSVLDVNDN
APEFPFKTKEIRVEEDTKVNSTVIPETQLQAEDRDKDDILFYTLQEMTAGASDYFSLVSV
NRPALRLDRPLDFYERPNMTFWLLVRDTPGENVEPSHTATATLVLNVVPADLRPPWFLPC
TFSDGYVCIQAQYHGAVPTGHILPSPLVRPGPIYAEDGDRGINQPIIYSIFRGNVNGTF
IIHPDSGNLTVARSVPSPMTFLLLVKGQQADLARYSVTQVTVEAVAAAGSPPRFPQSLYR
GTVARGAGAGVVVKDAAAPSQPLRIQAQDPEFSDLNSAITYRITNHSHFRMEGEVVLTTT
TLAQAGAFYAEVEAHNTVTSGTATTVIEIQVSEQEPPSTEAGGTTGPWTSTTSEVPRPPE
PSQGPSTTSSGGGTGPHPPSGTTLRPPTSSTPGGPPGAENSTSHQPATPGGDTAQTPKPG
TSQPMPPGVGTSTSHQPATPSGGTAQTPEPGTSQPMPPSMGTSTSHQPATPGGGTAQTPE
AGTSQPMPPGMGTSTSHQPTTPGGGTAQTPEPGTSQPMPLSKSTPSSGGGPSEDKRFSVV
DMAALGGVLGALLLLALLGLAVLVHKHYGPRLKCCSGKAPEPQPQGFDNQAFLPDHKANW
APVPSPTHDPKPAEAPMPAEPAPPGPASPGGAPEPPAAARAGGSPTAVRSILTKERRPEG
GYKAVWFGEDIGTEADVVVLNAPTLDVDGASDSGSGDEGEGAGRGGGPYDAPGGDDSYI
```

Important features of the protein:
Signal peptide:
Amino acids                                     1-25

Transmembrane domain:
Amino acids                                     662-684

N-glycosylation sites:
Amino acids                                     44-48;140-144;198-202;297-301;
                                                308-312;405-409;520-524

Glycosaminoglycan attachment sites:
Amino acids                                     490-494;647-651;813-817 cAMP- and cGMP-dependent protein kinase phosphorylation site:
Amino acids                                     655-659

Tyrosine kinase phosphorylation sites:
Amino acids                                     154-163;776-783

N-myristoylation sites:
Amino acids                                     57-63;102-108;255-261;294-300;
                                                366-372;426-432;441-447;513-519;
                                                517-523;530-536;548-554;550-556;
                                                581-587;592-598;610-616;612-618;
                                                623-629;648-654;666-672;667-673;
                                                762-768;763-769;780-786;809-815;
                                                821-827;833-839

Cadherins extracellular repeated domain signature:
Amino acids                                     112-123

FIGURE 55

```
GCAGCTGGGTTCTCCCGGTTCCCTTGGGCAGGTGCAGGGTCGGGTTCAAAGCCTCCGGAACGCGTTTTGGCCTG
ATTTGAGGAGGGGGCGGGGAGGGACCTGCGGCTTGCGGCCCCGCCCCTTCTCCGGCTCGCAGCCGACCGGTA
AGCCCGCCTCCTCCCTCGGCCGGCCCTGGGGCCGTGTCCGCCGGGCAACTCCAGCCGAGGCCTGGGCTTCTGCC
TGCAGGTGTCTGCGGCGAGGCCCCTAGGGTACAGCCCGATTTGGCCCCATGGTGGGTTTCGGGGCCAACCGGCG
GGCTGGCCGCCTGCCCTCTCGTGCTGGTGGTGCTGCTGGTGGTGATCGTCGTCCTCGCCTTCAACTACTGGA
GCATCTCCTCCCGCCACGTCCTGCTTCAGGAGGAGGTGGCCGAGCTGCAGGGCCAGGTCCAGCGCACCGAAGTG
GCCCGCGGGCGGCTGGAAAAGCGCAATTCGGACCTCTTGCTGTTGGTGGACACGCACAAGAAACAGATCGACCA
GAAGGAGGCCGACTACGGCCGCCTCAGCAGCCGGCTGCAGGCCAGAGAGGGCCTCGGGAAGAGATGCGAGGATG
ACAAGGTTAAACTACAGAACAACATATCGTATCAGATGGCAGACATACATCATTTAAAGGAGCAACTTGCTGAG
CTTCGTCAGGAATTTCTTCGACAAGAAGACCAGCTTCAGGACTATAGGAAGAACAATACTTACCTTGTGAAGAG
GTTAGAATATGAAAGTTTTCAGTGTGGACAGCAGATGAAGGAATTGAGAGCACAGCATGAAGAAATATTAAAA
AGTTAGCAGACCAGTTTTTAGAGGAACAAAAGCAAGAGACCCAAAAGATTCAATCAAATGATGGAAAGGAATTG
GATATAAACAATCAAGTAGTACCTAAAAATATTCCAAAAGTAGCTGAGAATGTTGCAGATAAGAATGAAGAACC
CTCAAGCAATCATATTCCACATGGGAAGAACAAATCAAAAGAGGTGGTGATGCAGGGATGCCTGGAATAGAAG
AGAATGACCTAGCAAAAGTTGATGATCTTCCCCCTGCTTTAAGGAAGCCTCCTATTTCAGTTTCTCAACATGAA
AGTCATCAAGCAATCTCCCATCTTCCAACTGGACAACCTCTCTCCCCAAATATGCCTCCAGATTCACACATAAA
CCACAATGGAAACCCCGGTACTTCAAAACAGAATCCTTCCAGTCCTCTTCAGCGTTTAATTCCAGGCTCAAACT
TGGACAGTGAACCCAGAATTCAAACAGATATACTAAAGCAGGCTACCAAGGACAGAGTCAGTGATTTCCATAAA
TTGAAGCAAAATGATGAAGAACGAGAGCTTCAAATGGATCCTGCAGACTATGGAAAGCAACATTTCAATGATGT
CCTTTAAGTCCTAAAGGAATGCTTCAGAAAACCTAAAGTGCTGTAAAATGAAATCATTCTACTTTGTCCTTTCT
GACTTTTGTTGTAAAGACGAATTGTATCAGTTGTAAAGATACATTGAGATAGAATTAAGGAAAAACTTTAATGA
AGGAATCTACCCATGTACATATGTGAACTTTTTCATATTGTATTATCAAGGTATAGACTTTTTTGGTTATGATA
CAGTTAAGCCAAAAACAGCTAATCTTTGCATCTAAAGCAAACTAATGTATATTTCACATTTTATTGAGCCGACT
TATTTCCACAAATAGATAAACAGGACAAAATAGTTGTACAGGTTATATGTGGCATAGCATAACCACAGTAAGAA
CAGAACAGATATTCAGCAGAAAACTTTTTATACTCTAATTCTTTTTTTTTTTTTTTGAGACAGAGTTTTAGTC
TTGTTTCCCAGGCTGGAGTGCAATGGCACAATCTTGGCTCACTGCAACCTCCGCCTCCTGGGTTCAGGCAATTT
TCCTGCCTCAGCCTCCCAAGTAGCTGGGATTACAGGCACCCACCACCATGCCCAGCTAATTTTTGTATTTTTAA
TAGAGAGCTAATAATTGTATATTTAATAAAGACGGGTTTCACCATGTTGGCCAGGCTGGTCTTGAACTCCTGAC
CTCAGGTGATCCTCCTGCATTGGCCTCCCAAAGTGCTGGAATTCCAGGCATGAGCCACTGCGCCCAGTCTACAC
ACTAATTCTTGTTAGCCCAACAGCTGTTCTGTTCTATCTACCCCTCATTTCACGCTCAAGGAGTCATACCTAGA
ATAGTTACACACAAGAGGGAAACTGGAAGCCAAACACTGTACAGTATTGTGTAGAAAGTCACCTCCCTACTCCT
TTTATTTTACATGAGTGCTGATGTGTTTTGGCAGATGAGCTTTCAGCTGAGGCCTGATGGAAATTGAGATAACCTG
CAAAGACATAACAGTATTTATGAGTTATATCTTAGTTCTTGAAATTGTGGAATGCATGATTGACAATATATTTT
TAATTTTTATTTTTTCAAGTAATACCAGTACTGTTTAACTATAGCCAGAACTGGCTAAAATTTTTATATTTTCA
GAGTTGAAGTTGGTGAAGACATTCATGATTTAAACACCAGATCCTGAAAGGGGTTAAATCTACTTTGAAATGAA
TCTGCAATCAGTATTTCAAAGCTTTTCTGGTAATTTTAGTGATCTTATTTGATTAGACTTTTTCAGAAGTACTA
AATAAGGAATTTTAACAGGTTTTTATTAATGCACAGATAAATAGAAGTACAGTGAGGTCTATAGCCATTTTATT
AAAATAGCTTAAAAGTTTGTAAAAAAATGAATCTTTGTAATTACTTAATATGTTAGTTAAGAACCCGTCAAGCT
TATATTTGCTAGACTTACAAATTATTTTAAATGCATTTATCTTTTTTGACACTATTCAGTGGAATGTGTAAGCT
AGCTAATTCTTGTTTTCTGATTTAAAGCACTTTTAAATCTTATCCTGCCCCCTAAAAACAAAAGGTTTTGATCA
CAAGGGGAAATTTAAGATTGTTAACCCTGTTTTTCAGAAGGGCTACTGTTAATTGCACATAAACATGAAATGTG
TTTTCCCCTGTGTACTAACACATTCTAGGCAAAATTCAAACTTATAGTGGTAAAGAAACAGGTTGTTCACTTGC
TGAGGTGCAAAAATTCTTAAGACTTCTGTTTGAAATTGCTCAATGACTAGGAAAAGATGTAGTAGTTTACTAAA
ATTGTTTTTCTACCATATCAAATTAAACAATTCATGCCTTTATAGGGTCAGGCCTACAATGAATAGGTATGGTG
GTTTCACAGAATTTTAAAATAGAGTTAAAGGGAAGTGATGTACATTTCGGGGCATTAGGGTAGGGAGATGAAT
CAAAAAATACCCCTAGTAATGCTTTATATTTAATACTGCAAAAGCTTTACAAATGGAAACCATGCAATTACCT
GCCTTAGTTCTTTTGTCATAAAAACAATCACTTGGTTGGTTGTATTGTAGCTATTACTTATACAGCAACATTTC
TTCAATTAGCAGTCTAGACATTTTATAAACAGAAATCTTGGACCAATTGATAATATTTCTGACTGTATTAATAT
TTTAGTGCTATAAAATACTATGTGAATCTCTTAAAAATCTGACATTTTACAGTCTGTATTAGACATACTGTTTTA
TAATGTTTTACTTCTGCCTTAAGATTTAGGTTTTTAAATGTATTTTGCCCTGAATTAAGTGTTAATTTGATG
GAAACTCTGCTTTTAAAATCATCATTTACTGGGTTCTAATAAATTAAAAATTAAACTTGAAAAAAAAAAAAAAA
AAAAAAAAAAAAAAAAAAAAAAAAAAAAAAAAAAAAAAAAAAAAAAAAAAAAAAAAAAAAAA
```

FIGURE 56

MVGFGANRRAGRLPSLVLVVLLVVIVVLAFNYWSISSRHVLLQEEVAELQGQVQRTEVAR
GRLEKRNSDLLLLVDTHKKQIDQKEADYGRLSSRLQAREGLGKRCEDDKVKLQNNISYQM
ADIHHLKEQLAELRQEFLRQEDQLQDYRKNNTYLVKRLEYESFQCGQQMKELRAQHEENI
KKLADQFLEEQKQETQKIQSNDGKELDINNQVVPKNIPKVAENVADKNEEPSSNHIPHGK
EQIKRGGDAGMPGIEENDLAKVDDLPPALRKPPISVSQHESHQAISHLPTGQPLSPNMPP
DSHINHNGNPGTSKQNPSSPLQRLIPGSNLDSEPRIQTDILKQATKDRVSDFHKLKQNDE
ERELQMDPADYGKQHFNDVL

Important features of the protein:
Signal peptide:
1-29

Transmembrane domain.
None

N-glycosylation site.
115-119
150-154 cAMP- and cGMP-dependent protein kinase phosphorylation site.
65-69

N-myristoylation site.
246-252
253-259
308-314

Amidation site.
101-105

FIGURE 57

```
GGATGGGCGAGCAGTCTGAATGCCAGAATGGATAACCGTTTTGCTACAGCATTTGTAATTGC
TTGTGTGCTTAGCCTCATTTCCACCATCTACATGGCAGCCTCCATTGGCACAGACTTCTGGT
ATGAATATCGAAGTCCAGTTCAAGAAAATTCCAGTGATTTGAATAAAAGCATCTGGGATGAA
TTCATTAGTGATGAGGCAGATGAAAGACTTATAATGATGCACTTTTTCGATACAATGGCAC
AGTGGGATTGTGGAGACGGTGTATCACCATACCCAAAAACATGCATTGGTATAGCCCACCAG
AAAGGACAGAGTCATTTGATGTGGTCACAAAATGTGTGAGTTTCACACTAACTGAGCAGTTC
ATGGAGAAATTTGTTGATCCCGGAAACCACAATAGCGGGATTGATCTCCTTAGGACCTATCT
TTGGCGTTGCCAGTTCCTTTTACCTTTTGTGAGTTTAGGTTTGATGTGCTTTGGGGCTTTGA
TCGGACTTTGTGCTTGCATTTGCCGAAGCTTATATCCCACCATTGCCACGGGCATTCTCCAT
CTCCTTGCAGATACCATGCTGTGAAGTCCAGGCCACATGGAGGTGTCCTGTGTAGATGCTCC
AGCTGAAATCCCAAGCTAAGCTCCCAACTGACAGCCAACATCATTTCCAGCCATGTGTGGA
GCCATCCTGGATGTCCAGCCTTAACAAGCCTTCAGAGGACTTCAGCCACAGCTATTATCTTA
CTACATCCTTGTGAGACTCTAATAAAGAACCAACTAGCTGAGCCCAATCAACCTATGGAACTG
ATAGAAATAAAATGAATTGTTGTTTTGTGCCGTT
```

FIGURE 58

```
></usr/seqdb2/sst/DNA/Dnaseqs.min/ss.DNA102880
><subunit 1 of 1, 184 aa, 1 stop
><MW: 21052, pI: 5.01, NX(S/T): 3
MDNRFATAFVIACVLSLISTIYMAASIGTDFWYEYRSPVQENSSDLNKSIWDEFISDEAD
EKTYNDALFRYNGTVGLWRRCITIPKNMHWYSPPERTESFDVVTKCVSFTLTEQFMEKFV
DPGNHNSGIDLLRTYLWRCQFLLPFVSLGLMCFGALIGLCACICRSLYPTIATGILHLLA
DTML
```

Important features of the protein:
Signal peptide:
Amino acids          1-20

Transmembrane domain:
Amino acids          142-163

N-glycosylation sites:
Amino acids          42-46;47-51;72-76;

N-myristoylation sites:
Amino acids          123-129;154-160;158-164

Prokaryotic membrane lipoprotein lipid attachment site:
Amino acids          152-163

FIGURE 59

```
GCGTGGACACCACCTCAGCCCACTGAGCAGGAGTCACAGCACGAAGACCAAGCGCAAAGCGA
CCCCTGCCCTCCATCCTGACTGCTCCTCCTAAGAGAGATGGCACCGGCCAGAGCAGGATTCT
GCCCCCTTCTGCTGCTTCTGCTGCTGGGGCTGTGGGTGGCAGAGATCCCAGTCAGTGCCAAG
CCCAAGGGCATGACCTCATCACAGTGGTTTAAAATTCAGCACATGCAGCCCAGCCCTCAAGC
ATGCAACTCAGCCATGAAAAACATTAACAAGCACACAAAACGGTGCAAAGACCTCAACACCT
TCCTGCACGAGCCTTTCTCCAGTGTGGCCGCCACCTGCCAGACCCCCAAAATAGCCTGCAAG
AATGGCGATAAAAACTGCCACCAGAGCCACGGGCCCGTGTCCCTGACCATGTGTAAGCTCAC
CTCAGGGAAGTATCCGAACTGCAGGTACAAAGAGAAGCGACAGAACAAGTCTTACGTAGTGG
CCTGTAAGCCTCCCCAGAAAAAGGACTCTCAGCAATTCCACCTGGTTCCTGTACACTTGGAC
AGAGTCCTTTAGGTTTCCAGACTGGCTTGCTCTTTGGCTGACCTTCAATTCCCTCTCCAGGA
CTCCGCACCACTCCCCTACACCCAGAGCATTCTCTTCCCCTCATCTCTTGGGGCTGTTCCTG
GTTCAGCCTCTGCTGGGAGGCTGAAGCTGACACTCTGGTGAGCTGAGCTCTAGAGGGATGGC
TTTTCATCTTTTTGTTGCTGTTTTCCCAGATGCTTATCCCCAAGAAACAGCAAGCTCAGGTC
TGTGGGTTCCCTGGTCTATGCCATTGCACATGTCTCCCCTGCCCCCTGGCATTAGGGCAGCA
TGACAAGGAGAGGAAATAAATGGAAGGGGGCAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAA
AAAAA
```

FIGURE 60

```
></usr/seqdb2/sst/DNA/Dnaseqs.min/ss.DNA105782
><subunit 1 of 1, 156 aa, 1 stop
><MW: 17472, pI: 10.01, NX(S/T): 1
MAPARAGFCPLLLLLLLGLWVAEIPVSAKPKGMTSSQWFKIQHMQPSPQACNSAMKNINK
HTKRCKDLNTFLHEPFSSVAATCQTPKIACKNGDKNCHQSHGPVSLTMCKLTSGKYPNCR
YKEKRQNKSYVVACKPPQKKDSQQFHLVPVHLDRVL
```

Important features of the protein:
Signal peptide:
Amino acids                1-22

N-glycosylation site:
Amino acids                127-131 cAMP- and cGMP-dependent protein kinase phosphorylation site:
Amino acids                139-143

N-myristoylation sites:
Amino acids                18-24;32-38

Pancreatic ribonuclease family signature:
Amino acids                65-72

Pancreatic ribonuclease family proteins:
Amino acids                49-93

FIGURE 61

CGGGTCATGCGCCGCCGCCTGTGGCTGGGCCTGGCCTGGCTGCTGCTGGCGCGGGCGCCGGA
CGCCGCGGGAACCCCGAGCGCGTCGCGGGGACCGCGCAGCTACCCGCACCTGGAGGGCGACGTG
CGCTGGCGGCGCCTCTTCTCCTCCACTCACTTCTTCCTGCGCGTGGATCCCGGCGGCCGCGT
GCAGGGCACCCGCTGGCGCCACGGCCAGGACAGCATCCTGGAGATCCGCTCTGTACACGTGG
GCGTCGTGGTCATCAAAGCAGTGTCCTCAGGCTTCTACGTGGCCATGAACCGCCGGGGCCGC
CTCTACGGGTCGCGACTCTACACCGTGGACTGCAGGTTCCGGGAGCGCATCGAAGAGAACGG
CCACAACACCTACGCCTCACAGCGCTGGCGCCGCCGCGGCCAGCCCATGTTCCTGGCGCTGG
ACAGGAGGGGGGGCCCCGGCCAGGCGGCCGGACGCGGCGGTACCACCTGTCCGCCCACTTC
CTGCCCGTCCTGGTCTCCTGAG

FIGURE 62

```
></usr/seqdb2/sst/DNA/Dnaseqs.min/ss.DNA108912
><subunit 1 of 1, 170 aa, 1 stop
><MW: 19663, pI: 11.81, NX(S/T): 0
MRRRLWLGLAWLLLARAPDAAGTPSASRGPRSYPHLEGDVRWRRLFSSTHFFLRVDPGGR
VQGTRWRHGQDSILEIRSVHVGVVVIKAVSSGFYVAMNRRGRLYGSRLYTVDCRFRERIE
ENGHNTYASQRWRRRGQPMFLALDRRGGPRPGGRTRRYHLSAHFLPVLVS
```

Important features of the protein:
Signal peptide:
Amino acids                 1-17

N-myristoylation site:
Amino acids                 22-28

HBGF/FGF family proteins:
Amino acids                 74-125;139-166

FIGURE 63

ATCCCTCGACCTCGACCCACGCGTCCGCTGGAAGGTGGCGTGCCCTCCTCTGGCTGGTACCA
TGCAGCTCCCACTGGCCCTGTGTCTCGTCTGCCTGCTGGTACACACAGCCTTCCGTGTAGTG
GAGGGCCAGGGGTGGCAGGCGTTCAAGAATGATGCCACGGAAATCATCCCCGAGCTCGGAGA
GTACCCCGAGCCTCCACCGGAGCTGGAGAACAACAAGACCATGAACCGGGCGGAGAACGGAG
GGCGGCCTCCCCACCACCCCTTTGAGACCAAAGACGTGTCCGAGTACAGCTGCCGCGAGCTG
CACTTCACCCGCTACGTGACCGATGGGCCGTGCCGCAGCGCCAAGCCGGTCACCGAGCTGGT
GTGCTCCGGCCAGTGCGGCCCGGCGCGCCTGCTGCCCAACGCCATCGGCCGCGGCAAGTGGT
GGCGACCTAGTGGGCCCGACTTCCGCTGCATCCCCGACCGCTACCGCGCGCAGCGCGTGCAG
CTGCTGTGTCCCGGTGGTGAGGCGCCGCGCGCGCGCAAGGTGCGCCTGGTGGCCTCGTGCAA
GTGCAAGCGCCTCACCCGCTTCCACAACCAGTCGGAGCTCAAGGACTTCGGGACCGAGGCCG
CTCGGCCGCAGAAGGGCCGGAAGCCGCGGCCCCGCGCCCGGAGCGCCAAAGCCAACCAGGCC
GAGCTGGAGAACGCCTACTAGAGCCCGCCGCGCCCCTCCCCACCGGCGGGCGCCCCGGCCC
TGAACCCGCGCCCCACATTTCTGTCCTCTGCGCGTGGTTTGATTGTTTATATTTCATTGTAA
ATGCCTGCAACCCAGGGCAGGGGCTGAGACCTTCCAGGCCCTGAGGAATCCCGGGCGCCGG
CAAGGCCCCCCTCAGCCCGCCAGCTGAGGGGTCCCACGGGGCAGGGGAGGGAATTGAGAGTC
ACAGACACTGAGCCACGCAGCCCCGCCTCTGGGGCCGCCTACCTTTGCTGGTCCCACTTCAG
AGGAGGCAGAAATGGAAGCATTTTCACCGCCCTGGGGTTTTAAGGGAGCGGTGTGGGAGTGG
GAAAGTCCAGGGACTGGTTAAGAAAGTTGGATAAGATTCCCCCTTGCACCTCGCTGCCCATC
AGAAAGCCTGAGGCGTGCCCAGAGCACAAGACTGGGGGCAACTGTAGATGTGGTTTCTAGTCC
TGGCTCTGCCACTAACTTCCTGTGTAACCTTGAACTACACAATTCTCCTTCGGGACCTCAAT
TTCCACTTTGTAAAATGAGGGTGGAGGTGGGAATAGGATCTCGAGGAGACTATTGGCATATG
ATTCCAAGGACTCCAGTGCCTTTTGAATGGGCAGAGGTGAGAGAGAGAGAGAGAAAGAGAGA
GAATGAATGCAGTTGCATTGATTCAGTGCCAAGGTCACTTCCAGAATTCAGAGTTGTGATGC
TCTCTTCTGACAGCCAAAGATGAAAACAAACAGAAAAAAAAAGTAAAGAGTCTATTTATG
GCTGACATATTTACGGCTGACAAACTCCTGGAAGAAGCTATGCTGCTTCCCAGCCTGGCTTC
CCCGGATGTTTGGCTACCTCCACCCCTCCATCTCAAAGAAATAACATCATCCATTGGGGTAG
AAAAGGAGAGGGTCCGAGGGTGGTGGGAGGGATAGAAATCACATCCGCCCCAACTTCCCAAA
GAGCAGCATCCCTCCCCCGACCCATAGCCATGTTTTAAAGTCACCTTCCGAAGAGAAGTGAA
AGGTTCAAGGACACTGGCCTTGCAGGCCCGAGGGAGCAGCCATCACAAACTCACAGACCAGC
ACATCCCTTTTGAGACACCGCCTTCTGCCCACCACTCACGGACACATTTCTGCCTAGAAAAC
AGCTTCTTACTGCTCTTACATGTGATGGCATATCTTACACTAAAGAATATTATTGGGGGAA
AAACTACAAGTGCTGTACATATGCTGAGAAACTGCAGAGCATAATAGCTGCCACCCAAAAAT
CTTTTTGAAAATCATTTCCAGACAACCTCTTACTTTCTGTGTAGTTTTAATTGTTAAAAAA
AAAAAGTTTTAAACAGAAGCACATGACATATGAAAGCCTGCAGGACTGGTCGTTTTTTTGGC
AATTCTTCCACGTGGGACTTGTCCACAAGAATGAAAGTAGTGGTTTTAAAGAGTTAAGTTA
CATATTTATTTTCTCACTTAAGTTATTTATGCAAAAGTTTTTCTTGTAGAATGACAATGT
TAATATTGCTTTATGAATTAACAGTCTGTTCTTCCAGAGTCCAGAGACATTGTTAATAAAGA
CAATGAATCATGAAAAAAAAAAAAAAAAAAAAA

FIGURE 64

```
</usr/seqdb2/sst/DNA/Dnaseqs.min/ss.DNA115253
<subunit 1 of 1, 213 aa, 1 stop
<MW: 24031, pI: 9.59, NX(S/T): 2
MQLPLALCLVCLLVHTAFRVVEGQGWQAFKNDATEIIPELGEYPEPPPELENNKTMNRAE
NGGRPPHHPFETKDVSEYSCRELHFTRYVTDGPCRSAKPVTELVCSGQCGPARLLPNAIG
RGKWWRPSGPDFRCIPDRYRAQRVQLLCPGGEAPRARKVRLVASCKCKRLTRFHNQSELK
DFGTEAARPQKGRKPRPRARSAKANQAELENAY
```

Important features of the protein:
Signal peptide:
Amino acids                 1-16

N-glycosylation sites:
Amino acids                 53-57;175-179 cAMP- and cGMP-dependent protein kinase phosphorylation site:
Amino acids                 168-172

N-myristoylation site:
Amino acids                 183-189

Amidation site:
Amino acids                 191-195

FIGURE 65

CCCACTCGGCGGTTTGGCGGGAGGGAGGGGCTTTGCGCAGGCCCCGCTCCCGCCCCGCCTCC
ATGCGGCCCGCCCCGATTGCGCTGTGGCTGCGCCTGGTCTTGGCCCTGGCCCTTGTCCGCCC
CCGGGCTGTGGGGTGGGCCCCGGTCCGAGCCCCATCTATGTCAGCAGCTGGGCCGTCCAGG
TGTCCCAGGGTAACCGGGAGGTCGAGCGCCTGGCACGCAAATTCGGCTTCGTCAACCTGGGG
CCGATCTTCTCTGACGGGCAGTACTTTCACCTGCGGCACCGGGGCGTGGTCCAGCAGTCCCT
GACCCCGCACTGGGGCCACCGCCTGCACCTGAAGAAAAACCCCAAGGTGCAGTGGTTCCAGC
AGCAGACGCTGCAGCGGCGGGTGAAACGCTCTGTCGTGGTGCCCACGGACCCCTGGTTCTCC
AAGCAGTGGTACATGAACAGCGAGCCCAACCAGACCTGAGCATCCTGCAGGCCTGGAGTCA
GGGGCTGTCAGGCCAGGGCATCGTGGTCTCTGTGCTGGACGATGGCATCGAGAAGGACCACC
CGGACCTCTGGGCCAACTACGACCCCCTGGCCAGCTATGACTTCAATGACTACGACCCGGAC
CCCCAGCCCCGCTACACCCCCAGCAAAGAGAACCGGCACGGGACCCGCTGTGCTGGGGAGGT
GGCCGCGATGGCCAACAATGGCTTCTGTGGTGTGGGGGTCGCTTTCAACGCCCGAATCGGAG
GCGTACGGATGCTGGACGGTACCATCACCGATGTCATCGAGGCCCAGTCGCTGAGCCTGCAG
CCGCAGCACATCCACATTTACAGCGCCAGCTGGGGTCCCGAGGACGACGGCCGCACGGTGGA
CGGCCCCGGCATCCTCACCCGCGAGGCCTTCCGGCGTGGTGTGACCAAGGGCCGCGGCGGGC
TGGGCACGCTCTTCATCTGGGCCTCGGGCAACGGCGGCCTGCACTACGACAACTGCAACTGC
GACGGCTACACCAACAGCATCCACACGCTTTCCGTGGGCAGCACCACCCAGCAGGGCCGCGT
GCCCTGGTACAGCGAAGCCTGCGCCTCCACCCTCACCACCACCTACAGCAGCGGCGTGGCCA
CCGACCCCCAGATCGTCACCACGGACCTGCATCACGGGTGCACAGACCAGCACACGGGCACC
TCGGCCTCAGCCCCACTGGCGGCCGGCATGATCGCCCTAGCGCTGGAGGCCAACCCGTTCCT
GACGTGGAGAGACATGCAGCACCTGGTGGTCCGCGCGTCCAAGCCGGCGCACCTGCAGGCCG
AGGACTGGAGGACCAACGGCGTGGGCGCCAAGTGAGCCATCACTACGGATACGGGCTGCTG
GACGCCGGGCTGCTGGTGGACACCGCCCGCACCTGGCTGCCCACCCAGCCGCAGAGGAAGTG
CGCCGTCCGGGTCCAGAGCCGCCCCACCCCCATCCTGCCGCTGATCTACATCAGGGAAAACG
TATCGGCCTGCGCCGGCCTCCACAACTCCATCCGCTCGCTGGAGCACGTGCAGGCGCAGCTG
ACGCTGTCCTACAGCCGGCGCGGAGACCTGGAGATCTCGCTCACCAGCCCCATGGGCACGCG
CTCCACACTCGTGGCCATACGACCCTTGGACGTCAGCACTGAAGGCTACAACAACTGGGTCT
TCATGTCCACCCACTTCTGGGATGAGAACCCACAGGGCGTGTGGACCCTGGGCCTAGAGAAC
AAGGGCTACTATTTCAACACGGGGACGTTGTACCGCTACACGCTGCTGCTCTATGGGACGGC
CGAGGACATGACAGCGCGGCCTACAGGCCCCCAGGTGACCAGCAGCGCGTGTGTGCAGCGGGAC
ACAGAGGGGCTGTGCCAGGCGTGTGACGGCCCCGCCTACATCCTGGGACAGCTCTGCCTGGC
CTACTGCCCCCGCGGTTCTTCAACCACACAAGGCTGGTGACCGCTGGGCCTGGGCACACGG
CGGCGCCCGCGCTGAGGGTCTGCTCCAGCTGCCATGCCTCCTGCTACACCTGCCGCGGCGGC
TCCCCGAGGGACTGCACCTCCTGTCCCCCATCCTCCACGCTGGACCAGCAGCAGGGCTCCTG
CATGGGACCCACCACCCCCGACAGCCGCCCCGGCTTAGAGCTGCCGCCTGTCCCCACCACCG
CTGCCCAGCCTCGGCCATGGTGCTGAGCCTCCTGGCCGTGACCCTCGGAGGCCCCGTCCTCT
GCGGCATGTCCATGGACCTCCCACTATACGCCTGGCTCTCCGTGCCAGGGCCACCCCCACC
AAACCCCAGGTCTGGCTGCCAGCTGGAACCTGAAGTTGTCAGCTCAGAAAGCGACCTTGCCC
CCGCCTGGGTCCCTGACAGGCACTGCTGCCATGCTGCCTCCCAGGCTGGCCCCAGAGGAGC
GAGCACCAGCACCCGACGCCTGGCCTGCCAGGGATGGCCCCGTGGAACCCCGAAGCCTGGC
GGGAGAGAGAGAGAGAGAAGTCTCCTCTGCATTTTGGGTTTGGGCAGGAGTGGGCTGGGGGG
AGAGGCTGGAGCACCCCAAAAGCCAGGGGAAAGTGGAGGGAGAGAAACGTGACACTGTCCGT
CTCGGGCACCGCGTCCAACCTCAGAGTTTGCAAATAAAGGTTGCTTAGAAGGTGAA

FIGURE 66

```
></usr/seqdb2/sst/DNA/Dnaseqs.min/ss.DNA119302
><subunit 1 of 1, 755 aa, 1 stop
><MW: 82785, pI: 8.71, NX(S/T): 2
MRPAPIALWLRLVLALALVRPRAVGWAPVRAPIYVSSWAVQVSQGNREVERLARKFGFVN
LGPIFSDGQYFHLRHRGVVQQSLTPHWGHRLHLKKNPKVQWFQQQTLQRRVKRSVVVPTD
PWFSKQWYMNSEAQPDLSILQAWSQGLSGQGIVVSVLDDGIEKDHPDLWANYDPLASYDF
NDYDPDPQPRYTPSKENRHGTRCAGEVAAMANNGFCGVGVAFNARIGGVRMLDGTITDVI
EAQSLSLQPQHIHIYSASWGPEDDGRTVDGPGILTREAFRRGVTKGRGGLGTLFIWASGN
GGLHYDNCNCDGYTNSIHTLSVGSTTQQGRVPWYSEACASTLTTTYSSGVATDPQIVTTD
LHHGCTDQHTGTSASAPLAAGMIALALEANPFLTWRDMQHLVVRASKPAHLQAEDWRTNG
VGRQVSHHYGYGLLDAGLLVDTARTWLPTQPQRKCAVRVQSRPTPILPLIYIRENVSACA
GLHNSIRSLEHVQAQLTLSYSRRGDLEISLTSPMGTRSTLVAIRPLDVSTEGYNNWVFMS
THFWDENPQGVWTLGLENKGYYFNTGTLYRYTLLLYGTAEDMTARPTGPQVTSSACVQRD
TEGLCQACDGPAYILGQLCLAYCPPRFFNHTRLVTAGPGHTAAPALRVCSSCHASCYTCR
GGSPRDCTSCPPSSTLDQQQGSCMGPTTPDSRPRLRAAACPHHRCPASAMVLSLLAVTLG
GPVLCGMSMDLPLYAWLSRARATPTKPQVWLPAGT
```

Important features of the protein:
Signal peptide:
Amino acids                    1-21
Transmembrane domain:
Amino acids                    706-730

N-glycosylation sites:
Amino acids                    475-479;629-633

Glycosaminoglycan attachment sites:
Amino acids                    148-152;298-302

N-myristoylation sites:
Amino acids                    151-157;200-206;217-223;219-225;
                               282-288;288-294;371-377;432-438;
                               481-487;515-521;603-609

Prokaryotic membrane lipoprotein lipid attachment site:
Amino acids                    586-597

Cell attachment sequence:
Amino acids                    503-506

Serine proteases, subtilase family, aspartic acid active site:
Amino acids                    154-166

Serine proteases, subtilase family, histidine active site:
Amino acids                    199-210

Serine proteases, subtilase family, serine active site:
Amino acids                    371-382

Cytochrome c family heme-binding site signature:
Amino acids                    649-655

FIGURE 67

ATGAGGAAGCTCCAGGGCAGGATGGTTTACCTGCCTGGACAGCAAGATGATGGCTACACTAG
CCCCCATTCTCTGGGCGCCTGGATTTGCCCACCAGATCTCCTCACCTCTTGCCCTTCACCTC
CTGCTGTACCTACAAGGTCTCCCCGATTCTCATCTGCCCATAATCATGGACACAGCCCCAGG
ATGTGCAGGACTCTCAGGGACCATCTGGAGTTCCAGCTGGAATCTGGGCCTGGTGGAGTGGG
AGTGGGGCAGGGGCCTGCATTGGGCTGACTTAGAGAGCACAGTTATTCCATCCATATGGAAA
TAAACATTTTGGATTCCTGATC

FIGURE 68

></usr/seqdb2/sst/DNA/Dnaseqs.min/ss.DNA119536
><subunit 1 of 1, 88 aa, 1 stop
><MW: 9645, pI: 5.45, NX(S/T): 0
MMATLAPILWAPGFAHQISSPLALHLLLYLQGLPDSHLPIIMDTAPGCAGLSGTIWSSSW
NLGLVEWEWGRGLHWADLESTVIPSIWK

Signal sequence:
Amino acids              1-15

N-myristoylation sites:
Amino acids              32-38;50-56;53-59;72-78

FIGURE 69

```
TTTGCAGTGGGGTCCTCCTCTGGCCTCCTGCCCCTCCTGCTGCTGCTGCTGCTTCCATTGCT
GGCAGCCCAGGGTGGGGGTGGCCTGCAGGCAGCGCTGCTGGCCCTTGAGGTGGGGCTGGTGG
GTCTGGGGGCCTCCTACCTGCTCCTTTGTACAGCCCTGCACCTGCCCTCCAGTCTTTTCCTA
CTCCTGGCCCAGGGTACCGCACTGGGGGCCGTCCTGGGCCTGAGCTGGCGCCGAGGCCTCAT
GGGTGTTCCCCTGGGCCTTGGAGCTGCCTGGCTCTTAGCTTGGCCAGGCCTAGCTCTACCTC
TGGTGGCTATGGCAGCGGGGGGCAGATGGGTGCGGCAGCAGGGCCCCGGGTGCGCGGGGC
ATATCTCGACTCTGGTTGCGGGTTCTGCTGCGCCTGTCACCCATGGCCTTCCGGGCCCTGCA
GGGCTGTGGGGCTGTGGGGGACCGGGGTCTGTTTGCACTGTACCCCAAAACCAACAAGGATG
GCTTCCGCAGCCGCCTGCCCGTCCTGGGCCCCGGCGGCGTAATCCCCGCACCACCCAACAC
CCATTAGCTCTGTTGGCAAGGGTCTGGGTCCTGTGCAAGGGCTGGAACTGGCGTCTGGCACG
GGCCAGCCAGGGTTTAGCATCCCACTTGCCCCGTGGGCCATCCACACACTGGCCAGCTGGG
GCCTGCTTCGGGGTGAACGGCCCACCCGAATCCCCCGGCTACTACCACGCAGCCAGCGCCAG
CTAGGGCCCCCTGCCTCCCGCCAGCCACTGCCAGGGACTCTAGCCGGGCGGAGGTCACGCAC
CCGCCAGTCCCGGGCCCTGCCCCCTGGAGGTAGCTGACTCCAGCCCTTCCAGCCCAAATCT
AGAGCATTGAGCACTTTATCTCCCACGACTCAGTGAAGTTTCTCCAGTCCCTAGTCCTCTCT
TTTCACCCACCTTCCTCAGTTTGCTCACTTACCCCAGGCCCAGCCCTTCGGACCTCTAGACA
GGCAGCCTCCTCAGCTGTGGAGTCCAGCAGTCACTCTGTGTTCTCCTGGCGCTCCTCCCCTA
AGTTATTGCTGTTCGCCCGCTGTGTGTGCTCATCCTCACCCTCATTGACTCAGGCCTGGGGC
CAGGGGTGGTGGAGGGTGGGAAGAGTCATGTTTTTTTTCTCCTCTTTGATTTTGTTTTTCTG
TCTCCCTTCCAACCTGTCCCCTTCCCCCCACCAAAAAAAXXXXXXXXXXXXXXXXXXXXXXX
XXXXXXXXXXXXAAAAAAAAAAAAAAAAAAAAAAAAAAAAAAAAAAAAAAAAAAAAAAAAA
```

FIGURE 70

></usr/seqdb2/sst/DNA/Dnaseqs.min/ss.DNA119542
><subunit 1 of 1, 197 aa, 1 stop
><MW: 21992, pI: 12.18, NX(S/T): 0
MGVPLGLGAAWLLAWPGLALPLVAMAAGGRWVRQQGPRVRRGISRLWLRVLLRLSPMAFR
ALQGCGAVGDRGLFALYPKTNKDGFRSRLPVPGPRRRNPRTTQHPLALLARVWVLCKGWN
WRLARASQGLASHLPPWAIHTLASWGLLRGERPTRIPRLLPRSQRQLGPPASRQPLPGTL
AGRRSRTRQSRALPPWR

Important features of the protein:
Signal peptide:
Amino acids                    1-21

N-myristoylation sites:
Amino acids                    2-8;6-12;146-152;178-184

Amidation site:
Amino acids                    181-185

FIGURE 71

```
GTTTGGGGGTTGTTTGGGATTAGTGAAGCTACTGCCTTTGCCGCCAGCGCAGCCTCAGAGTT
TGATTATTTGCAATGTCAGGCTTTGAAAACTTAAACACGGATTTCTACCAGACAAGTTACAG
CATCGATGATCAGTCACAGCAGTCCTATGATTATGGAGGAAGTGGAGGACCCTATAGCAAAC
AGTATGCTGGCTATGACTATTCGCAGCAAGGCAGATTTGTCCCTCCAGACATGATGCAGCCA
CAACAGCCATACACCGGGCAGATTTACCAGCCAACTCAGGCATATACTCCAGCTTCACCTCA
GCCTTTCTATGGAAACAACTTTGAGGATGAGCCACCTTTATTAGAAGAGTTAGGTATCAATTTT
GACCACATCTGGCAAAAAACACTAACAGTATTACATCCGTTAAAAGTAGCAGATGGCAGCAT
CATGAATGAAACTGATTTGGCAGGTCCAATGGTTTTTTGCCTTGCTTTTGGAGCCACATTGC
TACTGGCTGGCAAAATCCAGTTTGGCTATGTATACGGGATCAGTGCAATTGGATGTCTAGGA
ATGTTTTGTTTATTAAACTTAATGAGTATGACAGGTGTTTCATTTGGTTGTGTGGCAAGTGT
CCTTGGATATTGTCTTCTGCCCATGATCCTACTTTCCAGCTTTGCAGTGATATTTTCTTTGC
AAGGAATGGTAGGAATCATTCTCACTGCTGGGATTATTGGATGGTGTAGTTTTTCTGCTTCC
AAAATATTTATTTCTGCATTAGCCATGGAAGGACAGCAACTTTTAGTAGCATATCCTTGCGC
TTTGTTATATGGAGTCTTTGCCCTGATTTCCGTCTTTTGAAAATTTATCTGGGATGTGGACA
TCAGTGGGCCAGATGTACAAAAAGGACCTTGAACTCTTAAATTGGACCAGCAAACTGCTGCA
GCGCAACTCTCATGCAGATTTACATTTGACTGTTGGAGCAATGAAAGTAAACGTGTATCTCT
TGTTCATTTTATAGAACTTTTGCATACTATATTGGATTTACCTGCGGTGTGACTAGCTTTA
AATGTTTGTGTTTATACAGATAAGAAATGCTATTTCTTTCTGGTTCCTGCAGCCATTGAAAA
ACCTTTTTCCTTGCAAATTATAATGTTTTTGATAGATTTTATCAACTGTGGGAAACCAAAC
ACAAAGCTGATAACCTTTCTTAAAAACGACCCAGTCACAGTAAAGAAGACACAAGACGGCCG
GGCGTGGTAGCTCACGCCTGTAATCCCAGCACTTTGGGAGGCCGAGGCGGGCGGATCACAAG
GGCAGGAGATCGAGACCATCCTGGTTAACACGGTGAAACCCCGACTCTACTAAAACTACAAA
AAAAATTAGCTGGGCGTGGTGGCGGGCGCCTGTAGTCCCAGCTACTCAGGAGGCTGAGGCAG
GAGAAGTGTGAACCCAGGAGGCGGAGCTTGCAGTGAGCCGAGATCACACCACTGCACTCCAT
CCAGCCTGGGTGACAGGGTGAGACTCTGTCTCAAAAAAAAAAAAAAAAGGAGACACAAGACT
TACTGCAAAAATATTTTTCCAAGGATTTAGGAAAGAAAAATTGCCTTGTATTCTCAAGTCAG
GTAACTCAAAGCAAAAAGTGATCCAAATGTAGAGTATGAGTTTGCACTCCAAAAATTTGAC
ATTACTGTAAATTATCTCATGGAATTTTTGCTAAAATTCAGAGATACGGGAAGTTCACAATC
TACCTCATTGTAGACATGAAATGCGAACACTTACTTACATATTAATGTTAACTCAACCTTAG
GGACCTGGAATGGTTGCATTAATGCTATAATCGTTGGATCGCCACATTTCCCAAAAATAATA
AAAAATCACTAACCTTTTTAAGGAAAATATTTAAAGTTTTACAAAATTCAATATTGCAAT
TATCAATGTAAAGTACATTTGAATGCTTATTAAAACTTTCCCAATTAATTTT
```

FIGURE 72

```
></usr/seqdb2/sst/DNA/Dnaseqs.min/ss.DNA143498
><subunit 1 of 1, 257 aa, 1 stop
><MW: 27989, pI: 4.16, NX(S/T): 1
MSGFENLNTDFYQTSYSIDDQSQQSYDYGGSGGPYSKQYAGYDYSQQGRFVPPDMMQPQQ
PYTGQIYQPTQAYTPASPQPFYGNNFEDEPPLLEELGINFDHIWQKTLTVLHPLKVADGS
IMNETDLAGPMVFCLAFGATLLLAGKIQFGYVYGISAIGCLGMFCLLNLMSMTGVSFGCV
ASVLGYCLLPMILLSSFAVIFSLQGMVGIILTAGIIGWCSFSASKIFISALAMEGQQLLV
AYPCALLYGVFALISVF
```

Transmembrane domain:
Amino acids          129-145;184-203

N-glycosylation sites:
Amino acids          123-127

N-myristoylation sites:
Amino acids          32-38;119-125;174-180;178-184;208-214

Prokaryotic membrane lipoprotein lipid attachment site:
Amino acids          150-161;169-180

FIGURE 73

```
ACACTGGCCAAAACGCGGCTCGCCCTCGGCTGCGCTCGGCTCCCGCGGGCGCTCGGCCCCGA
GCCCCTCCTCCCCCTACCCGCCGGCCGGACAGGGAGGAGCCAATGGCTGGGCCTGCCATCCA
CACCGCTCCCATGCTGTTCCTCGTCCTCCTGCTGCCCCAGCTGAGCCTGGCAGGCGCCCTTG
CACCTGGGACCCCTGCCCGGAACCTCCCTGAGAATCACATTGACCTCCCAGGCCCAGCGCTG
TGGACGCCTCAGGCCAGCCACCACCGCCGGCGGGGCCCGGGCAAGAAGGAGTGGGGCCCAGG
CCTGCCCAGCCAGGCCCAGGATGGGGCTGTGGTCACCGCCACCAGGCAGGCCTCCAGGCTGC
CAGAGGCTGAGGGGCTGCTGCCTGAGCAGAGTCCTGCAGGCCTGCTGCAGGACAAGGACCTG
CTCCTGGGACTGGCATTGCCCTACCCCGAGAAGGAGAACAGACCTCCAGGTTGGGAGAGGAC
CAGGAAACGCAGCAGGGAGCACAAGAGACGCAGGGACAGGTTGAGGCTGCACCAAGGCCGAG
CCTTGGTCCGAGGTCCCAGCTCCCTGATGAAGAAGGCAGAGCTCTCCGAAGCCCAGGTGCTG
GATGCAGCCATGGAGGAATCCTCCACCAGCCTGGCGCCCACCATGTTCTTTCTCACCACCTT
TGAGGCAGCACCTGCCACAGAAGAGTCCCTGATCCTGCCCGTCACCTCCCTGCGGCCCCAGC
AGGCACAGCCCAGGTCTGACGGGGAGGTGATGCCCACGCTGGACATGGCCTTGTTCGACTGG
ACCGATTATGAAGACTTAAAACCTGATGGTTGGCCCTCTGCAAAGAAGAAAGAGAAACACCG
CGGTAAACTCTCCAGTGATGGTAACGAAACATCACCAGCCGAAGGGGAACCATGCGACCATC
ACCAAGACTGCCTGCCAGGGACTTGCTGCGACCTGCGGGAGCATCTCTGCACACCCCACAAC
CGAGGCCTCAACAACAAATGCTTCGATGACTGCATGTGTGTGGAAGGGCTGCGCTGCTATGC
CAAATTCCACCGGAACCGCAGGGTTACACGGAGGAAAGGGCGCTGTGTGGAGCCCGAGACGG
CCAACGGCGACCAGGGATCCTTCATCAACGTCTAGCGGCCCCGCGGGACTGGGGACTGAGCC
CAGGAGGTTTGCACAAGCCGGGCGATTTGTTTGTAACTAGCAGTGGGAGATCAAGTTGGGGA
ACAGATGGCTGAGGCTGCAGACTCAGGCCCAGGACACTCAACCCC
```

FIGURE 74

```
></usr/seqdb2/sst/DNA/Dnaseqs.min/ss.DNA145583
><subunit 1 of 1, 348 aa, 1 stop
><MW: 38536, pI: 8.24, NX(S/T): 1
MAGPAIHTAPMLFLVLLLPQLSLAGALAPGTPARNLPENHIDLPGPALWTPQASHHRRRG
PGKKEWGPGLPSQAQDGAVVTATRQASRLPEAEGLLPEQSPAGLLQDKDLLLGLALPYPE
KENRPPGWERTRKRSREHKRRRDRLRLHQGRALVRGPSSLMKKAELSEAQVLDAAMEESS
TSLAPTMFFLTTFEAAPATEESLILPVTSLRPQQAQPRSDGEVMPTLDMALFDWTDYEDL
KPDGWPSAKKKEKHRGKLSSDGNETSPAEGEPCDHHQDCLPGTCCDLREHLCTPHNRGLN
NKCFDDCMCVEGLRCYAKFHRNRRVTRRKGRCVEPETANGDQGSFINV
```

Important features of the protein:
Signal peptide:
Amino acids            1-24

N-glycosylation site:
Amino acids            263-267 cAMP- and cGMP-dependent protein kinase phosphorylation site:
Amino acids            132-136;323-327

N-myristoylation sites:
Amino acids            77-83;343-349

Amidation site:
Amino acids            61-65

FIGURE 75

CAGAAGGGCAAAAACATTGACTGCCTCAAGGTCTCAAGCACCAGTCTTCACCGCGGAAAGCA
TGTTGTGGCTGTTCCAATCGCTCCTGTTTGTCTTCTGCTTTGGCCCAGGGAATGTAGTTTCA
CAAAGCAGCTTAACCCCATTGATGGTGAACGGGATTCTGGGGGAGTCAGTAACTCTTCCCCT
GGAGTTTCCTGCAGGAGAGAAGGTCAACTTCATCACTTGGCTTTTCAATGAAACATCTCTTG
CCTTCATAGTACCCCATGAAACCAAAAGTCCAGAAATCCACGTGACTAATCCGAAACAGGGA
AAGCGACTGAACTTCACCCAGTCCTACTCCCTGCAACTCAGCAACCTGAAGATGGAAGACAC
AGGCTCTTACAGAGCCCAGATATCCACAAAGACCTCTGCAAAGCTGTCCAGTTACACTCTGA
GGATATTAAGACAACTGAGGAACATACAAGTTACCAATCACAGTCAGCTATTTCAGAATATG
ACCTGTGAGCTCCATCTGACTTGCTCTGTGGAGGATGCAGATGACAATGTCTCATTCAGATG
GGAGGCCTTGGGAAACACACTTTCAAGTCAGCCAAACCTCACTGTCTCCTGGGACCCCAGGA
TTTCCAGTGAACAGGACTACACCTGCATAGCAGAGAATGCTGTCAGTAATTTATCCTTCTCT
GTCTCTGCCCAGAAGCTTTGCGAAGATGTTAAAATTCAATATACAGATACCAAAATGATTCT
GTTTATGGTTTCTGGGATATGCATAGTCTTCGGTTTCATCATACTGCTGTTACTTGTTTTGA
GGAAAAGAAGAGATTCCCTATCTTTGTCTACTCAGCGAACACAGGGCCCCGCAGAGTCCGCA
AGGAACCTAGAGTATGTTTCAGTGTCTCCAACGAACAACACTGTGTATGCTTCAGTCACTCA
TTCAAACAGGGAAACAGAAATCTGGACACCTAGAGAAATGATACTATCACAATTTACTCCA
CAATTAATCATTCCAAAGAGAGTAAACCCACTTTTTCCAGGGCAACTGCCCTTGACAATGTC
GTGTAAGTTGCTGAAAGGCCTCAGAGGAATTCGGGAATGACACGTCTTCTGATCCATGAGA
CAGAACAAAGAACAGGAAGCTTGGTTCCTGTTGTTCCTGGCAACAGAATTTGAATATCTAGG
ATAGGATGATCACCTCCAGTCCTTCGGACTTAAACCTGCCTACCTGAGTCAAACACCTAAGG
ATAACATCATTTCCAGCATGTGGTTCAAATAATATTTTCCAATCCACTTCAGGCCAAAACAT
GCTAAAGATAACACACCAGCACATTGACTCTCTCTTTGATAACTAAGCAAATGGAATTATGG
TTGACAGAGAGTTTATGATCCAGAAGACAACCACTTCTCTCCTTTTAGAAAGCAGCAGGATT
GACTTATTGAGAAATAATGCAGTGTGTTGGTTACATGTGTAGTCTCTGGAGTTGGATGGGCC
CATCCTGATACAAGTTGAGCATCCCTTGTCTGAAATGCTTGGGATTAGAAATGTTTCAGATT
TCAATTTTTTTTCAGATTTTGGAATATTTGCATTATATTTAGCGGTTGAGTATCCAAATCCA
AAAATCCAAAATTCAAAATGCTCCAATAAGCATTTCCCTTGAGTTTCATTGATGTCGATGCA
GTGCTCAAAATCTCAGATTTTGGAGCAATTTGGATATTGGATTTTTGGATTTGGGATGCTCA
ACTTGTACAATGTTTATTAGACACATCTCCTGGGACATACTGCCTAACCTTTTGGAGCCTTA
GTCTCCCAGACTGAAAAAGGAAGAGGATGGTATTACATCAGCTCCATTGTTTGAGCCAAGAA
TCTAAGTC

FIGURE 76

```
></usr/seqdb2/sst/DNA/Dnaseqs.min/ss.DNA161000
><subunit 1 of 1, 332 aa, 1 stop
><MW: 37345, pI: 6.72, NX(S/T): 10
MLWLFQSLLFVFCFGPGNVVSQSSLTPLMVNGILGESVTLPLEFPAGEKVNFITWLFNET
SLAFIVPHETKSPEIHVTNPKQGKRLNFTQSYSLQLSNLKMEDTGSYRAQISTKTSAKLS
SYTLRILRQLRNIQVTNHSQLFQNMTCELHLTCSVEDADDNVSFRWEALGNTLSSQPNLT
VSWDPRISSEQDYTCIAENAVSNLSFSVSAQKLCEDVKIQYTDTKMILFMVSGICIVFGF
IILLLLVLRKRRDSLSLSTQRTQGPAESARNLEYVSVSPTNNTVYASVTHSNRETEIWTP
RENDTITIYSTINHSKESKPTFSRATALDNVV
```

Important features of the protein:
Signal peptide:
Amino acids                     1-13

Transmembrane domain:
Amino acids                     228-247

N-glycosylation sites:
Amino acids                     58-62;87-91;137-141;144-148;161-165;
                                178-182;203-207;281-285;303-307;
                                313-317 cAMP- and cGMP-dependent protein kinase phosphorylation site:
Amino acids                     251-255

Tyrosine kinase phosphorylation sites:
Amino acids                     100-108;186-194

N-myristoylation sites:
Amino acids                     17-23;105-111;170-176

Amidation site:
Amino acids                     82-86

Immunoglobulin domain:
Amino acids                     35-111

FIGURE 77

GATCCCTCGACCTCGACCCACGCGTCCGCTCTTTAATGCTTTCTTTTTAAGAGATCACCTTC
TGACTTCTCACAGAAGAGGTTAACTATTACCTGTGGGAAGTCAGAAGGTGATCTCTTTAATG
CTTTCTTTTTAAGAATTTTTCAAATTGAGACTAATTGCAGAGGTTCCAGTTGACCAGCATTC
ATAGGAATGAAGACAAACACAGAGATGGTGTGTCTAAGAAACTTCAAAAGGTGTAGACCTCC
TGACTGAAGCATATTGGATTTATTTAATTTTTTTCACTGTATTTCTGTCCTCCTACAAGGGA
AAGTCATGATTACACTAACTGAGCTAAAATGCTTAGCAGATGCCCAGTCATCTTATCACATC
TTAAAACCATGGTGGGACGTCTTCTGGTATTACATCACACTGATCATGCTGCTGGTGGCCGTG
CTGGCCGGAGCTCTCCAGCTGACGCAGAGCAGGGTTCTGTGCTGTCTTCCATGCAAAGTGGA
ATTTGACAATCACTGTGCCGTGCCTTGGGACATCCTGAAAGCCAGCATGAACACATCCTCTA
ATCCTGGGACACCGCTTCCGCTCCCCCTCCGAATTCAGAATGACCTCCACCGACAGCAGTAC
TCCTATATTGATGCCGTCTGTTACGAGAAACAGCTCCATTGGTTTGCAAAGTTTTTCCCCTA
TCTGGTGCTCTTGCACACGCTCATCTTTGCAGCCTGCAGCAACTTTTGGCTTCACTACCCCA
GTACCAGTTCCAGGCTCGAGCATTTTGTGGCCATCCTTCACAAGTGCTTCGATTCTCCATGG
ACCACCCGCGCCCTTTCAGAAACAGTGGCTGAGCAGTCAGTGAGGCCTCTGAAACTCTCCAA
GTCCAAGATTTTGCTTTCGTCCTCAGGGTGTTCAGCTGACATAGATTCCGGCAAACAGTCAT
TGCCCTACCCACAGCCAGGTTTGGAGTCAGCTGGTATAGAAAGCCCAACTTCCAGTGGCCTG
GACAAGAAGGAGGGTGAACAGGCCAAAGCCATCTTTGAAAAAGTGAAAAGATTCCGCATGCA
TGTGGAGCAGAAGGACATCATTTATAGAGTATATCTGAAACAGATAATAGTCAAAGTCATTT
TGTTTGTGCTCATCATAACTTATGTTCCATATTTTTTAACCCACATCACTCTTGAAATCGAC
TGTTCAGTTGATGTGCAGGCTTTTACAGGATATAAGCGCTACCAGTGTGTCTATTCCTTGGC
AGAAATCTTTAAGGTCCTGGCTTCATTTTATGTCATTTTGGTTATACTTTATGGTCTGACCT
CTTCCTACAGCCTGTGGTGGATGCTGAGGAGTTCCCTGAAGCAATATTCCTTTGAGGCGTTA
AGAGAAAAAGCAACTACAGTGACATCCCTGATGTCAAGAATGACTTTGCCTTCATCCTTCA
TCTGGCTGATCAGTATGATCCTCTTTATTCCAAACGCTTCTCCATATTCCTATCAGAGGTCA
GTGAGAACAAACTGAAACAGATCAACCTCAATAATGAATGGACAGTTGAGAAACTGAAAAGT
AAGCTTGTGAAAAATGCCCAGGACAAGATAGAACTGCATCTTTTATGCTCAACGGTCTTCC
AGACAATGTCTTTGAGTTAACTGAAATGGAAGTGCTAAGCCTGGAGCTTATCCCAGAGGTGA
AGCTGCCCTCTGCAGTCTCACAGCTGGTCAACCTCAAGGAGCTTCGTGTGTACCATTCATCT
CTGGTCGTAGACCATCCTGCACTGGCCTTTCTAGAGGAGAATTTAAAAATCCTCCGCCTGAA
ATTTACTGAAATGGGAAAAATCCCACGCTGGGTATTTCACCTCAAGAATCTCAAGGAACTTT
ATCTTTCGGGCTGTGTTCTCCCTGAACAGTTGAGTACTATGCAGTTGGAGGGCTTTCAGGAC
TTAAAAAATCTAAGGACCCTGTACTTGAAGAGCAGCCTCTCCCGGATCCCACAAGTTGTTACA
GACCTCCTGCCTTCATTGCAGAAACTGTCCCTTGATAATGAGGGAAGCAAACTGGTTGTGTT
GAACAACTTGAAAAGATGGTCAATCTGAAAGCCTAGAACTGATCAGCTGTGACCTGGAAC
GCATCCCACATTCCATTTTCAGCCTGAATAATTTGCATGAGTTAGACCTAAGGGAAAATAAC
CTTAAAACTGTGGAAGAGATTAGCTTTCAGCATCTTCAGAATCTTTCCTGCTTAAAGTTGTG
GCACAATAACATTGCTTATATTCCTGCACAGATTGGGGCATTATCTAACCTAGAGCAGCTCT
CTTTGGACCATAATAATATTGAGAATCTGCCCTTGCAGCTTTTCCTATGCACTAAACTACAT
TATTTGGATCTAAGCTATAACCACTTGACCTTCATTCCAGAAGAAATCCAGTATCTGAGTAA
TTTGCAGTACTTTGCTGTGACCAACAACAATATTGAGATGCTACCAGATGGGCTGTTTCAGT
GCAAAAGCTGCAGTGTTTACTTTTGGGGAAAAATAGCTTGATGAATTTGTCCCCTCATGTG
GGTGAGCTGTCAAACCTTACTCATCTGGAGCTCATTGGTAATTACCTGGAAACACTTCCTCC
TGAACTAGAAGGATGTCAGTCCCTAAAACGGAACTGTCTGATTGTTGAGGAGAACTTGCTCA
ATACTCTTCCTCTCCCTGTAACAGAACGTTTACAGACGTGCTTAGACAAATGTTGACTTAAA
GAAAAGAGACCCGTGTTTCAAAATCATTTTTAAAAGTATGCTCGGCCGGGCGTGGTGGCTCA
TGCCTATAATCCCAGCACTTTGGGAGGCCAAGATGGGCGGATTGCTTGAGGTCAGGAGTTCG
AGACCAGTCTGGCCAACCTGGTGAAACCCCATCTCTGCTAAAACTACAAAAAAATTAGCCAG
GCGTGGTGGCGTGCGCCTGTAATCCCAGCTACTTGGGAGGCTGACGCAGGGGAATTGCTTGA
ACCAGGGAGGTGGAGGTTGCAGTGAGCCGAGATTGTGCCACTGTACACCAGCCTGGGTGACA
GAGCAAGACTCTTATCTCAAAAAAAAAAAAAAA

FIGURE 78

```
></usr/seqdb2/sst/DNA/Dnaseqs.min/ss.DNA161005
><subunit 1 of 1, 802 aa, 1 stop
><MW: 92235, pI: 6.80, NX(S/T): 5
MITLTELKCLADAQSSYHILKPWWDVFWYYITLIMLLVAVLAGALQLTQSRVLCCLPCKV
EFDNHCAVPWDILKASMNTSSNPGTPLPLPLRIQNDLHRQQYSYIDAVCYEKQLHWFAKF
FPYLVLLHTLIFAACSNFWLHYPSTSSRLEHFVAILHKCFDSPWTTRALSETVAEQSVRP
LKLSKSKILLSSSGCSADIDSGKQSLPYPQPGLESAGIESPTSSGLDKKEGEQAKAIFEK
VKRFRMHVEQKDIIYRVYLKQIIVKVILFVLIITYVPYFLTHITLEIDCSVDVQAFTGYK
RYQCVYSLAEIFKVLASFYVILVILYGLTSSYSLWWMLRSSLKQYSFEALREKSNYSDIP
DVKNDFAFILHLADQYDPLYSKRFSIFLSEVSENKLKQINLNNEWTVEKLKSKLVKNAQD
KIELHLFMLNGLPDNVFELTEMEVLSLELIPEVKLPSAVSQLVNLKELRVYHSSLVVDHP
ALAFLEENLKILRLKFTEMGKIPRWVFHLKNLKELYLSGCVLPEQLSTMQLEGFQDLKNL
RTLYLKSSLSRIPQVVTDLLPSLQKLSLDNEGSKLVVLNNLKKMVNLKSLELISCDLERI
PHSIFSLNNLHELDLRENNLKTVEEISFQHLQNLSCLKLWHNNIAYIPAQIGALSNLEQL
SLDHNNIENLPLQLFLCTKLHYLDLSYNHLTFIPEEIQYLSNLQYFAVTNNNIEMLPDGL
FQCKKLQCLLLGKNSLMNLSPHVGELSNLTHLELIGNYLETLPPELEGCQSLKRNCLIVE
ENLLNTLPLPVTERLQTCLDKC
```

Important features of the protein:

Signal peptide:
Amino acids                 1-46

Transmembrane domains:
Amino acids                 118-138;261-281;311-332

N-glycosylation sites:
Amino acids                 78-82;355-359;633-637;748-752 cAMP- and cGMP-dependent protein kinase phosphorylation site:
Amino acids                 382-386

Tyrosine kinase phosphorylation site:
Amino acids                 21-30

N-myristoylation sites:
Amino acids                 212-218;327-333;431-437;652-658;
                            719-725

Prokaryotic membrane lipoprotein lipid attachment site:
Amino acids                 125-136

Leucine zipper pattern:
Amino acids                 468-490

Leucine Rich Repeat:
Amino acids                 609-632; 748-770

FIGURE 79

CGGACGCGTGGGCCGCGCTCCCTCACGGCCCCTCGGCGGCGCCCGTCGGATCCGGCCTCTCT
CTGCGCCCCGGGGCGCGCCACCTCCCCGCCGGAGGTGTCCACGCGTCCGGCCGTCCATCCGT
CCGTCCTCCTGGGGCCGGCGCTGACCATGCCCAGCGGCTGCCGCTGCCTGCATCTCGTGTG
CCTGTTGTGCATTCTGGGGGCTCCCGGTCAGCCTGTCCGAGCCGATGACTGCAGCTCCCACT
GTGACCTGGCCCACGGCTGCTGTGCACCTGACGGCTCCTGCAGGTGTGACCCGGGCTGGGAG
GGGCTGCACTGTGAGCGCTGTGTGAGGATGCCTGGCTGCCAGCACGGTACCTGCCACCAGCC
ATGGCAGTGCATCTGCCACAGTGGCTGGGCAGGCAAGTTCTGTGACAAAGATGAACATATCT
GTACCACGCAGTCCCCCTGCCAGAATGGAGGCCAGTGCATGTATGACGGGGCGGTGAGTAC
CATTGTGTGTGCTTACCAGGCTTCCATGGGCGTGACTGCGAGCGCAAGGCTGGACCCTGTGA
ACAGGCAGGCTCCCCATGCCGCAATGGCGGGCAGTGCCAGGACGACCAGGGCTTTGCTCTCA
ACTTCACGTGCCGCTGCTTGGTGGGCTTTGTGGGTGCCCGCTGTGAGGTAAATGTGGATGAC
TGCCTGATGCGGCCTTGTGCTAACGGTGCCACCTGCCTTGACGGCATAAACCGCTTCTCCTG
CCTCTGTCCTGAGGGCTTTGCTGGACGCTTCTGCACCATCAACCTGGATGACTGTGCCAGCC
GCCCATGCCAGAGAGGGGCCCGCTGTCGGGACCGTGTCCACGACTTCGACTGCCTCTGCCCC
AGTGGCTATGGTGGCAAGACCTGTGAGCTTGTCTTACCTGTCCCAGACCCCCCAACCACAGTG
GACACCCCTCTAGGGCCCACCTCAGCTGTAGTGGTACCTGCTACGGGCCAGCCCCCCACAG
CGCAGGGGCTGGTCTGCTGCGGATCTCAGTGAAGGAGGTGGTGCGGAGGCAAGAGGCTGGGC
TAGGTGAGCCTAGCTTGGTGGCCCTGGTGGTGTTTGGGGCCCTCACTGCTGCCCTGGTTCTG
GCTACTGTGTTGCTGACCCTGAGGGCCTGGCGCCGGGGTGTCTGCCCCCCTGGACCCTGTTG
CTACCCTGCCCCACACTATGCTCCAGCGTGCCAGGACCAGGAGTGTCAGGTTAGCATGCTGC
CAGCAGGGCTCCCCCTGCCACGTGACTTGCCCCCTGAGCCTGGAAAGACCACAGCACTGTGA
TGGAGGTGGGGCTTTCTGGCCCCCTTCCTCACCTCTTCCACCCCTCAGACTGGAGTGGTCC
GTTCTCACCACCCTTCAGCTTGGGTACACACACAGAGGAGACCTCAGCCTCACACCAGAAAT
ATTATTTTTTTAATACACAGAATGTAAGATGGAATTTTATCAAATAAAACTATGAAAATGCA
AAAAAAAAAAAAAAA

FIGURE 80

```
></usr/seqdb2/sst/DNA/Dnaseqs.min/ss.DNA170245
><subunit 1 of 1, 383 aa, 1 stop
><MW: 40548, pI: 6.48, NX(S/T): 1
MPSGCRCLHLVCLLCILGAPGQPVRADDCSSHCDLAHGCCAPDGSCRCDPGWEGLHCERC
VRMPGCQHGTCHQPWQCICHSGWAGKFCDKDEHICTTQSPCQNGGQCMYDGGGEYHCVCL
PGFHGRDCERKAGPCEQAGSPCRNGGQCQDDQGFALNFTCRCLVGFVGARCEVNVDDCLM
RPCANGATCLDGINRFSCLCPEGFAGRFCTINLDDCASRPCQRGARCRDRVHDFDCLCPS
GYGGKTCELVLPVPDPPTTVDTPLGPTSAVVVPATGPAPHSAGAGLLRISVKEVVRRQEA
GLGEPSLVALVVFGALTAALVLATVLLTLRAWRRGVCPPGPCCYPAPHYAPACQDQECQV
SMLPAGLPLPRDLPPEPGKTTAL
```

Important features of the protein:
Signal peptide:
Amino acids                1-21

Transmembrane domain:
Amino acids                306-331

N-glycosylation site:
Amino acids                157-160

Glycosaminoglycan attachment site:
Amino acids                240-243

N-myristoylation sites:
Amino acids                44-49;65-70;243-248;314-319

Aspartic acid and asparagine hydroxylation sites:
Amino acids                189-200;227-238

EGF-like domain cysteine pattern signature:
Amino acids                46-57;77-88;117-128;160-171;198-209;
                           236-247

Zinc finger, C3HC4 type, signature:
Amino acids                7-16

EGF-like domain proteins:
Amino acids                46-58;77-89;117-129;160-172;198-210;
                           216-228;236-248

FIGURE 81

GTTTGTTGCTCAAACCGAGTTCTGGAGAACGCCATCAGCTCGCTGCTTAAAATTAAACCACA
GGTTCCATTATGGGTCGACTTGATGGGAAAGTCATCATCCTGACGGCCGCTGCTCAGGGGAT
TGGCCAAGCAGCTGCCTTAGCTTTTGCAAGAGAAGGTGCCAAAGTCATAGCCACAGACATTA
ATGAGTCCAAACTTCAGGAACTGGAAAAGTACCCGGGTATTCAAACTCGTGTCCTTGATGTC
ACAAAGAAGAAACAAATTGATCAGTTTGCCAGTGAAGTTGAGAGACTTGATGTTCTCTTTAAT
GTTGCTGGTTTTGTCCATCATGGAACTGTCCTGGATTGTGAGGAGAAAGACTGGGACTTCTC
GATGAATCTCAATGTGCGCAGCATGTACCTGATGATCAAGGCATTCCTTCCTAAAATGCTTG
CTCAGAAATCTGGCAATATTATCAACATGTCTTCTGTGGCTTCCAGCGTCAAAGGAGTTGTG
AACAGATGTGTGTACAGCACAACCAAGGCAGCCGTGATTGGCCTCACAAAATCTCTGGCTGC
AGATTTCATCCAGCAGGGCATCAGGTGCAACTGTGTGTGCCCAGGAACAGTTGATACGCCAT
CTCTACAAGAAAGAATACAAGCCAGAGGAAATCCTGAAGAGGCACGGAATGATTTCCTGAAG
AGACAAAAGACGGGAAGATTCGCAACTGCAGAAGAAATAGCCATGCTCTGCGTGTATTTGGC
TTCTGATGAATCTGCTTATGTAACTGGTAACCCTGTCATCATTGATGGAGGCTGGAGCTTGT
GATTTTAGGATCTCCATGGTGGGAAGGAAGGCAGGCCCTTCCTATCCACAGTGAACCTGGTT
ACGAAGAAAACTCACCAATCATCTCCTTCCTGTTAATCACATGTTAATGAAAATAAGCTCTT
TTTAATGATGTCACTGTTTGCAAGAGTCTGATTCTTTAAGTATATTAATCTCTTTGTAATCT
CTTCTGAAATCATTGTAAAGAAATAAAAATATTGAACTCAT

FIGURE 82

```
></usr/seqdb2/sst/DNA/Dnaseqs.min/ss.DNA171771
><subunit 1 of 1, 245 aa, 1 stop
><MW: 26711, pI: 8.00, NX(S/T): 2
MGRLDGKVIILTAAAQGIGQAAALAFAREGAKVIATDINESKLQELEKYPGIQTRVLDVT
KKKQIDQFASEVERLDVLFNVAGFVHHGTVLDCEEKDWDFSMNLNVRSMYLMIKAFLPKM
LAQKSGNIINMSSVASSVKGVVNRCVYSTTKAAVIGLTKSLAADFIQQGIRCNCVCPGTV
DTPSLQERIQARGNPEEARNDFLKRQKTGRFATAEEIAMLCVYLASDESAYVTGNPVIID
GGWSL Important features of the protein:
Signal peptide:
Amino acids               1-20

N-glycosylation sites:
Amino acids               39-43;130-134

Tyrosine kinase phosphorylation site:
Amino acids               42-50

N-myristoylation sites:
Amino acids               17-23;19-25;126-132;156-162;169-175

Short-chain dehydrogenases/reductases family proteins:
Amino acids               7-19;73-83;127-164; 169-178

Short chain dehydrogenase:
Amino acids               7-183
```

FIGURE 83

```
GGGCGGCGGCGGCAGCGGTTGGAGGTTGTAGGACCGGCGAGGAATAGGAATCATGGCGGCTG
CGCTGTTCGTGCTGCTGGGATTCGCGCTGCTGGGCACCCACGGAGCCTCCGGGGCTGCCGGC
TTCGTCCAGGCGCCGCTGTCCAGCAGAGGTGGGTGGGGGGCAGTGTGGAGCTGCACTGCGA
GGCCGTGGGCAGCCCGGTGCCCGAGATCCAGTGGTGGTTTGAAGGGCAGGGTCCCAACGACA
CCTGCTCCCAGCTCTGGGACGGCGCCCGGCTGGACCGCGTCCACATCCACGCCACCTACCAC
CAGCACGCGGCCAGCACCATCTCCATCGACACGCTCGTGGAGGAGGACACGGGCACTTACGA
GTGCCGGGCCAGCAACGACCCGGATCGCAACCACCTGACCCGGGCGCCAGGGTCAAGTGGG
TCCGCGCCCAGGCAGTCGTGCTAGTCCTGGAACCCGGCACAGTCTTCACTACCGTAGAAGAC
CTTGGCTCCAAGATACTCCTCACCTGCTCCTTGAATGACAGCGCCACAGAGGTCACAGGGCA
CCGCTGGCTGAAGGGGGCGTGGTGCTGAAGGAGGACGCGCTGCCCGGCCAGAAAACGGAGT
TCAAGGTGGACTCCGACGACCAGTGGGGAGAGTACTCCTGCGTCTTCCTCCCCGAGCCCATG
GGCACGGCCAACATCCAGCTCCACGGGCCTCCCAGAGTGAAGGCTGTGAAGTCGTCAGAACA
CATCAACGAGGGGGAGACGGCCATGCTGGTCTGCAAGTCAGAGTCCGTGCCACCTGTCACTG
ACTGGGCCTGGTACAAGATCACTGACTCTGAGGACAAGGCCCTCATGAACGGCTCCGAGAGC
AGGTTCTTCGTGAGTTCCTCGCAGGGCCGGTCAGAGCTACACATTGAGAACCTGAACATGGA
GGCCGACCCCGGCCAGTACCGGTGCAACGGCACCAGCTCCAAGGGCTCCGACCAGGCCATCA
TCACGCTCCGCGTGCGCAGCCACCTGGCCGCCCTCTGGCCCTTCCTGGGCATCGTGGCTGAG
GTGCTGGTGCTGGTCACCATCATCTTCATCTACGAGAAGCGCCGGAAGCCCGAGGACGTCCT
GGATGATGACGACGCCGGCTCTGCACCCCTGAAGAGCAGCGGGCAGCACCAGAATGACAAAG
GCAAGAACGTCCGCCAGAGGAACTCTTCCTGAGGCAGGTGGCCCGAGGACGCTCCCTGCTCC
ACGTCTGCGCCGCCGCCGGAGTCCACTCCCAGTGCTTGCAAGATTCCAAGTTCTCACCTCTT
AAAGAAAACCCACCCCGTAGATTCCCATCATACACTTCCTTCTTTTTTAAAAAAGTTGGGTT
TTCTCCATTCAGGATTCTGTTCCTTAGGTTTTTTCCTTCTGAAGTGTTTCACGAGAGCCCG
GGAGCTGCTGCCCTGCGGCCCCGTCTGTGGCTTTCAGCCTCTGGGTCTGAGTCATGGCCGGG
TGGGCGGCACAGCCTTCTCCACTGGCCGGAGTCAGTGCCAGGTCCTTGCCCTTTGTGGAAAGTC
ACAGGTCACACGAGGGGCCCCGTGTCCTGCCTGTCTGAAGCCAATGCTGTCTGGTTGCGCCA
TTTTTGTGCTTTTATGTTTAATTTTATGAGGGCCACGGGTCTGTGTTCGACTCAGCCTCAGG
GACGACTCTGACCTCTTGGCCACAGAGGACTCACTTGCCCACACCGAGGGCGACCCCGTCAC
AGCCTCAAGTCACTCCCAAGCCCCCTCCTTGTCTGTGCATCCGGGGCAGCTCTGGAGGGGG
TTTGCTGGGGAACTGGCGCCATCGCCGGGACTCCAGAACGCAGAAGCCTCCCCAGCTCACC
CCTGGAGGACGGCCGGCTCTCTATAGCACCAGGGCTCACGTGGGAACCCCCCTCCCACCCAC
CGCCACAATAAAGATCGCCCCCACCTCCACCCAAAAA
```

FIGURE 84

```
></usr/seqdb2/sst/DNA/Dnaseqs.min/ss.DNA173157
><subunit 1 of 1, 385 aa, 1 stop
><MW: 42200, pI: 5.57, NX(S/T): 5
MAAALFVLLGFALLGTHGASGAAGFVQAPLSQQRWVGGSVELHCEAVGSPVPEIQWWFEG
QGPNDTCSQLWDGARLDRVHIHATYHQHAASTISIDTLVEEDTGTYECRASNDPDRNHLT
RAPRVKWVRAQAVVLVLEPGTVFTTVEDLGSKILLTCSLNDSATEVTGHRWLKGGVVLKE
DALPGQKTEFKVDSDDQWGEYSCVFLPEPMGTANIQLHGPPRVKAVKSSEHINEGETAML
VCKSESVPPVTDWAWYKITDSEDKALMNGSESRFFVSSSQGRSELHIENLNMEADPGQYR
CNGTSSKGSDQAIITLRVRSHLAALWPFLGIVAEVLVLVTIIFIYEKRRKPEDVLDDDDA
GSAPLKSSGQHQNDKGKNVRQRNSS
```

Important features of the protein:
Signal peptide:
Amino acids               1-18

Transmembrane domain:
Amino acids               320-343

N-glycosylation sites:
Amino acids               64-68;160-164;268-272;302-306

N-myristoylation sites:
Amino acids               15-21;18-24;60-66;104-110;140-146;
                          297-303;308-314;369-375

Immunoglobulin domain:
Amino acids               37-110;150-205;235-303

FIGURE 85

GGCTCGAGCAAAGACATACGAACAGGGAGGAAGGCCGACTGAAAGAAAGACGGAGAAGAGGA
GAGAGAAGCCAGGGCCGAGCGTGCCAGCAGGCGGATGGAGGGCGGCCTGGTGGAGGAGGAGA
CGTAGTGGCCTGGGCTGAGCTGGGTGGCCGGGAGAAGCGGGTGCCTCAGAGTGGGGGTGGG
GGCATGGGAGGGGCAGGCATTCTGCTGCTGCTGCTGGCTGGGCGGGGGTGGTGGTGGCCTGG
AGACCCCAAAGGGAAAGTGTCCCCTGCGCTGCTCCTGCTCTAAAGACAGCGCCCTGTGTGA
GGGCTCCCCGGACCTGCCCGTCAGCTTCTCTCCGACCCTGCTGTCACTCTCACTCGTCAGGA
CGGGAGTCACCCAGCTGAAGGCCGGCAGCTTCCTGAGAATTCCGTCTCTGCACCTGCTCCTC
TTCACCTCCAACTCCTTCTCCGTGATTGAGGACGATGCATTTGCGGGCCTGTCCCACCTGCA
GTACCTCTTCATCGAGGACAATGAGATTGGCTCCATCTCTAAGAATGCCCTCAGAGGACTTC
GCTCGCTTACACACCTAAGCCTGGCCAATAACCATCTGGAGACCCTCCCCAGATTCCTGTTC
CGAGGCCTGGACACCCTTACTCACGTGGACCTCCGCGGGAACCCGTTCCAGTGTGACTGCCG
CGTCCTCTGGCTCCTGCAGTGGATGCCCACCGTGAATGCCAGCGTGGGGACCGGCGCCTGTG
CGGGCCCCGCCTCCCTGAGCCACATGCAGCTCCACCACCTCGACCCCAAGACTTTCAAGTGC
AGAGCCATAGGTGGGGGGCTTTCCCGATGGGGTGGGAGGCGGGAGATCTGGGGGAAAGGCTG
CCAGGGCCAAGAGGCTCGTCTCACTCCCTGCCCTGCCATTTCCCGGAGTGGGAAGACCCTGA
GCAAGCAGCACTGCCTTCCTGAGCCCCAGTTTTCTCATCTGTAAAGTGGGGGTAATAAACAG
TGATATAGG

FIGURE 86

```
></usr/seqdb2/sst/DNA/Dnaseqs.min/ss.DNA175734
><subunit 1 of 1, 261 aa, 1 stop
><MW: 28231, pI: 9.28, NX(S/T): 1
MGGAGILLLLLAGAGVVVAWRPPKGKCPLRCSCSKDSALCEGSPDLPVSFSPTLLSLSLV
RTGVTQLKAGSFLRIPSLHLLLFTSNSFSVIEDDAFAGLSHLQYLFIEDNEIGSISKNAL
RGLRSLTHLSLANNHLETLPRFLFRGLDTLTHVDLRGNPFQCDCRVLWLLQWMPTVNASV
GTGACAGPASLSHMQLHHLDPKTFKCRAIGGGLSRWGGRREIWGKGCQGQEARLTPCPAI
SRSGKTLSKQHCLPEPQFSHL
```

Important features of the protein:
Signal peptide:
Amino acids                 1-19

N-glycosylation site:
Amino acids                 177-181

N-myristoylation sites:
Amino acids                 15-21;181-186;210-215

Amidation site:
Amino acids                 217-220

Microbodies C-terminal targeting signal:
Amino acids                 259-262

ATP/GTP-binding site motif A (P-loop):
Amino acids                 239-246

Leucine zipper pattern:
Amino acids                 129-150

Leucine Rich Repeat:
Amino acids                 53-76; 149-171

Leucine rich repeat C-terminal domain:
Amino acids                 158-207

FIGURE 87

```
CGGACGCGTGGGGCGGCGAGAGCAGCTGCAGTTCGCATCTCAGGCAGTACCTAGAGGAGCTG
CCGGTGCCTCCTCAGAACATCTCCTGATCGCTACCCAGGACCAGGCACCAAGGACAGGGAGT
CCCAGGCGCACACCCCCATTCTGGGTCCCCAGGCCCAGACCCCCACTCTGCCACAGGTTG
CATCTTGACCTGGTCCTCCTGCAGAAGTGGCCCCTGTGGTCCTGCTCTGAGACTCGTCCCTG
GGCGCCCTGCAGCCCCTTTCTATGACTCCATCTGGATTTGGCTGGCTGTGGGGACGCGGTC
CGAGGGGCGGCCTGGCTCTCAGCGTGGTGGCAGCCAGCTCTCTGGCCACCATGGCAAATGCT
GAGATCTGAGGGGACAAGGCTCTACAGCCTCAGCCAGGGCACTCAGCTGTTGCAGGGTGTG
```ATG```GAGAACAAAGCTATGTACCTACACACCGTCAGCGACTGTGACACCAGCTCCATCTGTGA
GGATTCCTTTGATGGCAGGAGCCTGTCCAAGCTGAACCTGTGTGAGGATGGTCCATGTCACA
AACGGCGGGCAAGCATCTGCTGTACCCAGCTGGGGTCCCTGTCGGCCCTGAAGCATGCTGTC
CTGGGGCTCTACCTGCTGGTCTTCCTGATTCTTGTGGGCATCTTCATCTTAGCAGGGCCACC
GGGACCCAAAGGTGATCAGGGGGATGAAGGAAAGGAAGGCAGGCCTGGCATCCCTGGATTGC
CTGGACTTCGAGGTCTGCCCGGGGAGAGAGGTACCCCAGGATTGCCCGGGCCCAAGGGCGAT
GATGGGAAGCTGGGGCCACAGGACCAATGGGCATGCGTGGGTTCAAAGGTGACCGAGGCCC
AAAAGGAGAGAAAGGAGAGAAAGGAGACAGAGCTGGGGATGCCAGTGGCGTGGAGGCCCCGA
TGATGATCCGCCTGGTGAATGGCTCAGGTCCGCACGAGGGCCGCGTGGAAGTGTACCACGAC
CGGCGCTGGGGCACCGTGTGTGACGACGGCTGGGACAAGAAGGACGGAGACGTGGTGTGCCG
CATGCTCGGCTTCCGCGGTGTGGAGGAGGTGTACCGCACAGCTCGATTCGGGCAAGGCACTG
GGAGGATCTGGATGGATGACGTTGCCTGCAAGGGCACAGAGGAAACCATCTTCCGCTGCAGC
TTCTCCAAATGGGGGTGACAAACTGTGGACATGCCGAAGATGCCAGCGTGACATGCAACAG
ACAC```TGA```AAGTGGGCAGAGCCCAAGTTCGGGGTCCTGCACAGAGCACCCTTGCTGCATCCCT
GGGGTGGGGCACAGCTCGGGGCCACCCTGACCATGCCTCGACCACACCCCGTCCAGCATTCT
CAGTCCTCACACCTGCATCCCAGGACCGTGGGGGCCGGTCGTCATTTCCCTCTTGAACATGT
GCTCCGAAGTATAACTCTGGGACCTACTGCCCGTCTCTCTCTTCCACCAGGTTCCTGCATGA
GGAGCCCTGATCAACTGGATCACCACTTTGCCCAGCCTCTGAACACCATGCACCAGGCCTCA
ATATCCCAGTTCCCTTTGGCCTTTTAGTTACAGGTGAATGCTGAGAATGTGTCAGAGACAAG
TGCAGCAGCAGCGATGGTTGGTAGTATAGATCATTTACTCTTCAGACAATTCCCAAACCTCC
ATTAGTCCAAGAGTTTCTACATCTTCCTCCCCAGCAAGAGGCAACGTCAAGTGATGAATTTC
CCCCCTTTACTCTGCCTCTGCTCCCCATTTGCTAGTTTGAGGAAGTGACATAGAGGAGAAGC
CAGCTGTAGGGGCAAGAGGGAAATGCAAGTCACCTGCAGGAATCCAGCTAGATTTGGAGAAG
GGAATGAAACTAACATTGAATGACTACCATGGCACGCTAAATAGTATCTTGGGTGCCAAATTCA
TGTATCCACTTAGCTGCATTGGTCCAGGGCATGTCAGTCTGGATACAGCCTTACCTTCAGGT
AGCACTTAACTGGTCCATTCACCTAGACTGCAAGTAAGAAGACAAAATGACTGAGACCGTGT
GCCCACCTGAACTTATTGTCTTTACTTGGCCTGAGCTAAAAGCTTGGGTGCAGGACCTGTGT
AACTAGAAAGTTGCCTACTTCAGAACCTCCAGGGCGTGAGTGCAAGGTCAAACATGACTGGC
TTCCAGGCCGACCATCAATGTAGGAGGAGAGCTGATGTGGAGGGTGACATGGGGCTGCCCA
TGTTAAACCTGAGTCCAGTGCTCTGGCATTGGGCAGTCACGGTTAAAGCCAAGTCATGTGTG
TCTCAGCTGTTTGGAGGTGATGATTTTGCATCTTCCAAGCCTCTTCAGGTGTGAATCTGTGG
TCAGGAAAACACAAGTCCTAATGGAACCCTTAGGGGGAAGGAAATGAAGATTCCCTATAAC
CTCTGGGGGTGGGGAGTAGGAATAAGGGGCCTTGGGCCTCCATAAATCTGCAATCTGCACCC
TCCTCCTAGAGACAGGGAGATCGTGTTCTGCTTTTTACATGAGGAGCAGAACTGGGCCATAC
ACGTGTTCAAGAACTAGGGGAGCTACCTGGTAGCAAGTGAGTGCAGACCCACCTCACCTTGG
GGGAATCTCAAACTCATAGGCCTCAGATACACGATCACCTGTCATATCAGGTGAGCACTGGC
CTGCTTGGGGAGAGACCTGGGCCCCTCCAGGTGTAGGAACAGCAACACTCCTGGCTGACAAC
TAAGCCAATATGGCCCTAGGTCATTCTTGCTTCCAATATGCTTGCCACTCCTTAAATGTCCT
AATGATGAGAAACTCTCTTTCTGACCAATTGCTATGTTTACATAACACGCATGTACTCATGC
ATCCCTTGCCAGAGCCCATATATGTATGCATATATAAACATAGCACTTTTTACTACATAGCT
CAGCACATTGCAAGGTTTGCATTTAAGTT
```

FIGURE 88

></usr/seqdb2/sst/DNA/Dnaseqs.min/ss.DNA176108
><subunit 1 of 1, 270 aa, 1 stop
><MW: 28871, pI: 7.09, NX(S/T): 1
MENKAMYLHTVSDCDTSSICEDSFDGRSLSKLNLCEDGPCHKRRASICCTQLGSLSALKH
AVLGLYLLVFLILVGIFILAGPPGPKGDQGDEGKEGRPGIPGLPGLRGLPGERGTPGLPG
PKGDDGKLGATGPMGMRGFKGDRGPKGEKGDRAGDASGVEAPMMIRLVNGSGPHEGR
VEVYHDRRWGTVCDDGWDKKDGDVVCRMLGFRGVEEVYRTARFGQGTGRIWMDDVACKGT
EETIFRCSFSKWGVTNCGHAEDASVTCNRH

Transmembrane domain:
Amino acids                55-80

N-glycosylation site:
Amino acids                172-175 cAMP- and cGMP-dependent protein kinase phosphorylation site:
Amino acids                43-46

Tyrosine kinase phosphorylation site:
Amino acids                212-218

N-myristoylation sites:
Amino acids                53-58;224-229;239-244;253-258

Speract receptor repeated domain signature:
Amino acids                173-211

Scavenger receptor cysteine-rich domain:
Amino acids                171-268

Collagen Collagen triple helix repeat:
Amino acids                90-149

FIGURE 89

GTCGCCGCGAGGGACGCAGAGAGCACCCTCCACGCCCAGATGCCTGCGTAGTTTTTGTGACC
AGTCCGCTCCTGCCTCCCCCTGGGGCAGTAGAGGGGGAGCGATGGAGAACTGGACTGGCAGG
CCCTGGCTGTATCTGCTGCTGCTTCTGTCCCTCCCTCAGCTCTGCTTGGATCAGGAGGTGTT
GTCCGGACACTCTCTTCAGACACCTACAGAGGAGGGCCAGGGCCCCGAAGGTGTCTGGGGAC
CTTGGGTCCAGTGGGCCTCTTGCTCCCAGCCCTGCGGGGTGGGGGTGCAGCGCAGGAGCCGG
ACATGTCAGCTCCCTACAGTGCAGCTCCACCCGAGTCTGCCCCTCCCTCCCCGGCCCCAAG
ACATCCAGAAGCCCTCCTCCCCGGGGCCAGGGTCCCAGACCCCAGACTTCTCCAGAAACCC
TCCCCTTGTACAGGACACAGTCTCGGGGAAGGGGTGGCCCACTTCGAGGTCCCGCTTCCCAC
CTAGGGAGAGAGGAGACCCAGGAGATTCGAGCGGCCAGGAGGTCCGGCTTCGAGACCCCAT
CAAGCCAGGAATGTTCGGTTATGGGAGAGTGCCCTTTGCATTGCCACTGCACCGGAACCGCA
GGCACCCTCGGAGCCCACCCAGATCTGAGCTGTCCCTGATCTCTTCTAGAGGGGAAGAGGCT
ATTCCGTCCCTACTCCAAGAGCAGAGCCATTCTCCGCAAACGGCAGCCCCCAAACTGAGCT
CCCTCCCACAGAACTGTCTGTCCACACCCCATCCCCCCAAGCAGAACCTCTAAGCCCTGAAA
CTGCTCAGACAGAGGTGGCCCCCAGAACCAGGCCTGCCCCCTACGGCATCACCCCAGAGCC
CAGGCCTCTGGCACAGAGCCCCCTCACCCACGCACTCCTTAGGAGAAGGTGGCTTCTTCCG
TGCATCCCCTCAGCCACGAAGGCCAAGTTCCCAGGGTTGGGCCAGTCCCCAGGTAGCAGGGA
GACGCCTGATCCTTTTCCTTCGGTCCCTCGGGGCCGAGGCCAGCAGGGCCAAGGGCCTTGG
GGAACGGGGGGGACTCCTCACGGGCCCCGCCTGGAGCCTGACCCTCAGCACCCGGGCGCCTG
GCTGCCCCTGCTGAGCAACGGCCCCCATGCCAGCTCCCTCTGGAGCCTCTTTGCTCCCAGTA
GCCCTATTCCAAGATGTTCTGGGGAGAGTGAACAGCTAAGAGCCTGCAGCCAAGCGCCCTGC
CCCCCTGAGCAGCCAGACCCCGGGCCCTGCAGTGCGCAGCCTTTAACTCCCAGGAATTCATG
GGCCAGCTGTATCAGTGGGAGCCCTTCACTGAAGTCCAGGGCTCCCAGCGCTGTGAACTGAA
CTGCCGGCCCCGTGGCTTCCGCTTCTATGTCCGTCACACTGAAAAGGTCCAGGATGGGACCC
TGTGTCAGCCTGGAGCCCCTGACATCTGTGTGGCTGGACGCTGTCTGAGCCCCGGCTGTGAT
GGGATCCTTGGCTCTGGCAGGCGTCCTGATGGCTGTGGAGTCTGTGGGGGTGATGATTCTAC
CTGTCGCCTTGTTTCGGGGAACCTCACTGACCGAGGGGGCCCCCTGGGCTATCAGAAGATCT
TGTGGATTCCAGCGGGAGCCTTGCGGCTCCAGATTGCCCAGCTCCGGCCTAGCTCCAACTAC
CTGGCACTTCGTGGCCCTGGGGGCCGGTCCATCATCAATGGGAACTGGGCTGTGGATCCCCC
TGGGTCCTACAGGGCCGGCGGGACCGTCTTTCGATATAACCGTCCTCCCAGGGAGGAGGGCA
AAGGGGAGAGTCTGTCGGCTGAAGGCCCCACCACCCAGCCTGTGGATGTCTATATGATCTTT
CAGGAGGAAAACCCAGGCGTTTTTTATCAGTATGTCATCTCTTCACCTCCTCCAATCCTTGA
GAACCCCACCCCAGAGCCCCTGTCCCCAGCTTCAGCCGGAGATTCTGAGGGTGGAGCCCC
CACTTGCTCCGGCACCCCGCCCAGCCCGGACCCCAGGCACCCTCCAGCGTCAGGTGCGGATC
CCCCAGATGCCCGCCCCGCCCCATCCCAGGACACCCCTGGGGTCTCCAGCTGCGTACTGGAA
ACGAGTGGGACACTCTGCATGCTCAGCGTCCTGCGGGAAAGGTGTCTGGCGCCCCATTTTCC
TCTGCATCTCCCGTGAGTCGGGAGAGGAACTGGATGAACGCAGCTGTGCCGCGGGTGCCAGG
CCCCAGCCTCCCCTGAACCCTGCCACGGCACCCATGCCCCCATACTGGGAGGCTGGCGA
GTGGACATCCTGCAGCCGCTCCTGTGGCCCCGGCACCCAGCACCGCCAGCTGCAGTGCCGGC
AGGAATTTGGGGGGGTGGCTCCTCGGTGCCCCGGAGCGCTGTGGACATCTCCCCGGCCC
AACATCACCCAGTCTTGCCAGCTGCGCCTCTGTGGCCATTGGGAAGTTGGCTCTCCTTGGAG
CCAGTGCTCCGTGCGGTGCGGCCGGGCCAGAGAAGCCGGCAGGTTCGCTGTGTTGGGAACA
ACGGTGATGAAGTGAGCGAGCAGGAGTGTGCGTCAGGCCCCCACAGCCCCCAGCAGAGAG
GCCTGTGACATGGGGCCCTGTACTACTGCCTGGTTCCACAGCGACTGGAGCTCCAAGGTGAG
CCCGGAACCCCCAGCCATATCCTGCATCCTGGGTAACCATGCCCAGGACACCTCAGCCTTTC
CAGCATAGCTCAATAAACTTGTATTGATC

FIGURE 90

```
></usr/seqdb2/sst/DNA/Dnaseqs.min/ss.DNA190710
><subunit 1 of 1, 877 aa, 1 stop
><MW: 95132, pI: 8.77, NX(S/T): 5
MENWTGRPWLYLLLLLSLPQLCLDQEVLSGHSLQTPTEEGQGPEGVWGPWVQWASCSQPC
GVGVQRRSRTCQLPTVQLHPSLPLPPRPPRHPEALLPRGQGPRPQTSPETLPLYRTQSRG
RGGPLRGPASHLGREETQEIRAARRSRLRDPIKPGMFGYGRVPFALPLHRNRRHPRSPPR
SELSLISSRGEEAIPSPTPRAEPFSANGSPQTELPPTELSVHTPSPQAEPLSPETAQTEV
APRTRPAPLRHHPRAQASGTEPPSPTHSLGEGGFFRASPQPRRPSSQGWASPQVAGRRPD
PFPSVPRGRGQQGQGPWGTGGTPHGPRLEPDPQHPGAWLPLLSNGPHASSLWSLFAPSSP
IPRCSGESEQLRACSQAPCPPEQPDPRALQCAAFNSQEFMGQLYQWEPFTEVQGSQRCEL
NCRPRGFRFYVRHTEKVQDGTLCQPGAPDICVAGRCLSPGCDGILGSGRRPDGCGVCGGD
DSTCRLVSGNLTDRGGPLGYQKILWIPAGALRLQIAQLRPSSNYLALRGPGGRSIINGNW
AVDPPGSYRAGGTVFRYNRPPREEGKGESLSAEGPTTQPVDVYMIFQEENPGVFYQYVIS
SPPPILENPTPEPPVPQLQPEILRVEPPLAPAPRPARTPGTLQRQVRIPQMPAPPHPRTP
LGSPAAYWKRVGHSACSASCGKGVWRPIFLCISRESGEELDERSCAAGARPPASPEPCHG
TPCPPYWEAGEWTSCSRSCGPGTQHRQLQCRQEFGGGGSSVPPERCGHLPRPNITQSCQL
RLCGHWEVGSPWSQCSVRCGRGQRSRQVRCVGNNGDEVSEQECASGPPQPPSREACDMGP
CTTAWFHSDWSSKVSPEPPAISCILGNHAQDTSAFPA
```

Important features of the protein:

Signal peptide:
Amino acids          1-24

N-glycosylation sites:
Amino acids          3-6;490-493;773-776 cAMP- and cGMP-dependent protein kinase phosphorylation site:
Amino acids          282-285

N-myristoylation sites:
Amino acids          208-213;414-419;463-468;473-478;475-480;
478-483;495-500;546-551;662-667;755-760;
756-761;789-794

Amidation sites:
Amino acids          295-298;467-470

Leucine zipper pattern:
Amino acids          504-526

VWFC domain proteins:
Amino acids          53-67;732-746;792-806

Thrombospondin type 1 domain:
Amino acids          48-87;727-783;787-841

FIGURE 91

```
CGAGTATTTTCCCACCATCTCCAGCCGGAAACTGACCAAGAACTCTGAGGCGGATGGCATGT
TCGCGTACGTCTTCCATGATGAGTTCGTGGCCTCGATGATTAAGATCCCTTCGGACACCTTC
ACCATCATCCCTGACTTTGATATCTACTATGTCTATGGTTTTAGCAGTGGCAACTTTGTCTA
CTTTTTGACCCTCCAACCTGAGATGGTGTCTCCACCAGGCTCCACCACCAAGGAGCAGGTGT
ATACATCCAAGCTCGTGAGGCTTTGCAAGGAGGACACAGCCTTCAACTCCTATGTAGAGGTG
CCCATTGGCTGTGAGCGCAGTGGGGTGGAGTACCGCCTGCTGCAGGCTGCCTACCTGTCCAA
AGCGGGGGCCGTGCTTGGCAGGACCCTTGGAGTCCATCCAGATGATGACCTGCTCTTCACCG
TCTTCTCCAAGGGCCAGAAGCGGAAATGAAATCCCTGGATGAGTCGGCCTGTGCATCTTC
ATCTTGAAGCAGATAAATGACCGCATTAAGGAGCGGCTGCAGTCTTGTTACCGGGGCGAGGG
CACGCTGGACCTGGCCTGGCTCAAGGTGAAGGACATCCCCTGCAGCAGTGCGCTCTTAACCA
TTGACGATAACTTCTGTGGCCTGGACATGAATGCTCCCCTGGGAGTGTCCGACATGGTGCGT
GGAATTCCCGTCTTCACGGAGGACAGGGACCGCATGACGTCTGTCATCGCATATGTCTACAA
GAACCACTCTCTGGCCTTTGTGGGCACCAAAAGTGGCAAGCTGAAGAAGGTGCCTGGTACCA
GCCTCTGCCCTACCCTTGAGCTACAGACGGGACCCCGATCCCACAGAGCAACAGTGACTCTG
GAACTCCTGTTCTCCAGCTGTTCATCAAACTGAGAAAAACTTCAGAGCTGTGTAGGCTTATT
TAGTGTGTTGTCAGCCTTGGATATTGGAAAATGGAAACAGATGAGACACATCTACCTCCCTG
TGACCCCAGCCATACATCATAGCTCATGTCCTGCCACCCCAAGTCCTTAGGGAAAAAGACT
TTGGAGAATGTGTCTCTGCTTAGCTTGGCTAGGTAGTTGGTCTCTTTTCTCTGCCCCAAGCG
TCCCCTGGGTAATTTTGGACAATGGAGTGTAGGCATGTTTGACTCTTGTGGTGTTATCACTT
GTATATGTCAGTGAAACTAACTGATTCTCCCATCGGAATATAGTTATCTCTTGGGCCTGATA
TATGGTAGGATAACCTTATGCTCATCTGTCCACTTCTGCAGCCAAGTCGCCTGGCCAGTGTG
TGTGTGTGTGTGTGTGTGTGTGTGTGTGTGTATGCTTATCTGTGTTTAAAGGTGTGTG
TGCATACACAGGGCAGAGAGGATGGAGCCCACCGTACTGCAGCATCATGTAATTAACTCAGT
GCTCAGAACCATCCCAGCCTCTGCGGGAAGAGAAAAGTAAGCCAACAGTGCCTGATGAGCT
GATCATATGTGCAAAAGCTCTGTTGGCATCTGGTCCAGGAGAGCACCCAAAAAAGTTAATT
GGTGTTGTCCAGTCTCCTTTCCTTAAGACTATGGTTACAACAAAGCGTGAGCAGTGTCTCCT
GCATGGCCACTATCCAGCACAATTCCATAATTCCCCCATAGAGCCGGTGGGGAGGAGGAGGT
GAGTGGCGAAGGAAGTGGAAACACTTGGTGTCATGTGCTCCTATCATTTCTACTAGCTTACT
GGGAAATAAAGTGTAGTCAAGAGTGTATGAAGGCAAGATGTAAAATTAGCGACTGGTGCTAA
TCTGGTTACTTGAAAACAAGTGAAAGTGCTGTAGATTTGTTCTGTTGCTAAGAACCACCACA
CTAAACCTCGTATAGTTCCTGGAGGATATACAACAGTGTAATTCTCTTTAGGGTGTGCCACA
GGTTCCTGGCCTGTGGGAGGGAATGAATCAGGAGGGCTCTTGAGAACCTTCATCTGTGTGCT
TGCACTGAAAGTGAGTCCCAAAGCTGGAGATTTAGTGAGAGCAGGCAACCCCTCTGTGTCTC
ACTGTCCATATTCTGGAGGCAGAGGTTTGTAACAGGCCATGTGCACCTGCATAGGGATGGGT
AAAGCAAGGACTTTGAAAGAGTTGAAAAGCATTATAAACAGTTGTTCAGAAATACGTCCCAG
GAGTTCCATGTGAAACTGGCTCTGTGTGCATTGAAGCATGGCTGTTGGGAATTCTAACTGGT
CCAACACTCCTGCAAAACAATGTGTAAATATTTAGGAAGAAACTTGAAAATAGTCAAATCCT
TTGAACTGGTGACAATTTTTTAAAGAATCAATTCTAATTTGTTTCAAGGGTAATAATCACCA
AGATACACATTTCAGCATTTATTTAGTCTATCAAAAATTGGAATTGATATATACACTCATTT
ATAGGAGAATGGTTAGGTAGATTTGGTATATTTATGTAGTCATTGAAAACTTAGTTTATAAA
GGCCAATCTTGTAACTGATTCTTGTGTGATAACATTCAGTGAAAAGCATGAGACAATTAGA
AAGCATGATACAATGAATAAAATAAAAACTGGAAAGAGAACCATCAAAATGCTAA
```

FIGURE 92

```
></usr/seqdb2/sst/DNA/Dnaseqs.min/ss.DNA190803
><subunit 1 of 1, 280 aa, 1 stop
><MW: 31222, pI: 7.40, NX(S/T): 1
MFAYVFHDEFVASMIKIPSDTFTIIPDFDIYYVYGFSSGNFVYFLTLQPEMVSPPGSTTK
EQVYTSKLVRLCKEDTAFNSYVEVPIGCERSGVEYRLLQAAYLSKAGAVLGRTLGVHPDD
DLLFTVFSKGQKRKMKSLDESALCIFILKQINDRIKERLQSCYRGEGTLDLAWLKVKDIP
CSSALLTIDDNFCGLDMNAPLGVSDMVRGIPVFTEDRDRMTSVIAYVYKNHSLAFVGTKS
GKLKKVPGTSLCPTLELQTGPRSHRATVTLELLFSSCSSN
```

Important features of the protein:

N-glycosylation site:
Amino acids            230-233

N-myristoylation sites:
Amino acids            87-92;107-112;194-199;237-242

FIGURE 93

```
CCTTATCAGACAAAGGACGAGATGGAAAATACAAGATAATTTACAGTGGAGAAGAATTAGAA
TGTAACCTGAAAGATCTTAGACCAGCAACAGATTATCATGTGAGGGTGTATGCCATGTACAA
TTCCGTAAAGGGATCCTGCTCCGAGCCTGTTAGCTTCACCACCCACAGCTGTGCACCCGAGT
GTCCTTTCCCCCCTAAGCTGGCACATAGGAGCAAAAGTTCACTAACCCTGCAGTGGAAGGCA
CCAATTGACAACGGTTCAAAAATCACCAACTACCTTTTAGAGTGGGATGAGGGAAAAGAAA
TAGTGGTTTCAGACAGTGCTTCTTCGGGAGCCAGAAGCACTGCAAGTTGACAAAGCTTTGTC
CGGCAATGGGGTACACATTCAGGCTGGCCGCTCGAAACGACATTGGCACCAGTGGTTATAGC
CAAGAGGTGGTGTGCTACACATTAGGAAATATCCCTCAGATGCCTTCTGCACTAAGGCTGGT
TCGAGCTGGCATCACATGGGTCACGTTGCAGTGGAGTAAGCCAGAAGGCTGTTCACCCGAGG
AAGTGATCACCTACACCTTGGAAATTCAGGAGGATGAAAATGATAACCTTTTCCACCCAAAA
TACACTGGAGAGGATTTAACCTGTACTGTGAAAAATCTCAAAAGAAGCACACAGTATAAATT
CAGGCTGACTGCTTCTAATACGGAAGGAAAAAGCTGTCCAAGCGAAGTTCTTGTTTGTACGA
CGAGTCCTGACAGGCCTGGACCTCCTACCAGACCGCTTGTCAAAGGCCCAGTTACATCTCAT
GGCTTTAGTGTCAAATGGGATCCCCCTAAGGACAATGGTGGTTCAGAAATCCTCAAGTACTT
GCTAGAGATTACTGATGGAAATTCTGAAGCGAATCAGTGGGAAGTGGCCTACAGTGGGTCGG
CTACCGAATACACCTTCACCCACTTGAAACCAGGCACTTTGTACAAACTCCGAGCATGCTGC
ATCAGTACCGGCGGACACAGCCAGTGTTCTGAAAGTCTCCCTGTTCGCACACTAAGCATTGC
ACCAGGTCAATGTCGACCACCGAGGGTTTTGGGTAGACCAAAGCACAAAGAAGTCCACTTAG
AGTGGGATGTTCCTGCATCGGAAAGTGGCTGTGAGGTCTCAGAGTACAGCGTGGAGATGACG
GAGCCCGAAGACGTAGCCTCGGAAGTGTACCATGGCCCAGAGCTGGAGTGCACCGTCGGCAA
CCTGCTTCCTGGAACCGTGTATCGCTTCCGGGTGAGGGCTCTGAATGATGGAGGGTATGGTC
CCTATTCTGATGTCTCAGAAATTACCACTGCTGCAGGGCCTCCTGGACAATGCAAAGCACCT
TGTATTTCTTGTACACCTGATGGATGTGTCTTAGTGGGTTGGGAGAGTCCTGATAGTTCTGG
TGCTGACATCTCAGAGTACAGGTTGGAATGGGGAGAAGATGAAGAATCCTTAGAACTCATTT
ATCATGGGACAGACACCCGTTTTGAAATAAGAGACCTGTTGCCTGCTGCACAGTATTGCTGT
AGACTACAGGCCTTCAATCAAGCAGGGGCAGGGCCGTACAGTGAACTTGTCCTTTGCCAGAC
GCCAGCGTCTGCCCCTGACCCGTCTCCACTCTCTGTGTCCTGGAGGAGGAGCCCCTTGATGCC
TACCCTGATTCACCTTCTGCGTGCCTTGTACTGAACTGGGAAGAGCCGTGCAATAACGGATC
TGAAATCCTTGCTTACACCATTGATCTAGGAGACACTAGCATTACCGTGGGCAACACCACCA
TGCATGTTATGAAAGATCTCCTTCCAGAAACCACCTACCGGATCAGAATTCAGGCTATAAAT
GAAATTGGAGCTGGACCATTTAGTCAGTTCATTAAAGCAAAAACTCGGCCATTACCACCCTT
GCCTCCTAGGCTAGAATGTGCTGCTGCTGGTCCTCAGAGCCTGAAGCTAAAATGGGGAGACA
GTAACTCCAAGACACATGCTGCTGAGGACATTGTGTACACACTACAGCTGGAGGACAGAAAC
AAGAGGTTTATTTCAATCTACAGAGGACCCAGCCACACCTACAAGGTCCAGAGACTGACGGA
ATTCACATGCTACTCCTTCAGAATCCAGGCAGCAAGCGAGGCTGGAGAAGGGCCCTTCTCAG
AAACCTATACCTTCAGCACAACCAAAAGTGTCCCCCCCACCATCAAAGCACCTCGAGTAACA
CAGTTAGAAGTAAATTCATGTGAAATTTTATGGGAGACGGTACCATCAATGAAAGGTGACCC
TGTTAACTACATTCTGCAGGTATTGGTTGGAAGAGAATCTGAGTACAAACAGGTGTACAAGG
GAGAAGAAGCCACATTCCAAATCTCAGGCCTCCAGACCAACACAGACTACAGGTTCCGCGTA
TGTGCGTGTCGTCGCTGTTTAGACACCTCTCAGGAGCTAAGCGGAGCCTTCAGCCCCTCTGC
GGCTTTTGTATTACAACGAAGTGAGGTCATGCTTACAGGGGACATGGGGAGCTTAGATGATC
CCAAAATGAAGAGCATGATGCCTACTGATGAACAGTTTGCAGCCATCATTGTGCTTGGCTTT
GCAACTTTGTCCATTTTATTTGCCTTTATATTACAGTACTTCTTAATGAAGTAACCCAACA
AAACTAGAGGTATGAATTAATGCTACACATTTTAATACACACATTTATTCAGATACTCCCCT
TTTTAAAGCCCTTTTGTTTTTTGATTTATATACTCTGTTTTACAGATTTAGCTAGAAAAAAA
ATGTCAGTGTTTTGGTGCACCTTTTTGAAATGCAAAACTAGGAAAAGGTTAAACTGGATTTT
TTTTTAAAAAAAAAAAAAAAAAAAAAAAAA
```

FIGURE 94

```
></usr/seqdb2/sst/DNA/Dnaseqs.min/ss.DNA191064
><subunit 1 of 1, 847 aa, 1 stop
><MW: 93607, pI: 5.33, NX(S/T): 3
MYNSVKGSCSEPVSFTTHSCAPECPFPPKLAHRSKSSLTLQWKAPIDNGSKITNYLLEWD
EGKRNSGFRQCFFGSQKHCKLTKLCPAMGYTFRLAARNDIGTSGYSQEVVCYTLGNIPQM
PSALRLVRAGITWVTLQWSKPEGCSPEEVITYTLEIQEDENDNLFHPKYTGEDLTCTVKN
LKRSTQYKFRLTASNTEGKSCPSEVLVCTTSPDRPGPPTRPLVKGPVTSHGFSVKWDPPK
DNGGSEILKYLLEITDGNSEANQWEVAYSGSATEYTFTHLKPGTLYKLRACCISTGGHSQ
CSESLPVRTLSIAPGQCRPPRVLGRPKHKEVHLEWDVPASESGCEVSEYSVEMTEPEDVA
SEVYHGPELECTVGNLLPGTVYRFVRALNDGGYGPYSDVSEITTAAGPPGQCKAPCISC
TPDGCVLVGWESPDSSGADISEYRLEWGEDEESLELIYHGTDTRFEIRDLLPAAQYCCRL
QAFNQAGAGPYSELVLCQTPASAPDPVSTLCVLEEEPLDAYPDSPSACLVLNWEEPCNNG
SEILAYTIDLGDTSITVGNTTMHVMKDLLPETTYRIRIQAINEIGAGPFSQFIKAKTRPL
PPLPPRLECAAAGPQSLKLKWGDSNSKTHAAEDIVYTLQLEDRNKRFISIYRGPSHTYKV
QRLTEFTCYSFRIQAASEAGEGPFSETYTFSTTKSVPPTIKAPRVTQLEVNSCEILWETV
PSMKGDPVNYILQVLVGRESEYKQVYKGEEATFQISGLQTNTDYRFRVCACRRCLDTSQE
LSGAFSPSAAFVLQRSEVMLTGDMGSLDDPKMKSMMPTDEQFAAIIVLGFATLSILFAFI
LQYFLMK
```

Important features of the protein:

Transmembrane domain:
Amino acids              823-843

N-glycosylation sites:
Amino acids              48-51;539-542;559-562 cAMP- and cGMP-dependent protein kinase phosphorylation site:
Amino acids              63-66;182-185

Tyrosine kinase phosphorylation sites:
Amino acids              387-394;662-669

N-myristoylation sites:
Amino acids              49-54;257-262;343-348;437-442;757-762

Amidation site:
Amino acids              61-64

ATP/GTP-binding site motif A (P-loop):
Amino acids              193-200

Fibronectin type III domain:
Amino acids              22-106;118-203;215-302;314-398;
                         410-492;504-590;601-685;697-778

FIGURE 95A

```
CAATTCGGCCTCGCTCCTTGTGATTGCGCTAAACCTTCCGTCCTCAGCTGAGAACGCTCCACCACCTCCCCGGA
TCGCTCATCTCTTGGCTGCCCTCCCACTGTTCCTGATGTTATTTTACTCCCCGTATCCCCTACTCGTTCTTCAC
AATTCTGTAGGTGAGTGGTTCCAGCTGGTGCCTGGCCTGTGTCTCTTGGATGCCCTGTGGCTTCAGTCCGTCTC
CTGTTGCCCACCACCTCGTCCCTGGGCCGCCTGATACCCCAGCCCAACAGCTAAGGTGTGGATGGACAGTAGGG
GGCTGGCTTCTCTCACTGGTCAGGGGTCTTCTCCCCTGTCTGCCTCCCGGAGCTAGGACTGCAGAGGGGCCTAT
CATGGTGCTTGCAGGCCCCCTGGCTGTCTCGCTGTTGCTGCCCAGCCTCACACTGCTGGTGTCCCACCTCTCCA
GCTCCCAGGATGTCTCCAGTGAGCCCAGCAGTGAGCAGCAGCTGTGCGCCCTTAGCAAGCACCCCACCGTGGCC
TTTGAAGACCTGCAGCCGTGGGTCTCTAACTTCACCTACCCTGGAGCCCGGGATTTCTCCCAGCTGGCTTTGGA
CCCCTCCGGGAACCAGCTCATCGTGGGAGCCAGGAACTACCTCTTCAGACTCAGCCTTGCCAATGTCTCTCTTC
TTCAGGCCACAGAGTGGGCCTCCAGTGAGGACACGCGCCGCTCCTGCCAAAGCAAAGGGAAGACTGAGGAGGAG
TGTCAGAACTACGTGCGAGTCCTGATCGTCGCCGGCCGGAAGGTGTTCATGTGTGGAACCAATGCCTTTTCCCC
CATGTGCACCAGCAGACAGGTGGGGAACCTCAGCCGGACTATTGAGAAGATCAATGGTGTGGCCCGCTGCCCCT
ATGACCCACGCCACAACTCCACAGCTGTCATCTCCTCCCAGGGGGAGCTCTATGCAGCCACGGTCATCGACTTC
TCAGGTCGGGACCCTGCCATCTACCGCAGCCTGGGCAGTGGGCCACCGCTTCGCACTGCCCAATATAACTCCAAG
TGGCTTAATGAGCCAAACTTCGTGGCAGCCTATGATATTGGCTGTTTGCATACTTCTTCCTGCGGGAGAACGC
AGTGGAGCACGACTGTGGACGCACCGTGTACTCTCGCGTGGCCCGCGTGTGCAAGAATGACGTGGGGGGCCGAT
TCCTGCTGGAGGACACATGGACCACATTCATGAAGGCCCGGCTCAACTGCTCCCGCCCGGGCGAGGTCCCCTTC
TACTATAACGAGCTGCAGAGTGCCTTCCACTTGCCGGAGCAGGACCTCATCTATGGAGTTTTCACAACCAACGT
AAACAGCATCGCGGCTTCTGCTGTCTGCGCCTTCAACCTCAGTGCTATCTCCCAGGCTTTCAATGGCCCATTTC
GCTACCAGGAGAACCCCAGGGCTGCCTGGCTCCCCATAGCCAACCCCATCCCCAATTTCCAGTGTGGCACCCTG
CCTGAGACCGGTCCCAACGAGAACCTGACGGAGCGCAGCCTGCAGGACGCGCAGCGCCTCTTCCTGATGAGCGA
GGCCGTGCAGCCGGTGACACCCGAGCCCTGTGTCACCCAGGACAGCGTGCGCTTCTCACACCTCGTGGTGGACC
TGGTGCAGGCTAAAGACACGCTCTACCATGTACTCTACATTGGCACCGAGTCGGGCACCATCCTGAAGGCGCTG
TCCACGGCGAGCCGCAGCCTCCACGGCTGCTACCTGGAGGAGCTGCACGTGCTGCCCCCGGGCGCCGCGAGCC
CCTGCGCAGCCTGCGCATCCTGCACAGCGCCCGCGCGCTCTTCGTGGGGCTGAGAGACGGCGTCCTGCGGGTCC
CACTGGAGAGGTGCGCCGCCTACCGCAGCCAGGGGGCATGCCTGGGGGCCCGGGACCCGTACTGTGGCTGGGAC
GGGAAGCAGCAACGTTGCAGCACACTCGAGGACAGCTCCAACATGAGCCTCTGGACCCAGAACATCACCGCCTG
TCCTGTGCGGAATGTGACACGGGATGGGGGCTTCGGCCCATGGTCACCATGGCAACCATGTGAGCACTTGGATG
GGGACAACTCAGGCTCTTGCCTGTGTCGAGCTCGATCCTGTGATTCCCCTCGACCCCGCTGTGGGGGCCTTGAC
TGCCTGGGGCCAGCCATCCACATCGCCAACTGCTCCAGGAATGGGGCGTGGACCCCGTGGTCATCGTGGGCGCT
GTGCAGCACGTCCTGTGGCATCGGCTTCCAGGTCCGCCAGCGAAGTTGCAGCAACCCTGCTCCCCGCCACGGGGC
CGCATCTTCGTGGGCAAGAGCCGGGAGGAACGGTTCTGTAATGAGAACACGCCTTGCCCGGTGCCCATCTTCTG
GGCTTCCTGGGGCTCCTGGAGCAAGTGCAGCAGCAACTGTGGAGGGGCATGCAGTCGCGGCGTCGGGCCTGCG
AGAACGGCAACTCCTGCCTGGGCTGCGGCGAGTTCAAGACGTGCAACCCCGAGGGCTGCCCCGAAGTGCGGCGC
AACACCCCCTGGACGCCGTGGCTGCCCGTGAACGTGACGCAGGGCGGGGCACGGCAGGAGCAGGCAGGTTCCGCTT
CACCTGCCGCGCGCCCCTTGCAGACCCGCACGGCCTGCAGTTCGGCAGGAGAAGGACCGAGACGAGGACCTGTC
CCGCGGACGGCTCCGGCTCCTGCGACACCGACGCCCTGGTGGAGGTCCTCCTGCGCAGCGGGAGCACCTCCCCG
CACACGGTGAGCGGGGCTGGGCCGCCTGGGGCCCGTGGTCGTCCTGCTCCCGGGACTGCCAGCTGGGCTTCCG
CGTCCGCAAGAGAACGTGCACTAACCCGGAGCCCCGCAACGGGGGCCTGCCCTGCGTGGGCGATGCTGCCGAGT
ACCAGGACTGCAACCCCCAGGCTTGCCCAGTTCGGGGTGCTTGGTCCTGCTGGACCTCATGGTCTCCATGCTCA
GCTTCCTGTGGTGGGGGTCACTATCAACGCACCCGTTCCTGCACCAGCCCCGCACCCTCCCCAGGTGAGGACAT
CTGTCTCGGGCTGCACACGGAGGAGGCACTATGTGCCACACAGGCCTGCCCAGGCTGGTCGCCCTGGTCTGAGT
GGAGTAAGTGCACTGACGACGGAGCCCAGAGCCGAAGCCGGCACTGTGAGGAGCTCCTCCCAGGGTCCAGCGCC
TGTGCTGGAAACAGCAGCCAGAGCCGCCCCTGCCCCTACAGCGAGATTCCCGTCATCCTGCCAGCCTCCAGCAT
GGAGGAGGCCACCGACTGTGCAGGTAAAAGAAACCGGACCTACCTCATGCTGCGGTCCTCCCAGCCCTCCAGCA
CCCCACTCCAAAGTCTGGACTCTTTCCACATCCTGCTCCAGACAGCCAAGCTTTGTTGGGGTCCCCACTGCTTT
GAGATGGGTTCAATCTCATCCACTTGGTGGCCACGGGCATCTCCTGCTTCTTGGGCTCTGGGCTCCTGACCCTA
GCAGTGTACCTGTCTTGCCAGCACTGCCAGCGTCAGTCCCAGGAGTCCACACTGGTCCATCCTGCCACCCCCAACC
ATTTGCACTACAAGGGCGGAGGCACCCCGAAGAATGAAAAGTACACACCCATGGAATTCAAGACCCTGAACAAG
AATAACTTGATCCCTGATGACAGAGCCAACTTCTACCCATTGCAGCAGACCAATGTGTACACGACTACTTACTA
CCCAAGCCCCCTGAACAAACACAGCTTCCGGCCCGAGGCCTCACCTGGACAACGGTGCTTCCCCAACAGCTGAT
ACCGCCGTCCTGGGGACTTGGGCTTCTTGCCTTCATAAGGCACAGAGCAGATGGAGATGGGACAGTGGAGCCAG
TTTGGTTTTCTCCCTCTGCACTAGGCCAAGAACTTGCTGCCTTGCCTGTGGGGGTCCCATCCGGCTTCAGAGA
GCTCTGGCTGGCATTGACCATGGGGAAAGGCTGGTTTCAGGCTGACATATGGCCGCAGGTCCAGTTCAGCCC
AGGTCTCTCATGGTTATCTTCCAACCCACTGTCACGCTGACACTATGCTGCCATGCCTGGGCTGTGGACCTACT
GGGCATTTGAGGAATTGGAGAATGGAGATGGCAAGAGGGCAGGCTTTTAAGTTTGGGTTGGAGACAACTTCCTG
TGGCCCCCACAAGCTGAGTCTGGCCTTCTCCAGCTGGCCCCAAAAAAGGCCTTTGCTACATCCTGATTATCTCT
GAAAGTAATCAATCAAGTGGCTCCAGTAGCTCTGGATTTTCTGCCAGGGCTGGGCCATTGTGGTGCTGCCCAG
TATGACATGGGACCAAGGCCAGCGCAGGTTATCCACCTCTGCCTGGAAGTCTATACTCTACCCAGGGCATCCT
CTGGTCAGAGGCAGTGAGTACTGGGAACTGGAGGCTGACCTGTGCTTAGAAGTCCTTTAATCTGGGCTGGTACA
GGCCTCAGCCTTGCCCTCAATGCACGAAAGGTGGCCCAGGAGAGAGGATCAATGCCATAGGAGGCAGAAGTCTG
GCCTCTGTGCCTCTATGGAGACTATCTTCCAGTTGCTGCTCAACAGAGTTGTTGGCTGAGACCTGCTTGGGAGT
```

FIGURE 95B

```
CTCTGCTGGCCCTTCATCTGTTCAGGAACACACACACACACACACTCACACACGCACACACAATCACAATTTGC
TACAGCAACAAAAAAGACATTGGGCTGTGGCATTATTAATTAAAGATGATATCCAGTC
```

FIGURE 96

```
></usr/seqdb2/sst/DNA/Dnaseqs.min/ss.DNA194909
><subunit 1 of 1, 1092 aa, 1 stop
><MW: 119324, pI: 8.13, NX(S/T): 14
MPCGFSPSPVAHHLVPGPPDTPAQQLRCGWTVGGWLLSLVRGLLPCLPPGARTAEGPIMV
LAGPLAVSLLLPSLTLLVSHLSSSQDVSSEPSSEQQLCALSKHPTVAFEDLQPWVSNFTY
PGARDFSQLALDPSGNQLIVGARNYLFRLSLANVSLLQATEWASSEDTRRSCQSKGKTEE
ECQNYVRVLIVAGRKVFMCGTNAFSPMCTSRQVGNLSRTIEKINGVARCPYDPRHNSTAV
ISSQGELYAATVIDFSGRDPAIYRSLGSGPPLRTAQYNSKWLNEPNFVAAYDIGLFAYFF
LRENAVEHDCGRTVYSRVARVCKNDVGGRFLLEDTWTTFMKARLNCSRPGEVPFYYNELQ
SAFHLPEQDLIYGVFTTNVNSIAASAVCAFNLSAISQAFNGPFRYQENPRAAWLPIANPI
PNFQCGTLPETGPNENLTERSLQDAQRLFLMSEAVQPVTPEPCVTQDSVRFSHLVVDLVQ
AKDTLYHVLYIGTESGTILKALSTASRSLHGCYLEELHVLPPGRREPLRSLRILHSARAL
FVGLRDGVLRVPLERCAAYRSQGACLGARDPYCGWDGKQQRCSTLEDSSNMSLWTQNITA
CPVRNVTRDGGFGPWSPWQPCEHLDGDNSGSCLCRARSCDSPRPRCGGLDCLGPAIHIAN
CSRNGAWTPWSSWALCSTSCGIGFQVRQRSCSNPAPRHGGRIFVGKSREERFCNENTPCP
VPIFWASWGSWSKCSSNCGGGMQSRRRACENGNSCLGCGEFKTCNPEGCPEVRRNTPWTP
WLPVNVTQGGARQEQRFRFTCRAPLADPHGLQFGRRRTETRTCPADGSGSCDTDALVEVL
LRSGSTSPHTVSGGWAAWGPWSSCSRDCELGFRVRKRTCTNPEPRNGGLPCVGDAAEYQD
CNPQACPVRGAWSCWTSWSPCSASCGGGHYQRTRSCTSPAPSPGEDICLGLHTEEALCAT
QACPGWSPWSEWSKCTDDGAQSRSRHCEELLPGSSACAGNSSQSRPCPYSEIPVILPASS
MEEATDCAGKRNRTYLMLRSSQPSSTPLQSLDSFHILLQTAKLCWGPHCFEMGSISSTWW
PRASPASWALGS
```

Important features of the protein:

Signal peptide:
Amino acids          1-42

Transmembrane domain:
Amino acids          56-79;373-395

N-glycosylation sites:
Amino acids          117-120;153-156;215-218;236-239;345-348;391-394;
436-439;590-593;597-600;605-608;660-663;785-788;
1000-1003;1032-1035 cAMP- and cGMP-dependent protein kinase phosphorylation sites:
Amino acids          773-776;815-818;875-878

Tyrosine kinase phosphorylation site:
Amino acids          177-185;348-355

N-myristoylation sites:
Amino acids          42-47;50-55;373-378;492-497;543-548;563-568;
630-635;647-652;740-745;810-815;827-832;829-834;
853-858;887-892;910-915;993-998;1073-1078

Amidation sites:
Amino acids          192-195;522-525;813-816;1028-1031

ATP/GTP-binding site motif A (P-loop):
Amino acids          700-707

Cytochrome c oxidase subunit II, copper A binding region signature:
Amino acids          921-929

Growth factor and cytokines receptors family signature 2:
Amino acids          967-973

Sema domain:
Amino acids          126-537

Plexin repeat:
Amino acids          555-602

Thrombospondin type 1 domain:
Amino acids          613-661;668-719;726-769;856-906;913-963;967-1007

FIGURE 97

```
CAAGCCCTCCCAGCATCCCCTCTCCTGTGTTCCTCCCCAGTTCTCTACTCAGAGTTGACTGACCAGAGATTTAT
CAGCTTGGAGGGCTGGAGGTGTGGATCCATGGGGTAGCCTCAACGCATCTGCCCCTCCACCCCAGCCAGCTCAT
GGGCCACGTGGCCTGGCCCAGCCTCAGCACCCAGGGCCAGTGAACAGAGCCCTGGCTGGAGTCCAAACATGTGG
GGCCTGGTGAGGCTCCTGCTGGCCTGGCTGGGTGGCTGGGGCTGCATGGGGCGTCTGGCAGCCCCAGCCCGGGC
CTGGGCAGGGTCCCGGGAACACCCAGGGCCTGCTCTGCTGCGGACTCGAAGGAGCTGGGTCTGGAACCAGTTCT
TTGTCATTGAGGAATATGCTGGTCCAGAGCCTGTTCTCATTGGCAAGCTGCACTCGGATGTTGACCGGGGAGAG
GGCCGCACCAAGTACCTGTTGACCGGGGAGGGGGCAGGCACCGTATTTGTGATTGATGAGGCCACAGGCAATAT
TCATGTTACCAAGAGCCTTGACCGGGAGGAAAAGGCGCAATATGTGCTACTGGCCCAAGCCGTGGACCGAGCCT
CCAACCGGCCCTGGAGCCCCATCAGAGTTCATCATCAAAGTGCAAGACATCAACGACAATCCACCCATTTTT
CCCCTTGGGCCCTACCATGCCACCGTGCCCGAGATGTCCAATGTCGGGACATCAGTGATCCAGGTGACTGCTCA
CGATGCTGATGACCCCAGCTATGGGAACAGTGCCAAGCTGGTGTACACTGTTCTGGATGGACTGCCTTTCTTCT
CTGTGGACCCCAGACTGGAGTGGTGCGTACAGCCATCCCCAACATGGACCGGGAGACACAGGAGGAGTTCTTG
GTGGTGATCCAGGCCAAGGACATGGGCGGCCACATGGGGGGGCTGTCAGGCAGCACTACGGTGACTGTCACGCT
CAGCGATGTCAACGACAACCCCCCAAGTTCCCACAGAGCCTATACCAGTTCTCCGTGGTGGAGACAGCTGGAC
CTGGCACACTGGTGGGCCGGCTCCGGGCCCAGGACCCAGACCTGGGGACAACGCCCTGATGGCATACAGCATC
CTGGATGGGGAGGGGTCTGAGGCCTTCAGCATCAGCACAGACTTGCAGGGTCGAGACGGGCTCCTCACTGTCCG
CAAGCCCCTAGACTTTGAGAGCCAGCGCTCCTACTCCTTCCGTGTCGAGGCCACCAACACGCTCATTGACCCAGCC
TATCTGCGGCGAGGGCCCTTCAAGGATGTGGCCTCTGTGCGTGTGGCAGTGCAAGATGCCCCAGAGCCACCTGC
CTTCACCCAGGCTGCCTACCACCTGACAGTGCCTGAGAACAAGGCCCCGGGGACCCTGGTAGGCCAGATCTCCG
CGGCTGACCTGGACTCCCCTGCCAGCCCAATCAGATACTCCATCCTCCCCCACTCAGATCCGGAGCGTTGCTTC
TCTATCCAGCCCGAGGAAGGCACCATCCATACAGCAGCACCCTGGATCGCGAGGCTCGCGCCTGGCACAACCT
CACTGTGCTGGCTACAGAGCTCGACAGTTCTGCACAGGCCTCGCGCGTGCAAGTGGCCATCCAGACCCTGGATG
AGAATGACAATGCTCCCCAGCTGGCTGAGCCCTACGATACTTTTGTGTGTGACTCTGCAGCTCCTGGCCAGCTG
ATTCAGGTCATCCGGGCCCTGGACAGAGATGAAGTTGGCAACAGTAGCCATGTCTCCTTTCAAGGTCCTCTGGG
CCCTGATGCCAACTTTACTGTCCAGGACAACCGAGATGGCTCCGCCAGCCTGCTGCTGCCCTCCCGCCCTGCTC
CACCCCGCCATGCCCCCTACTTGGTTCCCATAGAACTGTGGGACTGGGGGCAGCCGGCGCTGAGCAGCACTGCC
ACAGTGACTGTTAGTGTGTGCCGCTGCCAGCCTGACGGCTCTGTGGCATCCTGCTGGCCTGAGGCTCACCTCTC
AGCTGCTGGGCTCAGCACCGGCGCCCTGCTTGCCATCATCACCTGTGTGGGTGCCCTGCTTGCCCTGGTGGTGC
TCTTCGTGGCCCTGCGGCGGCAGAAGCAAGAAGCACTGATGGTACTGGAGGAGGAGGACGTCCGAGAGAACATC
ATCACCTACGACGACGAGGGCGGCGGCGAGGAGGACACCGAGGCCTTCGACATCACGGCCTTGCAGAACCCGGA
CGGGGCGGCCCCCCGGCCGCCCCTCCCGCGCGCCGAGACGTGTTGCCCCGGGCCCGGGTGTCGCGCCAGC
CCAGACCCCCCGGCCCCGCCGACGTGGCGCAGCTCCTGGCGCTGCGGCTCCGCGAGGCGGACGAGGACCCCGGC
GTACCCCCGTACGACTCGGTGCAGGTGTACGGCTACGAGGGCCGGGCTCCTCTTGCGGCTCCCTCAGCTCCCT
GGGCTCCGGCAGCGAAGCCGGCGGCGCCCCGGCCCCGCGGAGCCGCTGGACGACTGGGGTCCGCTCTTCCGCACC
CTGGCCGAGCTGTATGGGGCCAAGGAGCCCCCGGCCCCTGAGCGCCCGGGCTGGCCCGGCCCACCGCGGGGGG
GGGGCAGCGGGCACAGGCCCTCTGAGTGAGCCCCACGGGGTCCAGGCGGGCGGCAGCAGCCCAGGGGCCCCAGG
CCTCCTCCCTGTCCTTGTGTCCCTCCTTGCTTCCCCGGGGCACCCTCGCTCTCACCTCCCTCCTCCTGAGTCGG
TGTGTGTGTCTCTCTCCAGGAATCTTTGTCTCTATCTGTGACACGCTCCTCTGTCCGGGCCTGGGTTTCCTGCC
CTGGCCCTGGCCCTGCGATCTCTCACTGTGATTCCTCTCCTTCCTCCGTGGCGTTTTGTCTCTGCAGTTCTGAA
GCTCACACATAGTCTCCCTGCGTCTTCCTTGCCCATACACATGCTCTGTGTCTGTCTCCTGCCCACATCTCCCT
TCCTTCTCTCTGGGTCCCTGTGACTGGCTTTTTGTTTTTTTCTGTTGTCCATCCCAAAATCAAGAGAAACTTCC
AGCCACTGCTGCCCACCCTCCTGCAGGGGATGTTGTGCCCCAGACCTGCCTGCATGGTTCCATCCATTACTCAT
GGCCTCAGCCTCATCCTGGCTCCACTGGCCTCCAGCTGAGAGAGGGAACCAGCCTGCCTCCCAGGGCAAGAGCT
CCAGCCTCCCGTGTGGCCGCCTCCCTGGAGCTCTGCCCAGCTGCCAGCTTCCCCTGGGCATCCCAGCCCTGGGC
ATTGTCTTGTGTGCTTCCTGAGGGAGTAGGGAAAGGAAAGGGGGAGGCGGCTGGGGAAGGGGAAAGAGGGAGGA
AGGGGAGGGGCCTCCATCTCTAATTTCATAATAAACAAACACTTTATTTTGTAAAAC
```

FIGURE 98

MWGLVRLLLAWLGGWGCMGRLAAPARAWAGSREHPGPALLRTRRSWVWNQFFVIEEYAGP
EPVLIGKLHSDVDRGEGRTKYLLTGEGAGTVFVIDEATGNIHVTKSLDREEKAQYVLLAQ
AVDRASNRPLEPPSEFIIKVQDINDNPPIFPLGPYHATVPEMSNVGTSVIQVTAHDADDP
SYGNSAKLVYTVLDGLPFFSVDPQTGVVRTAIPNMDRETQEEFLVVIQAKDMGGHMGGLS
GSTTVTVTLSDVNDNPPKFPQSLYQFSVVETAGPGTLVGRLRAQDPDLGDNALMAYSILD
GEGSEAFSISTDLQGRDGLLTVRKPLDFESQRSYSFRVEATNTLIDPAYLRRGPFKDVAS
VRVAVQDAPEPPAFTQAAYHLTVPENKAPGTLVGQISAADLDSPASPIRYSILPHSDPER
CFSIQPEEGTIHTAAPLDREARAWHNLTVLATELDSSAQASRVQVAIQTLDENDNAPQLA
EPYDTFVCDSAAPGQLIQVIRALDRDEVGNSSHVSFQGPLGPDANFTVQDNRDGSASLLL
PSRPAPPRHAPYLVPIELWDWGQPALSSTATVTVSVCRCQPDGSVASCWPEAHLSAAGLS
TGALLAIITCVGALLALVVLFVALRRQKQEALMVLEEEDVRENIITYDDEGGGEEDTEAF
DITALQNPDGAAPPAPGPPARRDVLPRARVSRQPRPPGPADVAQLLALRLREADEDPGVP
PYDSVQVYGYEGRGSSCGSLSSLGSGSEAGGAPGPAEPLDDWGPLFRTLAELYGAKEPPA
P

Signal peptide:
Amino acids        1-16

Transmembrane domain:
Amino acids        597-624

N-glycosylation sites:
Amino acids        446-449;510-513;525-528

N-myristoylation sites:
Amino acids        13-18;206-211;233-238;237-242;238-243;275-280;390-395;
                   394-399;429-434;583-588;598-603;602-607;612-617;
                   734-739;738-743;746-751

ATP synthase c subunit signature:
Amino acids        691-712

Cadherins extracellular repeated domain signature:
Amino acids        138-148;247-257

Cadherin domain:
Amino acids        50-141;155-250;264-366;379-470;483-577

Cadherin cytoplasmic region:
Amino acids        625-776

FIGURE 99

```
GCCAACACTGGCCAAACATATGGGGCTGGAATCTCAACATCGGTCACTGGGACCTCAATATT
TGGAGCCGGAACCCCACAATTTGGAACACAGACCCCAATATTTGGAGCAGAACCCCAAGATT
TGACATCTAAAACCTCAAGCCTGGAGCTGAACTCTGAATTCTGGGCCTGGGACCTTGAAATC
TGGGACTGGATTTCCAGTACTGTACCCTGGAACCCACTCTTGGGGACCTGAACCCTGGGATT
CAGGCCTCAAATTCCAAGATCTGGACTGTGGATTCCAAGGGGCCTGAACCCGAGTTTGGGC
CTGAAGTCCTTGCTGCAGACCTGAGTGCTTAAATCTGGGCTTGAGACCTCCCAATCTTGAC
TCAGCACCCAATATCTGAATGCAGAACCCCGGGATCGGATCTCAGACTCTAAACCCCACCG
TTTGGCTGCTTAGCATCCCAAGACTGGACCTGGGAGACCCTGACCCTGAACAACCCAAACTG
GACCCGTAAAACTGGACCCTAGAGGCCCAATATTTAGGGGTCTGGAACCCCGAGTATTAAGG
TCTGGAGACTCCGTTGCCACAGATTTGAGCCGAGTCAGGACACAGTCCCTCTACAGAAGCCT
TGGGGACAGGAAAAGCATGACCAGATGCTCCCTCCAGAGCCCTGACCTCTGACTCCCCTGGA
GCTAGGACTCTGCTCCCTGGGGCTGCTTCTAGCTCAGGACACCCTGCCCGCGATGGCCATC
CTCCCGTTGCTCCTGTGCCTGCTGCCGCTGGCCCCTGCCTCATCCCCACCCAGTCAGCCAC
ACCCAGCCCATGTCCCCGCCGCTGCCGCTGCCAGACACAGTCGCTGCCCCTAAGCGTGCTGT
GCCCAGGGGCAGGCCTCCTGTTCGTGCCACCCTCGCTGGACCGCCGGGCAGCCGAGCTGCGG
CTGGCAGACAACTTCATCGCCTCCGTGCGCCGCCGCGACCTGGCCAACATGACAGGCCTGCT
GCATCTGAGCCTGTCGCGGAACACCATCCGCCACGTGGCTGCCGGCGCCTTCGCCGACCTGC
GGGCCCTGCGTGCCCTGCACCTGGATGGCAACCGGCTGACCTCACTGGGCGAGGGCCAGCTG
CGCGGCCTGGTCAACTTGCGCCACCTCATCCTCAGCAACAACCAGCTGGCAGCGCTGGCGGC
CGGCGCCCTGGATGATTGTGCCGAGACACTGGAGGACCTCGACCTCCTACAACAACCTCG
AGCAGCTGCCCTGGGAGGCCCTGGGCCGCCTGGGCAACGTCAACACGTTGGGCCTCGACCAC
AACCTGCTGGCTTCTGTGCCCGGCGCTTTTTCCCGCCTGCACAAGCTGGCCCGGCTGGACAT
GACCTCCAACCGCCTGACCACAATCCCACCCGACCCACTCTTCTCCCGCCTGCCCCTGCTCG
CCAGGCCCCGGGGCTCGCCCGCCTCTGCCCTGGTGCTGGCCTTTGGCGGGAACCCCCTGCAC
TGCAACTGCGAGCTGGTGTGGCTGCGTCGCCTGGCGCGGGAGGACGACCTCGAGGCCTGCGC
GTCCCCACCTGCTCTGGGCGGCCGCTACTTCTGGGCGGTGGGCGAGGAGGAGTTTGTCTGCG
AGCCGCCCGTGGTGACTCACCGCTCACCACCTCTGGCTGTGCCCGCAGGTCGGCCGGCTGCC
CTGCGCTGCCGGGCAGTGGGGGACCCAGAGCCCCGTGTGCGTTGGGTGTCACCCCAGGGCCG
GCTGCTAGGCAACTCAAGCCGTGCCCGCGCCTTCCCCAATGGGACGCTGGAGCTGCTGGTCA
CCGAGCCGGGTGATGGTGGCATCTTCACCTGCATTGCGGCCAATGCAGCTGGCGAGGCCACA
GCTGCTGTGGAGCTGACTGTGGGTCCCCACCACCTCCTCAGCTAGCCAACAGCACCAGCTG
TGACCCCCGCGGGACGGGGATCCTGATGCTCTCACCCCACCCTCCGCTGCCTCTGCTTCTG
CCAAGGTGGCCGACACTGGGCCCCTACCGACCGTGGCGTCCAGGTGACTGAGCACGGGGCC
ACAGCTGCTCTTGTCCAGTGGCCGGATCAGCGGCCTATCCCGGGCATCGCATGTACCAGAT
CCAGTACAACAGCTCGGCTGATGACATCCTCGTCTACAGGATGATCCCGGCGGAGAGCCGCT
CGTTCCTGCTGACGGACCTGGCGTCAGGCCGGACCTACGATCTGTGCGTGCTCGCCGTGTAT
GAGGACAGCGCCACGGGGCTCACGGCCACGCGGCCTGTGGGCTGCGCCCGCTTCTCCACCGAA
CCTGCGCTGCGGCCATGCGGGGCGCCGCACGCTCCCTTCCTGGGCGGCACGATGATCATCGC
GCTGGGCGGCGTCATCGTAGCCTCGGTACTGGTCTTCATCTTCGTGCTGCTAATGCGCTACA
AGGTGCACGGCGGCCAGCCCCCGGCAAGGCCAAGATTCCCGCGCCTGTTAGCAGCGTTTGC
TCCCAGACCAACGGCGCCCTGGGCCCCACGCCCACGCCCGCCCCGCCCGCCCCGGAGCCCGC
GGCGCTCAGGGCCCACACCGTGGTCCAGCTGGACTGCGAGCCCTGGGGGCCCGGCCACGAAC
CTGTGGGACCCTAGCCAGGCGCCCCCCCTCTAAGGGTCCTCTGGCCCCACGGACAGCAGGA
CCCGGACACCCTGTGGGACCTGGCCTCAAACTCACCAAATCGCTCATGGTTTTTAAAACTCT
GATGGGGAGGGTGTCGGGGACACCGGGGCAAAACAAGAAAGTCCTATTTTTCCAAAAAAAAA
AAAAAAAAAAAAAAAAAAAAAAAAAAAAAAAAAAAAAAAAAAAAAAAAAAAAAAAAAAAAAA
```

FIGURE 100

```
></usr/seqdb2/sst/DNA/Dnaseqs.min/ss.DNA213858
><subunit 1 of 1, 627 aa, 1 stop
><MW: 66189, pI: 7.31, NX(S/T): 5
MAILPLLLCLLPLAPASSPPQSATPSPCPRRCRCQTQSLPLSVLCPGAGLLFVPPSLDRR
AAELRLADNFIASVRRRDLANMTGLLHLSLSRNTIRHVAAGAFADLRALRALHLDGNRLT
SLGEGQLRGLVNLRHLILSNNQLAALAAGALDDCAETLEDLDLSYNNLEQLPWEALGRLG
NVNTLGLDHNLLASVPGAFSRLHKLARLDMTSNRLTTIPPDPLFSRLPLLARPRGSPASA
LVLAFGGNPLHCNCELVWLRRLAREDDLEACASPPALGGRYFWAVGEEEFVCEPPVVTHR
SPPLAVPAGRPAALRCRAVGDPEPRVRWVSPQGRLLGNSSRARAFPNGTLELLVTEPGDG
GIFTCIAANAAGEATAAVELTVGPPPPQLANSTSCDPPRDGDPDALTPPSAASASAKVA
DTGPPTDRGVQVTEHGATAALVQWPDQRPIPGIRMYQIQYNSSADDILVYRMIPAESRSF
LLTDLASGRTYDLCVLAVYEDSATGLTATRPVGCARFSTEPALRPCGAPHAPFLGGTMII
ALGGVIVASVLVFIFVLLMRYKVHGGQPPGKAKIPAPVSSVCSQTNGALGPTPTPAPPAP
EPAALRAHTVVQLDCEPWGPGHEPVGP
```

Important features of the protein:

Signal peptide:
Amino acids          1-16

Transmembrane domain:
Amino acids          35-55; 536-556

N-glycosylation sites:
Amino acids          81-84;338-341;347-350;392-395;461-464

N-myristoylation sites:
Amino acids          116-121;125-130;180-185;186-191;235-240;
                     360-365;361-366;429-434;436-441;505-510;
                     544-549;566-571

Leucine Rich Repeat:
Amino acids          60-83;84-107;108-131;132-155;157-180;
                     181-203;204-227

Leucine rich repeat C-terminal domain:
Amino acids          248-293

Immunoglobulin domain:
Amino acids          309-367

Fibronectin type III domain:
Amino acids          424-504

FIGURE 101

```
    CGACTCCATAACCGTGGCCTTGGCCCCAGTCCCCCTGACTTCCGGACTTCAGACCAGATACTGCCCATATCCCC
    TTATGAAGTCTTGGCCAGGCAACCCCTAGGGTGTACGTTTTCTAAAGATTAAAGAGGCGGTGCTAAGCTGCAGA
    CGGACTTGCGACTCAGCCACTGGTGTAAGTCAGGCGGGAGGTGGCGCCCAATAAGCTCAAGAGAGGAGGCGGGT
 5  TCTGGAAAAAGGCCAATAGCCTGTGAAGGCGAGTCTAGCAGCAACCAATAGCTATGAGCGAGAGGCGGGACTCT
    GAGGGAAGTCAATCGCTGCCGCAGGTACCGCCAATGGCTTTTGGCGGGGCGTTCCCCAACCCTGCCCTCTCTC
    ATGACCCCGCTCCGGGATTATGGCCGGACTGGGCTGCTGGCGCTGCGGACGCTGCCAGGGCCCAGCTGGGTGC
    GAGGCTCGGGCCCTTCCGTGCTGAGCCGCCTGCAGGACGCGGCCGTGGTGCGGCCTGGCTTCCTGAGCACGGCA
    GAGGAGGAGACGCTGAGCCGAGAACTGGAGCCCGAGCTGCGCCGCCGCCGCTACGAATACGATCACTGGGACGC
10  GGCCATCCACGGCTTCCGAGAGACAGAGAAGTCGCGCTGGTCAGAAGCCAGCCGGGCCATCCTGCAGCGCGTGC
    AGGCGGCCGCCTTTGGCCCCGGCCAGACCCTGCTCTCCTCCGTGCACGTGCTGGACCTGGAAGCCCGCGGCTAC
    ATCAAGCCCCACGTGGACAGCATCAAGTTCTGCGGGGCCACCATCGCCGGCCTGTCTCTCCTGTCTCCCAGCGT
    TATGCGGCTGGTGCACACCCAGGAGCCGGGGGAGTGGCTGGAACTCTTGCTGGAGCCGGGCTCCCTCTACATCC
    TTAGGGGCTCAGCCCGTTATGACTTCTCCCATGAGATCCTTCGGGATGAAGAGTCCTTCTTTGGGGAACGCCGG
15  ATTCCCCGGGGCCGGCGCATCTCCGTGATCTGCCGCTCCCTCCCTGAGGGCATGGGGCCAGGGGAGTCTGGACA
    GCCGCCCCCAGCCTGCTGACCCCCAGCTTTCTACAGACACCAGATTTGTGAATAAAGTTGGGGAATGGACAGCCT
```

FIGURE 102

MAGTGLLALRTLPGPSWVRGSGPSVLSRLQDAAVVRPGFLSTAEEETLSRELEPELRRRRYEYDHWDAAIHGFR
ETEKSRWSEASRAILQRVQAAAFGPGQTLLSSVHVLDLEARGYIKPHVDSIKFCGATIAGLSLLSPSVMRLVHT
QEPGEWLELLLEPGSLYILRGSARYDFSHEILRDEESFFGERRIPRGRRISVICRSLPEGMGPGESGQPPPAC

Important features of the protein:

Signal peptide:
1-18

Transmembrane domain:
None cAMP- and cGMP-dependent protein kinase phosphorylation site.
    196-199

N-myristoylation site.
    20-25
    129-134
    208-213

Amidation site.
    194-197

FIGURE 103

```
CTCCCCGGCGCCGCAGGCAGCGTCCTCCTCCGAAGCAGCTGCACCTGCAACTGGGCAGCCTGGACCCTCGTGCC
CTGTTCCCGGGACCTCGCGCAGGGGGCGCCCCGGGACACCCCCTGCGGGCCGGGTGGAGGAGGAAGAGGAGGAG
GAGGAAGAAGACGTGGACAAGGACCCCCATCCTACCCAGAACACCTGCCTGCGCTGCCGCCACTTCTCTTTAAG
GGAGAGGAAAAGAGAGCCTAGGAGAACCATGGGGGGCTGCGAAGTCCGGGAATTTCTTTTGCAATTTGGTTTCT
TCTTGCCTCTGCTGACAGCGTGGCCAGGCGACTGCAGTCACGTCTCCAACAACCAAGTTGTGTTGCTTGATACA
ACAACTGTACTGGGAGAGCTAGGATGGAAAACATATCCATTAAATGGGTGGGATGCCATCACTGAAATGGATGA
ACATAATAGGCCCATTCACACATACCAGGTATGTAATGTAATGGAACCAAACCAAAACAACTGGCTTCGTACAA
ACTGGATCTCCCGTGATGCAGCTCAGAAAATTTATGTGGAAATGAAATTCACACTAAGGGATTGTAACAGCATC
CCATGGGTCTTGGGGACTTGCAAAGAAACATTTAATCTGTTTTATATGGAATCAGATGAGTCCCACGGAATTAA
ATTCAAGCCAAACCAGTATACAAAGATCGACACAATTGCTGCTGATGAGAGTTTTACCCAGATGGATTTGGGTG
ATCGCATCCTCAAACTCAACACTGAAATTCGTGAGGTGGGGCCTATAGAAAGGAAAGGATTTTATCTGGCTTTT
CAAGACATTGGGGCGTGCATTGCCCTGGTTTCAGTCCGTGTTTTCTACAAGAAATGCCCCTTCACTGTTCGTAA
CTTGGCCATGTTTCCTGATACCATTCCAAGGGTTGATTCCTCCTCTTTGGTTGAAGTACGGGGTTCTTGTGTCA
AGAGTGCTGAAGAGCGTGACACTCCTAAACTGTATTGTGGAGCTGATGGAGATTGGCTGGTTCCTCTTGGAAGG
TGCATCTGCAGTACAGGATATGAAGAAATTGAGGGTTCTTGCCATGCTTGCAGACCAGGATTCTATAAAGCTTT
TGCTGGGAACACAAAATGTTCTAAATGTCCTCCACACAGTTTAACATACATGGAAGCAACTTCTGTCTGTCAGT
GTGAAAAGGGTTATTTCCGAGCTGAAAAGACCCACCTTCTATGGCATGTACCAGGCCACCTTCAGCTCCTAGG
AATGTGGTTTTTAACATCAATGAAACAGCCCTTATTTTGGAATGGAGCCCACCAAGTGACACAGGAGGGAGAAA
AGATCTCACATACAGTGTAATCTGTAAGAAATGTGGCTTAGACACCAGCCAGTGTGAGGACTGTGGTGGAGGAC
TCCGCTTCATCCCAAGACATACAGGCCTGATCAACAATTCCGTGATAGTACTTGACTTTGTGTCTCACGTGAAT
TACACCTTTGAAATAGAAGCAATGAATGGAGTTTCTGAGTTGAGTTTTTCTCCCAAGCCATTCACAGCTATTAC
AGTGACCACGGATCAAGATGCACCTTCCCTGATAGGTGTGGTAAGGAAGGACTGGGCATCCAAAATAGCATTGCC
CTATCATGGCAAGCACCTGCTTTTTCCAATGGAGCCATTCTGGACTACGAGATCAAGTACTATGAGAAAGAACA
TGAGCAGCTGACCTACTCTTCCACAAGGTCCAAAGCCCCCAGTGTCATCATCACAGGTCTTAAGCCAGCCACCA
AATATGTATTTCACATCCGAGTGAGAACTGCGACAGGATACAGTGGCTACAGTCAGAAATTTGAATTTGAAACA
GGAGATGAAACTTCTGACATGGCAGCAGAACAAGGACAGATTCTCGTGATAGCCACCGCCGCTGTTGGCGGATT
CACTCTCCTCGTCATCCTCACTTTATTCTTCTTGATCACTGGGAGATGTCAGTGGTACATAAAAGCCAAGATGA
AGTCAGAAGAGAAGAGAAGAAACCACTTACAGAATGGGCATTTGCGCTTCCCGGGAATTAAAACTTACATTGAT
CCAGATACATATGAAGACCCATCCCTAGCAGTCCATGAATTTGCAAAGGAGATTGATCCCTCAAGAATTCGTAT
TGAGAGAGTCATTGGGGCAGGTGAATTTGGAGAAGTCTGTAGTGGGCGTTTGAAGACACCAGGGAAAAGAGAGA
TCCCAGTTGCCATTAAAACTTTGAAAGGTGGCCACATGGATCGGCAAGAAGAGATTTTCTAAGAGAAGCTAGT
ATCATGGGCCAGTTTGACCATCCAAACATCATTCGCCTAGAAGGGGTTGTCACCAAAAGATCCTTCCCGGCCAT
TGGGGTGGAGGCGTTTTGCCCCAGCTTCCTGAGGGCAGGGTTTTAAATAGCATCCAGGCCCCGCATCCAGTGC
CAGGGGGAGGATCTTTGCCCCCCAGGATTCCTGCTGGCAGACCAGTAATGATTGTGGTGGAATATATGGAGAAT
GGATCCCTAGACTCCTTTTTGCGGAAGCATGATGGCCACTTCACAGTCATCCAGTTGGTCGGAATGCTCCGAGG
CATTGCATCAGGCATGAAGTATCTTTCTGATATGGGTTATGTTCATCGAGACCTAGCGGCTCGGAATATACTGG
TCAATAGCAACTTAGTATGCAAAGTTTCTGATTTTGGTCTCTCCAGAGTGCTGGAAGATGATCCAGAAGCTGCT
TATACAACAACTGGTGGAAAAATCCCCATAAGGTGGACAGCCCCAGAAGCCATCGCCTACAGAAAATTCTCCTC
AGCAAGCGATGCATGGAGCTATGGCATTGTCATGTGGGAGGTCATGTCCTATGGAGAGACCTTATTGGGAAATG
TCTAACCAAGATGTCATTCTGTCCATTGAAGAAGGGTACAGACTTCCAGCTCCCATGGGCTGTCCAGCATCTCT
ACACCAGCTGATGCTCCACTGCTGGCAGAAGGAGAGAAATCACAGACCAAAATTTACTGACATTGTCAGCTTCC
TTGACAAACTGATCCGAAATCCCAGTGCCCTTCACACCCTGGTGGAGGACATCCTTGTAATGCCAGAGTCCCCT
GGTGAAGTTCCGGAATATCCTTTGTTTGTCACAGTTGGTGACTGGCTAGATTCTATAAAGATGGGGCAATACAA
GAATAACTTCGTGGCAGCAGGGTTTACAACATTTGACCTGATTTCAAGAATGAGCATTGATGACATTAGAAGAA
TTGGAGTCATACTTATTGGACACCAGAGACGAATAGTCAGCAGCATACAGACTTTACGTTTACACATGATGCAC
ATACAGGAGAAGGGATTTCATGTATGAAAGTACCACAAGCACCTGTGTTTTGTGCCTCAGCATTTCTAAAATGA
ACGATATCCTCTCTACTACTCTCTCTTCTGATTCTCCAAACATCACTTCACAAACTGCAGTCTTCTGTTCAGAC
TATAGGCACACACCTTATGTTTATGCTTCCAACCAGGATTTTAAAATCATGCTACATAAATCCGTTCTGAATAA
CCTGCAACTAAAAAAAAAAAAAAAAAAAA
```

FIGURE 104

```
></usr/seqdb2/sst/DNA/Dnaseqs.min/ss.DNA222653
><subunit 1 of 1, 1036 aa, 1 stop
><MW: 116379, pI: 6.94, NX(S/T): 5
MGGCEVREFLLQFGFFLPLLTAWPGDCSHVSNNQVVLLDTTTVLGELGWKTYPLNGWDAI
TEMDEHNRPIHTYQVCNVMEPNQNNWLRTNWISRDAAQKIYVEMKFTLRDCNSIPWVLGT
CKETFNLFYMESDESHGIKFKPNQYTKIDTIAADESFTQMDLGDRILKLNTEIREVGPIE
RKGFYLAFQDIGACIALVSVRVFYKKCPFTVRNLAMFPDTIPRVDSSSLVEVRGSCVKSA
EERDTPKLYCGADGDWLVPLGRCICSTGYEEIEGSCHACRPGFYKAFAGNTKCSKCPPHS
LTYMEATSVCQCEKGYFRAEKDPPSMACTRPPSAPRNVVFNINETALILEWSPPSDTGGR
KDLTYSVICKKCGLDTSQCEDCGGGLRFIPRHTGLINNSVIVLDFVSHVNYTFEIEAMNG
VSELSFSPKPFTAITVTTDQDAPSLIGVVRKDWASQNSIALSWQAPAFSNGAILDYEIKY
YEKEHEQLTYSSTRSKAPSVIITGLKPATKYVFHIRVRTATGYSGYSQKFEFETGDETSD
MAAEQGQILVIATAAVGGFTLLVILTLFFLITGRCQWYIKAKMKSEEKRRNHLQNGHLRF
PGIKTYIDPDTYEDPSLAVHEFAKEIDPSRIRIERVIGAGEFGEVCSGRLKTPGKREIPV
AIKTLKGGHMDRQRRDFLREASIMGQFDHPNIIRLEGVVTKRSFPAIGVEAFCPSFLRAG
FLNSIQAPHPVPGGGSLPPRIPAGRPVMIVVEYMENGSLDSFLRKHDGHFTVIQLVGMLR
GIASGMKYLSDMGYVHRDLAARNILVNSNLVCKVSDFGLSRVLEDDPEAAYTTTGGKIPI
RWTAPEAIAYRKFSSASDAWSYGIVMWEVMSYGERPYWEMSNQDVILSIEEGYRLPAPMG
CPASLHQLMLHCWQKERNHRPKFTDIVSFLDKLIRNPSALHTLVEDILVMPESPGEVPEY
PLFVTVGDWLDSIKMGQYKNNFVAAGFTTFDLISRMSIDDIRRIGVILIGHQRRIVSSIQ
TLRLHMMHIQEKGFHV
```

Important features of the protein:
Signal peptide:
Amino acids               1-22

Transmembrane domain:
Amino acids               551-571

N-glycosylation sites:
Amino acids               343-346;397-400;410-413;756-759 cAMP- and cGMP-dependent protein kinase phosphorylation site:
Amino acids               851-854

Tyrosine kinase phosphorylation sites:
Amino acids               483-490;604-612;787-794

N-myristoylation sites:
Amino acids               192-197;274-279;289-294;373-378;394-399;504-509;
                                 757-762;777-782;781-786;900-905;976-981

Amidation site:
Amino acids               358-361;653-656

Tyrosine protein kinases specific active-site signature:
Amino acids               794-806

Receptor tyrosine kinase class V signature 1:
Amino acids               192-208

Ephrin receptor ligand binding domain:
Amino acids               34-207 pkinase Protein kinase domain:
Amino acids               631-927

Fibronectin type III domain:
Amino acids               332-425;440-527

SAM domain (Sterile alpha motif):
Amino acids               959-1023

FIGURE 105

```
GGCGGCGGGCTGCGCGGAGCGGCGTCCCCTGCAGCCGCGGACCGAGGCAGCGGCGGCACCTGCCGGCCGAGCAA
TGCCAAGTGAGTACACCTATGTGAAACTGAGAAGTGATTGCTCGAGGCCTTCCCTGCAATGGTACACCCGAGCT
CAAAGCAAGATGAGAAGGCCCAGCTTGTTATTAAAAGACATCCTCAAATGTACATTGCTTGTGTTTGGAGTGTG
GATCCTTTATATCCTCAAGTTAAATTATACTACTGAAGAATGTGACATGAAAAAAATGCATTATGTGGACCCTG
ACCATGTAAAGAGAGCTCAGAAATATGCTCAGCAAGTCTTGCAGAAGGAATGTCGTCCCAAGTTTGCCAAGACA
TCAATGGCGCTGTTATTTGAGCACAGGTATAGCGTGGACTTACTCCCTTTTGTGCAGAAGGCCCCCAAAGACAG
TGAAGCTGAGTCCAAGTACGATCCTCCTTTTGGGTTCCGGAAGTTCTCCAGTAAAGTCCAGACCCTCTTGGAAC
TCTTGCCAGAGCACGACCTCCCTGAACACTTGAAAGCCAAGACCTGTCGGCGCTGTGTGGTTATTGGAAGCGGA
GGAATACTGCACGGATTAGAACTGGGCCACACCCTGAACCAGTTCGATGTTGTGATAAGGTTAAACAGTGCACC
AGTTGAGGGATATTCAGAACATGTTGGAAATAAAACTACTATAAGGATGACTTATCCAGAGGGCGCACCACTGT
CTGACCTTGAATATTATTCCAATGACTTATTTGTTGCTGTTTTATTTAAGAGTGTTGATTTCAACTGGCTTCAA
GCAATGGTAAAAAAGGAAACCCTGCCATTCTGGGTACGACTCTTCTTTTGGAAGCAGGTGGCAGAAAAAATCCC
ACTGCAGCCAAAACATTTCAGGATTTTGAATCCAGTTATCATCAAAGAGACTGCCTTTGACATCCTTCAGTACT
CAGAGCCTCAGTCAAGGTTCTGGGGCCGAGATAAGAACGTCCCCACAATCGGTGTCATTGCCGTTGTCTTAGCC
ACACATCTGTGCGATGAAGTCAGTTTGGCGGGTTTTGGATATGACCTCAATCAACCCAGAACACCTTTGCACTA
CTTCGACAGTCAATGCATGGCTGCTATGAACTTTCAGACCATGCATAATGTGACAACGGAAACCAAGTTCCTCT
TAAAGCTGGTCAAAGAGGGAGTGGTGAAAGATCTCAGTGGAGGCATTGATCGTGAATTTTGAACACAGAAAACC
TCAGTTGAAAATGCAACTCTAACTCTGAGAGCTGTTTTGACAGCCTTCTTGATGTATTTCTCCATCCTGCAGA
TACTTTGAAGTGCAGCTCATGTTTTTAACTTTTAATTTAAAAACACAAAAAAATTTTAGCTCTTCCCACTTTT
TTTTTCCTATTTATTTGAGGTCAGTGTTTGTTTTGCACACCATTTTGTAAATGAAACTTAAGAATTGAATTGG
AAAGACTTCTCAAAGAGAATTGTATGTAACGATGTTGTATTGATTTTAAGAAAGTAATTTAATTTGTAAAACT
TCTGCTCGTTTACACTGCACATTGAATACAGGTAACTAATTGGAAGGAGAGGGAGGTCACTCTTTTGATGGTG
GCCCTGAACCTCATTCTGGTTCCCTGCTGCGCTGCTTGGTGTGACCCACGGAGGATCCACTCCCAGGATGACGT
GCTCCGTAGCTCTGCTGCTGATACTGGGTCTGCGATGCAGCGGCGTGAGGCCTGGGCTGGTTGGAGAAGGTCAC
AACCCTTCTCTGTTGGTCTGCCTTCTGCTGAAAGACTCGAGAACCAACCAGGGAAGCTGTCCTGGAGGTCCCTG
GTCGGAGAGGGACATAGAATCTGTGACCTCTGACAACTGTGAAGCCACCCTGGGCTACAGAAACCACAGTCTTC
CCAGCAATTATTACAATTCTTGAATTCCTTGGGATTTTTTACTGCCCTTTCAAAGCACTTAAGTGTTAGATCT
AACGTGTTCCAGTGTCTGTCTGAGGTGACTTAAAAAATCAGAACAAAACTTCTATTATCCAGAGTCATGGAGA
GTACACCCTTTCCAGGAATAATGTTTTGGGAAACACTGAAATGAAATCTTCCCAGTATTATAAATTGTGTATTTAA
```

FIGURE 106

></usr/seqdb2/sst/DNA/Dnaseqs.min/ss.DNA96897
><subunit 1 of 1, 362 aa, 1 stop
><MW: 41736, pI: 8.80, NX(S/T): 3
MRRPSLLLKDILKCTLLVFGVWILYILKLNYTTEECDMKKMHYVDPDHVKRAQKYAQQVLQK
ECRPKFAKTSMALLFEHRYSVDLLPFVQKAPKDSEAESKYDPPFGFRKFSSKVQTLLELLPE
HDLPEHLKAKTCRRCVVIGSGGILHGLELGHTLNQFDVVIRLNSAPVEGYSEHVGNKTTIRM
TYPEGAPLSDLEYYSNDLFVAVLFKSVDFNWLQAMVKKETLPFWVRLFFWKQVAEKIPLQPK
HFRILNPVIIKETAFDILQYSEPQSRFWGRDKNVPTIGVIAVVLATHLCDEVSLAGFGYDLN
QPRTPLHYFDSQCMAAMNFQTMHNVTTETKFLLKLVKEGVVKDLSGGIDREF

Important features of the protein:

Transmembrane domain:
Amino acids          11-27;281-297

N-glycosylation sites:
Amino acids          30-34;180-184;334-338 cAMP- and cGMP-dependent protein kinase phosphorylation site:
Amino acids          2-6;109-113;223-227

N-myristoylation sites:
Amino acids          146-152;150-156;179-185;191-197

FIGURE 107

```
TGACGCGGGGCGCCAGCTGCCAACTTCGCGCGCGGAGCTCCCCGGCGGTGCAGTCCCGTCCCGGCGGCGCGG
GCGGCATGAAGACTAGCCGCCGCGGCCGAGCGCTCCTGGCCGTGGCCCTGAACCTGCTGGCGCTGCTGTTCG
CCACCACCGCTTTCCTCACCACGCACTGGTGCCAGGGCACGCAGCGGGTCCCCAAGCCGGGCTGCGGCCAGG
GCGGGCGCGCCAACTGCCCCAACTCGGGCGCCAACGCCACGGCCAACGGCACCGCCGCCCCGCCGCCGCCG
CCGCCGCCGCCACCGCCTCGGGGAACGGCCCCCCTGGCGGCGCGCTCTACAGCTGGGAGACCGGCGACGACC
GCTTCCTCTTCAGGAATTTCCACACCGGCATCTGGTACTCGTGCGAGGAGGAGCTCAGCGGGCTTGGTGAAA
AATGTCGCAGCTTCATTGACCTGGCCCCGGCGTCGGAGAAAGGCCTCCTGGGAATGGTCGCCCACATGATGT
ACACGCAGGTGTTCCAGGTCACCGTGAGCCTCGGTCCTGAGGACTGGAGACCCCATTCCTGGGACTACGGGT
GGTCCTTCTGCCTGGCGTGGGGCTCCTTTACCTGCTGCATGGCAGCCTCTGTCACCACGCTCAACTCCTACA
CCAAGACGGTCATTGAGTTCCGGCACAAGCGCAAGGTCTTTGAGCAGGGCTACCGGGAAGAGCCGACCTTCA
TAGACCCTGAGGCCATCAAGTACTTCCGGGAGAGGATGGAGAAGAGGGACGGGAGCGAGGAGGACTTTCACT
TAGACTGCCGCCACGAGAGATACCCTGCCCGACACCAGCCACACATGGCGGATTCCTGGCCCCGGAGCTCCG
CACAGGAAGCACCAGAGCTGAACCGACAGTGCTGGGTCTTGGGGCACTGGGTGTGACCAAGACCTCAACCTG
GCCCGCGGACCTCAGGCCATCGCTGGCACCAGCCCTGCTGCAAGACCACCAGAGTGGTGCCCCCAGAACCC
TGGCCTGTGTGCCGTGAACTCAGTCAGCCTGCGTGGGAGATGCCAGGCCTGTCCTGCCCATCGCTGCCTGGG
TCCCATGGCCTTGGAAATGGGGCCAGGGCAGGCCCAAGGGAATGCACAGGGCTGCACAGAGTGACTTTGGGA
CAGCAGCCCCGGACTCTTGCCATCATCACATGAGCCCTGCTGGGCACAGCTGCGATGCCAGGAGACACATGG
CCACTGGCCACTGAATGGCTGGCACCCACAAGCCAGTCAGGTGCCCAGAGGGGCAGAGCCCTTTGGGGGGCA
GAGAGTGGCTTCCTGAAGGAGGGGGCAGTGGCGCAGGCACTGCAGGGGTGTCACACAGCAGGCACACAGCAG
GGGCTCAATAAATGCTTGTTGAACTTGTTTT
```

FIGURE 108

```
MKTSRRGRALLAVALNLLALLFATTAFLTTHWCQGTQRVPKPGCGQGGRANCPNSGANATANGTAAPAAAA
AAATASGNGPPGGALYSWETGDDRFLFRNFHTGIWYSCEEELSGLGEKCRSFIDLAPASEKGLLGMVAHMM
YTQVFQVTVSLGPEDWRPHSWDYGWSFCLAWGSFTCCMAASVTTLNSYTKTVIEFRHKRKVFEQGYREEPT
FIDPEAIKYFRERMEKRDGSEEDFHLDCRHERYPARHQPHMADSWPRSSAQEAPELNRQCWVLGHWV
```

Important features of the protein:

Signal peptide:
1-26

Transmembrane domain:
169-189

N-glycosylation site.
    58-61
    62-65

Glycosaminoglycan attachment site.
    77-80
    114-117

Tyrosine kinase phosphorylation site.
    202-208

N-myristoylation site.
    43-48
    47-52
    56-61
    84-89
    104-109
    174-179

FIGURE 109

```
GATTACCAAGCAAGAACAGCTAAAATGAAAGCCATCATTCATCTTACTCTTCTTGCTCTCCT
TTCTGTAAACACAGCCACCAACCAAGGCAACTCAGCTGATGCTGTAACAACCACAGAAACTG
CGACTAGTGGTCCTACAGTAGCTGCAGCTGATACCACTGAAACTAATTTCCCTGAAACTGCT
AGCACCACAGCAAATACACCTTCTTTCCCAACAGCTACTTCACCTGCTCCCCCATAATTAG
TACACATAGTTCCTCCACAATTCCTACACCTGCTCCCCCATAATTAGTACACATAGTTCCT
CCACAATTCCTATACCTACTGCTGCAGACAGTGAGTCAACCACAAATGTAAATTCATTAGCT
ACCTCTGACATAATCACCGCTTCATCTCCAAATGATGGATTAATCACAATGGTTCCTTCTGA
AACACAAAGTAACAATGAAATGTCCCCACCACAGAAGACAATCAATCATCAGGGCCTCCCA
CTGGCACCGCTTTATTGGAGACCAGCACCCTAAACAGCACAGGTCCCAGCAATCCTTGCCAA
GATGATCCCTGTGCAGATAATTCGTTATGTGTTAAGCTGCATAATACAAGTTTTTGCCTGTG
TTTAGAAGGGTATTACTACAACTCTTCTACATGTAAGAAAGGAAAGGTATTCCCTGGGAAGATT
TCAGTGACAGTATCAGAAACATTTGACCCAGAAGAGAAACATTCCATGGCCTATCAAGACTT
GCATAGTGAAATTACTAGCTTGTTTAAAGATGTATTTGGCACATCTGTTTATGGACAGACTG
TAATTCTTACTGTAAGCACATCTCTGTCACCAAGATCTGAAATGCGTGCTGATGACAAGTTT
GTTAATGTAACAATAGTAACAATTTTGGCAGAAACCACAAGTGACAATGAGAAGACTGTGAC
TGAGAAAATTAATAAAGCAATTAGAAGTAGCTCAAGCAACTTTCTAAACTATGATTTGACCC
TTCGGTGTGATTATTATGGCTGTAACCAGACTGCGGATGACTGCCTCAATGGTTTAGCATGC
GATTGCAAATCTGACCTGCAAAGGCCTAACCCACAGAGCCCTTTCTGCGTTGCTTCCAGTCT
CAAGTGTCCTGATGCCTGCAACGCACAGCACAAGCAATGCTTAATAAAGAAGAGTGGTGGGG
CCCCTGAGTGTGCGTGCGTGCCCGGCTACCAGGAAGATGCTAATGGGAACTGCCAAAAGTGT
GCATTTGGCTACAGTGGACTCGACTGTAAGGACAAATTTCAGCTGATCCTCACTATTGTGGG
CACCATCGCTGGCATTGTCATTCTCAGCATGATAATTGCATTGATTGTCACAGCAAGATCAA
ATAACAAAACGAAGCATATTGAAGAAGAGAACTTGATTGACGAAGACTTTCAAAATCTAAAA
CTGCGGTCGACAGGCTTCACCAATCTTGGAGCAGAAGGGAGCGTCTTTCCTAAGGTCAGGAT
AACGGCCTCCAGAGACAGCCAGATGCAAAATCCCTATTCAAGCCACAGCAGCATGCCCCGCC
CTGACTATTAGAATCATAAGAATGTGGAACCCGCCATGGCCCCAACCAATGTACAAGCTAT
TATTTAGAGTGTTTAGAAAGACTGATGGAGAAGTGAGCACCAGTAAGATCTGGCCTCCGGG
GTTTTTCTTCCATCTGACATCTGCCAGCCTCTCTGAATGGAAGTTGTGAATGTTTGCAACGA
ATCCAGCTCACTTGCTAAATAAGAATCTATGACATTAAATGTAGTAGATGCTATTAGCGCTT
GTCAGAGAGGTGGTTTTCTTCAATCAGTACAAAGTACTGAGACAATGGTTAGGGTTGTTTTC
TTAATTCTTTTCCTGGTAGGGCAACAAGAACCATTTCCAATCTAGAGGAAAGCTCCCCAGCA
TTGCTTGCTCCTGGGCAAACATTGCTCTTGAGTTAAGTGACCTAATTCCCCTGGGAGACATA
CGCATCAACTGTGGAGGTCCGAGGGGATGAGAAGGGATACCACCATCTTTCAAGGGTCACA
AGCTCACTCTCTGACAAGTCAGAATAGGGACACTGCTTCTATCCCTCCAATGGAGAGATTCT
GGCAACCTTTGAACAGCCCAGAGCTTGCAACCTAGCCTCACCCAAGAAGACTGGAAAGAGAC
ATATCTCTCAGCTTTTTCAGGAGGCGTGCCTGGGAATCCAGGAACTTTTTGATGCTAATTAG
AAGGCCTGGACTAAAAATGTCCACTATGGGGTGCACTCTACAGTTTTTGAAATGCTAGGAGG
CAGAAGGGGCAGAGAGTAAAAAACATGACCTGGTAGAAGGAAGAGAGGCAAAGGAAACTGGG
TGGGAGGATCAATTAGAGAGGAGGCACCTGGGATCCACCTTCTTCCTTAGGTCCCCTCCTC
CATCAGCAAAGGAGCACTTCTCTAATCATGCCCTCCCGAAGACTGGCTGGGAGAAGGTTTAAAA
ACAAAAATCCAGGAGTAAGAGCCTTAGGTCAGTTTGAAATTGGAGACAAACTGTCTGGCAA
AGGGTGCGAGAGGGAGCTTGTGCTCAGGAGTCCAGCCGCCCAGCCTCGGGGTGTAGGTTTCT
GAGGTGTGCCATTGGGGCCTCAGCCTTCTCTGGTGACAGAGGCTCAGCTGTGGCCACCAACA
CACAACCACACACACACAACCACACACACAAATGGGGGCAACCACATCCAGTACAAGCTTTT
ACAAATGTTATTAGTGTCCTTTTTTATTTCTAATGCCTTGTCCTCTTAAAAGTTATTTTATT
TGTTATTATTATTTGTTCTTGACTGTTAATTGTGAATGGTAATGCAATAAAGTGCCTTTGTT
AGATGGTGAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAA
```

FIGURE 110

```
></usr/seqdb2/sst/DNA/Dnaseqs.min/ss.DNA142930
><subunit 1 of 1, 512 aa, 1 stop
><MW: 54535, pI: 4.89, NX(S/T): 7
MKAIIHLTLLALLSVNTATNQGNSADAVTTTETATSGPTVAAADTTETNFPETASTTANT
PSFPTATSPAPPIISTHSSSTIPTPAPPIISTHSSSTIPIPTAADSESTTNVNSLATSDI
ITASSPNDGLITMVPSETQSNNEMSPTTEDNQSSGPPTGTALLETSTLNSTGPSNPCQDD
PCADNSLCVKLHNTSFCLCLEGYYYNSSTCKKGKVFPGKISVTVSETFDPEEKHSMAYQD
LHSEITSLFKDVFGTSVYGQTVILTVSTSLSPRSEMRADDKFVNVTIVTILAETTSDNEK
TVTEKINKAIRSSSSNFLNYDLTLRCDYYGCNQTADDCLNGLACDCKSDLQRPNPQSPFC
VASSLKCPDACNAQHKQCLIKKSGGAPECACVPGYQEDANGNCQKCAFGYSGLDCKDKFQ
LILTIVGTIAGIVILSMIIALIVTARSNNKTKHIEEENLIDEDFQNLKLRSTGFTNLGAE
GSVFPKVRITASRDSQMQNPYSSHSSMPRPDY
```

Important features of the protein:
Signal peptide:
Amino acids        1-17

Transmembrane domain:
Amino acids        421-442

N-glycosylation sites:
Amino acids        151-155;169-173;193-197;206-210;284-288;
                   332-336;449-453

N-myristoylation sites:
Amino acids        330-336;385-391;427-433;478-484

SEA domain:
Amino acids        212-328

FIGURE 111

```
CTGGGACTTGGCTTTCTCCGGATAAGCGGCGGCACCGGCGTCAGCGATGACCGTGCAGAGAC
TCGTGGCCGCGGCCGTGCTGGTGGCCCTGGTCTCACTCATCCTCAACAACGTGGCGGCCTTC
ACCTCCAACTGGGTGTGCCAGACGCTGGAGGATGGGCGCAGGCGCAGCGTGGGGCTGTGGAG
GTCCTGCTGGCTGGTGGACAGGACCCGGGGAGGGCCGAGCCCTGGGCCAGAGCCGGCCAGG
TGGACGCACATGACTGTGAGGCGCTGGGCTGGGGCTCCGAGGCAGCCGGCTTCCAGGAGTCC
CGAGGCACCGTCAAACTGCAGTTCGACATGATGCGCGCCTGCAACCTGGTGGCCACGGCCGC
GCTCACCGCAGGCCAGCTCACCTTCCTCCTGGGGCTGGTGGGCCTGCCCCTGCTGTCACCCG
ACGCCCCGTGCTGGGAGGAGGCCATGGCCGCTGCATTCCAACTGGCGAGTTTTGTCCTGGTC
ATCGGGCTCGTGACTTTCTACAGAATTGGCCCATACACCAACCTGTCCTGGTCCTGCTACCT
GAACATTGGCGCCTGCCTTCTGGCCACGCTGGCGGCAGCCATGCTCATCTGGAACATTCTCC
ACAAGAGGGAGGACTGCATGGCCCCCGGGTGATTGTCATCAGCCGCTCCCTGACAGCGCGC
TTTCGCCGTGGGCTGGACAATGACTACGTGGAGTCACCATGCTGAGTCGCCCTTCTCAGCGC
TCCATCAACGCACACCTGCTATCGTGGAACAGCCTAGAAACCAAGGGACTCCACCACCAAGT
CACTTCCCCTGCTCGTGCAGAGGCACGGGATGAGTCTGGGTGACCTCTGCGCCATGCGTGCG
AGACACGTGTGCGTTTACTGTTATGTCGGTCATATGTCTGTACGTGTCGTGGGCCAACCTCG
TTCTGCCTCCAGC
```

FIGURE 112

```
></usr/seqdb2/sst/DNA/Dnaseqs.min/ss.DNA147253
><subunit 1 of 1, 226 aa, 1 stop
><MW: 24540, pI: 8.27, NX(S/T): 1
MTVQRLVAAAVLVALVSLILNNVAAFTSNWVCQTLEDGRRRSVGLWRSCWLVDRTRGGPS
PGARAGQVDAHDCEALGWGSEAAGFQESRGTVKLQFDMMRACNLVATAALTAGQLTFLLG
LVGLPLLSPDAPCWEEAMAAAFQLASFVLVIGLVTFYRIGPYTNLSWSCYLNIGACLLAT
LAAAMLIWNILHKREDCMAPRVIVISRSLTARFRRGLDNDYVESPC
```

Important features of the protein:
Signal peptide:
Amino acids            1-25

Transmembrane domains:
Amino acids            105-125;139-157;169-188

N-glycosylation site:
Amino acids            164-168 cAMP- and cGMP-dependent protein kinase phosphorylation site:
Amino acids            39-43

Tyrosine kinase phosphorylation site:
Amino acids            214-222

N-myristoylation sites:
Amino acids            44-50;62-68;66-72;79-85

Amidation site:
Amino acids            37-41

FIGURE 113

```
GACTTTACCACTACTCGCTATAGAGCCCTGGTCAAGTTCTCTCCACCTCTCTATCTATGTCT
CAGTTTCTTCATCTGTAACATCAAATGAATAATAATACCAATCTCCTAGACTTCATAAGAGG
ATTAACAAAGACAAAATATGGGAAAAACATAACATGGCGTCCCATAATTATTAGATCTTATT
ATTGACACTAAAATGGCATTAAAATTACCAAAAGGAAGACAGCATCTGTTTCCTCTTTGGTC
CTGAGCTGGTTAAAAGGAACACTGGTTGCCTGAACAGTCACACTTGCAACCATGATGCCTAA
ACATTGCTTTCTAGGCTTCCTCATCAGTTTCTTCCTTACTGGTGTAGCAGGAACTCAGTCAA
CGCATGAGTCTCTGAAGCCTCAGAGGGTACAATTTCAGTCCCGAAATTTTCACAACATTTTG
CAATGGCAGCCTGGGAGGGCACTTACTGGCAACAGCAGTGTCTATTTTGTGCAGTACAAAAT
ATATGGACAGAGACAATGGAAAAATAAAGAAGACTGTTGGGGTACTCAAGAACTCTCTTGTG
ACCTTACCAGTGAAACCTCAGACATACAGGAACCTTATTACGGGAGGGTGAGGGCGGCCTCG
GCTGGGAGCTACTCAGAATGGAGCATGACGCCGCGGTTCACTCCCTGGTGGGAAACAAAAT
AGATCCTCCAGTCATGAATATAACCCAAGTCAATGGCTCTTTGTTGGTAATTCTCCATGCTC
CAAATTTACCATATAGATACCAAAAGGAAAAAAATGTATCTATAGAAGATTACTATGAACTA
CTATACCGAGTTTTTATAATTAACAATTCACTAGAAAAGGAGCAAAAGGTTTATGAAGGGGC
TCACAGAGCGGTTGAAATTGAAGCTCTAACACCACACTCCAGCTACTGTGTAGTGGCTGAAA
TATATCAGCCCATGTTAGACAGAAGAAGTCAGAGAAGTGAAGAGAGATGTGTGGAAATTCCA
TGACTTGTGGAATTTGGCATTCAGCAATGTGGAAATTCTAAAGCTCCCTGAGAACAGGATGA
CTCGTGTTTGAAGGATCTTATTTAAAATTGTTTTTGTATTTTCTTAAAGCAATATTCACTGT
TACACCTTGGGGACTTCTTTGTTTACCCATTCTTTTATCCTTTATATTTCATTTGTAAACTA
TATTTGAACGACATTCCCCCCGAAAAATTGAAATGTAAAGATGAGGCAGAGAATAAAGTGTT
CTATGAAATTCAGAACTTTATTTCTGAATGTAACATCCCTAATAACAACCTTCATTCTTCTA
ATACAGCAAAATAAAAATTTAACAACCAAGGAATAGTATTTAAGAAAATGTTGAATAATTT
TTTTAAAATAGCATTACAGACTGAG
```

FIGURE 114

```
></usr/seqdb2/sst/DNA/Dnaseqs.min/ss.DNA149927
><subunit 1 of 1, 231 aa, 1 stop
><MW: 26980, pI: 7.06, NX(S/T): 5
MMPKHCFLGFLISFFLTGVAGTQSTHESLKPQRVQFQSRNFHNILQWQPGRALTGNSSVY
FVQYKIYGQRQWKNKEDCWGTQELSCDLTSETSDIQEPYYGRVRAASAGSYSEWSMTPRF
TPWWETKIDPPVMNITQVNGSLLVILHAPNLPYRYQKEKNVSIEDYYELLYRVFIINNSL
EKEQKVYEGAHRAVEIEALTPHSSYCVVAEIYQPMLDRRSQRSEERCVEIP
```

Important features of the protein:
Signal peptide:
Amino acids          1-21

N-glycosylation sites:
Amino acids          56-60;134-138;139-143;160-164;177-181

N-myristoylation sites:
Amino acids          18-24;21-27;189-195

PRO4407 POLYPEPTIDES

This application is a continuation of, and claims priority under 35 USC §120 to, U.S. application Ser. No. 10/197,942 filed Jul. 18, 2002, now abandoned, which is a continuation of, and claims priority under 35 USC §120 to, PCT Application PCT/US01/27099 filed Aug. 29, 2001, which is a continuation-in-part of, and claims priority under 35 USC §120 to, PCT Application PCT/US99/28551 filed Dec. 2, 1999, which claims priority under 35 USC §119 to US Provisional Application 60/162,506 filed Oct. 29, 1999 and US Provisional Application 60/131,271 filed Apr. 27, 1999.

FIELD OF THE INVENTION

The present invention relates generally to the identification and isolation of novel DNA and to the recombinant production of novel polypeptides.

BACKGROUND OF THE INVENTION

Extracellular proteins play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Secreted proteins have various industrial applications, including as pharmaceuticals, diagnostics, biosensors and bioreactors. Most protein drugs available at present, such as thrombolytic agents, interferons, interleukins, erythropoietins, colony stimulating factors, and various other cytokines, are secretory proteins. Their receptors, which are membrane proteins, also have potential as therapeutic or diagnostic agents. Efforts are being undertaken by both industry and academia to identify new, native secreted proteins. Many efforts are focused on the screening of mammalian recombinant DNA libraries to identify the coding sequences for novel secreted proteins. Examples of screening methods and techniques are described in the literature [see, for example, Klein et al., *Proc. Natl. Acad. Sci.* 93:7108-7113 (1996); U.S. Pat. No. 5,536,637)].

Membrane-bound proteins and receptors can play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesion molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immunoadhesins, for instance, can be employed as therapeutic agents to block receptor-ligand interactions. The membrane-bound proteins can also be employed for screening of potential peptide or small molecule inhibitors of the relevant receptor/ligand interaction.

Efforts are being undertaken by both industry and academia to identify new, native receptor or membrane-bound proteins. Many efforts are focused on the screening of mammalian recombinant DNA libraries to identify the coding sequences for novel receptor or membrane-bound proteins.

SUMMARY OF THE INVENTION

In one embodiment, the invention provides an isolated nucleic acid molecule comprising a nucleotide sequence that encodes a PRO polypeptide.

In one aspect, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule encoding a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule comprising the coding sequence of a full-length PRO polypeptide cDNA as disclosed herein, the coding sequence of a PRO polypeptide lacking the signal peptide as disclosed herein, the coding sequence of an extracellular domain of a transmembrane PRO polypeptide, with or without the signal peptide, as disclosed herein or the coding sequence of any other specifically defined fragment of the full-length amino acid sequence as disclosed herein, or (b) the complement of the DNA molecule of (a).

In a further aspect, the invention concerns an isolated nucleic acid molecule comprising a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule that encodes the same mature polypeptide encoded by any of the human protein cDNAs deposited with the ATCC as disclosed herein, or (b) the complement of the DNA molecule of (a).

Another aspect the invention provides an isolated nucleic acid molecule comprising a nucleotide sequence encoding a PRO polypeptide which is either transmembrane domain-deleted or transmembrane domain-inactivated, or is complementary to such encoding nucleotide sequence, wherein the transmembrane domain(s) of such polypeptide are disclosed herein. Therefore, soluble extracellular domains of the herein described PRO polypeptides are contemplated.

Another embodiment is directed to fragments of a PRO polypeptide coding sequence, or the complement thereof, that may find use as, for example, hybridization probes, for encoding fragments of a PRO polypeptide that may optionally encode a polypeptide comprising a binding site for an anti-PRO antibody or as antisense oligonucleotide probes. Such nucleic acid fragments are usually at least about 10 nucleotides in length, alternatively at least about 15 nucleotides in length, alternatively at least about 20 nucleotides in length, alternatively at least about 30 nucleotides in length, alternatively at least about 40 nucleotides in length, alternatively at least about 50 nucleotides in length, alternatively at least about 60 nucleotides in length, alternatively at least about 70 nucleotides in length, alternatively at least about 80 nucleotides in length, alternatively at least about 90 nucleotides in length, alternatively at least about 100 nucleotides in length, alternatively at least about 110 nucleotides in length, alternatively at least about 120 nucleotides in length, alternatively at least about 130 nucleotides in length, alternatively at least about 140 nucleotides in length, alternatively at least about 150 nucleotides in length, alternatively at least about 160 nucleotides in length, alternatively at least about 170 nucleotides in length, alternatively at least about 180 nucleotides in length, alternatively at least about 190 nucleotides in length, alternatively at least about 200 nucleotides in length, alternatively at least about 250 nucleotides in length, alternatively at least about 300 nucleotides in length, alternatively at least about 350 nucleotides in length, alternatively at least about 400 nucleotides in length, alternatively at least about 450 nucleotides in length, alternatively at least about 500 nucleotides in length, alternatively at least about 600 nucleotides in length, alternatively at least about 700 nucleotides in length, alternatively at least about 800 nucleotides in length, alternatively at least about 900 nucleotides in length and alternatively at least about 1000 nucleotides in length, wherein in this context the term "about" means the referenced nucleotide sequence length plus or minus 10% of that referenced length. It is noted that novel fragments of a PRO polypeptide-encoding nucleotide sequence may be determined in a routine manner by aligning the PRO polypeptide-encoding nucleotide sequence with other known nucleotide sequences using any of a number of well known sequence alignment programs and determining which PRO polypeptide-encoding nucleotide sequence fragment(s) are novel. All of such PRO polypeptide-encoding nucleotide sequences are contemplated herein. Also contemplated are the PRO polypeptide fragments encoded by these nucleotide molecule fragments, preferably those PRO polypeptide fragments that comprise a binding site for an anti-PRO antibody.

In another embodiment, the invention provides isolated PRO polypeptide encoded by any of the isolated nucleic acid sequences hereinabove identified.

In a certain aspect, the invention concerns an isolated PRO polypeptide, comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a further aspect, the invention concerns an isolated PRO polypeptide comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to an amino acid sequence encoded by any of the human protein cDNAs deposited with the ATCC as disclosed herein.

In a specific aspect, the invention provides an isolated PRO polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

Another aspect the invention provides an isolated PRO polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

In yet another embodiment, the invention concerns agonists and antagonists of a native PRO polypeptide as defined herein. In a particular embodiment, the agonist or antagonist is an anti-PRO antibody or a small molecule.

In a further embodiment, the invention concerns a method of identifying agonists or antagonists to a PRO polypeptide which comprise contacting the PRO polypeptide with a candidate molecule and monitoring a biological activity mediated by said PRO polypeptide. Preferably, the PRO polypeptide is a native PRO polypeptide.

In a still further embodiment, the invention concerns a composition of matter comprising a PRO polypeptide, or an agonist or antagonist of a PRO polypeptide as herein described, or an anti-PRO antibody, in combination with a carrier. Optionally, the carrier is a pharmaceutically acceptable carrier.

Another embodiment of the present invention is directed to the use of a PRO polypeptide, or an agonist or antagonist thereof as hereinbefore described, or an anti-PRO antibody, for the preparation of a medicament useful in the treatment of a condition which is responsive to the PRO polypeptide, an agonist or antagonist thereof or an anti-PRO antibody.

In other embodiments of the present invention, the invention provides vectors comprising DNA encoding any of the herein described polypeptides. Host cell comprising any such vector are also provided. By way of example, the host cells may be CHO cells, E. coli, or yeast. A process for producing any of the herein described polypeptides is further provided and comprises culturing host cells under conditions suitable for expression of the desired polypeptide and recovering the desired polypeptide from the cell culture.

In other embodiments, the invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

In another embodiment, the invention provides an antibody which binds, preferably specifically, to any of the above or below described polypeptides. Optionally, the antibody is a monoclonal antibody, humanized antibody, antibody fragment or single-chain antibody.

In yet other embodiments, the invention provides oligonucleotide probes which may be useful for isolating genomic and cDNA nucleotide sequences, measuring or detecting expression of an associated gene or as antisense probes, wherein those probes may be derived from any of the above or below described nucleotide sequences. Preferred probe lengths are described above.

In yet other embodiments, the present invention is directed to methods of using the PRO polypeptides of the present invention for a variety of uses based upon the functional biological assay data presented in the Examples below.

BRIEF DESCRIPTION OF THE DRAWINGS

FIG. 1 shows a nucleotide sequence (SEQ ID NO:1) of a native sequence PRO281 cDNA, wherein SEQ ID NO:1 is a clone designated herein as "DNA 16422-1209".

FIG. 2 shows the amino acid sequence (SEQ ID NO:2) derived from the coding sequence of SEQ ID NO:1 shown in FIG. 1.

FIG. 3 shows a nucleotide sequence (SEQ ID NO:3) of a native sequence PRO1560 cDNA, wherein SEQ ID NO:3 is a clone designated herein as "DNA19902-1669".

FIG. 4 shows the amino acid sequence (SEQ ID NO:4) derived from the coding sequence of SEQ ID NO:3 shown in FIG. 3.

FIG. 5 shows a nucleotide sequence (SEQ ID NO:5) of a native sequence PRO189 cDNA, wherein SEQ ID NO:5 is a clone designated herein as "DNA21624-1391".

FIG. 6 shows the amino acid sequence (SEQ ID NO:6) derived from the coding sequence of SEQ ID NO:5 shown in FIG. 5.

FIG. 7 shows a nucleotide sequence (SEQ ID NO:7) of a native sequence PRO240 cDNA, wherein SEQ ID NO:7 is a clone designated herein as "DNA34387-1138".

FIG. 8 shows the amino acid sequence (SEQ ID NO:8) derived from the coding sequence of SEQ ID NO:7 shown in FIG. 7.

FIG. 9 shows a nucleotide sequence (SEQ ID NO:9) of a native sequence PRO256 cDNA, wherein SEQ ID NO:9 is a clone designated herein as "DNA35880-1160".

FIG. 10 shows the amino acid sequence (SEQ ID NO:10) derived from the coding sequence of SEQ ID NO:9 shown in FIG. 9.

FIG. 11 shows a nucleotide sequence (SEQ ID NO:11) of a native sequence PRO306 cDNA, wherein SEQ ID NO:11 is a clone designated herein as "DNA39984-1221".

FIG. 12 shows the amino acid sequence (SEQ ID NO:12) derived from the coding sequence of SEQ ID NO:11 shown in FIG. 11.

FIG. 13 shows a nucleotide sequence (SEQ ID NO:13) of a native sequence PRO540 cDNA, wherein SEQ ID NO:13 is a clone designated herein as "DNA44189-1322".

FIG. 14 shows the amino acid sequence (SEQ ID NO:14) derived from the coding sequence of SEQ ID NO:13 shown in FIG. 13.

FIG. 15 shows a nucleotide sequence (SEQ ID NO:15) of a native sequence PRO773 cDNA, wherein SEQ ID NO:15 is a clone designated herein as "DNA48303-2829".

FIG. 16 shows the amino acid sequence (SEQ ID NO:16) derived from the coding sequence of SEQ ID NO:15 shown in FIG. 15.

FIG. 17 shows a nucleotide sequence (SEQ ID NO:17) of a native sequence PRO698 cDNA, wherein SEQ ID NO:17 is a clone designated herein as "DNA48320-1433".

FIG. 18 shows the amino acid sequence (SEQ ID NO:18) derived from the coding sequence of SEQ ID NO:17 shown in FIG. 17.

FIG. 19 shows a nucleotide sequence (SEQ ID NO:19) of a native sequence PRO3567 cDNA, wherein SEQ ID NO:19 is a clone designated herein as "DNA56049-2543".

FIG. 20 shows the amino acid sequence (SEQ ID NO:20) derived from the coding sequence of SEQ ID NO:19 shown in FIG. 19.

FIG. 21 shows a nucleotide sequence (SEQ ID NO:21) of a native sequence PRO826 cDNA, wherein SEQ ID NO:21 is a clone designated herein as "DNA57694-1341".

FIG. 22 shows the amino acid sequence (SEQ ID NO:22) derived from the coding sequence of SEQ ID NO:21 shown in FIG. 21.

FIG. 23 shows a nucleotide sequence (SEQ ID NO:23) of a native sequence PRO 1002 cDNA, wherein SEQ ID NO:23 is a clone designated herein as "DNA59208-1373".

FIG. 24 shows the amino acid sequence (SEQ ID NO:24) derived from the coding sequence of SEQ ID NO:23 shown in FIG. 23.

FIG. 25 shows a nucleotide sequence (SEQ ID NO:25) of a native sequence PRO 1068 cDNA, wherein SEQ ID NO:25 is a clone designated herein as "DNA59214-1449".

FIG. 26 shows the amino acid sequence (SEQ ID NO:26) derived from the coding sequence of SEQ ID NO:25 shown in FIG. 25.

FIG. 27 shows a nucleotide sequence (SEQ ID NO:27) of a native sequence PRO 1030 cDNA, wherein SEQ ID NO:27 is a clone designated herein as "DNA59485-1336".

FIG. 28 shows the amino acid sequence (SEQ ID NO:28) derived from the coding sequence of SEQ ID NO:27 shown in FIG. 27.

FIG. 29 shows a nucleotide sequence (SEQ ID NO:29) of a native sequence PRO1313 cDNA, wherein SEQ ID NO:29 is a clone designated herein as "DNA64966-1575".

FIG. 30 shows the amino acid sequence (SEQ ID NO:30) derived from the coding sequence of SEQ ID NO:29 shown in FIG. 29.

FIG. 31 shows a nucleotide sequence (SEQ ID NO:31) of a native sequence PRO6071 cDNA, wherein SEQ ID NO:31 is a clone designated herein as "DNA82403-2959".

FIG. 32 shows the amino acid sequence (SEQ ID NO:32) derived from the coding sequence of SEQ ID NO:31 shown in FIG. 31.

FIG. 33 shows a nucleotide sequence (SEQ ID NO:33) of a native sequence PRO4397 cDNA, wherein SEQ ID NO:33 is a clone designated herein as "DNA83505-2606".

FIG. 34 shows the amino acid sequence (SEQ ID NO:34) derived from the coding sequence of SEQ ID NO:33 shown in FIG. 33.

FIG. 35 shows a nucleotide sequence (SEQ ID NO:35) of a native sequence PRO4344 cDNA, wherein SEQ ID NO:35 is a clone designated herein as "DNA84927-2585".

FIG. 36 shows the amino acid sequence (SEQ ID NO:36) derived from the coding sequence of SEQ ID NO:35 shown in FIG. 35.

FIG. 37 shows a nucleotide sequence (SEQ ID NO:37) of a native sequence PRO4407 cDNA, wherein SEQ ID NO:37 is a clone designated herein as "DNA92264-2616".

FIG. 38 shows the amino acid sequence (SEQ ID NO:38) derived from the coding sequence of SEQ ID NO:37 shown in FIG. 37.

FIG. 39 shows a nucleotide sequence (SEQ ID NO:39) of a native sequence PRO4316 cDNA, wherein SEQ ID NO:39 is a clone designated herein as "DNA94713-2561".

FIG. 40 shows the amino acid sequence (SEQ ID NO:40) derived from the coding sequence of SEQ ID NO:39 shown in FIG. 39.

FIG. 41 shows a nucleotide sequence (SEQ ID NO:41) of a native sequence PRO5775 cDNA, wherein SEQ ID NO:41 is a clone designated herein as "DNA96869-2673".

FIG. 42 shows the amino acid sequence (SEQ ID NO:42) derived from the coding sequence of SEQ ID NO:41 shown in FIG. 41.

FIG. 43 shows a nucleotide sequence (SEQ ID NO:43) of a native sequence PRO6016 cDNA, wherein SEQ ID NO:43 is a clone designated herein as "DNA96881-2699".

FIG. 44 shows the amino acid sequence (SEQ ID NO:44) derived from the coding sequence of SEQ ID NO:43 shown in FIG. 43.

FIG. 45 shows a nucleotide sequence (SEQ ID NO:45) of a native sequence PRO4499 cDNA, wherein SEQ ID NO:45 is a clone designated herein as "DNA96889-2641".

FIG. 46 shows the amino acid sequence (SEQ ID NO:46) derived from the coding sequence of SEQ ID NO:45 shown in FIG. 45.

FIG. 47 shows a nucleotide sequence (SEQ ID NO:47) of a native sequence PRO4487 cDNA, wherein SEQ ID NO:47 is a clone designated herein as "DNA96898-2640".

FIG. 48 shows the amino acid sequence (SEQ ID NO:48) derived from the coding sequence of SEQ ID NO:47 shown in FIG. 47.

FIG. 49 shows a nucleotide sequence (SEQ ID NO:49) of a native sequence PRO4980 cDNA, wherein SEQ ID NO:49 is a clone designated herein as "DNA97003-2649".

FIG. 50 shows the amino acid sequence (SEQ ID NO:50) derived from the coding sequence of SEQ ID NO:49 shown in FIG. 49.

FIG. 51 shows a nucleotide sequence (SEQ ID NO:51) of a native sequence PRO6018 cDNA, wherein SEQ ID NO:51 is a clone designated herein as "DNA98565-2701".

FIG. 52 shows the amino acid sequence (SEQ ID NO:52) derived from the coding sequence of SEQ ID NO:51 shown in FIG. 51.

FIG. 53 shows a nucleotide sequence (SEQ ID NO:53) of a native sequence PRO7168 cDNA, wherein SEQ ID NO:53 is a clone designated herein as "DNA102846-2742".

FIG. 54 shows the amino acid sequence (SEQ ID NO:54) derived from the coding sequence of SEQ ID NO:53 shown in FIG. 53.

FIG. 55 shows a nucleotide sequence (SEQ ID NO:55) of a native sequence PRO6308 cDNA, wherein SEQ ID NO:55 is a clone designated herein as "DNA102847-2726".

FIG. 56 shows the amino acid sequence (SEQ ID NO:56) derived from the coding sequence of SEQ ID NO:55 shown in FIG. 55.

FIG. 57 shows a nucleotide sequence (SEQ ID NO:57) of a native sequence PRO6000 cDNA, wherein SEQ ID NO:57 is a clone designated herein as "DNA102880-2689".

FIG. 58 shows the amino acid sequence (SEQ ID NO:58) derived from the coding sequence of SEQ ID NO:57 shown in FIG. 57.

FIG. 59 shows a nucleotide sequence (SEQ ID NO:59) of a native sequence PRO6006 cDNA, wherein SEQ ID NO:59 is a clone designated herein as "DNA105782-2693".

FIG. 60 shows the amino acid sequence (SEQ ID NO:60) derived from the coding sequence of SEQ ID NO:59 shown in FIG. 59.

FIG. 61 shows a nucleotide sequence (SEQ ID NO:61) of a native sequence PRO5800 cDNA, wherein SEQ ID NO:61 is a clone designated herein as "DNA108912-2680".

FIG. 62 shows the amino acid sequence (SEQ ID NO:62) derived from the coding sequence of SEQ ID NO:61 shown in FIG. 61.

FIG. 63 shows a nucleotide sequence (SEQ ID NO:63) of a native sequence PRO7476 cDNA, wherein SEQ ID NO:63 is a clone designated herein as "DNA115253-2757".

FIG. 64 shows the amino acid sequence (SEQ ID NO:64) derived from the coding sequence of SEQ ID NO:63 shown in FIG. 63.

FIG. 65 shows a nucleotide sequence (SEQ ID NO:65) of a native sequence PRO6496 cDNA, wherein SEQ ID NO:65 is a clone designated herein as "DNA119302-2737".

FIG. 66 shows the amino acid sequence (SEQ ID NO:66) derived from the coding sequence of SEQ ID NO:65 shown in FIG. 65.

FIG. 67 shows a nucleotide sequence (SEQ ID NO:67) of a native sequence PRO7422 cDNA, wherein SEQ ID NO:67 is a clone designated herein as "DNA119536-2752".

FIG. 68 shows the amino acid sequence (SEQ ID NO:68) derived from the coding sequence of SEQ ID NO:67 shown in FIG. 67.

FIG. 69 shows a nucleotide sequence (SEQ ID NO:69) of a native sequence PRO7431 cDNA, wherein SEQ ID NO:69 is a clone designated herein as "DNA119542-2754".

FIG. 70 shows the amino acid sequence (SEQ ID NO:70) derived from the coding sequence of SEQ ID NO:69 shown in FIG. 69.

FIG. 71 shows a nucleotide sequence (SEQ ID NO:71) of a native sequence PRO10275 cDNA, wherein SEQ ID NO:71 is a clone designated herein as "DNA143498-2824".

FIG. 72 shows the amino acid sequence (SEQ ID NO:72) derived from the coding sequence of SEQ ID NO:71 shown in FIG. 71.

FIG. 73 shows a nucleotide sequence (SEQ ID NO:73) of a native sequence PRO 10268 cDNA, wherein SEQ ID NO:73 is a clone designated herein as "DNA145583-2820".

FIG. 74 shows the amino acid sequence (SEQ ID NO:74) derived from the coding sequence of SEQ ID NO:73 shown in FIG. 73.

FIG. 75 shows a nucleotide sequence (SEQ ID NO:75) of a native sequence PRO20080 cDNA, wherein SEQ ID NO:75 is a clone designated herein as "DNA161000-2896".

FIG. 76 shows the amino acid sequence (SEQ ID NO:76) derived from the coding sequence of SEQ ID NO:75 shown in FIG. 75.

FIG. 77 shows a nucleotide sequence (SEQ ID NO:77) of a native sequence PRO21207 cDNA, wherein SEQ ID NO:77 is a clone designated herein as "DNA161005-2943".

FIG. 78 shows the amino acid sequence (SEQ ID NO:78) derived from the coding sequence of SEQ ID NO:77 shown in FIG. 77.

FIG. 79 shows a nucleotide sequence (SEQ ID NO:79) of a native sequence PRO28633 cDNA, wherein SEQ ID NO:79 is a clone designated herein as "DNA170245-3053".

FIG. 80 shows the amino acid sequence (SEQ ID NO:80) derived from the coding sequence of SEQ ID NO:79 shown in FIG. 79.

FIG. 81 shows a nucleotide sequence (SEQ ID NO:81) of a native sequence PRO20933 cDNA, wherein SEQ ID NO:81 is a clone designated herein as "DNA171771-2919".

FIG. 82 shows the amino acid sequence (SEQ ID NO:82) derived from the coding sequence of SEQ ID NO:81 shown in FIG. 81.

FIG. 83 shows a nucleotide sequence (SEQ ID NO:83) of a native sequence PRO21383 cDNA, wherein SEQ ID NO:83 is a clone designated herein as "DNA173157-2981".

FIG. 84 shows the amino acid sequence (SEQ ID NO:84) derived from the coding sequence of SEQ ID NO:83 shown in FIG. 83.

FIG. 85 shows a nucleotide sequence (SEQ ID NO:85) of a native sequence PRO21485 cDNA, wherein SEQ ID NO:85 is a clone designated herein as "DNA175734-2985".

FIG. 86 shows the amino acid sequence (SEQ ID NO:86) derived from the coding sequence of SEQ ID NO:85 shown in FIG. 85.

FIG. 87 shows a nucleotide sequence (SEQ ID NO:87) of a native sequence PRO28700 cDNA, wherein SEQ ID NO:87 is a clone designated herein as "DNA176108-3040".

FIG. 88 shows the amino acid sequence (SEQ ID NO:88) derived from the coding sequence of SEQ ID NO:87 shown in FIG. 87.

FIG. 89 shows a nucleotide sequence (SEQ ID NO:89) of a native sequence PRO34012 cDNA, wherein SEQ ID NO:89 is a clone designated herein as "DNA190710-3028".

FIG. 90 shows the amino acid sequence (SEQ ID NO:90) derived from the coding sequence of SEQ ID NO:89 shown in FIG. 89.

FIG. 91 shows a nucleotide sequence (SEQ ID NO:91) of a native sequence PRO34003 cDNA, wherein SEQ ID NO:91 is a clone designated herein as "DNA190803-3019".

FIG. 92 shows the amino acid sequence (SEQ ID NO:92) derived from the coding sequence of SEQ ID NO:91 shown in FIG. 91.

FIG. 93 shows a nucleotide sequence (SEQ ID NO:93) of a native sequence PRO34274 cDNA, wherein SEQ ID NO:93 is a clone designated herein as "DNA191064-3069".

FIG. 94 shows the amino acid sequence (SEQ ID NO:94) derived from the coding sequence of SEQ ID NO:93 shown in FIG. 93.

FIGS. 95A-95B shows a nucleotide sequence (SEQ ID NO:95) of a native sequence PRO34001 cDNA, wherein SEQ ID NO:95 is a clone designated herein as "DNA194909-3013".

FIG. 96 shows the amino acid sequence (SEQ ID NO:96) derived from the coding sequence of SEQ ID NO:95 shown in FIGS. 95A-95B.

FIG. 97 shows a nucleotide sequence (SEQ ID NO:97) of a native sequence PRO34009 cDNA, wherein SEQ ID NO:97 is a clone designated herein as "DNA203532-3029".

FIG. 98 shows the amino acid sequence (SEQ ID NO:98) derived from the coding sequence of SEQ ID NO:97 shown in FIG. 97.

FIG. 99 shows a nucleotide sequence (SEQ ID NO:99) of a native sequence PRO34192 cDNA, wherein SEQ ID NO:99 is a clone designated herein as "DNA213858-3060".

FIG. 100 shows the amino acid sequence (SEQ ID NO:100) derived from the coding sequence of SEQ ID NO:99 shown in FIG. 99.

FIG. 101 shows a nucleotide sequence (SEQ ID NO:101) of a native sequence PRO34564 cDNA, wherein SEQ ID NO:101 is a clone designated herein as "DNA216676-3083".

FIG. 102 shows the amino acid sequence (SEQ ID NO:102) derived from the coding sequence of SEQ ID NO:101 shown in FIG. 101.

FIG. 103 shows a nucleotide sequence (SEQ ID NO:103) of a native sequence PRO35444 cDNA, wherein SEQ ID NO:103 is a clone designated herein as "DNA222653-3104".

FIG. 104 shows the amino acid sequence (SEQ ID NO:104) derived from the coding sequence of SEQ ID NO:103 shown in FIG. 103.

FIG. 105 shows a nucleotide sequence (SEQ ID NO:105) of a native sequence PRO5998 cDNA, wherein SEQ ID NO:105 is a clone designated herein as "DNA96897-2688".

FIG. 106 shows the amino acid sequence (SEQ ID NO:106) derived from the coding sequence of SEQ ID NO:105 shown in FIG. 105.

FIG. 107 shows a nucleotide sequence (SEQ ID NO:107) of a native sequence PRO 19651 cDNA, wherein SEQ ID NO:107 is a clone designated herein as "DNA 142917-3081".

FIG. 108 shows the amino acid sequence (SEQ ID NO:108) derived from the coding sequence of SEQ ID NO:107 shown in FIG. 107.

FIG. 109 shows a nucleotide sequence (SEQ ID NO:109) of a native sequence PRO20221 cDNA, wherein SEQ ID NO:109 is a clone designated herein as "DNA142930-2914".

FIG. 110 shows the amino acid sequence (SEQ ID NO:110) derived from the coding sequence of SEQ ID NO:109 shown in FIG. 109.

FIG. 111 shows a nucleotide sequence (SEQ ID NO:111) of a native sequence PRO21434 cDNA, wherein SEQ ID NO:111 is a clone designated herein as "DNA 147253-2983".

FIG. 112 shows the amino acid sequence (SEQ ID NO:112) derived from the coding sequence of SEQ ID NO:111 shown in FIG. 111.

FIG. 113 shows a nucleotide sequence (SEQ ID NO:113) of a native sequence PRO 19822 cDNA, wherein SEQ ID NO:113 is a clone designated herein as "DNA 149927-2887".

FIG. 114 shows the amino acid sequence (SEQ ID NO:114) derived from the coding sequence of SEQ ID NO:113 shown in FIG. 113.

DETAILED DESCRIPTION OF THE PREFERRED EMBODIMENTS

I. Definitions

The terms "PRO polypeptide" and "PRO" as used herein and when immediately followed by a numerical designation refer to various polypeptides, wherein the complete designation (i.e., PRO/number) refers to specific polypeptide sequences as described herein. The terms "PRO/number polypeptide" and "PRO/number" wherein the term "number" is provided as an actual numerical designation as used herein encompass native sequence polypeptides and polypeptide variants (which are further defined herein). The PRO polypeptides described herein may be isolated from a variety of sources, such as from human tissue types or from another source, or prepared by recombinant or synthetic methods. The term "PRO polypeptide" refers to each individual PRO/number polypeptide disclosed herein. All disclosures in this specification which refer to the "PRO polypeptide" refer to each of the polypeptides individually as well as jointly. For example, descriptions of the preparation of, purification of, derivation of, formation of antibodies to or against, administration of, compositions containing, treatment of a disease with, etc., pertain to each polypeptide of the invention-individually. The term "PRO polypeptide" also includes variants of the PRO/number polypeptides disclosed herein.

A "native sequence PRO polypeptide" comprises a polypeptide having the same amino acid sequence as the corresponding PRO polypeptide derived from nature. Such native sequence PRO polypeptides can be isolated from nature or can be produced by recombinant or synthetic means. The term "native sequence PRO polypeptide" specifically encompasses naturally-occurring truncated or secreted forms of the specific PRO polypeptide (e.g., an extracellular domain sequence), naturally-occurring variant forms (e.g., alternatively spliced forms) and naturally-occurring allelic variants of the polypeptide. In various embodiments of the invention, the native sequence PRO polypeptides disclosed herein are mature or full-length native sequence polypeptides comprising the full-length amino acids sequences shown in the accompanying figures. Start and stop codons are shown in bold font and underlined in the figures. However, while the PRO polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the PRO polypeptides.

The PRO polypeptide "extracellular domain" or "ECD" refers to a form of the PRO polypeptide which is essentially free of the transmembrane and cytoplasmic domains. Ordinarily, a PRO polypeptide ECD will have less than 1% of such transmembrane and/or cytoplasmic domains and preferably, will have less than 0.5% of such domains. It will be understood that any transmembrane domains identified for the PRO polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a PRO polypeptide may contain from about 5 or fewer amino acids on either side of the transmembrane domain/extracellular domain boundary as identified in the Examples or specification and such polypeptides, with or without the associated signal peptide, and nucleic acid encoding them, are contemplated by the present invention.

The approximate location of the "signal peptides" of the various PRO polypeptides disclosed herein are shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., Prot. Eng. 10:1-6 (1997) and von Heinje et al., Nucl. Acids. Res. 14:4683-4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"PRO polypeptide variant" means an active PRO polypeptide as defined above or below having at least about 80% amino acid sequence identity with a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Such PRO polypeptide variants include, for instance, PRO polypeptides wherein one or more amino acid residues are added, or deleted, at the N- or C-terminus of the full-length native amino acid sequence. Ordinarily, a PRO polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other specifically defined fragment of a full-length PRO polypeptide sequence as disclosed herein. Ordinarily, PRO variant polypeptides are at least about 10 amino acids in length, alternatively at least about 20 amino acids in length, alternatively at least about 30 amino acids in length, alternatively at least about 40 amino acids in length, alternatively at least about 50 amino acids in length, alternatively at least about 60 amino acids in length, alternatively at least about 70 amino acids in length, alternatively at least about 80 amino acids in length, alternatively at least about 90 amino acids in length, alternatively at least about 100 amino acids in length, alternatively at least about 150 amino acids in length, alternatively at least about 200 amino acids in length, alternatively at least about 300 amino acids in length, or more.

"Percent (%) amino acid sequence identity" with respect to the PRO polypeptide sequences identified herein is defined as the percentage of amino acid residues in a candidate sequence that are identical with the amino acid residues in the specific PRO polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "PRO", wherein "PRO" represents the amino acid sequence of a hypothetical PRO polypeptide of interest, "Comparison Protein" represents the amino acid sequence of a polypeptide against which the "PRO" polypeptide of interest is being compared, and "X, Y" and "Z" each represent different hypothetical amino acid residues.

Unless specifically stated otherwise, all % amino acid sequence identity values used herein are obtained as described in the immediately preceding paragraph using the ALIGN-2 computer program. However, % amino acid sequence identity values may also be obtained as described below by using the WU-BLAST-2 computer program (Altschul et al., *Methods in Enzymology* 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the PRO polypeptide of interest having a sequence derived from the native PRO polypeptide and the comparison amino acid sequence of interest (i.e., the sequence against which the PRO polypeptide of interest is being compared which may be a PRO variant polypeptide) as determined by WU-BLAST-2 by (b) the total number of amino acid residues of the PRO polypeptide of interest. For example, in the statement "a polypeptide comprising an the amino acid sequence A which has or having at least 80% amino acid sequence identity to the amino acid sequence B", the amino acid sequence A is the comparison amino acid sequence of interest and the amino acid sequence B is the amino acid sequence of the PRO polypeptide of interest.

Percent amino acid sequence identity may also be determined using the sequence comparison program NCBI-BLAST2 (Altschul et al., *Nucleic Acids Res.* 25:3389-3402 (1997)). The NCBI-BLAST2 sequence comparison program may be obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"PRO variant polynucleotide" or "PRO variant nucleic acid sequence" means a nucleic acid molecule which encodes an active PRO polypeptide as defined below and which has at least about 80% nucleic acid sequence identity with a nucleotide acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Ordinarily, a PRO variant polynucleotide will have at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity with a nucleic acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal sequence, as disclosed herein or any other fragment of a full-length PRO polypeptide sequence as disclosed herein. Variants do not encompass the native nucleotide sequence.

Ordinarily, PRO variant polynucleotides are at least about 30 nucleotides in length, alternatively at least about 60 nucleotides in length, alternatively at least about 90 nucleotides in length, alternatively at least about 120 nucleotides in length, alternatively at least about 150 nucleotides in length, alternatively at least about 180 nucleotides in length, alternatively at least about 210 nucleotides in length, alternatively at least about 240 nucleotides in length, alternatively at least about 270 nucleotides in length, alternatively at least about 300 nucleotides in length, alternatively at least about 450 nucleotides in length, alternatively at least about 600 nucleotides in length, alternatively at least about 900 nucleotides in length, or more.

"Percent (%) nucleic acid sequence identity" with respect to PRO-encoding nucleic acid sequences identified herein is defined as the percentage of nucleotides in a candidate sequence that are identical with the nucleotides in the PRO nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "PRO-DNA", wherein "PRO-DNA" represents a hypothetical PRO-encoding nucleic acid sequence of interest, "Comparison DNA" represents the nucleotide sequence of a nucleic acid molecule against which the "PRO-DNA" nucleic acid molecule of interest is being compared, and "N", "L" and "V" each represent different hypothetical nucleotides.

Unless specifically stated otherwise, all % nucleic acid sequence identity values used herein are obtained as described in the immediately preceding paragraph using the ALIGN-2 computer program. However, % nucleic acid sequence identity values may also be obtained as described below by using the WU-BLAST-2 computer program (Altschul et al., *Methods in Enzymology* 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % nucleic acid sequence identity value is determined by dividing (a) the number of matching identical nucleotides between the nucleic acid sequence of the PRO polypeptide-encoding nucleic acid molecule of interest having a sequence derived from the native sequence PRO polypeptide-encoding nucleic acid and the comparison nucleic acid molecule of interest (i.e., the sequence against which the PRO polypeptide-encoding nucleic acid molecule of interest is being compared which may be a variant PRO polynucleotide) as determined by WU-BLAST-2 by (b) the total number of nucleotides of the PRO polypeptide-encoding nucleic acid molecule of interest. For example, in the statement "an isolated nucleic acid molecule comprising a nucleic acid sequence A which has or having at least 80% nucleic acid sequence identity to the nucleic acid sequence B", the nucleic acid sequence A is the comparison nucleic acid molecule of interest and the nucleic acid sequence B is the nucleic acid sequence of the PRO polypeptide-encoding nucleic acid molecule of interest.

Percent nucleic acid sequence identity may also be determined using the sequence comparison program NCBI-BLAST2 (Altschul et al., Nucleic Acids Res. 25:3389-3402 (1997)). The NCBI-BLAST2 sequence comparison program may be obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, PRO variant polynucleotides are nucleic acid molecules that encode an active PRO polypeptide and which are capable of hybridizing, preferably under stringent hybridization and wash conditions, to nucleotide sequences encoding a full-length PRO polypeptide as disclosed herein. PRO variant polypeptides may be those that are encoded by a PRO variant polynucleotide.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO polypeptide natural environment will not be present. Ordinarily, however, isolated polypeptide will be prepared by at least one purification step.

An "isolated" PRO polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers, for example, single anti-PRO monoclonal antibodies (including agonist, antagonist, and neutralizing antibodies), anti-PRO antibody compositions with polyepitopic specificity, single chain anti-PRO antibodies, and fragments of anti-PRO antibodies (see below). The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a PRO polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesion") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesion part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Active" or "activity" for the purposes herein refers to form(s) of a PRO polypeptide which retain a biological and/or an immunological activity of native or naturally-occurring PRO, wherein "biological" activity refers to a biological function (either inhibitory or stimulatory) caused by a native or naturally-occurring PRO other than the ability to induce the production of an antibody against an antigenic epitope possessed by a native or naturally-occurring PRO and an "immunological" activity refers to the ability to induce the production of an antibody against an antigenic epitope possessed by a native or naturally-occurring PRO.

The term "antagonist" is used in the broadest sense, and includes any molecule that partially or fully blocks, inhibits, or neutralizes a biological activity of a native PRO polypeptide disclosed herein. In a similar manner, the term "agonist" is used in the broadest sense and includes any molecule that mimics a biological activity of a native PRO polypeptide disclosed herein. Suitable agonist or antagonist molecules specifically include agonist or antagonist antibodies or antibody fragments, fragments or amino acid sequence variants of native PRO polypeptides, peptides, antisense oligonucleotides, small organic molecules, etc. Methods for identifying agonists or antagonists of a PRO polypeptide may comprise contacting a PRO polypeptide with a candidate agonist or antagonist molecule and measuring a detectable change in one or more biological activities normally associated with the PRO polypeptide.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8(10): 1057-1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

The word "label" when used herein refers to a detectable compound or composition which is conjugated directly or indirectly to the antibody so as to generate a "labeled" antibody. The label may be detectable by itself (e.g. radio-isotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a PRO polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

An "effective amount" of a polypeptide disclosed herein or an agonist or antagonist thereof is an amount sufficient to carry out a specifically stated purpose. An "effective amount" may be determined empirically and in a routine manner, in relation to the stated purpose.

Table 1

```
/*
 *
 * C-C increased from 12 to 15
 * Z is average of EQ
 * B is average of ND
 * match with stop is _M; stop-stop = 0; J (joker) match = 0
 */
define  _M    -8       /* value of a match with a stop */ int     _day[26][26] = {
/*     A  B  C  D  E  F  G  H  I  J  K  L  M  N  O  P  Q  R  S  T  U  V  W  X  Y  Z*/
/* A */ { 2, 0,-2, 0, 0,-4, 1,-1,-1, 0,-1,-2,-1, 0,_M, 1, 0,-2, 1, 1, 0, 0,-6, 0,-3, 0},
/* B */ { 0, 3,-4, 3, 2,-5, 0, 1,-2, 0, 0,-3,-2, 2,_M,-1, 1, 0, 0, 0, 0,-2,-5, 0,-3, 1},
/* C */ {-2,-4,15,-5,-5,-4,-3,-3,-2, 0,-5,-6,-5,-4,_M,-3,-5,-4, 0,-2, 0,-2,-8, 0, 0,-5},
/* D */ { 0, 3,-5, 4, 3,-6, 1, 1,-2, 0, 0,-4,-3, 2,_M,-1, 2,-1, 0, 0, 0,-2,-7, 0,-4, 2},
/* E */ { 0, 2,-5, 3, 4,-5, 0, 1,-2, 0, 0,-3,-2, 1,_M,-1, 2,-1, 0, 0, 0,-2,-7, 0,-4, 3},
/* F */ {-4,-5,-4,-6,-5, 9,-5,-2, 1, 0,-5, 2, 0,-4,_M,-5,-5,-4,-3,-3, 0,-1, 0, 0, 7,-5},
/* G */ { 1, 0,-3, 1, 0,-5, 5,-2,-3, 0,-2,-4,-3, 0,_M,-1,-1,-3, 1, 0, 0,-1,-7, 0,-5, 0},
/* H */ {-1, 1,-3, 1, 1,-2,-2, 6,-2, 0, 0,-2,-2, 2,_M, 0, 3, 2,-1,-1, 0,-2,-3, 0, 0, 2},
/* I */ {-1,-2,-2,-2,-2, 1,-3,-2, 5, 0,-2, 2, 2,-2,_M,-2,-2,-2,-1, 0, 0, 4,-5, 0,-1,-2},
/* J */ { 0, 0, 0, 0, 0, 0, 0, 0, 0, 0, 0, 0, 0, 0,_M, 0, 0, 0, 0, 0, 0, 0, 0, 0, 0, 0},
/* K */ {-1, 0,-5, 0, 0,-5,-2, 0,-2, 0, 5,-3, 0, 1,_M,-1, 1, 3, 0, 0, 0,-2,-3, 0,-4, 0},
/* L */ {-2,-3,-6,-4,-3, 2,-4,-2, 2, 0,-3, 6, 4,-3,_M,-3,-2,-3,-3,-1, 0, 2,-2, 0,-1,-2},
/* M */ {-1,-2,-5,-3,-2, 0,-3,-2, 2, 0, 0, 4, 6,-2,_M,-2,-1, 0,-2,-1, 0, 2,-4, 0,-2,-1},
/* N */ { 0, 2,-4, 2, 1,-4, 0, 2,-2, 0, 1,-3,-2, 2,_M,-1, 1, 0, 1, 0, 0,-2,-4, 0,-2, 1},
/* O */ {_M,_M,_M,_M,_M,_M,_M,_M,_M,_M,_M,_M,_M,_M, 0,_M,_M,_M,_M,_M,_M,_M,_M,_M,_M,_M},
/* P */ { 1,-1,-3,-1,-1,-5,-1, 0,-2, 0,-1,-3,-2,-1,_M, 6, 0, 0, 1, 0, 0,-1,-6, 0,-5, 0},
/* Q */ { 0, 1,-5, 2, 2,-5,-1, 3,-2, 0, 1,-2,-1, 1,_M, 0, 4, 1,-1,-1, 0,-2,-5, 0,-4, 3},
/* R */ {-2, 0,-4,-1,-1,-4,-3, 2,-2, 0, 3,-3, 0, 0,_M, 0, 1, 6, 0,-1, 0,-2, 2, 0,-4, 0},
/* S */ { 1, 0, 0, 0, 0,-3, 1,-1,-1, 0, 0,-3,-2, 1,_M, 1,-1, 0, 2, 1, 0,-1,-2, 0,-3, 0},
/* T */ { 1, 0,-2, 0, 0,-3, 0,-1, 0, 0, 0,-1,-1, 0,_M, 0,-1,-1, 1, 3, 0, 0,-5, 0,-3, 0},
/* U */ { 0, 0, 0, 0, 0, 0, 0, 0, 0, 0, 0, 0, 0, 0,_M, 0, 0, 0, 0, 0, 0, 0, 0, 0, 0, 0},
/* V */ { 0,-2,-2,-2,-2,-1,-1,-2, 4, 0,-2, 2, 2,-2,_M,-1,-2,-2,-1, 0, 0, 4,-6, 0,-2,-2},
/* W */ {-6,-5,-8,-7,-7, 0,-7,-3,-5, 0,-3,-2,-4,-4,_M,-6,-5, 2,-2,-5, 0,-6,17, 0, 0,-6},
/* X */ { 0, 0, 0, 0, 0, 0, 0, 0, 0, 0, 0, 0, 0, 0,_M, 0, 0, 0, 0, 0, 0, 0, 0, 0, 0, 0},
/* Y */ {-3,-3, 0,-4,-4, 7,-5, 0,-1, 0,-4,-1,-2,-2,_M,-5,-4,-4,-3,-3, 0,-2, 0, 0,10,-4},
/* Z */ { 0, 1,-5, 2, 3,-5, 0, 2,-2, 0, 0,-2,-1, 1,_M, 0, 3, 0, 0, 0, 0,-2,-6, 0,-4, 4}
};
```

Table 1 (cont')

```
/*
*/
#include <stdio.h>
include <ctype.h> define  MAXJMP   16        /* max jumps in a diag */
define  MAXGAP   24        /* don't continue to penalize gaps larger than this */
#define  JMPS     1024      /* max jmps in an path */
define  MX       4         /* save if there's at least MX-1 bases since last jmp */ define  DMAT     3         /* value of matching bases */
define  DMIS     0         /* penalty for mismatched bases */
#define  DINS0    8         /* penalty for a gap */
#define  DINS1    1         /* penalty per base */
#define  PINS0    8         /* penalty for a gap */
define  PINS1    4         /* penalty per residue */ struct jmp {
        short          n[MAXJMP];      /* size of jmp (neg for dely) */
        unsigned short x[MAXJMP];      /* base no. of jmp in seq x */
};                                     /* limits seq to 2^16 -1 */ struct diag {
        int       score;               /* score at last jmp */
        long      offset;              /* offset of prev block */
        short     ijmp;                /* current jmp index */
        struct jmp jp;                 /* list of jmps */
};

struct path {
        int    spc;                    /* number of leading spaces */
        short  n[JMPS];                /* size of jmp (gap) */
        int    x[JMPS];                /* loc of jmp (last elem before gap) */
};

char    *ofile;                        /* output file name */
char    *namex[2];                     /* seq names: getseqs() */
char    *prog;                         /* prog name for err msgs */
char    *seqx[2];                      /* seqs: getseqs() */
int     dmax;                          /* best diag: nw() */
int     dmax0;                         /* final diag */
int     dna;                           /* set if dna: main() */
int     endgaps;                       /* set if penalizing end gaps */
int     gapx, gapy;                    /* total gaps in seqs */
int     len0, len1;                    /* seq lens */
int     ngapx, ngapy;                  /* total size of gaps */
int     smax;                          /* max score: nw() */
int     *xbm;                          /* bitmap for matching */
long    offset;                        /* current offset in jmp file */
struct  diag  *dx;                     /* holds diagonals */
struct  path  pp[2];                   /* holds path for seqs */ char    *calloc(), *malloc(), *index(), *strcpy();
char    *getseq(), *g_calloc();
```

Table 1 (cont')

```
/* Needleman-Wunsch alignment program
 *
 * usage: progs file1 file2
 *   where file1 and file2 are two dna or two protein sequences.
 *   The sequences can be in upper- or lower-case an may contain ambiguity
 *   Any lines beginning with ';', '>' or '<' are ignored
 *   Max file length is 65535 (limited by unsigned short x in the jmp struct)
 *   A sequence with 1/3 or more of its elements ACGTU is assumed to be DNA
 *   Output is in the file "align.out"
 *
 * The program may create a tmp file in /tmp to hold info about traceback.
 * Original version developed under BSD 4.3 on a vax 8650
 */
include "nw.h"
#include "day.h"

static  _dbval[26] = {
        1,14,2,13,0,0,4,11,0,0,12,0,3,15,0,0,0,5,6,8,8,7,9,0,10,0
};

static  _pbval[26] = {
        1, 2|(1<<('D'-'A'))|(1<<('N'-'A')), 4, 8, 16, 32, 64,
        128, 256, 0xFFFFFFFF, 1<<10, 1<<11, 1<<12, 1<<13, 1<<14,
        1<<15, 1<<16, 1<<17, 1<<18, 1<<19, 1<<20, 1<<21, 1<<22,
        1<<23, 1<<24, 1<<25|(1<<('E'-'A'))|(1<<('Q'-'A'))
};

main(ac, av)                                                                    main
        int     ac;
        char    *av[];
{
        prog = av[0];
        if (ac != 3) {
                fprintf(stderr,"usage: %s file1 file2\n", prog);
                fprintf(stderr,"where file1 and file2 are two dna or two protein sequences.\n");
                fprintf(stderr,"The sequences can be in upper- or lower-case\n");
                fprintf(stderr,"Any lines beginning with ';' or '<' are ignored\n");
                fprintf(stderr,"Output is in the file \"align.out\"\n");
                exit(1);
        }
        namex[0] = av[1];
        namex[1] = av[2];
        seqx[0] = getseq(namex[0], &len0);
        seqx[1] = getseq(namex[1], &len1);
        xbm = (dna)? _dbval : _pbval;

endgaps = 0;            /* 1 to penalize endgaps */
        ofile = "align.out";    /* output file */ nw();                   /* fill in the matrix, get the possible jmps */
        readjmps();             /* get the actual jmps */
        print();                /* print stats, alignment */ cleanup(0);             /* unlink any tmp files */
}
```

Table 1 (cont')

```
/* do the alignment, return best score: main()
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw()
{
        char            *px, *py;         /* seqs and ptrs */
        int             *ndely, *dely;    /* keep track of dely */
        int             ndelx, delx;      /* keep track of delx */
        int             *tmp;             /* for swapping row0, row1 */
        int             mis;              /* score for each type */
        int             ins0, ins1;       /* insertion penalties */
        register        id;               /* diagonal index */
        register        ij;               /* jmp index */
        register        *col0, *col1;     /* score for curr, last row */
        register        xx, yy;           /* index into seqs */ dx = (struct diag *)g_calloc("to get diags", len0+len1+1, sizeof(struct diag));

ndely = (int *)g_calloc("to get ndely", len1+1, sizeof(int));
        dely  = (int *)g_calloc("to get dely",  len1+1, sizeof(int));
        col0  = (int *)g_calloc("to get col0",  len1+1, sizeof(int));
        col1  = (int *)g_calloc("to get col1",  len1+1, sizeof(int));
        ins0  = (dna)? DINS0 : PINS0;
        ins1  = (dna)? DINS1 : PINS1;

smax = -10000;
        if (endgaps) {
                for (col0[0] = dely[0] = -ins0, yy = 1; yy <= len1; yy++) {
                        col0[yy] = dely[yy] = col0[yy-1] - ins1;
                        ndely[yy] = yy;
                }
                col0[0] = 0;        /* Waterman Bull Math Biol 84 */
        }
        else
                for (yy = 1; yy <= len1; yy++)
                        dely[yy] = -ins0;

/* fill in match matrix
         */
        for (px = seqx[0], xx = 1; xx <= len0; px++, xx++) {
                /* initialize first entry in col
                 */
                if (endgaps) {
                        if (xx == 1)
                                col1[0] = delx = -(ins0+ins1);
                        else
                                col1[0] = delx = col0[0] - ins1;
                        ndelx = xx;
                }
                else {
                        col1[0] = 0;
                        delx = -ins0;
                        ndelx = 0;
                }
``` nw

Table 1 (cont')

...nw

```
for (py = seqx[1], yy = 1; yy < = len1; py++, yy++) {
        mis = col0[yy-1];
        if (dna)
                mis += (xbm[*px-'A']&xbm[*py-'A'])? DMAT : DMIS;
        else
                mis += _day[*px-'A'][*py-'A'];

/* update penalty for del in x seq;
         * favor new del over ongong del
         * ignore MAXGAP if weighting endgaps
         */
        if (endgaps || ndely[yy] < MAXGAP) {
                if (col0[yy] - ins0 > = dely[yy]) {
                        dely[yy] = col0[yy] - (ins0+ins1);
                        ndely[yy] = 1;
                } else {
                        dely[yy] -= ins1;
                        ndely[yy]++;
                }
        } else {
                if (col0[yy] - (ins0+ins1) > = dely[yy]) {
                        dely[yy] = col0[yy] - (ins0+ins1);
                        ndely[yy] = 1;
                } else
                        ndely[yy]++;
        }

/* update penalty for del in y seq;
         * favor new del over ongong del
         */
        if (endgaps || ndelx < MAXGAP) {
                if (col1[yy-1] - ins0 > = delx) {
                        delx = col1[yy-1] - (ins0+ins1);
                        ndelx = 1;
                } else {
                        delx -= ins1;
                        ndelx++;
                }
        } else {
                if (col1[yy-1] - (ins0+ins1) > = delx) {
                        delx = col1[yy-1] - (ins0+ins1);
                        ndelx = 1;
                } else
                        ndelx++;
        }

/* pick the maximum score; we're favoring
         * mis over any del and delx over dely
         */
```

Table 1 (cont')

...nw

```
                id = xx - yy + len1 - 1;
                if (mis >= delx && mis >= dely[yy])
                        col1[yy] = mis;
                else if (delx >= dely[yy]) {
                        col1[yy] = delx;
                        ij = dx[id].ijmp;
                        if (dx[id].jp.n[0] && (!dna || (ndelx >= MAXJMP
                            && xx > dx[id].jp.x[ij]+MX) || mis > dx[id].score+DINS0)) {
                                dx[id].ijmp++;
                                if (++ij >= MAXJMP) {
                                        writejmps(id);
                                        ij = dx[id].ijmp = 0;
                                        dx[id].offset = offset;
                                        offset += sizeof(struct jmp) + sizeof(offset);
                                }
                        }
                        dx[id].jp.n[ij] = ndelx;
                        dx[id].jp.x[ij] = xx;
                        dx[id].score = delx;
                }
                else {
                        col1[yy] = dely[yy];
                        ij = dx[id].ijmp;
                        if (dx[id].jp.n[0] && (!dna || (ndely[yy] >= MAXJMP
                            && xx > dx[id].jp.x[ij]+MX) || mis > dx[id].score+DINS0)) {
                                dx[id].ijmp++;
                                if (++ij >= MAXJMP) {
                                        writejmps(id);
                                        ij = dx[id].ijmp = 0;
                                        dx[id].offset = offset;
                                        offset += sizeof(struct jmp) + sizeof(offset);
                                }
                        }
                        dx[id].jp.n[ij] = -ndely[yy];
                        dx[id].jp.x[ij] = xx;
                        dx[id].score = dely[yy];
                }
                if (xx == len0 && yy < len1) {
                        /* last col
                        */
                        if (endgaps)
                                col1[yy] -= ins0+ins1*(len1-yy);
                        if (col1[yy] > smax) {
                                smax = col1[yy];
                                dmax = id;
                        }
                }
        }
        if (endgaps && xx < len0)
                col1[yy-1] -= ins0+ins1*(len0-xx);
        if (col1[yy-1] > smax) {
                smax = col1[yy-1];
                dmax = id;
        }
        tmp = col0; col0 = col1; col1 = tmp;
}
(void) free((char *)ndely);
(void) free((char *)dely);
(void) free((char *)col0);
(void) free((char *)col1);                              }
```

Table 1 (cont')

```
/*
 *
 * print() -- only routine visible outside this module
 *
 * static:
 * getmat() -- trace back best path, count matches: print()
 * pr_align() -- print alignment of described in array p[]: print()
 * dumpblock() -- dump a block of lines with numbers, stars: pr_align()
 * nums() -- put out a number line: dumpblock()
 * putline() -- put out a line (name, [num], seq, [num]): dumpblock()
 * stars() - -put a line of stars: dumpblock()
 * stripname() -- strip any path and prefix from a seqname
 */ include "nw.h"

define SPC     3
#define P_LINE  256     /* maximum output line */
define P_SPC   3       /* space between name or num and seq */ extern  _day[26][26];
int     olen;           /* set output line length */
FILE    *fx;            /* output file */ print()                                                                 print
{
        int     lx, ly, firstgap, lastgap;      /* overlap */ if ((fx = fopen(ofile, "w")) == 0) {
                fprintf(stderr,"%s: can't write %s\n", prog, ofile);
                cleanup(1);
        }
        fprintf(fx, " <first sequence: %s (length = %d)\n", namex[0], len0);
        fprintf(fx, " <second sequence: %s (length = %d)\n", namex[1], len1);
        olen = 60;
        lx = len0;
        ly = len1;
        firstgap = lastgap = 0;
        if (dmax < len1 - 1) {          /* leading gap in x */
                pp[0].spc = firstgap = len1 - dmax - 1;
                ly -= pp[0].spc;
        }
        else if (dmax > len1 - 1) {     /* leading gap in y */
                pp[1].spc = firstgap = dmax - (len1 - 1);
                lx -= pp[1].spc;
        }
        if (dmax0 < len0 - 1) {         /* trailing gap in x */
                lastgap = len0 - dmax0 -1;
                lx -= lastgap;
        }
        else if (dmax0 > len0 - 1) {    /* trailing gap in y */
                lastgap = dmax0 - (len0 - 1);
                ly -= lastgap;
        }
        getmat(lx, ly, firstgap, lastgap);
        pr_align();
}
```

30

Table 1 (cont')

```
/*
 * trace back the best path, count matches
 */
static
getmat(lx, ly, firstgap, lastgap)
         int        lx, ly;                  /* "core" (minus endgaps) */
         int        firstgap, lastgap;       /* leading trailing overlap */
{
         int        nm, i0, i1, siz0, siz1;
         char       outx[32];
         double     pct;
         register   n0, n1;
         register char  *p0, *p1;

/* get total matches, score
          */
         i0 = i1 = siz0 = siz1 = 0;
         p0 = seqx[0] + pp[1].spc;
         p1 = seqx[1] + pp[0].spc;
         n0 = pp[1].spc + 1;
         n1 = pp[0].spc + 1;

nm = 0;
         while ( *p0 && *p1 ) {
                 if (siz0) {
                         p1++;
                         n1++;
                         siz0--;
                 }
                 else if (siz1) {
                         p0++;
                         n0++;
                         siz1--;
                 }
                 else {
                         if (xbm[*p0-'A']&xbm[*p1-'A'])
                                 nm++;
                         if (n0++ == pp[0].x[i0])
                                 siz0 = pp[0].n[i0++];
                         if (n1++ == pp[1].x[i1])
                                 siz1 = pp[1].n[i1++];
                         p0++;
                         p1++;
                 }
         }

/* pct homology:
          * if penalizing endgaps, base is the shorter seq
          * else, knock off overhangs and take shorter core
          */
         if (endgaps)
                 lx = (len0 < len1)? len0 : len1;
         else
                 lx = (lx < ly)? lx : ly;
         pct = 100.*(double)nm/(double)lx;
         fprintf(fx, "\n");
         fprintf(fx, " <%d match%s in an overlap of %d: %.2f percent similarity\n",
                 nm, (nm == 1)? "" : "es", lx, pct);
``` getmat

Table 1 (cont')

```
                fprintf(fx, "<gaps in first sequence: %d", gapx);                    ...getmat
                if (gapx) {
                        (void) sprintf(outx, " (%d %s%s)",
                                ngapx, (dna)? "base":"residue", (ngapx == 1)? "":"s");
  5                     fprintf(fx,"%s", outx);

fprintf(fx, ", gaps in second sequence: %d", gapy);
                if (gapy) {
                        (void) sprintf(outx, " (%d %s%s)",
 10                             ngapy, (dna)? "base":"residue", (ngapy == 1)? "":"s");
                        fprintf(fx,"%s", outx);
                }
                if (dna)
                        fprintf(fx,
 15                     "\n<score: %d (match = %d, mismatch = %d, gap penalty = %d + %d per base)\n",
                        smax, DMAT, DMIS, DINS0, DINS1);
                else
                        fprintf(fx,
                        "\n<score: %d (Dayhoff PAM 250 matrix, gap penalty = %d + %d per residue)\n",
 20                     smax, PINS0, PINS1);
                if (endgaps)
                        fprintf(fx,
                        "<endgaps penalized. left endgap: %d %s%s, right endgap: %d %s%s\n",
                        firstgap, (dna)? "base" : "residue", (firstgap == 1)? "" : "s",
 25                     lastgap, (dna)? "base" : "residue", (lastgap == 1)? "" : "s");
                else
                        fprintf(fx, "<endgaps not penalized\n");
        }

30     static          nm;             /* matches in core -- for checking */
        static          lmax;           /* lengths of stripped file names */
        static          ij[2];          /* jmp index for a path */
        static          nc[2];          /* number at start of current line */
        static          ni[2];          /* current elem number -- for gapping */
 35     static          siz[2];
        static char     *ps[2];         /* ptr to current element */
        static char     *po[2];         /* ptr to next output char slot */
        static char     out[2][P_LINE]; /* output line */
        static char     star[P_LINE];   /* set by stars() */
 40
        /*
         * print alignment of described in struct path pp[]
         */
        static
 45     pr_align()                                                                   pr_align
        {
                int             nn;     /* char count */
                int             more;
                register        i;
 50
                for (i = 0, lmax = 0; i < 2; i++) {
                        nn = stripname(namex[i]);
                        if (nn > lmax)
                                lmax = nn;
 55
                        nc[i] = 1;
                        ni[i] = 1;
                        siz[i] = ij[i] = 0;
                        ps[i] = seqx[i];
 60                     po[i] = out[i];                         }
```

Table 1 (cont')

```
        for (nn = nm = 0, more = 1; more; ) {                             ...pr_align
                for (i = more = 0; i < 2; i++) {
                        /*
 5                       * do we have more of this sequence?
                         */
                        if (!*ps[i])
                                continue;
10                      more++;

if (pp[i].spc) {      /* leading space */
                                *po[i]++ = ' ';
                                pp[i].spc--;
15                      }
                        else if (siz[i]) {    /* in a gap */
                                *po[i]++ = '-';
                                siz[i]--;
                        }
20                      else {                /* we're putting a seq element
                                               */
                                *po[i] = *ps[i];
                                if (islower(*ps[i]))
                                        *ps[i] = toupper(*ps[i]);
25                              po[i]++;
                                ps[i]++;

/*
                                 * are we at next gap for this seq?
30                               */
                                if (ni[i] == pp[i].x[ij[i]]) {
                                        /*
                                         * we need to merge all gaps
                                         * at this location
35                                       */
                                        siz[i] = pp[i].n[ij[i]++];
                                        while (ni[i] == pp[i].x[ij[i]])
                                                siz[i] += pp[i].n[ij[i]++];
                                }
40                              ni[i]++;
                        }
                }
                if (++nn == olen || !more && nn) {
                        dumpblock();
45                      for (i = 0; i < 2; i++)
                                po[i] = out[i];
                        nn = 0;
                }
        }
50  }
    /*
     * dump a block of lines, including numbers, stars: pr_align()
     */
55  static
    dumpblock()                                                           dumpblock
    {
            register i;

60          for (i = 0; i < 2; i++)
                    *po[i]-- = '\0';
```

Table 1 (cont')

...dumpblock

```
            (void) putc('\n', fx);
            for (i = 0; i < 2; i++) {
                    if (*out[i] && (*out[i] != ' ' || *(po[i]) != ' ')) {
                            if (i == 0)
                                    nums(i);
                            if (i == 0 && *out[1])
                                    stars();
                            putline(i);
                            if (i == 0 && *out[1])
                                    fprintf(fx, star);
                            if (i == 1)
                                    nums(i);
                    }
            }
    }
    /*
     * put out a number line: dumpblock()
     */
    static
    nums(ix)
            int     ix;     /* index in out[] holding seq line */
    {
            char    nline[P_LINE];
            register i, j;
            register char *pn, *px, *py;

for (pn = nline, i = 0; i < lmax+P_SPC; i++, pn++)
                    *pn = ' ';
            for (i = nc[ix], py = out[ix]; *py; py++, pn++) {
                    if (*py == ' ' || *py == '-')
                            *pn = ' ';
                    else {
                            if (i%10 == 0 || (i == 1 && nc[ix] != 1)) {
                                    j = (i < 0)? -i : i;
                                    for (px = pn; j; j /= 10, px--)
                                            *px = j%10 + '0';
                                    if (i < 0)
                                            *px = '-';
                            }
                            else
                                    *pn = ' ';
                            i++;
                    }
            }
            *pn = '\0';
            nc[ix] = i;
            for (pn = nline; *pn; pn++)
                    (void) putc(*pn, fx);
            (void) putc('\n', fx);
    }
    /*
     * put out a line (name, [num], seq, [num]): dumpblock()
     */
    static
    putline(ix)
            int     ix;                     {
``` nums putline

34

Table 1 (cont')

...putline

```
              int           i;
              register char *px;

for (px = namex[ix], i = 0; *px && *px != ':'; px++, i++)
                      (void) putc(*px, fx);
              for (; i < lmax+P_SPC; i++)
                      (void) putc(' ', fx);

/* these count from 1:
               * ni[] is current element (from 1)
               * nc[] is number at start of current line
               */
              for (px = out[ix]; *px; px++)
                      (void) putc(*px&0x7F, fx);
              (void) putc('\n', fx);
      }

/*
       * put a line of stars (seqs always in out[0], out[1]): dumpblock()
       */
      static
      stars()                                                                    stars
      {
              int           i;
              register char *p0, *p1, cx, *px;

if (!*out[0] || (*out[0] == ' ' && *(po[0]) == ' ') ||
                  !*out[1] || (*out[1] == ' ' && *(po[1]) == ' '))
                      return;
              px = star;
              for (i = lmax+P_SPC; i; i--)
                      *px++ = ' ';

for (p0 = out[0], p1 = out[1]; *p0 && *p1; p0++, p1++) {
                      if (isalpha(*p0) && isalpha(*p1)) {
                              if (xbm[*p0-'A']&xbm[*p1-'A']) {
                                      cx = '*';
                                      nm++;
                              }
                              else if (!dna && _day[*p0-'A'][*p1-'A'] > 0)
                                      cx = '.';
                              else
                                      cx = ' ';
                      }
                      else
                              cx = ' ';
                      *px++ = cx;
              }
              *px++ = '\n';
              *px = '\0';
      }
```

Table 1 (cont')

```
/*
 * strip path or prefix from pn, return len: pr_align()
 */
static
stripname(pn)                                                    stripname
        char       *pn;     /* file name (may be path) */
{
        register char     *px, *py;

py = 0;
        for (px = pn; *px; px++)
                if (*px == '/')
                        py = px + 1;
        if (py)
                (void) strcpy(pn, py);
        return(strlen(pn));

}
```

Table 1 (cont')

```
/*
 * cleanup() -- cleanup any tmp file
 * getseq() -- read in seq, set dna, len, maxlen
 * g_calloc() -- calloc() with error checkin
 * readjmps() -- get the good jmps, from tmp file if necessary
 * writejmps() -- write a filled array of jmps to a tmp file: nw()
 */
include "nw.h"
include <sys/file.h> char    *jname = "/tmp/homgXXXXXX";        /* tmp file for jmps */
FILE    *fj;

int     cleanup();                          /* cleanup tmp file */
long    lseek();

/*
 * remove any tmp file if we blow
 */
cleanup(i)                                                                      cleanup
        int     i;
{
        if (fj)
                (void) unlink(jname);
        exit(i);
}

/*
 * read, return ptr to seq, set dna, len, maxlen
 * skip lines starting with ';', '<', or '>'
 * seq in upper or lower case
 */
char    *
getseq(file, len)                                                               getseq
        char    *file;       /* file name */
        int     *len;        /* seq len */
{
        char            line[1024], *pseq;
        register char   *px, *py;
        int             natgc, tlen;
        FILE            *fp;

if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc() failed to get %d bytes for %s\n", prog, tlen+6, file);
                exit(1);
        }
        pseq[0] = pseq[1] = pseq[2] = pseq[3] = '\0';
```

Table 1 (cont')

...getseq

```
            py = pseq + 4;
            *len = tlen;
            rewind(fp);
            while (fgets(line, 1024, fp)) {
                    if (*line == ';' || *line == '<' || *line == '>')
                            continue;
                    for (px = line; *px != '\n'; px++) {
                            if (isupper(*px))
                                    *py++ = *px;
                            else if (islower(*px))
                                    *py++ = toupper(*px);
                            if (index("ATGCU",*(py-1)))
                                    natgc++;
                    }
            }
            *py++ = '\0';
            *py = '\0';
            (void) fclose(fp);
            dna = natgc > (tlen/3);
            return(pseq+4);
    }
    char    *
    g_calloc(msg, nx, sz)                                                       g_calloc
            char    *msg;           /* program, calling routine */
            int     nx, sz;         /* number and size of elements */
    {
            char    *px, *calloc();

if ((px = calloc((unsigned)nx, (unsigned)sz)) == 0) {
                    if (*msg) {
                            fprintf(stderr, "%s: g_calloc() failed %s (n=%d, sz=%d)\n", prog, msg, nx, sz);
                            exit(1);
                    }
            }
            return(px);
    }
    /*
     * get final jmps from dx[] or tmp file, set pp[], reset dmax: main()
     */
    readjmps()                                                                  readjmps
    {
            int     fd = -1;
            int     siz, i0, i1;
            register i, j, xx;

if (fj) {
                    (void) fclose(fj);
                    if ((fd = open(jname, O_RDONLY, 0)) < 0) {
                            fprintf(stderr, "%s: can't open() %s\n", prog, jname);
                            cleanup(1);
                    }
            }
            for (i = i0 = i1 = 0, dmax0 = dmax, xx = len0; ; i++) {
                    while (1) {
                            for (j = dx[dmax].ijmp; j >= 0 && dx[dmax].jp.x[j] >= xx; j--)
                                    ;
```

Table 1 (cont')

...readjmps

```
                if (j < 0 && dx[dmax].offset && fj) {
                        (void) lseek(fd, dx[dmax].offset, 0);
                        (void) read(fd, (char *)&dx[dmax].jp, sizeof(struct jmp));
                        (void) read(fd, (char *)&dx[dmax].offset, sizeof(dx[dmax].offset));
                        dx[dmax].ijmp = MAXJMP-1;
                }
                else
                        break;
        }
        if (i >= JMPS) {
                fprintf(stderr, "%s: too many gaps in alignment\n", prog);
                cleanup(1);
        }
        if (j >= 0) {
                siz = dx[dmax].jp.n[j];
                xx = dx[dmax].jp.x[j];
                dmax += siz;
                if (siz < 0) {              /* gap in second seq */
                        pp[1].n[i1] = -siz;
                        xx += siz;
                        /* id = xx - yy + len1 - 1
                         */
                        pp[1].x[i1] = xx - dmax + len1 - 1;
                        gapy++;
                        ngapy -= siz;
/* ignore MAXGAP when doing endgaps */
                        siz = (-siz < MAXGAP || endgaps)? -siz : MAXGAP;
                        i1++;
                }
                else if (siz > 0) {    /* gap in first seq */
                        pp[0].n[i0] = siz;
                        pp[0].x[i0] = xx;
                        gapx++;
                        ngapx += siz;
/* ignore MAXGAP when doing endgaps */
                        siz = (siz < MAXGAP || endgaps)? siz : MAXGAP;
                        i0++;
                }
        }
        else
                break;
}

/* reverse the order of jmps
 */
for (j = 0, i0--; j < i0; j++, i0--) {
        i = pp[0].n[j]; pp[0].n[j] = pp[0].n[i0]; pp[0].n[i0] = i;
        i = pp[0].x[j]; pp[0].x[j] = pp[0].x[i0]; pp[0].x[i0] = i;
}
for (j = 0, i1--; j < i1; j++, i1--) {
        i = pp[1].n[j]; pp[1].n[j] = pp[1].n[i1]; pp[1].n[i1] = i;
        i = pp[1].x[j]; pp[1].x[j] = pp[1].x[i1]; pp[1].x[i1] = i;
}
if (fd >= 0)
        (void) close(fd);
if (fj) {
        (void) unlink(jname);
        fj = 0;
        offset = 0;
}
```

Table 1 (cont')

```
/*
 * write a filled jmp struct offset of the prev one (if any): nw()
 */
writejmps(ix)                                                                writejmps
        int     ix;
{
        char    *mktemp();

if (!fj) {
                if (mktemp(jname) < 0) {
                        fprintf(stderr, "%s: can't mktemp() %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
}
```

TABLE 2

| PRO | XXXXXXXXXXXXXXX | (Length = 15 amino acids) |
|---|---|---|
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the PRO polypeptide) = 5 divided by 15 = 33.3%

TABLE 3

| PRO | XXXXXXXXXX | (Length = 10 amino acids) |
|---|---|---|
| Comparison Protein | XXXXXYYYYYZZYZ | (Length = 15 amino acids) |

% amino acid sequence identity = (the number of identically matching amino acid residues between the two polypeptide sequences as determined by ALIGN-2) divided by (the total number of amino acid residues of the PRO polypeptide) = 5 divided by 10 = 50%

TABLE 4

| PRO-DNA | NNNNNNNNNNNNNN | (Length = 14 nucleotides) |
|---|---|---|
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 6 divided by 14 = 42.9%

TABLE 5

| PRO-DNA | NNNNNNNNNNNN | (Length = 12 nucleotides) |
|---|---|---|
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 4 divided by 12 = 33.3%

II. Compositions and Methods of the Invention

A. Full-Length PRO Polypeptides

The present invention provides newly identified and isolated nucleotide sequences encoding polypeptides referred to in the present application as PRO polypeptides. In particular, cDNAs encoding various PRO polypeptides have been identified and isolated, as disclosed in further detail in the Examples below. It is noted that proteins produced in separate expression rounds may be given different PRO numbers but the UNQ number is unique for any given DNA and the encoded protein, and will not be changed. However, for sake of simplicity, in the present specification the protein encoded by the full length native nucleic acid molecules disclosed herein as well as all further native homologues and variants included in the foregoing definition of PRO, will be referred to as "PRO/number", regardless of their origin or mode of preparation.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the PRO polypeptides and encoding nucleic acids described herein, Applicants have identified what is believed to be the reading frame best identifiable with the sequence information available at the time.

B. PRO Polypeptide Variants

In addition to the full-length native sequence PRO polypeptides described herein, it is contemplated that PRO variants can be prepared. PRO variants can be prepared by introducing appropriate nucleotide changes into the PRO DNA, and/or by synthesis of the desired PRO polypeptide. Those skilled in the art will appreciate that amino acid changes may alter post-translational processes of the PRO, such as changing the number or position of glycosylation sites or altering the membrane anchoring characteristics.

Variations in the native full-length sequence PRO or in various domains of the PRO described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO that results in a change in the amino acid sequence of the PRO as compared with the native sequence PRO. Optionally the variation is by substitution of at least one amino acid with any other amino acid in one or more of the domains of the PRO. Guidance in determining which amino acid residue may be inserted, substituted or deleted without adversely affecting the desired activity may be found by comparing the sequence of the PRO with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

PRO polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the PRO polypeptide.

PRO fragments may be prepared by any of a number of conventional techniques. Desired peptide fragments may be chemically synthesized. An alternative approach involves generating PRO fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, PRO polypeptide fragments share at least one biological and/or immunological activity with the native PRO polypeptide disclosed herein.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the PRO polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., Nucl. Acids Res., 13:4331 (1986); Zoller et al., Nucl. Acids Res., 10:6487 (1987)], cassette mutagenesis [Wells et al., Gene, 34:315 (1985)], restriction selection mutagenesis [Wells et al., Philos. Trans. R. Soc. London SerA, 317:415 (1986)] or other known techniques can be performed on the cloned DNA to produce the PRO variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, Science, 244: 1081-1085 (1989)]. Alanine is also typically preferred because it is the most common amino acid. Further, it is frequently found in both buried and exposed positions [Creighton, The Proteins, (W. H. Freeman & Co., N.Y.); Chothia, J. Mol. Biol., 150:1 (1976)]. If alanine substitution does not yield adequate amounts of variant, an isoteric amino acid can be used.

C. Modifications of PRO

Covalent modifications of PRO are included within the scope of this invention. One type of covalent modification includes reacting targeted amino acid residues of a PRO polypeptide with an organic derivatizing agent that is capable of reacting with selected side chains or the N- or C-terminal residues of the PRO. Derivatization with bifunctional agents is useful, for instance, for crosslinking PRO to a water-insoluble support matrix or surface for use in the method for purifying anti-PRO antibodies, and vice-versa. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, Proteins: Structure and Molecular Properties, W. H. Freeman & Co., San Francisco, pp. 79-86 (1983)], acetylation of the N-terminal amine, and amidation of any C-terminal carboxyl group.

Another type of covalent modification of the PRO polypeptide included within the scope of this invention comprises altering the native glycosylation pattern of the polypeptide. "Altering the native glycosylation pattern" is intended for purposes herein to mean deleting one or more carbohydrate moieties found in native sequence PRO (either by removing the underlying glycosylation site or by deleting the glycosylation by chemical and/or enzymatic means), and/or adding one or more glycosylation sites that are not present in the native sequence PRO. In addition, the phrase includes qualitative changes in the glycosylation of the native proteins, involving a change in the nature and proportions of the various carbohydrate moieties present.

Addition of glycosylation sites to the PRO polypeptide may be accomplished by altering the amino acid sequence. The alteration may be made, for example, by the addition of, or substitution by, one or more serine or threonine residues to the native sequence PRO (for O-linked glycosylation sites). The PRO amino acid sequence may optionally be altered through changes at the DNA level, particularly by mutating the DNA encoding the PRO polypeptide at preselected bases such that codons are generated that will translate into the desired amino acids.

Another means of increasing the number of carbohydrate moieties on the PRO polypeptide is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259-306 (1981).

Removal of carbohydrate moieties present on the PRO polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal.

*Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of PRO comprises linking the PRO polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The PRO of the present invention may also be modified in a way to form a chimeric molecule comprising PRO fused to another, heterologous polypeptide or amino acid sequence.

In one embodiment, such a chimeric molecule comprises a fusion of the PRO with a tag polypeptide which provides an epitope to which an anti-tag antibody can selectively bind. The epitope tag is generally placed at the amino- or carboxyl-terminus of the PRO. The presence of such epitope-tagged forms of the PRO can be detected using an antibody against the tag polypeptide. Also, provision of the epitope tag enables the PRO to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

In an alternative embodiment, the chimeric molecule may comprise a fusion of the PRO with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a PRO polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of PRO

The description below relates primarily to production of PRO by culturing cells transformed or transfected with a vector containing PRO nucleic acid. It is, of course, contemplated that alternative methods, which are well known in the art, may be employed to prepare PRO. For instance, the PRO sequence, or portions thereof, may be produced by direct peptide synthesis using solid-phase techniques [see, e.g., Stewart et al., *Solid-Phase Peptide Synthesis*, W. H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO may be chemically synthesized separately and combined using chemical or enzymatic methods to produce the full-length PRO.

1. Isolation of DNA Encoding PRO

DNA encoding PRO may be obtained from a cDNA library prepared from tissue believed to possess the PRO mRNA and to express it at a detectable level. Accordingly, human PRO DNA can be conveniently obtained from a cDNA library prepared from human tissue, such as described in the Examples. The PRO-encoding gene may also be obtained from a genomic library or by known synthetic procedures (e.g., automated nucleic acid synthesis).

Libraries can be screened with probes (such as antibodies to the PRO or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases.

Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et at., supra.

Methods of eukaryotic cell transfection and prokaryotic cell transformation are known to the ordinarily skilled artisan, for example, CaCl$_2$, CaPO$_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene,* 23:315 (1983) and WO 89/05859 published 29 Jun. 1989. For mammalian cells without such cell walls, the calcium phosphate precipitation method of Graham and van der Eb, *Virology,* 52:456-457 (1978) can be employed. General aspects of mammalian cell host system transfections have been described in U.S. Pat. No. 4,399,216. Transformations into yeast are typically carried out according to the method of Van Solingen et al., *J. Bact.,* 130:946 (1977) and Hsiao et al., *Proc. Natl. Acad. Sci. (USA),* 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology,* 185:527-537 (1990) and Mansour et al., *Nature,* 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli.* Various *E. coli* strains are publicly available, such as *E. coli* K12 strain MM294 (ATCC 31,446); *E. coli* X1776 (ATCC 31,537); *E. coli* strain W3110 (ATCC 27,325) and K5772 (ATCC 53,635). Other suitable prokaryotic host cells include Enterobacteriaceae such as *Escherichia,* e.g., *E. coli, Enterobacter, Erwinia, Klebsiella, Proteus, Salmonella,* e.g., *Salmonella typhimurium, Serratia,* e.g., *Serratia marcescans,* and *Shigella,* as well as Bacilli such as *B. subtilis* and *B. licheniformis* (e.g., *B. licheniformis* 41P disclosed in DD 266,710 published 12 Apr. 1989), *Pseudomonas* such as *P. aeruginosa,* and *Streptomyces.* These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for PRO-encoding vectors. *Saccharomyces cerevisiae* is a commonly used lower eukaryotic host microorganism. Others include *Schizosaccharomyces pombe* (Beach and Nurse, *Nature,* 290: 140 [1981]; EP 139,383 published 2 May 1985); *Kluyveromyces* hosts (U.S. Pat. No. 4,943,529; Fleer et al., *Bio/Technology,* 9:968-975 (1991)) such as, e.g., *K. lactis* (MW98-8C, CBS683, CBS4574; Louvencourt et al., *J. Bacteriol.,* 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology,* 8:135 (1990)), *K. thermotolerans,* and *K. manrianus; yarrowia* (EP 402,226); *Pichia pastoris* (EP 183,070; Sreekrishna et al., *J. Basic Microbiol.,* 28:265-278 [1988]); *Candida; Trichoderma reesia* (EP 244,234); *Neurospora crassa* (Case et at., *Proc. Natl. Acad. Sci. USA,* 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.,* 112:284-289 [1983]; Tilburn et al., *Gene,* 26:205-221 [1983]; Yelton et al., *Proc. Natl. Acad. Sci. USA,* 81: 1470-1474 [1984]) and *A. niger* (Kelly and Hynes, *EMBO J.,* 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis,* and *Rhodotorula.* A list of specific species that are exemplary of this class of yeasts may be found in C. Anthony, *The Biochemistry of Methylotrophs,* 269 (1982).

Suitable host cells for the expression of glycosylated PRO are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.,* 36:59 (1977)); Chinese hamster ovary cells/-DHFR (CHO, Urlaub and Chasin, *Proc. Natl. Acad. Sci. USA,* 77:4216 (1980)); mouse sertoli cells (TM4, Mather, *Biol. Reprod.,* 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and use of a Replicable Vector

The nucleic acid (e.g., cDNA or genomic DNA) encoding PRO may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO-encoding DNA that is inserted into the vector. The signal sequence may be a prokaryotic signal sequence selected, for example, from the group of the alkaline phosphatase, penicillinase, 1 pp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the PRO-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1[Jones, *Genetics*, 85:12 (1977)].

Expression and cloning vectors usually contain a promoter operably linked to the PRO-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21-25 (1983)]. Promoters for use in bacterial systems also will contain a Shine-Dalgarno (S.D.) sequence operably linked to the DNA encoding PRO.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the PRO coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO.

Still other methods, vectors, and host cells suitable for adaptation to the synthesis of PRO in recombinant vertebrate cell culture are described in Gething et al., *Nature*, 293:620-625 (1981); Mantei et al., *Nature*, 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO polypeptide or against a synthetic peptide based on the DNA sequences provided herein or against exogenous sequence fused to PRO DNA and encoding a specific antibody epitope.

5. Purification of Polypeptide

Forms of PRO may be recovered from culture medium or from host cell lysates. If membrane-bound, it can be released from the membrane using a suitable detergent solution (e.g. Triton-X 100) or by enzymatic cleavage. Cells employed in expression of PRO can be disrupted by various physical or chemical means, such as freeze-thaw cycling, sonication, mechanical disruption, or cell lysing agents.

It may be desired to purify PRO from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular PRO produced.

E. Uses for PRO

Nucleotide sequences (or their complement) encoding PRO have various applications in the art of molecular biology, including uses as hybridization probes, in chromosome and gene mapping and in the generation of anti-sense RNA and DNA. PRO nucleic acid will also be useful for the preparation of PRO polypeptides by the recombinant techniques described herein.

The full-length native sequence PRO gene, or portions thereof, may be used as hybridization probes for a cDNA library to isolate the full-length PRO cDNA or to isolate still other cDNAs (for instance, those encoding naturally-occurring variants of PRO or PRO from other species) which have a desired sequence identity to the native PRO sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence PRO. By way of example, a screening method will comprise isolating the coding region of the PRO gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the PRO gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the PRO nucleic acids include antisense or sense oligonucleotides comprising a singe-stranded nucleic acid sequence (either RNA or DNA) capable of binding to target PRO mRNA (sense) or PRO DNA (antisense) sequences. Antisense or sense oligonucleotides, according to the present invention, comprise a fragment of the coding region of PRO DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of PRO proteins. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 bases in length, about 10 bases in length, about 15 bases in length, about 20 bases in length, about 25 bases in length, about 30 bases in length, about 35 bases in length, about 40 bases in length, about 45 bases in length, about 50 bases in length, about 55 bases in length, about 60 bases in length, about 65 bases in length, about 70 bases in length, about 75 bases in length, about 80 bases in length, about 85 bases in length, about 90 bases in length, about 95 bases in length, about 100 bases in length, or more.

The probes may also be employed in PCR techniques to generate a pool of sequences for identification of closely related PRO coding sequences.

Nucleotide sequences encoding a PRO can also be used to construct hybridization probes for mapping the gene which encodes that PRO and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for PRO encode a protein which binds to another protein (example, where the PRO is a receptor), the PRO can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor PRO can be used to isolate correlative ligand(s). Screening assays can be designed to find lead compounds that mimic the biological activity of a native PRO or a receptor for PRO. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode PRO or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding PRO can be used to clone genomic DNA encoding PRO in accordance with established techniques and the genomic sequences used to generate transgenic animals that contain cells which express DNA encoding PRO. Methods for generating transgenic animals, particularly animals such as mice or rats, have become conventional in the art and are described, for example, in U.S. Pat. Nos. 4,736,866 and 4,870,009. Typically, particular cells would be targeted for PRO transgene incorporation with tissue-specific enhancers. Transgenic animals that include a copy of a transgene encoding PRO introduced into the germ line of the animal at an embryonic stage can be used to examine the effect of increased expression of DNA encoding PRO. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of PRO can be used to construct a PRO "knockout" animal which has a defective or altered gene encoding PRO as a result of homologous recombination between the endogenous gene encoding PRO and altered genomic DNA encoding PRO introduced into an embryonic stem cell of the animal. For example, cDNA encoding PRO can be used to clone genomic DNA encoding PRO in accordance with established techniques. A portion of the genomic DNA encoding PRO can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knock-out animals can be characterized for instance, for their ability to defend against certain pathological conditions and for their development of pathological conditions due to absence of the PRO polypeptide.

Nucleic acid encoding the PRO polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

The PRO polypeptides described herein may also be employed as molecular weight markers for protein electrophoresis purposes and the isolated nucleic acid sequences may be used for recombinantly expressing those markers.

The nucleic acid molecules encoding the PRO polypeptides or fragments thereof described herein are useful for chromosome identification. In this regard, there exists an ongoing need to identify new chromosome markers, since relatively few chromosome marking reagents, based upon actual sequence data are presently available. Each PRO nucleic acid molecule of the present invention can be used as a chromosome marker.

The PRO polypeptides and nucleic acid molecules of the present invention may also be used diagnostically for tissue typing, wherein the PRO polypeptides of the present invention may be differentially expressed in one tissue as compared to another, preferably in a diseased tissue as compared to a normal tissue of the same tissue type. PRO nucleic acid molecules will find use for generating probes for PCR, Northern analysis, Southern analysis and Western analysis.

The PRO polypeptides described herein may also be employed as therapeutic agents. The PRO polypeptides of the present invention can be formulated according to known methods to prepare pharmaceutically useful compositions, whereby the PRO product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumim, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for be determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a PRO polypeptide or agonist or antagonist thereof is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a PRO polypeptide is desired in a formulation with release characteristics suitable for the treatment of any disease or disorder requiring administration of the PRO polypeptide, microencapsulation of the PRO polypeptide is contemplated. Microencapsulation of recombinant proteins; for sustained release has been successfully performed with human growth hormone (rhGH), interferon-(rhIFN), interleukin-2, and MN rgp120. Johnson et al., *Nat. Med.,* 2:795-799 (1996); Yasuda, *Biomed. Ther.,* 27: 1221-1223 (1993); Hora et al., *Bio/Technology.* 8:755-758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1-41.

This invention encompasses methods of screening compounds to identify those that mimic the PRO polypeptide (agonists) or prevent the effect of the PRO polypeptide (antagonists). Screening assays for antagonist drug candidates are designed to identify compounds that bind or complex with the PRO polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a PRO polypeptide encoded by a nucleic acid identified herein under conditions and for a time sufficient to allow these two components to interact.

In binding assays, the interaction is binding and the complex formed can be isolated or detected in the reaction mixture. In a particular embodiment, the PRO polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the PRO polypeptide and drying. Alternatively, an immobilized antibody, e.g., a monoclonal antibody, specific for the PRO polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)*, 340:245-246 (1989); Chien et al., *Proc. Natl. Acad. Sci. USA*, 88:9578-9582 (1991)) as disclosed by Chevray and Nathans, *Proc. Natl. Acad. Sci. USA*, 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a PRO polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the PRO polypeptide may be added to a cell along with the compound to be screened for a particular activity and the ability of the compound to inhibit the activity of interest in the presence of the PRO polypeptide indicates that the compound is an antagonist to the PRO polypeptide. Alternatively, antagonists may be detected by combining the PRO polypeptide and a potential antagonist with membrane-bound PRO polypeptide receptors or recombinant receptors under appropriate conditions for a competitive inhibition assay. The PRO polypeptide can be labeled, such as by radioactivity, such that the number of PRO polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.*, 1(2): Chapter 5 (1991). Preferably, expression cloning is employed wherein polyadenylated RNA is prepared from a cell responsive to the PRO polypeptide and a cDNA library created from this RNA is divided into pools and used to transfect COS cells or other cells that are not responsive to the PRO polypeptide. Transfected cells that are grown on glass slides are exposed to labeled PRO polypeptide. The PRO polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled PRO polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled PRO polypeptide in the presence of the candidate compound. The ability of the compound to enhance or block this interaction could then be measured.

More specific examples of potential antagonists include an oligonucleotide that binds to the fusions of immunoglobulin with PRO polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the PRO polypeptide that recognizes the receptor but imparts no effect, thereby competitively inhibiting the action of the PRO polypeptide.

Another potential PRO polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature PRO polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.,* 6:3073 (1979); Cooney et al., *Science,* 241: 456(1988); Dervan et al., *Science,* 251:1360(1991)), thereby preventing transcription and the production of the PRO polypeptide. The antisense RNA oligonucleotide hybridizes to the mRNA in vivo and blocks translation of the mRNA molecule into the PRO polypeptide (antisense—Okano, *Neurochem.,* 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the PRO polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the PRO polypeptide, thereby blocking the normal biological activity of the PRO polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology,* 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Diagnostic and therapeutic uses of the herein disclosed molecules may also be based upon the positive functional assay hits disclosed and described below.

F. Anti-PRO Antibodies

The present invention further provides anti-PRO antibodies. Exemplary antibodies include polyclonal, monoclonal, humanized, bispecific, and heteroconjugate antibodies.

1. Polyclonal Antibodies

The anti-PRO antibodies may comprise polygonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the PRO polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-PRO antibodies may, alternatively, be monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the PRO polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice,* Academic Press, (1986) pp.

59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, J. Immunol., 133:3001 (1984); Brodeur et al., Monoclonal Antibody Production Techniques and Applications, Marcel Dekker, Inc., New York, (1987) pp. 51-63].

The culture medium in which the hybridoma cells are cultured can then be assayed for the presence of monoclonal antibodies directed against PRO. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fe region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-PRO antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol. 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779-783 (1992); Lonberg et al., *Nature* 368 856-859 (1994); Morrison, *Nature* 368, 812-13 (1994); Fishwild et al., *Nature Biotechnology* 14, 845-51 (1996); Neuberger, *Nature Biotechnology* 14, 826 (1996); Lonberg and Huszar, *Intern. Rev. Immunol.* 1365-93 (1995).

The antibodies may also be affinity matured using known selection and/or mutagenesis methods as described above. Preferred affinity matured antibodies have an affinity which is five times, more preferably 10 times, even more preferably 20 or 30 times greater than the starting antibody (generally murine, humanized or human) from which the matured antibody is prepared.

4. Bispecific Antibodies

Bispecific antibodies are monoclonal, preferably human or humanized, antibodies that have binding specificities for at least two different antigens. In the present case, one of the binding specificities is for the PRO, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.*, 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175:217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994).

Antibodies with more than two valencies are contemplated. For example, trispecific antibodies can be prepared. Tutt et al., *J. Immunol.* 147:60 (1991).

Exemplary bispecific antibodies may bind to two different epitopes on a given PRO polypeptide herein. Alternatively, an anti-PRO polypeptide arm may be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular PRO polypeptide. Bispecific antibodies may also be used to localize cytotoxic agents to cells which express a particular PRO polypeptide. These antibodies possess a PRO-binding arm and an arm which binds a cytotoxic agent or a radionuclide chelator, such as EOTUBE, DPTA, DOTA, or TETA. Another bispecific antibody of interest binds the PRO polypeptide and further binds tissue factor (TF).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.,* 176: 1191-1195 (1992) and Shopes, *J. Immunol.,* 148: 2918-2922 (1992). Homodimeric antibodies with enhanced anti-tumor activity may also be prepared using heterobifunctional cross-linkers as described in Wolff et al. *Cancer Research,* 53: 2560-2565 (1993). Alternatively, an antibody can be engineered that has dual Fc regions and may thereby have enhanced complement lysis and ADCC capabilities. See Stevenson et al., *Anti-Cancer Drug Design.* 3: 219-230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

8. Immunoliposomes

The antibodies disclosed herein may also be formulated as immunoliposomes. Liposomes containing the antibody are prepared by methods known in the art, such as described in Epstein et al., *Proc. Natl. Acad. Sci. USA,* 82: 3688 (1985); Hwang et al., *Proc. Natl. Acad. Sci. USA,* 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.,* 257: 286-288 (1982) via a disulfide-interchange reaction. A chemotherapeutic agent (such as Doxorubicin) is optionally contained within the liposome. See Gabizon et al., *J. National Cancer Inst.,* 81(19): 1484 (1989).

9. Pharmaceutical Compositions of Antibodies

Antibodies specifically binding a PRO polypeptide identified herein, as well as other molecules identified by the screening assays disclosed hereinbefore, can be administered for the treatment of various disorders in the form of pharmaceutical compositions.

If the PRO polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco el al., *Proc. Natl. Acad. Sci. USA*, 90: 7889-7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences*, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

G. Uses for Anti-PRO Antibodies

The anti-PRO antibodies of the invention have various utilities. For example, anti-PRO antibodies may be used in diagnostic assays for PRO, e.g., detecting its expression (and in some cases, differential expression) in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147-158].

The antibodies used in the diagnostic assays can be labeled with a detectable moiety. The detectable moiety should be capable of producing, either directly or indirectly, a detectable signal. For example, the detectable moiety may be a radioisotope, such as $^{3}H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13: 1014 (1974); Pain et al., *J. Immunol. Meth.*, 40:219 (1981); and Nygren, *J. Histochem. and Cytochem.*, 30:407 (1982).

Anti-PRO antibodies also are useful for the affinity purification of PRO from recombinant cell culture or natural sources. In this process, the antibodies against PRO are immobilized on a suitable support, such a Sephadex resin or filter paper, using methods well known in the art. The immobilized antibody then is contacted with a sample containing the PRO to be purified, and thereafter the support is washed with a suitable solvent that will remove substantially all the material in the sample except the PRO, which is bound to the immobilized antibody. Finally, the support is washed with another suitable solvent that will release the PRO from the antibody.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Extracellular Domain Homology Screening to Identify Novel Polypeptides and cDNA Encoding Therefor The extracellular domain (ECD) sequences (including the secretion signal sequence, if any) from about 950 known secreted proteins from the Swiss-Prot public database were used to search EST databases. The EST databases included public databases (e.g., Dayhoff, GenBank), and proprietary databases (e.g. LIFESEQ™, Incyte Pharmaceuticals, Palo Alto, Calif.). The search was performed using the computer program BLAST or BLAST-2 (Altschul et al., *Methods in Enzymology* 266:460480 (1996)) as a comparison of the ECD protein sequences to a 6 frame translation of the EST sequences. Those comparisons with a BLAST score of 70 (or in some cases 90) or greater that did not encode known proteins were clustered and assembled into consensus DNA sequences with the program "phrap" (Phil Green, University of Washington, Seattle, Wash.).

Using this extracellular domain homology screen, consensus DNA sequences were assembled relative to the other identified EST sequences using phrap. In addition, the consensus DNA sequences obtained were often (but not always) extended using repeated cycles of BLAST or BLAST-2 and phrap to extend the consensus sequence as far as possible using the sources of EST sequences discussed above.

Based upon the consensus sequences obtained as described above, oligonucleotides were then synthesized and used to identify by PCR a cDNA library that contained the sequence of interest and for use as probes to isolate a clone of the full-length coding sequence for a PRO polypeptide. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the primer pairs.

The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253:1278-1280 (1991)) in the unique XhoI and NotI sites.

Example 2

Isolation of cDNA Clones by Amylase Screening

1. Preparation of Oligo dT Primed cDNA Library mRNA was isolated from a human tissue of interest using reagents and protocols from Invitrogen, San Diego, Calif. (Fast Track 2). This RNA was used to generate an oligo dT primed cDNA library in the vector pRK5D using reagents and protocols from Life Technologies, Gaithersburg, Md. (Super Script Plasmid System). In this procedure, the double stranded cDNA was sized to greater than 1000 bp and the SalI/NotI linkered cDNA was cloned into XhoI/NotI cleaved vector. pRK5D is a cloning vector that has an sp6 transcription initiation site followed by an SfiI restriction enzyme site preceding the XhoI/NotI cDNA cloning sites.

2. Preparation of Random Primed cDNA Library

A secondary cDNA library was generated in order to preferentially represent the 5' ends of the primary cDNA clones. Sp6 RNA was generated from the primary library (described above), and this RNA was used to generate a random primed cDNA library in the vector pSST-AMY.0 using reagents and protocols from Life Technologies (Super Script Plasmid System, referenced above). In this procedure the double stranded cDNA was sized to 500-1000 bp, linkered with blunt to NotI adaptors, cleaved with SfiI, and cloned into SfiI/NotI cleaved vector. pSST-AMY.0 is a cloning vector that has a yeast alcohol dehydrogenase promoter preceding the cDNA cloning sites and the mouse amylase sequence (the mature sequence without the secretion signal) followed by the yeast alcohol dehydrogenase terminator, after the cloning sites. Thus, cDNAs cloned into this vector that are fused in frame with amylase sequence will lead to the secretion of amylase from appropriately transfected yeast colonies.

3. Transformation and Detection

DNA from the library described in paragraph 2 above was chilled on ice to which was added electrocompetent DH10B bacteria (Life Technologies, 20 ml). The bacteria and vector mixture was then electroporated as recommended by the manufacturer. Subsequently, SOC media (Life Technologies, 1 ml) was added and the mixture was incubated at 37° C. for 30 minutes. The transformants were then plated onto 20 standard 150 mm LB plates containing ampicillin and incubated for 16 hours (37° C.). Positive colonies were scraped off the plates and the DNA was isolated from the bacterial pellet using standard protocols, e.g. CsCl-gradient. The purified DNA was then carried on to the yeast protocols below.

The yeast methods were divided into three categories: (1) Transformation of yeast with the plasmid/cDNA combined vector; (2) Detection and isolation of yeast clones secreting amylase; and (3) PCR amplification of the insert directly from the yeast colony and purification of the DNA for sequencing and further analysis.

The yeast strain used was HD56-5A (ATCC-90785). This strain has the following genotype: MAT alpha, ura3-52, leu2-3, leu2-112, his3-11, his3-15, MAL$^+$, SUC$^+$, GAL$^+$. Preferably, yeast mutants can be employed that have deficient post-translational pathways. Such mutants may have translocation deficient alleles in sec71, sec72, sec62, with truncated sec71 being most preferred. Alternatively, antagonists (including antisense nucleotides and/or ligands) which interfere with the normal operation of these genes, other proteins implicated in this post translation pathway (e.g., SEC61p, SEC72p, SEC62p, SEC63p, TDJ1p or SSA1p-4p) or the complex formation of these proteins may also be preferably employed in combination with the amylase-expressing yeast.

Transformation was performed based on the protocol outlined by Gietz et al., *Nucl. Acid. Res.*, 20:1425 (1992). Transformed cells were then inoculated from agar into YEPD complex media broth (100 ml) and grown overnight at 30° C. The YEPD broth was prepared as described in Kaiser et al., *Methods in Yeast Genetics*, Cold Spring Harbor Press, Cold Spring Harbor, N.Y., p. 207 (1994). The overnight culture was then diluted to about 2×10$^6$ cells/ml (approx. OD$_{600}$=0.1) into fresh YEPD broth (500 ml) and regrown to 1×10$^7$ cells/ml (approx. OD$_{600}$=0.4-0.5).

The cells were then harvested and prepared for transformation by transfer into GS3 rotor bottles in a Sorval GS3 rotor at 5,000 rpm for 5 minutes, the supernatant discarded, and then resuspended into sterile water, and centrifuged again in 50 ml falcon tubes at 3,500 rpm in a Beckman GS-6KR centrifuge. The supernatant was discarded and the cells were subsequently washed with LiAc/TE (10 ml, 10 mM Tris-HCl, 1 mM EDTA pH 7.5, 100 mM Li$_2$OOCCH$_3$), and resuspended into LiAc/TE (2.5 ml).

Transformation took place by mixing the prepared cells (100 µl) with freshly denatured single stranded salmon testes DNA (Lofstrand Labs, Gaithersburg, Md.) and transforming DNA (1 µg, vol. <10 µl) in microfuge tubes. The mixture was mixed briefly by vortexing, then 40% PEG/TE (600 µl, 40% polyethylene glycol-4000, 10 mM Tris-HCl, 1 mM EDTA, 100 mM Li$_2$OOCCH$_3$, pH 7.5) was added. This mixture was gently mixed and incubated at 30° C. while agitating for 30 minutes. The cells were then heat shocked at 42° C. for 15 minutes, and the reaction vessel centrifuged in a microfuge at 12,000 rpm for 5-10 seconds, decanted and resuspended into TE (500 μl, 10 mM Tris-HCl, 1 mM EDTA pH 7.5) followed by recentrifugation. The cells were then diluted into TE (1 ml) and aliquots (200 μl) were spread onto the selective media previously prepared in 150 mm growth plates (VWR).

Alternatively, instead of multiple small reactions, the transformation was performed using a single, large scale reaction, wherein reagent amounts were scaled up accordingly.

The selective media used was a synthetic complete dextrose agar lacking uracil (SCD-Ura) prepared as described in Kaiser et al., *Methods in Yeast Genetics*, Cold Spring Harbor Press, Cold Spring Harbor, N.Y., p. 208-210 (1994). Transformants were grown at 30° C. for 2-3 days.

The detection of colonies secreting amylase was performed by including red starch in the selective growth media. Starch was coupled to the red dye (Reactive Red-120, Sigma) as per the procedure described by Biely et al., *Anal. Biochem.*, 172:176-179 (1988). The coupled starch was incorporated into the SCD-Ura agar plates at a final concentration of 0.15% (w/v), and was buffered with potassium phosphate to a pH of 7.0 (50-100 mM final concentration).

The positive colonies were picked and streaked across fresh selective media (onto 150 mm plates) in order to obtain well isolated and identifiable single colonies. Well isolated single colonies positive for amylase secretion were detected by direct incorporation of red starch into buffered SCD-Ura agar. Positive colonies were determined by their ability to break down starch resulting in a clear halo around the positive colony visualized directly.

4. Isolation of DNA by PCR Amplification

When a positive colony was isolated, a portion of it was picked by a toothpick and diluted into sterile water (30 μl) in a 96 well plate. At this time, the positive colonies were either frozen and stored for subsequent analysis or immediately amplified. An aliquot of cells (5 μl) was used as a template for the PCR reaction in a 25 μl volume containing: 0.5 μl Klentaq (Clontech, Palo Alto, Calif.); 4.0 μl 10 mM dNTP's (Perkin Elmer-Cetus); 2.5 μl Kentaq buffer (Clontech); 0.25 μl forward oligo 1; 0.25 μl reverse oligo 2; 12.5 μl distilled water. The sequence of the forward oligonucleotide 1 was:

5'-TGTAAAACGACGGCCAGT
TAAATAGACCTGCAATTATTAATCT-3' (SEQ ID NO:115)

The sequence of reverse oligonucleotide 2 was:
5'-CAGGAAACAGCTATGACC
ACCTGCACACCTGCAAATCCATT-3' (SEQ ID NO:116)

PCR was then performed as follows:

| a. | | Denature | 92° C., | 5 minutes |
|---|---|---|---|---|
| b. | 3 cycles of: | Denature | 92° C., | 30 seconds |
| | | Anneal | 59° C., | 30 seconds |
| | | Extend | 72° C., | 60 seconds |
| c. | 3 cycles of: | Denature | 92° C., | 30 seconds |
| | | Anneal | 57° C., | 30 seconds |
| | | Extend | 72° C., | 60 seconds |
| d. | 25 cycles of: | Denature | 92° C., | 30 seconds |
| | | Anneal | 55° C., | 30 seconds |
| | | Extend | 72° C., | 60 seconds |
| e. | | Hold | 4° C. | |

The underlined regions of the oligonucleotides annealed to the ADH promoter region and the amylase region, respectively, and amplified a 307 bp region from vector pSST-AMY.0 when no insert was present. Typically, the first 18 nucleotides of the 5' end of these oligonucleotides contained annealing sites for the sequencing primers. Thus, the total product of the PCR reaction from an empty vector was 343 bp. However, signal sequence-fused cDNA resulted in considerably longer nucleotide sequences.

Following the PCR, an aliquot of the reaction (5 μl) was examined by agarose gel electrophoresis in a 1% agarose gel using a Tris-Borate-EDTA (TBE) buffering system as described by Sambrook et al., supra. Clones resulting in a single strong PCR product larger than 400 bp were further analyzed by DNA sequencing after purification with a 96 Qiaquick PCR clean-up column (Qiagen Inc., Chatsworth, Calif.).

Example 3

Isolation of cDNA Clones using Signal Algorithm Analysis

Various polypeptide-encoding nucleic acid sequences were identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals. Use of this algorithm resulted in the identification of numerous polypeptide-encoding nucleic acid sequences.

Example 4

Isolation of cDNA Clones Encoding Human PRO Polypeptides

Using the techniques described in Examples 1 to 3 above, numerous full-length cDNA clones were identified as encoding PRO polypeptides as disclosed herein. These cDNAs were then deposited under the terms of the Budapest Treaty with the American Type Culture Collection, 10801 University Blvd., Manassas, Va. 20110-2209, USA (ATCC) as shown in Table 7 below.

TABLE 7

| Material | ATCC Dep. No. | Deposit Date |
|---|---|---|
| DNA16422-1209 | 209929 | Jun. 2, 1998 |
| DNA19902-1669 | 203454 | Nov. 3, 1998 |
| DNA21624-1391 | 209917 | Jun. 2, 1998 |
| DNA34387-1138 | 209260 | Sep. 16, 1997 |
| DNA35880-1160 | 209379 | Oct. 16, 1997 |
| DNA39984-1221 | 209435 | Nov. 7, 1997 |

TABLE 7-continued

| Material | ATCC Dep. No. | Deposit Date |
| --- | --- | --- |
| DNA44189-1322 | 209699 | Mar. 26, 1998 |
| DNA48303-2829 | PTA-1342 | Feb. 8, 2000 |
| DNA48320-1433 | 209904 | May 27, 1998 |
| DNA56049-2543 | 203662 | Feb. 9, 1999 |
| DNA57694-1341 | 203017 | Jun. 23, 1998 |
| DNA59208-1373 | 209881 | May 20, 1998 |
| DNA59214-1449 | 203046 | Jul. 1, 1998 |
| DNA59485-1336 | 203015 | Jun. 23, 1998 |
| DNA64966-1575 | 203575 | Jan. 12, 1999 |
| DNA82403-2959 | PTA-2317 | Aug. 1, 2000 |
| DNA83505-2606 | PTA-132 | May 25, 1999 |
| DNA84927-2585 | 203865 | Mar. 23, 1999 |
| DNA92264-2616 | 203969 | Apr. 27, 1999 |
| DNA94713-2561 | 203835 | Mar. 9, 1999 |
| DNA96869-2673 | PTA-255 | Jun. 22, 1999 |
| DNA96881-2699 | PTA-553 | Aug. 17, 1999 |
| DNA96889-2641 | PTA-119 | May 25, 1999 |
| DNA96898-2640 | PTA-122 | May 25, 1999 |
| DNA97003-2649 | PTA-43 | May 11, 1999 |
| DNA98565-2701 | PTA-481 | Aug. 3, 1999 |
| DNA102846-2742 | PTA-545 | Aug. 17, 1999 |
| DNA102847-2726 | PTA-517 | Aug. 10, 1999 |
| DNA102880-2689 | PTA-383 | Jul. 20, 1999 |
| DNA105782-2683 | PTA-387 | Jul. 20, 1999 |
| DNA108912-2680 | PTA-124 | May, 25, 1999 |
| DNA115253-2757 | PTA-612 | Aug. 31, 1999 |
| DNA119302-2737 | PTA-520 | Aug. 10, 1999 |
| DNA119536-2752 | PTA-551 | Aug. 17, 1999 |
| DNA119542-2754 | PTA-619 | Aug. 31, 1999 |
| DNA143498-2824 | PTA-1263 | Feb. 2, 2000 |
| DNA145583-2820 | PTA-1179 | Jan. 11, 2000 |
| DNA161000-2896 | PTA-1731 | Apr. 18, 2000 |
| DNA161005-2943 | PTA-2243 | Jun. 27, 2000 |
| DNA170245-3053 | PTA-2952 | Jan. 23, 2001 |
| DNA171771-2919 | PTA-1902 | May 23, 2000 |
| DNA173157-2981 | PTA-2388 | Aug. 8, 2000 |
| DNA175734-2985 | PTA-2455 | Sep. 12, 2000 |
| DNA176108-3040 | PTA-2824 | Dec. 19, 2000 |
| DNA190710-3028 | PTA-2822 | Dec. 19, 2000 |
| DNA190803-3019 | PTA-2785 | Dec. 12, 2000 |
| DNA191064-3069 | PTA-3016 | Feb. 6, 2001 |
| DNA194909-3013 | PTA-2779 | Dec. 12, 2000 |
| DNA203532-3029 | PTA-2823 | Dec. 19, 2000 |
| DNA213858-3060 | PTA-2958 | Jan. 23, 2001 |
| DNA216676-3083 | PTA-3157 | Mar. 6, 2001 |
| DNA222653-3104 | PTA-3330 | Apr. 24, 2001 |
| DNA96897-2688 | PTA-379 | Jul. 20, 1999 |
| DNA142917-3081 | PTA-3155 | Mar. 6, 2001 |
| DNA142930-2914 | PTA-1901 | May 23, 2000 |
| DNA147253-2983 | PTA-2405 | Aug. 22, 2000 |
| DNA149927-2887 | PTA-1782 | Apr. 25, 2000 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit and for at least five (5) years after the most recent request for the furnishing of a sample of the deposit received by the depository. The deposits will be made available by ATCC under the terms of the Budapest Treaty, and subject to an agreement between Genentech, Inc. and ATCC, which assures that all restrictions imposed by the depositor on the availability to the public of the deposited material will be irrevocably removed upon the granting of the pertinent U.S. patent, assures availability of the progeny to one determined by the U.S. Commissioner of Patents and Trademarks to be entitled thereto according to 35 USC § 122 and the Commissioner's rules pursuant thereto (including 37 CFR § 1.14 with particular reference to 886 OG 638.

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Example 5

Use of PRO as a Hybridization Probe

The following method describes use of a nucleotide sequence encoding PRO as a hybridization probe.

DNA comprising the coding sequence of full-length or mature PRO as disclosed herein is employed as a probe to screen for homologous DNAs (such as those encoding naturally-occurring variants of PRO) in human tissue cDNA libraries or human tissue genomic libraries.

Hybridization and washing of filters containing either library DNAs is performed under the following high stringency conditions. Hybridization of radiolabeled PRO-derived probe to the filters is performed in a solution of 50% formamide, 5×SSC, 0.1% SDS, 0.1% sodium pyrophosphate, 50 mM sodium phosphate, pH 6.8, 2× Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence PRO can then be identified using standard techniques known in the art.

Example 6

Expression of PRO in *E. coli*

This example illustrates preparation of an unglycosylated form of PRO by recombinant expression in *E. coli*.

The DNA sequence encoding PRO is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO coding region, lambda transcriptional terminator, and an argu gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO protein can then be purified using a metal chelating column under conditions that allow tight binding of the protein.

PRO may be expressed in *E. coli* in a poly-His tagged form, using the following procedure. The DNA encoding PRO is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA(tonA) lon galE rpoHts(htpRts) clpP(lacIq). Transformants are first grown in LB containing 50 mg/ml carbenicillin at 30° C. with shaking until an O.D.600 of 3-5 is reached. Cultures are then diluted 50-100 fold into CRAP media (prepared by mixing 3.57 g $(NH_4)_2SO_4$, 0.71 g sodium citrate.$2H_2O$, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

*E. coli* paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbipchem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded PRO polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Many of the PRO polypeptides disclosed herein were successfully expressed as described above.

Example 7

Expression of PRO in Mammalian Cells

This example illustrates preparation of a potentially glycosylated form of PRO by recombinant expression in mammalian cells.

The vector, pRK5 (see EP 307,247, published Mar. 15, 1989), is employed as the expression vector. Optionally, the PRO DNA is ligated into pRK5 with selected restriction enzymes to allow insertion of the PRO DNA using ligation methods such as described in Sambrook et al., supra. The resulting vector is called pRK5-PRO.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-PRO DNA is mixed with about 1 μg DNA encoding the VA RNA gene [Thimmappaya et al., *Cell*, 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO polypeptide. The cultures containing transfected cells may undergo further incubation (in serum free medium) and the medium is tested in selected bioassays.

In an alternative technique, PRO may be introduced into 293 cells transiently using the dextran sulfate method described by Somparyrac et al., *Proc. Natl. Acad. Sci.*, 12:7575 (1981). 293 cells are grown to maximal density in a spinner flask and 700 μg pRK5-PRO DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed PRO can then be concentrated and purified by any selected method, such as dialysis and/or column chromatography.

In another embodiment, PRO can be expressed in CHO cells. The pRK5-PRO can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of PRO polypeptide, the culture medium may be replaced with serum free medium. Preferably, the cultures are incubated for about 6 days, and then the conditioned medium is harvested. The medium containing the expressed PRO can then be concentrated and purified by any selected method.

Epitope-tagged PRO may also be expressed in host CHO cells. The PRO may be subcloned out of the pRK5 vector. The subclone insert can undergo PCR to fuse in frame with a selected epitope tag such as a poly-his tag into a Baculovirus expression vector. The poly-his tagged PRO insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO can then be concentrated and purified by any selected method, such as by $Ni^{2+}$-chelate affinity chromatography.

PRO may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Qiagen), Dosper® or Fugene® (Boehringer Mannheim). The cells are grown as described in Lucas et al., supra. Approximately $3 \times 10^7$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 µm filtered PS20 with 5% 0.2 µm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2 \times 10^6$ cells/mL. On day 0, the cell number pH ie determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 µm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 µL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Many of the PRO polypeptides disclosed herein were successfully expressed as described above.

Example 8

Expression of PRO in Yeast

The following method describes recombinant expression of PRO in yeast.

First, yeast expression vectors are constructed for intracellular production or secretion of PRO from the ADH2/GAPDH promoter. DNA encoding PRO and the promoter is inserted into suitable restriction enzyme sites in the selected plasmid to direct intracellular expression of PRO. For secretion, DNA encoding PRO can be cloned into the selected plasmid, together with DNA encoding the ADH2/GAPDH promoter, a native PRO signal peptide or other mammalian signal peptide, or, for example, a yeast alpha-factor or invertase secretory signal/leader sequence, and linker sequences (if needed) for expression of PRO.

Yeast cells, such as yeast strain AB 110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO can subsequently be isolated and purified by removing the yeast cells from the fermentation medium by centrifugation and then concentrating the medium using selected cartridge filters. The concentrate containing PRO may further be purified using selected column chromatography resins.

Many of the PRO polypeptides disclosed herein were successfully expressed as described above.

Example 9

Expression of PRO in Baculovirus-infected Insect Cells

The following method describes recombinant expression of PRO in Baculovirus-infected insect cells.

The sequence coding for PRO is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding PRO or the desired portion of the coding sequence of PRO such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged PRO can then be purified, for example, by $Ni^{2+}$-chelate affinity chromatography as follows. Extracts are prepared from recombinant virus-infected Sf9 cells as described by Rupert et al., *Nature*, 362:175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged PRO are pooled and dialyzed against loading buffer.

Alternatively, purification of the IgG tagged (or Fc tagged) PRO can be performed using known chromatography techniques, including for instance, Protein A or protein G column chromatography.

Many of the PRO polypeptides disclosed herein were successfully expressed as described above.

Example 10

Preparation of Antibodies that Bind PRO

This example illustrates preparation of monoclonal antibodies which can specifically bind PRO.

Techniques for producing the monoclonal antibodies are known in the art and are described, for instance, in Goding, supra. Immunogens that may be employed include purified PRO, fusion proteins containing PRO, and cells expressing recombinant PRO on the cell surface. Selection of the immunogen can be made by the skilled artisan without undue experimentation.

Mice, such as Balb/c, are immunized with the PRO immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-PRO antibodies.

After a suitable antibody titer has been detected, the animals "positive" for antibodies can be injected with a final intravenous injection of PRO. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO. Determination of "positive" hybridoma cells secreting the desired monoclonal antibodies against PRO is within the skill in the art.

The positive hybridoma cells can be injected intraperitoneally into syngeneic Balb/c mice to produce ascites containing the anti-PRO monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 11

Purification of PRO Polypeptides using Specific Antibodies

Native or recombinant PRO polypeptides may be purified by a variety of standard techniques in the art of protein purification. For example, pro-PRO polypeptide, mature PRO polypeptide, or pre-PRO polypeptide is purified by immunoaffinity chromatography using antibodies specific for the PRO polypeptide of interest. In general, an immunoaffinity column is constructed by covalently coupling the anti-PRO polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of PRO polypeptide by preparing a fraction from cells containing PRO polypeptide in a soluble form. This preparation is derived by solubilization of the whole cell or of a subcellular fraction obtained via differential centrifugation by the addition of detergent or by other methods well known in the art. Alternatively, soluble PRO polypeptide containing a signal sequence may be secreted in useful quantity into the medium in which the cells are grown.

A soluble PRO polypeptide-containing preparation is passed over the immunoaffinty column, and the column is washed under conditions that allow the preferential absorbance of PRO polypeptide (e.g., high ionic strength buffers in the presence of detergent). Then, the column is eluted under conditions that disrupt antibody/PRO polypeptide binding (e.g., a low pH buffer such as approximately pH 2-3, or a high concentration of a chaotrope such as urea or thiocyanate ion), and PRO polypeptide is collected.

Example 12

Drug Screening

This invention is particularly useful for screening compounds by using PRO polypeptides or binding fragment thereof in any of a variety of drug screening techniques. The PRO polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the PRO polypeptide or fragment. Drugs are screened against such transformed cells in competitive binding assays. Such cells, either in viable or fixed form, can be used for standard binding assays. One may measure, for example, the formation of complexes between PRO polypeptide or a fragment and the agent being tested. Alternatively, one can examine the diminution in complex formation between the PRO polypeptide and its target cell or target receptors caused by the agent being tested.

Thus, the present invention provides methods of screening for drugs or any other agents which can affect a PRO polypeptide-associated disease or disorder. These methods comprise contacting such an agent with an PRO polypeptide or fragment thereof and assaying (I) for the presence of a complex between the agent and the PRO polypeptide or fragment, or (ii) for the presence of a complex between the PRO polypeptide or fragment and the cell, by methods well known in the art. In such competitive binding assays, the PRO polypeptide or fragment is typically labeled. After suitable incubation, free PRO polypeptide or fragment is separated from that present in bound form, and the amount of free or uncomplexed label is a measure of the ability of the particular agent to bind to PRO polypeptide or to interfere with the PRO polypeptide/cell complex.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a PRO polypeptide, the peptide test compounds are reacted with PRO polypeptide and washed. Bound PRO polypeptide is detected by methods well known in the art. Purified PRO polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding PRO polypeptide specifically compete with a test compound for binding to PRO polypeptide or fragments thereof. In this manner, the antibodies can be used to detect the presence of any peptide which shares one or more antigenic determinants with PRO polypeptide.

Example 13

Rational Drug Design

The goal of rational drug design is to produce structural analogs of biologically active polypeptide of interest (i.e., a PRO polypeptide) or of small molecules with which they interact, e.g., agonists, antagonists, or inhibitors. Any of these examples can be used to fashion drugs which are more active or stable forms of the PRO polypeptide or which enhance or interfere with the function of the PRO polypeptide in vivo (cf., Hodgson, *Bio/Technology,* 9: 19-21 (1991)).

In one approach, the three-dimensional structure of the PRO polypeptide, or of an PRO polypeptide-inhibitor complex, is determined by x-ray crystallography, by computer modeling or, most typically, by a combination of the two approaches. Both the shape and charges of the PRO polypeptide must be ascertained to elucidate the structure and to determine active site(s) of the molecule. Less often, useful information regarding the structure of the PRO polypeptide may be gained by modeling based on the structure of homologous proteins. In both cases, relevant structural information is used to design analogous PRO polypeptide-like molecules or to identify efficient inhibitors. Useful examples of rational drug design may include molecules which have improved activity or stability as shown by Braxton and Wells, *Biochemistry,* 31:7796-7801 (1992) or which act as inhibitors, agonists, or antagonists of native peptides as shown by Athauda et al., *J. Biochem.*, 113:742-746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the PRO polypeptide may be made available to perform such analytical studies as X-ray crystallography. In addition, knowledge of the PRO polypeptide amino acid sequence provided herein will provide guidance to those employing computer modeling techniques in place of or in addition to x-ray crystallography.

Example 14

Ability of PRO Polypeptides to Stimulate the Release of Proteoglycans from Cartilage (Assay 97)

The ability of various PRO polypeptides to stimulate the release of proteoglycans from cartilage tissue was tested as follows.

The metacarphophalangeal joint of 4-6 month old pigs was aseptically dissected, and articular cartilage was removed by free hand slicing being careful to avoid the underlying bone. The cartilage was minced and cultured in bulk for 24 hours in a humidified atmosphere of 95% air, 5% $CO_2$ in serum free (SF) media (DME/F12 1:1) with 0.1% BSA and 100 U/ml penicillin and 100 µg/ml streptomycin. After washing three times, approximately 100 mg of articular cartilage was aliquoted into micronics tubes and incubated for an additional 24 hours in the above SF media. PRO polypeptides were then added at 1% either alone or in combination with 18 ng/ml interleukin-1α, a known stimulator of proteoglycan release from cartilage tissue. The supernatant was then harvested and assayed for the amount of proteoglycans using the 1,9-dimethyl-methylene blue (DMB) colorimetric assay (Farndale and Buttle, *Biochem. Biophys. Acta* 883:173-177 (1985)). A positive result in this assay indicates that the test polypeptide will find use, for example, in the treatment of sports-related joint problems, articular cartilage defects, osteoarthritis or rheumatoid arthritis.

When various PRO polypeptides were tested in the above assay, the polypeptides demonstrated a marked ability to stimulate release of proteoglycans from cartilage tissue both basally and after stimulation with interleukin-1α and at 24 and 72 hours after treatment, thereby indicating that these PRO polypeptides are useful for stimulating proteoglycan release from cartilage tissue. As such, these PRO polypeptides are useful for the treatment of sports-related joint problems, articular cartilage defects, osteoarthritis or rheumatoid arthritis. PRO6018 polypeptide testing positive in this assay.

Example 15

Human Microvascular Endothelial Cell Proliferation (Assay 146)

This assay is designed to determine whether PRO polypeptides of the present invention show the ability to induce proliferation of human microvascular endothelial cells in culture and, therefore, function as useful growth factors.

On day 0, human microvascular endothelial cells were plated in 96-well plates at 1000 cells/well per 100 microliter and incubated overnight in complete media [EBM-2 growth media, plus supplements: IGF-1; ascorbic acid; VEGF; hEGF; hFGF; hydrocortisone, gentamicin (GA-1000), and fetal bovine serum (FBS, Clonetics)]. On day 1, complete media was replaced by basal media [EBM-2 plus 1% FBS] and addition of PRO polypeptides at 1%, 0.1% and 0.01%. On day 7, an assessment of cell proliferation was performed using the ViaLight HS kit [ATP/luciferase Lumitech]. Results are expressed as % of the cell growth observed with control buffer.

The following PRO polypeptides stimulated human microvascular endothelial cell proliferation in this assay: PRO1313, PRO20080, and PRO21383.

The following PRO polypeptides inhibited human microvascular endothelial cell proliferation in this assay: PRO6071, PRO4487, and PRO6006.

Example 16

Microarray Analysis to Detect Overexpression of PRO Polypeptides in Cancerous Tumors Nucleic acid microarrays, often containing thousands of gene sequences, are useful for identifying differentially expressed genes in diseased tissues as compared to their normal counterparts. Using nucleic acid microarrays, test and control mRNA samples from test and control tissue samples are reverse transcribed and labeled to generate cDNA probes. The cDNA probes are then hybridized to an array of nucleic acids immobilized on a solid support. The array is configured such that the sequence and position of each member of the array is known. For example, a selection of genes known to be expressed in certain disease states may be arrayed on a solid support. Hybridization of a labeled probe with a particular array member indicates that the sample from which the probe was derived expresses that gene. If the hybridization signal of a probe from a test (disease tissue) sample is greater than hybridization signal of a probe from a control (normal tissue) sample, the gene or genes overexpressed in the disease tissue are identified. The implication of this result is that an overexpressed protein in a diseased tissue is useful not only as a diagnostic marker for the presence of the disease condition, but also as a therapeutic target for treatment of the disease condition.

The methodology of hybridization of nucleic acids and microarray technology is well known in the art. In the present example, the specific preparation of nucleic acids for hybridization and probes, slides, and hybridization conditions are all detailed in U.S. Provisional Patent Application Ser. No. 60/193,767, filed on Mar. 31, 2000 and which is herein incorporated by reference.

In the present example, cancerous tumors derived from various human tissues were studied for PRO polypeptide-encoding gene expression relative to non-cancerous human tissue in an attempt to identify those PRO polypeptides which are overexpressed in cancerous tumors. Cancerous human tumor tissue from any of a variety of different human tumors was obtained and compared to a "universal" epithelial control sample which was prepared by pooling non-cancerous human tissues of epithelial origin, including liver, kidney, and lung. mRNA isolated from the pooled tissues represents a mixture of expressed gene products from these different tissues. Microarray hybridization experiments using the pooled control samples generated a linear plot in a 2-color analysis. The slope of the line generated in a 2-color analysis was then used to normalize the ratios of (test:control detection) within each experiment. The normalized ratios from various experiments were then compared and used to identify clustering of gene expression. Thus, the pooled "universal control" sample not only allowed effective relative gene expression determinations in a simple 2-sample comparison, it also allowed multi-sample comparisons across several experiments.

In the present experiments, nucleic acid probes derived from the herein described PRO polypeptide-encoding nucleic acid sequences were used in the creation of the microarray and RNA from a panel of nine different tumor tissues (listed below) were used for the hybridization thereto. A value based upon the normalized ratio:experimental ratio was designated as a "cutoff ratio". Only values that were above this cutoff ratio were determined to be significant. Table 8 below shows the results of these experiments, demonstrating that various PRO polypeptides of the present invention are significantly overexpressed in various human tumor tissues, as compared to a non-cancerous human tissue control or other human tumor tissues. As described above, these data demonstrate that the PRO polypeptides of the present invention are useful not only as diagnostic markers for the presence of one or more cancerous tumors, but also serve as therapeutic targets for the treatment of those tumors.

TABLE 8

| Molecule | is overexpressed in: | as compared to normal control: |
|---|---|---|
| PRO240 | breast tumor | universal normal control |
| PRO240 | lung tumor | universal normal control |
| PRO256 | colon tumor | universal normal control |
| PRO256 | lung tumor | universal normal control |
| PRO256 | breast tumor | universal normal control |
| PRO306 | colon tumor | universal normal control |
| PRO306 | lung tumor | universal normal control |
| PRO540 | lung tumor | universal normal control |
| PRO540 | colon tumor | universal normal control |
| PRO773 | breast tumor | universal normal control |
| PRO773 | colon tumor | universal normal control |
| PRO698 | colon tumor | universal normal control |
| PRO698 | breast tumor | universal normal control |
| PRO698 | lung tumor | universal normal control |
| PRO698 | prostate tumor | universal normal control |
| PRO698 | rectal tumor | universal normal control |
| PRO3567 | colon tumor | universal normal control |
| PRO3567 | breast tumor | universal normal control |
| PRO3567 | lung tumor | universal normal control |
| PRO826 | colon tumor | universal normal control |
| PRO826 | lung tumor | universal normal control |
| PRO826 | breast tumor | universal normal control |
| PRO826 | rectal tumor | universal normal control |
| PRO826 | liver tumor | universal normal control |
| PRO1002 | colon tumor | universal normal control |
| PRO1002 | lung tumor | universal normal control |
| PRO1068 | colon tumor | universal normal control |
| PRO1068 | breast tumor | universal normal control |
| PRO1030 | colon tumor | universal normal control |
| PRO1030 | breast tumor | universal normal control |
| PRO1030 | lung tumor | universal normal control |
| PRO1030 | prostate tumor | universal normal control |
| PRO1030 | rectal tumor | universal normal control |

TABLE 8-continued

| Molecule | is overexpressed in: | as compared to normal control: |
|---|---|---|
| PRO4397 | colon tumor | universal normal control |
| PRO4397 | breast tumor | universal normal control |
| PRO4344 | colon tumor | universal normal control |
| PRO4344 | lung tumor | universal normal control |
| PRO4344 | rectal tumor | universal normal control |
| PRO4407 | colon tumor | universal normal control |
| PRO4407 | breast tumor | universal normal control |
| PRO4407 | lung tumor | universal normal control |
| PRO4407 | liver tumor | universal normal control |
| PRO4407 | rectal tumor | universal normal control |
| PRO4316 | colon tumor | universal normal control |
| PRO4316 | prostate tumor | universal normal control |
| PRO5775 | colon tumor | universal normal control |
| PRO6016 | colon tumor | universal normal control |
| PRO4980 | breast tumor | universal normal control |
| PRO4980 | colon tumor | universal normal control |
| PRO4980 | lung tumor | universal normal control |
| PRO6018 | colon tumor | universal normal control |
| PRO7168 | colon tumor | universal normal control |
| PRO6000 | colon tumor | universal normal control |
| PRO6006 | colon tumor | universal normal control |
| PRO5800 | colon tumor | universal normal control |
| PRO5800 | breast tumor | universal normal control |
| PRO5800 | lung tumor | universal normal control |
| PRO5800 | rectal tumor | universal normal control |
| PRO7476 | colon tumor | universal normal control |
| PRO10268 | colon tumor | universal normal control |
| PRO6496 | colon tumor | universal normal control |
| PRO6496 | breast tumor | universal normal control |
| PRO6496 | lung tumor | universal normal control |
| PRO7422 | colon tumor | universal normal control |
| PRO7431 | colon tumor | universal normal control |
| PRO28633 | colon tumor | universal normal control |
| PRO28633 | lung tumor | universal normal control |
| PRO28633 | liver tumor | universal normal control |
| PRO21485 | colon tumor | universal normal control |
| PRO28700 | breast tumor | universal normal control |
| PRO28700 | lung tumor | universal normal control |
| PRO28700 | colon tumor | universal normal control |
| PRO34012 | colon tumor | universal normal control |
| PRO34012 | lung tumor | universal normal control |
| PRO34003 | colon tumor | universal normal control |
| PRO34003 | lung tumor | universal normal control |
| PRO34001 | colon tumor | universal normal control |
| PRO34009 | colon tumor | universal normal control |
| PRO34009 | breast tumor | universal normal control |
| PRO34009 | lung tumor | universal normal control |
| PRO34009 | rectal tumor | universal normal control |
| PRO34192 | colon tumor | universal normal control |
| PRO34564 | colon tumor | universal normal control |
| PRO35444 | colon tumor | universal normal control |
| PRO5998 | colon tumor | universal normal control |
| PRO5998 | lung tumor | universal normal control |
| PRO5998 | kidney tumor | universal normal control |
| PRO19651 | colon tumor | universal normal control |
| PRO20221 | liver tumor | universal normal control |
| PRO21434 | liver tumor | universal normal control |

Example 17

Fetal Hemoglobin Induction in an Erythroblastic Cell Line (Assay 107)

This assay is useful for screening PRO polypeptides for the ability to induce the switch from adult hemoglobin to fetal hemoglobin in an erythroblastic cell line. Molecules testing positive in this assay are expected to be useful for therapeutically treating various mammalian hemoglobin-associated disorders such as the various thalassemias. The assay is performed as follows. Erythroblastic cells are plated in standard growth medium at 1000 cells/well in a 96 well format. PRO polypeptides are added to the growth medium at a concentration of 0.2% or 2% and the cells are incubated for 5 days at 37° C. As a positive control, cells are treated with 100 μM hemin and as a negative control, the cells are untreated. After 5 days, cell lysates are prepared and analyzed for the expression of gamma globin (a fetal marker). A positive in the assay is a gamma globin level at least 2-fold above the negative control.

PRO20080 polypeptide tested positive in this assay.

Example 18

Microarray Analysis to Detect Overexpression of PRO Polypeptides in HUVEC Cells Treated with Growth Factors This assay is designed to determine whether PRO polypeptides of the present invention show the ability to induce angiogenesis by stimulating endothelial cell tube formation in HUVEC cells.

Nucleic acid microarrays, often containing thousands of gene sequences, are useful for identifying differentially expressed genes in tissues exposed to various stimuli (e.g., growth factors) as compared to their normal, unexposed counterparts. Using nucleic acid microarrays, test and control mRNA samples from test and control tissue samples are reverse transcribed and labeled to generate cDNA probes. The cDNA probes are then hybridized to an array of nucleic acids immobilized on a solid support. The array is configured such that the sequence and position of each member of the array is known. Hybridization of a labeled probe with a particular array member indicates that the sample from which the probe was derived expresses that gene. If the hybridization signal of a probe from a test (exposed tissue) sample is greater than hybridization signal of a probe from a control (normal, unexposed tissue) sample, the gene or genes overexpressed in the exposed tissue are identified. The implication of this result is that an overexpressed protein in an exposed tissue may be involved in the functional changes within the tissue following exposure to the stimuli (e.g., tube formation).

The methodology of hybridization of nucleic acids and microarray technology is well known in the art. In the present example, the specific preparation of nucleic acids for hybridization and probes, slides, and hybridization conditions are all detailed in U.S. Provisional Patent Application Ser. No. 60/193,767, filed on Mar. 31, 2000 and which is herein incorporated by reference.

In the present example, HUVEC cells grown in either collagen gels or fibrin gels were induced to form tubes by the addition of various growth factors. Specifically, collagen gels were prepared as described previously in Yang et al., *American J. Pathology*, 1999, 155(3):887-895 and Xin et al., *American J. Pathology*, 2001, 158(3): 1111-1120. Following gelation of the HUVEC cells, IX basal medium containing M199 supplemented with 1% FBS, 1× ITS, 2 mM L-glutamine, 50 μg/ml ascorbic acid, 26.5 mM $NaHCO_3$, 100 U/ml penicillin and 100 U/ml streptomycin was added. Tube formation was elicited by the inclusion in the culture media of either a mixture of phorbol myrsitate acetate (50 nM), vascular endothelial cell growth factor (40 ng/ml) and basic fibroblast growth factor (40 ng/ml) ("PMA growth factor mix") or hepatocyte growth factor (40 ng/ml) and vascular endothelial cell growth factor (40 ng/ml) (HGF/VEGF mix) for the indicated period of time. Fibrin Gels were prepared by suspending Huvec ($4\times10^5$ cells/ml) in M199 containing 1% fetal bovine serum (Hyclone) and human fibrinogen (2.5 mg/ml). Thrombin (50 U/ml) was then added to the fibrinogen suspension at a ratio of 1 part thrombin solution:30 parts fibrinogen suspension. The solution was then layered onto 10 cm tissue culture plates (total volume: 15 ml/plate) and allowed to solidify at 37° C. for 20 min. Tissue culture media (10 ml of BM containing PMA (50 nM), bFGF (40 ng/ml) and VEGF (40 ng/ml)) was then added and the cells incubated at 37° C. in 5% $CO_2$ in air for the indicated period of time.

Total RNA was extracted from the HUVEC cells incubated for 0, 4, 8, 24, 40 and 50 hours in the different matrix and media combinations using a TRIzol extraction followed by a second purification using RNAeasy Mini Kit (Qiagen). The total RNA was used to prepare cRNA which was then hybridized to the microarrays.

In the present experiments, nucleic acid probes derived from the herein described PRO polypeptide-encoding nucleic acid sequences were used in the creation of the microarray and RNA from the HUVEC cells described above were used for the hybridization thereto. Pairwise comparisons were made using time 0 chips as a baseline. Three replicate samples were analyzed for each experimental condition and time. Hence there were 3 time 0 samples for each treatment and 3 replicates of each successive time point. Therefore, a 3 by 3 comparison was performed for each time point compared against each time 0 point. This resulted in 9 comparisons per time point. Only those genes that had increased expression in all three non-time-0 replicates in each of the different matrix and media combinations as compared to any of the three time zero replicates were considered positive. Although this stringent method of data analysis does allow for false negatives, it minimizes false positives.

PRO281, PRO1560, PRO189, PRO4499, PRO6308, PRO6000, PRO10275, PRO21207, PRO20933, and PRO34274 tested positive in this assay.

Example 19

Tumor Versus Normal Differential Tissue Expression Distribution

Oligonucleotide probes were constructed from some of the PRO polypeptide-encoding nucleotide sequences shown in the accompanying figures for use in quantitative PCR amplification reactions. The oligonucleotide probes were chosen so as to give an approximately 200-600 base pair amplified fragment from the 3' end of its associated template in a standard PCR reaction. The oligonucleotide probes were employed in standard quantitative PCR amplification reactions with cDNA libraries isolated from different human tumor and normal human tissue samples and analyzed by agarose gel electrophoresis so as to obtain a quantitative determination of the level of expression of the PRO polypeptide-encoding nucleic acid in the various tumor and normal tissues tested. β-actin was used as a control to assure that equivalent amounts of nucleic acid was used in each reaction. Identification of the differential expression of the PRO polypeptide-encoding nucleic acid in one or more tumor tissues as compared to one or more normal tissues of the same tissue type renders the molecule useful diagnostically for the determination of the presence or absence of tumor in a subject suspected of possessing a tumor as well as therapeutically as a target for the treatment of a tumor in a subject possessing such a tumor. These assays provided the following results:

(1) DNA 161005-2943 molecule is very highly expressed in human umbilical vein endothelial cells (HUVEC), substantia niagra, hippocampus and dendrocytes; highly expressed in lymphoblasts; expressed in spleen, prostate, uterus and macrophages; and is weakly expressed in cartilage and heart. Among a panel of normal and tumor tissues examined, it is expressed in esophageal tumor, and is not expressed in normal esophagus, normal stomach, stomach tumor, normal kidney, kidney tumor, normal lung, lung tumor, normal rectum, rectal tumor, normal liver and liver tumor.

(2) DNA170245-3053 molecule is highly expressed in cartilage, testis, adrenal gland, and uterus, and not expressed in HUVEC, colon tumor, heart, placenta, bone marrow, spleen and aortic endothelial cells. In a panel of tumor and normal tissue samples examined, the DNA170245-3053 molecule was found to be expressed in normal esophagus and esophagial tumor, expressed in normal stomach and in stomach tumor, not expressed in normal kidney, but expressed in kidney tumor, not expressed in normal lung, but expressed in lung tumor, not expressed in normal rectum nor in rectal tumor, and not expressed in normal liver, but is expressed in liver tumor.

(3) DNA173157-2981 molecule is significantly expressed in the following tissues: cartilage, testis, HUVEC, heart, placenta, bone marrow, adrenal gland, prostate, spleen, aortic endothelial cells, and uterus. When these assays were conducted on a tumor tissue panel, it was found that the DNA 173157-2981 molecule is significantly expressed in the following tissues: normal esophagus and esophagial tumor, normal stomach and stomach tumor, normal kidney and kidney tumor, normal lung and lung tumor, normal rectum and rectal tumor, normal liver and liver tumor, and colon tumor.

(4) DNA175734-2985 molecule is significantly expressed in the adrenal gland and the uterus. The DNA 175734-2985 molecule is not significantly expressed in the following tissues: cartilage, testis, HUVEC, colon tumor, heart, placenta, bone marrow, prostate, spleen and aortic endothelial cells. Screening of a tumor panel revealed that DNA175734-2985 is significantly expressed in normal esophagus but not in esophagial tumor. Similarly, while highly expressed in normal rectum, DNA175734-2985 is expressed to a lesser extent in rectal tumor. DNA 175734-2985 is expressed equally in normal stomach and stomach tumor as well as normal liver and liver tumor. While not expressed in normal kidney, DNA175734-2985 is highly expressed in kidney tumor.

(5) DNA 176108-3040 molecule is highly expressed in prostate and uterus, expressed in cartilage, testis, heart, placenta, bone marrow, adrenal gland and spleen, and not significantly expressed in HUVEC, colon tumor, and aortic endothelial cells. In a panel of tumor and normal tissue samples examined, the DNA 176108-3040 molecule was found to be highly expressed in normal esophagus, but expressed at lower levels in esophagial tumor, highly expressed in normal stomach, and expressed at a lower level in stomach tumor, expressed in kidney and in kidney tumor, expressed in normal rectum and at a lower level in rectal tumor, and expressed in normal liver and not expressed in liver tumor.

(6) DNA191064-3069 molecule is significantly expressed in the following tissues: cartilage, testis, HUVEC, heart, placenta, bone marrow, adrenal gland, prostate, spleen, aortic endothelial cells, and uterus and not significantly expressed in colon tumor. In a panel of tumor and normal tissue samples, the DNA 191064-3069 molecule was found to be expressed in normal esophagus and in esophagial tumors, expressed in normal stomach and in stomach tumors, expressed in normal kidney and in kidney tumors, expressed in normal lung and in lung tumors, expressed in normal rectum and in rectal tumors, expressed in normal liver and in liver tumors.

(7) DNA 194909-3013 molecule is highly expressed in placenta, and expressed in cartilage, testis, HUVEC, colon tumor, heart, bone marrow, adrenal gland, prostate, spleen, aortic endothelial cells and uterus. In a panel of tumor and normal tissue samples examined, the DNA194909-3013 molecule was found to be expressed in normal esophagus and expressed at a lower level in esophagial tumor, not expressed in normal stomach nor stomach tumor, expressed in normal kidney and kidney tumor, expressed in normal lung and lung tumor, expressed in normal rectum and rectal tumor, and not expressed in normal liver, but is expressed in liver tumor.

(8) The PRO34009 encoding genes of the invention (DNA203532-3029) were screened in normal tissues and the following primary tumors and the resulting values are reported below.

Tumor Panel:

PRO34009 encoding genes were expressed 39.3 fold higher in lung tumor than normal lung. It is expressed 9.5 fold higher in esophagial tumors than normal esophagus. It is expressed 6.7 fold higher in kidney tumor than normal kidney. It is expressed 4.0 fold higher in colon tumor than normal colon. It is expressed 2.7 fold higher in stomach tumor than normal stomach. It is expressed at similar levels in normal rectum and rectal tumor, normal liver and liver tumor, normal uterus and uterine tumor.

Normal Panel:

For the normal tissue values, the normal tissue with the highest expression, in this case normal thymus, was given a value of 1 and all other normal tissues were given a value of less than 1, and described as expressed, weakly expressed or not expressed, based on their expression relative to thymus. PRO34009 encoding genes were expressed in normal thymus. It is weakly expressed in lymphoblast, spleen, heart, fetal limb, fetal lung, placenta, HUVEC, testis, fetal kidney, uterus, prostate, macrophage, substantia nigra, hippocampus, liver, skin, esophagus, stomach, rectum, kidney, thyroid, skeletal muscle, or fetal articular cartilage. It is not expressed in bone marrow, fetal liver, colon, lung or dendrocytes.

(9) DNA213858-3060 molecule is not significantly expressed in cartilage, testis, HUVEC, colon tumor, heart, placenta, bone marrow, adrenal gland, prostate, spleen, aortic endothelial cells or uterus. In a panel of tumor and normal tissue samples examined, the DNA213858-3060 molecule was found to be expressed in normal esophagus and esophagial tumor, expressed in normal stomach and in stomach tumor, expressed in normal kidney and and kidney tumor, expressed in normal lung and in lung tumor, expressed in normal rectum and in rectal tumor, and expressed in normal liver and in liver tumor.

(10) DNA216676-3083 molecule is significantly expressed in the following tissues: testis, heart, bone marrow, and uterus, and not significantly expressed in the following tissues: cartilage, HUVEC, colon tumor, placenta, adrenal gland, prostate, spleen, or aortic endothelial cells In a panel of tumor and normal tissues samples examined, the DNA216676-3083 molecule was found to be expressed in normal esophagus and esophagial tumor, not expressed in normal stomach, but is expressed in stomach tumor, not expressed in normal kidney nor in kidney tumor, not expressed in normal lung, but is expressed in lung tumor, not expressed in normal rectum, but is expressed in rectal tumor, and not expressed in normal liver nor in liver tumor.

(11) DNA222653-3104 molecule is significantly expressed testis, and not significantly expressed in cartilage, HUVEC, colon tumor, heart, placenta, bone marrow, adrenal gland, prostate, spleen, aortic endothelial cells and uterus. In a panel of tumor and normal tissue samples examined, the DNA22653-3104 molecule was not expressed in normal esophagus, esophagial tumor, normal stomach, stomach tumor, normal kidney, kidney tumor, normal lung, lung tumor, normal rectum, rectal tumor, normal liver and liver tumor.

Example 20

Guinea Pig Vascular Leak (Assay 51)

This assay is designed to determine whether PRO polypeptides of the present invention show the ability to induce vascular permeability. Polypeptides testing positive in this assay are expected to be useful for the therapeutic treatment of conditions which would benefit from enhanced vascular permeability including, for example, conditions which may benefit from enhanced local immune system cell infiltration.

Hairless guinea pigs weighing 350 grams or more were anesthetized with Ketamine (75-80 mg/kg) and 5 mg/kg Xylazine intramuscularly. Test samples containing the PRO polypeptide or a physiological buffer without the test polypeptide are injected into skin on the back of the test animals with 100 µl per injection site intradermally. There were approximately 16-24 injection sites per animal. One ml of Evans blue dye (1% in PBS) is then injected intracardially. Skin vascular permeability responses to the compounds (i.e., blemishes at the injection sites of injection) are visually scored by measuring the diameter (in mm) of blue-colored leaks from the site of injection at 1 and 6 hours post administration of the test materials. The mm diameter of blueness at the site of injection is observed and recorded as well as the severity of the vascular leakage. Blemishes of at least 5 mm in diameter are considered positive for the assay when testing purified proteins, being indicative of the ability to induce vascular leakage or permeability. A response greater than 7 mm diameter is considered positive for conditioned media samples. Human VEGF at 0.1 µg/100 µl is used as a positive control, inducing a response of 15-23 mm diameter.

PRO19822 polypeptides tested positive in this assay.

Example 21

Skin Vascular Permeability Assay (Assay 64)

This assay shows that certain polypeptides of the invention stimulate an immune response and induce inflammation by inducing mononuclear cell, eosinophil and PMN infiltration at the site of injection of the animal. Compounds which stimulate an immune response are useful therapeutically where stimulation of an immune response is beneficial. This skin vascular permeability assay is conducted as follows. Hairless guinea pigs weighing 350 grams or more are anesthetized with ketamine (75-80 mg/Kg) and 5 mg/Kg xylazine intramuscularly (IM). A sample of purified polypeptide of the invention or a conditioned media test sample is injected intradermally onto the backs of the test animals with 100 µl per injection site: It is possible to have about 10-30, preferably about 16-24, injection sites per animal. One µl of Evans blue dye (1% in physiologic buffered saline) is injected intracardially. Blemishes at the injection sites are then measured (mm diameter) at 1 hr and 6 hr post injection. Animals were sacrificed at 6 hrs after injection. Each skin injection site is biopsied and fixed in formalin. The skins are then prepared for histopathologic evaluation. Each site is evaluated for inflammatory cell infiltration into the skin. Sites with visible inflammatory cell inflammation are scored as positive. Inflammatory cells may be neutrophilic, eosinophilic, monocytic or lymphocytic. At least a minimal perivascular infiltrate at the injection site is scored as positive, no infiltrate at the site of injection is scored as negative.

PRO19822 polypeptide tested positive in this assay.

SEQUENCE LISTING

```
<160> NUMBER OF SEQ ID NOS: 116

<210> SEQ ID NO 1
<211> LENGTH: 1943
<212> TYPE: DNA
<213> ORGANISM: Homo Sapien

<400> SEQUENCE: 1
cggacgcgtg ggtgcgaggc gaaggtgacc ggggaccgag catttcagat          50
ctgctcggta gacctggtgc accaccacca tgttggctgc aaggctggtg         100
tgtctccgga cactaccttc tagggttttc cacccagctt tcaccaaggc         150
ctcccctgtt gtgaagaatt ccatcacgaa gaatcaatgg ctgttaacac         200
ctagcaggga atatgccacc aaaacaagaa ttgggatccg gcgtgggaga         250
actggccaag aactcaaaga ggcagcattg gaaccatcga tggaaaaaat         300
atttaaaatt gatcagatgg gaagatggtt tgttgctgga ggggctgctg         350
ttggtcttgg agcattgtgc tactatggct tgggactgtc taatgagatt         400
```

-continued

```
ggagctattg aaaaggctgt aatttggcct cagtatgtca aggatagaat      450
tcattccacc tatatgtact tagcagggag tattggttta acagctttgt      500
ctgccatagc aatcagcaga acgcctgttc tcatgaactt catgatgaga      550
ggctcttggg tgacaattgg tgtgaccttt gcagccatgg ttggagctgg      600
aatgctggta cgatcaatac catatgacca gagcccaggc ccaaagcatc      650
ttgcttggtt gctacattct ggtgtgatgg gtgcagtggt ggctcctctg      700
acaatattag ggggtcctct tctcatcaga gctgcatggt acacagctgg      750
cattgtggga ggcctctcca ctgtggccat gtgtgcgccc agtgaaaagt      800
ttctgaacat gggtgcaccc ctgggagtgg gcctgggtct cgtctttgtg      850
tcctcattgg gatctatgtt cttccacct accaccgtgg ctggtgccac       900
tctttactca gtggcaatgt acggtggatt agttcttttc agcatgttcc      950
ttctgtatga tacccagaaa gtaatcaagc gtgcagaagt atcaccaatg     1000
tatggagttc aaaatatga tcccattaac tcgatgctga gtatctacat      1050
ggatacatta aatatattta tgcgagttgc aactatgctg gcaactggag     1100
gcaacagaaa gaaatgaagt gactcagctt ctggcttctc tgctacatca     1150
aatatcttgt ttaatggggc agatatgcat taaatagttt gtacaagcag     1200
ctttcgttga agtttagaag ataagaaaca tgtcatcata tttaaatgtt     1250
ccggtaatgt gatgcctcag gtctgccttt ttttctggag aataaatgca     1300
gtaatcctct cccaaataag cacacacatt ttcaattctc atgtttgagt     1350 gatttttaaaa tgttttggtg aatgtgaaaa ctaaagtttg tgtcatgaga    1400
atgtaagtct ttttctact ttaaaattta gtaggttcac tgagtaacta      1450
aaatttagca aacctgtgtt tgcatatttt tttggagtgc agaatattgt     1500
aattaatgtc ataagtgatt tggagctttg gtaaagggac cagagagaag     1550
gagtcacctg cagtcttttg tttttttaaa tacttagaac ttagcacttg     1600
tgttattgat tagtgaggag ccagtaagaa acatctgggt atttggaaac     1650
aagtggtcat tgttacattc atttgctgaa cttaacaaaa ctgttcatcc     1700
tgaaacaggc acaggtgatg cattctcctg ctgttgcttc tcagtgctct     1750 cttttccaata tagatgtggt catgtttgac ttgtacagaa tgttaatcat    1800
acagagaatc cttgatggaa ttatatatgt gtgtttact tttgaatgtt      1850 acaaaaggaa ataactttaa aactattctc aagagaaaat attcaaagca     1900
tgaaatatgt tgcttttcc agaatacaaa cagtatactc atg             1943
```

<210> SEQ ID NO 2
<211> LENGTH: 345
<212> TYPE: PRT
<213> ORGANISM: Homo Sapien

<400> SEQUENCE: 2

```
Met Leu Ala Ala Arg Leu Val Cys Leu Arg Thr Leu Pro Ser Arg
 1               5                  10                  15

Val Phe His Pro Ala Phe Thr Lys Ala Ser Pro Val Val Lys Asn
                20                  25                  30

Ser Ile Thr Lys Asn Gln Trp Leu Leu Thr Pro Ser Arg Glu Tyr
                35                  40                  45
```

```
Ala Thr Lys Thr Arg Ile Gly Ile Arg Arg Gly Arg Thr Gly Gln
             50                  55                  60

Glu Leu Lys Glu Ala Ala Leu Glu Pro Ser Met Glu Lys Ile Phe
             65                  70                  75

Lys Ile Asp Gln Met Gly Arg Trp Phe Val Ala Gly Gly Ala Ala
             80                  85                  90

Val Gly Leu Gly Ala Leu Cys Tyr Tyr Gly Leu Gly Leu Ser Asn
             95                 100                 105

Glu Ile Gly Ala Ile Glu Lys Ala Val Ile Trp Pro Gln Tyr Val
            110                 115                 120

Lys Asp Arg Ile His Ser Thr Tyr Met Tyr Leu Ala Gly Ser Ile
            125                 130                 135

Gly Leu Thr Ala Leu Ser Ala Ile Ala Ile Ser Arg Thr Pro Val
            140                 145                 150

Leu Met Asn Phe Met Met Arg Gly Ser Trp Val Thr Ile Gly Val
            155                 160                 165

Thr Phe Ala Ala Met Val Gly Ala Gly Met Leu Val Arg Ser Ile
            170                 175                 180

Pro Tyr Asp Gln Ser Pro Gly Pro Lys His Leu Ala Trp Leu Leu
            185                 190                 195

His Ser Gly Val Met Gly Ala Val Val Ala Pro Leu Thr Ile Leu
            200                 205                 210

Gly Gly Pro Leu Leu Ile Arg Ala Ala Trp Tyr Thr Ala Gly Ile
            215                 220                 225

Val Gly Gly Leu Ser Thr Val Ala Met Cys Ala Pro Ser Glu Lys
            230                 235                 240

Phe Leu Asn Met Gly Ala Pro Leu Gly Val Gly Leu Gly Leu Val
            245                 250                 255

Phe Val Ser Ser Leu Gly Ser Met Phe Leu Pro Pro Thr Thr Val
            260                 265                 270

Ala Gly Ala Thr Leu Tyr Ser Val Ala Met Tyr Gly Gly Leu Val
            275                 280                 285

Leu Phe Ser Met Phe Leu Leu Tyr Asp Thr Gln Lys Val Ile Lys
            290                 295                 300

Arg Ala Glu Val Ser Pro Met Tyr Gly Val Gln Lys Tyr Asp Pro
            305                 310                 315

Ile Asn Ser Met Leu Ser Ile Tyr Met Asp Thr Leu Asn Ile Phe
            320                 325                 330

Met Arg Val Ala Thr Met Leu Ala Thr Gly Gly Asn Arg Lys Lys
            335                 340                 345

<210> SEQ ID NO 3
<211> LENGTH: 1110
<212> TYPE: DNA
<213> ORGANISM: Homo Sapien

<400> SEQUENCE: 3
ccaatcgccc ggtgcggtgg tgcagggtct cgggctagtc atggcgtccc         50
cgtctcggag actgcagact aaaccagtca ttacttgttt caagagcgtt        100
ctgctaatct acactttat tttctggatc actggcgtta tccttcttgc         150
agttggcatt tggggcaagg tgagcctgga gaattacttt tctcttttaa        200
atgagaaggc caccaatgtc cccttcgtgc tcattgctac tggtaccgtc        250
```

-continued

```
attattcttt tgggcacctt tggttgtttt gctacctgcc gagcttctgc    300
atggatgcta aaactgtatg caatgtttct gactctcgtt tttttggtcg    350
aactggtcgc tgccatcgta ggatttgttt tcagacatga gattaagaac    400
agctttaaga ataattatga aaggctttg aagcagtata actctacagg     450
agattataga agccatgcag tagacaagat ccaaaatacg ttgcattgtt    500
gtggtgtcac cgattataga gattggacag atactaatta ttactcagaa    550
aaaggatttc ctaagagttg ctgtaaactt gaagattgta ctccacagag    600
agatgcagac aaagtaaaca atgaaggttg ttttataaag gtgatgacca    650
ttatagagtc agaaatggga gtcgttgcag gaatttcctt tggagttgct    700
tgcttccaac tgattggaat ctttctcgcc tactgccwct ctcgtgccat    750
aacaaataac cagtatgaga tagtgtaacc caatgtatct gtgggcctat    800
tcctctctac ctttaaggac atttagggtc cccctgtga attagaaagt     850
tgcttggctg agaactgac aacactactt actgatagac caaaaaacta     900
caccagtagg ttgattcaat caagatgtat gtagacctaa aactacacca    950
ataggctgat tcaatcaaga tccgtgctcg cagtgggctg attcaatcaa   1000
gatgtatgtt tgctatgttc taagtccacc ttctatccca ttcatgttag   1050
atcgttgaaa ccctgtatcc ctctgaaaca ctggaagagc tagtaaattg   1100
taaatgaagt                                               1110
```

<210> SEQ ID NO 4
<211> LENGTH: 245
<212> TYPE: PRT
<213> ORGANISM: Homo Sapien
<220> FEATURE:
<221> NAME/KEY: unsure
<222> LOCATION: 233
<223> OTHER INFORMATION: unknown amino acid

<400> SEQUENCE: 4

```
Met Ala Ser Pro Ser Arg Arg Leu Gln Thr Lys Pro Val Ile Thr
 1               5                  10                  15

Cys Phe Lys Ser Val Leu Leu Ile Tyr Thr Phe Ile Phe Trp Ile
                20                  25                  30

Thr Gly Val Ile Leu Leu Ala Val Gly Ile Trp Gly Lys Val Ser
                35                  40                  45

Leu Glu Asn Tyr Phe Ser Leu Leu Asn Glu Lys Ala Thr Asn Val
                50                  55                  60

Pro Phe Val Leu Ile Ala Thr Gly Thr Val Ile Ile Leu Leu Gly
                65                  70                  75

Thr Phe Gly Cys Phe Ala Thr Cys Arg Ala Ser Ala Trp Met Leu
                80                  85                  90

Lys Leu Tyr Ala Met Phe Leu Thr Leu Val Phe Leu Val Glu Leu
                95                 100                 105

Val Ala Ala Ile Val Gly Phe Val Phe Arg His Glu Ile Lys Asn
               110                 115                 120

Ser Phe Lys Asn Asn Tyr Glu Lys Ala Leu Lys Gln Tyr Asn Ser
               125                 130                 135

Thr Gly Asp Tyr Arg Ser His Ala Val Asp Lys Ile Gln Asn Thr
               140                 145                 150

Leu His Cys Cys Gly Val Thr Asp Tyr Arg Asp Trp Thr Asp Thr
```

```
                    155                 160                 165
Asn Tyr Tyr Ser Glu Lys Gly Phe Pro Lys Ser Cys Cys Lys Leu
                170                 175                 180

Glu Asp Cys Thr Pro Gln Arg Asp Ala Asp Lys Val Asn Asn Glu
                185                 190                 195

Gly Cys Phe Ile Lys Val Met Thr Ile Ile Glu Ser Glu Met Gly
                200                 205                 210

Val Val Ala Gly Ile Ser Phe Gly Val Ala Cys Phe Gln Leu Ile
                215                 220                 225

Gly Ile Phe Leu Ala Tyr Cys Xaa Ser Arg Ala Ile Thr Asn Asn
                230                 235                 240

Gln Tyr Glu Ile Val
            245

<210> SEQ ID NO 5
<211> LENGTH: 1373
<212> TYPE: DNA
<213> ORGANISM: Homo Sapien

<400> SEQUENCE: 5
ggggccgcgg tctagggcgg ctacgtgtgt tgccatagcg accattttgc         50
attaactggt tggtagcttc tatcctgggg gctgagcgac tgcgggccag        100
ctcttcccct actccctctc ggctccttgt ggcccaaagg cctaaccggg        150
gtccggcggt ctggcctagg gatcttcccc gttgccccct tggggcggga        200
tggctgcgga agaagaagac gaggtggagt gggtagtgga gagcatcgcg        250
gggttcctgc gaggcccaga ctggtccatc cccatcttgg actttgtgga        300
acagaaatgt gaagttaact gcaaaggagg gcatgtgata actccaggaa        350
gcccagagcc ggtgattttg gtggcctgtg ttccccttgt ttttgatgat        400
gaagaagaaa gcaaattgac ctatacagag attcatcagg aatacaaaga        450
actagttgaa aagctgttag aaggttacct caaagaaatt ggaattaatg        500
aagatcaatt tcaagaagca tgcacttctc ctcttgcaaa acccatacα        550 tcacaggcca ttttgcaacc tgtgttggca gcagaagatt ttactatctt        600
taaagcaatg atggtccaga aaacattga atgcagctg caagccattc         650 gaataattca agagagaaat ggtgtattac ctgactgctt aaccgatggc        700
tctgatgtgg tcagtgacct tgaacacgaa gagatgaaaa tcctgaggga        750
agttcttaga aaatcaaaag aggaaatatga ccaggaagaa gaaaggaaga       800
ggaaaaaaca gttatcagag gctaaaacag aagagcccac agtgcattcc        850
agtgaagctg caataatgaa taattcccaa ggggatggtg aacattttgc        900
acacccaccc tcagaagtta aaatgcattt tgctaatcag tcaatagaac        950
ctttgggaag aaaagtggaa aggtctgaaa cttcctccct cccacaaaaa       1000
ggcctgaaga ttcctggctt agagcatgcg agcattgaag gaccaatagc       1050
aaacttatca gtacttggaa cagaagaact tcggcaacga gaacactatc       1100
tcaagcagaa gagagataag ttgatgtcca tgagaaagga tatgaggact       1150
aaacagatac aaaatatgga gcagaaagga aacccactg gggaggtaga        1200 ggaaatgaca gagaaaccag aaatgacagc agaggagaag caaacattac       1250
taaagaggag attgcttgca gagaaactca agaagaagt tattaataag        1300
```

```
taataattaa gaacaattta acaaaatgga agttcaaatt gtcttaaaaa    1350
taaattattt agtccttaca ctg                                  1373
```

<210> SEQ ID NO 6
<211> LENGTH: 367
<212> TYPE: PRT
<213> ORGANISM: Homo Sapien

<400> SEQUENCE: 6

```
Met Ala Ala Glu Glu Asp Glu Val Glu Trp Val Val Glu Ser
 1               5                  10                  15

Ile Ala Gly Phe Leu Arg Gly Pro Asp Trp Ser Ile Pro Ile Leu
                20                  25                  30

Asp Phe Val Glu Gln Lys Cys Glu Val Asn Cys Lys Gly Gly His
                35                  40                  45

Val Ile Thr Pro Gly Ser Pro Glu Pro Val Ile Leu Val Ala Cys
                50                  55                  60

Val Pro Leu Val Phe Asp Asp Glu Glu Ser Lys Leu Thr Tyr
                65                  70                  75

Thr Glu Ile His Gln Glu Tyr Lys Glu Leu Val Lys Leu Leu
                80                  85                  90

Glu Gly Tyr Leu Lys Glu Ile Gly Ile Asn Glu Asp Gln Phe Gln
                95                  100                 105

Glu Ala Cys Thr Ser Pro Leu Ala Lys Thr His Thr Ser Gln Ala
                110                 115                 120

Ile Leu Gln Pro Val Leu Ala Ala Glu Asp Phe Thr Ile Phe Lys
                125                 130                 135

Ala Met Met Val Gln Lys Asn Ile Glu Met Gln Leu Gln Ala Ile
                140                 145                 150

Arg Ile Ile Gln Glu Arg Asn Gly Val Leu Pro Asp Cys Leu Thr
                155                 160                 165

Asp Gly Ser Asp Val Val Ser Asp Leu Glu His Glu Glu Met Lys
                170                 175                 180

Ile Leu Arg Glu Val Leu Arg Lys Ser Lys Glu Glu Tyr Asp Gln
                185                 190                 195

Glu Glu Glu Arg Lys Arg Lys Lys Gln Leu Ser Glu Ala Lys Thr
                200                 205                 210

Glu Glu Pro Thr Val His Ser Ser Glu Ala Ala Ile Met Asn Asn
                215                 220                 225

Ser Gln Gly Asp Gly Glu His Phe Ala His Pro Ser Glu Val
                230                 235                 240

Lys Met His Phe Ala Asn Gln Ser Ile Glu Pro Leu Gly Arg Lys
                245                 250                 255

Val Glu Arg Ser Glu Thr Ser Ser Leu Pro Gln Lys Gly Leu Lys
                260                 265                 270

Ile Pro Gly Leu Glu His Ala Ser Ile Glu Gly Pro Ile Ala Asn
                275                 280                 285

Leu Ser Val Leu Gly Thr Glu Glu Leu Arg Gln Arg Glu His Tyr
                290                 295                 300

Leu Lys Gln Lys Arg Asp Lys Leu Met Ser Met Arg Lys Asp Met
                305                 310                 315

Arg Thr Lys Gln Ile Gln Asn Met Glu Gln Lys Gly Lys Pro Thr
                320                 325                 330
```

```
Gly Glu Val Glu Glu Met Thr Glu Lys Pro Glu Met Thr Ala Glu
                335                 340                 345

Glu Lys Gln Thr Leu Leu Lys Arg Arg Leu Leu Ala Glu Lys Leu
                350                 355                 360

Lys Glu Glu Val Ile Asn Lys
                365

<210> SEQ ID NO 7
<211> LENGTH: 932
<212> TYPE: DNA
<213> ORGANISM: Homo Sapien
<220> FEATURE:
<221> NAME/KEY: unsure
<222> LOCATION: 911
<223> OTHER INFORMATION: unknown base

<400> SEQUENCE: 7
gggaacggaa aatggcgcct cacggcccgg gtagtcttac gaccctggtg            50
ccctgggctg ccgccctgct cctcgctctg ggcgtggaaa gggctctggc           100
gctacccgag atatgcaccc aatgtccagg gagcgtgcaa aatttgtcaa           150
aagtggcctt ttattgtaaa acgacacgag agctaatgct gcatgcccgt           200
tgctgcctga atcagaaggg caccatcttg gggctggatc tccagaactg           250
ttctctggag gaccctggtc caaactttca tcaggcacat accactgtca           300
tcatagacct gcaagcaaac cccctcaaag gtgacttggc caacaccttc           350
cgtggcttta ctcagctcca gactctgata ctgccacaac atgtcaactg           400
tcctggagga attaatgcct ggaatactat cacctcttat atagacaacc           450
aaatctgtca agggcaaaag aacctttgca ataacactgg ggacccagaa           500
atgtgtcctg agaatggatc ttgtgtacct gatggtccag gtcttttgca           550
gtgtgtttgt gctgatggtt tccatggata caagtgtatg cgccagggct           600
cgttctcact gcttatgttc ttcgggattc tgggagccac cactctatcc           650
gtctccattc tgctttgggc gacccagcgc cgaaaagcca agacttcatg           700
aactacatag gtcttaccat tgacctaaga tcaatctgaa ctatcttagc           750
ccagtcaggg agctctgctt cctagaaagg catctttcgc cagtggattc           800
gcctcaaggt tgaggccgcc attggaagat gaaaaattgc actcccttgg           850
tgtagacaaa taccagttcc cattggtgtt gttgcctata ataaacactt           900 tttcttttttt naaaaaaaaa aaaaaaaaaa aa                              932

<210> SEQ ID NO 8
<211> LENGTH: 229
<212> TYPE: PRT
<213> ORGANISM: Homo Sapien

<400> SEQUENCE: 8

Met Ala Pro His Gly Pro Gly Ser Leu Thr Thr Leu Val Pro Trp
  1               5                  10                  15

Ala Ala Ala Leu Leu Leu Ala Leu Gly Val Glu Arg Ala Leu Ala
                 20                  25                  30

Leu Pro Glu Ile Cys Thr Gln Cys Pro Gly Ser Val Gln Asn Leu
                 35                  40                  45

Ser Lys Val Ala Phe Tyr Cys Lys Thr Thr Arg Glu Leu Met Leu
                 50                  55                  60
```

-continued

```
His Ala Arg Cys Cys Leu Asn Gln Lys Gly Thr Ile Leu Gly Leu
                65                  70                  75
Asp Leu Gln Asn Cys Ser Leu Glu Asp Pro Gly Pro Asn Phe His
            80                  85                  90
Gln Ala His Thr Thr Val Ile Ile Asp Leu Gln Ala Asn Pro Leu
        95                  100                 105
Lys Gly Asp Leu Ala Asn Thr Phe Arg Gly Phe Thr Gln Leu Gln
    110                 115                 120
Thr Leu Ile Leu Pro Gln His Val Asn Cys Pro Gly Gly Ile Asn
125                 130                 135
Ala Trp Asn Thr Ile Thr Ser Tyr Ile Asp Asn Gln Ile Cys Gln
            140                 145                 150
Gly Gln Lys Asn Leu Cys Asn Asn Thr Gly Asp Pro Glu Met Cys
        155                 160                 165
Pro Glu Asn Gly Ser Cys Val Pro Asp Gly Pro Gly Leu Leu Gln
    170                 175                 180
Cys Val Cys Ala Asp Gly Phe His Gly Tyr Lys Cys Met Arg Gln
185                 190                 195
Gly Ser Phe Ser Leu Leu Met Phe Phe Gly Ile Leu Gly Ala Thr
            200                 205                 210
Thr Leu Ser Val Ser Ile Leu Leu Trp Ala Thr Gln Arg Arg Lys
        215                 220                 225
Ala Lys Thr Ser
```

<210> SEQ ID NO 9
<211> LENGTH: 2482
<212> TYPE: DNA
<213> ORGANISM: Homo Sapien

<400> SEQUENCE: 9

```
gggggagaag gcggccgagc cccagctctc cgagcaccgg gtcggaagcc            50
gcgacccgag ccgcgcagga agctgggacc ggaacctcgg cggacccggc           100
cccacccaac tcacctgcgc aggtcaccag caccctcgga acccagaggc           150
ccgcgctctg aaggtgaccc cctggggag gaaggcgatg gccctgcga             200
ggacgatggc ccgcgcccgc ctcgcccggg ccggcatccc tgccgtcgcc           250
ttgtggcttc tgtgcacgct cggcctccag ggcacccagg ccgggccacc           300
gcccgcgccc cctgggctgc ccgcgggagc cgactgcctg aacagcttta           350
ccgccggggt gcctggcttc gtgctggaca ccaacgcctc ggtcagcaac           400
ggagctacct tcctggagtc ccccaccgtg cgccggggct gggactgcgt           450
gcgcgcctgc tgcaccaccc agaactgcaa cttggcgcta gtggagctgc           500
agcccgaccg cggggaggac gccatcgccg cctgcttcct catcaactgc           550
ctctacgagc agaacttcgt gtgcaagttc gcgcccaggg agggcttcat           600
caactacctc acgagggaag tgtaccgctc ctaccgccag ctgcggaccc           650
agggctttgg agggtctggg atccccaagg cctgggcagg catagacttg           700
aaggtacaac cccaggaacc cctggtgctg aaggatgtgg aaaacacaga           750
ttggcgccta ctgcggggtg acacggatgt cagggtagag aggaaagacc           800
caaaccaggt ggaactgtgg ggactcaagg aaggcaccta cctgttccag           850
ctgacagtga ctagctcaga ccacccagag gacacggcca acgtcacagt           900
```

-continued

| | |
|---|---|
| cactgtgctg tccaccaagc agacagaaga ctactgcctc gcatccaaca | 950 |
| aggtgggtcg ctgccggggc tctttcccac gctggtacta tgaccccacg | 1000 |
| gagcagatct gcaagagttt cgtttatgga ggctgcttgg caacaagaa | 1050 |
| caactacctt cgggaagaag agtgcattct agcctgtcgg ggtgtgcaag | 1100 |
| gtgggccttt gagaggcagc tctgggctc aggcgacttt cccccagggc | 1150 |
| ccctccatgg aaaggcgcca tccagtgtgc tctggcacct gtcagcccac | 1200 |
| ccagttccgc tgcagcaatg gctgctgcat cgacagtttc ctggagtgtg | 1250 |
| acgacacccc caactgcccc gacgcctccg acgaggctgc ctgtgaaaaa | 1300 |
| tacacgagtg gctttgacga gctccagcgc atccatttcc ccagtgacaa | 1350 |
| agggcactgc gtgacctgc cagacacagg actctgcaag gagagcatcc | 1400 |
| cgcgctggta ctacaacccc ttcagcgaac actgcgcccg ctttacctat | 1450 |
| ggtggttgtt atggcaacaa gaacaacttt gaggaagagc agcagtgcct | 1500 |
| cgagtcttgt cgcggcatct ccaagaagga tgtgtttggc ctgaggcggg | 1550 |
| aaatccccat tccagcaca ggctctgtgg agatggctgt cacagtgttc | 1600 |
| ctggtcatct gcattgtggt ggtggtagcc atcttgggtt actgcttctt | 1650 |
| caagaaccag agaaaggact ccacggaca ccaccaccac ccaccaccca | 1700 |
| cccctgccag ctccactgtc tccactaccg aggacacgga gcacctggtc | 1750 |
| tataaccaca ccacccggcc cctctgagcc tgggtctcac cggctctcac | 1800 |
| ctggccctgc ttcctgcttg ccaaggcaga ggcctgggct gggaaaaact | 1850 |
| ttggaaccag actcttgcct gtttcccagg cccactgtgc ctcagagacc | 1900 |
| agggctccag cccctcttgg agaagtctca gctaagctca cgtcctgaga | 1950 |
| aagctcaaag gtttggaagg agcagaaaac ccttgggcca gaagtaccag | 2000 |
| actagatgga cctgcctgca taggagtttg gaggaagttg gagttttgtt | 2050 |
| tcctctgttc aaagctgcct gtccctaccc catggtgcta ggaagaggag | 2100 |
| tggggtggtg tcagaccctg gaggccccaa ccctgtcctc ccgagctcct | 2150 |
| cttccatgct gtgcgcccag ggctgggagg aaggacttcc ctgtgtagtt | 2200 |
| tgtgctgtaa agagttgctt tttgtttatt taatgctgtg gcatgggtga | 2250 |
| agaggagggg aagaggcctg tttggcctct ctgtcctctc ttcctcttcc | 2300 |
| cccaagattg agctctctgc ccttgatcag ccccacctg gcctagacca | 2350 |
| gcagacagag ccaggagagg ctcagctgca ttccgcagcc cccacccca | 2400 |
| aggttctcca acatcacagc ccagcccacc cactgggtaa taaaagtggt | 2450 |
| ttgtggaaaa aaaaaaaaa aaaaaaaaa aa | 2482 |

<210> SEQ ID NO 10
<211> LENGTH: 529
<212> TYPE: PRT
<213> ORGANISM: Homo Sapien

<400> SEQUENCE: 10

Met Ala Pro Ala Arg Thr Met Ala Arg Ala Arg Leu Ala Pro Ala
1               5                   10                  15

Gly Ile Pro Ala Val Ala Leu Trp Leu Leu Cys Thr Leu Gly Leu
                20                  25                  30

Gln Gly Thr Gln Ala Gly Pro Pro Pro Ala Pro Pro Gly Leu Pro

-continued

```
                35                  40                  45
Ala Gly Ala Asp Cys Leu Asn Ser Phe Thr Ala Gly Val Pro Gly
                50                  55                  60
Phe Val Leu Asp Thr Asn Ala Ser Val Ser Asn Gly Ala Thr Phe
                65                  70                  75
Leu Glu Ser Pro Thr Val Arg Arg Gly Trp Asp Cys Val Arg Ala
                80                  85                  90
Cys Cys Thr Thr Gln Asn Cys Asn Leu Ala Leu Val Glu Leu Gln
                95                 100                 105
Pro Asp Arg Gly Glu Asp Ala Ile Ala Ala Cys Phe Leu Ile Asn
               110                 115                 120
Cys Leu Tyr Glu Gln Asn Phe Val Cys Lys Phe Ala Pro Arg Glu
               125                 130                 135
Gly Phe Ile Asn Tyr Leu Thr Arg Glu Val Tyr Arg Ser Tyr Arg
               140                 145                 150
Gln Leu Arg Thr Gln Gly Phe Gly Gly Ser Gly Ile Pro Lys Ala
               155                 160                 165
Trp Ala Gly Ile Asp Leu Lys Val Gln Pro Gln Glu Pro Leu Val
               170                 175                 180
Leu Lys Asp Val Glu Asn Thr Asp Trp Arg Leu Leu Arg Gly Asp
               185                 190                 195
Thr Asp Val Arg Val Glu Arg Lys Asp Pro Asn Gln Val Glu Leu
               200                 205                 210
Trp Gly Leu Lys Glu Gly Thr Tyr Leu Phe Gln Leu Thr Val Thr
               215                 220                 225
Ser Ser Asp His Pro Glu Asp Thr Ala Asn Val Thr Val Thr Val
               230                 235                 240
Leu Ser Thr Lys Gln Thr Glu Asp Tyr Cys Leu Ala Ser Asn Lys
               245                 250                 255
Val Gly Arg Cys Arg Gly Ser Phe Pro Arg Trp Tyr Tyr Asp Pro
               260                 265                 270
Thr Glu Gln Ile Cys Lys Ser Phe Val Tyr Gly Gly Cys Leu Gly
               275                 280                 285
Asn Lys Asn Asn Tyr Leu Arg Glu Glu Cys Ile Leu Ala Cys
               290                 295                 300
Arg Gly Val Gln Gly Gly Pro Leu Arg Gly Ser Ser Gly Ala Gln
               305                 310                 315
Ala Thr Phe Pro Gln Gly Pro Ser Met Glu Arg Arg His Pro Val
               320                 325                 330
Cys Ser Gly Thr Cys Gln Pro Thr Gln Phe Arg Cys Ser Asn Gly
               335                 340                 345
Cys Cys Ile Asp Ser Phe Leu Glu Cys Asp Asp Thr Pro Asn Cys
               350                 355                 360
Pro Asp Ala Ser Asp Glu Ala Ala Cys Glu Lys Tyr Thr Ser Gly
               365                 370                 375
Phe Asp Glu Leu Gln Arg Ile His Phe Pro Ser Asp Lys Gly His
               380                 385                 390
Cys Val Asp Leu Pro Asp Thr Gly Leu Cys Lys Glu Ser Ile Pro
               395                 400                 405
Arg Trp Tyr Tyr Asn Pro Phe Ser Glu His Cys Ala Arg Phe Thr
               410                 415                 420
Tyr Gly Gly Cys Tyr Gly Asn Lys Asn Asn Phe Glu Glu Glu Gln
               425                 430                 435
```

```
Gln Cys Leu Glu Ser Cys Arg Gly Ile Ser Lys Lys Asp Val Phe
            440                 445                 450

Gly Leu Arg Arg Glu Ile Pro Ile Pro Ser Thr Gly Ser Val Glu
            455                 460                 465

Met Ala Val Thr Val Phe Leu Val Ile Cys Ile Val Val Val Val
            470                 475                 480

Ala Ile Leu Gly Tyr Cys Phe Phe Lys Asn Gln Arg Lys Asp Phe
            485                 490                 495

His Gly His His His Pro Pro Pro Thr Pro Ala Ser Ser Thr
            500                 505                 510

Val Ser Thr Thr Glu Asp Thr Glu His Leu Val Tyr Asn His Thr
            515                 520                 525

Thr Arg Pro Leu

<210> SEQ ID NO 11
<211> LENGTH: 1899
<212> TYPE: DNA
<213> ORGANISM: Homo Sapien

<400> SEQUENCE: 11
```

| | | | | | |
|---|---|---|---|---|---|
| gtgctgggct | ttttcagaca | agtgcatctc | ctaaccaggt | cacatttcag | 50 |
| ccgcgaccca | ctctccgcca | gtcaccggag | gcagaccgcg | ggaggagagc | 100 |
| tgaggacagc | cgcgtgcgct | tcgccagcag | cggggtggga | ggaaggacat | 150 |
| taaaatactg | cagaagtcaa | gaccccccca | ggtcgaaccc | agaccacgat | 200 |
| gcgcgccccg | ggctgcgggc | ggctggtgct | gccgctgctg | ctcctggccg | 250 |
| cggcagccct | ggccgaaggc | gacgccaagg | ggctcaagga | gggcgagacc | 300 |
| cccggcaatt | tcatggagga | cgagcaatgg | ctgtcgtcca | tctcgcagta | 350 |
| cagcggcaag | atcaagcact | ggaaccgctt | ccgagacgaa | gtggaggatg | 400 |
| actatatcaa | gagctgggag | gacaatcagc | aaggagatga | agccctggat | 450 |
| accaccaagg | acccctgcca | gaaggtgaag | tgcagccgcc | acaaggtgtg | 500 |
| cattgcccag | ggctaccagc | gggccatgtg | catcagtcgc | aagaagctgg | 550 |
| agcacaggat | caagcagccg | accgtgaaac | tccatggaaa | caaagactcc | 600 |
| atctgcaagc | cctgccacat | ggcccagctt | gcctctgtct | gcggctcaga | 650 |
| tggccacact | tacagctctg | tgtgtaagct | ggagcaacag | gcgtgcctga | 700 |
| gcagcaagca | gctggcggtg | cgatgcgagg | gcccctgccc | ctgccccacg | 750 |
| gagcaggctg | ccacctccac | cgccgatggc | aaaccagaga | cttgcaccgg | 800 |
| tcaggacctg | gctgacctgg | gagatcggct | gcgggactgg | ttccagctcc | 850 |
| ttcatgagaa | ctccaagcag | aatggctcag | ccagcagtgt | agccggcccg | 900 |
| gccagcgggc | tggacaagag | cctgggggcc | agctgcaagg | actccattgg | 950 |
| ctggatgttc | tccaagctgg | acaccagtgc | tgacctcttc | ctggaccaga | 1000 |
| cggagctggc | cgccatcaac | ctggacaagt | acagggtctg | catccgtccc | 1050 |
| ttcttcaact | cctgtgacac | ctacaaggat | ggccgggtct | ctactgctga | 1100 |
| gtggtgcttc | tgcttctgga | gggagaagcc | cccctgcctg | cagagctggg | 1150 |
| agcgcatcca | gatccaggag | gccgccaaga | agaagccagg | catcttcatc | 1200 |
| ccgagctgcg | acgaggatgg | ctactaccgg | aagatgcagt | gtgaccagag | 1250 |

```
cagcggtgac tgctggcgtg tggaccagct gggcctggag ctgactggca        1300
cgcgcacgca tgggagcccc gactgcgatg acatcgtggg cttctcgggg        1350
gactttggaa gcggtgtcgg ctgggaggat gaggaggaga aggagacgga        1400
ggaagcaggc gaggaggccg aggaggagga gggcgaggca ggcgaggctg        1450
acgacggggg ctacatctgg tagacgccct caggagccgg ctgccggggg        1500
ggactcaaca gcagagctct gagcagcagc aggcaacttc gagaacggat        1550
ccagaaatgc agtcagaagg accctgctcc acctgggggg actgggagtg        1600
tgagtgtgca tggcatgtgt gtggcacaga tggctgggac gggtgacagt        1650
gtgagtgcat gtgtgcatgc atgtgtgtat gtgtgtgtgt gtgtggcatg        1700
cgctgacaaa tgtgtccttg atccacactg ctcctggcag agtgagtcac        1750
ccaaaggccc cttcggcctc cttgtagctg ttttctttcc ttttgttgtt        1800
ggttttaaaa tacattcaca cacaaataca aaaaaaaaaa aaaaaaaaaa        1850
aaaaaaaaaa aaaaaaaaaa aaaaaaaaaa aaaaaaaaaa aaaaaaaa         1899
```

<210> SEQ ID NO 12
<211> LENGTH: 424
<212> TYPE: PRT
<213> ORGANISM: Homo Sapien

<400> SEQUENCE: 12

```
Met Arg Ala Pro Gly Cys Gly Arg Leu Val Leu Pro Leu Leu Leu
 1               5                  10                  15

Leu Ala Ala Ala Leu Ala Glu Gly Asp Ala Lys Gly Leu Lys
                20                  25                  30

Glu Gly Glu Thr Pro Gly Asn Phe Met Glu Asp Glu Gln Trp Leu
                35                  40                  45

Ser Ser Ile Ser Gln Tyr Ser Gly Lys Ile Lys His Trp Asn Arg
                50                  55                  60

Phe Arg Asp Glu Val Glu Asp Asp Tyr Ile Lys Ser Trp Glu Asp
                65                  70                  75

Asn Gln Gln Gly Asp Glu Ala Leu Asp Thr Thr Lys Asp Pro Cys
                80                  85                  90

Gln Lys Val Lys Cys Ser Arg His Lys Val Cys Ile Ala Gln Gly
                95                 100                 105

Tyr Gln Arg Ala Met Cys Ile Ser Arg Lys Lys Leu Glu His Arg
               110                 115                 120

Ile Lys Gln Pro Thr Val Lys Leu His Gly Asn Lys Asp Ser Ile
               125                 130                 135

Cys Lys Pro Cys His Met Ala Gln Leu Ala Ser Val Cys Gly Ser
               140                 145                 150

Asp Gly His Thr Tyr Ser Ser Val Cys Lys Leu Glu Gln Gln Ala
               155                 160                 165

Cys Leu Ser Ser Lys Gln Leu Ala Val Arg Cys Glu Gly Pro Cys
               170                 175                 180

Pro Cys Pro Thr Glu Gln Ala Ala Thr Ser Thr Ala Asp Gly Lys
               185                 190                 195

Pro Glu Thr Cys Thr Gly Gln Asp Leu Ala Asp Leu Gly Asp Arg
               200                 205                 210

Leu Arg Asp Trp Phe Gln Leu Leu His Glu Asn Ser Lys Gln Asn
               215                 220                 225
```

-continued

| | | | | | | | | | | | |
|---|---|---|---|---|---|---|---|---|---|---|---|
|Gly|Ser|Ala|Ser|Ser|Val|Ala|Gly|Pro|Ala|Ser|Gly|Leu|Asp|Lys|
| | |230| | | |235| | | |240| |

Ser Leu Gly Ala Ser Cys Lys Asp Ser Ile Gly Trp Met Phe Ser
           245              250              255

Lys Leu Asp Thr Ser Ala Asp Leu Phe Leu Asp Gln Thr Glu Leu
           260              265              270

Ala Ala Ile Asn Leu Asp Lys Tyr Glu Val Cys Ile Arg Pro Phe
           275              280              285

Phe Asn Ser Cys Asp Thr Tyr Lys Asp Gly Arg Val Ser Thr Ala
           290              295              300

Glu Trp Cys Phe Cys Phe Trp Arg Glu Lys Pro Pro Cys Leu Ala
           305              310              315

Glu Leu Glu Arg Ile Gln Ile Gln Glu Ala Ala Lys Lys Lys Pro
           320              325              330

Gly Ile Phe Ile Pro Ser Cys Asp Glu Asp Gly Tyr Tyr Arg Lys
           335              340              345

Met Gln Cys Asp Gln Ser Ser Gly Asp Cys Trp Arg Val Asp Gln
           350              355              360

Leu Gly Leu Glu Leu Thr Gly Thr Arg Thr His Gly Ser Pro Asp
           365              370              375

Cys Asp Asp Ile Val Gly Phe Ser Gly Asp Phe Gly Ser Gly Val
           380              385              390

Gly Trp Glu Asp Glu Glu Lys Glu Thr Glu Glu Ala Gly Glu
           395              400              405

Glu Ala Glu Glu Glu Glu Gly Glu Ala Gly Glu Ala Asp Asp Gly
           410              415              420

Gly Tyr Ile Trp

<210> SEQ ID NO 13
<211> LENGTH: 2680
<212> TYPE: DNA
<213> ORGANISM: Homo Sapien

<400> SEQUENCE: 13

| | |
|---|---|
| tgcggcgacc gtcgtacacc atgggcctcc acctccgccc ctaccgtgtg | 50 |
| gggctgctcc cggatggcct cctgttcctc ttgctgctgc taatgctgct | 100 |
| cgcggaccca cgctcccggg ccggacgtca ccccccagtg gtgctggtcc | 150 |
| ctggtgattt gggtaaccaa ctggaagcca agctggacaa gccgacagtg | 200 |
| gtgcactacc tctgctccaa gaagaccgaa agctacttca caatctggct | 250 |
| gaacctggaa ctgctgctgc tgtcatcat tgactgctgg attgacaata | 300 |
| tcaggctggt ttacaacaaa acatccaggg ccacccagtt tcctgatggt | 350 |
| gtggatgtac gtgtccctgg ctttgggaag accttctcac tggagttcct | 400 |
| ggaccccagc aaaagcagcg tgggttccta tttccacacc atggtggaga | 450 |
| gccttgtggg ctgggctac acacggggtg aggatgtccg aggggctccc | 500 |
| tatgactggc gccgagcccc aaatgaaaac gggccctact tcctggccct | 550 |
| ccgcgagatg atcgaggaga gtaccagct gtatgggggc cccgtggtgc | 600 |
| tggttgccca cagtatgggc aacatgtaca cgctctactt tctgcagcgg | 650 |
| cagccgcagg cctggaagga caagtatatc cgggccttcg tgtcactggg | 700 |
| tgcgccctgg gggggcgtgg ccaagaccct gcgcgtcctg gcttcaggag | 750 |

-continued

| | |
|---|---|
| acaacaaccg gatcccagtc atcgggcccc tgaagatccg ggagcagcag | 800 |
| cggtcagctg tctccaccag ctggctgctg ccctacaact acacatggtc | 850 |
| acctgagaag gtgttcgtgc agacacccac aatcaactac acactgcggg | 900 |
| actaccgcaa gttcttccag gacatcggct ttgaagatgg ctggctcatg | 950 |
| cggcaggaca cagaagggct ggtggaagcc acgatgccac ctggcgtgca | 1000 |
| gctgcactgc ctctatggta ctggcgtccc cacaccagac tccttctact | 1050 |
| atgagagctt ccctgaccgt gaccctaaaa tctgctttgg tgacggcgat | 1100 |
| ggtactgtga acttgaagag tgccctgcag tgccaggcct ggcagagccg | 1150 |
| ccaggagcac caagtgttgc tgcaggagct gccaggcagc gagcacatcg | 1200 |
| agatgctggc caacgccacc accctggcct atctgaaacg tgtgctcctt | 1250 |
| gggccctgac tcctgtgcca caggactcct gtggctcggc cgtggacctg | 1300 |
| ctgttggcct ctgggctgt catggcccac gcgttttgca aagtttgtga | 1350 |
| ctcaccattc aaggccccga gtcttggact gtgaagcatc tgccatgggg | 1400 |
| aagtgctgtt tgttatcctt tctctgtggc agtgaagaag gaagaaatga | 1450 |
| gagtctagac tcaagggaca ctggatggca agaatgctgc tgatggtgga | 1500 |
| actgctgtga ccttaggact ggctccacag ggtggactgg ctgggcccctg | 1550 |
| gtcccagtcc ctgcctgggg ccatgtgtcc ccctattcct gtgggctttt | 1600 |
| catacttgcc tactgggccc tggccccgca gccttcctat gagggatgtt | 1650 |
| actgggctgt ggtcctgtac ccagaggtcc cagggatcgg ctcctggccc | 1700 |
| ctcgggtgac ccttcccaca caccagccac agataggcct gccactggtc | 1750 |
| atgggtagct agagctgctg gcttccctgt ggcttagctg gtggccagcc | 1800 |
| tgactggctt cctgggcgag cctagtagct cctgcaggca ggggcagttt | 1850 |
| gttgcgttct tcgtggttcc caggccctgg gacatctcac tccactccta | 1900 |
| cctcccttac caccaggagc attcaagctc tggattgggc agcagatgtg | 1950 |
| cccccagtcc cgcaggctgt gttccagggg ccctgatttc ctcggatgtg | 2000 |
| ctattggccc caggactgaa gctgcctccc ttcaccctgg gactgtggtt | 2050 |
| ccaaggatga gagcagggt tggagccatg gccttctggg aacctatgga | 2100 |
| gaaagggaat ccaaggaagc agccaaggct gctcgcagct tccctgagct | 2150 |
| gcacctcttg ctaaccccac catcacactg ccaccctgcc ctagggtctc | 2200 |
| actagtacca agtgggtcag cacagggctg aggatggggc tcctatccac | 2250 |
| cctggccagc acccagctta gtgctgggac tagcccagaa acttgaatgg | 2300 |
| gaccctgaga gagccagggg tcccctgagg cccccctagg ggctttctgt | 2350 |
| ctgccccagg gtgctccatg gatctccctg tggcagcagg catggagagt | 2400 |
| cagggctgcc ttcatggcag taggctctaa gtgggtgact ggccacaggc | 2450 |
| cgagaaaagg gtacagcctc taggtgggt tcccaaagac gccttcaggc | 2500 |
| tggactgagc tgctctccca cagggtttct gtgcagctgg attttctctg | 2550 |
| ttgcatacat gcctggcatc tgtctcccct tgttcctgag tggccccaca | 2600 |
| tggggctctg agcaggctgt atctggattc tggcaataaa agtactctgg | 2650 |
| atgctgtaaa aaaaaaaaaa aaaaaaaaa | 2680 |

-continued

```
<210> SEQ ID NO 14
<211> LENGTH: 412
<212> TYPE: PRT
<213> ORGANISM: Homo Sapien

<400> SEQUENCE: 14

Met Gly Leu His Leu Arg Pro Tyr Arg Val Gly Leu Leu Pro Asp
 1               5                  10                  15

Gly Leu Leu Phe Leu Leu Leu Leu Met Leu Leu Ala Asp Pro
                20                  25                  30

Ala Leu Pro Ala Gly Arg His Pro Val Val Leu Val Pro Gly
                35                  40                  45

Asp Leu Gly Asn Gln Leu Glu Ala Lys Leu Asp Lys Pro Thr Val
                50                  55                  60

Val His Tyr Leu Cys Ser Lys Lys Thr Glu Ser Tyr Phe Thr Ile
                65                  70                  75

Trp Leu Asn Leu Glu Leu Leu Leu Pro Val Ile Ile Asp Cys Trp
                80                  85                  90

Ile Asp Asn Ile Arg Leu Val Tyr Asn Lys Thr Ser Arg Ala Thr
                95                  100                 105

Gln Phe Pro Asp Gly Val Asp Val Arg Val Pro Gly Phe Gly Lys
                110                 115                 120

Thr Phe Ser Leu Glu Phe Leu Asp Pro Ser Lys Ser Ser Val Gly
                125                 130                 135

Ser Tyr Phe His Thr Met Val Glu Ser Leu Val Gly Trp Gly Tyr
                140                 145                 150

Thr Arg Gly Glu Asp Val Arg Gly Ala Pro Tyr Asp Trp Arg Arg
                155                 160                 165

Ala Pro Asn Glu Asn Gly Pro Tyr Phe Leu Ala Leu Arg Glu Met
                170                 175                 180

Ile Glu Glu Met Tyr Gln Leu Tyr Gly Gly Pro Val Val Leu Val
                185                 190                 195

Ala His Ser Met Gly Asn Met Tyr Thr Leu Tyr Phe Leu Gln Arg
                200                 205                 210

Gln Pro Gln Ala Trp Lys Asp Lys Tyr Ile Arg Ala Phe Val Ser
                215                 220                 225

Leu Gly Ala Pro Trp Gly Gly Val Ala Lys Thr Leu Arg Val Leu
                230                 235                 240

Ala Ser Gly Asp Asn Asn Arg Ile Pro Val Ile Gly Pro Leu Lys
                245                 250                 255

Ile Arg Glu Gln Gln Arg Ser Ala Val Ser Thr Ser Trp Leu Leu
                260                 265                 270

Pro Tyr Asn Tyr Thr Trp Ser Pro Glu Lys Val Phe Val Gln Thr
                275                 280                 285

Pro Thr Ile Asn Tyr Thr Leu Arg Asp Tyr Arg Lys Phe Phe Gln
                290                 295                 300

Asp Ile Gly Phe Glu Asp Gly Trp Leu Met Arg Gln Asp Thr Glu
                305                 310                 315

Gly Leu Val Glu Ala Thr Met Pro Pro Gly Val Gln Leu His Cys
                320                 325                 330

Leu Tyr Gly Thr Gly Val Pro Thr Pro Asp Ser Phe Tyr Tyr Glu
                335                 340                 345

Ser Phe Pro Asp Arg Asp Pro Lys Ile Cys Phe Gly Asp Gly Asp
                350                 355                 360
```

```
Gly Thr Val Asn Leu Lys Ser Ala Leu Gln Cys Gln Ala Trp Gln
            365                 370                 375
Ser Arg Gln Glu His Gln Val Leu Leu Gln Glu Leu Pro Gly Ser
            380                 385                 390
Glu His Ile Glu Met Leu Ala Asn Ala Thr Thr Leu Ala Tyr Leu
            395                 400                 405
Lys Arg Val Leu Leu Gly Pro
            410

<210> SEQ ID NO 15
<211> LENGTH: 1371
<212> TYPE: DNA
<213> ORGANISM: Homo Sapien

<400> SEQUENCE: 15
cagagcagat aatggcaagc atggctgccg tgctcacctg ggctctggct         50
cttctttcag cgttttcggc cacccaggca cggaaaggct tctgggacta        100
cttcagccag accagcgggg acaaaggcag ggtggagcag atccatcagc        150
agaagatggc tcgcgagccc gcgaccctga agacagcctt gagcaagac         200 ctcaacaata tgaacaagtt cctggaaaag ctgaggcctc tgagtgggag        250
cgaggctcct cggctcccac aggacccggt gggcatgcgg cggcagctgc        300
aggaggagtt ggaggaggtg aaggctcgcc tccagcccta catggcagag        350
gcgcacgagc tggtgggctg gaatttggag ggcttgcggc agcaactgaa        400
gccctacacg atggatctga tggagcaggt ggccctgcgc gtgcaggagc        450
tgcaggagca gttgcgcgtg tgggggaag  acaccaaggc ccagttgctg        500
gggggcgtgg acgaggcttg ggctttgctg cagggactgc agagccgcgt        550
ggtgcaccac accggccgct tcaaagagct cttccaccca tacgccgaga        600
gcctggtgag cggcatcggg cgccacgtgc aggagctgca ccgcagtgtg        650
gctccgcacg ccccgccag ccccgcgcgc tcagtcgct gcgtgcaggt         700 gctctcccgg aagctcacgc tcaaggccaa ggccctgcac gcacgcatcc        750
agcagaacct ggaccagctg cgcgaagagc tcagcagagc cttgcaggc         800 actgggactg aggaagggc cggcccggac ccctagatgc tctccgagga         850
ggtgcgccag cgacttcagg ctttccgcca ggacacctac ctgcagatag        900
ctgccttcac tcgcgccatc gaccaggaga ctgaggaggt ccagcagcag        950
ctggcgccac ctccaccagg ccacagtgcc ttcgccccag agtttcaaca       1000
aacagacagt ggcaaggttc tgagcaagct gcaggcccgt ctggatgacc       1050
tgtgggaaga catcactcac agccttcatg accagggcca cagccatctg       1100
ggggacccct gaggatctac ctgcccaggc ccattcccag cttcttgtct       1150
ggggagcctt ggctctgagc ctctagcatg gttcagtcct tgaaagtggc       1200
ctgttgggtg gagggtggaa ggtcctgtgc aggacaggga ggccaccaaa       1250
ggggctgctg tctcctgcat atccagcctc ctgcgactcc ccaatctgga       1300
tgcattacat tcaccaggct ttgcaaaaaa aaaaaaaaaa aaaaaaaaa        1350 aaaaaaaaaa aaaaaaaaaa a                                     1371

<210> SEQ ID NO 16
<211> LENGTH: 274
```

<212> TYPE: PRT
<213> ORGANISM: Homo Sapien

<400> SEQUENCE: 16

```
Met Ala Ser Met Ala Ala Val Leu Thr Trp Ala Leu Ala Leu Leu
 1               5                  10                  15
Ser Ala Phe Ser Ala Thr Gln Ala Arg Lys Gly Phe Trp Asp Tyr
                20                  25                  30
Phe Ser Gln Thr Ser Gly Asp Lys Gly Arg Val Glu Gln Ile His
                35                  40                  45
Gln Gln Lys Met Ala Arg Glu Pro Ala Thr Leu Lys Asp Ser Leu
                50                  55                  60
Glu Gln Asp Leu Asn Asn Met Asn Lys Phe Leu Glu Lys Leu Arg
                65                  70                  75
Pro Leu Ser Gly Ser Glu Ala Pro Arg Leu Pro Gln Asp Pro Val
                80                  85                  90
Gly Met Arg Arg Gln Leu Gln Glu Glu Leu Glu Val Lys Ala
                95                 100                 105
Arg Leu Gln Pro Tyr Met Ala Glu Ala His Glu Leu Val Gly Trp
               110                 115                 120
Asn Leu Glu Gly Leu Arg Gln Gln Leu Lys Pro Tyr Thr Met Asp
               125                 130                 135
Leu Met Glu Gln Val Ala Leu Arg Val Gln Glu Leu Gln Glu Gln
               140                 145                 150
Leu Arg Val Val Gly Glu Asp Thr Lys Ala Gln Leu Leu Gly Gly
               155                 160                 165
Val Asp Glu Ala Trp Ala Leu Leu Gln Gly Leu Gln Ser Arg Val
               170                 175                 180
Val His His Thr Gly Arg Phe Lys Glu Leu Phe His Pro Tyr Ala
               185                 190                 195
Glu Ser Leu Val Ser Gly Ile Gly Arg His Val Gln Glu Leu His
               200                 205                 210
Arg Ser Val Ala Pro His Ala Pro Ala Ser Pro Ala Arg Leu Ser
               215                 220                 225
Arg Cys Val Gln Val Leu Ser Arg Lys Leu Thr Leu Lys Ala Lys
               230                 235                 240
Ala Leu His Ala Arg Ile Gln Gln Asn Leu Asp Gln Leu Arg Glu
               245                 250                 255
Glu Leu Ser Arg Ala Phe Ala Gly Thr Gly Thr Glu Glu Gly Ala
               260                 265                 270
Gly Pro Asp Pro
```

<210> SEQ ID NO 17
<211> LENGTH: 2854
<212> TYPE: DNA
<213> ORGANISM: Homo Sapien

<400> SEQUENCE: 17

| | |
|---|---|
| ctaagaggac aagatgaggc ccggcctctc atttctccta gcccttctgt | 50 |
| tcttccttgg ccaagctgca ggggatttgg gggatgtggg acctccaatt | 100 |
| cccagccccg gcttcagctc tttcccaggt gttgactcca gctccagctt | 150 |
| cagctccagc tccaggtcgg gctccagctc cagccgcagc ttaggcagcg | 200 |
| gaggttctgt gtcccagttg ttttccaatt tcaccggctc cgtggatgac | 250 |

-continued

```
cgtgggacct gccagtgctc tgtttccctg ccagacacca cctttcccgt         300
ggacagagtg gaacgcttgg aattcacagc tcatgttctt tctcagaagt         350
ttgagaaaga actttctaaa gtgagggaat atgtccaatt aattagtgtg         400
tatgaaaaga aactgttaaa cctaactgtc cgaattgaca tcatggagaa         450
ggataccatt tcttacactg aactggactt cgagctgatc aaggtagaag         500
tgaaggagat ggaaaaactg gtcatacagc tgaaggagag ttttggtgga         550
agctcagaaa ttgttgacca gctggaggtg gagataagaa atatgactct         600
cttggtagag aagcttgaga cactagacaa aaacaatgtc cttgccattc         650
gccgagaaat cgtggctctg aagaccaagc tgaaagagtg tgaggcctct         700
aaagatcaaa acacccctgt cgtccaccct cctcccactc cagggagctg         750
tggtcatggt ggtgtggtga acatcagcaa accgtctgtg gttcagctca         800
actggagagg gttttcttat ctatatggtg cttggggtag ggattactct         850
ccccagcatc caaacaaagg actgtattgg gtggcgccat gaatacaga          900 tgggagactg ttggagtatt atagactgta caacacactg gatgatttgc         950
tattgtatat aaatgctcga gagttgcgga tcacctatgg ccaaggtagt        1000
ggtacagcag tttacaacaa caacatgtac gtcaacatgt acaacaccgg        1050
gaatattgcc agagttaacc tgaccaccaa cacgattgct gtgactcaaa        1100
ctctccctaa tgctgcctat aataaccgct tttcatatgc taatgttgct        1150
tggcaagata ttgactttgc tgtggatgag aatggattgt gggttattta        1200
ttcaactgaa gccagcactg gtaacatggt gattagtaaa ctcaatgaca        1250
ccacacttca ggtgctaaac acttggtata ccaagcagta taaaccatct        1300
gcttctaacg ccttcatggt atgtgggtt ctgtatgcca cccgtactat         1350
gaacaccaga acagaagaga ttttttacta ttatgacaca aacacaggga        1400
aagagggcaa actagacatt gtaatgcata agatgcagga aaaagtgcag        1450
agcattaact ataccccttt tgaccagaaa ctttatgtct ataacgatgg        1500
ttaccttctg aattatgatc tttctgtctt gcagaagccc cagtaagctg        1550
tttaggagtt agggtgaaag agaaaatgtt tgttgaaaaa atagtcttct        1600
ccacttactt agatatctgc agggtgtct aaaagtgtgt tcatttttgca        1650 gcaatgttta ggtgcatagt tctaccacac tagagatcta ggacatttgt        1700
cttgatttgg tgagttctct tgggaatcat ctgcctcttc aggcgcattt        1750
tgcaataaag tctgtctagg gtgggattgt cagaggtcta ggggcactgt        1800
gggcctagtg aagcctactg tgaggaggct tcactagaag ccttaaatta        1850
ggaattaagg aacttaaaac tcagtatggc gtctagggat tctttgtaca        1900
ggaaatattg cccaatgact agtcctcatc catgtagcac cactaattct        1950
tccatgcctg gaagaaacct ggggacttag ttaggtagat taatatctgg        2000
agctcctcga gggaccaaat ctccaacttt ttttcccct cactagcacc         2050 tggaatgatg ctttgtatgt ggcagataag taaatttggc atgcttatat        2100
attctacatc tgtaaagtgc tgagttttat ggagagaggc ttttttatgc        2150
attaaattgt acatggcaaa taaatcccag aaggatctgt agatgaggca        2200
cctgcttttt cttttctctc attgtccacc ttactaaaag tcagtagaat        2250
```

```
cttctacctc ataacttcct tccaaaggca gctcagaaga ttagaaccag         2300
acttactaac caattccacc ccccaccaac cccttctac tgcctacttt          2350 aaaaaaatta atagttttct atggaactga tctaagatta gaaaaattaa        2400
ttttctttaa tttcattatg acttttatt tacatgactc taagactata          2450
agaaaatctg atggcagtga caaagtgcta gcatttattg ttatctaata        2500
aagaccttgg agcatatgtg caacttatga gtgtatcagt tgttgcatgt        2550 aattttgcc tttgtttaag cctggaactt gtaagaaaat gaaaatttaa         2600
tttttttttc taggacgagc tatagaaaag ctattgagag tatctagtta        2650
atcagtgcag tagttggaaa ccttgctggt gtatgtgatg tgcttctgtg        2700
cttttgaatg actttatcat ctagtctttg tctattttc ctttgatgtt         2750 caagtcctag tctataggat tggcagttta aatgctttac tccccctttt        2800
aaaataaatg attaaaatgt gctttgaaaa aaaaaaaaa aaaaaaaaa          2850 aaaa                                                           2854
```

<210> SEQ ID NO 18
<211> LENGTH: 510
<212> TYPE: PRT
<213> ORGANISM: Homo Sapien

<400> SEQUENCE: 18

```
Met Arg Pro Gly Leu Ser Phe Leu Leu Ala Leu Leu Phe Phe Leu
 1               5                  10                  15

Gly Gln Ala Ala Gly Asp Leu Gly Asp Val Gly Pro Pro Ile Pro
                20                  25                  30

Ser Pro Gly Phe Ser Ser Phe Pro Gly Val Asp Ser Ser Ser
                35                  40                  45

Phe Ser Ser Ser Arg Ser Gly Ser Ser Ser Arg Ser Leu
                50                  55                  60

Gly Ser Gly Gly Ser Val Ser Gln Leu Phe Ser Asn Phe Thr Gly
                65                  70                  75

Ser Val Asp Asp Arg Gly Thr Cys Gln Cys Ser Val Ser Leu Pro
                80                  85                  90

Asp Thr Thr Phe Pro Val Asp Arg Val Glu Arg Leu Glu Phe Thr
                95                  100                 105

Ala His Val Leu Ser Gln Lys Phe Glu Lys Glu Leu Ser Lys Val
                110                 115                 120

Arg Glu Tyr Val Gln Leu Ile Ser Val Tyr Glu Lys Lys Leu Leu
                125                 130                 135

Asn Leu Thr Val Arg Ile Asp Ile Met Glu Lys Asp Thr Ile Ser
                140                 145                 150

Tyr Thr Glu Leu Asp Phe Glu Leu Ile Lys Val Glu Val Lys Glu
                155                 160                 165

Met Glu Lys Leu Val Ile Gln Leu Lys Glu Ser Phe Gly Gly Ser
                170                 175                 180

Ser Glu Ile Val Asp Gln Leu Glu Val Glu Ile Arg Asn Met Thr
                185                 190                 195

Leu Leu Val Glu Lys Leu Glu Thr Leu Asp Lys Asn Asn Val Leu
                200                 205                 210

Ala Ile Arg Arg Glu Ile Val Ala Leu Lys Thr Lys Leu Lys Glu
                215                 220                 225
```

-continued

```
Cys Glu Ala Ser Lys Asp Gln Asn Thr Pro Val His Pro Pro
            230                 235                 240

Pro Thr Pro Gly Ser Cys Gly His Gly Gly Val Val Asn Ile Ser
            245                 250                 255

Lys Pro Ser Val Val Gln Leu Asn Trp Arg Gly Phe Ser Tyr Leu
            260                 265                 270

Tyr Gly Ala Trp Gly Arg Asp Tyr Ser Pro Gln His Pro Asn Lys
            275                 280                 285

Gly Leu Tyr Trp Val Ala Pro Leu Asn Thr Asp Gly Arg Leu Leu
            290                 295                 300

Glu Tyr Tyr Arg Leu Tyr Asn Thr Leu Asp Asp Leu Leu Tyr
            305                 310                 315

Ile Asn Ala Arg Glu Leu Arg Ile Thr Tyr Gly Gln Gly Ser Gly
            320                 325                 330

Thr Ala Val Tyr Asn Asn Asn Met Tyr Val Asn Met Tyr Asn Thr
            335                 340                 345

Gly Asn Ile Ala Arg Val Asn Leu Thr Thr Asn Thr Ile Ala Val
            350                 355                 360

Thr Gln Thr Leu Pro Asn Ala Ala Tyr Asn Asn Arg Phe Ser Tyr
            365                 370                 375

Ala Asn Val Ala Trp Gln Asp Ile Asp Phe Ala Val Asp Glu Asn
            380                 385                 390

Gly Leu Trp Val Ile Tyr Ser Thr Glu Ala Ser Thr Gly Asn Met
            395                 400                 405

Val Ile Ser Lys Leu Asn Asp Thr Thr Leu Gln Val Leu Asn Thr
            410                 415                 420

Trp Tyr Thr Lys Gln Tyr Lys Pro Ser Ala Ser Asn Ala Phe Met
            425                 430                 435

Val Cys Gly Val Leu Tyr Ala Thr Arg Thr Met Asn Thr Arg Thr
            440                 445                 450

Glu Glu Ile Phe Tyr Tyr Tyr Asp Thr Asn Thr Gly Lys Glu Gly
            455                 460                 465

Lys Leu Asp Ile Val Met His Lys Met Gln Glu Lys Val Gln Ser
            470                 475                 480

Ile Asn Tyr Asn Pro Phe Asp Gln Lys Leu Tyr Val Tyr Asn Asp
            485                 490                 495

Gly Tyr Leu Leu Asn Tyr Asp Leu Ser Val Leu Gln Lys Pro Gln
            500                 505                 510

<210> SEQ ID NO 19
<211> LENGTH: 663
<212> TYPE: DNA
<213> ORGANISM: Homo Sapien

<400> SEQUENCE: 19
gcaccgcaga cggcgcggat cgcagggagc cggtccgccg ccggaacggg        50
agcctgggtg tgcgtgtgga gtccggactc gtgggagacg atcgcgatga       100
acacggtgct gtcgcgggcg aactcactgt tcgccttctc gctgagcgtg       150
atggcggcgc tcaccttcgg ctgcttcatc accaccgcct tcaaagacag       200
gagcgtcccg gtgcggctgc acgtctcgcg gatcatgcta aaaaatgtag       250
aagatttcac tggacctaga gaagaagtg atctggatt tatcacattt         300 gatataactg ctgatctaga gaatatattt gattggaatg ttaagcagtt       350
```

```
gtttctttat ttatcagcag aatattcaac aaaaaataat gctctgaacc         400
aagttgtcct atgggacaag attgttttga gaggtgataa tccgaagctg         450
ctgctgaaag atatgaaaac aaatatttt ttctttgacg atggaaatgg          500
tctcaaggga acaggaatg tcactttgac cctgtcttgg aacgtcgtac          550
caaatgctgg aattctacct cttgtgacag gatcaggaca cgtatctgtc         600
ccatttccag atacatatga ataacgaag agttattaaa ttattctgaa          650
tttgaaacaa aaa                                                 663
```

```
<210> SEQ ID NO 20
<211> LENGTH: 180
<212> TYPE: PRT
<213> ORGANISM: Homo Sapien

<400> SEQUENCE: 20

Met Asn Thr Val Leu Ser Arg Ala Asn Ser Leu Phe Ala Phe Ser
 1               5                  10                  15

Leu Ser Val Met Ala Ala Leu Thr Phe Gly Cys Phe Ile Thr Thr
                20                  25                  30

Ala Phe Lys Asp Arg Ser Val Pro Val Arg Leu His Val Ser Arg
                35                  40                  45

Ile Met Leu Lys Asn Val Glu Asp Phe Thr Gly Pro Arg Glu Arg
                50                  55                  60

Ser Asp Leu Gly Phe Ile Thr Phe Asp Ile Thr Ala Asp Leu Glu
                65                  70                  75

Asn Ile Phe Asp Trp Asn Val Lys Gln Leu Phe Leu Tyr Leu Ser
                80                  85                  90

Ala Glu Tyr Ser Thr Lys Asn Asn Ala Leu Asn Gln Val Val Leu
                95                 100                 105

Trp Asp Lys Ile Val Leu Arg Gly Asp Asn Pro Lys Leu Leu Leu
               110                 115                 120

Lys Asp Met Lys Thr Lys Tyr Phe Phe Phe Asp Asp Gly Asn Gly
               125                 130                 135

Leu Lys Gly Asn Arg Asn Val Thr Leu Thr Leu Ser Trp Asn Val
               140                 145                 150

Val Pro Asn Ala Gly Ile Leu Pro Leu Val Thr Gly Ser Gly His
               155                 160                 165

Val Ser Val Pro Phe Pro Asp Thr Tyr Glu Ile Thr Lys Ser Tyr
               170                 175                 180
```

```
<210> SEQ ID NO 21
<211> LENGTH: 415
<212> TYPE: DNA
<213> ORGANISM: Homo Sapien

<400> SEQUENCE: 21
aaacttgacg ccatgaagat cccggtcctt cctgccgtgg tgctcctctc          50
cctcctggtg ctccactctg cccagggagc caccctgggt ggtcctgagg         100
aagaaagcac cattgagaat tatgcgtcac gacccgaggc ctttaacacc         150
ccgttcctga acatcgacaa attgcgatct gcgtttaagg ctgatgagtt         200
cctgaactgg cacgccctct ttgagtctat caaaaggaaa cttcctttcc         250
tcaactggga tgcctttcct aagctgaaag gactgaggag cgcaactcct         300
```

```
gatgcccagt gaccatgacc tccactggaa gagggggcta gcgtgagcgc         350
tgattctcaa cctaccataa ctctttcctg cctcaggaac tccaataaaa         400
cattttccat ccaaa                                               415
```

<210> SEQ ID NO 22
<211> LENGTH: 99
<212> TYPE: PRT
<213> ORGANISM: Homo Sapien

<400> SEQUENCE: 22

```
Met Lys Ile Pro Val Leu Pro Ala Val Val Leu Leu Ser Leu Leu
 1               5                  10                  15

Val Leu His Ser Ala Gln Gly Ala Thr Leu Gly Gly Pro Glu Glu
                20                  25                  30

Glu Ser Thr Ile Glu Asn Tyr Ala Ser Arg Pro Glu Ala Phe Asn
                35                  40                  45

Thr Pro Phe Leu Asn Ile Asp Lys Leu Arg Ser Ala Phe Lys Ala
                50                  55                  60

Asp Glu Phe Leu Asn Trp His Ala Leu Phe Glu Ser Ile Lys Arg
                65                  70                  75

Lys Leu Pro Phe Leu Asn Trp Asp Ala Phe Pro Lys Leu Lys Gly
                80                  85                  90

Leu Arg Ser Ala Thr Pro Asp Ala Gln
                95
```

<210> SEQ ID NO 23
<211> LENGTH: 866
<212> TYPE: DNA
<213> ORGANISM: Homo Sapien

<400> SEQUENCE: 23

```
tctcagactc ttggaagggg ctatactaga cacacaaaga cagccccaag          50
aaggacggtg gagtagtgtc ctcgctaaaa gacagtagat atgcaacgcc         100
tcttgctcct gccctttctc ctgctgggaa cagtttctgc tcttcatctg         150
gagaatgatg cccccatct ggagagccta gagacacagg cagacctagg          200
ccaggatctg gatagttcaa aggagcagga gagagacttg gctctgacgg         250
aggaggtgat tcaggcagag ggagaggagg tcaaggcttc tgcctgtcaa         300
gacaactttg aggatgagga agccatggag tcggacccag ctgccttaga         350
caaggacttc cagtgcccca gggaagaaga cattgttgaa gtgcagggaa         400
gtccaaggtg caagacctgc cgctacctat tggtgcggac tcctaaaact         450
tttgcagaag ctcagaatgt ctgcagcaga tgctacggag gcaaccttgt         500
ctctatccat gacttcaact tcaactatcg cattcagtgc tgcactagca         550
cagtcaacca agcccaggtc tggattggag caacctcag gggctggttc          600 ctgtggaagc ggttttgctg gactgatggg agccactgga attttgctta         650
ctggtcccca gggcaacctg ggaatgggca aggctcctgt gtggccctat         700
gcaccaaagg aggttattgg cgacgagctc aatgcgacaa gcaactgccc         750
ttcgtctgct ccttctaagc cagcggcacg gagaccctgc cagcagctcc         800
ctcccgtccc ccaacctctc ctgctcataa atccagactt cccacagcaa         850
aaaaaaaaaa aaaaaa                                              866
```

<210> SEQ ID NO 24
<211> LENGTH: 225
<212> TYPE: PRT
<213> ORGANISM: Homo Sapien

<400> SEQUENCE: 24

Met Gln Arg Leu Leu Leu Pro Phe Leu Leu Leu Gly Thr Val
 1               5                  10                  15

Ser Ala Leu His Leu Glu Asn Asp Ala Pro His Leu Glu Ser Leu
            20                  25                  30

Glu Thr Gln Ala Asp Leu Gly Gln Asp Leu Asp Ser Ser Lys Glu
        35                  40                  45

Gln Glu Arg Asp Leu Ala Leu Thr Glu Val Ile Gln Ala Glu
    50                  55                  60

Gly Glu Glu Val Lys Ala Ser Ala Cys Gln Asp Asn Phe Glu Asp
65                  70                  75

Glu Glu Ala Met Glu Ser Asp Pro Ala Ala Leu Asp Lys Asp Phe
                80                  85                  90

Gln Cys Pro Arg Glu Glu Asp Ile Val Glu Val Gln Gly Ser Pro
            95                  100                 105

Arg Cys Lys Thr Cys Arg Tyr Leu Leu Val Arg Thr Pro Lys Thr
        110                 115                 120

Phe Ala Glu Ala Gln Asn Val Cys Ser Arg Cys Tyr Gly Gly Asn
    125                 130                 135

Leu Val Ser Ile His Asp Phe Asn Phe Asn Tyr Arg Ile Gln Cys
            140                 145                 150

Cys Thr Ser Thr Val Asn Gln Ala Gln Val Trp Ile Gly Gly Asn
                155                 160                 165

Leu Arg Gly Trp Phe Leu Trp Lys Arg Phe Cys Trp Thr Asp Gly
            170                 175                 180

Ser His Trp Asn Phe Ala Tyr Trp Ser Pro Gly Gln Pro Gly Asn
        185                 190                 195

Gly Gln Gly Ser Cys Val Ala Leu Cys Thr Lys Gly Gly Tyr Trp
    200                 205                 210

Arg Arg Ala Gln Cys Asp Lys Gln Leu Pro Phe Val Cys Ser Phe
            215                 220                 225

<210> SEQ ID NO 25
<211> LENGTH: 584
<212> TYPE: DNA
<213> ORGANISM: Homo Sapien

<400> SEQUENCE: 25
caacagaagc caagaaggaa gccgtctatc ttgtggcgat catgtataag        50
ctggcctcct gctgtttgct tttcacagga ttcttaaatc ctctcttatc       100
tcttcctctc cttgactcca gggaaatatc ctttcaactc tcagcacctc       150
atgaagacgc gcgcttaact ccggaggagc tagaaagagc ttcccttcta       200
cagatattgc agagatgct gggtgcagaa agagggata ttctcaggaa         250 agcagactca gtaccaaca tttttaaccc aagaggaaat tgagaaagt         300 ttcaggattt ctctggacaa gatcctaaca ttttactgag tcatcttttg       350
gccagaatct ggaaaccata caagaaacgt gagactcctg attgcttctg       400
gaaatactgt gtctgaagtg aaataagcat ctgttagtca gctcagaaac       450

| | |
|---|---|
| acccatctta gaatatgaaa aataacacaa tgcttgattt gaaaacagtg | 500 |
| tggagaaaaa ctaggcaaac tacaccctgt tcattgttac ctggaaaata | 550 |
| aatcctctat gttttgcaca aaaaaaaaaa aaaa | 584 |

<210> SEQ ID NO 26
<211> LENGTH: 124
<212> TYPE: PRT
<213> ORGANISM: Homo Sapien

<400> SEQUENCE: 26

```
Met Tyr Lys Leu Ala Ser Cys Cys Leu Leu Phe Thr Gly Phe Leu
  1               5                  10                  15

Asn Pro Leu Leu Ser Leu Pro Leu Leu Asp Ser Arg Glu Ile Ser
                 20                  25                  30

Phe Gln Leu Ser Ala Pro His Glu Asp Ala Arg Leu Thr Pro Glu
                 35                  40                  45

Glu Leu Glu Arg Ala Ser Leu Leu Gln Ile Leu Pro Glu Met Leu
                 50                  55                  60

Gly Ala Glu Arg Gly Asp Ile Leu Arg Lys Ala Asp Ser Ser Thr
                 65                  70                  75

Asn Ile Phe Asn Pro Arg Gly Asn Leu Arg Lys Phe Gln Asp Phe
                 80                  85                  90

Ser Gly Gln Asp Pro Asn Ile Leu Leu Ser His Leu Leu Ala Arg
                 95                 100                 105

Ile Trp Lys Pro Tyr Lys Lys Arg Glu Thr Pro Asp Cys Phe Trp
                110                 115                 120

Lys Tyr Cys Val
```

<210> SEQ ID NO 27
<211> LENGTH: 920
<212> TYPE: DNA
<213> ORGANISM: Homo Sapien

<400> SEQUENCE: 27

| | |
|---|---|
| caagtaaatg cagcactagt gggtgggatt gaggtatgcc ctggtgcata | 50 |
| aatagagact cagctgtgct ggcacactca gaagcttgga ccgcatccta | 100 |
| gccgccgact cacacaaggc aggtgggtga ggaaatccag agttgccatg | 150 |
| gagaaaattc cagtgtcagc attcttgctc cttgtggccc tctcctacac | 200 |
| tctggccaga gataccacag tcaaacctgg agccaaaaag gacacaaagg | 250 |
| actctcgacc caaactgccc cagaccctct ccagaggttg gggtgaccaa | 300 |
| ctcatctgga ctcagacata tgaagaagct ctatataaat ccaagacaag | 350 |
| caacaaaccc ttgatgatta ttcatcactt ggatgagtgc ccacacagtc | 400 |
| aagctttaaa gaaagtgttt gctgaaaata agaaatccaa gaaattggca | 450 |
| gagcagtttg tcctcctcaa tctggtttat gaaacaactg acaaacacct | 500 |
| ttctcctgat ggccagtatg tccccaggat tatgtttgtt gacccatctc | 550 |
| tgacagttag agccgatatc actggaagat attcaaatcg tctctatgct | 600 |
| tacgaacctg cagatacagc tctgttgctt gacaacatga gaaagctct | 650 |
| caagttgctg aagactgaat tgtaaagaaa aaaatctcc aagcccttct | 700 |
| gtctgtcagg ccttgagact tgaaaccaga agaagtgtga agagactggc | 750 |
| tagtgtggaa gcatagtgaa cacactgatt aggttatggt ttaatgttac | 800 |

| aacaactatt ttttaagaaa aacaagtttt agaaatttgg tttcaagtgt | 850 |
| --- | --- |
| acatgtgtga aaacaatatt gtatactacc atagtgagcc atgattttct | 900 |
| aaaaaaaaaa ataaatgtta | 920 |

<210> SEQ ID NO 28
<211> LENGTH: 175
<212> TYPE: PRT
<213> ORGANISM: Homo Sapien

<400> SEQUENCE: 28

```
Met Glu Lys Ile Pro Val Ser Ala Phe Leu Leu Val Ala Leu
  1               5                  10                  15
Ser Tyr Thr Leu Ala Arg Asp Thr Thr Val Lys Pro Gly Ala Lys
                 20                  25                  30
Lys Asp Thr Lys Asp Ser Arg Pro Lys Leu Pro Gln Thr Leu Ser
                 35                  40                  45
Arg Gly Trp Gly Asp Gln Leu Ile Trp Thr Gln Thr Tyr Glu Glu
                 50                  55                  60
Ala Leu Tyr Lys Ser Lys Thr Ser Asn Lys Pro Leu Met Ile Ile
                 65                  70                  75
His His Leu Asp Glu Cys Pro His Ser Gln Ala Leu Lys Lys Val
                 80                  85                  90
Phe Ala Glu Asn Lys Glu Ile Gln Lys Leu Ala Glu Gln Phe Val
                 95                  100                 105
Leu Leu Asn Leu Val Tyr Glu Thr Thr Asp Lys His Leu Ser Pro
                 110                 115                 120
Asp Gly Gln Tyr Val Pro Arg Ile Met Phe Val Asp Pro Ser Leu
                 125                 130                 135
Thr Val Arg Ala Asp Ile Thr Gly Arg Tyr Ser Asn Arg Leu Tyr
                 140                 145                 150
Ala Tyr Glu Pro Ala Asp Thr Ala Leu Leu Leu Asp Asn Met Lys
                 155                 160                 165
Lys Ala Leu Lys Leu Leu Lys Thr Glu Leu
                 170                 175
```

<210> SEQ ID NO 29
<211> LENGTH: 1181
<212> TYPE: DNA
<213> ORGANISM: Homo Sapien

<400> SEQUENCE: 29

| aagaccctct ctttcgctgt ttgagagtct ctcggctcaa ggaccgggag | 50 |
| --- | --- |
| gtaagaggtt tgggactgcc ccggcaactc cagggtgtct ggtccacgac | 100 |
| ctatcctagg cgccatgggt gtgataggta tacagctggt tgttaccatg | 150 |
| gtgatggcca gtgtcatgca agagattata cctcactatt ctcttgctcg | 200 |
| atggctactc tgtaatggca gtttgaggtg gtatcaacat cctacagaag | 250 |
| aagaattaag aattcttgca gggaaacaac aaaaagggaa aaccaaaaaa | 300 |
| gataggaaat ataatggtca cattgaaagt aagccattaa ccattccaaa | 350 |
| ggatattgac cttcatctag aaacaaagtc agttacagaa gtggatactt | 400 |
| tagcattgca ttactttcca gaataccagt ggctggtgga tttcacagtg | 450 |
| gctgctacag ttgtgtatct agtaactgaa gtctactaca attttatgaa | 500 |

-continued

```
gcctacacag gaaatgaata tcagcttagt ctggtgccta cttgttttgt        550
cttttgcaat caaagttcta ttttcattaa ctacacacta ttttaaagta        600
gaagatggtg gtgaaagatc tgtttgtgtc acctttggat ttttttttctt       650 tgtcaaagca atggcagtgt tgattgtaac agaaaattat ctggaatttg        700
gacttgaaac agggtttaca aattttttcag acagtgcgat gcagtttctt       750
gaaaagcaag gtttagaatc tcagagtcct gtttcaaaac ttactttcaa        800 attttttcctg gctatttttct gttcattcat tggggctttt ttgacatttc      850
ctggattacg actggctcaa atgcatctgg atgccctgaa tttggcaaca        900
gaaaaaatta cacaaacttt acttcatatc aacttcttgg caccttttatt      950 tatggttttg ctctgggtaa aaccaatcac caaagactac attatgaacc       1000
caccactggg caaagaaatt tccccatctg aagatgaag ataatagtat       1050 ctaactcaca aggttatcat tggaataaat gaaagaacac atgtaatgca       1100
accagctgga attaagtgct taataaatgt tcttttcact gctttgcctc       1150
atcagaatta aaatagaaat acttgactag t                           1181
```

<210> SEQ ID NO 30
<211> LENGTH: 307
<212> TYPE: PRT
<213> ORGANISM: Homo Sapien

<400> SEQUENCE: 30

```
Met Gly Val Ile Gly Ile Gln Leu Val Val Thr Met Val Met Ala
 1               5                  10                  15

Ser Val Met Gln Lys Ile Ile Pro His Tyr Ser Leu Ala Arg Trp
                20                  25                  30

Leu Leu Cys Asn Gly Ser Leu Arg Trp Tyr Gln His Pro Thr Glu
                35                  40                  45

Glu Glu Leu Arg Ile Leu Ala Gly Lys Gln Gln Lys Gly Lys Thr
                50                  55                  60

Lys Lys Asp Arg Lys Tyr Asn Gly His Ile Glu Ser Lys Pro Leu
            65                  70                  75

Thr Ile Pro Lys Asp Ile Asp Leu His Leu Glu Thr Lys Ser Val
            80                  85                  90

Thr Glu Val Asp Thr Leu Ala Leu His Tyr Phe Pro Glu Tyr Gln
            95                 100                 105

Trp Leu Val Asp Phe Thr Val Ala Ala Thr Val Val Tyr Leu Val
           110                 115                 120

Thr Glu Val Tyr Tyr Asn Phe Met Lys Pro Thr Gln Glu Met Asn
           125                 130                 135

Ile Ser Leu Val Trp Cys Leu Leu Val Leu Ser Phe Ala Ile Lys
           140                 145                 150

Val Leu Phe Ser Leu Thr Thr His Tyr Phe Lys Val Glu Asp Gly
           155                 160                 165

Gly Glu Arg Ser Val Cys Val Thr Phe Gly Phe Phe Phe Val
           170                 175                 180

Lys Ala Met Ala Val Leu Ile Val Thr Glu Asn Tyr Leu Glu Phe
           185                 190                 195

Gly Leu Glu Thr Gly Phe Thr Asn Phe Ser Asp Ser Ala Met Gln
           200                 205                 210

Phe Leu Glu Lys Gln Gly Leu Glu Ser Gln Ser Pro Val Ser Lys
```

```
                    215                 220                 225
Leu Thr Phe Lys Phe Phe Leu Ala Ile Phe Cys Ser Phe Ile Gly
                230                 235                 240
Ala Phe Leu Thr Phe Pro Gly Leu Arg Leu Ala Gln Met His Leu
                245                 250                 255
Asp Ala Leu Asn Leu Ala Thr Glu Lys Ile Thr Gln Thr Leu Leu
                260                 265                 270
His Ile Asn Phe Leu Ala Pro Leu Phe Met Val Leu Leu Trp Val
                275                 280                 285
Lys Pro Ile Thr Lys Asp Tyr Ile Met Asn Pro Pro Leu Gly Lys
                290                 295                 300
Glu Ile Ser Pro Ser Gly Arg
                305

<210> SEQ ID NO 31
<211> LENGTH: 513
<212> TYPE: DNA
<213> ORGANISM: Homo Sapien

<400> SEQUENCE: 31
gtagcatagt gtgcagttca ctggaccaaa agctttggct gcacctcttc            50
tggaaagctg gccatggggc tcttcatgat cattgcaatt ctgctgttcc           100
agaaacccac agtaaccgaa caacttaaga gtgctggaa taactatgta            150 caaggacatt gcaggaaaat ctgcagagta atgaagtgc ctgaggcact            200 atgtgaaaat gggagatact gttgcctcaa tatcaaggaa ctggaagcat           250
gtaaaaaaat tacaaagcca cctcgtccaa agccagcaac acttgcactg           300
actcttcaag actatgttac aataatagaa aatttcccaa gcctgaagac           350
acagtctaca taaatcaaat acaatttcgt tttcacttgc ttctcaacct           400
agtctaataa actaaggtga tgagatatac atcttcttcc ttctggtttc           450
ttgatcctta aaatgacctt cgagcatatt ctaataaagt gcattgccag           500
ttaaaaaaaa aaa                                                   513

<210> SEQ ID NO 32
<211> LENGTH: 99
<212> TYPE: PRT
<213> ORGANISM: Homo Sapien

<400> SEQUENCE: 32

Met Gly Leu Phe Met Ile Ile Ala Ile Leu Leu Phe Gln Lys Pro
 1               5                  10                  15
Thr Val Thr Glu Gln Leu Lys Lys Cys Trp Asn Asn Tyr Val Gln
                20                  25                  30
Gly His Cys Arg Lys Ile Cys Arg Val Asn Glu Val Pro Glu Ala
                35                  40                  45
Leu Cys Glu Asn Gly Arg Tyr Cys Cys Leu Asn Ile Lys Glu Leu
                50                  55                  60
Glu Ala Cys Lys Lys Ile Thr Lys Pro Pro Arg Pro Lys Pro Ala
                65                  70                  75
Thr Leu Ala Leu Thr Leu Gln Asp Tyr Val Thr Ile Ile Glu Asn
                80                  85                  90
Phe Pro Ser Leu Lys Thr Gln Ser Thr
                95
```

```
<210> SEQ ID NO 33
<211> LENGTH: 2684
<212> TYPE: DNA
<213> ORGANISM: Homo Sapien
<220> FEATURE:
<221> NAME/KEY: unsure
<222> LOCATION: 2636-2637
<223> OTHER INFORMATION: unknown base

<400> SEQUENCE: 33
```

| | |
|---|---:|
| cggacgcgtg ggcgctgagc cccggaggcc agggcgtccg gggctgcgcc | 50 |
| acttccgagg gccgagcgct gccggtcccg gcggtgcgac acggccggga | 100 |
| ggaggagaac aacgcaaggg gctcaaccgt cggtcgctgg agcccccccc | 150 |
| ggggcgtggc ctcccgcccc ctcagctggg gagggcgggg ctcgctgccc | 200 |
| cctgctgccg actgcgaccc ttacagggga gggagggcgc aggccgcgcg | 250 |
| gagatgagga ggaggctgcg cctacgcagg gacgcattgc tcacgctgct | 300 |
| ccttggcgcc tccctgggcc tcttactcta tgcgcagcgc gacggcgcgg | 350 |
| ccccgacggc gagcgcgccg cgagggcgag ggagggcggc accgaggccc | 400 |
| acccccggac cccgcgcgtt ccagttaccc gacgcgggtg cagccccgcc | 450 |
| ggcctacgaa ggggacacac cggcgccgcc cacgcctacg ggacccttg  | 500 |
| acttcgcccg ctatttgcgc gccaaggacc agcggcggtt tccactgctc | 550 |
| attaaccagc cgcacaagtg ccgcggcgac ggcgcacccg gtggccgccc | 600 |
| ggacctgctt attgctgtca agtcggtggc agaggacttc gagcggcgcc | 650 |
| aagccgtgcg ccagacgtgg ggcgcggagg gtcgcgtgca gggggcgctg | 700 |
| gtgcgccgcg tgttcttgct gggcgtgccc aggggcgcag gctcgggcgg | 750 |
| ggccgacgaa gttggggagg gcgcgcgaac ccactggcgc gccctgctgc | 800 |
| gggccgagag ccttgcgtat gcggacatcc tgctctgggc cttcgacgac | 850 |
| accttttta acctaacgct caaggagatc cactttctag cctgggcctc | 900 |
| agctttctgc cccgacgtgc gcttcgtttt aagggcgac gcagatgtgt  | 950 |
| tcgtgaacgt gggaaatctc ctggagttcc tggcgccgcg ggaccggcg  | 1000 |
| caagacctgc ttgctggtga cgtaattgtg catgcgcggc ccatccgcac | 1050 |
| gcgggctagc aagtactaca tccccgaggc cgtgtacggc ctgccgcct  | 1100 |
| atccggccta cgcgggcggc ggtggctttg tgctttccgg ggccacgctg | 1150 |
| caccgcctgg ctggcgcctg tgcgcaggtc gagctcttcc ccatcgacga | 1200 |
| cgtctttctg ggcatgtgtc tgcagcgcct gcggctcacg cccgagcctc | 1250 |
| accctgcctt ccgcaccttt ggcatccccc agccttcagc cgcgccgcat | 1300 |
| ttgagcacct tcgaccctg cttttaccgt gagctggttg tagtgcacgg  | 1350 |
| gctctcggcc gctgacatct ggcttatgtg gcgcctgctg cacgggccgc | 1400 |
| atgggccagc ctgtgcgcat ccacagcctg tcgctgcagg ccccttccaa | 1450 |
| tgggactcct agctccccac tacagcccca agctcctaac tcagacccag | 1500 |
| aatggagccg gtttcccaga ttattgccgt gtatgtggtt cttccctgat | 1550 |
| caccaggtgc ctgtctccac aggatcccag gggatggggg ttaagcttgg | 1600 |
| ctcctggcgc tccaccctgc tggaaccagt tgaaacccgt gtaatggtga | 1650 |
| cccttttgagc gagccaaggc tgggtggtag atgaccatct cttgtccaac | 1700 |

-continued

| | |
|---|---|
| aggtcccaga gcagtggata tgtctggtcc tcctagtagc acagaggtgt | 1750 |
| gttctggtgt ggtggcaggg acttagggaa tcctaccact ctgctggatt | 1800 |
| tggaaccccc taggctgacg cggacgtatg cagaggctct caaggccagg | 1850 |
| ccccacaggg aggtggaggg gctccggccg ccacagcctg aattcatgaa | 1900 |
| cctggcaggc actttgccat agctcatctg aaaacagata ttatgcttcc | 1950 |
| cacaacctct cctgggccca ggtgtggctg agcaccaggg atggagccac | 2000 |
| acataaggga caaatgagtg cacggtccta cctagtcttt cctcacctcc | 2050 |
| tgaactcaca caacaatgcc agtctcccac tggaggctgt atcccctcag | 2100 |
| aggagccaag gaatgtcttc ccctgagatg ccaccactat taatttcccc | 2150 |
| atatgcttca accaccccct tgctcaaaaa accaataccc acacttacct | 2200 |
| taatacaaac atcccagcaa cagcacatgg caggccattg ctgagggcac | 2250 |
| aggtgcttta ttggagaggg gatgtgggca ggggataagg aaggttcccc | 2300 |
| cattccagga ggatgggaac agtcctggct gcccctgaca gtggggatat | 2350 |
| gcaaggggct ctggccaggc cacagtccaa atgggaagac accagtcagt | 2400 |
| cacaaaagtc gggagcgcca cacaaacctg gctataaggc ccaggaacca | 2450 |
| tataggagcc tgagacaggt cccctgcaca ttcatcatta aactatacag | 2500 |
| gatgaggctg tacatgagtt aattacaaaa gagtcatatt tacaaaaatc | 2550 |
| tgtacacaca tttgaaaaac tcacaaaatt gtcatctatg tatcacaagt | 2600 |
| tgctagaccc aaaatattaa aaatgggata aaattnnttt aaaaaaaaaa | 2650 |
| aaaaaaaaaa aaaaaaaaaa aaaaaaaaaa aaaa | 2684 |

<210> SEQ ID NO 34
<211> LENGTH: 402
<212> TYPE: PRT
<213> ORGANISM: Homo Sapien

<400> SEQUENCE: 34

Met Arg Arg Arg Leu Arg Leu Arg Arg Asp Ala Leu Leu Thr Leu
1               5                   10                  15

Leu Leu Gly Ala Ser Leu Gly Leu Leu Leu Tyr Ala Gln Arg Asp
            20                  25                  30

Gly Ala Ala Pro Thr Ala Ser Ala Pro Arg Gly Arg Gly Arg Ala
            35                  40                  45

Ala Pro Arg Pro Thr Pro Gly Pro Arg Ala Phe Gln Leu Pro Asp
            50                  55                  60

Ala Gly Ala Ala Pro Pro Ala Tyr Glu Gly Asp Thr Pro Ala Pro
            65                  70                  75

Pro Thr Pro Thr Gly Pro Phe Asp Phe Ala Arg Tyr Leu Arg Ala
            80                  85                  90

Lys Asp Gln Arg Arg Phe Pro Leu Leu Ile Asn Gln Pro His Lys
            95                  100                 105

Cys Arg Gly Asp Gly Ala Pro Gly Gly Arg Pro Asp Leu Leu Ile
            110                 115                 120

Ala Val Lys Ser Val Ala Glu Asp Phe Glu Arg Arg Gln Ala Val
            125                 130                 135

Arg Gln Thr Trp Gly Ala Glu Gly Arg Val Gln Gly Ala Leu Val
            140                 145                 150

-continued

```
Arg Arg Val Phe Leu Leu Gly Val Pro Arg Ala Gly Ser Gly
            155                 160                 165
Gly Ala Asp Glu Val Gly Glu Gly Ala Arg Thr His Trp Arg Ala
        170                 175                 180
Leu Leu Arg Ala Glu Ser Leu Ala Tyr Ala Asp Ile Leu Leu Trp
    185                 190                 195
Ala Phe Asp Asp Thr Phe Phe Asn Leu Thr Leu Lys Glu Ile His
200                 205                 210
Phe Leu Ala Trp Ala Ser Ala Phe Cys Pro Asp Val Arg Phe Val
        215                 220                 225
Phe Lys Gly Asp Ala Asp Val Phe Val Asn Val Gly Asn Leu Leu
    230                 235                 240
Glu Phe Leu Ala Pro Arg Asp Pro Ala Gln Asp Leu Leu Ala Gly
245                 250                 255
Asp Val Ile Val His Ala Arg Pro Ile Arg Thr Arg Ala Ser Lys
        260                 265                 270
Tyr Tyr Ile Pro Glu Ala Val Tyr Gly Leu Pro Ala Tyr Pro Ala
    275                 280                 285
Tyr Ala Gly Gly Gly Phe Val Leu Ser Gly Ala Thr Leu His
290                 295                 300
Arg Leu Ala Gly Ala Cys Ala Gln Val Glu Leu Phe Pro Ile Asp
        305                 310                 315
Asp Val Phe Leu Gly Met Cys Leu Gln Arg Leu Arg Leu Thr Pro
    320                 325                 330
Glu Pro His Pro Ala Phe Arg Thr Phe Gly Ile Pro Gln Pro Ser
335                 340                 345
Ala Ala Pro His Leu Ser Thr Phe Asp Pro Cys Phe Tyr Arg Glu
        350                 355                 360
Leu Val Val Val His Gly Leu Ser Ala Ala Asp Ile Trp Leu Met
    365                 370                 375
Trp Arg Leu Leu His Gly Pro His Gly Pro Ala Cys Ala His Pro
380                 385                 390
Gln Pro Val Ala Ala Gly Pro Phe Gln Trp Asp Ser
        395                 400
```

<210> SEQ ID NO 35
<211> LENGTH: 1643
<212> TYPE: DNA
<213> ORGANISM: Homo Sapien

<400> SEQUENCE: 35

| | | |
|---|---|---|
| agcagcctct gcccgacccg gctcgtgcgg accccaggac cgggcgcggg | 50 |
| acgcgtgcgt ccagcctccg gcgctgcgga gacccgcggc tgggtccggg | 100 |
| gaggccccaa acccgccccc gccagaaccc cgccccaaat tcccacctcc | 150 |
| tccagaagcc ccgcccactc ccgagccccg agagctccgc gcacctgggc | 200 |
| gccatccgcc ctggctccgc tgcacgagct ccacgcccgt accccggcgt | 250 |
| cacgctcagc ccgcggtgct cgcacacctg agactcatct cgcttcgacc | 300 |
| ccgccgccgc cgccgcccgg catcctgagc acggagacag tctccagctg | 350 |
| ccgttcatgc ttcctcccca gccttccgca gcccaccagg gaaggggcgg | 400 |
| taggagtggc ctttttaccaa agggaccggc gatgctctgc aggctgtgct | 450 |
| ggctggtctc gtacagcttg gctgtgctgt tgctcggctg cctgctcttc | 500 |

-continued

| | |
|---|---|
| ctgaggaagg cggccaagcc cgcaggagac cccacggccc accagccttt | 550 |
| ctgggctccc ccaacacccc gtcacagccg gtgtccaccc aaccacacag | 600 |
| tgtctagcgc ctctctgtcc ctgcctagcc gtcaccgtct cttcttgacc | 650 |
| tatcgtcact gccgaaattt ctctatcttg ctggagcctt caggctgttc | 700 |
| caaggatacc ttcttgctcc tggccatcaa gtcacagcct ggtcacgtgg | 750 |
| agcgacgtgc ggctatccgc agcacgtggg gcagggtggg gggatgggct | 800 |
| agggggccggc agctgaagct ggtgttcctc ctaggggtgg caggatccgc | 850 |
| tcccccagcc cagctgctgg cctatgagag tagggagttt gatgacatcc | 900 |
| tccagtggga cttcactgag gacttcttca acctgacgct caaggagctg | 950 |
| cacctgcagc gctgggtggt ggctgcctgc cccaggcccc atttcatgct | 1000 |
| aaagggagat gacgatgtct ttgtccacgt ccccaacgtg ttagagttcc | 1050 |
| tggatggctg ggacccagcc caggacctcc tggtgggaga tgtcatccgc | 1100 |
| caagccctgc ccaacaggaa cactaaggtc aaatacttca tcccaccctc | 1150 |
| aatgtacagg gccacccact acccacccta tgctggtggg ggaggatatg | 1200 |
| tcatgtccag agccacagtg cggcgcctcc aggctatcat ggaagatgct | 1250 |
| gaactcttcc ccattgatga tgtctttgtg ggtatgtgcc tgaggaggct | 1300 |
| ggggctgagc cctatgcacc atgctggctt caagacattt ggaatccggc | 1350 |
| ggccctggga ccccttagac ccctgcctgt ataggggggct cctgctggtt | 1400 |
| caccgcctca gccccctcga gatgtggacc atgtgggcac tggtgacaga | 1450 |
| tgagggctc aagtgtgcag ctggccccat accccagcgc tgaagggtgg | 1500 |
| gttgggcaac agcctgagag tggactcagt gttgattctc tatcgtgatg | 1550 |
| cgaaattgat gcctgctgct ctacagaaaa tgccaacttg gttttttaac | 1600 |
| tcctctcacc ctgttagctc tgattaaaaa cactgcaacc caa | 1643 |

<210> SEQ ID NO 36
<211> LENGTH: 378
<212> TYPE: PRT
<213> ORGANISM: Homo Sapien

<400> SEQUENCE: 36

```
Met Leu Pro Pro Gln Pro Ser Ala Ala His Gln Gly Arg Gly Gly
  1               5                  10                  15

Arg Ser Gly Leu Leu Pro Lys Gly Pro Ala Met Leu Cys Arg Leu
                 20                  25                  30

Cys Trp Leu Val Ser Tyr Ser Leu Ala Val Leu Leu Gly Cys
                 35                  40                  45

Leu Leu Phe Leu Arg Lys Ala Ala Lys Pro Ala Gly Asp Pro Thr
                 50                  55                  60

Ala His Gln Pro Phe Trp Ala Pro Pro Thr Pro Arg His Ser Arg
                 65                  70                  75

Cys Pro Pro Asn His Thr Val Ser Ser Ala Ser Leu Ser Leu Pro
                 80                  85                  90

Ser Arg His Arg Leu Phe Leu Thr Tyr Arg His Cys Arg Asn Phe
                 95                 100                 105

Ser Ile Leu Leu Glu Pro Ser Gly Cys Ser Lys Asp Thr Phe Leu
                110                 115                 120

Leu Leu Ala Ile Lys Ser Gln Pro Gly His Val Glu Arg Arg Ala
```

```
                    125                 130                 135
Ala Ile Arg Ser Thr Trp Gly Arg Val Gly Gly Trp Ala Arg Gly
                140                 145                 150

Arg Gln Leu Lys Leu Val Phe Leu Leu Gly Val Ala Gly Ser Ala
            155                 160                 165

Pro Pro Ala Gln Leu Leu Ala Tyr Glu Ser Arg Glu Phe Asp Asp
        170                 175                 180

Ile Leu Gln Trp Asp Phe Thr Glu Asp Phe Asn Leu Thr Leu
    185                 190                 195

Lys Glu Leu His Leu Gln Arg Trp Val Val Ala Ala Cys Pro Gln
            200                 205                 210

Ala His Phe Met Leu Lys Gly Asp Asp Asp Val Phe Val His Val
            215                 220                 225

Pro Asn Val Leu Glu Phe Leu Asp Gly Trp Asp Pro Ala Gln Asp
            230                 235                 240

Leu Leu Val Gly Asp Val Ile Arg Gln Ala Leu Pro Asn Arg Asn
            245                 250                 255

Thr Lys Val Lys Tyr Phe Ile Pro Pro Ser Met Tyr Arg Ala Thr
            260                 265                 270

His Tyr Pro Pro Tyr Ala Gly Gly Gly Gly Tyr Val Met Ser Arg
            275                 280                 285

Ala Thr Val Arg Arg Leu Gln Ala Ile Met Glu Asp Ala Glu Leu
            290                 295                 300

Phe Pro Ile Asp Asp Val Phe Val Gly Met Cys Leu Arg Arg Leu
            305                 310                 315

Gly Leu Ser Pro Met His His Ala Gly Phe Lys Thr Phe Gly Ile
            320                 325                 330

Arg Arg Pro Leu Asp Pro Leu Asp Pro Cys Leu Tyr Arg Gly Leu
            335                 340                 345

Leu Leu Val His Arg Leu Ser Pro Leu Glu Met Trp Thr Met Trp
            350                 355                 360

Ala Leu Val Thr Asp Glu Gly Leu Lys Cys Ala Ala Gly Pro Ile
            365                 370                 375

Pro Gln Arg

<210> SEQ ID NO 37
<211> LENGTH: 1226
<212> TYPE: DNA
<213> ORGANISM: Homo Sapien

<400> SEQUENCE: 37
atgaaagtga taatcaggca gcccaaatga ttgttaataa ggatcaaatg        50
agatcgtgta tgtgggtcca atcaattgat tctacacaaa ggagcctggg       100
gaggggccat ggtgccaatg cacttactgg ggagactgga gaagccgctt       150
ctcctcctgt gctgcgcctc cttcctactg ggctggcttt gctgggcat        200 aaagacggac atcaccccg ttgcttattt ctttctcaca ttgggtggct        250
tcttcttgtt tgcctatctc ctggtccggt ttctggaatg ggggcttcgg       300
tcccagctcc aatcaatgca gactgagagc ccagggccct caggcaatgc       350
acgggacaat gaagcctttg aagtgccagt ctatgaagag gccgtggtgg       400
gactagaatc ccagtgccgc ccccaagagt tggaccaacc accccctac        450 agcactgttg tgataccccc agcacctgag aggaacaac ctagccatcc        500
```

```
agaggggtcc aggagagcca aactggaaca gaggcgaatg gcctcagagg        550
ggtccatggc ccaggaagga agccctggaa gagctccaat caaccttcgg        600
cttcggggac cacgggctgt gtccactgct cctgatctgc agagcttggc        650
ggcagtcccc acattagagc ctctgactcc accccctgcc tatgatgtct        700
gctttggtca ccctgatgat gatagtgttt tttatgagga caactgggca        750
ccccttaaa  tgactctccc aagatttctc ttctctccac accagacctc        800
gttcatttga ctaacatttt ccagcgccta ctatgtgtca gaaacaagtg        850
tttctgcctg gacatcataa atggggactt ggaccctgag gagagtcagg        900
ccacggtaag cccttcccag ctgagatatg ggtggcataa tttgagtctt        950
ctggcaacat ttggtgacct accccatatc caatatttcc agcgttagat       1000
tgaggatgag gtagggaggt gatccagaga aggcggagaa ggaagaagta       1050
acctctgagt ggcggctatt gcttctgttc caggtgctgt tcgagctgtt       1100
agaaccctta ggcttgacag ctttgtgagt tattattgaa aaatgaggat       1150
tccaagagtc agaggagttt gataatgtgc acgagggcac actgctagta       1200
aataacatta aataactgg  aatgaa                                  1226
```

```
<210> SEQ ID NO 38
<211> LENGTH: 216
<212> TYPE: PRT
<213> ORGANISM: Homo Sapien

<400> SEQUENCE: 38

Met Val Pro Met His Leu Leu Gly Arg Leu Glu Lys Pro Leu Leu
1               5                   10                  15

Leu Leu Cys Cys Ala Ser Phe Leu Leu Gly Leu Ala Leu Leu Gly
                20                  25                  30

Ile Lys Thr Asp Ile Thr Pro Val Ala Tyr Phe Phe Leu Thr Leu
            35                  40                  45

Gly Gly Phe Phe Leu Phe Ala Tyr Leu Leu Val Arg Phe Leu Glu
        50                  55                  60

Trp Gly Leu Arg Ser Gln Leu Gln Ser Met Gln Thr Glu Ser Pro
    65                  70                  75

Gly Pro Ser Gly Asn Ala Arg Asp Asn Glu Ala Phe Glu Val Pro
            80                  85                  90

Val Tyr Glu Glu Ala Val Val Gly Leu Glu Ser Gln Cys Arg Pro
        95                  100                 105

Gln Glu Leu Asp Gln Pro Pro Tyr Ser Thr Val Val Ile Pro
    110                 115                 120

Pro Ala Pro Glu Glu Glu Gln Pro Ser His Pro Glu Gly Ser Arg
            125                 130                 135

Arg Ala Lys Leu Glu Gln Arg Arg Met Ala Ser Glu Gly Ser Met
        140                 145                 150

Ala Gln Glu Gly Ser Pro Gly Arg Ala Pro Ile Asn Leu Arg Leu
    155                 160                 165

Arg Gly Pro Arg Ala Val Ser Thr Ala Pro Asp Leu Gln Ser Leu
            170                 175                 180

Ala Ala Val Pro Thr Leu Glu Pro Leu Thr Pro Pro Ala Tyr
        185                 190                 195

Asp Val Cys Phe Gly His Pro Asp Asp Asp Ser Val Phe Tyr Glu
```

|  |  | 200 |  | 205 |  | 210 |  |
|---|---|---|---|---|---|---|---|

Asp Asn Trp Ala Pro Pro
              215

<210> SEQ ID NO 39
<211> LENGTH: 2770
<212> TYPE: DNA
<213> ORGANISM: Homo Sapien

<400> SEQUENCE: 39

| | | | | | |
|---|---|---|---|---|---|
| cccacgcgtc | cggcggctac | acacctaggt | gcggtgggct | tcgggtgggg | 50 |
| ggcctgcagc | tagctgatgg | caagggagga | atagcagggg | tgggggattgt | 100 |
| ggtgtgcgag | aggtcccgcg | gacgggggc | tcgggggtct | cttcagacga | 150 |
| gattcccttc | aggcttgggc | cgggtccctt | cgcacggaga | tcccaatgaa | 200 |
| cgcgggcccc | tggaggccgg | tggttgggc | ttctccgcgt | cggggatggg | 250 |
| gccggtaccc | tagcccgttt | ccagcgcctc | agtcggttcc | ccatgccctc | 300 |
| agaggtggcc | cggggcaagc | gcgccgcct | cttcttcgct | gcggtggcca | 350 |
| tcgtgctggg | gctaccgctc | tggtggaaga | ccacggagac | ctaccgggcc | 400 |
| tcgttgcctt | actcccagat | cagtggcctg | aatgccttc | agctccgcct | 450 |
| catggtgcct | gtcactgtcg | tgtttacgcg | ggagtcagtg | ccctggacg | 500 |
| accaggagaa | gctgcccttc | accgttgtgc | atgaaagaga | gattcctctg | 550 |
| aaatacaaaa | tgaaaatcaa | atgccgtttc | cagaaggcct | atcggagggc | 600 |
| tttggaccat | gaggaggagg | ccctgtcatc | gggcagtgtg | caagaggcag | 650 |
| aagccatgtt | agatgagcct | caggaacaag | cggagggctc | cctgactgtg | 700 |
| tacgtgatat | ctgaacactc | ctcacttctt | ccccaggaca | tgatgagcta | 750 |
| cattgggccc | aagaggacag | cagtggtgcg | ggggataatg | caccgggagg | 800 |
| cctttaacat | cattggccgc | cgcatagtcc | aggtggccca | ggccatgtct | 850 |
| ttgactgagg | atgtgcttgc | tgctgctctg | gctgaccacc | ttccagagga | 900 |
| caagtggagc | gctgagaaga | ggcggcctct | caagtccagc | ttgggctatg | 950 |
| agatcacctt | cagtttactc | aacccagacc | ccaagtccca | tgatgtctac | 1000 |
| tgggacattg | aggggctgt | ccggcgctat | gtgcaacctt | tcctgaatgc | 1050 |
| cctcggtgcc | gctggcaact | tctctgtgga | ctctcagatt | ctttactatg | 1100 |
| caatgttggg | ggtgaatccc | cgctttgact | cagcttcctc | cagctactat | 1150 |
| ttggacatgc | acagcctccc | ccatgtcatc | aacccagtgg | agtcccggct | 1200 |
| gggatccagt | gctgcctcct | tgtaccctgt | gctcaacttt | ctactctacg | 1250 |
| tgcctgagct | tgcacactca | ccgctgtaca | ttcaggacaa | ggatggcgct | 1300 |
| ccagtggcca | ccaatgcctt | ccatagtccc | cgctggggtg | gcattatggt | 1350 |
| atataatgtt | gactccaaaa | cctataatgc | ctcagtgctg | ccagtgagag | 1400 |
| tcgaggtgga | catggtgcga | gtgatggagg | tgttcctggc | acagttgcgg | 1450 |
| ttgctctttg | ggattgctca | gcccagctg | cctccaaaat | gcctgctttc | 1500 |
| agggcctacg | agtgaagggc | taatgacctg | ggagctagac | cggctgctct | 1550 |
| gggctcggtc | agtggagaac | ctggccacag | ccaccaccac | ccttacctcc | 1600 |
| ctggcgcagc | ttctgggcaa | gatcagcaac | attgtcatta | aggacgacgt | 1650 |

-continued

```
ggcatctgag gtgtacaagg ctgtagctgc cgtccagaag tcggcagaag          1700
agttggcgtc tgggcacctg gcatctgcct ttgtcgccag ccaggaagct          1750
gtgacatcct ctgagcttgc cttctttgac ccgtcactcc tccacctcct          1800
ttatttccct gatgaccaga agtttgccat ctacatccca ctcttcctgc          1850
ctatggctgt gcccatcctc ctgtccctgg tcaagatctt cctggagacc          1900
cgcaagtcct ggagaaagcc tgagaagaca gactgagcag ggcagcacct          1950
ccataggaag ccttcctttc tggccaaggt gggcggtgtt agattgtgag          2000
gcacgtacat ggggcctgcc ggaatgactt aaatatttgt ctccagtctc          2050
cactgttggc tctccagcaa ccaaagtaca acactccaag atgggttcat          2100
cttttcttcc tttcccattc acctggctca atcctcctcc accaccaggg          2150
gcctcaaaag gcacatcatc cgggtctcct tatcttgttt gataaggctg          2200
ctgcctgtct ccctctgtgg caaggactgt ttgttctttt gccccatttc          2250
tcaacatagc acattgtgc actgagagga gggagcatta tgggaaagtc           2300
cctgccttcc acacctctct ctagtccctg tgggacagcc ctagcccctg          2350
ctgtcatgaa ggggccaggc attggtcacc tgtgggacct tctccctcac          2400
tcccctccct cctagttggc tttgtctgtc aggtgcagtc tggcgggagt          2450
ccaggaggca gcagctcagg acatggtgct gtgtgtgtgt gtgtgtgtgt          2500
gtgtgtgtgt gtgtgtgtca gaggttccag aaagttccag atttggaatc          2550
aaacagtcct gaattcaaat ccttgttttt gcacttattg tctggagagc          2600
tttggataag gtattgaatc tctctgagcc tcagttttc atttgttcaa           2650 atggcactga tgatgtctcc cttacaagat ggttgtgagg agtaaatgtg          2700
atcagcatgt aaagtgtctg gcgtgtagta ggctcttaat aaacactggc          2750
tgaatatgaa ttggaatgat                                           2770
```

<210> SEQ ID NO 40
<211> LENGTH: 547
<212> TYPE: PRT
<213> ORGANISM: Homo Sapien

<400> SEQUENCE: 40

```
Met Pro Ser Glu Val Ala Arg Gly Lys Arg Ala Ala Leu Phe Phe
  1               5                  10                  15

Ala Ala Val Ala Ile Val Leu Gly Leu Pro Leu Trp Trp Lys Thr
                 20                  25                  30

Thr Glu Thr Tyr Arg Ala Ser Leu Pro Tyr Ser Gln Ile Ser Gly
             35                  40                  45

Leu Asn Ala Leu Gln Leu Arg Leu Met Val Pro Val Thr Val Val
         50                  55                  60

Phe Thr Arg Glu Ser Val Pro Leu Asp Asp Gln Glu Lys Leu Pro
     65                  70                  75

Phe Thr Val Val His Glu Arg Glu Ile Pro Leu Lys Tyr Lys Met
                 80                  85                  90

Lys Ile Lys Cys Arg Phe Gln Lys Ala Tyr Arg Arg Ala Leu Asp
             95                 100                 105

His Glu Glu Glu Ala Leu Ser Ser Gly Ser Val Gln Glu Ala Glu
            110                 115                 120

Ala Met Leu Asp Glu Pro Gln Glu Gln Ala Glu Gly Ser Leu Thr
```

-continued

```
                125                 130                 135
Val Tyr Val Ile Ser Glu His Ser Ser Leu Leu Pro Gln Asp Met
            140                 145                 150
Met Ser Tyr Ile Gly Pro Lys Arg Thr Ala Val Val Arg Gly Ile
            155                 160                 165
Met His Arg Glu Ala Phe Asn Ile Ile Gly Arg Arg Ile Val Gln
            170                 175                 180
Val Ala Gln Ala Met Ser Leu Thr Glu Asp Val Leu Ala Ala Ala
            185                 190                 195
Leu Ala Asp His Leu Pro Glu Asp Lys Trp Ser Ala Glu Lys Arg
            200                 205                 210
Arg Pro Leu Lys Ser Ser Leu Gly Tyr Glu Ile Thr Phe Ser Leu
            215                 220                 225
Leu Asn Pro Asp Pro Lys Ser His Asp Val Tyr Trp Asp Ile Glu
            230                 235                 240
Gly Ala Val Arg Arg Tyr Val Gln Pro Phe Leu Asn Ala Leu Gly
            245                 250                 255
Ala Ala Gly Asn Phe Ser Val Asp Ser Gln Ile Leu Tyr Tyr Ala
            260                 265                 270
Met Leu Gly Val Asn Pro Arg Phe Asp Ser Ala Ser Ser Ser Tyr
            275                 280                 285
Tyr Leu Asp Met His Ser Leu Pro His Val Ile Asn Pro Val Glu
            290                 295                 300
Ser Arg Leu Gly Ser Ser Ala Ala Ser Leu Tyr Pro Val Leu Asn
            305                 310                 315
Phe Leu Leu Tyr Val Pro Glu Leu Ala His Ser Pro Leu Tyr Ile
            320                 325                 330
Gln Asp Lys Asp Gly Ala Pro Val Ala Thr Asn Ala Phe His Ser
            335                 340                 345
Pro Arg Trp Gly Gly Ile Met Val Tyr Asn Val Asp Ser Lys Thr
            350                 355                 360
Tyr Asn Ala Ser Val Leu Pro Val Arg Val Glu Val Asp Met Val
            365                 370                 375
Arg Val Met Glu Val Phe Leu Ala Gln Leu Arg Leu Leu Phe Gly
            380                 385                 390
Ile Ala Gln Pro Gln Leu Pro Pro Lys Cys Leu Leu Ser Gly Pro
            395                 400                 405
Thr Ser Glu Gly Leu Met Thr Trp Glu Leu Asp Arg Leu Leu Trp
            410                 415                 420
Ala Arg Ser Val Glu Asn Leu Ala Thr Ala Thr Thr Thr Leu Thr
            425                 430                 435
Ser Leu Ala Gln Leu Leu Gly Lys Ile Ser Asn Ile Val Ile Lys
            440                 445                 450
Asp Asp Val Ala Ser Glu Val Tyr Lys Ala Val Ala Ala Val Gln
            455                 460                 465
Lys Ser Ala Glu Glu Leu Ala Ser Gly His Leu Ala Ser Ala Phe
            470                 475                 480
Val Ala Ser Gln Glu Ala Val Thr Ser Ser Glu Leu Ala Phe Phe
            485                 490                 495
Asp Pro Ser Leu Leu His Leu Leu Tyr Phe Pro Asp Asp Gln Lys
            500                 505                 510
Phe Ala Ile Tyr Ile Pro Leu Phe Leu Pro Met Ala Val Pro Ile
            515                 520                 525
```

Leu Leu Ser Leu Val Lys Ile Phe Leu Glu Thr Arg Lys Ser Trp
          530                 535                 540

Arg Lys Pro Glu Lys Thr Asp
              545

<210> SEQ ID NO 41
<211> LENGTH: 1964
<212> TYPE: DNA
<213> ORGANISM: Homo Sapien

<400> SEQUENCE: 41

| | |
|---|---:|
| ccagctgcag agaggaggag gtgagctgca gagaagagga ggttggtgtg | 50 |
| gagcacaggc agcaccgagc ctgccccgtg agctgagggc ctgcagtctg | 100 |
| cggctggaat caggatagac accaaggcag accccccaga gatgctgaag | 150 |
| cctctttgga aagcagcagt ggcccccaca tggccatgct ccatgccgcc | 200 |
| ccgccgcccg tgggacagag aggctggcac gttgcaggtc ctgggagcgc | 250 |
| tggctgtgct gtggctgggc tccgtggctc ttatctgcct cctgtggcaa | 300 |
| gtgccccgtc ctcccacctg ggccaggtg cagcccaagg acgtgcccag | 350 |
| gtcctgggag catggctcca gcccagcttg ggagcccctg aagcagagg | 400 |
| ccaggcagca gagggactcc tgccagcttg tccttgtgga aagcatcccc | 450 |
| caggacctgc catctgcagc cggcagcccc tctgcccagc ctctgggcca | 500 |
| ggcctggctg cagctgctgg acactgccca ggagagcgtc cacgtggctt | 550 |
| catactactg gtccctcaca gggcctgaca tcggggtcaa cgactcgtct | 600 |
| tcccagctgg gagaggctct tctgcagaag ctgcagcagc tgctgggcag | 650 |
| gaacatttcc ctggctgtgg ccaccagcag cccgacactg gccaggacat | 700 |
| ccaccgacct gcaggttctg gctgcccgag gtgcccatgt acgacaggtg | 750 |
| cccatggggc ggctcaccag gggtgttttg cactccaaat tctgggttgt | 800 |
| ggatggacgc cacatataca tgggcagtgc caacatggac tggcggtctc | 850 |
| tgacgcaggt gaaggagctt ggcgctgtca tctataactg cagccacctg | 900 |
| gcccaagacc tggagaagac cttccagacc tactgggtac tggggtgcc | 950 |
| caaggctgtc ctccccaaaa cctggcctca gaacttctca tctcacttca | 1000 |
| accgtttcca gccttccac ggcctctttg atggggtgcc caccactgcc | 1050 |
| tacttctcag cgtcgccacc agcactctgt ccccagggcc gcacccggga | 1100 |
| cctggaggcg ctgctggcgg tgatggggag cgcccaggag ttcatctatg | 1150 |
| cctccgtgat ggagtatttc cccaccacgc gcttcagcca ccccccgagg | 1200 |
| tactggccgg tgctggacaa cgcgctgcgg cggcagcct tcggcaaggg | 1250 |
| cgtgcgcgtg cgcctgctgg tcggctgcgg actcaacacg accccacca | 1300 |
| tgttccccta cctgcggtcc ctgcaggcgc tcagcaaccc cgcggccaac | 1350 |
| gtctctgtgg acgtgaaagt cttcatcgtg ccggtgggga accattccaa | 1400 |
| catcccattc agcagggtga accacagcaa gttcatggtc acggagaagg | 1450 |
| cagcctacat aggcacctcc aactggtcgg aggattactt cagcagcacg | 1500 |
| gcggggtgg gcttggtggt cacccagagc cctggcgcgc agcccgcggg | 1550 |
| ggccacggtg caggagcagc tgcggcagct ctttgagcgg gactggagtt | 1600 |

-continued

| | |
|---|---|
| cgcgctacgc cgtcggcctg gacggacagg ctccgggcca ggactgcgtt | 1650 |
| tggcagggct gagggggggcc tcttttttctc tcggcgaccc cgccccgcac | 1700 |
| gcgccctccc ctctgacccc ggcctgggct tcagccgctt cctcccgcaa | 1750 |
| gcagcccggg tccgcactgc gccaggagcc gcctgcgacc gcccgggcgt | 1800 |
| cgcaaaccgc ccgcctgctc tctgatttcc gagtccagcc ccccctgagc | 1850 |
| cccacctcct ccagggagcc ctccaggaag ccccttccct gactcctggc | 1900 |
| ccacaggcca ggcctaaaaa aaactcgtgg cttcaaaaaa aaaaaaaaaa | 1950 |
| aaaaaaaaaa aaaa | 1964 |

<210> SEQ ID NO 42
<211> LENGTH: 489
<212> TYPE: PRT
<213> ORGANISM: Homo Sapien

<400> SEQUENCE: 42

Met Pro Pro Arg Arg Pro Trp Asp Arg Glu Ala Gly Thr Leu Gln
 1               5                  10                  15

Val Leu Gly Ala Leu Ala Val Leu Trp Leu Gly Ser Val Ala Leu
                20                  25                  30

Ile Cys Leu Leu Trp Gln Val Pro Arg Pro Thr Trp Gly Gln
                35                  40                  45

Val Gln Pro Lys Asp Val Pro Arg Ser Trp Glu His Gly Ser Ser
                50                  55                  60

Pro Ala Trp Glu Pro Leu Glu Ala Glu Ala Arg Gln Gln Arg Asp
                65                  70                  75

Ser Cys Gln Leu Val Leu Val Glu Ser Ile Pro Gln Asp Leu Pro
                80                  85                  90

Ser Ala Ala Gly Ser Pro Ser Ala Gln Pro Leu Gly Gln Ala Trp
                95                 100                 105

Leu Gln Leu Leu Asp Thr Ala Gln Glu Ser Val His Val Ala Ser
               110                 115                 120

Tyr Tyr Trp Ser Leu Thr Gly Pro Asp Ile Gly Val Asn Asp Ser
               125                 130                 135

Ser Ser Gln Leu Gly Glu Ala Leu Leu Gln Lys Leu Gln Gln Leu
               140                 145                 150

Leu Gly Arg Asn Ile Ser Leu Ala Val Ala Thr Ser Ser Pro Thr
               155                 160                 165

Leu Ala Arg Thr Ser Thr Asp Leu Gln Val Leu Ala Ala Arg Gly
               170                 175                 180

Ala His Val Arg Gln Val Pro Met Gly Arg Leu Thr Arg Gly Val
               185                 190                 195

Leu His Ser Lys Phe Trp Val Val Asp Gly Arg His Ile Tyr Met
               200                 205                 210

Gly Ser Ala Asn Met Asp Trp Arg Ser Leu Thr Gln Val Lys Glu
               215                 220                 225

Leu Gly Ala Val Ile Tyr Asn Cys Ser His Leu Ala Gln Asp Leu
               230                 235                 240

Glu Lys Thr Phe Gln Thr Tyr Trp Val Leu Gly Val Pro Lys Ala
               245                 250                 255

Val Leu Pro Lys Thr Trp Pro Gln Asn Phe Ser Ser His Phe Asn
               260                 265                 270

Arg Phe Gln Pro Phe His Gly Leu Phe Asp Gly Val Pro Thr Thr

```
                   275                 280                 285
Ala Tyr Phe Ser Ala Ser Pro Pro Ala Leu Cys Pro Gln Gly Arg
               290                 295                 300
Thr Arg Asp Leu Glu Ala Leu Leu Ala Val Met Gly Ser Ala Gln
               305                 310                 315
Glu Phe Ile Tyr Ala Ser Val Met Glu Tyr Phe Pro Thr Thr Arg
               320                 325                 330
Phe Ser His Pro Pro Arg Tyr Trp Pro Val Leu Asp Asn Ala Leu
               335                 340                 345
Arg Ala Ala Ala Phe Gly Lys Gly Val Arg Val Arg Leu Leu Val
               350                 355                 360
Gly Cys Gly Leu Asn Thr Asp Pro Thr Met Phe Pro Tyr Leu Arg
               365                 370                 375
Ser Leu Gln Ala Leu Ser Asn Pro Ala Ala Asn Val Ser Val Asp
               380                 385                 390
Val Lys Val Phe Ile Val Pro Val Gly Asn His Ser Asn Ile Pro
               395                 400                 405
Phe Ser Arg Val Asn His Ser Lys Phe Met Val Thr Glu Lys Ala
               410                 415                 420
Ala Tyr Ile Gly Thr Ser Asn Trp Ser Glu Asp Tyr Phe Ser Ser
               425                 430                 435
Thr Ala Gly Val Gly Leu Val Val Thr Gln Ser Pro Gly Ala Gln
               440                 445                 450
Pro Ala Gly Ala Thr Val Gln Glu Gln Leu Arg Gln Leu Phe Glu
               455                 460                 465
Arg Asp Trp Ser Ser Arg Tyr Ala Val Gly Leu Asp Gly Gln Ala
               470                 475                 480
Pro Gly Gln Asp Cys Val Trp Gln Gly
               485

<210> SEQ ID NO 43
<211> LENGTH: 1130
<212> TYPE: DNA
<213> ORGANISM: Homo Sapien

<400> SEQUENCE: 43
gggcctggcg atccggatcc cgcaggcgcg ctggctgcgc tgcccggctg          50
tctgtcgtca tggtggggcc ctgggtgtat ctggtggcgg cagttttgct         100
catcggcctg atcctcttcc tgactcgcag ccggggtcgg gcggcagcag         150
ctgacggaga accactgcac aatgaggaag agagggcagg agcaggccag         200
gtaggccgct ctttgcccca ggagtctgaa gaacagagaa ctggaagcag         250
accccggcgt cggagggact tgggcagccg tctacaggcc cagcgtcgag         300
cccagcgagt ggcctgggaa gacggggatg agaatgtggg tcaaactgtt         350
attccagccc aggaggaaga aggcattgag aagccagcag aagttcaccc         400
aacagggaaa attggagcca agaaactacg gaagctagag aaaaacagg          450 ctcgaaaggc tcagcgagag gcagaggagg ctgaacgtga agaacggaaa         500
cgcctagagt cccaacgtga ggccgaatgg aagaaggaag aggaacggct         550
tcgcctgaag gaagaacaga aggaggagga agagaggaag gctcaggagg         600
agcaggcccg gcgggatcac gaggagtacc tgaaactgaa ggaggccttc         650
gtggtagaag aagaaggtgt tagcgaaacc atgactgagg agcagtctca         700
```

|  |  |
|---|---|
| cagcttcctg acagaattca tcaattacat caagaagtcc aaggttgtgc | 750 |
| ttttggaaga tctggctttc cagatgggcc taaggactca ggacgccata | 800 |
| aaccgcatcc aggacctgct gacggagggg actctaacag gtgtgattga | 850 |
| cgaccggggc aagtttatct acataacccc agaggaactg gctgccgtgg | 900 |
| ccaatttcat ccgacagcgg ggccgggtgt ccatcacaga gcttgcccag | 950 |
| gccagcaact ccctcatctc ctggggccag gacctccctg cccaggcttc | 1000 |
| agcctgactc cagtccttcc ttgagtgtat cctgtggcct acatgtgtct | 1050 |
| tcatccttcc ctaatgccgt cttggggcag ggatggaata tgaccagaaa | 1100 |
| gttgtggatt aaaggcctgt gaatactgaa | 1130 |

<210> SEQ ID NO 44
<211> LENGTH: 315
<212> TYPE: PRT
<213> ORGANISM: Homo Sapien

<400> SEQUENCE: 44

Met Val Gly Pro Trp Val Tyr Leu Val Ala Ala Val Leu Leu Ile
 1               5                  10                  15

Gly Leu Ile Leu Phe Leu Thr Arg Ser Arg Gly Arg Ala Ala Ala
                20                  25                  30

Ala Asp Gly Glu Pro Leu His Asn Glu Glu Arg Ala Gly Ala
                35                  40                  45

Gly Gln Val Gly Arg Ser Leu Pro Gln Glu Ser Glu Gln Arg
                50                  55                  60

Thr Gly Ser Arg Pro Arg Arg Arg Asp Leu Gly Ser Arg Leu
                65                  70                  75

Gln Ala Gln Arg Arg Ala Gln Arg Val Ala Trp Glu Asp Gly Asp
                80                  85                  90

Glu Asn Val Gly Gln Thr Val Ile Pro Ala Gln Glu Glu Gly
                95                 100                 105

Ile Glu Lys Pro Ala Glu Val His Pro Thr Gly Lys Ile Gly Ala
               110                 115                 120

Lys Lys Leu Arg Lys Leu Glu Glu Lys Gln Ala Arg Lys Ala Gln
               125                 130                 135

Arg Glu Ala Glu Glu Ala Glu Arg Glu Lys Arg Leu Glu
               140                 145                 150

Ser Gln Arg Glu Ala Glu Trp Lys Lys Glu Glu Arg Leu Arg
               155                 160                 165

Leu Lys Glu Glu Gln Lys Glu Glu Glu Arg Lys Ala Gln Glu
               170                 175                 180

Glu Gln Ala Arg Arg Asp His Glu Glu Tyr Leu Lys Leu Lys Glu
               185                 190                 195

Ala Phe Val Val Glu Glu Gly Val Ser Glu Thr Met Thr Glu
               200                 205                 210

Glu Gln Ser His Ser Phe Leu Thr Glu Phe Ile Asn Tyr Ile Lys
               215                 220                 225

Lys Ser Lys Val Val Leu Leu Glu Asp Leu Ala Phe Gln Met Gly
               230                 235                 240

Leu Arg Thr Gln Asp Ala Ile Asn Arg Ile Gln Asp Leu Leu Thr
               245                 250                 255

Glu Gly Thr Leu Thr Gly Val Ile Asp Asp Arg Gly Lys Phe Ile

|  |  |  |  |  |  |
|---|---|---|---|---|---|
| | | 260 | | 265 | 270 |
| Tyr | Ile | Thr | Pro | Glu | Glu | Leu | Ala | Ala | Val | Ala | Asn | Phe | Ile | Arg |
| | | 275 | | 280 | 285 |
| Gln | Arg | Gly | Arg | Val | Ser | Ile | Thr | Glu | Leu | Ala | Gln | Ala | Ser | Asn |
| | | 290 | | 295 | 300 |
| Ser | Leu | Ile | Ser | Trp | Gly | Gln | Asp | Leu | Pro | Ala | Gln | Ala | Ser | Ala |
| | | 305 | | 310 | 315 |

<210> SEQ ID NO 45
<211> LENGTH: 1977
<212> TYPE: DNA
<213> ORGANISM: Homo Sapien

<400> SEQUENCE: 45

| | |
|---|---|
| acgggccgca gcggcagtga cgtagggttg gcgcacggat ccgttgcggc | 50 |
| tgcagctctg cagtcgggcc gttccttcgc cgccgccagg ggtagcggtg | 100 |
| tagctgcgca gcgtcgcgcg cgctaccgca cccaggttcg gcccgtaggc | 150 |
| gtctggcagc ccggcgccat cttcatcgag cgccatggcc gcagcctgcg | 200 |
| ggccgggagc ggccgggtac tgcttgctcc tcggcttgca tttgtttctg | 250 |
| ctgaccgcgg gccctgccct gggctggaac gaccctgaca gaatgttgct | 300 |
| gcgggatgta aaagctctta ccctccacta tgaccgctat accacctccc | 350 |
| gcaggctgga tcccatccca cagttgaaat gtgttggagg cacagctggt | 400 |
| tgtgattctt ataccccaaa agtcatacag tgtcagaaca aaggctggga | 450 |
| tgggtatgat gtacagtggg aatgtaagac ggacttagat attgcataca | 500 |
| aatttggaaa aactgtggtg agctgtgaag gctatgagtc ctctgaagac | 550 |
| cagtatgtac taagaggttc ttgtggcttg gagtataatt tagattatac | 600 |
| agaacttggc ctgcagaaac tgaaggagtc tggaaagcag cacggctttg | 650 |
| cctctttctc tgattattat tataagtggt cctcggcgga ttcctgtaac | 700 |
| atgagtggat tgattaccat cgtggtactc cttgggatcg cctttgtagt | 750 |
| ctataagctg ttcctgagtg acgggcagta ttctcctcca ccgtactctg | 800 |
| agtatcctcc attttcccac cgttaccaga gattcaccaa ctcagcagga | 850 |
| cctcctcccc caggctttaa gtctgagttc acaggaccac agaatactgg | 900 |
| ccatggtgca acttctggtt ttggcagtgc ttttacagga caacaaggat | 950 |
| atgaaaattc aggaccaggg ttctggacag gcttgggaac tggtggaata | 1000 |
| ctaggatatt tgtttggcag caatagagcg gcaacaccct tctcagactc | 1050 |
| gtggtactac ccgtcctatc ctcctcctcta ccctggcacg tggaataggg | 1100 |
| cttactcacc ccttcatgga ggctcgggca gctattcggt atgttcaaac | 1150 |
| tcagacacga aaccagaac tgcatcagga tatggtggta ccaggagacg | 1200 |
| ataaagtaga aagttggagt caaacactgg atgcagaaat tttggatttt | 1250 |
| tcatcacttt ctctttagaa aaaaagtact acctgttaac aattgggaaa | 1300 |
| agggatatt caaagttcct gtggtgttat gtccagtgta gctttttgta | 1350 |
| ttctattatt tgaggctaaa agttgatgtg tgacaaaata cttatgtgtt | 1400 |
| gtatgtcagt gtaacatgca gatgtatatt gcagttttg aaagtgatca | 1450 |
| ttactgtgga atgctaaaaa tacattaatt tctaaaacct gtgatgccct | 1500 |

-continued

```
aagaagcatt aagaatgaag gtgttgtact aatagaaact aagtacagaa       1550
aatttcagtt ttaggtggtt gtagctgatg agttattacc tcatagagac       1600
tataatattc tatttggtat tatattattt gatgtttgct gttcttcaaa       1650
catttaaatc aagctttgga ctaattatgc taatttgtga gttctgatca       1700
cttttgagct ctgaagcttt gaatcattca gtggtggaga tggccttctg       1750
gtaactgaat attaccttct gtaggaaaag gtggaaaata agcatctaga       1800
aggttgttgt gaatgactct gtgctggcaa aaatgcttga aacctctata       1850
tttctttcgt tcataagagg taaggtcaa attttcaac aaaagtcttt         1900 taataacaaa agcatgcagt tctctgtgaa atctcaaata ttgttgtaat       1950
agtctgtttc aatcttaaaa agaatca                                1977
```

<210> SEQ ID NO 46
<211> LENGTH: 339
<212> TYPE: PRT
<213> ORGANISM: Homo Sapien

<400> SEQUENCE: 46

```
Met Ala Ala Ala Cys Gly Pro Gly Ala Ala Gly Tyr Cys Leu Leu
 1               5                  10                  15

Leu Gly Leu His Leu Phe Leu Leu Thr Ala Gly Pro Ala Leu Gly
                20                  25                  30

Trp Asn Asp Pro Asp Arg Met Leu Leu Arg Asp Val Lys Ala Leu
                35                  40                  45

Thr Leu His Tyr Asp Arg Tyr Thr Thr Ser Arg Arg Leu Asp Pro
                50                  55                  60

Ile Pro Gln Leu Lys Cys Val Gly Gly Thr Ala Gly Cys Asp Ser
                65                  70                  75

Tyr Thr Pro Lys Val Ile Gln Cys Gln Asn Lys Gly Trp Asp Gly
                80                  85                  90

Tyr Asp Val Gln Trp Glu Cys Lys Thr Asp Leu Asp Ile Ala Tyr
                95                 100                 105

Lys Phe Gly Lys Thr Val Val Ser Cys Glu Gly Tyr Glu Ser Ser
               110                 115                 120

Glu Asp Gln Tyr Val Leu Arg Gly Ser Cys Gly Leu Glu Tyr Asn
               125                 130                 135

Leu Asp Tyr Thr Glu Leu Gly Leu Gln Lys Leu Lys Glu Ser Gly
               140                 145                 150

Lys Gln His Gly Phe Ala Ser Phe Ser Asp Tyr Tyr Lys Trp
               155                 160                 165

Ser Ser Ala Asp Ser Cys Asn Met Ser Gly Leu Ile Thr Ile Val
               170                 175                 180

Val Leu Leu Gly Ile Ala Phe Val Val Tyr Lys Leu Phe Leu Ser
               185                 190                 195

Asp Gly Gln Tyr Ser Pro Pro Tyr Ser Glu Tyr Pro Pro Phe
               200                 205                 210

Ser His Arg Tyr Gln Arg Phe Thr Asn Ser Ala Gly Pro Pro Pro
               215                 220                 225

Pro Gly Phe Lys Ser Glu Phe Thr Gly Pro Gln Asn Thr Gly His
               230                 235                 240

Gly Ala Thr Ser Gly Phe Gly Ser Ala Phe Thr Gly Gln Gln Gly
               245                 250                 255
```

```
Tyr Glu Asn Ser Gly Pro Gly Phe Trp Thr Gly Leu Gly Thr Gly
            260                 265                 270

Gly Ile Leu Gly Tyr Leu Phe Gly Ser Asn Arg Ala Ala Thr Pro
            275                 280                 285

Phe Ser Asp Ser Trp Tyr Tyr Pro Ser Tyr Pro Ser Tyr Pro
            290                 295                 300

Gly Thr Trp Asn Arg Ala Tyr Ser Pro Leu His Gly Gly Ser Gly
            305                 310                 315

Ser Tyr Ser Val Cys Ser Asn Ser Asp Thr Lys Thr Arg Thr Ala
            320                 325                 330

Ser Gly Tyr Gly Gly Thr Arg Arg Arg
            335

<210> SEQ ID NO 47
<211> LENGTH: 1766
<212> TYPE: DNA
<213> ORGANISM: Homo Sapien

<400> SEQUENCE: 47
```

| | | | | |
|---|---|---|---|---|
| cccggagccg | gggagggagg | gagcgaggtt | cggacaccgg | cggcggctgc | 50 |
| ctggcctttc | catgagcccg | cggcggaccc | tcccgcgccc | cctctcgctc | 100 |
| tgcctctccc | tctgcctctg | cctctgcctg | gccgcggctc | tgggaagtgc | 150 |
| gcagtccggg | tcgtgtaggg | ataaaaagaa | ctgtaaggtg | gtcttttccc | 200 |
| agcaggaact | gaggaagcgg | ctaacacccc | tgcagtacca | tgtcactcag | 250 |
| gagaaaggga | ccgaaagtgc | ctttgaagga | gaatacacac | atcacaaaga | 300 |
| tcctggaata | tataaatgtg | ttgtttgtgg | aactccattg | tttaagtcag | 350 |
| aaaccaaatt | tgactccggt | tcaggttggc | cttcattcca | cgatgtgatc | 400 |
| aattctgagg | caatcacatt | cacagatgac | ttttcctatg | ggatgcacag | 450 |
| ggtggaaaca | agctgctctc | agtgtggtgc | tcaccttggg | cacattttg | 500 |
| atgatgggcc | tcgtccaact | gggaaaagat | actgcataaa | ttcggctgcc | 550 |
| ttgtctttta | cacctgcgga | tagcagtggc | accgccgagg | gaggcagtgg | 600 |
| ggtcgccagc | ccggcccagg | cagacaaagc | ggagctctag | agtaatggag | 650 |
| agtgatggaa | acaaagtgta | cttaatgcac | agcttattaa | aaaaatcaaa | 700 |
| attgttatct | taatagatat | attttttcaa | aaactataag | ggcagttttg | 750 |
| tgctattgat | atttttttctt | cttttgctta | aacagaagcc | ctggccatcc | 800 |
| atgtattttg | caattgacta | gatcaagaac | tgtttatagc | tttagcaaat | 850 |
| ggagacagct | ttgtgaaact | tcttcacaag | ccacttatac | cctttggcat | 900 |
| tcttttcttt | gagcacatgg | cttcttttgc | agttttttccc | cctttgattc | 950 |
| agaagcagag | ggttcatggt | cttcaaacat | gaaaatagag | atctcctctg | 1000 |
| cagtgtagag | accagagctg | ggcagtgcag | ggcatggaga | cctgcaagac | 1050 |
| acatggcctt | gaggcctttg | cacagaccca | cctaagataa | ggttggagtg | 1100 |
| atgttttaat | gagactgttc | agctttgtgg | aaagtttgag | ctaaggtcat | 1150 |
| tttttttttt | ctcactgaaa | gggtgtgaag | gtctaaagtc | tttccttatg | 1200 |
| ttaaattgtt | gccagatcca | aaggggcata | ctgagtgttg | tggcagagaa | 1250 |
| gtaaacatta | ccacactgtt | aggcctttat | tttatttttat | tttccatcga | 1300 |
| aagcattgga | ggcccagtgc | aatggctcac | gcctgtgatc | ccagcacttt | 1350 |

| | |
|---|---|
| gggaggccaa ggcgggtgga tcacgaggtc aggagatgga gaccatcctg | 1400 |
| gctaacatgg tgaaacccocg tctctactaa aaatacgaaa aattagccag | 1450 |
| gcgtggtggt gggcacctgt agtcccagct actcaggagg ctgaggcagg | 1500 |
| agaatggcgt gaacccggaa ggcggagctt gcagttagcc gagatcatgc | 1550 |
| cactgcactc cagcctacat gacaatgtga cactccatct caaaaaataa | 1600 |
| taataataac aatataagaa ctagctgggc atggtggcgc atgcatgtag | 1650 |
| tcccagctac tcctgaggct cagtcaggag aatcgcttga acttgggagg | 1700 |
| cggaggttgc agtgagctga gctcatacca ctgcactcca gcctgaacag | 1750 |
| agtgagatcc tgtcaa | 1766 |

<210> SEQ ID NO 48
<211> LENGTH: 192
<212> TYPE: PRT
<213> ORGANISM: Homo Sapien

<400> SEQUENCE: 48

```
Met Ser Pro Arg Arg Thr Leu Pro Arg Pro Leu Ser Leu Cys Leu
 1               5                  10                  15
Ser Leu Cys Leu Cys Leu Cys Leu Ala Ala Ala Leu Gly Ser Ala
                20                  25                  30
Gln Ser Gly Ser Cys Arg Asp Lys Lys Asn Cys Lys Val Val Phe
                35                  40                  45
Ser Gln Gln Glu Leu Arg Lys Arg Leu Thr Pro Leu Gln Tyr His
                50                  55                  60
Val Thr Gln Glu Lys Gly Thr Glu Ser Ala Phe Glu Gly Glu Tyr
                65                  70                  75
Thr His His Lys Asp Pro Gly Ile Tyr Lys Cys Val Val Cys Gly
                80                  85                  90
Thr Pro Leu Phe Lys Ser Glu Thr Lys Phe Asp Ser Gly Ser Gly
                95                  100                 105
Trp Pro Ser Phe His Asp Val Ile Asn Ser Glu Ala Ile Thr Phe
                110                 115                 120
Thr Asp Asp Phe Ser Tyr Gly Met His Arg Val Glu Thr Ser Cys
                125                 130                 135
Ser Gln Cys Gly Ala His Leu Gly His Ile Phe Asp Asp Gly Pro
                140                 145                 150
Arg Pro Thr Gly Lys Arg Tyr Cys Ile Asn Ser Ala Ala Leu Ser
                155                 160                 165
Phe Thr Pro Ala Asp Ser Ser Gly Thr Ala Glu Gly Gly Ser Gly
                170                 175                 180
Val Ala Ser Pro Ala Gln Ala Asp Lys Ala Glu Leu
                185                 190
```

<210> SEQ ID NO 49
<211> LENGTH: 2065
<212> TYPE: DNA
<213> ORGANISM: Homo Sapien

<400> SEQUENCE: 49

| | |
|---|---|
| cccaaagagg tgaggagccg gcagcggggg cggctgtaac tgtgaggaag | 50 |
| gctgcagagt ggcgacgtct acgccgtagg ttggaggctg tggggggtgg | 100 |
| ccgggcgcca gctcccaggc cgcagaagtg acctgcggtg gagttccctc | 150 |

-continued

```
ctcgctgctg gagaacggag ggagaaggtt gctggccggg tgaaagtgcc       200
tccctctgct tgacggggct gaggggcccg aagtctaggg cgtccgtagt       250
cgccccggcc tccgtgaagc cccaggtcta gagatatgac ccgagagtgc       300
ccatctccgg ccccggggcc tggggctccg ctgagtggat cggtgctggc       350
agaggcggca gtagtgtttg cagtggtgct gagcatccac gcaaccgtat       400
gggaccgata ctcgtggtgc gccgtggccc tcgcagtgca ggccttctac       450
gtccaataca agtgggaccg gctgctacag cagggaagcg ccgtcttcca       500
gttccgaatg tccgcaaaca gtggcctatt gcccgcctcc atggtcatgc       550
ctttgcttgg actagtcatg aaggagcggt gccagactgc tgggaacccg       600
ttctttgagc gttttggcat tgtggtggca gccactggca tggcagtggc       650
cctcttctca tcagtgttgg cgctcggcat cactcgccca gtgccaacca       700
acacttgtgt catcttgggc ttggctggag gtgttatcat ttatatcatg       750
aagcactcgt tgagcgtggg ggaggtgatc gaagtcctgg aagtccttct       800
gatcttcgtt tatctcaaca tgatcctgct gtacctgctg ccccgctgct       850
tcacccctgg tgaggcactg ctggtattgg gtggcattag ctttgtcctc       900
aaccagctca tcaagcgctc tctgacactg gtggaaagtc aggggaccc        950
agtggacttc ttcctgctgg tggtggtagt agggatggta ctcatgggca      1000
ttttcttcag cactctgttt gtcttcatgg actcaggcac ctgggcctcc      1050
tccatcttct tccacctcat gacctgtgtg ctgagccttg gtgtggtcct      1100
accctggctg caccggctca tccgcaggaa tccctgctc tggcttcttc       1150
agtttctctt ccagacagac acccgcatct acctcctagc ctattggtct      1200
ctgctggcca ccttggcctg cctggtggtg ctgtaccaga tgccaagcg       1250
gtcatcttcc gagtccaaga agcaccaggc ccccaccatc gcccgaaagt      1300
atttccacct cattgtggta gccacctaca tcccaggtat catctttgac      1350
cggccactgc tctatgtagc cgccactgta tgcctggcgg tcttcatctt      1400
cctggagtat gtgcgctact tccgcatcaa gcctttgggt cacactctac      1450
ggagcttcct gtccctttt ctggatgaac gagacagtgg accactcatt       1500
ctgacacaca tctacctgct cctgggcatg tctcttccca tctggctgat      1550
ccccagaccc tgcacacaga agggtagcct gggaggagcc agggccctcg      1600
tcccctatgc cggtgtcctg gctgtgggtg tgggtgatac tgtggcctcc      1650
atcttcggta gcaccatggg ggagatccgc tggcctggaa ccaaaaagac      1700
ttttgagggg accatgacat ctatatttgc gcagatcatt tctgtagctc      1750
tgatcttaat ctttgacagt ggagtggacc taaaactacag ttatgcttgg     1800
attttggggt ccatcagcac tgtgtccctc ctggaagcat acactacaca      1850
gatagacaat ctccttctgc ctctctacct cctgatattg ctgatggcct      1900
agctgttaca gtgcagcagc agtgacggag gaaacagaca tggggagggt      1950
gaacagtccc cacagcagac agctacttgg gcatgaagag ccaaggtgtg      2000
aaaagcagat ttgattttc agttgattca gatttaaaat aaaaagcaaa       2050
gctctcctag ttcta                                            2065
```

<210> SEQ ID NO 50
<211> LENGTH: 538
<212> TYPE: PRT
<213> ORGANISM: Homo Sapien

<400> SEQUENCE: 50

```
Met Thr Arg Glu Cys Pro Ser Pro Ala Pro Gly Pro Gly Ala Pro
 1               5                  10                  15

Leu Ser Gly Ser Val Leu Ala Glu Ala Val Val Phe Ala Val
                20                  25                  30

Val Leu Ser Ile His Ala Thr Val Trp Asp Arg Tyr Ser Trp Cys
                35                  40                  45

Ala Val Ala Leu Ala Val Gln Ala Phe Tyr Val Gln Tyr Lys Trp
                50                  55                  60

Asp Arg Leu Leu Gln Gln Gly Ser Ala Val Phe Gln Phe Arg Met
                65                  70                  75

Ser Ala Asn Ser Gly Leu Leu Pro Ala Ser Met Val Met Pro Leu
                80                  85                  90

Leu Gly Leu Val Met Lys Glu Arg Cys Gln Thr Ala Gly Asn Pro
                95                  100                 105

Phe Phe Glu Arg Phe Gly Ile Val Val Ala Ala Thr Gly Met Ala
                110                 115                 120

Val Ala Leu Phe Ser Ser Val Leu Ala Leu Gly Ile Thr Arg Pro
                125                 130                 135

Val Pro Thr Asn Thr Cys Val Ile Leu Gly Leu Ala Gly Gly Val
                140                 145                 150

Ile Ile Tyr Ile Met Lys His Ser Leu Ser Val Gly Glu Val Ile
                155                 160                 165

Glu Val Leu Glu Val Leu Leu Ile Phe Val Tyr Leu Asn Met Ile
                170                 175                 180

Leu Leu Tyr Leu Leu Pro Arg Cys Phe Thr Pro Gly Glu Ala Leu
                185                 190                 195

Leu Val Leu Gly Gly Ile Ser Phe Val Leu Asn Gln Leu Ile Lys
                200                 205                 210

Arg Ser Leu Thr Leu Val Glu Ser Gln Gly Asp Pro Val Asp Phe
                215                 220                 225

Phe Leu Leu Val Val Val Gly Met Val Leu Met Gly Ile Phe
                230                 235                 240

Phe Ser Thr Leu Phe Val Phe Met Asp Ser Gly Thr Trp Ala Ser
                245                 250                 255

Ser Ile Phe Phe His Leu Met Thr Cys Val Leu Ser Leu Gly Val
                260                 265                 270

Val Leu Pro Trp Leu His Arg Leu Ile Arg Arg Asn Pro Leu Leu
                275                 280                 285

Trp Leu Leu Gln Phe Leu Phe Gln Thr Asp Thr Arg Ile Tyr Leu
                290                 295                 300

Leu Ala Tyr Trp Ser Leu Leu Ala Thr Leu Ala Cys Leu Val Val
                305                 310                 315

Leu Tyr Gln Asn Ala Lys Arg Ser Ser Glu Ser Lys Lys His
                320                 325                 330

Gln Ala Pro Thr Ile Ala Arg Lys Tyr Phe His Leu Ile Val Val
                335                 340                 345

Ala Thr Tyr Ile Pro Gly Ile Ile Phe Asp Arg Pro Leu Leu Tyr
                350                 355                 360
```

-continued

Val Ala Ala Thr Val Cys Leu Ala Val Phe Ile Phe Leu Glu Tyr
                365                 370                 375

Val Arg Tyr Phe Arg Ile Lys Pro Leu Gly His Thr Leu Arg Ser
            380                 385                 390

Phe Leu Ser Leu Phe Leu Asp Glu Arg Asp Ser Gly Pro Leu Ile
        395                 400                 405

Leu Thr His Ile Tyr Leu Leu Leu Gly Met Ser Leu Pro Ile Trp
    410                 415                 420

Leu Ile Pro Arg Pro Cys Thr Gln Lys Gly Ser Leu Gly Gly Ala
425                 430                 435

Arg Ala Leu Val Pro Tyr Ala Gly Val Leu Ala Val Gly Val Gly
                440                 445                 450

Asp Thr Val Ala Ser Ile Phe Gly Ser Thr Met Gly Glu Ile Arg
            455                 460                 465

Trp Pro Gly Thr Lys Lys Thr Phe Glu Gly Thr Met Thr Ser Ile
        470                 475                 480

Phe Ala Gln Ile Ile Ser Val Ala Leu Ile Leu Ile Phe Asp Ser
    485                 490                 495

Gly Val Asp Leu Asn Tyr Ser Tyr Ala Trp Ile Leu Gly Ser Ile
500                 505                 510

Ser Thr Val Ser Leu Leu Glu Ala Tyr Thr Thr Gln Ile Asp Asn
                515                 520                 525

Leu Leu Leu Pro Leu Tyr Leu Leu Ile Leu Leu Met Ala
            530                 535

<210> SEQ ID NO 51
<211> LENGTH: 3476
<212> TYPE: DNA
<213> ORGANISM: Homo Sapien

<400> SEQUENCE: 51

| | | |
|---|---|---|
| gctctatgcc gcctaccttg ctctcgccgc tgctgccgga gccgaagcag | 50 |
| agaaggcagc gggtcccgtg accgtcccga gagccccgcg ctcccgacca | 100 |
| gggggcgggg gcggccccgg ggagggcggg gcagggcgg ggggaagaaa | 150 |
| ggggggttttg tgctgcgccg ggagggccgg cgccctcttc cgaatgtcct | 200 |
| gcggccccag cctctcctca cgctcgcgca gtctccgccg cagtctcagc | 250 |
| tgcagctgca ggactgagcc gtgcacccgg aggagacccc cggaggaggc | 300 |
| gacaaacttc gcagtgccgc gacccaaccc cagccctggg tagcctgcag | 350 |
| catgcccag ctgttcctgc ccctgctggc agccctggtc ctggcccagg | 400 |
| ctcctgcagc tttagcagat gttctggaag gagacagctc agaggaccgc | 450 |
| gcttttcgcg tgcgcatcgc gggcgacgcg ccactgcagg gcgtgctcgg | 500 |
| cggcgccctc accatcccct tgccacgtcca ctacctgcgg ccaccgccga | 550 |
| gccgccgggc tgtgctgggc tctccgcggg tcaagtggac tttcctgtcc | 600 |
| cggggccggg aggcagaggt gctggtggcg cggggagtgc gcgtcaaggt | 650 |
| gaacgaggcc taccggttcc gcgtggcact gcctgcgtac ccagcgtcgc | 700 |
| tcaccgacgt ctccctggcg ctgagcgagc tgcgccccaa cgactcaggt | 750 |
| atctatcgct gtgaggtcca gcacggcatc gatgacagca gcgacgctgt | 800 |
| ggaggtcaag gtcaaagggg tcgtctttct ctaccgagag ggctctgccc | 850 |

-continued

| | |
|---|---|
| gctatgcttt ctcctttct ggggcccagg aggcctgtgc ccgcattgga | 900 |
| gcccacatcg ccaccccgga gcagctctat gccgcctacc ttgggggcta | 950 |
| tgagcaatgt gatgctggct ggctgtcgga tcagaccgtg aggtatccca | 1000 |
| tccagacccc acgagaggcc tgttacggag acatggatgg cttccccggg | 1050 |
| gtccggaact atggtgtggt ggacccggat gacctctatg atgtgtactg | 1100 |
| ttatgctgaa gacctaaatg agaactgtt cctgggtgac cctccagaga | 1150 |
| agctgacatt ggaggaagca cgggcgtact gccaggagcg gggtgcagag | 1200 |
| attgccacca cgggccaact gtatgcagcc tgggatggtg gcctggacca | 1250 |
| ctgcagccca gggtggctag ctgatggcag tgtgcgctac cccatcgtca | 1300 |
| cacccagcca gcgctgtggt gggggcttgc ctggtgtcaa gactctcttc | 1350 |
| ctcttcccca accagactgg cttccccaat aagcacagcc gcttcaacgt | 1400 |
| ctactgcttc cgagactcgg cccagccttc tgccatccct gaggcctcca | 1450 |
| acccagcctc caacccagcc tctgatggac tagaggctat cgtcacagtg | 1500 |
| acagagaccc tggaggaact gcagctgcct caggaagcca cagagagtga | 1550 |
| atcccgtggg gccatctact ccatccccat catggaggac ggaggaggtg | 1600 |
| gaagctccac tccagaagac ccagcagagg cccctaggac gctcctagaa | 1650 |
| tttgaaacac aatccatggt accgcccacg gggttctcag aagaggaagg | 1700 |
| taaggcattg gaggaagaag agaaatatga agatgaagaa gagaaagagg | 1750 |
| aggaagaaga agaggaggag gtggaggatg aggctctgtg ggcatggccc | 1800 |
| agcgagctca gcagcccggg ccctgaggcc tctctcccca ctgagccagc | 1850 |
| agcccaggag aagtcactct cccaggcgcc agcaagggca gtcctgcagc | 1900 |
| ctggtgcatc accacttcct gatggagagt cagaagcttc caggcctcca | 1950 |
| agggtccatg gaccacctac tgagactctg cccactccca gggagaggaa | 2000 |
| cctagcatcc ccatcacctt ccactctggt tgaggcaaga gaggtggggg | 2050 |
| aggcaactgg tggtcctgag ctatctgggg tccctcgagg agagagcgag | 2100 |
| gagacaggaa gctccgaggg tgccccttcc ctgcttccag ccacgggc | 2150 |
| ccctgagggt accagggagc tggaggcccc ctctgaagat aattctggaa | 2200 |
| gaactgcccc agcagggacc tcagtgcagg cccagccagt gctgcccact | 2250 |
| gacagcgcca gccgaggtgg agtggccgtg gtccccgcat caggtgactg | 2300 |
| tgtccccagc cctgccaca atggtgggac atgcttggag gaggaggaag | 2350 |
| gggtccgctg cctatgtctg cctggctatg ggggggacct gtgcgatgtt | 2400 |
| ggcctccgct tctgcaaccc cggctgggac gccttccagg gcgcctgcta | 2450 |
| caagcacttt tccacacgaa ggagctggga ggaggcagag acccagtgcc | 2500 |
| ggatgtacgg cgcgcatctg ccagcatca gcacacccga ggaacaggac | 2550 |
| ttcatcaaca accggtaccg ggagtaccag tggatcggac tcaacgacag | 2600 |
| gaccatcgaa ggcgacttct tgtggtcgga tggcgtcccc ctgctctatg | 2650 |
| agaactggaa ccctgggcag cctgacagct acttcctgtc tggagagaac | 2700 |
| tgcgtggtca tggtgtggca tgatcaggga caatggagtg acgtgccctg | 2750 |
| caactaccac ctgtcctaca cctgcaagat ggggctggtg tcctgtgggc | 2800 |
| cgccaccgga gctgccctg gctcaagtgt tcggccgccc acggctgcgc | 2850 |

```
tatgaggtgg acactgtgct tcgctaccgg tgccgggaag gactggccca      2900
gcgcaatctg ccgctgatcc gatgccaaga gaacggtcgt tgggaggccc      2950
cccagatctc ctgtgtgccc agaagacctg cccgagctct gcacccagag      3000
gaggacccag aaggacgtca ggggaggcta ctgggacgct ggaaggcgct      3050
gttgatcccc ccttccagcc ccatgccagg tccctagggg gcaaggcctt      3100
gaacactgcc ggccacagca ctgccctgtc acccaaattt tccctcacac      3150
cttgcgctcc cgccaccaca ggaagtgaca acatgacgag gggtggtgct      3200
ggagtccagg tgacagttcc tgaaggggct tctgggaaat acctaggagg      3250
ctccagccca gcccaggccc tctccccta  ccctgggcac cagatcttcc      3300
atcagggccg gagtaaatcc ctaagtgcct caactgccct ctccctggca      3350
gccatcttgt cccctctatt cctctaggga gcactgtgcc cactctttct      3400
gggttttcca agggaatggg cttgcaggat ggagtgtctg taaaatcaac      3450
aggaaataaa actgtgtatg agccca                                3476
```

<210> SEQ ID NO 52
<211> LENGTH: 911
<212> TYPE: PRT
<213> ORGANISM: Homo Sapien

<400> SEQUENCE: 52

```
Met Ala Gln Leu Phe Leu Pro Leu Leu Ala Ala Leu Val Leu Ala
 1               5                  10                  15

Gln Ala Pro Ala Leu Ala Asp Val Leu Glu Gly Asp Ser Ser
                20                  25                  30

Glu Asp Arg Ala Phe Arg Val Arg Ile Ala Gly Asp Ala Pro Leu
                35                  40                  45

Gln Gly Val Leu Gly Gly Ala Leu Thr Ile Pro Cys His Val His
                50                  55                  60

Tyr Leu Arg Pro Pro Ser Arg Arg Ala Val Leu Gly Ser Pro
                65                  70                  75

Arg Val Lys Trp Thr Phe Leu Ser Arg Gly Arg Glu Ala Glu Val
                80                  85                  90

Leu Val Ala Arg Gly Val Arg Val Lys Val Asn Glu Ala Tyr Arg
                95                 100                 105

Phe Arg Val Ala Leu Pro Ala Tyr Pro Ala Ser Leu Thr Asp Val
               110                 115                 120

Ser Leu Ala Leu Ser Glu Leu Arg Pro Asn Asp Ser Gly Ile Tyr
               125                 130                 135

Arg Cys Glu Val Gln His Gly Ile Asp Asp Ser Ser Asp Ala Val
               140                 145                 150

Glu Val Lys Val Lys Gly Val Val Phe Leu Tyr Arg Glu Gly Ser
               155                 160                 165

Ala Arg Tyr Ala Phe Ser Phe Ser Gly Ala Gln Glu Ala Cys Ala
               170                 175                 180

Arg Ile Gly Ala His Ile Ala Thr Pro Glu Gln Leu Tyr Ala Ala
               185                 190                 195

Tyr Leu Gly Gly Tyr Glu Gln Cys Asp Ala Gly Trp Leu Ser Asp
               200                 205                 210

Gln Thr Val Arg Tyr Pro Ile Gln Thr Pro Arg Glu Ala Cys Tyr
               215                 220                 225
```

-continued

```
Gly Asp Met Asp Gly Phe Pro Gly Val Arg Asn Tyr Gly Val Val
            230                 235                 240

Asp Pro Asp Asp Leu Tyr Asp Val Tyr Cys Tyr Ala Glu Asp Leu
            245                 250                 255

Asn Gly Glu Leu Phe Leu Gly Asp Pro Glu Lys Leu Thr Leu
            260                 265                 270

Glu Glu Ala Arg Ala Tyr Cys Gln Glu Arg Gly Ala Glu Ile Ala
            275                 280                 285

Thr Thr Gly Gln Leu Tyr Ala Ala Trp Asp Gly Gly Leu Asp His
            290                 295                 300

Cys Ser Pro Gly Trp Leu Ala Asp Gly Ser Val Arg Tyr Pro Ile
            305                 310                 315

Val Thr Pro Ser Gln Arg Cys Gly Gly Leu Pro Gly Val Lys
            320                 325                 330

Thr Leu Phe Leu Phe Pro Asn Gln Thr Gly Phe Pro Asn Lys His
            335                 340                 345

Ser Arg Phe Asn Val Tyr Cys Phe Arg Asp Ser Ala Gln Pro Ser
            350                 355                 360

Ala Ile Pro Glu Ala Ser Asn Pro Ala Ser Asn Pro Ala Ser Asp
            365                 370                 375

Gly Leu Glu Ala Ile Val Thr Val Thr Glu Thr Leu Glu Glu Leu
            380                 385                 390

Gln Leu Pro Gln Glu Ala Thr Glu Ser Glu Ser Arg Gly Ala Ile
            395                 400                 405

Tyr Ser Ile Pro Ile Met Glu Asp Gly Gly Gly Ser Ser Thr
            410                 415                 420

Pro Glu Asp Pro Ala Glu Ala Pro Arg Thr Leu Leu Glu Phe Glu
            425                 430                 435

Thr Gln Ser Met Val Pro Pro Thr Gly Phe Ser Glu Glu Glu Gly
            440                 445                 450

Lys Ala Leu Glu Glu Glu Lys Tyr Glu Asp Glu Glu Lys
            455                 460                 465

Glu Glu Glu Glu Glu Glu Glu Val Glu Asp Glu Ala Leu Trp
            470                 475                 480

Ala Trp Pro Ser Glu Leu Ser Ser Pro Gly Pro Glu Ala Ser Leu
            485                 490                 495

Pro Thr Glu Pro Ala Ala Gln Glu Lys Ser Leu Ser Gln Ala Pro
            500                 505                 510

Ala Arg Ala Val Leu Gln Pro Gly Ala Ser Pro Leu Pro Asp Gly
            515                 520                 525

Glu Ser Glu Ala Ser Arg Pro Pro Arg Val His Gly Pro Pro Thr
            530                 535                 540

Glu Thr Leu Pro Thr Pro Arg Glu Arg Asn Leu Ala Ser Pro Ser
            545                 550                 555

Pro Ser Thr Leu Val Glu Ala Arg Glu Val Gly Glu Ala Thr Gly
            560                 565                 570

Gly Pro Glu Leu Ser Gly Val Pro Arg Gly Glu Ser Glu Glu Thr
            575                 580                 585

Gly Ser Ser Glu Gly Ala Pro Ser Leu Leu Pro Ala Thr Arg Ala
            590                 595                 600

Pro Glu Gly Thr Arg Glu Leu Glu Ala Pro Ser Glu Asp Asn Ser
            605                 610                 615
```

```
Gly Arg Thr Ala Pro Ala Gly Thr Ser Val Gln Ala Gln Pro Val
                620                 625                 630

Leu Pro Thr Asp Ser Ala Ser Arg Gly Gly Val Ala Val Val Pro
                635                 640                 645

Ala Ser Gly Asp Cys Val Pro Ser Pro Cys His Asn Gly Gly Thr
                650                 655                 660

Cys Leu Glu Glu Glu Glu Gly Val Arg Cys Leu Cys Leu Pro Gly
                665                 670                 675

Tyr Gly Gly Asp Leu Cys Asp Val Gly Leu Arg Phe Cys Asn Pro
                680                 685                 690

Gly Trp Asp Ala Phe Gln Gly Ala Cys Tyr Lys His Phe Ser Thr
                695                 700                 705

Arg Arg Ser Trp Glu Glu Ala Glu Thr Gln Cys Arg Met Tyr Gly
                710                 715                 720

Ala His Leu Ala Ser Ile Ser Thr Pro Glu Glu Gln Asp Phe Ile
                725                 730                 735

Asn Asn Arg Tyr Arg Glu Tyr Gln Trp Ile Gly Leu Asn Asp Arg
                740                 745                 750

Thr Ile Glu Gly Asp Phe Leu Trp Ser Asp Gly Val Pro Leu Leu
                755                 760                 765

Tyr Glu Asn Trp Asn Pro Gly Gln Pro Asp Ser Tyr Phe Leu Ser
                770                 775                 780

Gly Glu Asn Cys Val Val Met Val Trp His Asp Gln Gly Gln Trp
                785                 790                 795

Ser Asp Val Pro Cys Asn Tyr His Leu Ser Tyr Thr Cys Lys Met
                800                 805                 810

Gly Leu Val Ser Cys Gly Pro Pro Glu Leu Pro Leu Ala Gln
                815                 820                 825

Val Phe Gly Arg Pro Arg Leu Arg Tyr Glu Val Asp Thr Val Leu
                830                 835                 840

Arg Tyr Arg Cys Arg Glu Gly Leu Ala Gln Arg Asn Leu Pro Leu
                845                 850                 855

Ile Arg Cys Gln Glu Asn Gly Arg Trp Glu Ala Pro Gln Ile Ser
                860                 865                 870

Cys Val Pro Arg Arg Pro Ala Arg Ala Leu His Pro Glu Glu Asp
                875                 880                 885

Pro Glu Gly Arg Gln Gly Arg Leu Leu Gly Arg Trp Lys Ala Leu
                890                 895                 900

Leu Ile Pro Pro Ser Ser Pro Met Pro Gly Pro
                905                 910

<210> SEQ ID NO 53
<211> LENGTH: 3316
<212> TYPE: DNA
<213> ORGANISM: Homo Sapien

<400> SEQUENCE: 53
ctgccaggtg acagccgcca agatggggtc ttgggccctg ctgtggcctc        50
ccctgctgtt caccgggctg ctcgtccgac ccccggggac catggcccag       100
gcccagtact gctctgtgaa caaggacatc tttgaagtag aggagaacac       150
aaatgtcacc gagccgctgg tggacatcca cgtcccggag ggccaggagg       200 tgacccctcgg agccttgtcc accccctttg catttcggat ccagggaaac      250
cagctgtttc tcaacgtgac tcctgattac gaggagaagt cactgcttga       300
```

-continued

```
ggctcagctg ctgtgtcaga gcggaggcac attggtgacc cagctaaggg       350
tgttcgtgtc agtgctggac gtcaatgaca atgcccccga attccccttt       400
aagaccaagg agataagggt ggaggaggac acgaaagtga actccaccgt       450
catccctgag acgcaactgc aggctgagga ccgcgacaag gacgacattc       500
tgttctacac cctccaggaa atgacagcag gtgccagtga ctacttctcc       550
ctggtgagtg taaaccgtcc cgccctgagg ctggaccggc ccctggactt       600
ctacgagcgg ccgaacatga ccttctggct gctggtgcgg gacactccag       650
gggagaatgt ggaacccagc cacactgcca ccgccacact agtgctgaac       700
gtggtgcccg ccgacctgcg gccccgtgg ttcctgccct gcaccttctc       750
agatggctac gtctgcattc aagctcagta ccacggggct gtccccacgg       800
ggcacatact gccatctccc ctcgtcctgc gtcccggacc catctacgct       850
gaggacggag accgcggcat caaccagccc atcatctaca gcatctttag       900
gggaaacgtg aatggtacat tcatcatcca cccagactcg gcaacctca       950 ccgtggccag gagtgtcccc agccccatga ccttccttct gctggtgaag       1000
ggccaacagg ccgaccttgc ccgctactca gtgacccagg tcaccgtgga       1050
ggctgtggct gcggccggga cccgccccg cttcccccag agcctgtatc       1100
gtggcaccgt ggcgcgtggc gctggagcgg gcgttgtggt caaggatgca       1150
gctgcccctt ctcagcctct gaggatccag gctcaggacc cggagttctc       1200
ggacctcaac tcggccatca catatcgaat taccaaccac tcacacttcc       1250
ggatggaggg agaggttgtg ctgaccacca ccacactggc acaggcggga       1300
gccttctacg cagaggttga ggcccacaac acggtgacct ctggcaccgc       1350
aaccacagtc attgagatac aagtttccga acaggagccc cctccacag       1400 aggctggagg aacaactggg ccctggacca gcaccacttc cgaggtcccc       1450 agacccctg agccctccca gggacccctcc acgaccagct ctgggggagg       1500
cacaggccct catccacccct ctggcacaac tctgaggcca ccaacctcgt       1550
ccacacccgg ggggccccg ggtgcagaaa acagcacctc ccaccaacca       1600
gccactcccg gtggggacac agcacagacc ccaaagccag gaacctctca       1650
gccgatgccc ccggtgtgg gaaccagcac ctcccaccaa ccagccacac       1700
ccagtggggg cacagcacag accccagagc caggaacctc tcagccgatg       1750
ccccccagta tgggaaccag cacctcccac caaccagcca cacccggtgg       1800
gggcacagca cagacccag aggcaggaac ctctcagccg atgcccccg       1850 gtatgggaac cagcacctcc caccaaccaa ccacacccgg tggggcaca       1900 gcacagaccc cagagccagg aacctctcag ccgatgcccc tcagcaagag       1950 cacccccatct tcaggtggcg gcccctcgga ggacaagcgc ttctcggtgg       2000
tggatatggc ggccctgggc ggggtgctgg gtgcgctgct gctgctggct       2050
ctccttggcc tcgccgtcct tgtccacaag cactatggcc ccggctcaa       2100 gtgctgctct ggcaaagctc cggagcccca gccccaaggc tttgacaacc       2150
aggcgttcct ccctgaccac aaggccaact gggcgcccgt cccagccccc       2200
acgcacgacc ccaagcccgc ggaggcaccg atgcccgcag agcccgcacc       2250
```

```
cccggccct gcctccccag gcggtgcccc tgagccccc gcagcggccc         2300 gagctggcgg aagccccacg gcggtgaggt ccatcctgac caaggagcgg       2350
cggccggagg gcgggtacaa ggccgtctgg tttggcgagg acatcgggac       2400
ggaggcagac gtggtcgttc tcaacgcgcc caccctggac gtggatggcg       2450
ccagtgactc cggcagcggc gacgagggca agggcgcggg gaggggtggg       2500
ggtccctacg atgcacccgg tggtgatgac tcctacatct aagtggcccc       2550
tccaccctct cccccagccg cacgggcact ggaggtctcg ctcccccagc       2600
ctccgacccg aggcagaata aagcaaggct cccgaaaccc aggccatggc       2650
gtggggcagg cgcgtgggtc cctgggggcc ccattcactc agtcccctgt       2700
cgtcattagc gcttgagccc aggtgtgcag atgaggcggt gggtctggcc       2750
acgctgtccc caccccaagg ctgcagcact tcccgtaaac cacctgcagt       2800
gcccgccgcc ttcccgaggc tctgtgccag ctagtctggg aagttcctct       2850
cccgctctaa ccacagcccg aggggggctc ccctcccccg acctgcacca       2900
gagatctcag gcaccggct caactcagac ctcccgctcc cgaccctaca        2950
cagagattgc ctggggaggc tgaggagccg atgcaaaccc caaggcgac        3000 gcacttggga gccggtggtc tcaaacacct gccggggtc ctagtcccct        3050 tctgaaatct acatgcttgg gttggagcgc agcagtaaac accctgccca      3100
gtgacctgga ctgaggcgcg ctgggggtgg gtgcgccgtg tggcctgagc      3150
aggagccaga ccaggaggcc tagggtgag agacacattc ccctcgctgc        3200
tcccaaagcc agagcccagg ctgggcgccc atgcccagaa ccatcaaggg      3250
atcccttgcg gcttgtcagc actttcccta atggaaatac accattaatt      3300
cctttccaaa tgtttt                                            3316
```

<210> SEQ ID NO 54
<211> LENGTH: 839
<212> TYPE: PRT
<213> ORGANISM: Homo Sapien

<400> SEQUENCE: 54

```
Met Gly Ser Trp Ala Leu Leu Trp Pro Pro Leu Leu Phe Thr Gly
 1               5                  10                  15

Leu Leu Val Arg Pro Pro Gly Thr Met Ala Gln Ala Gln Tyr Cys
            20                  25                  30

Ser Val Asn Lys Asp Ile Phe Glu Val Glu Asn Thr Asn Val
            35                  40                  45

Thr Glu Pro Leu Val Asp Ile His Val Pro Glu Gly Gln Glu Val
            50                  55                  60

Thr Leu Gly Ala Leu Ser Thr Pro Phe Ala Phe Arg Ile Gln Gly
            65                  70                  75

Asn Gln Leu Phe Leu Asn Val Thr Pro Asp Tyr Glu Glu Lys Ser
            80                  85                  90

Leu Leu Glu Ala Gln Leu Leu Cys Gln Ser Gly Gly Thr Leu Val
            95                  100                 105

Thr Gln Leu Arg Val Phe Val Ser Val Leu Asp Val Asn Asp Asn
            110                 115                 120

Ala Pro Glu Phe Pro Phe Lys Thr Lys Glu Ile Arg Val Glu Glu
            125                 130                 135
```

-continued

```
Asp Thr Lys Val Asn Ser Thr Val Ile Pro Glu Thr Gln Leu Gln
                140                 145                 150

Ala Glu Asp Arg Asp Lys Asp Ile Leu Phe Tyr Thr Leu Gln
        155                 160                 165

Glu Met Thr Ala Gly Ala Ser Asp Tyr Phe Ser Leu Val Ser Val
                170                 175                 180

Asn Arg Pro Ala Leu Arg Leu Asp Arg Pro Leu Asp Phe Tyr Glu
                185                 190                 195

Arg Pro Asn Met Thr Phe Trp Leu Leu Val Arg Asp Thr Pro Gly
                200                 205                 210

Glu Asn Val Glu Pro Ser His Thr Ala Thr Ala Thr Leu Val Leu
                215                 220                 225

Asn Val Val Pro Ala Asp Leu Arg Pro Pro Trp Phe Leu Pro Cys
                230                 235                 240

Thr Phe Ser Asp Gly Tyr Val Cys Ile Gln Ala Gln Tyr His Gly
                245                 250                 255

Ala Val Pro Thr Gly His Ile Leu Pro Ser Pro Leu Val Leu Arg
                260                 265                 270

Pro Gly Pro Ile Tyr Ala Glu Asp Gly Asp Arg Gly Ile Asn Gln
                275                 280                 285

Pro Ile Ile Tyr Ser Ile Phe Arg Gly Asn Val Asn Gly Thr Phe
                290                 295                 300

Ile Ile His Pro Asp Ser Gly Asn Leu Thr Val Ala Arg Ser Val
                305                 310                 315

Pro Ser Pro Met Thr Phe Leu Leu Leu Val Lys Gly Gln Gln Ala
                320                 325                 330

Asp Leu Ala Arg Tyr Ser Val Thr Gln Val Thr Val Glu Ala Val
                335                 340                 345

Ala Ala Ala Gly Ser Pro Pro Arg Phe Pro Gln Ser Leu Tyr Arg
                350                 355                 360

Gly Thr Val Ala Arg Gly Ala Gly Ala Val Val Lys Asp
                365                 370                 375

Ala Ala Ala Pro Ser Gln Pro Leu Arg Ile Gln Ala Gln Asp Pro
                380                 385                 390

Glu Phe Ser Asp Leu Asn Ser Ala Ile Thr Tyr Arg Ile Thr Asn
                395                 400                 405

His Ser His Phe Arg Met Glu Gly Glu Val Val Leu Thr Thr Thr
                410                 415                 420

Thr Leu Ala Gln Ala Gly Ala Phe Tyr Ala Glu Val Glu Ala His
                425                 430                 435

Asn Thr Val Thr Ser Gly Thr Ala Thr Val Ile Glu Ile Gln
                440                 445                 450

Val Ser Glu Gln Glu Pro Pro Ser Thr Glu Ala Gly Gly Thr Thr
                455                 460                 465

Gly Pro Trp Thr Ser Thr Ser Glu Val Pro Arg Pro Glu
                470                 475                 480

Pro Ser Gln Gly Pro Ser Thr Ser Ser Gly Gly Thr Gly
                485                 490                 495

Pro His Pro Pro Ser Gly Thr Thr Leu Arg Pro Pro Thr Ser Ser
                500                 505                 510

Thr Pro Gly Gly Pro Pro Gly Ala Glu Asn Ser Thr Ser His Gln
                515                 520                 525

Pro Ala Thr Pro Gly Gly Asp Thr Ala Gln Thr Pro Lys Pro Gly
```

|   |   |   |
|---|---|---|
| 530 | 535 | 540 |

Thr Ser Gln Pro Met Pro Pro Gly Val Gly Thr Ser Thr Ser His
        545                    550                    555

Gln Pro Ala Thr Pro Ser Gly Gly Thr Ala Gln Thr Pro Glu Pro
        560                    565                    570

Gly Thr Ser Gln Pro Met Pro Pro Ser Met Gly Thr Ser Thr Ser
        575                    580                    585

His Gln Pro Ala Thr Pro Gly Gly Thr Ala Gln Thr Pro Glu
        590                    595                    600

Ala Gly Thr Ser Gln Pro Met Pro Pro Gly Met Gly Thr Ser Thr
        605                    610                    615

Ser His Gln Pro Thr Thr Pro Gly Gly Gly Thr Ala Gln Thr Pro
        620                    625                    630

Glu Pro Gly Thr Ser Gln Pro Met Pro Leu Ser Lys Ser Thr Pro
        635                    640                    645

Ser Ser Gly Gly Gly Pro Ser Glu Asp Lys Arg Phe Ser Val Val
        650                    655                    660

Asp Met Ala Ala Leu Gly Gly Val Leu Gly Ala Leu Leu Leu Leu
        665                    670                    675

Ala Leu Leu Gly Leu Ala Val Leu Val His Lys His Tyr Gly Pro
        680                    685                    690

Arg Leu Lys Cys Cys Ser Gly Lys Ala Pro Glu Pro Gln Pro Gln
        695                    700                    705

Gly Phe Asp Asn Gln Ala Phe Leu Pro Asp His Lys Ala Asn Trp
        710                    715                    720

Ala Pro Val Pro Ser Pro Thr His Asp Pro Lys Pro Ala Glu Ala
        725                    730                    735

Pro Met Pro Ala Glu Pro Ala Pro Pro Gly Pro Ala Ser Pro Gly
        740                    745                    750

Gly Ala Pro Glu Pro Pro Ala Ala Ala Arg Ala Gly Ser Pro
        755                    760                    765

Thr Ala Val Arg Ser Ile Leu Thr Lys Glu Arg Pro Glu Gly
        770                    775                    780

Gly Tyr Lys Ala Val Trp Phe Gly Glu Asp Ile Gly Thr Glu Ala
        785                    790                    795

Asp Val Val Leu Asn Ala Pro Thr Leu Asp Val Asp Gly Ala
        800                    805                    810

Ser Asp Ser Gly Ser Gly Asp Glu Gly Glu Gly Ala Gly Arg Gly
        815                    820                    825

Gly Gly Pro Tyr Asp Ala Pro Gly Gly Asp Asp Ser Tyr Ile
        830                    835

<210> SEQ ID NO 55
<211> LENGTH: 3846
<212> TYPE: DNA
<213> ORGANISM: Homo Sapien

<400> SEQUENCE: 55

| | | | | | |
|---|---|---|---|---|---|
| gcagctgggt | tctcccggtt | cccttgggca | ggtgcagggt | cgggttcaaa | 50 |
| gcctccggaa | cgcgtttttgg | cctgatttga | ggagggggc | ggggagggac | 100 |
| ctgcggcttg | cggccccgcc | cccttctccg | gctcgcagcc | gaccggtaag | 150 |
| cccgcctcct | ccctcggccg | gcctggggc | cgtgtccgcc | gggcaactcc | 200 |
| agccgaggcc | tgggcttctg | cctgcaggtg | tctgcggcga | ggcccctagg | 250 |

-continued

```
gtacagcccg atttggcccc atggtgggtt tcggggccaa ccggcgggct      300
ggccgcctgc cctctctcgt gctggtggtg ctgctggtgg tgatcgtcgt      350
cctcgccttc aactactgga gcatctcctc ccgccacgtc ctgcttcagg      400
aggaggtggc cgagctgcag ggccaggtcc agcgcaccga agtggcccgc      450
gggcggctgg aaaagcgcaa ttcggacctc ttgctgttgg tggacacgca      500
caagaaacag atcgaccaga aggaggccga ctacggccgc ctcagcagcc      550
ggctgcaggc cagagagggc ctcgggaaga gatgcgagga tgacaaggtt      600
aaactacaga acaacatatc gtatcagatg gcagacatac atcatttaaa      650
ggagcaactt gctgagcttc gtcaggaatt tcttcgacaa gaagaccagc      700
ttcaggacta taggaagaac aatacttacc ttgtgaagag gttagaatat      750 gaaagtttc agtgtggaca gcagatgaag gaattgagag cacagcatga       800
agaaaatatt aaaaagttag cagaccagtt tttagaggaa caaaagcaag      850
agacccaaaa gattcaatca aatgatgaa aggaattgga tataaacaat       900
caagtagtac ctaaaaatat tccaaaagta gctgagaatg ttgcagataa      950
gaatgaagaa ccctcaagca atcatattcc acatgggaaa gaacaaatca      1000
aaagaggtgg tgatgcaggg atgcctggaa tagaagagaa tgacctagca      1050
aaagttgatg atcttccccc tgctttaagg aagcctccta tttcagtttc      1100
tcaacatgaa agtcatcaag caatctccca tcttccaact ggacaacctc      1150 tctcccaaa tatgcctcca gattcacaca taaaccacaa tggaaacccc       1200
ggtacttcaa aacagaatcc ttccagtcct cttcagcgtt taattccagg      1250
ctcaaacttg gacagtgaac ccagaattca aacagatata ctaaagcagg      1300
ctaccaagga cagagtcagt gatttccata aattgaagca aaatgatgaa      1350
gaacgagagc ttcaaatgga tcctgcagac tatggaaagc aacatttcaa      1400
tgatgtcctt taagtcctaa aggaatgctt cagaaaacct aaagtgctgt      1450
aaaatgaaat cattctactt tgtcctttct gactttttgt gtaaagacga      1500
attgtatcag ttgtaaagat acattgagat agaattaagg aaaaactta      1550 atgaaggaat gtacccatgt acatatgtga actttttcat attgtattat      1600
caaggtatag acttttttgg ttatgataca gttaagccaa aaacagctaa      1650
tctttgcatc taaagcaaac taatgtatat ttcacatttt attgagccga      1700
cttatttcca caaatagata aacaggacaa aatagttgta caggttatat      1750
gtggcatagc ataaccacag taagaacaga acagatattc agcagaaaac      1800
tttttatact ctaattcttt ttttttttt tttgagacag agttttagtc        1850
ttgtttccca ggctggagtg caatggcaca atcttggctc actgcaacct      1900
ccgcctcctg ggttcaggca ttttcctgc ctcagcctcc caagtagctg       1950
ggattacagg cacccaccac catgcccagc taatttttgt atttttaata      2000
gagagctaat aattgtatat ttaataaaga cgggtttcac catgttggcc      2050
aggctggtct tgaactcctg acctcaggtg atcctcctgc cttggcctcc      2100
caaagtgctg gaattccagg catgagccac tgcgcccagt ctacacacta      2150
attcttgtta gcccaacagc tgttctgttc tatctacccc tcatttcacg      2200
```

-continued

```
ctcaaggagt catacctaga atagttacac acaagaggga aactggaagc      2250
caaacactgt acagtattgt gtagaaagtc acctccctac tccttttatt      2300
ttacatgagt gctgatgtgt tttggcagat gagctttcag ctgaggcctg      2350
atggaaattg agataacctg caaagacata acagtattta tgagttatat      2400
cttagttctt gaaattgtgg aatgcatgat tgacaatata ttttttaattt     2450
ttatttttc aagtaatacc agtactgttt aactatagcc agaactggct       2500
aaaatttta tattttcaga gttgaagttg gtgaagacat tcatgattta       2550
aacaccagat cctgaaaggg gttaaatcta ctttgaaatg aatctgcaat      2600
cagtatttca agctttct ggtaatttta gtgatcttat ttgattagac        2650
tttttcagaa gtactaaata aggaattta acaggtttt attaatgcac        2700
agataaatag aagtacagtg aggtctatag ccattttatt aaaatagctt      2750
aaaagtttgt aaaaaatga atctttgtaa ttacttaata tgttagttaa       2800
gaacccgtca agcttatatt tgctagactt acaaattatt ttaaatgcat      2850
ttatctttt tgacactatt cagtggaatg tgtaagctag ctaattcttg       2900
ttttctgatt taaagcactt ttaaatctta tcctgccccc taaaaacaaa      2950
aggttttgat cacaagggga aatttaagat tgttaaccct gtttttcaga      3000
agggctactg ttaattgcac ataaacatga aatgtgtttt cccctgtgta      3050
ctaacacatt ctaggcaaaa ttcaaactta tagtggtaaa gaaacaggtt      3100
gttcacttgc tgaggtgcaa aaattcttaa gacttctgtt tgaaattgct      3150
caatgactag gaaaagatgt agtagtttac taaaattgtt tttctaccat      3200
atcaaattaa acaattcatg cctttatagg gtcaggccta caatgaatag      3250
gtatggtggt ttcacagaat tttaaaatag agttaaaggg aagtgatgta      3300
catttcgggg gcattagggt agggagatga atcaaaaaat acccctagta      3350
atgctttata ttttaatact gcaaaagctt tacaaatgga aaccatgcaa      3400
ttacctgcct tagttctttt gtcataaaaa caatcacttg gttggttgta      3450
ttgtagctat tacttataca gcaacatttc ttcaattagc agtctagaca      3500
ttttataaac agaaatcttg gaccaattga taatatttct gactgtatta      3550
atattttagt gctataaaat actatgtgaa tctcttaaaa atctgacatt      3600
ttacagtctg tattagacat actgttttta taatgttta cttctgcctt       3650
aagatttagg tttttaaat gtattttgc cctgaattaa gtgttaattt        3700
gatggaaact ctgcttttaa aatcatcatt tactgggttc taataaatta      3750
aaaattaaac ttgaaaaaaa aaaaaaaaaa aaaaaaaaaa aaaaaaaaaa      3800
aaaaaaaaaa aaaaaaaaaa aaaaaaaaaa aaaaaaaaaa aaaaa          3846
```

<210> SEQ ID NO 56
<211> LENGTH: 380
<212> TYPE: PRT
<213> ORGANISM: Homo Sapien

<400> SEQUENCE: 56

```
Met Val Gly Phe Gly Ala Asn Arg Arg Ala Gly Arg Leu Pro Ser
 1               5                  10                  15

Leu Val Leu Val Val Leu Leu Val Val Ile Val Val Leu Ala Phe
            20                  25                  30
```

```
Asn Tyr Trp Ser Ile Ser Arg His Val Leu Leu Gln Glu Glu
                35                  40                  45

Val Ala Glu Leu Gln Gly Gln Val Gln Arg Thr Glu Val Ala Arg
         50                  55                  60

Gly Arg Leu Glu Lys Arg Asn Ser Asp Leu Leu Leu Val Asp
                 65                  70                  75

Thr His Lys Lys Gln Ile Asp Gln Lys Glu Ala Asp Tyr Gly Arg
         80                  85                  90

Leu Ser Ser Arg Leu Gln Ala Arg Glu Gly Leu Gly Lys Arg Cys
                 95                 100                 105

Glu Asp Asp Lys Val Lys Leu Gln Asn Asn Ile Ser Tyr Gln Met
        110                 115                 120

Ala Asp Ile His His Leu Lys Glu Gln Leu Ala Glu Leu Arg Gln
        125                 130                 135

Glu Phe Leu Arg Gln Glu Asp Gln Leu Gln Asp Tyr Arg Lys Asn
        140                 145                 150

Asn Thr Tyr Leu Val Lys Arg Leu Glu Tyr Glu Ser Phe Gln Cys
        155                 160                 165

Gly Gln Gln Met Lys Glu Leu Arg Ala Gln His Glu Glu Asn Ile
        170                 175                 180

Lys Lys Leu Ala Asp Gln Phe Leu Glu Glu Gln Lys Gln Glu Thr
        185                 190                 195

Gln Lys Ile Gln Ser Asn Asp Gly Lys Glu Leu Asp Ile Asn Asn
        200                 205                 210

Gln Val Val Pro Lys Asn Ile Pro Lys Val Ala Glu Asn Val Ala
        215                 220                 225

Asp Lys Asn Glu Glu Pro Ser Ser Asn His Ile Pro His Gly Lys
        230                 235                 240

Glu Gln Ile Lys Arg Gly Gly Asp Ala Gly Met Pro Gly Ile Glu
        245                 250                 255

Glu Asn Asp Leu Ala Lys Val Asp Asp Leu Pro Pro Ala Leu Arg
        260                 265                 270

Lys Pro Pro Ile Ser Val Ser Gln His Glu Ser His Gln Ala Ile
        275                 280                 285

Ser His Leu Pro Thr Gly Gln Pro Leu Ser Pro Asn Met Pro Pro
        290                 295                 300

Asp Ser His Ile Asn His Asn Gly Asn Pro Gly Thr Ser Lys Gln
        305                 310                 315

Asn Pro Ser Ser Pro Leu Gln Arg Leu Ile Pro Gly Ser Asn Leu
        320                 325                 330

Asp Ser Glu Pro Arg Ile Gln Thr Asp Ile Leu Lys Gln Ala Thr
        335                 340                 345

Lys Asp Arg Val Ser Asp Phe His Lys Leu Lys Gln Asn Asp Glu
        350                 355                 360

Glu Arg Glu Leu Gln Met Asp Pro Ala Asp Tyr Gly Lys Gln His
        365                 370                 375

Phe Asn Asp Val Leu
        380

<210> SEQ ID NO 57
<211> LENGTH: 841
<212> TYPE: DNA
<213> ORGANISM: Homo Sapien
```

<400> SEQUENCE: 57

```
ggatgggcga gcagtctgaa tgccagaatg gataaccgtt ttgctacagc        50
atttgtaatt gcttgtgtgc ttagcctcat ttccaccatc tacatggcag       100
cctccattgg cacagacttc tggtatgaat atcgaagtcc agttcaagaa       150
aattccagtg atttgaataa aagcatctgg gatgaattca ttagtgatga       200
ggcagatgaa aagacttata atgatgcact ttttcgatac aatggcacag       250
tgggattgtg gagacggtgt atcaccatac ccaaaaacat gcattggtat       300
agcccaccag aaaggacaga gtcatttgat gtggtcacaa aatgtgtgag       350
tttcacacta actgagcagt tcatggagaa atttgttgat cccggaaacc       400
acaatagcgg gattgatctc cttaggacct atctttggcg ttgccagttc       450
cttttacctt ttgtgagttt aggtttgatg tgctttgggg ctttgatcgg       500
actttgtgct tgcatttgcc gaagcttata tcccaccatt gccacgggca       550
ttctccatct ccttgcagat accatgctgt gaagtccagg ccacatggag       600
gtgtcctgtg tagatgctcc agctgaaatc ccaagctaag ctcccaactg       650
acagccaaca tcatttccag ccatgtgtgg gagccatcct ggatgtccag       700
ccttaacaag cctcagagg acttcagcca cagctatatt cttactacat        750
ccttgtgaga ctctaataaa gaaccaacta gctgagccca atcaacctat       800
ggaactgata gaaataaaat gaattgttgt tttgtgccgt t                841
```

<210> SEQ ID NO 58
<211> LENGTH: 184
<212> TYPE: PRT
<213> ORGANISM: Homo Sapien

<400> SEQUENCE: 58

```
Met Asp Asn Arg Phe Ala Thr Ala Phe Val Ile Ala Cys Val Leu
  1               5                  10                  15

Ser Leu Ile Ser Thr Ile Tyr Met Ala Ala Ser Ile Gly Thr Asp
                 20                  25                  30

Phe Trp Tyr Glu Tyr Arg Ser Pro Val Gln Glu Asn Ser Ser Asp
                 35                  40                  45

Leu Asn Lys Ser Ile Trp Asp Glu Phe Ile Ser Asp Glu Ala Asp
                 50                  55                  60

Glu Lys Thr Tyr Asn Asp Ala Leu Phe Arg Tyr Asn Gly Thr Val
                 65                  70                  75

Gly Leu Trp Arg Arg Cys Ile Thr Ile Pro Lys Asn Met His Trp
                 80                  85                  90

Tyr Ser Pro Pro Glu Arg Thr Glu Ser Phe Asp Val Val Thr Lys
                 95                 100                 105

Cys Val Ser Phe Thr Leu Thr Glu Gln Phe Met Glu Lys Phe Val
                110                 115                 120

Asp Pro Gly Asn His Asn Ser Gly Ile Asp Leu Leu Arg Thr Tyr
                125                 130                 135

Leu Trp Arg Cys Gln Phe Leu Leu Pro Phe Val Ser Leu Gly Leu
                140                 145                 150

Met Cys Phe Gly Ala Leu Ile Gly Leu Cys Ala Cys Ile Cys Arg
                155                 160                 165

Ser Leu Tyr Pro Thr Ile Ala Thr Gly Ile Leu His Leu Leu Ala
                170                 175                 180
```

Asp Thr Met Leu

<210> SEQ ID NO 59
<211> LENGTH: 997
<212> TYPE: DNA
<213> ORGANISM: Homo Sapien

<400> SEQUENCE: 59

| | | | | | |
|---|---|---|---|---|---|
| gcgtggacac | cacctcagcc | cactgagcag | gagtcacagc | acgaagacca | 50 |
| agcgcaaagc | gacccctgcc | ctccatcctg | actgctcctc | ctaagagaga | 100 |
| tggcaccggc | cagagcagga | ttctgccccc | ttctgctgct | tctgctgctg | 150 |
| gggctgtggg | tggcagagat | cccagtcagt | gccaagccca | agggcatgac | 200 |
| ctcatcacag | tggtttaaaa | ttcagcacat | gcagcccagc | cctcaagcat | 250 |
| gcaactcagc | catgaaaaac | attaacaagc | acacaaaacg | gtgcaaagac | 300 |
| ctcaacacct | tcctgcacga | gcctttctcc | agtgtggccg | ccacctgcca | 350 |
| gacccccaaa | atagcctgca | agaatggcga | taaaaactgc | caccagagcc | 400 |
| acgggcccgt | gtccctgacc | atgtgtaagc | tcacctcagg | gaagtatccg | 450 |
| aactgcaggt | acaaagagaa | gcgacagaac | aagtcttacg | tagtggcctg | 500 |
| taagcctccc | cagaaaaagg | actctcagca | attccacctg | gttcctgtac | 550 |
| acttggacag | agtcctttag | gtttccagac | tggcttgctc | tttggctgac | 600 |
| cttcaattcc | ctctccagga | ctccgcacca | ctcccctaca | cccagagcat | 650 |
| tctcttcccc | tcatctcttg | gggctgttcc | tggttcagcc | tctgctggga | 700 |
| ggctgaagct | gacactctgg | tgagctgagc | tctagaggga | tggcttttca | 750 |
| tcttttgtt | gctgttttcc | cagatgctta | tccccaagaa | acagcaagct | 800 |
| caggtctgtg | ggttccctgg | tctatgccat | tgcacatgtc | tcccctgccc | 850 |
| cctggcatta | gggcagcatg | acaaggagag | gaaataaatg | gaaggggggc | 900 |
| aaaaaaaaaa | aaaaaaaaaa | aaaaaaaaaa | aaaaaaaaaa | aaaaaaaaaa | 950 |
| aaaaaaaaaa | aaaaaaaaaa | aaaaaaaaaa | aaaaaaaaaa | aaaaaaa | 997 |

<210> SEQ ID NO 60
<211> LENGTH: 156
<212> TYPE: PRT
<213> ORGANISM: Homo Sapien

<400> SEQUENCE: 60

Met Ala Pro Ala Arg Ala Gly Phe Cys Pro Leu Leu Leu Leu
 1               5                  10                  15

Leu Leu Gly Leu Trp Val Ala Glu Ile Pro Val Ser Ala Lys Pro
                20                  25                  30

Lys Gly Met Thr Ser Ser Gln Trp Phe Lys Ile Gln His Met Gln
                35                  40                  45

Pro Ser Pro Gln Ala Cys Asn Ser Ala Met Lys Asn Ile Asn Lys
                50                  55                  60

His Thr Lys Arg Cys Lys Asp Leu Asn Thr Phe Leu His Glu Pro
                65                  70                  75

Phe Ser Ser Val Ala Ala Thr Cys Gln Thr Pro Lys Ile Ala Cys
                80                  85                  90

Lys Asn Gly Asp Lys Asn Cys His Gln Ser His Gly Pro Val Ser
                95                  100                 105

```
Leu Thr Met Cys Lys Leu Thr Ser Gly Lys Tyr Pro Asn Cys Arg
                110                 115                 120

Tyr Lys Glu Lys Arg Gln Asn Lys Ser Tyr Val Val Ala Cys Lys
                125                 130                 135

Pro Pro Gln Lys Lys Asp Ser Gln Gln Phe His Leu Val Pro Val
                140                 145                 150

His Leu Asp Arg Val Leu
                155

<210> SEQ ID NO 61
<211> LENGTH: 520
<212> TYPE: DNA
<213> ORGANISM: Homo Sapien

<400> SEQUENCE: 61
cgggtcatgc gccgccgcct gtggctgggc ctggcctggc tgctgctggc          50
gcgggcgccg gacgccgcgg gaaccccgag cgcgtcgcgg ggaccgcgca         100
gctacccgca cctggagggc gacgtgcgct ggcggcgcct cttctcctcc         150
actcacttct tcctgcgcgt ggatcccggc ggccgcgtgc agggcacccg         200
ctggcgccac ggccaggaca gcatcctgga gatccgctct gtacacgtgg         250
gcgtcgtggt catcaaagca gtgtcctcag gcttctacgt ggccatgaac         300
cgccggggcc gcctctacgg gtcgcgactc tacaccgtgg actgcaggtt         350
ccgggagcgc atcgaagaga acggccacaa cacctacgcc tcacagcgct         400
ggcgccgccg cggccagccc atgttcctgg cgctggacag aggggggggg         450
ccccggccag gcggccggac gcggcggtac cacctgtccg cccacttcct         500
gcccgtcctg gtctcctgag                                          520

<210> SEQ ID NO 62
<211> LENGTH: 170
<212> TYPE: PRT
<213> ORGANISM: Homo Sapien

<400> SEQUENCE: 62

Met Arg Arg Arg Leu Trp Leu Gly Leu Ala Trp Leu Leu Leu Ala
  1                 5                  10                  15

Arg Ala Pro Asp Ala Ala Gly Thr Pro Ser Ala Ser Arg Gly Pro
                 20                  25                  30

Arg Ser Tyr Pro His Leu Glu Gly Asp Val Arg Trp Arg Arg Leu
                 35                  40                  45

Phe Ser Ser Thr His Phe Phe Leu Arg Val Asp Pro Gly Gly Arg
                 50                  55                  60

Val Gln Gly Thr Arg Trp Arg His Gly Gln Asp Ser Ile Leu Glu
                 65                  70                  75

Ile Arg Ser Val His Val Gly Val Val Ile Lys Ala Val Ser
                 80                  85                  90

Ser Gly Phe Tyr Val Ala Met Asn Arg Gly Arg Leu Tyr Gly
                 95                 100                 105

Ser Arg Leu Tyr Thr Val Asp Cys Arg Phe Arg Glu Arg Ile Glu
                110                 115                 120

Glu Asn Gly His Asn Thr Tyr Ala Ser Gln Arg Trp Arg Arg Arg
                125                 130                 135

Gly Gln Pro Met Phe Leu Ala Leu Asp Arg Arg Gly Gly Pro Arg
```

```
                   140                 145                 150
     Pro Gly Gly Arg Thr Arg Arg Tyr His Leu Ser Ala His Phe Leu
                   155                 160                 165
     Pro Val Leu Val Ser
                   170

<210> SEQ ID NO 63
<211> LENGTH: 2329
<212> TYPE: DNA
<213> ORGANISM: Homo Sapien

<400> SEQUENCE: 63
atccctcgac ctcgacccac gcgtccgctg gaaggtggcg tgccctcctc            50
tggctggtac catgcagctc ccactggccc tgtgtctcgt ctgcctgctg           100
gtacacacag ccttccgtgt agtggagggc caggggtggc aggcgttcaa           150
gaatgatgcc acgaaaatca tccccgagct cggagagtac cccgagcctc           200
caccggagct ggagaacaac aagaccatga accgggcgga aacggagggg           250
cggcctcccc accacccctt tgagaccaaa gacgtgtccg agtacagctg           300
ccgcgagctg cacttcaccc gctacgtgac cgatgggccg tgccgcagcg           350
ccaagccggt caccgagctg gtgtgctccg gccagtgcgg cccggcgcgc           400
ctgctgccca cgccatcgg ccgcggcaag tggtggcgac ctagtgggcc            450
cgacttccgc tgcatccccg accgctaccg cgcgcagcgc gtgcagctgc           500
tgtgtcccgg tggtgaggcg ccgcgcgcgc gcaaggtgcg cctggtggcc           550
tcgtgcaagt gcaagcgcct caccgcttc cacaaccagt cggagctcaa            600
ggacttcggg accgaggccg ctcggccgca gaagggccgg aagccgcggc           650
cccgcgcccg gagcgccaaa gccaaccagg ccgagctgga aacgcctac             700 tagagcccgc ccgcgcccct ccccaccggc gggcgccccg gccctgaacc           750
cgcgccccac atttctgtcc tctgcgcgtg gtttgattgt ttatatttca           800
ttgtaaatgc ctgcaaccca gggcagggg ctgagacctt ccaggccctg            850
aggaatcccg ggcgccggca aggccccct cagcccgcca gctgaggggt            900
cccacggggc aggggaggga attgagagtc acagacactg agccacgcag           950
ccccgcctct ggggccgcct acctttgctg gtcccacttc agaggaggca          1000
gaaatggaag cattttcacc gccctgggt tttaagggag cggtgtggga           1050
gtgggaaagt ccagggactg gttaagaaag ttggataaga ttccccttg            1100 cacctcgctg cccatcagaa agcctgaggc gtgcccagag cacaagactg          1150
ggggcaactg tagatgtggt ttctagtcct ggctctgcca ctaacttcct          1200
gtgtaacctt gaactacaca attctccttc gggacctcaa tttccacttt          1250
gtaaaatgag ggtggaggtg ggaataggat ctcgaggaga ctattggcat          1300
atgattccaa ggactccagt gccttttgaa tgggcagagg tgagagagag          1350
agagagaaag agagagaatg aatgcagttg cattgattca gtgccaaggt          1400
cacttccaga attcagagtt gtgatgctct cttctgacag ccaaagatga          1450
aaaacaaaca gaaaaaaaaa agtaaagagt ctatttatgg ctgacatatt          1500 tacgctgac aaactcctgg aagaagctat gctgcttccc agcctggctt           1550
ccccggatgt ttggctacct ccacccctcc atctcaaaga aataacatca          1600
```

```
tccattgggg tagaaaagga gagggtccga gggtggtggg agggatagaa         1650
atcacatccg ccccaacttc ccaaagagca gcatccctcc cccgacccat         1700
agccatgttt taaagtcacc ttccgaagag aagtgaaagg ttcaaggaca         1750
ctggccttgc aggcccgagg gagcagccat cacaaactca cagaccagca         1800 catcccttt  gagacaccgc cttctgccca ccactcacgg acacatttct         1850
gcctagaaaa cagcttctta ctgctcttac atgtgatggc atatcttaca         1900
ctaaaagaat attattgggg gaaaaactac aagtgctgta catatgctga         1950
gaaactgcag agcataatag ctgccaccca aaatcttt  tgaaaatcat          2000 ttccagacaa cctcttactt tctgtgtagt ttttaattgt taaaaaaaaa         2050 aagtttaaa  cagaagcaca tgacatatga aagcctgcag gactggtcgt         2100
ttttttggca attcttccac gtgggacttg tccacaagaa tgaaagtagt         2150 ggttttaaa  gagttaagtt acatatttat tttctcactt aagttattta         2200
tgcaaaagtt tttcttgtag agaatgacaa tgttaatatt gctttatgaa         2250
ttaacagtct gttcttccag agtccagaga cattgttaat aaagacaatg         2300
aatcatgaaa aaaaaaaaa  aaaaaaaa                                 2329
```

<210> SEQ ID NO 64
<211> LENGTH: 213
<212> TYPE: PRT
<213> ORGANISM: Homo Sapien

<400> SEQUENCE: 64

```
Met Gln Leu Pro Leu Ala Leu Cys Leu Val Cys Leu Leu Val His
 1               5                  10                  15

Thr Ala Phe Arg Val Val Glu Gly Gln Gly Trp Gln Ala Phe Lys
            20                  25                  30

Asn Asp Ala Thr Glu Ile Ile Pro Glu Leu Gly Glu Tyr Pro Glu
            35                  40                  45

Pro Pro Pro Glu Leu Glu Asn Asn Lys Thr Met Asn Arg Ala Glu
            50                  55                  60

Asn Gly Gly Arg Pro Pro His His Pro Phe Glu Thr Lys Asp Val
            65                  70                  75

Ser Glu Tyr Ser Cys Arg Glu Leu His Phe Thr Arg Tyr Val Thr
            80                  85                  90

Asp Gly Pro Cys Arg Ser Ala Lys Pro Val Thr Glu Leu Val Cys
            95                 100                 105

Ser Gly Gln Cys Gly Pro Ala Arg Leu Leu Pro Asn Ala Ile Gly
           110                 115                 120

Arg Gly Lys Trp Trp Arg Pro Ser Gly Pro Asp Phe Arg Cys Ile
           125                 130                 135

Pro Asp Arg Tyr Arg Ala Gln Arg Val Gln Leu Leu Cys Pro Gly
           140                 145                 150

Gly Glu Ala Pro Arg Ala Arg Lys Val Arg Leu Val Ala Ser Cys
           155                 160                 165

Lys Cys Lys Arg Leu Thr Arg Phe His Asn Gln Ser Glu Leu Lys
           170                 175                 180

Asp Phe Gly Thr Glu Ala Ala Arg Pro Gln Lys Gly Arg Lys Pro
           185                 190                 195

Arg Pro Arg Ala Arg Ser Ala Lys Ala Asn Gln Ala Glu Leu Glu
```

Asn Ala Tyr

<210> SEQ ID NO 65
<211> LENGTH: 2663
<212> TYPE: DNA
<213> ORGANISM: Homo Sapien

<400> SEQUENCE: 65

| | | | | |
|---|---|---|---|---|
| cccactcggc | ggtttggcgg | gagggagggg | ctttgcgcag | gccccgctcc | 50 |
| cgccccgcct | ccatgcggcc | cgccccgatt | gcgctgtggc | tgcgcctggt | 100 |
| cttggccctg | gccttgtcc | gccccgggc | tgtggggtgg | gccccggtcc | 150 |
| gagccccat | ctatgtcagc | agctgggccg | tccaggtgtc | ccagggtaac | 200 |
| cgggaggtcg | agcgcctggc | acgcaaattc | ggcttcgtca | acctggggcc | 250 |
| gatcttctct | gacgggcagt | actttcacct | gcggcaccgg | ggcgtggtcc | 300 |
| agcagtccct | gaccccgcac | tggggccacc | gcctgcacct | gaagaaaaac | 350 |
| cccaaggtgc | agtggttcca | gcagcagacg | ctgcagcggc | gggtgaaacg | 400 |
| ctctgtcgtg | gtgcccacgg | accctggtt | ctccaagcag | tggtacatga | 450 |
| acagcgaggc | ccaaccagac | ctgagcatcc | tgcaggcctg | gagtcagggg | 500 |
| ctgtcaggcc | agggcatcgt | ggtctctgtg | ctggacgatg | catcgagaa | 550 |
| ggaccacccg | gacctctggg | ccaactacga | ccccctggcc | agctatgact | 600 |
| tcaatgacta | cgacccggac | ccccagcccc | gctacacccc | cagcaaagag | 650 |
| aaccggcacg | ggacccgctg | tgctggggag | gtggccgcga | tggccaacaa | 700 |
| tggcttctgt | ggtgtggggg | tcgctttcaa | cgcccgaatc | ggaggcgtac | 750 |
| ggatgctgga | cggtaccatc | accgatgtca | tcgaggccca | gtcgctgagc | 800 |
| ctgcagccgc | agcacatcca | catttacagc | gccagctggg | gtcccgagga | 850 |
| cgacggccgc | acggtggacg | gccccggcat | cctcacccgc | gaggccttcc | 900 |
| ggcgtggtgt | gaccaagggc | cgcggcgggc | tgggcacgct | cttcatctgg | 950 |
| gcctcgggca | acggcggcct | gcactacgac | aactgcaact | gcgacggcta | 1000 |
| caccaacagc | atccacacgc | tttccgtggg | cagcaccacc | cagcagggcc | 1050 |
| gcgtgccctg | gtacagcgaa | gcctgcgcct | ccaccctcac | caccacctac | 1100 |
| agcagcggcg | tggccaccga | ccccagatc | gtcaccacgg | acctgcatca | 1150 |
| cgggtgcaca | gaccagcaca | cgggcacctc | ggcctcagcc | ccactggcgg | 1200 |
| ccggcatgat | cgccctagcg | ctggaggcca | acccgttcct | gacgtggaga | 1250 |
| gacatgcagc | acctggtggt | ccgcgcgtcc | aagccggcgc | acctgcaggc | 1300 |
| cgaggactgg | aggaccaacg | gcgtggggcg | ccaagtgagc | catcactacg | 1350 |
| gatacgggct | gctggacgcc | gggctgctgg | tggacaccgc | ccgcacctgg | 1400 |
| ctgcccaccc | agccgcagag | gaagtgcgcc | gtccgggtcc | agagccgccc | 1450 |
| cacccccatc | ctgccgctga | tctacatcag | ggaaaacgta | tcggcctgcg | 1500 |
| ccggcctcca | caactccatc | cgctcgctgg | agcacgtgca | ggcgcagctg | 1550 |
| acgctgtcct | acagccggcg | cggagacctg | gagatctcgc | tcaccagccc | 1600 |
| catgggcacg | cgctccacac | tcgtggccat | acgacccttg | gacgtcagca | 1650 |
| ctgaaggcta | caacaactgg | gtcttcatgt | ccacccactt | ctgggatgag | 1700 |

-continued

| | |
|---|---|
| aacccacagg gcgtgtggac cctgggccta gagaacaagg gctactattt | 1750 |
| caacacgggg acgttgtacc gctacacgct gctgctctat gggacggccg | 1800 |
| aggacatgac agcgcggcct acaggccccc aggtgaccag cagcgcgtgt | 1850 |
| gtgcagcggg acacagaggg gctgtgccag gcgtgtgacg gccccgccta | 1900 |
| catcctggga cagctctgcc tggcctactg ccccccgcgg ttcttcaacc | 1950 |
| acacaaggct ggtgaccgct gggcctgggc acacggcggc gcccgcgctg | 2000 |
| agggtctgct ccagctgcca tgcctcctgc tacacctgcc gcggcggctc | 2050 |
| cccgagggac tgcacctcct gtcccccatc ctccacgctg accagcagc | 2100 |
| agggctcctg catgggaccc accaccccg acagccgccc ccggcttaga | 2150 |
| gctgccgcct gtccccacca ccgctgccca gcctcggcca tggtgctgag | 2200 |
| cctcctggcc gtgaccctcg gaggccccgt cctctgcggc atgtccatgg | 2250 |
| acctcccact atacgcctgg ctctcccgtg ccagggccac cccaccaaa | 2300 |
| ccccaggtct ggctgccagc tggaacctga agttgtcagc tcagaaagcg | 2350 |
| accttgcccc cgcctgggtc cctgacaggc actgctgcca tgctgcctcc | 2400 |
| ccaggctggc cccagaggag cgagcaccag cacccgacgc ctggcctgcc | 2450 |
| agggatgggc cccgtggaac cccgaagcct ggcgggagag agagagagag | 2500 |
| aagtctcctc tgcattttgg gtttgggcag gagtgggctg gggggagagg | 2550 |
| ctggagcacc ccaaaagcca ggggaaagtg gagggagaga acgtgacac | 2600 |
| tgtccgtctc gggcaccgcg tccaacctca gagtttgcaa ataaaggttg | 2650 |
| cttagaaggt gaa | 2663 |

<210> SEQ ID NO 66
<211> LENGTH: 755
<212> TYPE: PRT
<213> ORGANISM: Homo Sapien

<400> SEQUENCE: 66

Met Arg Pro Ala Pro Ile Ala Leu Trp Leu Arg Leu Val Leu Ala
1               5                   10                  15

Leu Ala Leu Val Arg Pro Arg Ala Val Gly Trp Ala Pro Val Arg
                20                  25                  30

Ala Pro Ile Tyr Val Ser Ser Trp Ala Gln Val Ser Gln Gly
                35                  40                  45

Asn Arg Glu Val Glu Arg Leu Ala Arg Lys Phe Gly Phe Val Asn
                50                  55                  60

Leu Gly Pro Ile Phe Ser Asp Gly Gln Tyr Phe His Leu Arg His
                65                  70                  75

Arg Gly Val Val Gln Gln Ser Leu Thr Pro His Trp Gly His Arg
                80                  85                  90

Leu His Leu Lys Lys Asn Pro Lys Val Gln Trp Phe Gln Gln Gln
                95                  100                 105

Thr Leu Gln Arg Arg Val Lys Arg Ser Val Val Pro Thr Asp
                110                 115                 120

Pro Trp Phe Ser Lys Gln Trp Tyr Met Asn Ser Glu Ala Gln Pro
                125                 130                 135

Asp Leu Ser Ile Leu Gln Ala Trp Ser Gln Gly Leu Ser Gly Gln
                140                 145                 150

-continued

```
Gly Ile Val Val Ser Val Leu Asp Asp Gly Ile Glu Lys Asp His
            155                 160                 165

Pro Asp Leu Trp Ala Asn Tyr Asp Pro Leu Ala Ser Tyr Asp Phe
            170                 175                 180

Asn Asp Tyr Asp Pro Asp Pro Gln Pro Arg Tyr Thr Pro Ser Lys
            185                 190                 195

Glu Asn Arg His Gly Thr Arg Cys Ala Gly Glu Val Ala Ala Met
            200                 205                 210

Ala Asn Asn Gly Phe Cys Gly Val Gly Val Ala Phe Asn Ala Arg
            215                 220                 225

Ile Gly Gly Val Arg Met Leu Asp Gly Thr Ile Thr Asp Val Ile
            230                 235                 240

Glu Ala Gln Ser Leu Ser Leu Gln Pro Gln His Ile His Ile Tyr
            245                 250                 255

Ser Ala Ser Trp Gly Pro Glu Asp Asp Gly Arg Thr Val Asp Gly
            260                 265                 270

Pro Gly Ile Leu Thr Arg Glu Ala Phe Arg Arg Gly Val Thr Lys
            275                 280                 285

Gly Arg Gly Gly Leu Gly Thr Leu Phe Ile Trp Ala Ser Gly Asn
            290                 295                 300

Gly Gly Leu His Tyr Asp Asn Cys Asn Cys Asp Gly Tyr Thr Asn
            305                 310                 315

Ser Ile His Thr Leu Ser Val Gly Ser Thr Thr Gln Gln Gly Arg
            320                 325                 330

Val Pro Trp Tyr Ser Glu Ala Cys Ala Ser Thr Leu Thr Thr Thr
            335                 340                 345

Tyr Ser Ser Gly Val Ala Thr Asp Pro Gln Ile Val Thr Thr Asp
            350                 355                 360

Leu His His Gly Cys Thr Asp Gln His Thr Gly Thr Ser Ala Ser
            365                 370                 375

Ala Pro Leu Ala Ala Gly Met Ile Ala Leu Ala Leu Glu Ala Asn
            380                 385                 390

Pro Phe Leu Thr Trp Arg Asp Met Gln His Leu Val Val Arg Ala
            395                 400                 405

Ser Lys Pro Ala His Leu Gln Ala Glu Asp Trp Arg Thr Asn Gly
            410                 415                 420

Val Gly Arg Gln Val Ser His His Tyr Gly Tyr Gly Leu Leu Asp
            425                 430                 435

Ala Gly Leu Leu Val Asp Thr Ala Arg Thr Trp Leu Pro Thr Gln
            440                 445                 450

Pro Gln Arg Lys Cys Ala Val Arg Val Gln Ser Arg Pro Thr Pro
            455                 460                 465

Ile Leu Pro Leu Ile Tyr Ile Arg Glu Asn Val Ser Ala Cys Ala
            470                 475                 480

Gly Leu His Asn Ser Ile Arg Ser Leu Glu His Val Gln Ala Gln
            485                 490                 495

Leu Thr Leu Ser Tyr Ser Arg Arg Gly Asp Leu Glu Ile Ser Leu
            500                 505                 510

Thr Ser Pro Met Gly Thr Arg Ser Thr Leu Val Ala Ile Arg Pro
            515                 520                 525

Leu Asp Val Ser Thr Glu Gly Tyr Asn Asn Trp Val Phe Met Ser
            530                 535                 540

Thr His Phe Trp Asp Glu Asn Pro Gln Gly Val Trp Thr Leu Gly
```

```
                545                 550                 555

Leu Glu Asn Lys Gly Tyr Tyr Phe Asn Thr Gly Thr Leu Tyr Arg
            560                 565                 570

Tyr Thr Leu Leu Tyr Gly Thr Ala Glu Asp Met Thr Ala Arg
        575                 580                 585

Pro Thr Gly Pro Gln Val Thr Ser Ser Ala Cys Val Gln Arg Asp
            590                 595                 600

Thr Glu Gly Leu Cys Gln Ala Cys Asp Gly Pro Ala Tyr Ile Leu
            605                 610                 615

Gly Gln Leu Cys Leu Ala Tyr Cys Pro Pro Arg Phe Phe Asn His
            620                 625                 630

Thr Arg Leu Val Thr Ala Gly Pro Gly His Thr Ala Ala Pro Ala
            635                 640                 645

Leu Arg Val Cys Ser Ser Cys His Ala Ser Cys Tyr Thr Cys Arg
            650                 655                 660

Gly Gly Ser Pro Arg Asp Cys Thr Ser Cys Pro Pro Ser Ser Thr
            665                 670                 675

Leu Asp Gln Gln Gln Gly Ser Cys Met Gly Pro Thr Thr Pro Asp
            680                 685                 690

Ser Arg Pro Arg Leu Arg Ala Ala Cys Pro His His Arg Cys
            695                 700                 705

Pro Ala Ser Ala Met Val Leu Ser Leu Leu Ala Val Thr Leu Gly
            710                 715                 720

Gly Pro Val Leu Cys Gly Met Ser Met Asp Leu Pro Leu Tyr Ala
            725                 730                 735

Trp Leu Ser Arg Ala Arg Ala Thr Pro Thr Lys Pro Gln Val Trp
            740                 745                 750

Leu Pro Ala Gly Thr
            755

<210> SEQ ID NO 67
<211> LENGTH: 332
<212> TYPE: DNA
<213> ORGANISM: Homo Sapien

<400> SEQUENCE: 67
atgaggaagc tccagggcag gatggtttac ctgcctggac agcaagatga          50
tggctacact agcccccatt ctctgggcgc ctggatttgc ccaccagatc         100
tcctcacctc ttgcccttca cctcctgctg tacctacaag gtctccccga         150
ttctcatctg cccataatca tggacacagc cccaggatgt gcaggactct         200
cagggaccat ctggagttcc agctggaatc tgggcctggt ggagtgggag         250
tggggcaggg gcctgcattg ggctgactta gagagcacag ttattccatc         300
catatggaaa taaacatttt ggattcctga tc                            332

<210> SEQ ID NO 68
<211> LENGTH: 88
<212> TYPE: PRT
<213> ORGANISM: Homo Sapien

<400> SEQUENCE: 68

Met Met Ala Thr Leu Ala Pro Ile Leu Trp Ala Pro Gly Phe Ala
  1               5                  10                  15

His Gln Ile Ser Ser Pro Leu Ala Leu His Leu Leu Leu Tyr Leu
                20                  25                  30
```

```
Gln Gly Leu Pro Asp Ser His Leu Pro Ile Ile Met Asp Thr Ala
            35                  40                  45

Pro Gly Cys Ala Gly Leu Ser Gly Thr Ile Trp Ser Ser Trp
        50                  55                  60

Asn Leu Gly Leu Val Glu Trp Glu Trp Gly Arg Gly Leu His Trp
65                  70                  75

Ala Asp Leu Glu Ser Thr Val Ile Pro Ser Ile Trp Lys
            80                  85

<210> SEQ ID NO 69
<211> LENGTH: 1302
<212> TYPE: DNA
<213> ORGANISM: Homo Sapien
<220> FEATURE:
<221> NAME/KEY: unsure
<222> LOCATION: 1218-1253
<223> OTHER INFORMATION: unknown base

<400> SEQUENCE: 69
tttgcagtgg ggtcctcctc tggcctcctg cccctcctgc tgctgctgct              50
gcttccattg ctggcagccc agggtggggg tggcctgcag gcagcgctgc             100
tggcccttga ggtggggctg gtgggtctgg gggcctccta cctgctcctt             150
tgtacagccc tgcacctgcc ctccagtctt ttcctactcc tggcccaggg             200
taccgcactg ggggccgtcc tgggcctgag ctggcgccga ggcctcatgg             250
gtgttcccct gggccttgga gctgcctggc tcttagcttg ccaggcccta             300
gctctacctc tggtggctat ggcagcgggg ggcagatggg tgcggcagca             350 gggccccegg gtgcgccggg gcatatctcg actctggttg cgggttctgc             400
tgcgcctgtc acccatggcc ttccgggccc tgcagggctg tggggctgtg             450
ggggaccggg gtctgtttgc actgtacccc aaaaccaaca aggatggctt             500
ccgcagccgc ctgcccgtcc ctgggccccg gcggcgtaat cccgcacca              550 cccaacaccc attagctctg ttggcaaggg tctgggtcct gtgcaagggc             600
tggaactggc gtctggcacg ggccagccag ggtttagcat cccacttgcc             650
cccgtgggcc atccacacac tggccagctg ggcctgctt cggggtgaac              700 ggcccacccg aatccccegg ctactaccac gcagccagcg ccagctaggg             750 cccccctgcct cccgccagcc actgccaggg actctagccg gcggaggtc             800 acgcacccgc cagtcccggg ccctgccccc ctggaggtag ctgactccag             850
cccttccagc ccaaatctag agcattgagc actttatctc ccacgactca             900
gtgaagtttc tccagtccct agtcctctct tttcacccac cttcctcagt             950
ttgctcactt accccaggcc cagcccttcg gacctctaga caggcagcct            1000
cctcagctgt ggagtccagc agtcactctg tgttctcctg gcgctcctcc            1050
cctaagttat tgctgttcgc ccgctgtgtg tgctcatcct caccctcatt            1100
gactcaggcc tggggccagg ggtggtggag ggtgggaaga gtcatgtttt            1150
ttttctcctc tttgattttg tttttctgtc tcccttccaa cctgtcccct            1200 tcccccacc aaaaaaannn nnnnnnnnnn nnnnnnnnnn nnnnnnnnnn             1250
nnnaaaaaaa aaaaaaaaaa aaaaaaaaaa aaaaaaaaaa aaaaaaaaaa            1300
aa                                                                1302
```

```
<210> SEQ ID NO 70
<211> LENGTH: 197
<212> TYPE: PRT
<213> ORGANISM: Homo Sapien

<400> SEQUENCE: 70

Met Gly Val Pro Leu Gly Leu Gly Ala Ala Trp Leu Leu Ala Trp
 1               5                  10                  15

Pro Gly Leu Ala Leu Pro Leu Val Ala Met Ala Ala Gly Gly Arg
                20                  25                  30

Trp Val Arg Gln Gln Gly Pro Arg Val Arg Arg Gly Ile Ser Arg
            35                  40                  45

Leu Trp Leu Arg Val Leu Leu Arg Leu Ser Pro Met Ala Phe Arg
        50                  55                  60

Ala Leu Gln Gly Cys Gly Ala Val Gly Asp Arg Gly Leu Phe Ala
    65                  70                  75

Leu Tyr Pro Lys Thr Asn Lys Asp Gly Phe Arg Ser Arg Leu Pro
        80                  85                  90

Val Pro Gly Pro Arg Arg Arg Asn Pro Arg Thr Thr Gln His Pro
            95                 100                 105

Leu Ala Leu Leu Ala Arg Val Trp Val Leu Cys Lys Gly Trp Asn
               110                 115                 120

Trp Arg Leu Ala Arg Ala Ser Gln Gly Leu Ala Ser His Leu Pro
           125                 130                 135

Pro Trp Ala Ile His Thr Leu Ala Ser Trp Gly Leu Leu Arg Gly
       140                 145                 150

Glu Arg Pro Thr Arg Ile Pro Arg Leu Leu Pro Arg Ser Gln Arg
           155                 160                 165

Gln Leu Gly Pro Pro Ala Ser Arg Gln Pro Leu Pro Gly Thr Leu
           170                 175                 180

Ala Gly Arg Arg Ser Arg Thr Arg Gln Ser Arg Ala Leu Pro Pro
           185                 190                 195

Trp Arg

<210> SEQ ID NO 71
<211> LENGTH: 1976
<212> TYPE: DNA
<213> ORGANISM: Homo Sapien

<400> SEQUENCE: 71
gtttgggggt tgtttgggat tagtgaagct actgcctttg ccgccagcgc         50
agcctcagag tttgattatt tgcaatgtca ggctttgaaa acttaaacac        100
ggatttctac cagacaagtt acagcatcga tgatcagtca cagcagtcct        150
atgattatgg aggaagtgga ggaccctata gcaaacagta tgctggctat        200
gactattcgc agcaaggcag atttgtccct ccagacatga tgcagccaca        250
acagccatac accgggcaga tttaccagcc aactcaggca tatactccag        300
cttcacctca gcctttctat ggaaacaact ttgaggatga gccaccttta        350
ttagaagagt taggtatcaa ttttgaccac atctggcaaa aaacactaac        400
agtattacat ccgttaaaag tagcagatgg cagcatcatg aatgaaactg        450
atttggcagg tccaatggtt tttttgcctt cttttggagc cacattgcta        500
ctggctggca aaatccagtt tggctatgta tacgggatca gtgcaattgg        550
```

-continued

```
atgtctagga atgttttgtt tattaaactt aatgagtatg acaggtgttt           600
catttggttg tgtggcaagt gtccttggat attgtcttct gcccatgatc           650
ctactttcca gctttgcagt gatattttct ttgcaaggaa tggtaggaat           700
cattctcact gctgggatta ttggatggtg tagttttttct gcttccaaaa          750 tatttatttc tgcattagcc atggaaggac agcaacttt agtagcatat            800 ccttgcgctt tgttatatgg agtctttgcc ctgatttccg tcttttgaaa           850
atttatctgg gatgtggaca tcagtgggcc agatgtacaa aaaggacctt           900
gaactcttaa attggaccag caaactgctg cagcgcaact ctcatgcaga           950
tttacatttg actgttggag caatgaaagt aaacgtgtat ctcttgttca           1000
tttttataga acttttgcat actatattgg atttacctgc ggtgtgacta          1050
gctttaaatg tttgtgttta tacagataag aaatgctatt tctttctggt         1100
tcctgcagcc attgaaaaac cttttcctt gcaaattata atgtttttga          1150
tagattttta tcaactgtgg gaaaccaaac acaaagctga taacctttct         1200
taaaaacgac ccagtcacag taagaagac acaagacggc cgggcgtggt          1250
agctcacgcc tgtaatccca gcactttggg aggccgaggc gggcggatca         1300
caagggcagg agatcgagac catcctggtt aacacggtga aaccccgact         1350 ctactaaaaac tacaaaaaaa attagctggg cgtggtggcg ggcgcctgta         1400
gtcccagcta ctcaggaggc tgaggcagga gaagtgtgaa cccaggaggc         1450
ggagcttgca gtgagccgag atcacaccac tgcactccat ccagcctggg         1500
tgacagggtg agactctgtc tcaaaaaaaa aaaaaaagg agacacaaga          1550 cttactgcaa aaatatttt ccaaggattt aggaaagaaa aattgccttg         1600
tattctcaag tcaggtaact caaagcaaaa aagtgatcca aatgtagagt         1650
atgagtttgc actccaaaaa tttgacatta ctgtaaatta tctcatggaa         1700
tttttgctaa aattcagaga tacgggaagt tcacaatcta cctcattgta         1750
gacatgaaat gcgaacactt acttacatat taatgttaac tcaaccttag         1800
ggacctggaa tggttgcatt aatgctataa tcgttggatc gccacatttc         1850
ccaaaaataa taaaaaaatc actaacctt ttaaggaaa atatttaaag           1900 ttttacaaaa tcaatattg caattatcaa tgtaaagtac atttgaatgc          1950
ttattaaaac tttcccaatt aatttt                                    1976
```

<210> SEQ ID NO 72
<211> LENGTH: 257
<212> TYPE: PRT
<213> ORGANISM: Homo Sapien

<400> SEQUENCE: 72

```
Met Ser Gly Phe Glu Asn Leu Asn Thr Asp Phe Tyr Gln Thr Ser
  1               5                  10                  15

Tyr Ser Ile Asp Asp Gln Ser Gln Gln Ser Tyr Asp Tyr Gly Gly
                 20                  25                  30

Ser Gly Gly Pro Tyr Ser Lys Gln Tyr Ala Gly Tyr Asp Tyr Ser
                 35                  40                  45

Gln Gln Gly Arg Phe Val Pro Pro Asp Met Met Gln Pro Gln Gln
                 50                  55                  60

Pro Tyr Thr Gly Gln Ile Tyr Gln Pro Thr Gln Ala Tyr Thr Pro
```

```
                65                  70                  75
Ala Ser Pro Gln Pro Phe Tyr Gly Asn Asn Phe Glu Asp Glu Pro
                80                  85                  90

Pro Leu Leu Glu Glu Leu Gly Ile Asn Phe Asp His Ile Trp Gln
                95                 100                 105

Lys Thr Leu Thr Val Leu His Pro Leu Lys Val Ala Asp Gly Ser
               110                 115                 120

Ile Met Asn Glu Thr Asp Leu Ala Gly Pro Met Val Phe Cys Leu
               125                 130                 135

Ala Phe Gly Ala Thr Leu Leu Ala Gly Lys Ile Gln Phe Gly
               140                 145                 150

Tyr Val Tyr Gly Ile Ser Ala Ile Gly Cys Leu Gly Met Phe Cys
               155                 160                 165

Leu Leu Asn Leu Met Ser Met Thr Gly Val Ser Phe Gly Cys Val
               170                 175                 180

Ala Ser Val Leu Gly Tyr Cys Leu Leu Pro Met Ile Leu Leu Ser
               185                 190                 195

Ser Phe Ala Val Ile Phe Ser Leu Gln Gly Met Val Gly Ile Ile
               200                 205                 210

Leu Thr Ala Gly Ile Ile Gly Trp Cys Ser Phe Ser Ala Ser Lys
               215                 220                 225

Ile Phe Ile Ser Ala Leu Ala Met Glu Gly Gln Gln Leu Leu Val
               230                 235                 240

Ala Tyr Pro Cys Ala Leu Leu Tyr Gly Val Phe Ala Leu Ile Ser
               245                 250                 255

Val Phe

<210> SEQ ID NO 73
<211> LENGTH: 1285
<212> TYPE: DNA
<213> ORGANISM: Homo Sapien

<400> SEQUENCE: 73
acactggcca aaacgcggct cgccctcggc tgcgctcggc tcccgcgggc          50
gctcggcccc gagcccctcc tccccctacc cgccggccgg acagggagga         100
gccaatggct gggcctgcca tccacaccgc tcccatgctg ttcctcgtcc         150
tcctgctgcc ccagctgagc ctggcaggcg cccttgcacc tgggacccct         200
gcccggaacc tccctgagaa tcacattgac ctcccaggcc cagcgctgtg         250
gacgcctcag gccagccacc accgccggcg gggcccgggc aagaaggagt         300
ggggcccagg cctgcccagc caggcccagg atggggctgt ggtcaccgcc         350
accaggcagg cctccaggct gccagaggct gagggctgc tgcctgagca         400 gagtcctgca ggcctgctgc aggacaagga cctgctcctg ggactggcat        450
tgccctaccc cgagaaggag aacagacctc caggttggga gaggaccagg         500
aaacgcagca gggagcacaa gagacgcagg gacaggttga ggctgcacca         550
aggccgagcc ttggtccgag gtcccagctc cctgatgaag aaggcagagc         600
tctccgaagc ccaggtgctg gatgcagcca tggaggaatc ctccaccagc         650
ctggcgccca ccatgttctt tctcaccacc tttgaggcag cacctgccac         700
agaagagtcc ctgatcctgc ccgtcacctc cctgcggccc cagcaggcac         750
agcccaggtc tgacggggag gtgatgccca cgctggacat ggccttgttc         800
```

-continued

| | |
|---|---|
| gactggaccg attatgaaga cttaaaacct gatggttggc cctctgcaaa | 850 |
| gaagaaagag aaacaccgcg gtaaactctc cagtgatggt aacgaaacat | 900 |
| caccagccga aggggaacca tgcgaccatc accaagactg cctgccaggg | 950 |
| acttgctgcg acctgcggga gcatctctgc acaccccaca accgaggcct | 1000 |
| caacaacaaa tgcttcgatg actgcatgtg tgtggaaggg ctgcgctgct | 1050 |
| atgccaaatt ccaccggaac cgcagggtta cacggaggaa agggcgctgt | 1100 |
| gtggagcccg agacggccaa cggcgaccag ggatccttca tcaacgtcta | 1150 |
| gcggccccgc gggactgggg actgagccca ggaggtttgc acaagccggg | 1200 |
| cgatttgttt gtaactagca gtgggagatc aagttgggga acagatggct | 1250 |
| gaggctgcag actcaggccc aggacactca acccc | 1285 |

<210> SEQ ID NO 74
<211> LENGTH: 348
<212> TYPE: PRT
<213> ORGANISM: Homo Sapien

<400> SEQUENCE: 74

```
Met Ala Gly Pro Ala Ile His Thr Ala Pro Met Leu Phe Leu Val
  1               5                  10                  15

Leu Leu Pro Gln Leu Ser Leu Ala Gly Ala Leu Ala Pro Gly
             20                  25                  30

Thr Pro Ala Arg Asn Leu Pro Glu Asn His Ile Asp Leu Pro Gly
             35                  40                  45

Pro Ala Leu Trp Thr Pro Gln Ala Ser His His Arg Arg Arg Gly
             50                  55                  60

Pro Gly Lys Lys Glu Trp Gly Pro Gly Leu Pro Ser Gln Ala Gln
 65                  70                  75

Asp Gly Ala Val Val Thr Ala Thr Arg Gln Ala Ser Arg Leu Pro
             80                  85                  90

Glu Ala Glu Gly Leu Leu Pro Glu Gln Ser Pro Ala Gly Leu Leu
             95                 100                 105

Gln Asp Lys Asp Leu Leu Leu Gly Leu Ala Leu Pro Tyr Pro Glu
            110                 115                 120

Lys Glu Asn Arg Pro Pro Gly Trp Glu Arg Thr Arg Lys Arg Ser
            125                 130                 135

Arg Glu His Lys Arg Arg Arg Asp Arg Leu Arg Leu His Gln Gly
            140                 145                 150

Arg Ala Leu Val Arg Gly Pro Ser Ser Leu Met Lys Lys Ala Glu
            155                 160                 165

Leu Ser Glu Ala Gln Val Leu Asp Ala Met Glu Glu Ser Ser
            170                 175                 180

Thr Ser Leu Ala Pro Thr Met Phe Phe Leu Thr Thr Phe Glu Ala
            185                 190                 195

Ala Pro Ala Thr Glu Glu Ser Leu Ile Leu Pro Val Thr Ser Leu
            200                 205                 210

Arg Pro Gln Gln Ala Gln Pro Arg Ser Asp Gly Glu Val Met Pro
            215                 220                 225

Thr Leu Asp Met Ala Leu Phe Asp Trp Thr Asp Tyr Glu Asp Leu
            230                 235                 240

Lys Pro Asp Gly Trp Pro Ser Ala Lys Lys Glu Lys His Arg
            245                 250                 255
```

```
Gly Lys Leu Ser Ser Asp Gly Asn Glu Thr Ser Pro Ala Glu Gly
                260                 265                 270

Glu Pro Cys Asp His His Gln Asp Cys Leu Pro Gly Thr Cys Cys
                275                 280                 285

Asp Leu Arg Glu His Leu Cys Thr Pro His Asn Arg Gly Leu Asn
                290                 295                 300

Asn Lys Cys Phe Asp Asp Cys Met Cys Val Glu Gly Leu Arg Cys
                305                 310                 315

Tyr Ala Lys Phe His Arg Asn Arg Arg Val Thr Arg Arg Lys Gly
                320                 325                 330

Arg Cys Val Glu Pro Glu Thr Ala Asn Gly Asp Gln Gly Ser Phe
                335                 340                 345

Ile Asn Val

<210> SEQ ID NO 75
<211> LENGTH: 1868
<212> TYPE: DNA
<213> ORGANISM: Homo Sapien

<400> SEQUENCE: 75
```

| | | |
|---|---|---|
| cagaagggca aaaacattga ctgcctcaag gtctcaagca ccagtcttca | 50 |
| ccgcggaaag catgttgtgg ctgttccaat cgctcctgtt tgtcttctgc | 100 |
| tttggcccag ggaatgtagt ttcacaaagc agcttaaccc cattgatggt | 150 |
| gaacgggatt ctgggggagt cagtaactct tcccctggag tttcctgcag | 200 |
| gagagaaggt caacttcatc acttggcttt tcaatgaaac atctcttgcc | 250 |
| ttcatagtac cccatgaaac caaaagtcca gaaatccacg tgactaatcc | 300 |
| gaaacaggga agcgactga acttcaccca gtcctactcc ctgcaactca | 350 |
| gcaacctgaa gatggaagac acaggctctt acagagccca gatatccaca | 400 |
| aagacctctg caaagctgtc cagttacact ctgaggatat taagacaact | 450 |
| gaggaacata caagttacca atcacagtca gctatttcag aatatgacct | 500 |
| gtgagctcca tctgacttgc tctgtggagg atgcagatga caatgtctca | 550 |
| ttcagatggg aggccttggg aaacacactt caagtcagc caaacctcac | 600 |
| tgtctcctgg gaccccagga tttccagtga acaggactac acctgcatag | 650 |
| cagagaatgc tgtcagtaat ttatccttct ctgtctctgc ccagaagctt | 700 |
| tgcgaagatg ttaaaattca atatacagat accaaaatga ttctgtttat | 750 |
| ggtttctggg atatgcatag tcttcggttt catcatactg ctgttacttg | 800 |
| ttttgaggaa aagaagagat tccctatctt tgtctactca gcgaacacag | 850 |
| ggccccgcag agtccgcaag gaacctagag tatgtttcag tgtctccaac | 900 |
| gaacaacact gtgtatgctt cagtcactca ttcaaacagg gaaacagaaa | 950 |
| tctggacacc tagagaaaat gatactatca caatttactc cacaattaat | 1000 |
| cattccaaag agagtaaacc cacttttttcc agggcaactg cccttgacaa | 1050 |
| tgtcgtgtaa gttgctgaaa ggcctcagag gaattcggga atgacacgtc | 1100 |
| ttctgatccc atgagacaga acaaagaaca ggaagcttgg ttcctgttgt | 1150 |
| tcctggcaac agaatttgaa tatctaggat aggatgatca cctccagtcc | 1200 |
| ttcggactta aacctgccta cctgagtcaa acacctaagg ataacatcat | 1250 |

| | |
|---|---:|
| ttccagcatg tggttcaaat aatattttcc aatccacttc aggccaaaac | 1300 |
| atgctaaaga taacacacca gcacattgac tctctctttg ataactaagc | 1350 |
| aaatggaatt atggttgaca gagagtttat gatccagaag acaaccactt | 1400 |
| ctctcctttt agaaagcagc aggattgact tattgagaaa taatgcagtg | 1450 |
| tgttggttac atgtgtagtc tctggagttg gatgggccca tcctgataca | 1500 |
| agttgagcat cccttgtctg aaatgcttgg gattagaaat gtttcagatt | 1550 |
| tcaattttt ttcagatttt ggaatatttg cattatattt agcggttgag | 1600 |
| tatccaaatc caaaaatcca aaattcaaaa tgctccaata agcatttccc | 1650 |
| ttgagtttca ttgatgtcga tgcagtgctc aaaatctcag attttggagc | 1700 |
| aatttggata ttggattttt ggatttggga tgctcaactt gtacaatgtt | 1750 |
| tattagacac atctcctggg acatactgcc taaccttttg gagccttagt | 1800 |
| ctcccagact gaaaaggaa gaggatggta ttacatcagc tccattgttt | 1850 |
| gagccaagaa tctaagtc | 1868 |

<210> SEQ ID NO 76
<211> LENGTH: 332
<212> TYPE: PRT
<213> ORGANISM: Homo Sapien

<400> SEQUENCE: 76

```
Met Leu Trp Leu Phe Gln Ser Leu Leu Phe Val Phe Cys Phe Gly
 1               5                  10                  15

Pro Gly Asn Val Val Ser Gln Ser Ser Leu Thr Pro Leu Met Val
                20                  25                  30

Asn Gly Ile Leu Gly Glu Ser Val Thr Leu Pro Leu Glu Phe Pro
                35                  40                  45

Ala Gly Glu Lys Val Asn Phe Ile Thr Trp Leu Phe Asn Glu Thr
                50                  55                  60

Ser Leu Ala Phe Ile Val Pro His Glu Thr Lys Ser Pro Glu Ile
                65                  70                  75

His Val Thr Asn Pro Lys Gln Gly Lys Arg Leu Asn Phe Thr Gln
                80                  85                  90

Ser Tyr Ser Leu Gln Leu Ser Asn Leu Lys Met Glu Asp Thr Gly
                95                 100                 105

Ser Tyr Arg Ala Gln Ile Ser Thr Lys Thr Ser Ala Lys Leu Ser
               110                 115                 120

Ser Tyr Thr Leu Arg Ile Leu Arg Gln Leu Arg Asn Ile Gln Val
               125                 130                 135

Thr Asn His Ser Gln Leu Phe Gln Asn Met Thr Cys Glu Leu His
               140                 145                 150

Leu Thr Cys Ser Val Glu Asp Ala Asp Asn Val Ser Phe Arg
               155                 160                 165

Trp Glu Ala Leu Gly Asn Thr Leu Ser Ser Gln Pro Asn Leu Thr
               170                 175                 180

Val Ser Trp Asp Pro Arg Ile Ser Ser Glu Gln Asp Tyr Thr Cys
               185                 190                 195

Ile Ala Glu Asn Ala Val Ser Asn Leu Ser Phe Ser Val Ser Ala
               200                 205                 210

Gln Lys Leu Cys Glu Asp Val Lys Ile Gln Tyr Thr Asp Thr Lys
               215                 220                 225
```

```
Met Ile Leu Phe Met Val Ser Gly Ile Cys Ile Val Phe Gly Phe
            230                 235                 240

Ile Ile Leu Leu Leu Leu Val Leu Arg Lys Arg Arg Asp Ser Leu
            245                 250                 255

Ser Leu Ser Thr Gln Arg Thr Gln Gly Pro Ala Glu Ser Ala Arg
            260                 265                 270

Asn Leu Glu Tyr Val Ser Val Ser Pro Thr Asn Asn Thr Val Tyr
            275                 280                 285

Ala Ser Val Thr His Ser Asn Arg Glu Thr Glu Ile Trp Thr Pro
            290                 295                 300

Arg Glu Asn Asp Thr Ile Thr Ile Tyr Ser Thr Ile Asn His Ser
            305                 310                 315

Lys Glu Ser Lys Pro Thr Phe Ser Arg Ala Thr Ala Leu Asp Asn
            320                 325                 330

Val Val

<210> SEQ ID NO 77
<211> LENGTH: 3073
<212> TYPE: DNA
<213> ORGANISM: Homo Sapien

<400> SEQUENCE: 77
```

| | | | | |
|---|---|---|---|---|
| gatccctcga | cctcgaccca | cgcgtccgct | ctttaatgct | ttcttttaa | 50 |
| gagatcacct | tctgacttct | cacagaagag | gttaactatt | acctgtggga | 100 |
| agtcagaagg | tgatctcttt | aatgctttct | ttttaagaat | ttttcaaatt | 150 |
| gagactaatt | gcagaggttc | cagttgacca | gcattcatag | gaatgaagac | 200 |
| aaacacagag | atggtgtgtc | taagaaactt | caaaaggtgt | agacctcctg | 250 |
| actgaagcat | attggattta | tttaattttt | ttcactgtat | ttctgtcctc | 300 |
| ctacaaggga | aagtcatgat | tacactaact | gagctaaaat | gcttagcaga | 350 |
| tgcccagtca | tcttatcaca | tcttaaaacc | atggtgggac | gtcttctggt | 400 |
| attacatcac | actgatcatg | ctgctggtgg | ccgtgctggc | cggagctctc | 450 |
| cagctgacgc | agagcagggt | tctgtgctgt | cttccatgca | aagtggaatt | 500 |
| tgacaatcac | tgtgccgtgc | cttgggacat | cctgaaagcc | agcatgaaca | 550 |
| catcctctaa | tcctgggaca | ccgcttccgc | tcccctccg | aattcagaat | 600 |
| gacctccacc | gacagcagta | ctcctatatt | gatgccgtct | gttacgagaa | 650 |
| acagctccat | tggtttgcaa | agttttttcc | ctatctggtg | ctcttgcaca | 700 |
| cgctcatctt | tgcagcctgc | agcaactttt | ggcttcacta | ccccagtacc | 750 |
| agttccaggc | tcgagcattt | tgtggccatc | cttcacaagt | gcttcgattc | 800 |
| tccatggacc | acccgcgccc | tttcagaaac | agtggctgag | cagtcagtga | 850 |
| ggcctctgaa | actctccaag | tccaagattt | tgctttcgtc | ctcagggtgt | 900 |
| tcagctgaca | tagattccgg | caaacagtca | ttgccctacc | cacagccagg | 950 |
| tttggagtca | gctggtatag | aaagcccaac | ttccagtggc | ctggacaaga | 1000 |
| aggagggtga | acaggccaaa | gccatctttg | aaaaagtgaa | aagattccgc | 1050 |
| atgcatgtgg | agcagaagga | catcatttat | agagtatatc | tgaaacagat | 1100 |
| aatagtcaaa | gtcatttgt | ttgtgctcat | cataacttat | gttccatatt | 1150 |
| ttttaaccca | catcactctt | gaaatcgact | gttcagttga | tgtgcaggct | 1200 |

```
tttacaggat ataagcgcta ccagtgtgtc tattccttgg cagaaatctt      1250
taaggtcctg gcttcatttt atgtcatttt ggttatactt tatggtctga      1300
cctcttccta cagcctgtgg tggatgctga ggagttccct gaagcaatat      1350
tcctttgagg cgttaagaga aaaaagcaac tacagtgaca tccctgatgt      1400
caagaatgac tttgccttca tccttcatct ggctgatcag tatgatcctc      1450
tttattccaa acgcttctcc atattcctat cagaggtcag tgagaacaaa      1500
ctgaaacaga tcaacctcaa taatgaatgg acagttgaga aactgaaaag      1550
taagcttgtg aaaaatgccc aggacaagat agaactgcat ctttttatgc      1600
tcaacggtct tccagacaat gtctttgagt taactgaaat ggaagtgcta      1650
agcctggagc ttatcccaga ggtgaagctg ccctctgcag tctcacagct      1700
ggtcaacctc aaggagcttc gtgtgtacca ttcatctctg gtcgtagacc      1750
atcctgcact ggccttttcta gaggagaatt taaaaatcct ccgcctgaaa      1800
tttactgaaa tgggaaaaat cccacgctgg gtatttcacc tcaagaatct      1850
caaggaactt tatcttttcgg gctgtgttct ccctgaacag ttgagtacta      1900
tgcagttgga gggctttcag gacttaaaaa atctaaggac cctgtacttg      1950
aagagcagcc tctcccggat cccacaagtt gttacagacc tcctgccttc      2000
attgcagaaa ctgtcccttg ataatgaggg aagcaaactg gttgtgttga      2050
acaacttgaa aaagatggtc aatctgaaaa gcctagaact gatcagctgt      2100
gacctggaac gcatcccaca ttccattttc agcctgaata atttgcatga      2150
gttagaccta agggaaaata accttaaaac tgtggaagag attagctttc      2200
agcatcttca gaatctttcc tgcttaaagt tgtggcacaa taacattgct      2250
tatattcctg cacagattgg ggcattatct aacctagagc agctctcttt      2300
ggaccataat aatattgaga atctgccctt gcagcttttc ctatgcacta      2350
aactacatta tttggatcta agctataacc acttgacctt cattccagaa      2400
gaaatccagt atctgagtaa tttgcagtac tttgctgtga ccaacaacaa      2450
tattgagatg ctaccagatg ggctgtttca gtgcaaaaag ctgcagtgtt      2500
tacttttggg gaaaaatagc ttgatgaatt tgtcccctca tgtgggtgag      2550
ctgtcaaacc ttactcatct ggagctcatt ggtaattacc tggaaacact      2600
tcctcctgaa ctagaaggat gtcagtccct aaaacggaac tgtctgattg      2650
ttgaggagaa cttgctcaat actcttcctc tccctgtaac agaacgttta      2700
cagacgtgct tagacaaatg ttgacttaaa gaaaagagac ccgtgtttca      2750
aaatcatttt taaagtatgt ctcggccggg cgtggtggct catgcctata      2800
atcccagcac tttgggaggc caagatgggc ggattgcttg aggtcaggag      2850
ttcgagacca gtctggccaa cctggtgaaa ccccatctct gctaaaacta      2900
caaaaaaatt agccaggcgt ggtggcgtgc gcctgtaatc ccagctactt      2950
gggaggctga cgcaggggaa ttgcttgaac cagggaggtg gaggttgcag      3000
tgagccgaga ttgtgccact gtacaccagc ctgggtgaca gagcaagact      3050
cttatctcaa aaaaaaaaaa aaa                                   3073
```

<210> SEQ ID NO 78
<211> LENGTH: 802

```
<212> TYPE: PRT
<213> ORGANISM: Homo Sapien

<400> SEQUENCE: 78

Met Ile Thr Leu Thr Glu Leu Lys Cys Leu Ala Asp Ala Gln Ser
  1               5                  10                  15

Ser Tyr His Ile Leu Lys Pro Trp Trp Asp Val Phe Trp Tyr Tyr
                 20                  25                  30

Ile Thr Leu Ile Met Leu Leu Val Ala Val Leu Ala Gly Ala Leu
                 35                  40                  45

Gln Leu Thr Gln Ser Arg Val Leu Cys Cys Leu Pro Cys Lys Val
                 50                  55                  60

Glu Phe Asp Asn His Cys Ala Val Pro Trp Asp Ile Leu Lys Ala
 65                  70                  75

Ser Met Asn Thr Ser Ser Asn Pro Gly Thr Pro Leu Pro Leu Pro
                 80                  85                  90

Leu Arg Ile Gln Asn Asp Leu His Arg Gln Gln Tyr Ser Tyr Ile
                 95                 100                 105

Asp Ala Val Cys Tyr Glu Lys Gln Leu His Trp Phe Ala Lys Phe
                110                 115                 120

Phe Pro Tyr Leu Val Leu Leu His Thr Leu Ile Phe Ala Ala Cys
                125                 130                 135

Ser Asn Phe Trp Leu His Tyr Pro Ser Thr Ser Ser Arg Leu Glu
                140                 145                 150

His Phe Val Ala Ile Leu His Lys Cys Phe Asp Ser Pro Trp Thr
                155                 160                 165

Thr Arg Ala Leu Ser Glu Thr Val Ala Glu Gln Ser Val Arg Pro
                170                 175                 180

Leu Lys Leu Ser Lys Ser Lys Ile Leu Leu Ser Ser Ser Gly Cys
                185                 190                 195

Ser Ala Asp Ile Asp Ser Gly Lys Gln Ser Leu Pro Tyr Pro Gln
                200                 205                 210

Pro Gly Leu Glu Ser Ala Gly Ile Glu Ser Pro Thr Ser Ser Gly
                215                 220                 225

Leu Asp Lys Lys Glu Gly Glu Gln Ala Lys Ala Ile Phe Glu Lys
                230                 235                 240

Val Lys Arg Phe Arg Met His Val Glu Gln Lys Asp Ile Ile Tyr
                245                 250                 255

Arg Val Tyr Leu Lys Gln Ile Ile Val Lys Val Ile Leu Phe Val
                260                 265                 270

Leu Ile Ile Thr Tyr Val Pro Tyr Phe Leu Thr His Ile Thr Leu
                275                 280                 285

Glu Ile Asp Cys Ser Val Asp Val Gln Ala Phe Thr Gly Tyr Lys
                290                 295                 300

Arg Tyr Gln Cys Val Tyr Ser Leu Ala Glu Ile Phe Lys Val Leu
                305                 310                 315

Ala Ser Phe Tyr Val Ile Leu Val Ile Leu Tyr Gly Leu Thr Ser
                320                 325                 330

Ser Tyr Ser Leu Trp Trp Met Leu Arg Ser Ser Leu Lys Gln Tyr
                335                 340                 345

Ser Phe Glu Ala Leu Arg Glu Lys Ser Asn Tyr Ser Asp Ile Pro
                350                 355                 360

Asp Val Lys Asn Asp Phe Ala Phe Ile Leu His Leu Ala Asp Gln
                365                 370                 375
```

-continued

```
Tyr Asp Pro Leu Tyr Ser Lys Arg Phe Ser Ile Phe Leu Ser Glu
            380                 385                 390

Val Ser Glu Asn Lys Leu Lys Gln Ile Asn Leu Asn Asn Glu Trp
            395                 400                 405

Thr Val Glu Lys Leu Lys Ser Lys Leu Val Lys Asn Ala Gln Asp
            410                 415                 420

Lys Ile Glu Leu His Leu Phe Met Leu Asn Gly Leu Pro Asp Asn
            425                 430                 435

Val Phe Glu Leu Thr Glu Met Glu Val Leu Ser Leu Glu Leu Ile
            440                 445                 450

Pro Glu Val Lys Leu Pro Ser Ala Val Ser Gln Leu Val Asn Leu
            455                 460                 465

Lys Glu Leu Arg Val Tyr His Ser Ser Leu Val Val Asp His Pro
            470                 475                 480

Ala Leu Ala Phe Leu Glu Glu Asn Leu Lys Ile Leu Arg Leu Lys
            485                 490                 495

Phe Thr Glu Met Gly Lys Ile Pro Arg Trp Val Phe His Leu Lys
            500                 505                 510

Asn Leu Lys Glu Leu Tyr Leu Ser Gly Cys Val Leu Pro Glu Gln
            515                 520                 525

Leu Ser Thr Met Gln Leu Glu Gly Phe Gln Asp Leu Lys Asn Leu
            530                 535                 540

Arg Thr Leu Tyr Leu Lys Ser Ser Leu Ser Arg Ile Pro Gln Val
            545                 550                 555

Val Thr Asp Leu Leu Pro Ser Leu Gln Lys Leu Ser Leu Asp Asn
            560                 565                 570

Glu Gly Ser Lys Leu Val Leu Asn Asn Leu Lys Lys Met Val
            575                 580                 585

Asn Leu Lys Ser Leu Glu Leu Ile Ser Cys Asp Leu Glu Arg Ile
            590                 595                 600

Pro His Ser Ile Phe Ser Leu Asn Asn Leu His Glu Leu Asp Leu
            605                 610                 615

Arg Glu Asn Asn Leu Lys Thr Val Glu Glu Ile Ser Phe Gln His
            620                 625                 630

Leu Gln Asn Leu Ser Cys Leu Lys Leu Trp His Asn Asn Ile Ala
            635                 640                 645

Tyr Ile Pro Ala Gln Ile Gly Ala Leu Ser Asn Leu Glu Gln Leu
            650                 655                 660

Ser Leu Asp His Asn Asn Ile Glu Asn Leu Pro Leu Gln Leu Phe
            665                 670                 675

Leu Cys Thr Lys Leu His Tyr Leu Asp Leu Ser Tyr Asn His Leu
            680                 685                 690

Thr Phe Ile Pro Glu Glu Ile Gln Tyr Leu Ser Asn Leu Gln Tyr
            695                 700                 705

Phe Ala Val Thr Asn Asn Asn Ile Glu Met Leu Pro Asp Gly Leu
            710                 715                 720

Phe Gln Cys Lys Lys Leu Gln Cys Leu Leu Leu Gly Lys Asn Ser
            725                 730                 735

Leu Met Asn Leu Ser Pro His Val Gly Glu Leu Ser Asn Leu Thr
            740                 745                 750

His Leu Glu Leu Ile Gly Asn Tyr Leu Glu Thr Leu Pro Pro Glu
            755                 760                 765
```

| | | | | | | | | | | | |
|---|---|---|---|---|---|---|---|---|---|---|---|
| Leu | Glu | Gly | Cys | Gln | Ser | Leu | Lys | Arg | Asn | Cys | Leu | Ile | Val | Glu |
| | | 770 | | | | | 775 | | | | | 780 | | |
| Glu | Asn | Leu | Leu | Asn | Thr | Leu | Pro | Leu | Pro | Val | Thr | Glu | Arg | Leu |
| | | | 785 | | | | | 790 | | | | | 795 | |
| Gln | Thr | Cys | Leu | Asp | Lys | Cys |
| | | | 800 | | | |

<210> SEQ ID NO 79
<211> LENGTH: 1504
<212> TYPE: DNA
<213> ORGANISM: Homo Sapien

<400> SEQUENCE: 79

| | |
|---|---|
| cggacgcgtg ggccgcgctc cctcacggcc cctcggcggc gcccgtcgga | 50 |
| tccggcctct ctctgcgccc cggggcgcgc cacctccccg ccggaggtgt | 100 |
| ccacgcgtcc ggccgtccat ccgtccgtcc tcctggggc cggcgctgac | 150 |
| catgcccagc ggctgccgct gcctgcatct cgtgtgcctg ttgtgcattc | 200 |
| tgggggctcc cggtcagcct gtccgagccg atgactgcag ctcccactgt | 250 |
| gacctggccc acggctgctg tgcacctgac ggctcctgca ggtgtgaccc | 300 |
| gggctgggag gggctgcact gtgagcgctg tgtgaggatg cctggctgcc | 350 |
| agcacggtac ctgccaccag ccatggcagt gcatctgcca cagtggctgg | 400 |
| gcaggcaagt tctgtgacaa agatgaacat atctgtacca cgcagtcccc | 450 |
| ctgccagaat ggaggccagt gcatgtatga cgggggcggt gagtaccatt | 500 |
| gtgtgtgctt accaggcttc catgggcgtg actgcgagcg caaggctgga | 550 |
| ccctgtgaac aggcaggctc cccatgccgc aatggcgggc agtgccagga | 600 |
| cgaccagggc tttgctctca acttcacgtg ccgctgcttg gtgggctttg | 650 |
| tgggtgcccg ctgtgaggta aatgtggatg actgcctgat gcggccttgt | 700 |
| gctaacggtg ccacctgcct tgacggcata aaccgcttct cctgcctctg | 750 |
| tcctgagggc tttgctggac gcttctgcac catcaacctg gatgactgtg | 800 |
| ccagccgccc atgccagaga ggggcccgct gtcgggaccg tgtccacgac | 850 |
| ttcgactgcc tctgccccag tggctatgtg gcaagacct gtgagcttgt | 900 |
| cttacctgtc ccagaccccc caaccacagt ggacacccct ctagggccca | 950 |
| cctcagctgt agtggtacct gctacggggc cagcccccca cagcgcaggg | 1000 |
| gctggtctgc tgcggatctc agtgaaggag gtggtgcgga ggcaagaggc | 1050 |
| tgggctaggt gagcctagct tggtggccct ggtggtgttt ggggccctca | 1100 |
| ctgctgccct ggttctggct actgtgttgc tgaccctgag ggcctggcgc | 1150 |
| cggggtgtct gccccctgg accctgttgc taccctgccc cacactatgc | 1200 |
| tccagcgtgc caggaccagg agtgtcaggt tagcatgctg ccagcagggc | 1250 |
| tccccctgcc acgtgacttg cccctgagc ctggaaagac cacagcactg | 1300 |
| tgatggaggt gggggctttc tggccccctt cctcacctct tccaccctc | 1350 |
| agactggagt ggtccgttct caccaccctt cagcttgggt acacacacag | 1400 |
| aggagacctc agcctcacac cagaaatatt attttttaa tacacagaat | 1450 |
| gtaagatgga attttatcaa ataaaactat gaaaatgcaa aaaaaaaaaa | 1500 |
| aaaa | 1504 |

```
<210> SEQ ID NO 80
<211> LENGTH: 383
<212> TYPE: PRT
<213> ORGANISM: Homo Sapien

<400> SEQUENCE: 80

Met Pro Ser Gly Cys Arg Cys Leu His Leu Val Cys Leu Leu Cys
 1               5                  10                  15

Ile Leu Gly Ala Pro Gly Gln Pro Val Arg Ala Asp Asp Cys Ser
                20                  25                  30

Ser His Cys Asp Leu Ala His Gly Cys Cys Ala Pro Asp Gly Ser
                35                  40                  45

Cys Arg Cys Asp Pro Gly Trp Glu Gly Leu His Cys Glu Arg Cys
                50                  55                  60

Val Arg Met Pro Gly Cys Gln His Gly Thr Cys His Gln Pro Trp
                65                  70                  75

Gln Cys Ile Cys His Ser Gly Trp Ala Gly Lys Phe Cys Asp Lys
                80                  85                  90

Asp Glu His Ile Cys Thr Thr Gln Ser Pro Cys Gln Asn Gly Gly
                95                 100                 105

Gln Cys Met Tyr Asp Gly Gly Glu Tyr His Cys Val Cys Leu
               110                 115                 120

Pro Gly Phe His Gly Arg Asp Cys Glu Arg Lys Ala Gly Pro Cys
               125                 130                 135

Glu Gln Ala Gly Ser Pro Cys Arg Asn Gly Gly Gln Cys Gln Asp
               140                 145                 150

Asp Gln Gly Phe Ala Leu Asn Phe Thr Cys Arg Cys Leu Val Gly
               155                 160                 165

Phe Val Gly Ala Arg Cys Glu Val Asn Val Asp Asp Cys Leu Met
               170                 175                 180

Arg Pro Cys Ala Asn Gly Ala Thr Cys Leu Asp Gly Ile Asn Arg
               185                 190                 195

Phe Ser Cys Leu Cys Pro Glu Gly Phe Ala Gly Arg Phe Cys Thr
               200                 205                 210

Ile Asn Leu Asp Asp Cys Ala Ser Arg Pro Cys Gln Arg Gly Ala
               215                 220                 225

Arg Cys Arg Asp Arg Val His Asp Phe Asp Cys Leu Cys Pro Ser
               230                 235                 240

Gly Tyr Gly Gly Lys Thr Cys Glu Leu Val Leu Pro Val Pro Asp
               245                 250                 255

Pro Pro Thr Thr Val Asp Thr Pro Leu Gly Pro Thr Ser Ala Val
               260                 265                 270

Val Val Pro Ala Thr Gly Pro Ala Pro His Ser Ala Gly Ala Gly
               275                 280                 285

Leu Leu Arg Ile Ser Val Lys Glu Val Arg Arg Gln Glu Ala
               290                 295                 300

Gly Leu Gly Glu Pro Ser Leu Val Ala Leu Val Phe Gly Ala
               305                 310                 315

Leu Thr Ala Ala Leu Val Leu Ala Thr Val Leu Thr Leu Arg
               320                 325                 330

Ala Trp Arg Arg Gly Val Cys Pro Gly Pro Cys Cys Tyr Pro
               335                 340                 345

Ala Pro His Tyr Ala Pro Ala Cys Gln Asp Gln Glu Cys Gln Val
               350                 355                 360
```

Ser Met Leu Pro Ala Gly Leu Pro Leu Pro Arg Asp Leu Pro Pro
            365                 370                 375

Glu Pro Gly Lys Thr Thr Ala Leu
            380

<210> SEQ ID NO 81
<211> LENGTH: 1034
<212> TYPE: DNA
<213> ORGANISM: Homo Sapien

<400> SEQUENCE: 81

| | | | | |
|---|---|---|---|---|
| gtttgttgct | caaaccgagt | tctggagaac | gccatcagct | cgctgcttaa | 50 |
| aattaaacca | caggttccat | tatgggtcga | cttgatggga | agtcatcat | 100 |
| cctgacggcc | gctgctcagg | ggattggcca | agcagctgcc | ttagcttttg | 150 |
| caagagaagg | tgccaaagtc | atagccacag | acattaatga | gtccaaactt | 200 |
| caggaactgg | aaaagtaccc | gggtattcaa | actcgtgtcc | ttgatgtcac | 250 |
| aaagaagaaa | caaattgatc | agtttgccag | tgaagttgag | agacttgatg | 300 |
| ttctctttaa | tgttgctggt | tttgtccatc | atggaactgt | cctggattgt | 350 |
| gaggagaaag | actgggactt | ctcgatgaat | ctcaatgtgc | gcagcatgta | 400 |
| cctgatgatc | aaggcattcc | ttcctaaaat | gcttgctcag | aaatctggca | 450 |
| atattatcaa | catgtcttct | gtggcttcca | gcgtcaaagg | agttgtgaac | 500 |
| agatgtgtgt | acagcacaac | caaggcagcc | gtgattggcc | tcacaaaatc | 550 |
| tctggctgca | gatttcatcc | agcagggcat | caggtgcaac | tgtgtgtgcc | 600 |
| caggaacagt | tgatacgcca | tctctacaag | aaagaataca | agccagagga | 650 |
| aatcctgaag | aggcacggaa | tgatttcctg | aagagacaaa | agacgggaag | 700 |
| attcgcaact | gcagaagaaa | tagccatgct | ctgcgtgtat | ttggcttctg | 750 |
| atgaatctgc | ttatgtaact | ggtaaccctg | tcatcattga | tggaggctgg | 800 |
| agcttgtgat | tttaggatct | ccatggtggg | aaggaaggca | ggcccttcct | 850 |
| atccacagtg | aacctggtta | cgaagaaaac | tcaccaatca | tctccttcct | 900 |
| gttaatcaca | tgttaatgaa | aataagctct | ttttaatgat | gtcactgttt | 950 |
| gcaagagtct | gattctttaa | gtatattaat | ctctttgtaa | tctcttctga | 1000 |
| aatcattgta | aagaaataaa | aatattgaac | tcat | | 1034 |

<210> SEQ ID NO 82
<211> LENGTH: 245
<212> TYPE: PRT
<213> ORGANISM: Homo Sapien

<400> SEQUENCE: 82

Met Gly Arg Leu Asp Gly Lys Val Ile Ile Leu Thr Ala Ala Ala
  1               5                  10                  15

Gln Gly Ile Gly Gln Ala Ala Ala Leu Ala Phe Ala Arg Glu Gly
                 20                  25                  30

Ala Lys Val Ile Ala Thr Asp Ile Asn Glu Ser Lys Leu Gln Glu
                 35                  40                  45

Leu Glu Lys Tyr Pro Gly Ile Gln Thr Arg Val Leu Asp Val Thr
                 50                  55                  60

Lys Lys Lys Gln Ile Asp Gln Phe Ala Ser Glu Val Glu Arg Leu
             65                  70                  75

```
Asp Val Leu Phe Asn Val Ala Gly Phe Val His His Gly Thr Val
            80                  85                  90

Leu Asp Cys Glu Glu Lys Asp Trp Asp Phe Ser Met Asn Leu Asn
        95                 100                 105

Val Arg Ser Met Tyr Leu Met Ile Lys Ala Phe Leu Pro Lys Met
            110                 115                 120

Leu Ala Gln Lys Ser Gly Asn Ile Ile Asn Met Ser Ser Val Ala
            125                 130                 135

Ser Ser Val Lys Gly Val Val Asn Arg Cys Val Tyr Ser Thr Thr
            140                 145                 150

Lys Ala Ala Val Ile Gly Leu Thr Lys Ser Leu Ala Ala Asp Phe
            155                 160                 165

Ile Gln Gln Gly Ile Arg Cys Asn Cys Val Cys Pro Gly Thr Val
            170                 175                 180

Asp Thr Pro Ser Leu Gln Glu Arg Ile Gln Ala Arg Gly Asn Pro
            185                 190                 195

Glu Glu Ala Arg Asn Asp Phe Leu Lys Arg Gln Lys Thr Gly Arg
            200                 205                 210

Phe Ala Thr Ala Glu Glu Ile Ala Met Leu Cys Val Tyr Leu Ala
            215                 220                 225

Ser Asp Glu Ser Ala Tyr Val Thr Gly Asn Pro Val Ile Ile Asp
            230                 235                 240

Gly Gly Trp Ser Leu
            245

<210> SEQ ID NO 83
<211> LENGTH: 1961
<212> TYPE: DNA
<213> ORGANISM: Homo Sapien

<400> SEQUENCE: 83
gggcggcggc ggcagcggtt ggaggttgta ggaccggcga ggaataggaa         50
tcatggcggc tgcgctgttc gtgctgctgg gattcgcgct gctgggcacc        100
cacggagcct ccggggctgc cggcttcgtc aggcgccgc tgtcccagca         150 gaggtgggtg gggggcagtg tggagctgca ctgcgaggcc gtgggcagcc        200
cggtgcccga gatccagtgg tggtttgaag gcagggtcc caacgacacc         250 tgctcccagc tctgggacgg cgcccggctg accgcgtcc acatccacgc         300 cacctaccac cagcacgcgg ccagcaccat ctccatcgac acgctcgtgg        350
aggaggacac gggcacttac gagtgccggg ccagcaacga cccggatcgc        400
aaccacctga cccgggcgcc cagggtcaag tgggtccgcg cccaggcagt        450
cgtgctagtc ctggaacccg gcacagtctt cactaccgta gaagaccttg        500
gctccaagat actcctcacc tgctccttga atgacagcgc cacagaggtc        550
acagggcacc gctggctgaa gggggcgtg gtgctgaagg aggacgcgct         600
gcccggccag aaaacggagt tcaaggtgga ctccgacgac cagtggggag        650
agtactcctg cgtcttcctc cccgagccca tgggcacggc caacatccag        700
ctccacgggc ctcccagagt gaaggctgtg aagtcgtcag aacacatcaa        750
cgagggggag acggccatgc tggtctgcaa gtcagagtcc gtgccacctg        800
tcactgactg ggcctggtac aagatcactg actctgagga caaggcccctc       850
```

-continued

| | |
|---|---|
| atgaacggct ccgagagcag gttcttcgtg agttcctcgc agggccggtc | 900 |
| agagctacac attgagaacc tgaacatgga ggccgacccc ggccagtacc | 950 |
| ggtgcaacgg caccagctcc aagggctccg accaggccat catcacgctc | 1000 |
| cgcgtgcgca gccacctggc cgccctctgg cccttcctgg gcatcgtggc | 1050 |
| tgaggtgctg gtgctggtca ccatcatctt catctacgag aagcgccgga | 1100 |
| agcccgagga cgtcctggat gatgacgacg ccggctctgc acccctgaag | 1150 |
| agcagcgggc agcaccagaa tgacaaaggc aagaacgtcc gccagaggaa | 1200 |
| ctcttcctga ggcaggtggc ccgaggacgc tccctgctcc acgtctgcgc | 1250 |
| cgccgccgga gtccactccc agtgcttgca agattccaag ttctcacctc | 1300 |
| ttaaagaaaa cccaccccgt agattcccat catacacttc cttctttttt | 1350 |
| aaaaaagttg ggttttctcc attcaggatt ctgttcctta ggttttttc | 1400 |
| cttctgaagt gtttcacgag agcccgggag ctgctgccct gcggcccgt | 1450 |
| ctgtggcttt cagcctctgg gtctgagtca tggccgggtg ggcggcacag | 1500 |
| ccttctccac tggccggagt cagtgccagg tccttgccct ttgtggaaag | 1550 |
| tcacaggtca cacgaggggc cccgtgtcct gcctgtctga agccaatgct | 1600 |
| gtctggttgc gccattttg tgcttttatg tttaattta tgagggccac | 1650 |
| gggtctgtgt tcgactcagc ctcagggacg actctgacct cttggccaca | 1700 |
| gaggactcac ttgcccacac cgagggcgac cccgtcacag cctcaagtca | 1750 |
| ctcccaagcc ccctccttgt ctgtgcatcc gggggcagct ctggaggggg | 1800 |
| tttgctgggg aactggcgcc atcgccggga ctccagaacc gcagaagcct | 1850 |
| ccccagctca cccctggagg acggccggct ctctatagca ccaggctca | 1900 |
| cgtgggaacc cccctcccac ccaccgccac aataaagatc gcccccacct | 1950 |
| ccacccaaaa a | 1961 |

<210> SEQ ID NO 84
<211> LENGTH: 385
<212> TYPE: PRT
<213> ORGANISM: Homo Sapien

<400> SEQUENCE: 84

```
Met Ala Ala Ala Leu Phe Val Leu Leu Gly Phe Ala Leu Leu Gly
  1               5                  10                  15

Thr His Gly Ala Ser Gly Ala Ala Gly Phe Val Gln Ala Pro Leu
             20                  25                  30

Ser Gln Gln Arg Trp Val Gly Ser Val Glu Leu His Cys Glu
         35                  40                  45

Ala Val Gly Ser Pro Val Pro Glu Ile Gln Trp Trp Phe Glu Gly
         50                  55                  60

Gln Gly Pro Asn Asp Thr Cys Ser Gln Leu Trp Asp Gly Ala Arg
         65                  70                  75

Leu Asp Arg Val His Ile His Ala Thr Tyr His Gln His Ala Ala
             80                  85                  90

Ser Thr Ile Ser Ile Asp Thr Leu Val Glu Glu Asp Thr Gly Thr
             95                 100                 105

Tyr Glu Cys Arg Ala Ser Asn Asp Pro Asp Arg Asn His Leu Thr
            110                 115                 120

Arg Ala Pro Arg Val Lys Trp Val Arg Ala Gln Ala Val Val Leu
```

```
                125                 130                 135
Val Leu Glu Pro Gly Thr Val Phe Thr Thr Val Glu Asp Leu Gly
            140                 145                 150

Ser Lys Ile Leu Leu Thr Cys Ser Leu Asn Asp Ser Ala Thr Glu
            155                 160                 165

Val Thr Gly His Arg Trp Leu Lys Gly Val Val Leu Lys Glu
            170                 175                 180

Asp Ala Leu Pro Gly Gln Lys Thr Glu Phe Lys Val Asp Ser Asp
            185                 190                 195

Asp Gln Trp Gly Glu Tyr Ser Cys Val Phe Leu Pro Glu Pro Met
            200                 205                 210

Gly Thr Ala Asn Ile Gln Leu His Gly Pro Pro Arg Val Lys Ala
            215                 220                 225

Val Lys Ser Ser Glu His Ile Asn Glu Gly Glu Thr Ala Met Leu
            230                 235                 240

Val Cys Lys Ser Glu Ser Val Pro Pro Val Thr Asp Trp Ala Trp
            245                 250                 255

Tyr Lys Ile Thr Asp Ser Glu Asp Lys Ala Leu Met Asn Gly Ser
            260                 265                 270

Glu Ser Arg Phe Phe Val Ser Ser Gln Gly Arg Ser Glu Leu
            275                 280                 285

His Ile Glu Asn Leu Asn Met Glu Ala Asp Pro Gly Gln Tyr Arg
            290                 295                 300

Cys Asn Gly Thr Ser Ser Lys Gly Ser Asp Gln Ala Ile Ile Thr
            305                 310                 315

Leu Arg Val Arg Ser His Leu Ala Ala Leu Trp Pro Phe Leu Gly
            320                 325                 330

Ile Val Ala Glu Val Leu Val Leu Val Thr Ile Ile Phe Ile Tyr
            335                 340                 345

Glu Lys Arg Arg Lys Pro Glu Asp Val Leu Asp Asp Asp Asp Ala
            350                 355                 360

Gly Ser Ala Pro Leu Lys Ser Ser Gly Gln His Gln Asn Asp Lys
            365                 370                 375

Gly Lys Asn Val Arg Gln Arg Asn Ser Ser
            380                 385

<210> SEQ ID NO 85
<211> LENGTH: 1002
<212> TYPE: DNA
<213> ORGANISM: Homo Sapien

<400> SEQUENCE: 85
ggctcgagca aagacatacg aacagggagg aaggccgact gaaagaaaga        50
cggagaagag gagagagaag ccagggccga gcgtgccagc aggcggatgg       100
agggcggcct ggtggaggag gagacgtagt ggcctgggct gagctgggtg       150
ggccgggaga agcgggtgcc tcagagtggg ggtgggggca tgggaggggc       200
aggcattctg ctgctgctgc tggctggggc ggggtggtg gtggcctgga       250 gaccccaaa gggaaagtgt cccctgcgct gctcctgctc taaagacagc        300
gccctgtgtg agggctcccc ggacctgccc gtcagcttct ctccgaccct       350
gctgtcactc tcactcgtca ggacgggagt cacccagctg aaggccggca       400
gcttcctgag aattccgtct ctgcacctgc tcctcttcac ctccaactcc       450
```

-continued

```
ttctccgtga ttgaggacga tgcatttgcg ggcctgtccc acctgcagta          500
cctcttcatc gaggacaatg agattggctc catctctaag aatgcccyca          550
gaggacttcg ctcgcttaca cacctaagcc tggccaataa ccatctggag          600
accctcccca gattcctgtt ccgaggcctg gacacccyta ctcacgtgga          650
cctccgcggg aacccgttcc agtgtgactg ccgcgtcctc tggctcctgc          700
agtggatgcc caccgtgaat gccagcgtgg ggaccggcgc ctgtgcgggc          750
cccgcctccc tgagccacat gcagctccac cacctcgacc ccaagacttt          800
caagtgcaga gccataggtg gggggctttc ccgatgggt gggaggcggg           850 agatctgggg gaaaggctgc cagggccaag aggctcgtct cactccctgc          900
cctgccattt cccggagtgg gaagaccctg agcaagcagc actgccttcc          950
tgagccccag ttttctcatc tgtaaagtgg gggtaataaa cagtgatata         1000
gg                                                             1002
```

<210> SEQ ID NO 86
<211> LENGTH: 261
<212> TYPE: PRT
<213> ORGANISM: Homo Sapien

<400> SEQUENCE: 86

```
Met Gly Gly Ala Gly Ile Leu Leu Leu Leu Ala Gly Ala Gly
  1               5                  10                  15

Val Val Val Ala Trp Arg Pro Pro Lys Gly Lys Cys Pro Leu Arg
                 20                  25                  30

Cys Ser Cys Ser Lys Asp Ser Ala Leu Cys Glu Gly Ser Pro Asp
                 35                  40                  45

Leu Pro Val Ser Phe Ser Pro Thr Leu Leu Ser Leu Ser Leu Val
                 50                  55                  60

Arg Thr Gly Val Thr Gln Leu Lys Ala Gly Ser Phe Leu Arg Ile
                 65                  70                  75

Pro Ser Leu His Leu Leu Leu Phe Thr Ser Asn Ser Phe Ser Val
                 80                  85                  90

Ile Glu Asp Asp Ala Phe Ala Gly Leu Ser His Leu Gln Tyr Leu
                 95                 100                 105

Phe Ile Glu Asp Asn Glu Ile Gly Ser Ile Ser Lys Asn Ala Leu
                110                 115                 120

Arg Gly Leu Arg Ser Leu Thr His Leu Ser Leu Ala Asn Asn His
                125                 130                 135

Leu Glu Thr Leu Pro Arg Phe Leu Phe Arg Gly Leu Asp Thr Leu
                140                 145                 150

Thr His Val Asp Leu Arg Gly Asn Pro Phe Gln Cys Asp Cys Arg
                155                 160                 165

Val Leu Trp Leu Leu Gln Trp Met Pro Thr Val Asn Ala Ser Val
                170                 175                 180

Gly Thr Gly Ala Cys Ala Gly Pro Ala Ser Leu Ser His Met Gln
                185                 190                 195

Leu His His Leu Asp Pro Lys Thr Phe Lys Cys Arg Ala Ile Gly
                200                 205                 210

Gly Gly Leu Ser Arg Trp Gly Gly Arg Glu Ile Trp Gly Lys
                215                 220                 225

Gly Cys Gln Gly Gln Glu Ala Arg Leu Thr Pro Cys Pro Ala Ile
                230                 235                 240
```

Ser Arg Ser Gly Lys Thr Leu Ser Lys Gln His Cys Leu Pro Glu
            245                 250                 255

Pro Gln Phe Ser His Leu
            260

<210> SEQ ID NO 87
<211> LENGTH: 2945
<212> TYPE: DNA
<213> ORGANISM: Homo Sapien

<400> SEQUENCE: 87

| | | |
|---|---|---|
| cggacgcgtg gggcggcgag agcagctgca gttcgcatct caggcagtac | 50 |
| ctagaggagc tgccggtgcc tcctcagaac atctcctgat cgctacccag | 100 |
| gaccaggcac caaggacagg gagtcccagg cgcacacccc ccattctggg | 150 |
| tcccccaggc ccagaccccc actctgccac aggttgcatc ttgacctggt | 200 |
| cctcctgcag aagtggcccc tgtggtcctg ctctgagact cgtccctggg | 250 |
| cgcccctgca gccctttct atgactccat ctggatttgg ctggctgtgg | 300 |
| ggacgcggtc cgaggggcgg cctggctctc agcgtggtgg cagccagctc | 350 |
| tctggccacc atggcaaatg ctgagatctg aggggacaag gctctacagc | 400 |
| ctcagccagg ggcactcagc tgttgcaggg tgtgatggag aacaaagcta | 450 |
| tgtacctaca caccgtcagc gactgtgaca ccagctccat ctgtgaggat | 500 |
| tcctttgatg gcaggagcct gtccaagctg aacctgtgtg aggatggtcc | 550 |
| atgtcacaaa cggcgggcaa gcatctgctg tacccagctg ggtccctgt | 600 |
| cggccctgaa gcatgctgtc ctggggctct acctgctggt cttcctgatt | 650 |
| cttgtgggca tcttcatctt agcagggcca ccgggaccca aggtgatca | 700 |
| gggggatgaa ggaaaggaag caggcctgg catccctgga ttgcctggac | 750 |
| ttcgaggtct gcccggggag agaggtaccc caggattgcc cgggcccaag | 800 |
| ggcgatgatg ggaagctggg ggccacagga ccaatgggca tgcgtgggtt | 850 |
| caaaggtgac cgaggcccaa aggagagaa aggagagaaa ggagacagag | 900 |
| ctggggatgc cagtggcgtg gaggcccga tgatgatccg cctggtgaat | 950 |
| ggctcaggtc cgcacgaggg ccgcgtggaa gtgtaccacg accggcgctg | 1000 |
| gggcaccgtg tgtgacgacg ctgggacaa gaaggacgga cgtggtgt | 1050 |
| gccgcatgct cggcttccgc ggtgtggagg aggtgtaccg cacagctcga | 1100 |
| ttcgggcaag gcactgggag gatctggatg gatgacgttg cctgcaaggg | 1150 |
| cacagaggaa accatcttcc gctgcagctt ctccaaatgg ggggtgacaa | 1200 |
| actgtggaca tgccgaagat gccagcgtga catgcaacag acactgaaag | 1250 |
| tgggcagagc ccaagttcgg ggtcctgcac agagcaccct tgctgcatcc | 1300 |
| ctggggtggg gcacagctcg gggccaccct gaccatgcct cgaccacacc | 1350 |
| ccgtccagca ttctcagtcc tcacacctgc atcccaggac cgtggggcc | 1400 |
| ggtcgtcatt tccctcttga acatgtgctc cgaagtataa ctctgggacc | 1450 |
| tactgcccgt ctctctcttc caccaggttc ctgcatgagg agccctgatc | 1500 |
| aactggatca ccactttgcc cagcctctga acaccatgca ccaggcctca | 1550 |
| atatcccagt tccctttggc cttttagtta caggtgaatg ctgagaatgt | 1600 |

-continued

| | |
|---|---|
| gtcagagaca agtgcagcag cagcgatggt tggtagtata gatcatttac | 1650 |
| tcttcagaca attcccaaac ctccattagt ccaagagttt ctacatcttc | 1700 |
| ctccccagca agaggcaacg tcaagtgatg aatttccccc ctttactctg | 1750 |
| cctctgctcc ccatttgcta gtttgaggaa gtgacataga ggagaagcca | 1800 |
| gctgtagggg caagagggaa atgcaagtca cctgcaggaa tccagctaga | 1850 |
| tttggagaag ggaatgaaac taacattgaa tgactaccat ggcacgctaa | 1900 |
| atagtatctt gggtgccaaa ttcatgtatc cacttagctg cattggtcca | 1950 |
| gggcatgtca gtctggatac agccttacct tcaggtagca cttaactggt | 2000 |
| ccattcacct agactgcaag taagaagaca aaatgactga daccgtgtgc | 2050 |
| ccacctgaac ttattgtctt tacttggcct gagctaaaag cttgggtgca | 2100 |
| ggacctgtgt aactagaaag ttgcctactt cagaacctcc agggcgtgag | 2150 |
| tgcaaggtca acatgactg gcttccaggc cgaccatcaa tgtaggagga | 2200 |
| gagctgatgt ggagggtgac atgggggctg cccatgttaa acctgagtcc | 2250 |
| agtgctctgg cattgggcag tcacggttaa agccaagtca tgtgtgtctc | 2300 |
| agctgtttgg aggtgatgat tttgcatctt ccaagcctct tcaggtgtga | 2350 |
| atctgtggtc aggaaaacac aagtcctaat ggaacccta ggggggaagg | 2400 |
| aaatgaagat tccctataac ctctgggggt ggggagtagg aataaggggc | 2450 |
| cttgggcctc cataaatctg caatctgcac cctcctccta gagacaggga | 2500 |
| gatcgtgttc tgcttttac atgaggagca gaactgggcc atacacgtgt | 2550 |
| tcaagaacta ggggagctac ctggtagcaa gtgagtgcag acccacctca | 2600 |
| ccttggggga atctcaaact cataggcctc agatacacga tcacctgtca | 2650 |
| tatcaggtga gcactggcct gcttggggag agacctgggc ccctccaggt | 2700 |
| gtaggaacag caacactcct ggctgacaac taagccaata tggccctagg | 2750 |
| tcattcttgc ttccaatatg cttgccactc cttaaatgtc ctaatgatga | 2800 |
| gaaactctct ttctgaccaa ttgctatgtt tacataacac gcatgtactc | 2850 |
| atgcatccct tgccagagcc catatatgta tgcatatata aacatagcac | 2900 |
| tttttactac atagctcagc acattgcaag gtttgcattt aagtt | 2945 |

<210> SEQ ID NO 88
<211> LENGTH: 270
<212> TYPE: PRT
<213> ORGANISM: Homo Sapien

<400> SEQUENCE: 88

```
Met Glu Asn Lys Ala Met Tyr Leu His Thr Val Ser Asp Cys Asp
 1               5                  10                  15

Thr Ser Ser Ile Cys Glu Asp Ser Phe Asp Gly Arg Ser Leu Ser
                20                  25                  30

Lys Leu Asn Leu Cys Glu Asp Gly Pro Cys His Lys Arg Arg Ala
                35                  40                  45

Ser Ile Cys Cys Thr Gln Leu Gly Ser Leu Ala Leu Lys His
                50                  55                  60

Ala Val Leu Gly Leu Tyr Leu Leu Val Phe Leu Ile Leu Val Gly
                65                  70                  75

Ile Phe Ile Leu Ala Gly Pro Pro Gly Pro Lys Gly Asp Gln Gly
                80                  85                  90
```

```
Asp Glu Gly Lys Glu Gly Arg Pro Gly Ile Pro Gly Leu Pro Gly
             95                 100                 105
Leu Arg Gly Leu Pro Gly Glu Arg Gly Thr Pro Gly Leu Pro Gly
        110                 115                 120
Pro Lys Gly Asp Asp Gly Lys Leu Gly Ala Thr Gly Pro Met Gly
    125                 130                 135
Met Arg Gly Phe Lys Gly Asp Arg Gly Pro Lys Gly Glu Lys Gly
140                 145                 150
Glu Lys Gly Asp Arg Ala Gly Asp Ala Ser Gly Val Glu Ala Pro
            155                 160                 165
Met Met Ile Arg Leu Val Asn Gly Ser Gly Pro His Glu Gly Arg
        170                 175                 180
Val Glu Val Tyr His Asp Arg Arg Trp Gly Thr Val Cys Asp Asp
    185                 190                 195
Gly Trp Asp Lys Lys Asp Gly Asp Val Val Cys Arg Met Leu Gly
200                 205                 210
Phe Arg Gly Val Glu Glu Val Tyr Arg Thr Ala Arg Phe Gly Gln
            215                 220                 225
Gly Thr Gly Arg Ile Trp Met Asp Asp Val Ala Cys Lys Gly Thr
        230                 235                 240
Glu Glu Thr Ile Phe Arg Cys Ser Phe Ser Lys Trp Gly Val Thr
    245                 250                 255
Asn Cys Gly His Ala Glu Asp Ala Ser Val Thr Cys Asn Arg His
260                 265                 270
```

<210> SEQ ID NO 89
<211> LENGTH: 2758
<212> TYPE: DNA
<213> ORGANISM: Homo Sapien

<400> SEQUENCE: 89

| | |
|---|---:|
| gtcgccgcga gggacgcaga gagcaccctc cacgcccaga tgcctgcgta | 50 |
| gtttttgtga ccagtccgct cctgcctccc cctggggcag tagaggggga | 100 |
| gcgatggaga actggactgg caggccctgg ctgtatctgc tgctgcttct | 150 |
| gtccctccct cagctctgct ggatcagga ggtgttgtcc ggacactctc | 200 |
| ttcagacacc tacagaggag gccagggcc ccgaaggtgt ctggggacct | 250 |
| tgggtccagt gggcctcttg ctcccagccc tgcggggtgg gggtgcagcg | 300 |
| caggagccgg acatgtcagc tccctacagt gcagctccac ccgagtctgc | 350 |
| ccctcccctcc ccggcccca agacatccag aagccctcct ccccgggc | 400 |
| cagggtccca gaccccagac ttctccagaa accctcccct tgtacaggac | 450 |
| acagtctcgg ggaagggtg gcccacttcg aggtcccgct tcccacctag | 500 |
| ggagagagga gacccaggag attcgagcgg ccaggaggtc ccggcttcga | 550 |
| gaccccatca agccaggaat gttcggttat gggagagtgc cctttgcatt | 600 |
| gccactgcac cggaaccgca ggcaccctcg gagcccaccc agatctgagc | 650 |
| tgtccctgat ctcttctaga ggggaagagg ctattccgtc ccctactcca | 700 |
| agagcagagc cattctccgc aaacggcagc ccccaaactg agctccctcc | 750 |
| cacagaactg tctgtccaca ccccatcccc ccaagcagaa cctctaagcc | 800 |
| ctgaaactgc tcagacagag gtggccccca gaaccaggcc tgcccccta | 850 |

-continued

| | |
|---|---|
| cggcatcacc ccagagccca ggcctctggc acagagcccc cctcacccac | 900 |
| gcactcctta ggagaaggtg gcttcttccg tgcatccccc cagccacgaa | 950 |
| ggccaagttc ccaggttgg gccagtcccc aggtagcagg gagacgccct | 1000 |
| gatcctttc cttcggtccc tcgggccga ggccagcagg gccaagggcc | 1050 |
| ttggggaacg ggggggactc ctcacgggcc ccgcctggag cctgaccctc | 1100 |
| agcacccggg cgcctggctg cccctgctga gcaacggccc ccatgccagc | 1150 |
| tccctctgga gcctctttgc tcccagtagc cctattccaa gatgttctgg | 1200 |
| ggagagtgaa cagctaagag cctgcagcca agcgccctgc cccctgagc | 1250 |
| agccagaccc ccgggccctg cagtgcgcag cctttaactc ccaggaattc | 1300 |
| atgggccagc tgtatcagtg ggagcccttc actgaagtcc agggctccca | 1350 |
| gcgctgtgaa ctgaactgcc ggccccgtgg cttccgcttc tatgtccgtc | 1400 |
| acactgaaaa ggtccaggat gggacccttgt gtcagcctgg agccctgac | 1450 |
| atctgtgtgg ctggacgctg tctgagcccc ggctgtgatg ggatccttgg | 1500 |
| ctctggcagg cgtcctgatg gctgtggagt ctgtgggggt gatgattcta | 1550 |
| cctgtcgcct tgtttcgggg aacctcactg accgagggg ccccctgggc | 1600 |
| tatcagaaga tcttgtggat tccagcggga gccttgcggc tccagattgc | 1650 |
| ccagctccgg cctagctcca actacctggc acttcgtggc cctggggggcc | 1700 |
| ggtccatcat caatgggaac tgggctgtgg atccccctgg gtcctacagg | 1750 |
| gccggcggga ccgtctttcg atataaccgt cctcccaggg aggagggcaa | 1800 |
| agggagagt ctgtcggctg aaggccccac cacccagcct gtggatgtct | 1850 |
| atatgatctt tcaggaggaa aacccaggcg ttttttatca gtatgtcatc | 1900 |
| tcttcacctc ctccaatcct tgagaacccc accccagagc cccctgtccc | 1950 |
| ccagcttcag ccggagattc tgagggtgga gccccacttt gctccggcac | 2000 |
| cccgcccagc ccggaccccca ggcacccctc agcgtcaggt gcggatcccc | 2050 |
| cagatgcccg ccccgcccca tcccaggaca cccctgggggt ctccagctgc | 2100 |
| gtactgaaaa cgagtgggac actctgcatg ctcagcgtcc tgcgggaaag | 2150 |
| gtgtctggcg ccccatttc ctctgcatct cccgtgagtc gggagaggaa | 2200 |
| ctggatgaac gcagctgtgc cgcgggtgcc aggccccag cctcccctga | 2250 |
| accctgccac ggcaccccat gccccccata ctgggaggct ggcgagtgga | 2300 |
| catcctgcag ccgctcctgt ggccccggca cccagcaccg ccagctgcag | 2350 |
| tgccggcagg aatttggggg gggtggctcc tcggtgcccc cggagcgctg | 2400 |
| tggacatctc ccccggccca acatcaccca gtcttgccag ctgcgcctct | 2450 |
| gtggccattg ggaagttggc tctccttgga gccagtgctc cgtgcggtgc | 2500 |
| ggccggggcc agagaagccg gcaggttcgc tgtgttggga caacggtga | 2550 |
| tgaagtgagc gagcaggagt gtgcgtcagg ccccccacag ccccccagca | 2600 |
| gagaggcctg tgacatgggg ccctgtacta ctgcctggtt ccacagcgac | 2650 |
| tggagctcca aggtgagccc ggaaccccca gccatatcct gcatcctggg | 2700 |
| taaccatgcc caggacacct cagccttttcc agcatagctc aataaacttg | 2750 |
| tattgatc | 2758 |

```
<210> SEQ ID NO 90
<211> LENGTH: 877
<212> TYPE: PRT
<213> ORGANISM: Homo Sapien

<400> SEQUENCE: 90
```

| | | | | | | | | | | | | | | |
|---|---|---|---|---|---|---|---|---|---|---|---|---|---|---|
| Met | Glu | Asn | Trp | Thr | Gly | Arg | Pro | Trp | Leu | Tyr | Leu | Leu | Leu | Leu |
| 1 | | | | 5 | | | | | 10 | | | | | 15 |
| Leu | Ser | Leu | Pro | Gln | Leu | Cys | Leu | Asp | Gln | Glu | Val | Leu | Ser | Gly |
| | | | 20 | | | | | 25 | | | | | 30 | |
| His | Ser | Leu | Gln | Thr | Pro | Thr | Glu | Glu | Gly | Gln | Gly | Pro | Glu | Gly |
| | | | | 35 | | | | | 40 | | | | | 45 |
| Val | Trp | Gly | Pro | Trp | Val | Gln | Trp | Ala | Ser | Cys | Ser | Gln | Pro | Cys |
| | | | 50 | | | | | 55 | | | | | 60 | |
| Gly | Val | Gly | Val | Gln | Arg | Arg | Ser | Arg | Thr | Cys | Gln | Leu | Pro | Thr |
| 65 | | | | | 70 | | | | | 75 | | | | |
| Val | Gln | Leu | His | Pro | Ser | Leu | Pro | Leu | Pro | Pro | Arg | Pro | Pro | Arg |
| | | | | 80 | | | | | 85 | | | | | 90 |
| His | Pro | Glu | Ala | Leu | Leu | Pro | Arg | Gly | Gln | Gly | Pro | Arg | Pro | Gln |
| | | | | 95 | | | | | 100 | | | | | 105 |
| Thr | Ser | Pro | Glu | Thr | Leu | Pro | Leu | Tyr | Arg | Thr | Gln | Ser | Arg | Gly |
| | | | | 110 | | | | | 115 | | | | | 120 |
| Arg | Gly | Gly | Pro | Leu | Arg | Gly | Pro | Ala | Ser | His | Leu | Gly | Arg | Glu |
| | | | | 125 | | | | | 130 | | | | | 135 |
| Glu | Thr | Gln | Glu | Ile | Arg | Ala | Ala | Arg | Ser | Arg | Leu | Arg | Asp |
| | | | | 140 | | | | | 145 | | | | | 150 |
| Pro | Ile | Lys | Pro | Gly | Met | Phe | Gly | Tyr | Gly | Arg | Val | Pro | Phe | Ala |
| | | | | 155 | | | | | 160 | | | | | 165 |
| Leu | Pro | Leu | His | Arg | Asn | Arg | Arg | His | Pro | Arg | Ser | Pro | Pro | Arg |
| | | | | 170 | | | | | 175 | | | | | 180 |
| Ser | Glu | Leu | Ser | Leu | Ile | Ser | Ser | Arg | Gly | Glu | Glu | Ala | Ile | Pro |
| | | | | 185 | | | | | 190 | | | | | 195 |
| Ser | Pro | Thr | Pro | Arg | Ala | Glu | Pro | Phe | Ser | Ala | Asn | Gly | Ser | Pro |
| | | | | 200 | | | | | 205 | | | | | 210 |
| Gln | Thr | Glu | Leu | Pro | Pro | Thr | Glu | Leu | Ser | Val | His | Thr | Pro | Ser |
| | | | | 215 | | | | | 220 | | | | | 225 |
| Pro | Gln | Ala | Glu | Pro | Leu | Ser | Pro | Glu | Thr | Ala | Gln | Thr | Glu | Val |
| | | | | 230 | | | | | 235 | | | | | 240 |
| Ala | Pro | Arg | Thr | Arg | Pro | Ala | Pro | Leu | Arg | His | His | Pro | Arg | Ala |
| | | | | 245 | | | | | 250 | | | | | 255 |
| Gln | Ala | Ser | Gly | Thr | Glu | Pro | Pro | Ser | Pro | Thr | His | Ser | Leu | Gly |
| | | | | 260 | | | | | 265 | | | | | 270 |
| Glu | Gly | Gly | Phe | Phe | Arg | Ala | Ser | Pro | Gln | Pro | Arg | Arg | Pro | Ser |
| | | | | 275 | | | | | 280 | | | | | 285 |
| Ser | Gln | Gly | Trp | Ala | Ser | Pro | Gln | Val | Ala | Gly | Arg | Arg | Pro | Asp |
| | | | | 290 | | | | | 295 | | | | | 300 |
| Pro | Phe | Pro | Ser | Val | Pro | Arg | Gly | Arg | Gly | Gln | Gln | Gly | Gln | Gly |
| | | | | 305 | | | | | 310 | | | | | 315 |
| Pro | Trp | Gly | Thr | Gly | Gly | Thr | Pro | His | Gly | Pro | Arg | Leu | Glu | Pro |
| | | | | 320 | | | | | 325 | | | | | 330 |
| Asp | Pro | Gln | His | Pro | Gly | Ala | Trp | Leu | Pro | Leu | Leu | Ser | Asn | Gly |
| | | | | 335 | | | | | 340 | | | | | 345 |
| Pro | His | Ala | Ser | Ser | Leu | Trp | Ser | Leu | Phe | Ala | Pro | Ser | Ser | Pro |
| | | | | 350 | | | | | 355 | | | | | 360 |

-continued

```
Ile Pro Arg Cys Ser Gly Glu Ser Glu Gln Leu Arg Ala Cys Ser
            365                 370                 375

Gln Ala Pro Cys Pro Pro Glu Gln Pro Asp Pro Arg Ala Leu Gln
            380                 385                 390

Cys Ala Ala Phe Asn Ser Gln Glu Phe Met Gly Gln Leu Tyr Gln
            395                 400                 405

Trp Glu Pro Phe Thr Glu Val Gln Gly Ser Gln Arg Cys Glu Leu
            410                 415                 420

Asn Cys Arg Pro Arg Gly Phe Arg Phe Tyr Val Arg His Thr Glu
            425                 430                 435

Lys Val Gln Asp Gly Thr Leu Cys Gln Pro Gly Ala Pro Asp Ile
            440                 445                 450

Cys Val Ala Gly Arg Cys Leu Ser Pro Gly Cys Asp Gly Ile Leu
            455                 460                 465

Gly Ser Gly Arg Arg Pro Asp Gly Cys Gly Val Cys Gly Gly Asp
            470                 475                 480

Asp Ser Thr Cys Arg Leu Val Ser Gly Asn Leu Thr Asp Arg Gly
            485                 490                 495

Gly Pro Leu Gly Tyr Gln Lys Ile Leu Trp Ile Pro Ala Gly Ala
            500                 505                 510

Leu Arg Leu Gln Ile Ala Gln Leu Arg Pro Ser Ser Asn Tyr Leu
            515                 520                 525

Ala Leu Arg Gly Pro Gly Gly Arg Ser Ile Ile Asn Gly Asn Trp
            530                 535                 540

Ala Val Asp Pro Pro Gly Ser Tyr Arg Ala Gly Gly Thr Val Phe
            545                 550                 555

Arg Tyr Asn Arg Pro Pro Arg Glu Glu Gly Lys Gly Glu Ser Leu
            560                 565                 570

Ser Ala Glu Gly Pro Thr Thr Gln Pro Val Asp Val Tyr Met Ile
            575                 580                 585

Phe Gln Glu Glu Asn Pro Gly Val Phe Tyr Gln Tyr Val Ile Ser
            590                 595                 600

Ser Pro Pro Pro Ile Leu Glu Asn Pro Thr Pro Glu Pro Pro Val
            605                 610                 615

Pro Gln Leu Gln Pro Glu Ile Leu Arg Val Glu Pro Pro Leu Ala
            620                 625                 630

Pro Ala Pro Arg Pro Ala Arg Thr Pro Gly Thr Leu Gln Arg Gln
            635                 640                 645

Val Arg Ile Pro Gln Met Pro Ala Pro His Pro Arg Thr Pro
            650                 655                 660

Leu Gly Ser Pro Ala Ala Tyr Trp Lys Arg Val Gly His Ser Ala
            665                 670                 675

Cys Ser Ala Ser Cys Gly Lys Gly Val Trp Arg Pro Ile Phe Leu
            680                 685                 690

Cys Ile Ser Arg Glu Ser Gly Glu Leu Asp Glu Arg Ser Cys
            695                 700                 705

Ala Ala Gly Ala Arg Pro Pro Ala Ser Pro Glu Pro Cys His Gly
            710                 715                 720

Thr Pro Cys Pro Pro Tyr Trp Glu Ala Gly Glu Trp Thr Ser Cys
            725                 730                 735

Ser Arg Ser Cys Gly Pro Gly Thr Gln His Arg Gln Leu Gln Cys
            740                 745                 750

Arg Gln Glu Phe Gly Gly Gly Gly Ser Ser Val Pro Pro Glu Arg
```

Cys Gly His Leu Pro Arg Pro Asn Ile Thr Gln Ser Cys Gln Leu
            770                 775                 780

Arg Leu Cys Gly His Trp Glu Val Gly Ser Pro Trp Ser Gln Cys
        785                 790                 795

Ser Val Arg Cys Gly Arg Gly Gln Arg Ser Arg Gln Val Arg Cys
            800                 805                 810

Val Gly Asn Asn Gly Asp Glu Val Ser Glu Gln Glu Cys Ala Ser
            815                 820                 825

Gly Pro Pro Gln Pro Ser Arg Glu Ala Cys Asp Met Gly Pro
            830                 835                 840

Cys Thr Thr Ala Trp Phe His Ser Asp Trp Ser Ser Lys Val Ser
            845                 850                 855

Pro Glu Pro Pro Ala Ile Ser Cys Ile Leu Gly Asn His Ala Gln
            860                 865                 870

Asp Thr Ser Ala Phe Pro Ala
            875

<210> SEQ ID NO 91
<211> LENGTH: 2597
<212> TYPE: DNA
<213> ORGANISM: Homo Sapien

<400> SEQUENCE: 91

| | |
|---|---:|
| cgagtatttt cccaccatct ccagccggaa actgaccaag aactctgagg | 50 |
| cggatggcat gttcgcgtac gtcttccatg atgagttcgt ggcctcgatg | 100 |
| attaagatcc cttcggacac cttcaccatc atccctgact ttgatatcta | 150 |
| ctatgtctat ggttttagca gtggcaactt tgtctacttt ttgaccctcc | 200 |
| aacctgagat ggtgtctcca ccaggctcca ccaccaagga gcaggtgtat | 250 |
| acatccaagc tcgtgaggct ttgcaaggag gacacagcct tcaactccta | 300 |
| tgtagaggtg cccattggct gtgagcgcag tggggtggag taccgcctgc | 350 |
| tgcaggctgc ctacctgtcc aaagcggggg ccgtgcttgg caggacccct | 400 |
| ggagtccatc cagatgatga cctgctcttc accgtcttct ccaagggcca | 450 |
| gaagcggaaa atgaaatccc tggatgagtc ggccctgtgc atcttcatct | 500 |
| tgaagcagat aaatgaccgc attaaggagc ggctgcagtc ttgttaccgg | 550 |
| ggcgagggca cgctggacct ggcctggctc aaggtgaagg acatcccctg | 600 |
| cagcagtgcg ctcttaacca ttgacgataa cttctgtggc ctggacatga | 650 |
| atgctcccct gggagtgtcc gacatggtgc gtggaattcc cgtcttcacg | 700 |
| gaggacaggg accgcatgac gtctgtcatc gcatatgtct acaagaacca | 750 |
| ctctctggcc tttgtgggca ccaaaagtgg caagctgaag aaggtgcctg | 800 |
| gtaccagcct ctgccctacc cttgagctac agacgggacc ccgatcccac | 850 |
| agagcaacag tgactctgga actcctgttc tccagctgtt catcaaactg | 900 |
| agaaaaactt cagagctgtg taggcttatt tagtgtgttg tcagccttgg | 950 |
| atattggaaa atgaaacag atgagacaca tctacctccc tgtgacccca | 1000 |
| gccatacatc atagctcatg tcctgccacc ccaagtcctt agggaaaaaa | 1050 |
| gactttggag aatgtgtctc tgcttagctt ggctaggtag ttggtctctt | 1100 |
| ttctctgccc caagcgtccc ctgggtaatt ttggacaatg gagtgtaggc | 1150 |

-continued

```
atgtttgact cttgtggtgt tatcacttgt atatgtcagt gaaactaact      1200
gattctccca tcggaatata gttatctctt gggcctgata tatggtagga      1250
taaccttatg ctcatctgtc cacttctgca gccaagtcgc ctggccagtg      1300
tgtgtgtgtg tgtgtgtgtg tgtgtgtgtg tgtgtgtatg cttatctgtg      1350
tttaaaggtg tgtgtgcata cacagggcag agaggatgga gcccaccgta      1400
ctgcagcatc atgtaattaa ctcagtgctc agaaccatcc cagcctctgc      1450
gggaaagaga aaagtaagcc aacagtgcct gatgagctga tcatatgtgc      1500
aaaagctctg ttggcatctg tccaggaga gcacccaaaa aaagttaatt       1550
ggtgttgtcc agtctccttt ccttaagact atggttacaa caaagcgtga      1600
gcagtgtctc ctgcatggcc actatccagc acaattccat aattccccca      1650
tagagccggt ggggaggagg aggtgagtgg cgaaggaagt ggaaacactt      1700
ggtgtcatgt gctcctatca tttctactag cttactggga aataaagtgt      1750
agtcaagagt gtatgaaggc aagatgtaaa attagcgact ggtgctaatc      1800
tggttacttg aaaacaagtg aaagtgctgt agatttgttc tgttgctaag      1850
aaccaccaca ctaaacctcg tatagttcct ggaggatata caacagtgta      1900
attctcttta gggtgtgcca caggttcctg gcctgtggga gggaatgaat      1950
caggagggct cttgagaacc ttcatctgtg tgcttgcact gaaagtgagt      2000
cccaaagctg gagatttagt gagagcaggc aaccctctg tgtctcactg       2050 tccatattct ggaggcagag gtttgtaaca ggccatgtgc acctgcatag      2100
ggatgggtaa agcaaggact ttgaaagagt tgaaaagcat tataaacagt      2150
tgttcagaaa tacgtcccag gagttccatg tgaaactggc tctgtgtgca      2200
ttgaagcatg gctgttggga attctaactg gtccaacact cctgcaaaac      2250
aatgtgtaaa tatttaggaa gaaacttgaa aatagtcaaa tcctttgaac      2300
tggtgacaat ttttttaaaga atcaattcta atttgtttca agggtaataa     2350
tcaccaagat acacatttca gcatttattt agtctatcaa aaattggaat      2400
tgatatatac actcatttat aggagaatgg ttaggtagat ttggtatatt      2450
tatgtagtca ttgaaaactt agtttataaa ggccaatctt gtaactgatt      2500
cttgtgtgat aacattcagt gaaaaagcat gagacaatta gaaagcatga      2550
tacaatgaat aaaataaaaa ctggaaagag aaccatcaaa atgctaa        2597
```

<210> SEQ ID NO 92
<211> LENGTH: 280
<212> TYPE: PRT
<213> ORGANISM: Homo Sapien

<400> SEQUENCE: 92

```
Met Phe Ala Tyr Val Phe His Asp Glu Phe Val Ala Ser Met Ile
  1               5                  10                  15

Lys Ile Pro Ser Asp Thr Phe Thr Ile Ile Pro Asp Phe Asp Ile
                 20                  25                  30

Tyr Tyr Val Tyr Gly Phe Ser Ser Gly Asn Phe Val Tyr Phe Leu
                 35                  40                  45

Thr Leu Gln Pro Glu Met Val Ser Pro Pro Gly Ser Thr Thr Lys
                 50                  55                  60
```

-continued

```
Glu Gln Val Tyr Thr Ser Lys Leu Val Arg Leu Cys Lys Glu Asp
                 65                  70                  75

Thr Ala Phe Asn Ser Tyr Val Glu Val Pro Ile Gly Cys Glu Arg
                 80                  85                  90

Ser Gly Val Glu Tyr Arg Leu Leu Gln Ala Ala Tyr Leu Ser Lys
                 95                 100                 105

Ala Gly Ala Val Leu Gly Arg Thr Leu Gly Val His Pro Asp Asp
                110                 115                 120

Asp Leu Leu Phe Thr Val Phe Ser Lys Gly Gln Lys Arg Lys Met
                125                 130                 135

Lys Ser Leu Asp Glu Ser Ala Leu Cys Ile Phe Ile Leu Lys Gln
                140                 145                 150

Ile Asn Asp Arg Ile Lys Glu Arg Leu Gln Ser Cys Tyr Arg Gly
                155                 160                 165

Glu Gly Thr Leu Asp Leu Ala Trp Leu Lys Val Lys Asp Ile Pro
                170                 175                 180

Cys Ser Ser Ala Leu Leu Thr Ile Asp Asp Asn Phe Cys Gly Leu
                185                 190                 195

Asp Met Asn Ala Pro Leu Gly Val Ser Asp Met Val Arg Gly Ile
                200                 205                 210

Pro Val Phe Thr Glu Asp Arg Asp Arg Met Thr Ser Val Ile Ala
                215                 220                 225

Tyr Val Tyr Lys Asn His Ser Leu Ala Phe Val Gly Thr Lys Ser
                230                 235                 240

Gly Lys Leu Lys Lys Val Pro Gly Thr Ser Leu Cys Pro Thr Leu
                245                 250                 255

Glu Leu Gln Thr Gly Pro Arg Ser His Arg Ala Thr Val Thr Leu
                260                 265                 270

Glu Leu Leu Phe Ser Ser Cys Ser Ser Asn
                275                 280
```

<210> SEQ ID NO 93
<211> LENGTH: 2883
<212> TYPE: DNA
<213> ORGANISM: Homo Sapien

<400> SEQUENCE: 93

| | | |
|---|---|---|
| ccttatcaga caaaggacga gatggaaaat acaagataat ttacagtgga | 50 |
| gaagaattag aatgtaacct gaaagatctt agaccagcaa cagattatca | 100 |
| tgtgagggtg tatgccatgt acaattccgt aaagggatcc tgctccgagc | 150 |
| ctgttagctt caccacccac agctgtgcac ccgagtgtcc tttccccct | 200 |
| aagctggcac ataggagcaa aagttcacta accctgcagt ggaaggcacc | 250 |
| aattgacaac ggttcaaaaa tcaccaacta ccttttagag tgggatgagg | 300 |
| gaaaagaaa tagtggtttc agacagtgct tcttcgggag ccagaagcac | 350 |
| tgcaagttga caaagctttg tccggcaatg gggtacacat tcaggctggc | 400 |
| cgctcgaaac gacattggca ccagtggtta tagccaagag gtggtgtgct | 450 |
| acacattagg aaatatccct cagatgcctt ctgcactaag gctggttcga | 500 |
| gctggcatca catgggtcac gttgcagtgg agtaagccag aaggctgttc | 550 |
| acccgaggaa gtgatcacct acaccttgga aattcaggag gatgaaaatg | 600 |
| ataaccttt ccacccaaaa tacactggag aggatttaac ctgtactgtg | 650 |

-continued

| | |
|---|---|
| aaaaatctca aaagaagcac acagtataaa ttcaggctga ctgcttctaa | 700 |
| tacggaagga aaaagctgtc caagcgaagt tcttgtttgt acgacgagtc | 750 |
| ctgacaggcc tggacctcct accagaccgc ttgtcaaagg cccagttaca | 800 |
| tctcatggct ttagtgtcaa atgggatccc cctaaggaca atggtggttc | 850 |
| agaaatcctc aagtacttgc tagagattac tgatggaaat tctgaagcga | 900 |
| atcagtggga agtggcctac agtgggtcgg ctaccgaata caccttcacc | 950 |
| cacttgaaac caggcacttt gtacaaactc cgagcatgct gcatcagtac | 1000 |
| cggcggacac agccagtgtt ctgaaagtct ccctgttcgc acactaagca | 1050 |
| ttgcaccagg tcaatgtcga ccaccgaggg ttttgggtag accaaagcac | 1100 |
| aaagaagtcc acttagagtg ggatgttcct gcatcggaaa gtggctgtga | 1150 |
| ggtctcagag tacagcgtgg agatgacgga gcccgaagac gtagcctcgg | 1200 |
| aagtgtacca tggcccagag ctggagtgca ccgtcggcaa cctgcttcct | 1250 |
| ggaaccgtgt atcgcttccg ggtgagggct ctgaatgatg gagggtatgg | 1300 |
| tccctattct gatgtctcag aaattaccac tgctgcaggg cctcctggac | 1350 |
| aatgcaaagc accttgtatt tcttgtacac ctgatggatg tgtcttagtg | 1400 |
| ggttgggaga gtcctgatag ttctggtgct gacatctcag agtacaggtt | 1450 |
| ggaatgggga gaagatgaag aatccttaga actcatttat catgggacag | 1500 |
| acacccgttt tgaaataaga gacctgttgc ctgctgcaca gtattgctgt | 1550 |
| agactacagg ccttcaatca agcaggggca gggccgtaca gtgaacttgt | 1600 |
| cctttgccag acgccagcgt ctgcccctga ccccgtctcc actctctgtg | 1650 |
| tcctggagga ggagccccctt gatgcctacc ctgattcacc ttctgcgtgc | 1700 |
| cttgtactga actgggaaga gccgtgcaat aacggatctg aaatccttgc | 1750 |
| ttacaccatt gatctaggag acactagcat taccgtgggc aacaccacca | 1800 |
| tgcatgttat gaaagatctc cttccagaaa ccacctaccg gatcagaatt | 1850 |
| caggctataa atgaaattgg agctggacca tttagtcagt tcattaaagc | 1900 |
| aaaaactcgg ccattaccac ccttgcctcc taggctagaa tgtgctgctg | 1950 |
| ctggtcctca gagcctgaag ctaaaatggg gagacagtaa ctccaagaca | 2000 |
| catgctgctg aggacattgt gtacacacta cagctggagg acagaaacaa | 2050 |
| gaggtttatt tcaatctaca gaggacccag ccacacctac aaggtccaga | 2100 |
| gactgacgga attcacatgc tactccttca gaatccaggc agcaagcgag | 2150 |
| gctggagaag ggcccttctc agaaacctat accttcagca caaccaaaag | 2200 |
| tgtcccccccc accatcaaag cacctcgagt aacacagtta gaagtaaatt | 2250 |
| catgtgaaat tttatgggag acggtaccat caatgaaagg tgaccctgtt | 2300 |
| aactacattc tgcaggtatt ggttggaaga gaatctgagt acaaacaggt | 2350 |
| gtacaaggga gaagaagcca cattccaaat ctcaggcctc cagaccaaca | 2400 |
| cagactacag gttccgcgta tgtgcgtgtc gtcgctgttt agacacctct | 2450 |
| caggagctaa gcgagccttt cagcccctct gcggcttttg tattacaacg | 2500 |
| aagtgaggtc atgcttacag gggacatggg gagcttagat gatcccaaaa | 2550 |
| tgaagagcat gatgcctact gatgaacagt ttgcagccat cattgtgctt | 2600 |
| ggctttgcaa cttttgtcca ttttatttgcc tttatattac agtacttctt | 2650 |

-continued

```
aatgaagtaa acccaacaaa actagaggta tgaattaatg ctacacattt          2700
taatacacac atttattcag atactcccct ttttaaagcc cttttgtttt          2750
ttgatttata tactctgttt tacagattta gctagaaaaa aaatgtcagt          2800
gttttggtgc acctttttga aatgcaaaac taggaaaagg ttaaactgga          2850
ttttttttta aaaaaaaaaa aaaaaaaaaa aaa                           2883
```

<210> SEQ ID NO 94
<211> LENGTH: 847
<212> TYPE: PRT
<213> ORGANISM: Homo Sapien

<400> SEQUENCE: 94

```
Met Tyr Asn Ser Val Lys Gly Ser Cys Ser Glu Pro Val Ser Phe
  1               5                  10                  15

Thr Thr His Ser Cys Ala Pro Glu Cys Pro Phe Pro Lys Leu
                 20                  25                  30

Ala His Arg Ser Lys Ser Ser Leu Thr Leu Gln Trp Lys Ala Pro
                 35                  40                  45

Ile Asp Asn Gly Ser Lys Ile Thr Asn Tyr Leu Leu Glu Trp Asp
                 50                  55                  60

Glu Gly Lys Arg Asn Ser Gly Phe Arg Gln Cys Phe Phe Gly Ser
 65                  70                  75

Gln Lys His Cys Lys Leu Thr Lys Leu Cys Pro Ala Met Gly Tyr
                 80                  85                  90

Thr Phe Arg Leu Ala Ala Arg Asn Asp Ile Gly Thr Ser Gly Tyr
                 95                 100                 105

Ser Gln Glu Val Val Cys Tyr Thr Leu Gly Asn Ile Pro Gln Met
                110                 115                 120

Pro Ser Ala Leu Arg Leu Val Arg Ala Gly Ile Thr Trp Val Thr
                125                 130                 135

Leu Gln Trp Ser Lys Pro Glu Gly Cys Ser Pro Glu Glu Val Ile
                140                 145                 150

Thr Tyr Thr Leu Glu Ile Gln Glu Asp Glu Asn Asp Asn Leu Phe
                155                 160                 165

His Pro Lys Tyr Thr Gly Glu Asp Leu Thr Cys Thr Val Lys Asn
                170                 175                 180

Leu Lys Arg Ser Thr Gln Tyr Lys Phe Arg Leu Thr Ala Ser Asn
                185                 190                 195

Thr Glu Gly Lys Ser Cys Pro Ser Glu Val Leu Val Cys Thr Thr
                200                 205                 210

Ser Pro Asp Arg Pro Gly Pro Pro Thr Arg Pro Leu Val Lys Gly
                215                 220                 225

Pro Val Thr Ser His Gly Phe Ser Val Lys Trp Asp Pro Pro Lys
                230                 235                 240

Asp Asn Gly Gly Ser Glu Ile Leu Lys Tyr Leu Leu Glu Ile Thr
                245                 250                 255

Asp Gly Asn Ser Glu Ala Asn Gln Trp Glu Val Ala Tyr Ser Gly
                260                 265                 270

Ser Ala Thr Glu Tyr Thr Phe Thr His Leu Lys Pro Gly Thr Leu
                275                 280                 285

Tyr Lys Leu Arg Ala Cys Cys Ile Ser Thr Gly Gly His Ser Gln
                290                 295                 300
```

-continued

```
Cys Ser Glu Ser Leu Pro Val Arg Thr Leu Ser Ile Ala Pro Gly
            305                 310                 315

Gln Cys Arg Pro Pro Arg Val Leu Gly Arg Pro Lys His Lys Glu
            320                 325                 330

Val His Leu Glu Trp Asp Val Pro Ala Ser Glu Ser Gly Cys Glu
            335                 340                 345

Val Ser Glu Tyr Ser Val Glu Met Thr Glu Pro Glu Asp Val Ala
            350                 355                 360

Ser Glu Val Tyr His Gly Pro Glu Leu Glu Cys Thr Val Gly Asn
            365                 370                 375

Leu Leu Pro Gly Thr Val Tyr Arg Phe Arg Val Arg Ala Leu Asn
            380                 385                 390

Asp Gly Gly Tyr Gly Pro Tyr Ser Asp Val Ser Glu Ile Thr Thr
            395                 400                 405

Ala Ala Gly Pro Pro Gly Gln Cys Lys Ala Pro Cys Ile Ser Cys
            410                 415                 420

Thr Pro Asp Gly Cys Val Leu Val Gly Trp Glu Ser Pro Asp Ser
            425                 430                 435

Ser Gly Ala Asp Ile Ser Glu Tyr Arg Leu Glu Trp Gly Glu Asp
            440                 445                 450

Glu Glu Ser Leu Glu Leu Ile Tyr His Gly Thr Asp Thr Arg Phe
            455                 460                 465

Glu Ile Arg Asp Leu Leu Pro Ala Ala Gln Tyr Cys Cys Arg Leu
            470                 475                 480

Gln Ala Phe Asn Gln Ala Gly Ala Gly Pro Tyr Ser Glu Leu Val
            485                 490                 495

Leu Cys Gln Thr Pro Ala Ser Ala Pro Asp Pro Val Ser Thr Leu
            500                 505                 510

Cys Val Leu Glu Glu Pro Leu Asp Ala Tyr Pro Asp Ser Pro
            515                 520                 525

Ser Ala Cys Leu Val Leu Asn Trp Glu Glu Pro Cys Asn Asn Gly
            530                 535                 540

Ser Glu Ile Leu Ala Tyr Thr Ile Asp Leu Gly Asp Thr Ser Ile
            545                 550                 555

Thr Val Gly Asn Thr Thr Met His Val Met Lys Asp Leu Leu Pro
            560                 565                 570

Glu Thr Thr Tyr Arg Ile Arg Ile Gln Ala Ile Asn Glu Ile Gly
            575                 580                 585

Ala Gly Pro Phe Ser Gln Phe Ile Lys Ala Lys Thr Arg Pro Leu
            590                 595                 600

Pro Pro Leu Pro Pro Arg Leu Glu Cys Ala Ala Ala Gly Pro Gln
            605                 610                 615

Ser Leu Lys Leu Lys Trp Gly Asp Ser Asn Ser Lys Thr His Ala
            620                 625                 630

Ala Glu Asp Ile Val Tyr Thr Leu Gln Leu Glu Asp Arg Asn Lys
            635                 640                 645

Arg Phe Ile Ser Ile Tyr Arg Gly Pro Ser His Thr Tyr Lys Val
            650                 655                 660

Gln Arg Leu Thr Glu Phe Thr Cys Tyr Ser Phe Arg Ile Gln Ala
            665                 670                 675

Ala Ser Glu Ala Gly Glu Gly Pro Phe Ser Glu Thr Tyr Thr Phe
            680                 685                 690

Ser Thr Thr Lys Ser Val Pro Pro Thr Ile Lys Ala Pro Arg Val
```

-continued

```
                    695                 700                 705
Thr Gln Leu Glu Val Asn Ser Cys Glu Ile Leu Trp Glu Thr Val
                710                 715                 720
Pro Ser Met Lys Gly Asp Pro Val Asn Tyr Ile Leu Gln Val Leu
                725                 730                 735
Val Gly Arg Glu Ser Glu Tyr Lys Gln Val Tyr Lys Gly Glu Glu
                740                 745                 750
Ala Thr Phe Gln Ile Ser Gly Leu Gln Thr Asn Thr Asp Tyr Arg
                755                 760                 765
Phe Arg Val Cys Ala Cys Arg Arg Cys Leu Asp Thr Ser Gln Glu
                770                 775                 780
Leu Ser Gly Ala Phe Ser Pro Ser Ala Ala Phe Val Leu Gln Arg
                785                 790                 795
Ser Glu Val Met Leu Thr Gly Asp Met Gly Ser Leu Asp Asp Pro
                800                 805                 810
Lys Met Lys Ser Met Met Pro Thr Asp Glu Gln Phe Ala Ala Ile
                815                 820                 825
Ile Val Leu Gly Phe Ala Thr Leu Ser Ile Leu Phe Ala Phe Ile
                830                 835                 840
Leu Gln Tyr Phe Leu Met Lys
                845
```

<210> SEQ ID NO 95
<211> LENGTH: 4725
<212> TYPE: DNA
<213> ORGANISM: Homo Sapien

<400> SEQUENCE: 95

| | | |
|---|---|---|
| caattcggcc tcgctccttg tgattgcgct aaaccttccg tcctcagctg | 50 |
| agaacgctcc accacctccc cggatcgctc atctcttggc tgccctccca | 100 |
| ctgttcctga tgttatttta ctccccgtat ccccctactcg ttcttcacaa | 150 |
| ttctgtaggt gagtggttcc agctggtgcc tggcctgtgt ctcttggatg | 200 |
| ccctgtggct tcagtccgtc tcctgttgcc caccacctcg tccctgggcc | 250 |
| gcctgatacc ccagcccaac agctaaggtg tggatggaca gtaggggggct | 300 |
| ggcttctctc actggtcagg ggtcttctcc cctgtctgcc tcccggagct | 350 |
| aggactgcag aggggcctat catggtgctt gcaggccccc tggctgtctc | 400 |
| gctgttgctg cccagcctca cactgctggt gtcccacctc tccagctccc | 450 |
| aggatgtctc cagtgagccc agcagtgagc agcagctgtg cgcccttagc | 500 |
| aagcacccca ccgtggcctt tgaagacctg cagccgtggg tctctaactt | 550 |
| cacctaccct ggagcccggg atttctccca gctggctttg gaccccctccg | 600 |
| ggaaccagct catcgtggga gccaggaact acctcttcag actcagcctt | 650 |
| gccaatgtct ctcttcttca ggccacagag tgggcctcca gtgaggacac | 700 |
| gcgccgctcc tgccaaagca aagggaagac tgaggaggag tgtcagaact | 750 |
| acgtgcgagt cctgatcgtc gccggccgga aggtgttcat gtgtggaacc | 800 |
| aatgcctttt cccccatgtg caccagcaga caggtgggga acctcagccg | 850 |
| gactattgag aagatcaatg gtgtggcccg ctgcccctat gacccacgcc | 900 |
| acaactccac agctgtcatc tcctcccagg gggagctcta tgcagccacg | 950 |
| gtcatcgact tctcaggtcg ggaccctgcc atctaccgca gcctgggcag | 1000 |

| | |
|---|---|
| tgggccaccg cttcgcactg cccaatataa ctccaagtgg cttaatgagc | 1050 |
| caaacttcgt ggcagcctat gatattgggc tgtttgcata cttcttcctg | 1100 |
| cgggagaacg cagtggagca cgactgtgga cgcaccgtgt actctcgcgt | 1150 |
| ggcccgcgtg tgcaagaatg acgtggggg ccgattcctg ctggaggaca | 1200 |
| catggaccac attcatgaag gcccggctca actgctcccg cccgggcgag | 1250 |
| gtccccttct actataacga gctgcagagt gccttccact tgccggagca | 1300 |
| ggacctcatc tatggagttt tcacaaccaa cgtaaacagc atcgcggctt | 1350 |
| ctgctgtctg cgccttcaac ctcagtgcta tctcccaggc tttcaatggc | 1400 |
| ccatttcgct accaggagaa ccccaggggct gcctggctcc ccatagccaa | 1450 |
| ccccatcccc aatttccagt gtggcaccct gcctgagacc ggtcccaacg | 1500 |
| agaacctgac ggagcgcagc ctgcaggacg cgcagcgcct cttcctgatg | 1550 |
| agcgaggccg tgcagccggt gacacccgag ccctgtgtca cccaggacag | 1600 |
| cgtgcgcttc tcacacctcg tggtggacct ggtgcaggct aaagacacgc | 1650 |
| tctaccatgt actctacatt ggcaccgagt cgggcaccat cctgaaggcg | 1700 |
| ctgtccacgg cgagccgcag cctccacggc tgctacctgg aggagctgca | 1750 |
| cgtgctgccc ccgggcgcc gcgagcccct gcgcagcctg cgcatcctgc | 1800 |
| acagcgcccg cgcgctcttc gtgggctga gagacggcgt cctgcgggtc | 1850 |
| ccactggaga ggtgcgccgc ctaccgcagc caggggcat gcctgggggc | 1900 |
| ccggacccg tactgtggct gggacggaa gcagcaacgt tgcagcacac | 1950 |
| tcgaggacag ctccaacatg agcctctgga cccagaacat caccgcctgt | 2000 |
| cctgtgcgga atgtgacacg ggatggggc ttcggcccat ggtcaccatg | 2050 |
| gcaaccatgt gagcacttgg atggggacaa ctcaggctct tgcctgtgtc | 2100 |
| gagctcgatc ctgtgattcc cctcgacccc gctgtggggg ccttgactgc | 2150 |
| ctggggccag ccatccacat cgccaactgc tccaggaatg gggcgtggac | 2200 |
| cccgtggtca tcgtgggcgc tgtgcagcac gtcctgtggc atcggcttcc | 2250 |
| aggtccgcca gcgaagttgc agcaaccctg ctccccgcca cggggccgc | 2300 |
| atcttcgtgg gcaagagccg ggaggaacgg ttctgtaatg agaacacgcc | 2350 |
| ttgcccggtg cccatcttct gggcttcctg gggctcctgg agcaagtgca | 2400 |
| gcagcaactg tggagggggc atgcagtcgc ggcgtcgggc ctgcgagaac | 2450 |
| ggcaactcct gcctgggctg cggcgagttc aagacgtgca accccgaggg | 2500 |
| ctgccccgaa gtgcggcgca acacccctg gacgcgtgg ctgcccgtga | 2550 |
| acgtgacgca gggcggggca cggcaggagc agcggttccg cttcacctgc | 2600 |
| cgcgcgcccc ttgcagaccc gcacggcctg cagttcggca ggagaaggac | 2650 |
| cgagacgagg acctgtcccg cggacggctc cggctcctgc gacaccgacg | 2700 |
| ccctggtgga ggtcctcctg cgcagcggga gcacctcccc gcacacggtg | 2750 |
| agcgggggct gggccgcctg gggccgtgg tcgtcctgct cccgggactg | 2800 |
| cgagctgggc ttccgcgtcc gcaagagaac gtgcactaac ccggagcccc | 2850 |
| gcaacggggg cctgccctgc gtgggcgatg ctgccgagta ccaggactgc | 2900 |
| aaccccagg cttgcccagt tcggggtgct tggtcctgct ggacctcatg | 2950 |

-continued

| | |
|---|---|
| gtctccatgc tcagcttcct gtggtggggg tcactatcaa cgcacccgtt | 3000 |
| cctgcaccag ccccgcaccc tccccaggtg aggacatctg tctcgggctg | 3050 |
| cacacggagg aggcactatg tgccacacag gcctgcccag gctggtcgcc | 3100 |
| ctggtctgag tggagtaagt gcactgacga cggagcccag agccgaagcc | 3150 |
| ggcactgtga ggagctcctc ccagggtcca gcgcctgtgc tggaaacagc | 3200 |
| agccagagcc gcccctgccc ctacagcgag attcccgtca tcctgccagc | 3250 |
| ctccagcatg gaggaggcca ccgactgtgc aggtaaaaga aaccggacct | 3300 |
| acctcatgct gcgtcctcc cagccctcca gcaccccact ccaaagtctg | 3350 |
| gactcttttcc acatcctgct ccagacagcc aagctttgtt ggggtcccca | 3400 |
| ctgctttgag atgggttcaa tctcatccac ttggtggcca cgggcatctc | 3450 |
| ctgcttcttg ggctctgggc tcctgaccct agcagtgtac ctgtcttgcc | 3500 |
| agcactgcca gcgtcagtcc caggagtcca cactggtcca tcctgccacc | 3550 |
| cccaaccatt tgcactacaa gggcggaggc accccgaaga atgaaaagta | 3600 |
| cacacccatg gaattcaaga ccctgaacaa gaataacttg atccctgatg | 3650 |
| acagagccaa cttctaccca ttgcagcaga ccaatgtgta cacgactact | 3700 |
| tactacccaa gccccctgaa caaacacagc ttccggcccg aggcctcacc | 3750 |
| tggacaacgg tgcttcccca acagctgata ccgccgtcct ggggacttgg | 3800 |
| gcttcttgcc ttcataaggc acagagcaga tggagatggg acagtggagc | 3850 |
| cagtttggtt ttctccctct gcactaggcc aagaacttgc tgccttgcct | 3900 |
| gtgggggggtc ccatccggct tcagagagct ctggctggca ttgaccatgg | 3950 |
| gggaaagggc tggtttcagg ctgacatatg gccgcaggtc cagttcagcc | 4000 |
| caggtctctc atggttatct tccaacccac tgtcacgctg acactatgct | 4050 |
| gccatgcctg ggctgtggac ctactgggca tttgaggaat tggagaatgg | 4100 |
| agatggcaag agggcaggct tttaagtttg ggttggagac aacttcctgt | 4150 |
| ggcccccaca agctgagtct ggccttctcc agctggcccc aaaaaaggcc | 4200 |
| tttgctacat cctgattatc tctgaaagta atcaatcaag tggctccagt | 4250 |
| agctctggat tttctgccag ggctgggcca ttgtggtgct gccccagtat | 4300 |
| gacatgggac caaggccagc gcaggttatc cacctctgcc tggaagtcta | 4350 |
| tactctaccc agggcatccc tctggtcaga ggcagtgagt actgggaact | 4400 |
| ggaggctgac ctgtgcttag aagtcctta atctgggctg gtacaggcct | 4450 |
| cagccttgcc ctcaatgcac gaaaggtggc ccaggagaga ggatcaatgc | 4500 |
| cataggaggc agaagtctgg cctctgtgcc tctatggaga ctatcttcca | 4550 |
| gttgctgctc aacagagttg ttggctgaga cctgcttggg agtctctgct | 4600 |
| ggcccttcat ctgttcagga acacacacac acacacactc acacacgcac | 4650 |
| acacaatcac aatttgctac agcaacaaaa aagacattgg gctgtggcat | 4700 |
| tattaattaa agatgatatc cagtc | 4725 |

<210> SEQ ID NO 96
<211> LENGTH: 1092
<212> TYPE: PRT
<213> ORGANISM: Homo Sapien

<400> SEQUENCE: 96

```
Met Pro Cys Gly Phe Ser Pro Ser Pro Val Ala His His Leu Val
  1               5                  10                  15

Pro Gly Pro Pro Asp Thr Pro Ala Gln Gln Leu Arg Cys Gly Trp
                 20                  25                  30

Thr Val Gly Gly Trp Leu Leu Ser Leu Val Arg Gly Leu Leu Pro
                 35                  40                  45

Cys Leu Pro Pro Gly Ala Arg Thr Ala Glu Gly Pro Ile Met Val
                 50                  55                  60

Leu Ala Gly Pro Leu Ala Val Ser Leu Leu Pro Ser Leu Thr
                 65                  70                  75

Leu Leu Val Ser His Leu Ser Ser Gln Asp Val Ser Ser Glu
                 80                  85                  90

Pro Ser Ser Glu Gln Gln Leu Cys Ala Leu Ser Lys His Pro Thr
                 95                 100                 105

Val Ala Phe Glu Asp Leu Gln Pro Trp Val Ser Asn Phe Thr Tyr
                110                 115                 120

Pro Gly Ala Arg Asp Phe Ser Gln Leu Ala Leu Asp Pro Ser Gly
                125                 130                 135

Asn Gln Leu Ile Val Gly Ala Arg Asn Tyr Leu Phe Arg Leu Ser
                140                 145                 150

Leu Ala Asn Val Ser Leu Leu Gln Ala Thr Glu Trp Ala Ser Ser
                155                 160                 165

Glu Asp Thr Arg Arg Ser Cys Gln Ser Lys Gly Lys Thr Glu Glu
                170                 175                 180

Glu Cys Gln Asn Tyr Val Arg Val Leu Ile Val Ala Gly Arg Lys
                185                 190                 195

Val Phe Met Cys Gly Thr Asn Ala Phe Ser Pro Met Cys Thr Ser
                200                 205                 210

Arg Gln Val Gly Asn Leu Ser Arg Thr Ile Glu Lys Ile Asn Gly
                215                 220                 225

Val Ala Arg Cys Pro Tyr Asp Pro Arg His Asn Ser Thr Ala Val
                230                 235                 240

Ile Ser Ser Gln Gly Glu Leu Tyr Ala Ala Thr Val Ile Asp Phe
                245                 250                 255

Ser Gly Arg Asp Pro Ala Ile Tyr Arg Ser Leu Gly Ser Gly Pro
                260                 265                 270

Pro Leu Arg Thr Ala Gln Tyr Asn Ser Lys Trp Leu Asn Glu Pro
                275                 280                 285

Asn Phe Val Ala Ala Tyr Asp Ile Gly Leu Phe Ala Tyr Phe Phe
                290                 295                 300

Leu Arg Glu Asn Ala Val Glu His Asp Cys Gly Arg Thr Val Tyr
                305                 310                 315

Ser Arg Val Ala Arg Val Cys Lys Asn Asp Val Gly Gly Arg Phe
                320                 325                 330

Leu Leu Glu Asp Thr Trp Thr Thr Phe Met Lys Ala Arg Leu Asn
                335                 340                 345

Cys Ser Arg Pro Gly Glu Val Pro Phe Tyr Tyr Asn Glu Leu Gln
                350                 355                 360

Ser Ala Phe His Leu Pro Glu Gln Asp Leu Ile Tyr Gly Val Phe
                365                 370                 375

Thr Thr Asn Val Asn Ser Ile Ala Ala Ser Ala Val Cys Ala Phe
                380                 385                 390
```

```
Asn Leu Ser Ala Ile Ser Gln Ala Phe Asn Gly Pro Phe Arg Tyr
            395                 400                 405

Gln Glu Asn Pro Arg Ala Ala Trp Leu Pro Ile Ala Asn Pro Ile
        410                 415                 420

Pro Asn Phe Gln Cys Gly Thr Leu Pro Glu Thr Gly Pro Asn Glu
        425                 430                 435

Asn Leu Thr Glu Arg Ser Leu Gln Asp Ala Gln Arg Leu Phe Leu
        440                 445                 450

Met Ser Glu Ala Val Gln Pro Val Thr Pro Glu Pro Cys Val Thr
        455                 460                 465

Gln Asp Ser Val Arg Phe Ser His Leu Val Asp Leu Val Gln
        470                 475                 480

Ala Lys Asp Thr Leu Tyr His Val Leu Tyr Ile Gly Thr Glu Ser
        485                 490                 495

Gly Thr Ile Leu Lys Ala Leu Ser Thr Ala Ser Arg Ser Leu His
        500                 505                 510

Gly Cys Tyr Leu Glu Glu Leu His Val Leu Pro Pro Gly Arg Arg
        515                 520                 525

Glu Pro Leu Arg Ser Leu Arg Ile Leu His Ser Ala Arg Ala Leu
        530                 535                 540

Phe Val Gly Leu Arg Asp Gly Val Leu Arg Val Pro Leu Glu Arg
        545                 550                 555

Cys Ala Ala Tyr Arg Ser Gln Gly Ala Cys Leu Gly Ala Arg Asp
        560                 565                 570

Pro Tyr Cys Gly Trp Asp Gly Lys Gln Gln Arg Cys Ser Thr Leu
        575                 580                 585

Glu Asp Ser Ser Asn Met Ser Leu Trp Thr Gln Asn Ile Thr Ala
        590                 595                 600

Cys Pro Val Arg Asn Val Thr Arg Asp Gly Gly Phe Gly Pro Trp
        605                 610                 615

Ser Pro Trp Gln Pro Cys Glu His Leu Asp Gly Asp Asn Ser Gly
        620                 625                 630

Ser Cys Leu Cys Arg Ala Arg Ser Cys Asp Ser Pro Arg Pro Arg
        635                 640                 645

Cys Gly Gly Leu Asp Cys Leu Gly Pro Ala Ile His Ile Ala Asn
        650                 655                 660

Cys Ser Arg Asn Gly Ala Trp Thr Pro Trp Ser Ser Trp Ala Leu
        665                 670                 675

Cys Ser Thr Ser Cys Gly Ile Gly Phe Gln Val Arg Gln Arg Ser
        680                 685                 690

Cys Ser Asn Pro Ala Pro Arg His Gly Gly Arg Ile Phe Val Gly
        695                 700                 705

Lys Ser Arg Glu Glu Arg Phe Cys Asn Glu Asn Thr Pro Cys Pro
        710                 715                 720

Val Pro Ile Phe Trp Ala Ser Trp Gly Ser Trp Ser Lys Cys Ser
        725                 730                 735

Ser Asn Cys Gly Gly Gly Met Gln Ser Arg Arg Arg Ala Cys Glu
        740                 745                 750

Asn Gly Asn Ser Cys Leu Gly Cys Gly Glu Phe Lys Thr Cys Asn
        755                 760                 765

Pro Glu Gly Cys Pro Glu Val Arg Arg Asn Thr Pro Trp Thr Pro
        770                 775                 780

Trp Leu Pro Val Asn Val Thr Gln Gly Gly Ala Arg Gln Glu Gln
```

```
                785                 790                 795
Arg Phe Arg Phe Thr Cys Arg Ala Pro Leu Ala Asp Pro His Gly
            800                 805                 810
Leu Gln Phe Gly Arg Arg Thr Glu Thr Arg Thr Cys Pro Ala
            815                 820                 825
Asp Gly Ser Gly Ser Cys Asp Thr Asp Ala Leu Val Glu Val Leu
            830                 835                 840
Leu Arg Ser Gly Ser Thr Ser Pro His Thr Val Ser Gly Gly Trp
            845                 850                 855
Ala Ala Trp Gly Pro Trp Ser Ser Cys Ser Arg Asp Cys Glu Leu
            860                 865                 870
Gly Phe Arg Val Arg Lys Arg Thr Cys Thr Asn Pro Glu Pro Arg
            875                 880                 885
Asn Gly Gly Leu Pro Cys Val Gly Asp Ala Ala Glu Tyr Gln Asp
            890                 895                 900
Cys Asn Pro Gln Ala Cys Pro Val Arg Gly Ala Trp Ser Cys Trp
            905                 910                 915
Thr Ser Trp Ser Pro Cys Ser Ala Ser Cys Gly Gly Gly His Tyr
            920                 925                 930
Gln Arg Thr Arg Ser Cys Thr Ser Pro Ala Pro Ser Pro Gly Glu
            935                 940                 945
Asp Ile Cys Leu Gly Leu His Thr Glu Glu Ala Leu Cys Ala Thr
            950                 955                 960
Gln Ala Cys Pro Gly Trp Ser Pro Trp Ser Glu Trp Ser Lys Cys
            965                 970                 975
Thr Asp Asp Gly Ala Gln Ser Arg Ser Arg His Cys Glu Glu Leu
            980                 985                 990
Leu Pro Gly Ser Ser Ala Cys Ala Gly Asn Ser Ser Gln Ser Arg
            995                 1000                1005
Pro Cys Pro Tyr Ser Glu Ile Pro Val Ile Leu Pro Ala Ser Ser
            1010                1015                1020
Met Glu Glu Ala Thr Asp Cys Ala Gly Lys Arg Asn Arg Thr Tyr
            1025                1030                1035
Leu Met Leu Arg Ser Ser Gln Pro Ser Ser Thr Pro Leu Gln Ser
            1040                1045                1050
Leu Asp Ser Phe His Ile Leu Leu Gln Thr Ala Lys Leu Cys Trp
            1055                1060                1065
Gly Pro His Cys Phe Glu Met Gly Ser Ile Ser Ser Thr Trp Trp
            1070                1075                1080
Pro Arg Ala Ser Pro Ala Ser Trp Ala Leu Gly Ser
            1085                1090

<210> SEQ ID NO 97
<211> LENGTH: 3391
<212> TYPE: DNA
<213> ORGANISM: Homo Sapien

<400> SEQUENCE: 97
caagccctcc cagcatcccc tctcctgtgt cctccccag ttctctactc        50 agagttgact gaccagagat ttatcagctt ggagggctgg aggtgtggat       100
ccatggggta gcctcaacgc atctgcccct ccaccccagc cagctcatgg       150
gccacgtggc ctggcccagc ctcagcaccc agggccagtg aacagagccc       200
tggctggagt ccaaacatgt ggggcctggt gaggctcctg ctggcctggc       250
```

-continued

| | |
|---|---|
| tgggtggctg ggctgcatg gggcgtctgg cagccccagc ccgggcctgg | 300 |
| gcagggtccc gggaacaccc agggcctgct ctgctgcgga ctcgaaggag | 350 |
| ctgggtctgg aaccagttct ttgtcattga ggaatatgct ggtccagagc | 400 |
| ctgttctcat tggcaagctg cactcggatg ttgaccgggg agagggccgc | 450 |
| accaagtacc tgttgaccgg ggagggggca ggcaccgtat ttgtgattga | 500 |
| tgaggccaca ggcaatattc atgttaccaa gagccttgac cgggaggaaa | 550 |
| aggcgcaata tgtgctactg gcccaagccg tggaccgagc tccaaccggg | 600 |
| cccctggagc ccccatcaga gttcatcatc aaagtgcaag acatcaacga | 650 |
| caatccaccc attttccccc ttgggcccta ccatgccacc gtgcccgaga | 700 |
| tgtccaatgt cgggacatca gtgatccagg tgactgctca cgatgctgat | 750 |
| gaccccagct atgggaacag tgccaagctg gtgtacactg ttctggatgg | 800 |
| actgcctttc ttctctgtgg acccccagac tggagtggtg cgtacagcca | 850 |
| tccccaacat ggaccgggag acacaggagg agttcttggt ggtgatccag | 900 |
| gccaaggaca tgggcggcca catggggggg ctgtcaggca gcactacggt | 950 |
| gactgtcacg ctcagcgatg tcaacgacaa cccccccaag ttcccacaga | 1000 |
| gcctatacca gttctccgtg gtggagacag ctggacctgg cacactggtg | 1050 |
| ggccggctcc gggcccagga cccagacctg ggggacaacg ccctgatggc | 1100 |
| atacagcatc ctggatgggg aggggtctga ggccttcagc atcagcacag | 1150 |
| acttgcaggg tcgagacggg ctcctcactg tccgcaagcc cctagacttt | 1200 |
| gagagccagc gctcctactc cttccgtgtc gaggccacca cacgctcat | 1250 |
| tgacccagcc tatctgcggc gagggccctt caaggatgtg gcctctgtgc | 1300 |
| gtgtggcagt gcaagatgcc ccagagccac ctgccttcac ccaggctgcc | 1350 |
| taccacctga cagtgcctga aacaaggcc ccggggaccc tggtaggcca | 1400 |
| gatctccgcg gctgacctgg actcccctgc cagcccaatc agatactcca | 1450 |
| tcctccccca ctcagatccg gagcgttgct ctctctatcca gcccgaggaa | 1500 |
| ggcaccatcc atacagcagc acccctggat cgcgaggctc cgcgcctggca | 1550 |
| caacctcact gtgctggcta cagagctcga cagttctgca caggcctcgc | 1600 |
| gcgtgcaagt ggccatccag accctggatg agaatgacaa tgctccccag | 1650 |
| ctggctgagc cctacgatac ttttgtgtgt gactctgcag ctcctggcca | 1700 |
| gctgattcag gtcatccggg ccctggacag agatgaagtt ggcaacagta | 1750 |
| gccatgtctc cttcaaggt cctctggggcc ctgatgccaa ctttactgtc | 1800 |
| caggacaacc gagatggctc cgccagcctg ctgctgccct cccgccctgc | 1850 |
| tccacccgc catgccccct acttggttcc catagaactg tgggactggg | 1900 |
| ggcagccggc gctgagcagc actgccacag tgactgttag tgtgtgccgc | 1950 |
| tgccagcctg acggctctgt ggcatcctgc tggcctgagg ctcacctctc | 2000 |
| agctgctggg ctcagcaccg gcgccctgct tgccatcatc acctgtgtgg | 2050 |
| gtgccctgct tgccctggtg gtgctcttcg tggccctgcg gcggcagaag | 2100 |
| caagaagcac tgatggtact ggaggaggag gacgtccgag agaacatcat | 2150 |
| cacctacgac gacgagggcg gcggcgagga ggacaccgag gccttcgaca | 2200 |

-continued

| | |
|---|---|
| tcacggcctt gcagaacccg gacggggcgg cccccccggc gcccggccct | 2250 |
| cccgcgcgcc gagacgtgtt gccccgggcc cgggtgtcgc gccagcccag | 2300 |
| acccccccggc cccgccgacg tggcgcagct cctggcgctg cggctccgcg | 2350 |
| aggcggacga ggaccccggc gtaccccccgt acgactcggt gcaggtgtac | 2400 |
| ggctacgagg gccgcggctc ctcttgcggc tccctcagct ccctgggctc | 2450 |
| cggcagcgaa gccggcggcg ccccccggcc cgcggagccg ctggacgact | 2500 |
| ggggtccgct cttccgcacc ctggccgagc tgtatggggc caaggagccc | 2550 |
| ccggcccccct gagcgcccgg gctggcccgg cccaccgcgg ggggggggca | 2600 |
| gcgggcacag gccctctgag tgagcccccac ggggtccagg cgggcggcag | 2650 |
| cagcccaggg gccccaggcc tcctccctgt ccttgtgtcc ctccttgctt | 2700 |
| ccccggggca ccctcgctct cacctccctc ctcctgagtc ggtgtgtgtg | 2750 |
| tctctctcca ggaatctttg tctctatctg tgacacgctc ctctgtccgg | 2800 |
| gcctgggttt cctgccctgg ccctggccct gcgatctctc actgtgattc | 2850 |
| ctctccttcc tccgtggcgt tttgtctctg cagttctgaa gctcacacat | 2900 |
| agtctccctg cgtcttcctt gcccatacac atgctctgtg tctgtctcct | 2950 |
| gcccacatct cccttccttc tctctgggtc cctgtgactg gcttttttgtt | 3000 |
| tttttctgtt gtccatccca aaatcaagag aaacttccag ccactgctgc | 3050 |
| ccaccctcct gcaggggatg ttgtgcccca gacctgcctg catggttcca | 3100 |
| tccattactc atggcctcag cctcatcctg gctccactgg cctccagctg | 3150 |
| agagagggaa ccagcctgcc tcccagggca agagctccag cctcccgtgt | 3200 |
| ggccgcctcc ctggagctct gcccagctgc cagcttcccc tgggcatccc | 3250 |
| agccctgggc attgtcttgt gtgcttcctg agggagtagg gaaaggaaag | 3300 |
| ggggaggcgg ctgggaaggg ggaaagaggg aggaagggga ggggcctcca | 3350 |
| tctctaattt cataataaac aaacacttta ttttgtaaaa c | 3391 |

<210> SEQ ID NO 98
<211> LENGTH: 781
<212> TYPE: PRT
<213> ORGANISM: Homo Sapien

<400> SEQUENCE: 98

Met Trp Gly Leu Val Arg Leu Leu Ala Trp Leu Gly Gly Trp
1               5                   10                  15

Gly Cys Met Gly Arg Leu Ala Ala Pro Ala Arg Ala Trp Ala Gly
                20                  25                  30

Ser Arg Glu His Pro Gly Pro Ala Leu Leu Arg Thr Arg Arg Ser
            35                  40                  45

Trp Val Trp Asn Gln Phe Phe Val Ile Glu Glu Tyr Ala Gly Pro
        50                  55                  60

Glu Pro Val Leu Ile Gly Lys Leu His Ser Asp Val Asp Arg Gly
    65                  70                  75

Glu Gly Arg Thr Lys Tyr Leu Leu Thr Gly Glu Gly Ala Gly Thr
        80                  85                  90

Val Phe Val Ile Asp Glu Ala Thr Gly Asn Ile His Val Thr Lys
        95                  100                 105

Ser Leu Asp Arg Glu Glu Lys Ala Gln Tyr Val Leu Leu Ala Gln
        110                 115                 120

```
Ala Val Asp Arg Ala Ser Asn Arg Pro Leu Glu Pro Pro Ser Glu
            125                 130                 135

Phe Ile Ile Lys Val Gln Asp Ile Asn Asp Asn Pro Pro Ile Phe
            140                 145                 150

Pro Leu Gly Pro Tyr His Ala Thr Val Pro Glu Met Ser Asn Val
            155                 160                 165

Gly Thr Ser Val Ile Gln Val Thr Ala His Asp Ala Asp Pro
            170                 175                 180

Ser Tyr Gly Asn Ser Ala Lys Leu Val Tyr Thr Val Leu Asp Gly
            185                 190                 195

Leu Pro Phe Phe Ser Val Asp Pro Gln Thr Gly Val Val Arg Thr
            200                 205                 210

Ala Ile Pro Asn Met Asp Arg Glu Thr Gln Glu Glu Phe Leu Val
            215                 220                 225

Val Ile Gln Ala Lys Asp Met Gly Gly His Met Gly Gly Leu Ser
            230                 235                 240

Gly Ser Thr Thr Val Thr Val Thr Leu Ser Asp Val Asn Asp Asn
            245                 250                 255

Pro Pro Lys Phe Pro Gln Ser Leu Tyr Gln Phe Ser Val Val Glu
            260                 265                 270

Thr Ala Gly Pro Gly Thr Leu Val Gly Arg Leu Arg Ala Gln Asp
            275                 280                 285

Pro Asp Leu Gly Asp Asn Ala Leu Met Ala Tyr Ser Ile Leu Asp
            290                 295                 300

Gly Glu Gly Ser Glu Ala Phe Ser Ile Ser Thr Asp Leu Gln Gly
            305                 310                 315

Arg Asp Gly Leu Leu Thr Val Arg Lys Pro Leu Asp Phe Glu Ser
            320                 325                 330

Gln Arg Ser Tyr Ser Phe Arg Val Glu Ala Thr Asn Thr Leu Ile
            335                 340                 345

Asp Pro Ala Tyr Leu Arg Arg Gly Pro Phe Lys Asp Val Ala Ser
            350                 355                 360

Val Arg Val Ala Val Gln Asp Ala Pro Glu Pro Pro Ala Phe Thr
            365                 370                 375

Gln Ala Ala Tyr His Leu Thr Val Pro Glu Asn Lys Ala Pro Gly
            380                 385                 390

Thr Leu Val Gly Gln Ile Ser Ala Ala Asp Leu Asp Ser Pro Ala
            395                 400                 405

Ser Pro Ile Arg Tyr Ser Ile Leu Pro His Ser Asp Pro Glu Arg
            410                 415                 420

Cys Phe Ser Ile Gln Pro Glu Glu Gly Thr Ile His Thr Ala Ala
            425                 430                 435

Pro Leu Asp Arg Glu Ala Arg Ala Trp His Asn Leu Thr Val Leu
            440                 445                 450

Ala Thr Glu Leu Asp Ser Ser Ala Gln Ala Ser Arg Val Gln Val
            455                 460                 465

Ala Ile Gln Thr Leu Asp Glu Asn Asp Asn Ala Pro Gln Leu Ala
            470                 475                 480

Glu Pro Tyr Asp Thr Phe Val Cys Asp Ser Ala Ala Pro Gly Gln
            485                 490                 495

Leu Ile Gln Val Ile Arg Ala Leu Asp Arg Asp Glu Val Gly Asn
            500                 505                 510
```

-continued

```
Ser Ser His Val Ser Phe Gln Gly Pro Leu Gly Pro Asp Ala Asn
            515                 520                 525

Phe Thr Val Gln Asp Asn Arg Asp Gly Ser Ala Ser Leu Leu Leu
            530                 535                 540

Pro Ser Arg Pro Ala Pro Pro Arg His Ala Pro Tyr Leu Val Pro
            545                 550                 555

Ile Glu Leu Trp Asp Trp Gly Gln Pro Ala Leu Ser Ser Thr Ala
            560                 565                 570

Thr Val Thr Val Ser Val Cys Arg Cys Gln Pro Asp Gly Ser Val
            575                 580                 585

Ala Ser Cys Trp Pro Glu Ala His Leu Ser Ala Ala Gly Leu Ser
            590                 595                 600

Thr Gly Ala Leu Leu Ala Ile Ile Thr Cys Val Gly Ala Leu Leu
            605                 610                 615

Ala Leu Val Val Leu Phe Val Ala Leu Arg Arg Gln Lys Gln Glu
            620                 625                 630

Ala Leu Met Val Leu Glu Glu Asp Val Arg Glu Asn Ile Ile
            635                 640                 645

Thr Tyr Asp Asp Glu Gly Gly Gly Glu Glu Asp Thr Glu Ala Phe
            650                 655                 660

Asp Ile Thr Ala Leu Gln Asn Pro Asp Gly Ala Ala Pro Pro Ala
            665                 670                 675

Pro Gly Pro Pro Ala Arg Arg Asp Val Leu Pro Arg Ala Arg Val
            680                 685                 690

Ser Arg Gln Pro Arg Pro Pro Gly Pro Ala Asp Val Ala Gln Leu
            695                 700                 705

Leu Ala Leu Arg Leu Arg Glu Ala Asp Glu Asp Pro Gly Val Pro
            710                 715                 720

Pro Tyr Asp Ser Val Gln Val Tyr Gly Tyr Glu Gly Arg Gly Ser
            725                 730                 735

Ser Cys Gly Ser Leu Ser Ser Leu Gly Ser Gly Ser Glu Ala Gly
            740                 745                 750

Gly Ala Pro Gly Pro Ala Glu Pro Leu Asp Asp Trp Gly Pro Leu
            755                 760                 765

Phe Arg Thr Leu Ala Glu Leu Tyr Gly Ala Lys Glu Pro Pro Ala
            770                 775                 780

Pro
```

<210> SEQ ID NO 99
<211> LENGTH: 2855
<212> TYPE: DNA
<213> ORGANISM: Homo Sapien

<400> SEQUENCE: 99

| | |
|---|---:|
| gccaacactg gccaaacata tggggctgga atctcaacat cggtcactgg | 50 |
| gacctcaata tttggagccg gaaccccaca atttggaaca cagaccccaa | 100 |
| tatttggagc agaaccccaa gatttgacat ctaaaacctc aagcctggag | 150 |
| ctgaactctg aattctgggc ctgggacctt gaaatctggg actggatttc | 200 |
| cagtactgta ccctggaacc cactcttggg gacctgaacc ctgggattca | 250 |
| ggcctcaaat tccaagatct ggactgtggg attccaaggg gcctgaaccc | 300 |
| gagtttgggc ctgaagtcct tgctgcagac ctgagtgctt aaatctgggg | 350 |
| cttgagacct cccaatcttg actcagcacc ccaatatctg aatgcagaac | 400 |

-continued

| | |
|---|---|
| cccgggatcg gatctcagac tctaaacccc accgtttggc tgcttagcat | 450 |
| cccaagactg gacctgggag accctgaccc tgaacaaccc aaactggacc | 500 |
| cgtaaaactg gacccta gag gcccaatatt taggggtctg gaaccccgag | 550 |
| tattaaggtc tggagactcc gttgccacag atttgagccg agtcaggaca | 600 |
| cagtccctct acagaagcct tggggacagg aaaagcatga ccagatgctc | 650 |
| cctccagagc cctgacctct gactcccctg gagctaggac tctgctccct | 700 |
| ggggctgctt ctagctcagg acaccnctgc ccgcgatggc catcctcccg | 750 |
| ttgctcctgt gcctgctgcc gctggcccct gcctcatccc caccccagtc | 800 |
| agccacaccc agcccatgtc ccgccgctg ccgctgccag acacagtcgc | 850 |
| tgcccctaag cgtgctgtgc ccaggggcag gcctcctgtt cgtgccaccc | 900 |
| tcgctggacc gccgggcagc cgagctgcgg ctggcagaca acttcatcgc | 950 |
| ctccgtgcgc cgccgcgacc tggccaacat gacaggcctg ctgcatctga | 1000 |
| gcctgtcgcg gaacaccatc cgccacgtgg ctgccggcgc cttcgccgac | 1050 |
| ctgcgggccc tgcgtgccct gcacctggat ggcaaccggc tgacctcact | 1100 |
| gggcgagggc cagctgcgcg gcctggtcaa cttgcgccac ctcatcctca | 1150 |
| gcaacaacca gctggcagcg ctggcggccg gcgccctgga tgattgtgcc | 1200 |
| gagacactgg aggacctcga cctctcctac aacaacctcg agcagctgcc | 1250 |
| ctgggaggcc ctgggccgcc tgggcaacgt caacacgttg ggcctcgacc | 1300 |
| acaacctgct ggcttctgtg cccggcgctt tttcccgcct gcacaagctg | 1350 |
| gcccggctgg acatgacctc caaccgcctg accacaatcc cacccgaccc | 1400 |
| actcttctcc cgcctgcccc tgctcgccag gccccgggggc tcgcccgcct | 1450 |
| ctgcctggt gctggccttt ggcgggaacc ccctgcactg caactgcgag | 1500 |
| ctggtgtggc tgcgtcgcct ggcgcgggag gacgacctcg aggcctgcgc | 1550 |
| gtccccacct gctctgggcg gccgctactt ctgggcggtg ggcgaggagg | 1600 |
| agtttgtctg cgagccgccc gtggtgactc accgctcacc acctctggct | 1650 |
| gtgcccgcag gtcggccggc tgccctgcgc tgccgggcag tggggacccc | 1700 |
| agagccccgt gtgcgttggg tgtcacccca gggccggctg ctaggcaact | 1750 |
| caagccgtgc ccgcgccttc cccaatggga cgctggagct gctggtcacc | 1800 |
| gagccgggtg atggtggcat cttcacctgc attgcggcca atgcagctgg | 1850 |
| cgaggccaca gctgctgtgg agctgactgt ggtcccccca ccacctcctc | 1900 |
| agctagccaa cagcaccagc tgtgacccccc cgcgggacgg ggatcctgat | 1950 |
| gctctcaccc caccctccgc tgcctctgct tctgccaagg tggccgacac | 2000 |
| tgggcccccct accgaccgtg gcgtccaggt gactgagcac ggggccacag | 2050 |
| ctgctcttgt ccagtggccg gatcagcggc ctatcccggg catccgcatg | 2100 |
| taccagatcc agtacaacag ctcggctgat gacatcctcg tctacaggat | 2150 |
| gatcccggcg gagagccgct cgttcctgct gacggacctg cgtcaggcc | 2200 |
| ggacctacga tctgtgcgtg ctcgccgtgt atgaggacag cgccacgggg | 2250 |
| ctcacgccca cgcggcctgt gggctgcgcc cgcttctcca ccgaacctgc | 2300 |
| gctgcggcca tgcggggcgc cgcacgctcc cttcctgggc ggcacgatga | 2350 |

-continued

```
tcatcgcgct gggcggcgtc atcgtagcct cggtactggt cttcatcttc        2400
gtgctgctaa tgcgctacaa ggtgcacggc ggccagcccc ccggcaaggc        2450
caagattccc gcgcctgtta gcagcgtttg ctcccagacc aacggcgccc        2500
tgggccccac gcccacgccc gccccgcccg ccccggagcc cgcggcgctc        2550
agggcccaca ccgtggtcca gctggactgc gagccctggg ggcccggcca        2600
cgaacctgtg ggaccctagc caggcgcccc ccctctaag ggtcctctgg         2650 ccccacggac agcaggaccc ggacaccctg tgggacctgg cctcaaactc        2700
accaaatcgc tcatggtttt taaaactctg atggggaggg tgtcggggac        2750 accgggcaa aacaagaaag tcctatttttt ccaaaaaaa aaaaaaaaaa         2800 aaaaaaaaaa aaaaaaaaaa aaaaaaaaaa aaaaaaaaaa aaaaaaaaaa        2850
aaaaa                                                         2855
```

<210> SEQ ID NO 100
<211> LENGTH: 627
<212> TYPE: PRT
<213> ORGANISM: Homo Sapien

<400> SEQUENCE: 100

```
Met Ala Ile Leu Pro Leu Leu Cys Leu Leu Pro Leu Ala Pro
 1               5                  10                  15

Ala Ser Ser Pro Pro Gln Ser Ala Thr Pro Ser Pro Cys Pro Arg
             20                  25                  30

Arg Cys Arg Cys Gln Thr Gln Ser Leu Pro Leu Ser Val Leu Cys
             35                  40                  45

Pro Gly Ala Gly Leu Leu Phe Val Pro Pro Ser Leu Asp Arg Arg
             50                  55                  60

Ala Ala Glu Leu Arg Leu Ala Asp Asn Phe Ile Ala Ser Val Arg
             65                  70                  75

Arg Arg Asp Leu Ala Asn Met Thr Gly Leu Leu His Leu Ser Leu
             80                  85                  90

Ser Arg Asn Thr Ile Arg His Val Ala Ala Gly Ala Phe Ala Asp
             95                 100                 105

Leu Arg Ala Leu Arg Ala Leu His Leu Asp Gly Asn Arg Leu Thr
            110                 115                 120

Ser Leu Gly Glu Gly Gln Leu Arg Gly Leu Val Asn Leu Arg His
            125                 130                 135

Leu Ile Leu Ser Asn Asn Gln Leu Ala Ala Leu Ala Ala Gly Ala
            140                 145                 150

Leu Asp Asp Cys Ala Glu Thr Leu Glu Asp Leu Asp Leu Ser Tyr
            155                 160                 165

Asn Asn Leu Glu Gln Leu Pro Trp Glu Ala Leu Gly Arg Leu Gly
            170                 175                 180

Asn Val Asn Thr Leu Gly Leu Asp His Asn Leu Leu Ala Ser Val
            185                 190                 195

Pro Gly Ala Phe Ser Arg Leu His Lys Leu Ala Arg Leu Asp Met
            200                 205                 210

Thr Ser Asn Arg Leu Thr Thr Ile Pro Pro Asp Pro Leu Phe Ser
            215                 220                 225

Arg Leu Pro Leu Leu Ala Arg Pro Arg Gly Ser Pro Ala Ser Ala
            230                 235                 240

Leu Val Leu Ala Phe Gly Gly Asn Pro Leu His Cys Asn Cys Glu
```

```
                  245                 250                 255
Leu Val Trp Leu Arg Arg Leu Ala Arg Glu Asp Asp Leu Glu Ala
                  260                 265                 270
Cys Ala Ser Pro Pro Ala Leu Gly Gly Arg Tyr Phe Trp Ala Val
                  275                 280                 285
Gly Glu Glu Glu Phe Val Cys Glu Pro Pro Val Thr His Arg
                  290                 295                 300
Ser Pro Pro Leu Ala Val Pro Ala Gly Arg Pro Ala Ala Leu Arg
                  305                 310                 315
Cys Arg Ala Val Gly Asp Pro Glu Pro Arg Val Arg Trp Val Ser
                  320                 325                 330
Pro Gln Gly Arg Leu Leu Gly Asn Ser Ser Arg Ala Arg Ala Phe
                  335                 340                 345
Pro Asn Gly Thr Leu Glu Leu Leu Val Thr Glu Pro Gly Asp Gly
                  350                 355                 360
Gly Ile Phe Thr Cys Ile Ala Ala Asn Ala Ala Gly Glu Ala Thr
                  365                 370                 375
Ala Ala Val Glu Leu Thr Val Gly Pro Pro Pro Pro Gln Leu
                  380                 385                 390
Ala Asn Ser Thr Ser Cys Asp Pro Pro Arg Asp Gly Asp Pro Asp
                  395                 400                 405
Ala Leu Thr Pro Pro Ser Ala Ala Ser Ala Ser Ala Lys Val Ala
                  410                 415                 420
Asp Thr Gly Pro Pro Thr Asp Arg Gly Val Gln Val Thr Glu His
                  425                 430                 435
Gly Ala Thr Ala Ala Leu Val Gln Trp Pro Asp Gln Arg Pro Ile
                  440                 445                 450
Pro Gly Ile Arg Met Tyr Gln Ile Gln Tyr Asn Ser Ser Ala Asp
                  455                 460                 465
Asp Ile Leu Val Tyr Arg Met Ile Pro Ala Glu Ser Arg Ser Phe
                  470                 475                 480
Leu Leu Thr Asp Leu Ala Ser Gly Arg Thr Tyr Asp Leu Cys Val
                  485                 490                 495
Leu Ala Val Tyr Glu Asp Ser Ala Thr Gly Leu Thr Ala Thr Arg
                  500                 505                 510
Pro Val Gly Cys Ala Arg Phe Ser Thr Glu Pro Ala Leu Arg Pro
                  515                 520                 525
Cys Gly Ala Pro His Ala Pro Phe Leu Gly Gly Thr Met Ile Ile
                  530                 535                 540
Ala Leu Gly Gly Val Ile Val Ala Ser Val Leu Val Phe Ile Phe
                  545                 550                 555
Val Leu Leu Met Arg Tyr Lys Val His Gly Gly Gln Pro Gly
                  560                 565                 570
Lys Ala Lys Ile Pro Ala Pro Val Ser Ser Val Cys Ser Gln Thr
                  575                 580                 585
Asn Gly Ala Leu Gly Pro Thr Pro Thr Pro Ala Pro Pro Ala Pro
                  590                 595                 600
Glu Pro Ala Ala Leu Arg Ala His Thr Val Val Gln Leu Asp Cys
                  605                 610                 615
Glu Pro Trp Gly Pro Gly His Glu Pro Val Gly Pro
                  620                 625

<210> SEQ ID NO 101
```

-continued

```
<211> LENGTH: 1111
<212> TYPE: DNA
<213> ORGANISM: Homo Sapien

<400> SEQUENCE: 101
cgactccata accgtggcct tggccccagt cccctgact tccggacttc         50 agaccagata ctgcccatat cccttatga agtcttggcc aggcaacccc        100
tagggtgtac gttttctaaa gattaaagag gcggtgctaa gctgcagacg       150
gacttgcgac tcagccactg gtgtaagtca ggcgggaggt ggcgcccaat       200
aagctcaaga gaggaggcgg gttctggaaa aaggccaata gcctgtgaag       250
gcgagtctag cagcaaccaa tagctatgag cgagaggcgg gactctgagg       300
gaagtcaatc gctgccgcag gtaccgccaa tggcttttgg cggggggcgtt      350 ccccaaccct gccctctctc atgaccccgc tccgggatta tggccgggac       400
tgggctgctg gcgctgcgga cgctgccagg gcccagctgg gtgcgaggct       450
cgggcccttc cgtgctgagc cgcctgcagg acgcggccgt ggtgcggcct       500
ggcttcctga gcacggcaga ggaggagacg ctgagccgag aactggagcc       550
cgagctgcgc cgccgccgct acgaatacga tcactgggac gcggccatcc       600
acggcttccg agagacagag aagtcgcgct ggtcagaagc cagccgggcc       650
atcctgcagc gcgtgcaggc ggccgccttt ggccccggcc agaccctgct       700
ctcctccgtg cacgtgctgg acctggaagc ccgcggctac atcaagcccc       750
acgtggacag catcaagttc tgcggggcca ccatcgccgg cctgtctctc       800
ctgtctccca gcgttatgcg gctggtgcac acccaggagc cggggagtg        850 gctggaactc ttgctggagc cgggctccct ctacatcctt aggggctcag       900
cccgttatga cttctcccat gagatccttc gggatgaaga gtccttcttt       950
ggggaacgcc ggattccccg gggccggcgc atctccgtga tctgccgctc      1000
cctccctgag ggcatggggc caggggagtc tggacagccg ccccagcct      1050 gctgaccccc agctttctac agacaccaga tttgtgaata agttgggga      1100 atggacagcc t                                                1111
```

```
<210> SEQ ID NO 102
<211> LENGTH: 221
<212> TYPE: PRT
<213> ORGANISM: Homo Sapien

<400> SEQUENCE: 102

Met Ala Gly Thr Gly Leu Leu Ala Leu Arg Thr Leu Pro Gly Pro
  1               5                  10                  15

Ser Trp Val Arg Gly Ser Gly Pro Ser Val Leu Ser Arg Leu Gln
                 20                  25                  30

Asp Ala Ala Val Val Arg Pro Gly Phe Leu Ser Thr Ala Glu Glu
                 35                  40                  45

Glu Thr Leu Ser Arg Glu Leu Glu Pro Glu Leu Arg Arg Arg Arg
                 50                  55                  60

Tyr Glu Tyr Asp His Trp Asp Ala Ala Ile His Gly Phe Arg Glu
                 65                  70                  75

Thr Glu Lys Ser Arg Trp Ser Glu Ala Ser Arg Ala Ile Leu Gln
                 80                  85                  90

Arg Val Gln Ala Ala Ala Phe Gly Pro Gly Gln Thr Leu Leu Ser
```

```
                 95                 100                 105
Ser Val His Val Leu Asp Leu Glu Ala Arg Gly Tyr Ile Lys Pro
                110                 115                 120
His Val Asp Ser Ile Lys Phe Cys Gly Ala Thr Ile Ala Gly Leu
                125                 130                 135
Ser Leu Leu Ser Pro Ser Val Met Arg Leu Val His Thr Gln Glu
                140                 145                 150
Pro Gly Glu Trp Leu Glu Leu Leu Glu Pro Gly Ser Leu Tyr
                155                 160                 165
Ile Leu Arg Gly Ser Ala Arg Tyr Asp Phe Ser His Glu Ile Leu
                170                 175                 180
Arg Asp Glu Glu Ser Phe Phe Gly Glu Arg Arg Ile Pro Arg Gly
                185                 190                 195
Arg Arg Ile Ser Val Ile Cys Arg Ser Leu Pro Glu Gly Met Gly
                200                 205                 210
Pro Gly Glu Ser Gly Gln Pro Pro Ala Cys
                215                 220
```

<210> SEQ ID NO 103
<211> LENGTH: 3583
<212> TYPE: DNA
<213> ORGANISM: Homo Sapien

<400> SEQUENCE: 103

| | | |
|---|---|---|
| ctccccggcg ccgcaggcag cgtcctcctc cgaagcagct gcacctgcaa | | 50 |
| ctgggcagcc tggaccctcg tgccctgttc ccgggacctc gcgcaggggg | | 100 |
| cgccccggga cacccctgc gggccgggtg gaggaggaag aggaggagga | | 150 |
| ggaagaagac gtggacaagg accccatcc tacccagaac acctgcctgc | | 200 |
| gctgccgcca cttctcttta agggagagga aaagagagcc taggagaacc | | 250 |
| atgggggct gcgaagtccg ggaatttctt ttgcaatttg gtttcttctt | | 300 |
| gcctctgctg acagcgtggc caggcgactg cagtcacgtc tccaacaacc | | 350 |
| aagttgtgtt gcttgataca caactgtac tgggagagct aggatggaaa | | 400 |
| acatatccat taaatgggtg ggatgccatc actgaaatgg atgaacataa | | 450 |
| taggcccatt cacacatacc aggtatgtaa tgtaatggaa ccaaaccaaa | | 500 |
| acaactggct tcgtacaaac tggatctccc gtgatgcagc tcagaaaatt | | 550 |
| tatgtggaaa tgaaattcac actaagggat tgtaacagca tcccatgggt | | 600 |
| cttgggact tgcaaagaaa catttaatct gttttatatg gaatcagatg | | 650 |
| agtcccacgg aattaaattc aagccaaacc agtatacaaa gatcgacaca | | 700 |
| attgctgctg atgagagttt tacccagatg gatttgggtg atcgcatcct | | 750 |
| caaactcaac actgaaattc gtgaggtggg gcctatagaa aggaaaggat | | 800 |
| tttatctggc ttttcaagac attggggcgt gcattgccct ggtttcagtc | | 850 |
| cgtgttttct acaagaaatg ccccttcact gttcgtaact tggccatgtt | | 900 |
| tcctgatacc attccaaggg ttgattcctc ctctttggtt gaagtacggg | | 950 |
| gttcttgtgt gaagagtgct gaagagcgtg acactcctaa actgtattgt | | 1000 |
| ggagctgatg gagattggct ggttcctctt ggaaggtgca tctgcagtac | | 1050 |
| aggatatgaa gaaattgagg gttcttgcca tgcttgcaga ccaggattct | | 1100 |
| ataaagcttt tgctgggaac acaaaatgtt ctaaatgtcc tccacacagt | | 1150 |

```
ttaacataca tggaagcaac ttctgtctgt cagtgtgaaa agggttattt        1200
ccgagctgaa aaagacccac cttctatggc atgtaccagg ccaccttcag        1250
ctcctaggaa tgtggttttt aacatcaatg aaacagccct tattttggaa        1300
tggagcccac caagtgacac aggagggaga aaagatctca catacagtgt        1350
aatctgtaag aaatgtggct tagacaccag ccagtgtgag gactgtggtg        1400
gaggactccg cttcatccca agacatacag gcctgatcaa caattccgtg        1450
atagtacttg actttgtgtc tcacgtgaat tacacctttg aaatagaagc        1500
aatgaatgga gtttctgagt tgagttttt  tcccaagcca ttcacagcta        1550
ttacagtgac cacggatcaa gatgcacctt ccctgatagg tgtggtaagg        1600
aaggactggg catcccaaaa tagcattgcc ctatcatggc aagcacctgc        1650
tttttccaat ggagccattc tggactacga gatcaagtac tatgagaaag        1700
aacatgagca gctgacctac tcttccacaa ggtccaaagc ccccagtgtc        1750
atcatcacag gtcttaagcc agccaccaaa tatgtatttc acatccgagt        1800
gagaactgcg acaggataca gtggctacag tcagaaattt gaatttgaaa        1850
caggagatga aacttctgac atggcagcag aacaaggaca gattctcgtg        1900
atagccaccg ccgctgttgg cggattcact ctcctcgtca tcctcacttt        1950
attcttcttg atcactggga gatgtcagtg gtacataaaa gccaagatga        2000
agtcagaaga gaagagaaga aaccacttac agaatgggca tttgcgcttc        2050
ccgggaatta aaacttacat tgatccagat acatatgaag acccatccct        2100
agcagtccat gaatttgcaa aggagattga tccctcaaga attcgtattg        2150
agagagtcat tggggcaggt gaatttggag aagtctgtag tgggcgtttg        2200
aagacaccag ggaaaagaga gatcccagtt gccattaaaa cttgaaagg         2250
tggccacatg gatcggcaaa gaagagattt tctaagagaa gctagtatca        2300
tgggccagtt tgaccatcca aacatcattc gcctagaagg ggttgtcacc        2350
aaaagatcct tcccggccat tgggtggag  gcgttttgcc ccagcttcct        2400
gagggcaggt tttttaaata gcatccaggc cccgcatcca gtgccagggg        2450
gaggatcttt gccccccagg attcctgctg gcagaccagt aatgattgtg        2500
gtggaatata tggagaatgg atccctagac tccttttttgc ggaagcatga        2550
tggccacttc acagtcatcc agttggtcgg aatgctccga ggcattgcat        2600
caggcatgaa gtatctttct gatatgggtt atgttcatcg agacctagcg        2650
gctcggaata tactggtcaa tagcaactta gtatgcaaag tttctgattt        2700
tggtctctcc agagtgctgg aagatgatcc agaagctgct tatacaacaa        2750
ctggtggaaa aatccccata aggtggacag ccccagaagc catcgcctac        2800
agaaaattct cctcagcaag cgatgcatgg agctatggca ttgtcatgtg        2850
ggaggtcatg tcctatggag agagaccta  ttgggaaatg tctaaccaag        2900
atgtcattct gtccattgaa gaagggtaca gacttccagc tcccatgggc        2950
tgtccagcat ctctacacca gctgatgctc cactgctggc agaaggagag        3000
aaatcacaga ccaaaattta ctgacattgt cagcttcctt gacaaactga        3050
tccgaaatcc cagtgcccctt cacaccctgg tggaggacat ccttgtaatg        3100
```

-continued

| | |
|---|---|
| ccagagtccc ctggtgaagt tccggaatat cctttgtttg tcacagttgg | 3150 |
| tgactggcta gattctataa agatggggca atacaagaat aacttcgtgg | 3200 |
| cagcagggtt tacaacattt gacctgattt caagaatgag cattgatgac | 3250 |
| attagaagaa ttggagtcat acttattgga caccagagac gaatagtcag | 3300 |
| cagcatacag actttacgtt tacacatgat gcacatacag gagaagggat | 3350 |
| ttcatgtatg aaagtaccac aagcacctgt gttttgtgcc tcagcatttc | 3400 |
| taaaatgaac gatatcctct ctactactct ctcttctgat tctccaaaca | 3450 |
| tcacttcaca aactgcagtc ttctgttcag actataggca cacaccttat | 3500 |
| gtttatgctt ccaaccagga ttttaaaatc atgctacata aatccgttct | 3550 |
| gaataacctg caactaaaaa aaaaaaaaaa aaa | 3583 |

<210> SEQ ID NO 104
<211> LENGTH: 1036
<212> TYPE: PRT
<213> ORGANISM: Homo Sapien

<400> SEQUENCE: 104

```
Met Gly Gly Cys Glu Val Arg Glu Phe Leu Leu Gln Phe Gly Phe
 1               5                  10                  15

Phe Leu Pro Leu Leu Thr Ala Trp Pro Gly Asp Cys Ser His Val
                20                  25                  30

Ser Asn Asn Gln Val Val Leu Leu Asp Thr Thr Thr Val Leu Gly
                35                  40                  45

Glu Leu Gly Trp Lys Thr Tyr Pro Leu Asn Gly Trp Asp Ala Ile
                50                  55                  60

Thr Glu Met Asp Glu His Asn Arg Pro Ile His Thr Tyr Gln Val
                65                  70                  75

Cys Asn Val Met Glu Pro Asn Gln Asn Asn Trp Leu Arg Thr Asn
                80                  85                  90

Trp Ile Ser Arg Asp Ala Ala Gln Lys Ile Tyr Val Glu Met Lys
                95                  100                 105

Phe Thr Leu Arg Asp Cys Asn Ser Ile Pro Trp Val Leu Gly Thr
                110                 115                 120

Cys Lys Glu Thr Phe Asn Leu Phe Tyr Met Glu Ser Asp Glu Ser
                125                 130                 135

His Gly Ile Lys Phe Lys Pro Asn Gln Tyr Thr Lys Ile Asp Thr
                140                 145                 150

Ile Ala Ala Asp Glu Ser Phe Thr Gln Met Asp Leu Gly Asp Arg
                155                 160                 165

Ile Leu Lys Leu Asn Thr Glu Ile Arg Glu Val Gly Pro Ile Glu
                170                 175                 180

Arg Lys Gly Phe Tyr Leu Ala Phe Gln Asp Ile Gly Ala Cys Ile
                185                 190                 195

Ala Leu Val Ser Val Arg Val Phe Tyr Lys Lys Cys Pro Phe Thr
                200                 205                 210

Val Arg Asn Leu Ala Met Phe Pro Asp Thr Ile Pro Arg Val Asp
                215                 220                 225

Ser Ser Ser Leu Val Glu Val Arg Gly Ser Cys Val Lys Ser Ala
                230                 235                 240

Glu Glu Arg Asp Thr Pro Lys Leu Tyr Cys Gly Ala Asp Gly Asp
                245                 250                 255
```

-continued

```
Trp Leu Val Pro Leu Gly Arg Cys Ile Cys Ser Thr Gly Tyr Glu
            260                 265                 270

Glu Ile Glu Gly Ser Cys His Ala Cys Arg Pro Gly Phe Tyr Lys
            275                 280                 285

Ala Phe Ala Gly Asn Thr Lys Cys Ser Lys Cys Pro Pro His Ser
            290                 295                 300

Leu Thr Tyr Met Glu Ala Thr Ser Val Cys Gln Cys Glu Lys Gly
            305                 310                 315

Tyr Phe Arg Ala Glu Lys Asp Pro Pro Ser Met Ala Cys Thr Arg
            320                 325                 330

Pro Pro Ser Ala Pro Arg Asn Val Val Phe Asn Ile Asn Glu Thr
            335                 340                 345

Ala Leu Ile Leu Glu Trp Ser Pro Pro Ser Asp Thr Gly Gly Arg
            350                 355                 360

Lys Asp Leu Thr Tyr Ser Val Ile Cys Lys Lys Cys Gly Leu Asp
            365                 370                 375

Thr Ser Gln Cys Glu Asp Cys Gly Gly Gly Leu Arg Phe Ile Pro
            380                 385                 390

Arg His Thr Gly Leu Ile Asn Asn Ser Val Ile Val Leu Asp Phe
            395                 400                 405

Val Ser His Val Asn Tyr Thr Phe Glu Ile Glu Ala Met Asn Gly
            410                 415                 420

Val Ser Glu Leu Ser Phe Ser Pro Lys Pro Phe Thr Ala Ile Thr
            425                 430                 435

Val Thr Thr Asp Gln Asp Ala Pro Ser Leu Ile Gly Val Val Arg
            440                 445                 450

Lys Asp Trp Ala Ser Gln Asn Ser Ile Ala Leu Ser Trp Gln Ala
            455                 460                 465

Pro Ala Phe Ser Asn Gly Ala Ile Leu Asp Tyr Glu Ile Lys Tyr
            470                 475                 480

Tyr Glu Lys Glu His Glu Gln Leu Thr Tyr Ser Ser Thr Arg Ser
            485                 490                 495

Lys Ala Pro Ser Val Ile Ile Thr Gly Leu Lys Pro Ala Thr Lys
            500                 505                 510

Tyr Val Phe His Ile Arg Val Arg Thr Ala Thr Gly Tyr Ser Gly
            515                 520                 525

Tyr Ser Gln Lys Phe Glu Phe Glu Thr Gly Asp Glu Thr Ser Asp
            530                 535                 540

Met Ala Ala Glu Gln Gly Gln Ile Leu Val Ile Ala Thr Ala Ala
            545                 550                 555

Val Gly Gly Phe Thr Leu Leu Val Ile Leu Thr Leu Phe Phe Leu
            560                 565                 570

Ile Thr Gly Arg Cys Gln Trp Tyr Ile Lys Ala Lys Met Lys Ser
            575                 580                 585

Glu Glu Lys Arg Arg Asn His Leu Gln Asn Gly His Leu Arg Phe
            590                 595                 600

Pro Gly Ile Lys Thr Tyr Ile Asp Pro Asp Thr Tyr Glu Asp Pro
            605                 610                 615

Ser Leu Ala Val His Glu Phe Ala Lys Glu Ile Asp Pro Ser Arg
            620                 625                 630

Ile Arg Ile Glu Arg Val Ile Gly Ala Gly Glu Phe Gly Glu Val
            635                 640                 645

Cys Ser Gly Arg Leu Lys Thr Pro Gly Lys Arg Glu Ile Pro Val
```

-continued

```
                            650                 655                 660
Ala Ile Lys Thr Leu Lys Gly Gly His Met Asp Arg Gln Arg Arg
                    665                 670                 675
Asp Phe Leu Arg Glu Ala Ser Ile Met Gly Gln Phe Asp His Pro
                    680                 685                 690
Asn Ile Ile Arg Leu Glu Gly Val Val Thr Lys Arg Ser Phe Pro
                    695                 700                 705
Ala Ile Gly Val Glu Ala Phe Cys Pro Ser Phe Leu Arg Ala Gly
                    710                 715                 720
Phe Leu Asn Ser Ile Gln Ala Pro His Pro Val Pro Gly Gly Gly
                    725                 730                 735
Ser Leu Pro Pro Arg Ile Pro Ala Gly Arg Pro Val Met Ile Val
                    740                 745                 750
Val Glu Tyr Met Glu Asn Gly Ser Leu Asp Ser Phe Leu Arg Lys
                    755                 760                 765
His Asp Gly His Phe Thr Val Ile Gln Leu Val Gly Met Leu Arg
                    770                 775                 780
Gly Ile Ala Ser Gly Met Lys Tyr Leu Ser Asp Met Gly Tyr Val
                    785                 790                 795
His Arg Asp Leu Ala Ala Arg Asn Ile Leu Val Asn Ser Asn Leu
                    800                 805                 810
Val Cys Lys Val Ser Asp Phe Gly Leu Ser Arg Val Leu Glu Asp
                    815                 820                 825
Asp Pro Glu Ala Ala Tyr Thr Thr Thr Gly Gly Lys Ile Pro Ile
                    830                 835                 840
Arg Trp Thr Ala Pro Glu Ala Ile Ala Tyr Arg Lys Phe Ser Ser
                    845                 850                 855
Ala Ser Asp Ala Trp Ser Tyr Gly Ile Val Met Trp Glu Val Met
                    860                 865                 870
Ser Tyr Gly Glu Arg Pro Tyr Trp Glu Met Ser Asn Gln Asp Val
                    875                 880                 885
Ile Leu Ser Ile Glu Glu Gly Tyr Arg Leu Pro Ala Pro Met Gly
                    890                 895                 900
Cys Pro Ala Ser Leu His Gln Leu Met Leu His Cys Trp Gln Lys
                    905                 910                 915
Glu Arg Asn His Arg Pro Lys Phe Thr Asp Ile Val Ser Phe Leu
                    920                 925                 930
Asp Lys Leu Ile Arg Asn Pro Ser Ala Leu His Thr Leu Val Glu
                    935                 940                 945
Asp Ile Leu Val Met Pro Glu Ser Pro Gly Glu Val Pro Glu Tyr
                    950                 955                 960
Pro Leu Phe Val Thr Val Gly Asp Trp Leu Asp Ser Ile Lys Met
                    965                 970                 975
Gly Gln Tyr Lys Asn Asn Phe Val Ala Ala Gly Phe Thr Thr Phe
                    980                 985                 990
Asp Leu Ile Ser Arg Met Ser Ile Asp Asp Ile Arg Arg Ile Gly
                    995                 1000                1005
Val Ile Leu Ile Gly His Gln Arg Arg Ile Val Ser Ser Ile Gln
                        1010                1015                1020
Thr Leu Arg Leu His Met Met His Ile Gln Glu Lys Gly Phe His
                        1025                1030                1035
Val
```

-continued

<210> SEQ ID NO 105
<211> LENGTH: 2148
<212> TYPE: DNA
<213> ORGANISM: Homo Sapien

<400> SEQUENCE: 105

| | |
|---|---:|
| ggcggcggc tgcgcggagc ggcgtcccct gcagccgcgg accgaggcag | 50 |
| cggcggcacc tgccggccga gcaatgccaa gtgagtacac ctatgtgaaa | 100 |
| ctgagaagtg attgctcgag gccttccctg caatggtaca cccgagctca | 150 |
| aagcaagatg agaaggccca gcttgttatt aaaagacatc ctcaaatgta | 200 |
| cattgcttgt gtttggagtg tggatccttt atatcctcaa gttaaattat | 250 |
| actactgaaa aatgtgacat gaaaaaaatg cattatgtgg accctgacca | 300 |
| tgtaaagaga gctcagaaat atgctcagca agtcttgcag aaggaatgtc | 350 |
| gtcccaagtt tgccaagaca tcaatggcgc tgttatttga gcacaggtat | 400 |
| agcgtggact tactcccttt tgtgcagaag ccccccaaag acagtgaagc | 450 |
| tgagtccaag tacgatcctc cttttgggtt ccggaagttc tccagtaaag | 500 |
| tccagaccct cttggaactc ttgccagagc acgacctccc tgaacacttg | 550 |
| aaagccaaga cctgtcggcg ctgtgtggtt attggaagcg gaggaatact | 600 |
| gcacggatta gaactgggcc acaccctgaa ccagttcgat gttgtgataa | 650 |
| ggttaaacag tgcaccagtt gagggatatt cagaacatgt tggaaataaa | 700 |
| actactataa ggatgactta ccagagggc gcaccactgt ctgaccttga | 750 |
| atattattcc aatgacttat ttgttgctgt tttatttaag agtgttgatt | 800 |
| tcaactggct tcaagcaatg gtaaaaaagg aaaccctgcc attctgggta | 850 |
| cgactcttct tttggaagca ggtggcagaa aaaatcccac tgcagccaaa | 900 |
| acatttcagg atttgaatc cagttatcat caaagagact gcctttgaca | 950 |
| tccttcagta ctcagagcct cagtcaaggt tctggggccg agataagaac | 1000 |
| gtccccacaa tcggtgtcat tgccgttgtc ttagccacac atctgtgcga | 1050 |
| tgaagtcagt ttggcgggtt ttggatatga cctcaatcaa cccagaacac | 1100 |
| ctttgcacta cttcgacagt caatgcatgg ctgctatgaa ctttcagacc | 1150 |
| atgcataatg tgacaacgga aaccaagttc ctcttaaagc tggtcaaaga | 1200 |
| gggagtggtg aaagatctca gtggaggcat tgatcgtgaa ttttgaacac | 1250 |
| agaaaacctc agttgaaaat gcaactctaa ctctgagagc tgtttttgac | 1300 |
| agccttcttg atgtatttct ccatcctgca gatactttga agtgcagctc | 1350 |
| atgttttaa cttttaattt aaaaacacaa aaaaatttt agctcttccc | 1400 |
| actttttttt tcctatttat ttgaggtcag tgtttgtttt tgcacaccat | 1450 |
| tttgtaaatg aaacttaaga attgaattgg aaagacttct caaagagaat | 1500 |
| tgtatgtaac gatgttgtat tgatttttaa gaaagtaatt taatttgtaa | 1550 |
| aacttctgct cgtttacact gcacattgaa tacaggtaac taattggaag | 1600 |
| gagaggggag gtcactcttt tgatggtggc cctgaacctc attctggttc | 1650 |
| cctgctgcgc tgcttggtgt gacccacgga ggatccactc ccaggatgac | 1700 |
| gtgctccgta gctctgctgc tgatactggg tctgcgatgc agcggcgtga | 1750 |
| ggcctgggct ggttggagaa ggtcacaacc cttctctgtt ggtctgcctt | 1800 |

```
ctgctgaaag actcgagaac caaccaggga agctgtcctg gaggtccctg       1850
gtcggagagg gacatagaat ctgtgacctc tgacaactgt gaagccaccc       1900
tgggctacag aaaccacagt cttcccagca attattacaa ttcttgaatt       1950
ccttggggat tttttactgc cctttcaaag cacttaagtg ttagatctaa       2000
cgtgttccag tgtctgtctg aggtgactta aaaaatcaga acaaaacttc       2050
tattatccag agtcatggga gagtacaccc tttccaggaa taatgttttg       2100
ggaaacactg aaatgaaatc ttcccagtat tataaattgt gtatttaa        2148

<210> SEQ ID NO 106
<211> LENGTH: 362
<212> TYPE: PRT
<213> ORGANISM: Homo Sapien

<400> SEQUENCE: 106

Met Arg Arg Pro Ser Leu Leu Leu Lys Asp Ile Leu Lys Cys Thr
 1               5                  10                  15

Leu Leu Val Phe Gly Val Trp Ile Leu Tyr Ile Leu Lys Leu Asn
                20                  25                  30

Tyr Thr Thr Glu Glu Cys Asp Met Lys Lys Met His Tyr Val Asp
                35                  40                  45

Pro Asp His Val Lys Arg Ala Gln Lys Tyr Ala Gln Gln Val Leu
                50                  55                  60

Gln Lys Glu Cys Arg Pro Lys Phe Ala Lys Thr Ser Met Ala Leu
            65                  70                  75

Leu Phe Glu His Arg Tyr Ser Val Asp Leu Leu Pro Phe Val Gln
                80                  85                  90

Lys Ala Pro Lys Asp Ser Glu Ala Glu Ser Lys Tyr Asp Pro Pro
                95                 100                 105

Phe Gly Phe Arg Lys Phe Ser Ser Lys Val Gln Thr Leu Leu Glu
                110                 115                 120

Leu Leu Pro Glu His Asp Leu Pro Glu His Leu Lys Ala Lys Thr
                125                 130                 135

Cys Arg Arg Cys Val Val Ile Gly Ser Gly Gly Ile Leu His Gly
                140                 145                 150

Leu Glu Leu Gly His Thr Leu Asn Gln Phe Asp Val Val Ile Arg
                155                 160                 165

Leu Asn Ser Ala Pro Val Glu Gly Tyr Ser Glu His Val Gly Asn
                170                 175                 180

Lys Thr Thr Ile Arg Met Thr Tyr Pro Glu Gly Ala Pro Leu Ser
                185                 190                 195

Asp Leu Glu Tyr Tyr Ser Asn Asp Leu Phe Val Ala Val Leu Phe
                200                 205                 210

Lys Ser Val Asp Phe Asn Trp Leu Gln Ala Met Val Lys Lys Glu
                215                 220                 225

Thr Leu Pro Phe Trp Val Arg Leu Phe Phe Trp Lys Gln Val Ala
                230                 235                 240

Glu Lys Ile Pro Leu Gln Pro Lys His Phe Arg Ile Leu Asn Pro
                245                 250                 255

Val Ile Ile Lys Glu Thr Ala Phe Asp Ile Leu Gln Tyr Ser Glu
                260                 265                 270

Pro Gln Ser Arg Phe Trp Gly Arg Asp Lys Asn Val Pro Thr Ile
                275                 280                 285
```

-continued

```
Gly Val Ile Ala Val Leu Ala Thr His Leu Cys Asp Glu Val
            290                 295                 300

Ser Leu Ala Gly Phe Gly Tyr Asp Leu Asn Gln Pro Arg Thr Pro
        305                 310                 315

Leu His Tyr Phe Asp Ser Gln Cys Met Ala Ala Met Asn Phe Gln
        320                 325                 330

Thr Met His Asn Val Thr Thr Glu Thr Lys Phe Leu Leu Lys Leu
        335                 340                 345

Val Lys Glu Gly Val Val Lys Asp Leu Ser Gly Gly Ile Asp Arg
        350                 355                 360

Glu Phe

<210> SEQ ID NO 107
<211> LENGTH: 1399
<212> TYPE: DNA
<213> ORGANISM: Homo Sapien

<400> SEQUENCE: 107
tgacgcgggg cgccagctgc caacttcgcg cgcggagctc cccggcggtg           50
cagtcccgtc ccggcggcgc gggcggcatg aagactagcc gccgcggccg          100
agcgctcctg gccgtggccc tgaacctgct ggcgctgctg ttcgccacca          150
ccgctttcct caccacgcac tggtgccagg gcacgcagcg ggtccccaag          200
ccgggctgcg gccagggcgg gcgcgccaac tgccccaact cgggcgccaa          250
cgccacggcc aacggcaccg ccgcccccgc cgccgccgcc gccgccgcca          300
ccgcctcggg gaacgcccc cctggcggcg cgctctacag ctgggagacc           350
ggcgacgacc gcttcctctt caggaatttc cacaccggca tctggtactc          400
gtgcgaggag gagctcagcg ggcttggtga aaaatgtcgc agcttcattg          450
acctggcccc ggcgtcggag aaaggcctcc tgggaatggt cgcccacatg          500
atgtacacgc aggtgttcca ggtcaccgtg agcctcggtc ctgaggactg          550
gagaccccat tcctgggact acgggtggtc cttctgcctg gcgtggggct          600
cctttacctg ctgcatggca gcctctgtca ccacgctcaa ctcctacacc          650
aagacggtca ttgagttccg gcacaagcgc aaggtctttg agcagggcta          700 ccggaagag ccgaccttca tagaccctga ggccatcaag tacttccggg           750
agaggatgga gaagagggac gggagcgagg aggactttca cttagactgc          800
cgccacgaga gataccctgc ccgacaccag ccacacatgg cggattcctg          850
gccccggagc tccgcacagg aagcaccaga gctgaaccga cagtgctggg          900
tcttggggca ctgggtgtga ccaagaccta acctggcccc gcggacctca          950
ggccatcgct ggcaccagcc cctgctgcaa gaccaccaga gtggtgcccc         1000
cagaaccctg gcctgtgtgc cgtgaactca gtcagcctgc gtgggagatg         1050
ccaggcctgt cctgcccatc gctgcctggg tcccatggcc ttgaaatgg          1100 ggccagggca ggcccaaggg aatgcacagg gctgcacaga gtgactttgg         1150
gacagcagcc ccggactctt gccatcatca catgagccct gctgggcaca         1200
gctgcgatgc caggagacac atggccactg ccactgaat ggctggcacc          1250 cacaagccag tcaggtgccc agaggggcag agccctttgg ggggcagaga         1300
gtggcttcct gaaggagggg gcagtggcgc aggcactgca ggggtgtcac         1350
```
acagcaggca cacagcaggg gctcaataaa tgcttgttga acttgtttt           1399

<210> SEQ ID NO 108
<211> LENGTH: 280
<212> TYPE: PRT
<213> ORGANISM: Homo Sapien

<400> SEQUENCE: 108

Met Lys Thr Ser Arg Arg Gly Arg Ala Leu Leu Ala Val Ala Leu
 1               5                  10                  15

Asn Leu Leu Ala Leu Leu Phe Ala Thr Thr Ala Phe Leu Thr Thr
            20                  25                  30

His Trp Cys Gln Gly Thr Gln Arg Val Pro Lys Pro Gly Cys Gly
            35                  40                  45

Gln Gly Gly Arg Ala Asn Cys Pro Asn Ser Gly Ala Asn Ala Thr
        50                  55                  60

Ala Asn Gly Thr Ala Ala Pro Ala Ala Ala Ala Ala Ala Ala Thr
        65                  70                  75

Ala Ser Gly Asn Gly Pro Pro Gly Gly Ala Leu Tyr Ser Trp Glu
        80                  85                  90

Thr Gly Asp Asp Arg Phe Leu Phe Arg Asn Phe His Thr Gly Ile
        95                  100                 105

Trp Tyr Ser Cys Glu Glu Leu Ser Gly Leu Gly Glu Lys Cys
        110                 115                 120

Arg Ser Phe Ile Asp Leu Ala Pro Ala Ser Glu Lys Gly Leu Leu
        125                 130                 135

Gly Met Val Ala His Met Met Tyr Thr Gln Val Phe Gln Val Thr
        140                 145                 150

Val Ser Leu Gly Pro Glu Asp Trp Arg Pro His Ser Trp Asp Tyr
        155                 160                 165

Gly Trp Ser Phe Cys Leu Ala Trp Gly Ser Phe Thr Cys Cys Met
        170                 175                 180

Ala Ala Ser Val Thr Thr Leu Asn Ser Tyr Thr Lys Thr Val Ile
        185                 190                 195

Glu Phe Arg His Lys Arg Lys Val Phe Glu Gln Gly Tyr Arg Glu
        200                 205                 210

Glu Pro Thr Phe Ile Asp Pro Glu Ala Ile Lys Tyr Phe Arg Glu
        215                 220                 225

Arg Met Glu Lys Arg Asp Gly Ser Glu Glu Asp Phe His Leu Asp
        230                 235                 240

Cys Arg His Glu Arg Tyr Pro Ala Arg His Gln Pro His Met Ala
        245                 250                 255

Asp Ser Trp Pro Arg Ser Ser Ala Gln Glu Ala Pro Glu Leu Asn
        260                 265                 270

Arg Gln Cys Trp Val Leu Gly His Trp Val
        275                 280

<210> SEQ ID NO 109
<211> LENGTH: 2964
<212> TYPE: DNA
<213> ORGANISM: Homo Sapien

<400> SEQUENCE: 109
gattaccaag caagaacagc taaaatgaaa gccatcattc atcttactct           50
tcttgctctc ctttctgtaa acacagccac caaccaaggc aactcagctg           100

-continued

| | |
|---|---|
| atgctgtaac aaccacagaa actgcgacta gtggtcctac agtagctgca | 150 |
| gctgatacca ctgaaactaa tttccctgaa actgctagca ccacagcaaa | 200 |
| tacaccttct ttcccaacag ctacttcacc tgctccccccc ataattagta | 250 |
| cacatagttc ctccacaatt cctacacctg ctcccccccat aattagtaca | 300 |
| catagttcct ccacaattcc tatacctact gctgcagaca gtgagtcaac | 350 |
| cacaaatgta aattcattag ctacctctga cataatcacc gcttcatctc | 400 |
| caaatgatgg attaatcaca atggttcctt ctgaaacaca agtaacaat | 450 |
| gaaatgtccc ccaccacaga agacaatcaa tcatcagggc ctcccactgg | 500 |
| caccgcttta ttggagacca gcaccctaaa cagcacaggt cccagcaatc | 550 |
| cttgccaaga tgatccctgt gcagataatt cgttatgtgt taagctgcat | 600 |
| aatacaagtt tttgcctgtg tttagaaggg tattactaca actcttctac | 650 |
| atgtaagaaa ggaaaggtat tccctgggaa gatttcagtg acagtatcag | 700 |
| aaacatttga cccagaagag aaacattcca tggcctatca agacttgcat | 750 |
| agtgaaatta ctagcttgtt taaagatgta tttggcacat ctgtttatgg | 800 |
| acagactgta attcttactg taagcacatc tctgtcacca agatctgaaa | 850 |
| tgcgtgctga tgacaagttt gttaatgtaa caatagtaac aattttggca | 900 |
| gaaaccacaa gtgacaatga gaagactgtg actgagaaaa ttaataaagc | 950 |
| aattagaagt agctcaagca actttctaaa ctatgatttg acccttcggt | 1000 |
| gtgattatta tggctgtaac cagactgcgg atgactgcct caatggttta | 1050 |
| gcatgcgatt gcaaatctga cctgcaaagg cctaacccac agagcccttt | 1100 |
| ctgcgttgct tccagtctca agtgtcctga tgcctgcaac gcacagcaca | 1150 |
| agcaatgctt aataaagaag agtggtgggg cccctgagtg tgcgtgcgtg | 1200 |
| cccggctacc aggaagatgc taatgggaac tgccaaaagt gtgcatttgg | 1250 |
| ctacagtgga ctcgactgta aggacaaatt tcagctgatc ctcactattg | 1300 |
| tgggcaccat cgctggcatt gtcattctca gcatgataat tgcattgatt | 1350 |
| gtcacagcaa gatcaaataa caaaacgaag catattgaag aagagaactt | 1400 |
| gattgacgaa gactttcaaa atctaaaact gcggtcgaca ggcttcacca | 1450 |
| atcttggagc agaagggagc gtctttccta aggtcaggat aacggcctcc | 1500 |
| agagacagcc agatgcaaaa tccctattca agccacagca gcatgccccg | 1550 |
| ccctgactat tagaatcata agaatgtgga acccgccatg gcccccaacc | 1600 |
| aatgtacaag ctattattta gagtgtttag aaagactgat ggagaagtga | 1650 |
| gcaccagtaa agatctggcc tccgggggttt tcttccatc tgacatctgc | 1700 |
| cagcctctct gaatggaagt tgtgaatgtt tgcaacgaat ccagctcact | 1750 |
| tgctaaataa gaatctatga cattaaatgt agtagatgct attagcgctt | 1800 |
| gtcagagagg tggttttctt caatcagtac aaagtactga gacaatggtt | 1850 |
| aggtttgttt tcttaattct tttcctggta gggcaacaag aaccatttcc | 1900 |
| aatctagagg aaagctcccc agcattgctt gctcctgggc aaacattgct | 1950 |
| cttgagttaa gtgacctaat tcccctggga gacatacgca tcaactgtgg | 2000 |
| aggtccgagg ggatgagaag ggataccccac catctttcaa gggtcacaag | 2050 |

-continued

```
ctcactctct gacaagtcag aatagggaca ctgcttctat ccctccaatg      2100
gagagattct ggcaacccttt gaacagccca gagcttgcaa cctagcctca     2150
cccaagaaga ctggaaagag acatatctct cagcttttc aggaggcgtg       2200 cctgggaatc caggaacttt ttgatgctaa ttagaaggcc tggactaaaa      2250
atgtccacta tggggtgcac tctacagttt ttgaaatgct aggaggcaga      2300
aggggcagag agtaaaaaac atgacctggt agaaggaaga gaggcaaagg      2350
aaactgggtg gggaggatca attagagagg aggcacctgg gatccacctt      2400
cttccttagg tcccctcctc catcagcaaa ggagcacttc tctaatcatg      2450
ccctcccgaa gactggctgg gagaaggttt aaaaacaaaa aatccaggag      2500
taagagcctt aggtcagttt gaaattggag acaaactgtc tggcaaaggg     2550
tgcgagaggg agcttgtgct caggagtcca gccgcccagc ctcggggtgt      2600
aggtttctga ggtgtgccat tggggcctca gccttctctg gtgacagagg      2650
ctcagctgtg gccaccaaca cacaaccaca cacacacaac cacacacaca     2700
aatgggggca accacatcca gtacaagctt ttacaaatgt tattagtgtc     2750
cttttttatt tctaatgcct tgtcctctta aaagttattt tatttgttat     2800
tattatttgt tcttgactgt taattgtgaa tggtaatgca ataaagtgcc     2850
tttgttagat ggtgaaaaaa aaaaaaaaaa aaaaaaaaaa aaaaaaaaaa      2900
aaaaaaaaaa aaaaaaaaaa aaaaaaaaaa aaaaaaaaaa aaaaaaaaaa      2950
aaaaaaaaaa aaaa                                              2964
```

<210> SEQ ID NO 110
<211> LENGTH: 512
<212> TYPE: PRT
<213> ORGANISM: Homo Sapien

<400> SEQUENCE: 110

```
Met Lys Ala Ile Ile His Leu Thr Leu Leu Ala Leu Leu Ser Val
 1               5                  10                  15

Asn Thr Ala Thr Asn Gln Gly Asn Ser Ala Asp Ala Val Thr Thr
                20                  25                  30

Thr Glu Thr Ala Thr Ser Gly Pro Thr Val Ala Ala Asp Thr
                35                  40                  45

Thr Glu Thr Asn Phe Pro Glu Thr Ala Ser Thr Thr Ala Asn Thr
                50                  55                  60

Pro Ser Phe Pro Thr Ala Thr Ser Pro Ala Pro Ile Ile Ser
 65                  70                  75

Thr His Ser Ser Ser Thr Ile Pro Thr Pro Ala Pro Ile Ile
                80                  85                  90

Ser Thr His Ser Ser Ser Thr Ile Pro Ile Pro Thr Ala Ala Asp
                95                 100                 105

Ser Glu Ser Thr Thr Asn Val Asn Ser Leu Ala Thr Ser Asp Ile
               110                 115                 120

Ile Thr Ala Ser Ser Pro Asn Asp Gly Leu Ile Thr Met Val Pro
               125                 130                 135

Ser Glu Thr Gln Ser Asn Asn Glu Met Ser Pro Thr Thr Glu Asp
               140                 145                 150

Asn Gln Ser Ser Gly Pro Pro Thr Gly Thr Ala Leu Leu Glu Thr
               155                 160                 165
```

-continued

```
Ser Thr Leu Asn Ser Thr Gly Pro Ser Asn Pro Cys Gln Asp Asp
            170                 175                 180

Pro Cys Ala Asp Asn Ser Leu Cys Val Lys Leu His Asn Thr Ser
        185                 190                 195

Phe Cys Leu Cys Leu Glu Gly Tyr Tyr Tyr Asn Ser Ser Thr Cys
    200                 205                 210

Lys Lys Gly Lys Val Phe Pro Gly Lys Ile Ser Val Thr Val Ser
215                 220                 225

Glu Thr Phe Asp Pro Glu Lys His Ser Met Ala Tyr Gln Asp
            230                 235                 240

Leu His Ser Glu Ile Thr Ser Leu Phe Lys Asp Val Phe Gly Thr
        245                 250                 255

Ser Val Tyr Gly Gln Thr Val Ile Leu Thr Val Ser Thr Ser Leu
    260                 265                 270

Ser Pro Arg Ser Glu Met Arg Ala Asp Asp Lys Phe Val Asn Val
275                 280                 285

Thr Ile Val Thr Ile Leu Ala Glu Thr Thr Ser Asp Asn Glu Lys
            290                 295                 300

Thr Val Thr Glu Lys Ile Asn Lys Ala Ile Arg Ser Ser Ser Ser
        305                 310                 315

Asn Phe Leu Asn Tyr Asp Leu Thr Leu Arg Cys Asp Tyr Tyr Gly
    320                 325                 330

Cys Asn Gln Thr Ala Asp Asp Cys Leu Asn Gly Leu Ala Cys Asp
335                 340                 345

Cys Lys Ser Asp Leu Gln Arg Pro Asn Pro Gln Ser Pro Phe Cys
            350                 355                 360

Val Ala Ser Ser Leu Lys Cys Pro Asp Ala Cys Asn Ala Gln His
        365                 370                 375

Lys Gln Cys Leu Ile Lys Lys Ser Gly Gly Ala Pro Glu Cys Ala
    380                 385                 390

Cys Val Pro Gly Tyr Gln Glu Asp Ala Asn Gly Asn Cys Gln Lys
395                 400                 405

Cys Ala Phe Gly Tyr Ser Gly Leu Asp Cys Lys Asp Lys Phe Gln
            410                 415                 420

Leu Ile Leu Thr Ile Val Gly Thr Ile Ala Gly Ile Val Ile Leu
        425                 430                 435

Ser Met Ile Ile Ala Leu Ile Val Thr Ala Arg Ser Asn Asn Lys
    440                 445                 450

Thr Lys His Ile Glu Glu Asn Leu Ile Asp Glu Asp Phe Gln
            455                 460                 465

Asn Leu Lys Leu Arg Ser Thr Gly Phe Thr Asn Leu Gly Ala Glu
        470                 475                 480

Gly Ser Val Phe Pro Lys Val Arg Ile Thr Ala Ser Arg Asp Ser
    485                 490                 495

Gln Met Gln Asn Pro Tyr Ser Ser His Ser Ser Met Pro Arg Pro
500                 505                 510

Asp Tyr
```

<210> SEQ ID NO 111
<211> LENGTH: 943
<212> TYPE: DNA
<213> ORGANISM: Homo Sapien

<400> SEQUENCE: 111

-continued

```
ctgggacttg gctttctccg gataagcggc ggcaccggcg tcagcgatga      50
ccgtgcagag actcgtggcc gcggccgtgc tggtggccct ggtctcactc     100
atcctcaaca acgtggcggc cttcacctcc aactgggtgt gccagacgct     150
ggaggatggg cgcaggcgca gcgtggggct gtggaggtcc tgctggctgg     200
tggacaggac ccggggaggg ccgagccctg gggccagagc cggccaggtg     250
gacgcacatg actgtgaggc gctgggctgg ggctccgagg cagccggctt     300
ccaggagtcc cgaggcaccg tcaaactgca gttcgacatg atgcgcgcct     350
gcaacctggt ggccacggcc gcgctcaccg caggccagct caccttcctc     400
ctggggctgg tgggcctgcc cctgctgtca cccgacgccc cgtgctggga     450
ggaggccatg gccgctgcat tccaactggc gagttttgtc ctggtcatcg     500
ggctcgtgac tttctacaga attggcccat acaccaacct gtcctggtcc     550
tgctacctga acattggcgc ctgccttctg gccacgctgg cggcagccat     600
gctcatctgg aacattctcc acaagaggga ggactgcatg gcccccccggg     650
tgattgtcat cagccgctcc ctgacagcgc gctttcgccg tgggctggac     700
aatgactacg tggagtcacc atgctgagtc gcccttctca gcgctccatc     750
aacgcacacc tgctatcgtg aacagcctta gaaaccaagg gactccacca     800
ccaagtcact tcccctgctc gtgcagaggc acgggatgag tctgggtgac     850
ctctgcgcca tgcgtgcgag acacgtgtgc gtttactgtt atgtcggtca     900
tatgtctgta cgtgtcgtgg gccaacctcg ttctgcctcc agc            943
```

<210> SEQ ID NO 112
<211> LENGTH: 226
<212> TYPE: PRT
<213> ORGANISM: Homo Sapien

<400> SEQUENCE: 112

```
Met Thr Val Gln Arg Leu Val Ala Ala Val Leu Val Ala Leu
  1               5                  10                  15

Val Ser Leu Ile Leu Asn Asn Val Ala Ala Phe Thr Ser Asn Trp
                 20                  25                  30

Val Cys Gln Thr Leu Glu Asp Gly Arg Arg Ser Val Gly Leu
                 35                  40                  45

Trp Arg Ser Cys Trp Leu Val Asp Arg Thr Arg Gly Gly Pro Ser
                 50                  55                  60

Pro Gly Ala Arg Ala Gly Gln Val Asp Ala His Asp Cys Glu Ala
                 65                  70                  75

Leu Gly Trp Gly Ser Glu Ala Ala Gly Phe Gln Glu Ser Arg Gly
                 80                  85                  90

Thr Val Lys Leu Gln Phe Asp Met Met Arg Ala Cys Asn Leu Val
                 95                 100                 105

Ala Thr Ala Ala Leu Thr Ala Gly Gln Leu Thr Phe Leu Leu Gly
                110                 115                 120

Leu Val Gly Leu Pro Leu Leu Ser Pro Asp Ala Pro Cys Trp Glu
                125                 130                 135

Glu Ala Met Ala Ala Ala Phe Gln Leu Ala Ser Phe Val Leu Val
                140                 145                 150

Ile Gly Leu Val Thr Phe Tyr Arg Ile Gly Pro Tyr Thr Asn Leu
                155                 160                 165
```

```
Ser Trp Ser Cys Tyr Leu Asn Ile Gly Ala Cys Leu Leu Ala Thr
            170                 175                 180

Leu Ala Ala Ala Met Leu Ile Trp Asn Ile Leu His Lys Arg Glu
            185                 190                 195

Asp Cys Met Ala Pro Arg Val Ile Val Ile Ser Arg Ser Leu Thr
            200                 205                 210

Ala Arg Phe Arg Arg Gly Leu Asp Asn Asp Tyr Val Glu Ser Pro
            215                 220                 225

Cys

<210> SEQ ID NO 113
<211> LENGTH: 1389
<212> TYPE: DNA
<213> ORGANISM: Homo Sapien

<400> SEQUENCE: 113
```

| | | | | |
|---|---|---|---|---|
| gactttacca | ctactcgcta | tagagccctg | gtcaagttct | ctccacctct | 50 |
| ctatctatgt | ctcagtttct | tcatctgtaa | catcaaatga | ataataatac | 100 |
| caatctccta | gacttcataa | gaggattaac | aaagacaaaa | tatgggaaaa | 150 |
| acataacatg | gcgtcccata | attattagat | cttattattg | acactaaaat | 200 |
| ggcattaaaa | ttaccaaaag | gaagacagca | tctgtttcct | ctttggtcct | 250 |
| gagctggtta | aaaggaacac | tggttgcctg | aacagtcaca | cttgcaacca | 300 |
| tgatgcctaa | acattgcttt | ctaggcttcc | tcatcagttt | cttccttact | 350 |
| ggtgtagcag | gaactcagtc | aacgcatgag | tctctgaagc | tcagagggt | 400 |
| acaatttcag | tcccgaaatt | ttcacaacat | tttgcaatgg | cagcctggga | 450 |
| gggcacttac | tggcaacagc | agtgtctatt | ttgtgcagta | caaaatatat | 500 |
| ggacagagac | aatggaaaaa | taaagaagac | tgttggggta | ctcaagaact | 550 |
| ctcttgtgac | cttaccagtg | aaacctcaga | catacaggaa | ccttattacg | 600 |
| ggagggtgag | ggcggcctcg | gctgggagct | actcagaatg | gagcatgacg | 650 |
| ccgcggttca | ctccctggtg | ggaaacaaaa | atagatcctc | cagtcatgaa | 700 |
| tataacccaa | gtcaatggct | ctttgttggt | aattctccat | gctccaaatt | 750 |
| taccatatag | ataccaaaag | gaaaaaaatg | tatctataga | agattactat | 800 |
| gaactactat | accgagtttt | tataattaac | aattcactag | aaaaggagca | 850 |
| aaaggtttat | gaagggggctc | acagagcggt | tgaaattgaa | gctctaacac | 900 |
| cacactccag | ctactgtgta | gtggctgaaa | tatatcagcc | catgttagac | 950 |
| agaagaagtc | agagaagtga | agagagatgt | gtggaaattc | catgacttgt | 1000 |
| ggaatttggc | attcagcaat | gtggaaattc | taaagctccc | tgagaacagg | 1050 |
| atgactcgtg | tttgaaggat | cttatttaaa | attgtttttg | tattttctta | 1100 |
| aagcaatatt | cactgttaca | ccttggggac | ttctttgttt | acccattctt | 1150 |
| ttatccttta | tatttcattt | gtaaactata | tttgaacgac | attcccccg | 1200 |
| aaaaattgaa | atgtaaagat | gaggcagaga | ataaagtgtt | ctatgaaatt | 1250 |
| cagaacttta | tttctgaatg | taacatccct | aataacaacc | ttcattcttc | 1300 |
| taatacagca | aaataaaaat | ttaacaacca | aggaatagta | tttaagaaaa | 1350 |
| tgttgaaata | attttttaa | aatagcatta | cagactgag | | 1389 |

-continued

<210> SEQ ID NO 114
<211> LENGTH: 231
<212> TYPE: PRT
<213> ORGANISM: Homo Sapien

<400> SEQUENCE: 114

```
Met Met Pro Lys His Cys Phe Leu Gly Phe Leu Ile Ser Phe Phe
  1               5                  10                  15

Leu Thr Gly Val Ala Gly Thr Gln Ser Thr His Glu Ser Leu Lys
             20                  25                  30

Pro Gln Arg Val Gln Phe Gln Ser Arg Asn Phe His Asn Ile Leu
             35                  40                  45

Gln Trp Gln Pro Gly Arg Ala Leu Thr Gly Asn Ser Ser Val Tyr
             50                  55                  60

Phe Val Gln Tyr Lys Ile Tyr Gly Gln Arg Gln Trp Lys Asn Lys
 65                  70                  75

Glu Asp Cys Trp Gly Thr Gln Glu Leu Ser Cys Asp Leu Thr Ser
             80                  85                  90

Glu Thr Ser Asp Ile Gln Glu Pro Tyr Tyr Gly Arg Val Arg Ala
             95                 100                 105

Ala Ser Ala Gly Ser Tyr Ser Glu Trp Ser Met Thr Pro Arg Phe
            110                 115                 120

Thr Pro Trp Trp Glu Thr Lys Ile Asp Pro Pro Val Met Asn Ile
            125                 130                 135

Thr Gln Val Asn Gly Ser Leu Leu Val Ile Leu His Ala Pro Asn
            140                 145                 150

Leu Pro Tyr Arg Tyr Gln Lys Glu Lys Asn Val Ser Ile Glu Asp
            155                 160                 165

Tyr Tyr Glu Leu Leu Tyr Arg Val Phe Ile Ile Asn Asn Ser Leu
            170                 175                 180

Glu Lys Glu Gln Lys Val Tyr Glu Gly Ala His Arg Ala Val Glu
            185                 190                 195

Ile Glu Ala Leu Thr Pro His Ser Ser Tyr Cys Val Val Ala Glu
            200                 205                 210

Ile Tyr Gln Pro Met Leu Asp Arg Arg Ser Gln Arg Ser Glu Glu
            215                 220                 225

Arg Cys Val Glu Ile Pro
            230
```

<210> SEQ ID NO 115
<211> LENGTH: 43
<212> TYPE: DNA
<213> ORGANISM: Artificial Sequence
<220> FEATURE:
<223> OTHER INFORMATION: Synthetic Oligonucleotide Probe

<400> SEQUENCE: 115
tgtaaaacga cggccagtta aatagacctg caattattaa tct          43

<210> SEQ ID NO 116
<211> LENGTH: 41
<212> TYPE: DNA
<213> ORGANISM: Artificial Sequence
<220> FEATURE:
<223> OTHER INFORMATION: Synthetic Oligonucleotide Probe

<400> SEQUENCE: 116
caggaaacag ctatgaccac ctgcacacct gcaaatccat t            41

What is claimed is:

1. An isolated polypeptide comprising:
   (a) the amino acid sequence of the polypeptide of SEQ ID NO:38;
   (b) the amino acid sequence of the polypeptide of SEQ ID NO:38, lacking its associated signal peptide; or
   (c) the amino acid sequence of the polypeptide encoded by the full-length coding sequence of the cDNA deposited under ATCC accession number 203969.

2. The isolated polypeptide of claim 1 comprising the amino acid sequence of the polypeptide of SEQ ID NO:38.

3. The isolated polypeptide of claim 1 comprising the amino acid sequence of the polypeptide of SEQ ID NO:38, lacking its associated signal peptide.

4. The isolated polypeptide of claim 1 comprising the amino acid sequence of the polypeptide encoded by the full-length coding sequence of the cDNA deposited under ATCC accession number 203969.

5. A chimeric polypeptide comprising a polypeptide according to claim 1 fused to a heterologous polypeptide.

6. The chimeric polypeptide of claim 5, wherein said heterologous polypeptide is an epitope tag on an Fc region of an immunoglobulin.

* * * * *